United States Patent
Kodama et al.

(10) Patent No.: US 7,803,801 B2
(45) Date of Patent: Sep. 28, 2010

(54) AMINOPYRIDINE COMPOUNDS HAVING SYK INHIBITORY ACTIVITY

(75) Inventors: Yoshitoshi Kodama, Takatsuki (JP); Satoru Noji, Takatsuki (JP); Katsuaki Imamura, Takatsuki (JP); Ryo Mizojiri, Takatsuki (JP); Kenta Aoki, Takatsuki (JP); Hideo Takagi, Takatsuki (JP); Yuichi Naka, Takatsuki (JP); Goro Ito, Hadano (JP); Kiyotaka Shinoda, Takatsuki (JP); Akihito Fujiwara, Takatsuki (JP); Kazunori Kurihara, Takatsuki (JP); Masaru Tanaka, Takatsuki (JP)

(73) Assignee: Japan Tobacco, Inc., Tokyo (JP)

( * ) Notice: Subject to any disclaimer, the term of this patent is extended or adjusted under 35 U.S.C. 154(b) by 925 days.

(21) Appl. No.: 11/363,563

(22) Filed: Feb. 28, 2006

(65) Prior Publication Data

US 2006/0205731 A1 Sep. 14, 2006

Related U.S. Application Data

(60) Provisional application No. 60/658,885, filed on Mar. 4, 2005, provisional application No. 60/763,045, filed on Jan. 27, 2006.

(30) Foreign Application Priority Data

| Feb. 28, 2005 | (JP) | 2005-052469 |
| Jan. 19, 2006 | (JP) | 2006-011751 |

(51) Int. Cl.
C07D 401/00 (2006.01)
A61K 31/47 (2006.01)

(52) U.S. Cl. ............ 514/252.03; 514/255.05; 514/275; 514/332; 544/238; 544/329; 544/405; 546/256

(58) Field of Classification Search .............. None
See application file for complete search history.

(56) References Cited

U.S. PATENT DOCUMENTS

2005/0239800 A1* 10/2005 Wang et al. ............ 514/255.05

FOREIGN PATENT DOCUMENTS

| JP | 2003-528872 | 9/2003 |
| JP | 2004-203748 | 7/2004 |
| WO | WO 98/18782 | 5/1998 |
| WO | WO 01/72745 | 10/2001 |
| WO | WO 01/83485 A1 | 11/2001 |
| WO | WO 02/096905 A1 | 12/2002 |
| WO | WO 2004/016597 A2 | 2/2004 |
| WO | WO 2004/041810 A1 | 5/2004 |
| WO | WO 2004/067516 A1 | 8/2004 |
| WO | WO 2004/087698 A2 | 10/2004 |
| WO | WO 2004/087699 A2 | 10/2004 |

OTHER PUBLICATIONS

Simone, Oncology: Introduction, Cecil Textbook of Medicine, 20th Edition, vol. 1, pp. 1004-1010, 1996.*
Casanova et al., PubMed Abstract (Rev Neurol. 28(9):909-15) May 1999.*
Traxler, Protein Tyrosine Kinase Inhibitors in Cancer Treatment, Expert Opinion on Therapeutic Patents, 7(6):571-588, 1997.*
Naika (Internal medicine) 81, 485-490(1998).
Naika (Internal medicine) 69, 207-214(1992).
M.A. Giembycz, et al., "Propects for Selective Cyclic Nucleotide Phosphodiesterase Inhibitors in the Treatment of Bronchial Asthma", Clin. Exp. Allergy, 22, 337-344(1992).
John A. Lowe, et al., "The PDE IV Family of Calcium-independent Phosphodiesterase Enzyme", Drugs of the Future, 17, 799-807(1992).
Ronald E. Weishaar, et al., "Relationship Between Inhibition of Cardiac Muscle Phosphodiesterases, Changes in Cyclic Nucleotide Levels, and Contractile Response for CI-914 and Other Novel Cardiotonics", J. Cyclic Nucleotide and Protein Phosphorylation Res., 10, 551-564(1985).
Richard J. Heaslip, et al., "Bronchial vs. Cardiovascular Activities of Selective Phosphodiesterase Inhibitors in the Anesthetized Beta-Blocked Dog", J. Pharmacol. Exp. Ther., 257, 741-747(1991).
Ulrich Blank, at al., "Characterization of Truncated a Chain Products From Human, Rat, and Mouse High Affinity Receptor for Immunoglobulin E", E. J. Biol. Chem.266, p. 2639-2646, 1991.

(Continued)

Primary Examiner—Zinna N Davis
(74) Attorney, Agent, or Firm—Fitzpatrick, Cella, Harper & Scinto

(57) ABSTRACT

The present invention relates to an aminopyridine compound represented by the following general formula (I) or a salt thereof and an Syk inhibitor containing the compound or a salt thereof as an active ingredient. Here, $X^1, X^2, X^3, Z, Y^1, Y^2$ represent a carbon atom or a nitrogen atom, R, $R^1, R^5, R^6$ represent a hydrogen atom, an alkyl group, etc., and $R^7$ represents a hydrogen atom, a halogen atom, a nitro group, a cyano group, $-C_pH_{2(p-1)}(R^{a1})(R^{a2})-O-R^{a3}, -C(=O)-R^{d1}$, a 5- or 6-membered saturated heterocyclic group, an aromatic heterocyclic group, $-N(R^{h1})(R^{h2})$, etc. The aminopyridine compound of the present invention has not only high Syk inhibitory activity but also properties to selectively inhibit Syk.

(I)

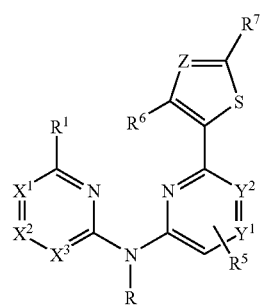

13 Claims, No Drawings

OTHER PUBLICATIONS

Lily Shiue, et al., "Syk is Activated by Phosphotyrosine-containing Peptides Representing the Tyrosine-based Activation Motifs of the High Affinityt Receptor for IgE", J. Biol. Chem. vol. 270. p. 10498-10502, 1995.

Lori E. Hutchinson, et al., "Fc∈RI-mediated Induction of Nuclear Factor of Activated T-cells", J. Biol. Chem. vol. 270, p. 16333-16338, 1995.

Mary T. Crowley, et al., "A Critical Role for Syk in Signal Transduction and Phagocytosis Mediated by Fcγ Receptors on Macrophages", J. Exp. Med. 186:1027-1039(1997).

Jill E. Hutchcroft, et al., "Association of the 72-kDa Protein-tyrosine Kinase PTK72 With the B Cell Antigen Receptor", J. Biol. Chem., 1992, vol. 267, p. 8613-8619.

Minoru Takata, et al., "Tyrosine Kinases Lyn and Syk Regulate B Cell Receptor-coupled $Ca^{2}+$ Mobilization Through Distinct Pathways", EMBO J., 1994, vol. 13, p. 1341-1349.

Shida Yousefi, et al., "Requirement of Lyn and Syk Tyrosine Kinases for the Prevention of Apoptosis by Cytokines in Human Eosinophils", J. Exp. Med., 1996, vol. 183, p. 1407-1414.

A. Poole, et al., "The Fc Receptor γ-chain and the Tyrosine Kinase Syk are Essential for Activation of Mouse Platelets by Collagen", EMBO J., 1997, vol. 16, p. 2333-2341.

Enrico Abignente, et al., "Research on Heterocyclic Compounds. XXVIII. Imidazo[1,2-c]Pyrimidines", IL Farmaco, 1991, vol. 46, p. 1099-1110.

Janet M. Oliver, et al., "Inhibition of Mast Cell Fc∈R1-mediated Signaling and Effector Function by the Syk-selective Inhibitor, Piceatannol", J. Biol. Chem. 269: 29697-29703 (1994).

* cited by examiner

AMINOPYRIDINE COMPOUNDS HAVING SYK INHIBITORY ACTIVITY

This application claims the benefit of priority of U.S. Provisional Application No. 60/658,885, filed Mar. 4, 2005, and No. 60/763,045, filed Jan. 27, 2006, which are incorporated by reference.

TECHNICAL FIELD

The present invention relates to a novel aminopyridine compound having Syk (Spleen tyrosine kinase) inhibitory effect and a therapeutic agent for allergic diseases comprising the compound as an active ingredient.

BACKGROUND ART

1. What is Allergic Disease Such as Bronchial Asthma

It is known that Type I (immediate) allergic reaction, which plays a central role in allergic diseases represented by bronchial asthma, allergic rhinitis, atopic dermatitis, is initiated by mutual action of an exogenous antigen such as pollen or house dust and immunoglobulin E (IgE) specific thereto. An allergen which has entered into the body is presented to helper T cells (Th cells) as an HLA ClassII molecule and a peptide fragment by antigen presenting cells such as macrophages, and Th cells are activated by antigen stimulation through T cell receptors and produce cytokines such as interleukin-4. Thereby production of a specific IgE antibody for the allergen by B cells is enhanced.

There exist receptors which bind to the produced IgE antibody with high affinity on the surface of the cells such as mast cell, basophil, monocyte and are referred to as high affinity IgE receptor (FcεRI). When IgE bound to FcεRI is crosslinked by polyvalent antigen, it is activated and various kinds of mediators are released. In other words, it is considered that the signal transfer from FcεRI into the cell triggers allergic disease such as bronchial asthma.

As mediators which mast cells release, there are preformed mediators such as histamine which is released to outside of the cells upon degranulation and mediators produced and released at an early stage of activation such as arachidonic acid metabolite. When these act on bronchi, bronchial smooth muscle contracts and airway becomes narrower due to swelling of mucosa, secretion of phlegm and so on, which causes asthmatic attack. When they act on skin, inflammation, swelling and itching occur and nettle-rashs and so on are caused. When they act on nasal mucosa, vascular permeability is increased and moisture in the blood gathers and a nasal mucosa swells up to cause a stuffy nose and bring about allergic rhinitis in which sneeze and a lot of nasal mucus are generated by nerve stimulation. When this reaction is caused in alimentary canal, enteric smooth muscle contracts, and enteric movement (peristaltic movement) abnormally increases to cause gastrointestinal allergy such as abdominal pain, vomiting and diarrhea.

As mediators released from mast cells, in addition to these, there are eosinophil chemotactic factor and cytokines which are accompanied with transcription and released after a delay through protein synthesis. This is considered as a cause of chronic inflammation (Non-Patent Document 1; Enshou-to-Men'eki (Inflammation and Immunity) vol. 7, no. 2, 1999, p. 165-171). Drawn by the eosinophil chemotactic factor and cytokine discharged from mast cells, eosinophil having strongly toxic chemical substance gathers to the site of allergic reaction and discharge chemical substances and cause a tissue injury. If this reaction is caused in bronchi, mucosa epithelium exfoliates, allowing an antigen to invade more easily, and allergic reaction is prolonged. As a result, asthma becomes refractory, in which airway hyperresponsiveness is enhanced, the airway becomes narrower due to swelling and phlegm and breathing cannot be performed freely, etc. The condition ranges from a symptom only with a chronic cough and phlegm to a serious condition with a fatal strong stroke. The number of patients has been increased steadily till now and is expected to increase further in the future, and development of an effective pharmaceutical drug is desired earnestly.

2. Existing Asthma Drug

At present, inhaled steroid as an anti-inflammatory drugs, β stimulant such as procaterol and xanthine derivatives such as aminophylline and theophylline as a bronchodilator are mainly used for the treatment of asthma. The inhaled steroid has a broad anti-inflammatory effect, and utility thereof as a therapeutic agent for asthma is high, but necessity of guidance of an appropriate inhalation method and existence of an asthmatic of steroid resistance have been pointed out (Non-Patent Document 2; ASTHMA 13-1, 69-73 (2000), Non-Patent Document 3; Naika (Internal medicine) 81, 485-490 (1998)). The bronchodilator activates adenylate cyclase, an enzyme which produces intracellular adenosine 3',5'-cyclic monophosphate (cAMP), or inhibits phosphodiesterase (PDE), an enzyme which decomposes cAMP, in airway smooth muscle and thereby increases the cAMP level in the cell and relieves contraction of the airway smooth muscle (Non-Patent Document 4; Naika (Internal medicine) 69, 207-214(1992)). It is known that increase in the intracellular cAMP level causes restraint of contraction in the airway smooth muscle (Non-Patent Document 5; Clin. Exp. Allergy, 22, 337-344(1992), Non-Patent Document 6; Drugs of the Future, 17, 799-807(1992)) and it is effective for improving asthmatic condition. It is known, however, that xanthine derivatives developes systemic side effect such as fall in blood pressure or cardiotonic action (Non-Patent Document 7; J. Cyclic Nucleotide and Protein Phosphorylation Res., 10, 551-564(1985), Non-Patent Document 8; J. Pharmacol. Exp. Ther., 257, 741-747(1991)), and that β stimulant is easy to cause desensitization while increased dose thereof produces side effects such as finger shivering and palpitation. Therefore, development of effective therapeutic agent for asthma free from such side effects is desired earnestly.

3. What Syk is

FcεRI has a basic structure common with the other immunoglobulin receptors (T cell receptor, B cell IgM receptor) and belongs to a superfamily referred to as multichain immune recognition receptor. FcεRI has a heterotetramer structure ($\alpha\beta\gamma_2$) consisting of respectively one α-chain and β-chain and two γ chains noncovalently bonded in the transmembrane region. The α-chain of FcεRI has two immunoglobulin (Ig) homologous domain in extracellular domain, and the immunoglobulin (Ig) homologous domain of C-terminal region binds IgE with high affinity (Non-Patent Document 9; E. J. Biol. Chem. 266, 1991, p. 2639-2646). The intracellular domain thereof is, however, relatively short, and even if the intracellular domain of C-terminal of the α-chain is cut off, there is caused no change in signal transduction. On the other hand, the extracellular domain of the γ-chain is short and it exists almost in the cell forming a homodimer with S—S linkage. Cut-off of the intracellular domain of the γ-chains brings about disruption of signal transfer, and the γ-chains are involved in intracellular signal transfer. The β-chain has a four-transmembrane structure, and both of the N-terminal and C-terminal ends exist in the cell. The β-chain has an effect of amplifying signal transfer, and intracellular signal transfer obviously attenuates when the β-chain is deleted. The β-chain and the γ-chain do not have endogenous enzymatic activity, and there is respectively a specific peptide sequence (immunoreceptor tyrosine-based activation motif: ITAM or antigen receptor activation motif: ARAM) domain based on two tyrosine residue in the intracellular domain. When subjected to tyrosine phosphorylation, they bind SH domain (Srk homology domein) of non-receptor type protein tyrosine kinase (protein tyrosine kinase: PTK) with high affinity.

As proteins tyrosine phosphorylated by aggregation of FcεRI, non-receptor type PTK such as Lyn, Syk and Btk, adapter molecule such as Shc and Grb2, PI3K, etc. have been identified in addition to the FcεRI β-chain and FcεRI γ-chain.

Syk is a molecule belonging to a subfamily referred to as Syk family along with ZAP-70 which is a PTK important in signaling through T cell receptor. It is not permanently associated with FcεRI γ-chain but it strongly bind ITAM of γ-chain tyrosine phosphorylated by Lyn after aggregation of FcεRI through SH2 domain of itself. It is known that Syk is subjected to autophosphorylation and phosphorylation by Lyn upon this binding and Syk causes further allosteric structural change, which enhances its activity (Non-Patent Document 10; J. Biol. Chem. Vol. 270. P. 10498-10502, 1995). The activated Syk induces formation of adapter molecular complex and activation of an enzyme and transfers a signal to the commom passway such as phospholipase CY (PLC γ), MAP kinase (MAPK) which is used by many receptors.

PLC γ is tyrosine phosphorylated by Syk and phosphatidylinositol-4,5-diphosphate (PI-4,5-$P_2$) is hydrolyzed to diacylglycerol (DAG) and inositol-1,4,5-triphosphate ($IP_3$). DAG induces activation of protein kinase C (PKC), and activation of PKC induces degranulation in combination with increase in the intracellular calcium level. In addition, Syk is associated with various adapter molecules having no kinase activity and having only SH2 domain and activates MAPK superfamily, and arachidonic acid metabolism is caused through phosphorylation of $PLA_2$. Activation of ERK, p38, JNK, etc. is involved in cytokine production of mast cell through transcription factors such as AP1 (Non-Patent Document 11; J. Biol. Chem. Vol. 270, p. 16333-16338, 1995).

It is reported that tyrosine phosphorylation of intracellular proteins and phagocytosis reaction, which are caused by immunoglobulin G (IgG) receptor (FcγR) stimulation, are remarkably restrained in a macrophage derived from a Syk deficient mouse (Non-Patent Document 12; Crowley, M. T. et al., J. Exp. Med. 186:1027-1039(1997)). Therefore, Syk plays an extremely important role in phagocytosis by macrophage via FcγR, and its participation in tissue injury caused by antibody-dependent cellular cytotoxicity (ADCC) is shown. Furthermore, Syk is involved in B cell activation (for example, Non-Patent Document 13; J. Biol. Chem., 1992, Vol. 267, p. 8613-8619 and Non-Patent Document 14; EMBO J., 1994, Vol. 13, p. 1341-1349), GM-CSFIL-5 induced eosinophil survival (for example, Non-Patent Document 15; J. Exp. Med., 1996, Vol. 183, p. 1407-1414), activation of blood platelet caused by collagen stimulation (for example, Non-Patent Document 16; EMBO J., 1997, Vol. 16, p. 2333-2341).

Accordingly, Syk inhibitor is expected to be useful as a therapeutic drug for diseases such as diseases derived from immediate allergy reaction and delayed inflammatory reaction (for example, bronchial asthma, allergic rhinitis, contact dermatitis, urticaria, food allergy, conjunctivitis, etc.) and diseases in which antibody participates, eosinophilic inflammation, diseases in which platelet activation participates. Particularly, it is considered to be very useful if it acts in an Syk specific manner without inhibiting Zap-70 which belongs to the same family and is expressed only in T cells.

4. Existing Syk Inhibitor (1) As a novel compound useful as a pharmaceutical drug having inhibitory activity on protein tyrosine kinase, particularly, Syk family tyrosine kinase, imidazo[1,2-c]pyrimidine derivatives represented by the following formula have been reported (Patent Document 1; Japanese Patent Laid-Open No. 2004-203748).

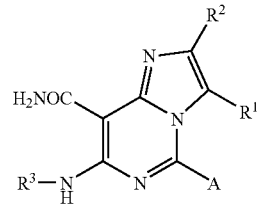

wherein $R^1$ and $R^2$ are hydrogen, lower alkyl, phenyl which may be substituted or heteroaryl, $R^3$ is hydrogen, lower alkyl, cycloalkyl, phenyl which may be substituted, heteroaryl or aralkyl, and A is hydrogen, lower alkyl, cycloalkyl, $R^4$, heteroaryl, $OR^5$, $SR^5$ or $NR^6R^7$.

(2) Abignente E. et al. have disclosed imidazo[1,2-c]pyrimidine derivatives having anti-inflammatory effect represented by the following general formula:

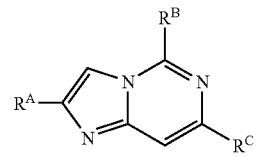

wherein $R^A$ is carboxy, ethoxycarbonyl, carbamoyl or carboxymethyl; $R^B$ is methyl or methoxy; and $R^C$ is methoxy, and methyl or chloro. (for example, Non-Patent Document 17; IL Farmaco, 1991, Vol. 46, p. 1099-1110).

(3) In addition, Yura T. et al. have disclosed imidazo[1,2-c] pyrimidine derivatives useful as an Syk inhibitor represented by the following general formula:

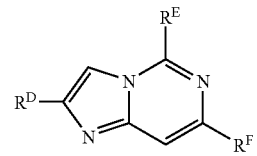

wherein $R^D$ is hydrogen, alkyl, carboxy, alkylcarbonyl or carbamoyl; $R^E$ is —$X^A$—$R^G$, heterocyclyl, carbocyclyl or a condensed ring; $X^A$ is S, O or NH; $R^G$ is aryl or heteroaryl; and $R^F$ is aryl or heteroaryl. (See for example, Patent Document 2; WO0183485).

(4) As a compound having Syk inhibitory effect, there have been reported 2-anilino pyrimidine derivatives represented by the following formula:

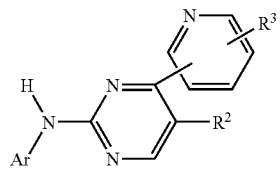

wherein, Ar represents an aromatic ring group which may be substituted, and $R^2$ represents H, halogen or a group represented by —$X^1$—$R^{2a}$ respectively. (See for example, Patent Document 3; WO9818782).

In addition, there has been a report about Piceatannol which is a natural product derived from a plant (Non-Patent Document 18; J. Biol. Chem. 269: 29697-29703(1994)).

(5) As a compound having Syk inhibitory effect, a compound represented by the following formula has been also reported (See Patent Document 4; WO02096905A1). The compound shown herein, however, exhibited an inhibitory effect against plural protein kinases and had an inhibitory effect against GSK3 and Aurora2 at the same level as against Syk.

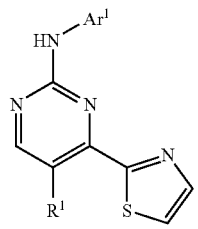

(6) Besides, a compound represented by the following formula has been also reported (Patent Document 5; WO2004016597A2).

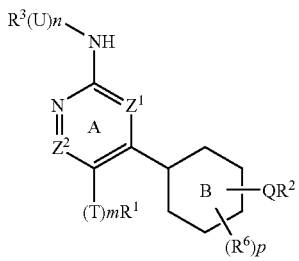

(7) In addition, thiazole derivatives represented by the following formula have been also reported (Patent Document 6; WO2004087698A2).

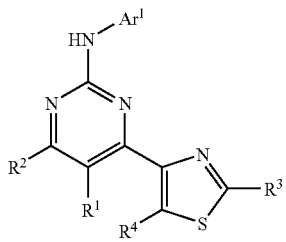

(8) In addition, as a thiazole derivative, a compound represented by the following formula has been also reported (Patent Document 7; WO2004087699A2).

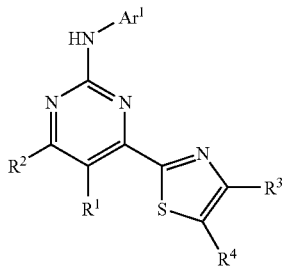

As stated above, plural Syk inhibitors have been reported till now, but these compounds had mainly pyrimidine skeleton and, in addition, showed an inhibitory effect against plural protein kinases and did not have a high Syk specificity.

Each of the compounds shown in above (1) to (8) inhibits not only Syk but also ZAP-70 expressing in T cells at the same level, and has poor selectivity.

5. With Regard to Known Aminopyridine Compounds (1) A compound represented by the following formula has been also reported (Patent Document 8; WO2004041810A1). However, the compound shown herein showed inhibitory activity to plural protein kinases including Jak, and the selectivity for Syk was never in a satisfiable level.

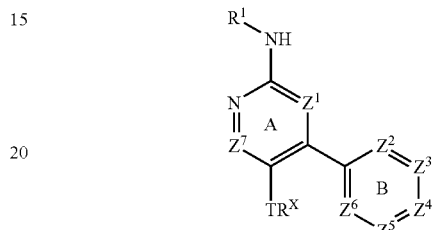

(2) Besides, a diaminopyrimidine derivative represented by the following formula has been reported as a PKC-theta inhibitor (Patent Document 9; WO2004067516A1).

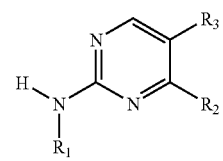

(3) In addition, 2-substituted-4-heteroaryl-pyrimidine derivatives as shown below are known as inhibitors of cyclin dependent kinase (CDK) (Patent Document 10; Japanese Patent Laid-Open No. 2003-528872).

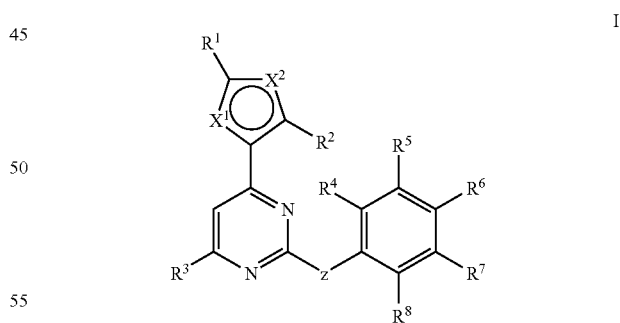

In the formula, $X^1$ is CH, $X^2$ is S; or one of $X^1$ and $X^2$ is S, the other of $X^1$ and $X^2$ is N; Z is NH, NHCO, NHSO$_2$, NHCH$_2$, CH$_2$, CH$_2$CH$_2$ or CH=CH; $R^1$, $R^2$ and $R^3$ are independently H, alkyl, aryl, aralkyl, heterocycle, halogeno, NO$_2$, CN, OH, alkoxy, aryloxy, NH$_2$, NH—R', N—(R')(R"), NH—COR', NH-aryl, N-(aryl)$_2$, COOH, COO—R', COO-aryl, CONH$_2$, CONH—R', CON—(R')(R"), CONH-aryl, CON-(aryl)$_2$, SO$_3$H, SO$_2$NH$_2$, CF$_3$, CO—R' or CO-aryl, wherein the alkyl group, aryl group, aralkyl group, heterocyclic group and NH-aryl group can be substituted with one or more groups selected from halogeno, $NO_2$, CN, OH, O-methyl, $NH_2$, COOH, $CONH_2$ and $CF_3$; at least one of groups $R^1$ and $R^2$ is other than H when $X^1$ or $X^2$ is S; $R^4$, $R^5$, $R^6$, $R^7$ and $R^8$ are independently from each other H, substituted or unsubstituted lower alkyl, halogeno, $NO_2$, CN, OH, substituted or unsubstituted alkoxy, $NH_2$, NH—R', alkyl-aryl, alkyl-heteroaryl, $NH(C=NH)NH_2$, $N(R')_3^+$, N—(R') (R''), COOH, COO—R', $CONH_2$, CONH—R', CON—(R')(R''), $SO_3H$, $SO_2NH_2$, $CF_3$ or $(CH_2)_nO(CH_2)_mNR'R''$, $(CH_2)_nCO_2(CH_2)_mOR'''$, wherein n is 0, 1, 2 or 3, m is 1, 2 or 3; and R', R'' and R''' are each independently an alkyl group which can be the same or different.

[Patent Document 1] Japanese Patent Laid-Open No. 2004

[Patent Document 2] WO0183485

[Patent Document 3] WO9818782

[Patent Document 4] WO02096905A1

[Patent Document 5] WO2004016597A2

[Patent Document 6] WO2004087698A2

[Patent Document 7] WO2004087699A2

[Patent Document 8] WO2004041810A1

[Patent Document 9] WO2004067516A1

[Patent Document 10] Japanese Patent Laid-Open No. 2003-528872

[Non-Patent Document 1] Enshou-to-Men'eki (Inflammation and Immunity) vol. 7, no. 2, 1999, p. 165-171

[Non-Patent Document 2] ASTHMA 13-1, 69-73 (2000)

[Non-Patent Document 3] Naika (Internal medicine) 81, 485-490(1998)

[Non-Patent Document 4] Naika (Internal medicine) 69, 207-214(1992)

[Non-Patent Document 5] Clin. Exp. Allergy, 22, 337-344 (1992)

[Non-Patent Document 6] Drugs of the Future, 17, 799-807 (1992)

[Non-Patent Document 7] J. Cyclic Nucleotide and Protein Phosphorylation Res., 10, 551-564(1985)

[Non-Patent Document 8] J. Pharmacol. Exp. Ther., 257, 741-747(1991)

[Non-Patent Document 9] E. J. Biol. Chem. 266, p. 2639-2646,

[Non-Patent Document 10] J. Biol. Chem. Vol. 270. P. 10498-10502, 1995

[Non-Patent Document 11] J. Biol. Chem. Vol. 270, p. 16333-16338, 1995

[Non-Patent Document 12] Crowley, M. T. et al., J. Exp. Med. 186:1027-1039(1997)

[Non-Patent Document 13] J. Biol. Chem., 1992, Vol. 267, p. 8613-8619

[Non-Patent Document 14] EMBO J., 1994, Vol. 13, p. 1341-1349

[Non-Patent Document 15] J. Exp. Med., 1996, Vol. 183, p. 1407-1414

[Non-Patent Document 16] EMBO J., 1997, Vol. 16, p. 2333-2341

[Non-Patent Document 17] IL Farmaco, 1991, Vol. 46, p. 1099-1110

[Non-Patent Document 18] J. Biol. Chem. 269: 29697-29703 (1994)

DISCLOSURE OF THE INVENTION

Problems to be Solved by the Invention

The Syk inhibitors heretofore reported had low specificity (selectivity) and showed inhibitory effect against plural protein kinases and therefore, they had possibility to cause immune suppression action in addition to controlling inflammatory reaction. Under such circumstances, pharmaceutical drugs having not only high inhibitory effect against Syk but also high selectivity for Syk have been earnestly desired.

Accordingly, an object of the present invention is to provide a novel compound which represents highly inhibitory activity to Syk.

Another object of the present invention is to provide a pharmaceutical composition containing such a compound as an active ingredient, more specifically, an Syk inhibitor, a drug for allergic diseases, a drug for bronchial asthma, a drug for allergic rhinitis, a drug for allergic dermatitis, a drug for autoimmune diseases, a drug for rheumatoid arthritis, a drug for systemic lupus erythematosus, a drug for multiple sclerosis, a drug for malignant tumor, a drug for B-lymphoma, B-cell leukemia and a pharmaceutical composition of these to be used in combination with other antiallergic therapeutic drugs.

Means for Solving the Problems

The present inventors have conducted intensive researches for the compounds which selectively inhibit Syk, and as a result, have found that a novel aminopyridine compound represented by the following general formula (I) has specific and excellent inhibitory effect against Syk and is useful as a therapeutic or preventive agent of the diseases such as allergia in which Syk is involved. This finding has led to the completion of the present invention.

Specifically the present invention is as follows.

1. An aminopyridine compound represented by the following general formula (I):

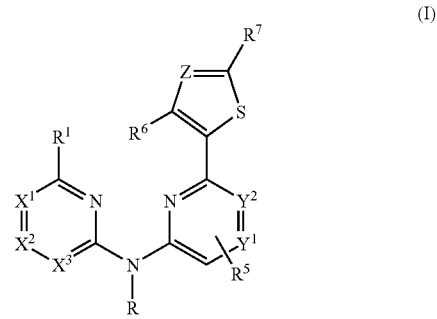

wherein $X^1$ represents (1) —$C(R^2)$= or (2) a nitrogen atom;

$X^2$ represents (1) —$C(R^3)$= or (2) a nitrogen atom;

$X^3$ represents (1) —C($R^4$)= or (2) a nitrogen atom;

Z represents (1) a nitrogen atom or (2) —C($R^{6'}$)=;

$Y^1$ represents (1) —CH= or (2) a nitrogen atom;

$Y^2$ represents (1) —CH=, or, (2) a nitrogen atom;

R represents (1) a hydrogen atom, (2) a $C_{1-6}$ alkyl group or (3) an acyl group;

$R^1$ represents (1) a hydrogen atom, (2) a $C_{1-6}$ alkyl group or (3) a halogen atom;

$R^2$ represents (1) a hydrogen atom, (2) a $C_{1-6}$ alkyl group or (3) a halogen atom;

$R^3$ represents (1) a hydrogen atom, (2) a halogen atom, (3) —N($R^{31}$)($R^{32}$)

wherein $R^{31}$ and $R^{32}$ represent represent a hydrogen atom or a $C_{1-6}$ alkyl group, (4) a hydroxyl group, (5) a $C_{1-6}$ alkoxy group, wherein the $C_{1-6}$ alkyl group in the $C_{1-6}$ alkoxy group may be substituted with a substituent selected from the following group Aa:

[Group Aa]

a. a hydroxyl group, b. a $C_{1-6}$ alkoxy group, c. —N($R^{31}$)($R^{32}$), wherein $R^{31}$ and $R^{32}$ are the same as above, d. —COO$R^{33}$, wherein $R^{33}$ represents a hydrogen atom or a $C_{1-6}$ alkyl group, e. —CO—N($R^{31}$)($R^{32}$), wherein $R^{31}$ and $R^{32}$ are the same as above, and f. a halogen atom, (6) an aralkoxy group, (7) an acyl group, (8) a saturated heterocyclic group or an aromatic heterocyclic group, wherein the heterocyclic group may be substituted with a $C_{1-6}$ alkyl group, and the saturated heterocyclic group may partially have a double bond, (9) a $C_{1-6}$ alkyl group, wherein the $C_{1-6}$ alkyl group may be substituted with a substituent selected from the following group Ab:

[group Ab]

a. a hydroxyl group, b. —COO$R^{33}$, wherein $R^{33}$ is the same as the above, c. —CO—N($R^{31}$)($R^{32}$), wherein $R^{31}$ and $R^{32}$ are the same as above, and d. a halogen atom,

(10) —COO$R^{33}$, wherein $R^{33}$ is the same as the above,

(11) —CO—N($R^{31}$)($R^{32}$), wherein $R^{31}$ and $R^{32}$ are the same as above, or

(12) a cyano group, or $R^3$ together with $R^2$ may form —C=C—C=C—;

$R^4$ represents (1) a hydrogen atom, (2) a $C_{1-6}$ alkyl group or (3) a nitro group;

$R^5$ represents (1) a hydrogen atom, (2) a $C_{1-6}$ alkyl group, wherein the $C_{1-6}$ alkyl group may be substituted with a hydroxyl group or a $C_{1-6}$ alkoxy group, (3) —COO$R^{51}$, wherein $R^{51}$ represents a hydrogen atom or a $C_{1-6}$ alkyl group, or (4) a nitro group;

$R^6$ and $R^{6'}$ may be the same or different and each represent (1) a hydrogen atom, (2) a $C_{1-6}$ alkyl group, wherein the $C_{1-6}$ alkyl group may be substituted with a hydroxyl group or a $C_{1-6}$ alkoxy group, (3) —COO$R^{61}$, wherein $R^{61}$ represents a hydrogen atom or a $C_{1-6}$ alkyl group, (4) —N($R^{62}$)($R^{63}$)

wherein $R^{62}$ and $R^{63}$ may be the same or different and each represent a hydrogen atom, a $C_{1-6}$ alkyl group, a $C_{1-6}$ alkoxy group or an acyl group, (5) —CO—N($R^{62}$)($R^{63}$)

wherein $R^{62}$ and $R^{63}$ are the same as above, or (6) an acyl group;

$R^7$ represents a hydrogen atom, a halogen atom, a nitro group, a cyano group, or the following $R^a$, $R^b$, $R^c$, $R^d$, $R^e$, $R^f$, $R^g$ or $R^h$;

$R^a$ represents —$C_pH_{2(p-1)}$($R^{a1}$)($R^{a2}$)—O—$R^{a3}$, wherein (1) p represents an integer from 1 to 6, (2) $R^{a1}$ represents a hydrogen atom or a $C_{1-6}$ alkyl group, (3) $R^{a2}$ represents a hydrogen atom, a $C_{1-6}$ alkyl group, an aralkyl group or an aryl group, wherein the $C_{1-6}$ alkyl group, aralkyl group and aryl group may be substituted with a substituent respectively selected from the following group Ba:

[Group Ba]

a. a hydroxyl group, b. a carboxy group, c. a $C_{1-6}$ alkoxycarbonyl group, d. an amino group, e. a $C_{1-6}$ alkylamino group, f. a di-$C_{1-6}$ alkylamino group, g. an acyloxy group and h. a halogen atom.

(4) $R^{a3}$ represents a hydrogen atom, an acyl group, —CON($R^{a31}$)($R^{a32}$) or a $C_{1-6}$ alkyl group, wherein the alkyl group may be substituted with a $C_{1-6}$ alkoxycarbonyl group or —CON($R^{a31}$)($R^{a32}$)

wherein $R^{a31}$ and $R^{a32}$ may be the same or different and each represent a hydrogen atom, an acyl group, wherein the acyl group may be substituted with a hydroxyl group or a carboxy group, a $C_{1-6}$ alkyl group (wherein $C_{1-6}$ alkyl group may be substituted with a substituent selected from a hydroxyl group, a carboxy group, a $C_{1-6}$ alkoxycarbonyl group, a carbamoyl group, a $C_{1-6}$ alkylcarbamoyl group and a di-$C_{1-6}$ alkylcarbamoyl group, a $C_{1-6}$ alkoxycarbonyl group or a $C_{1-6}$ alkylsulfonyl group, or $R^{a31}$ and $R^{a32}$ together with the adjacent nitrogen atom may form a 5- or 6-membered saturated heterocyclic group which has one or more nitrogen atoms, wherein the saturated heterocyclic group may be substituted with a hydroxyl group, an oxo group, an aralkylamino group or an acylamino group;

$R^b$ represents —$C_pH_{2(p-1)}$($R^{b1}$)($R^{b2}$)—N— ($R^{b3}$)($R^{b4}$), wherein (1) p represents an integer from 1 to 6, (2) $R^{b1}$ represents a hydrogen atom or a $C_{1-6}$ alkyl group, (3) $R^{b2}$ represents a. a hydrogen atom, b. an aralkyl group, wherein the aralkyl group may be substituted with a hydroxyl group, a $C_{1-6}$ alkoxy group which may be substituted with a hydroxyl group, an aralkyloxy group or —N($R^{b21}$)($R^{b22}$), wherein $R^{b21}$ and $R^{b22}$ may be the same or different and each represent a hydrogen atom, a $C_{1-6}$ alkyl group, an acyl group, a carbonyl group, a $C_{1-6}$ alkoxycarbonyl group or an aralkoxycarbonzyl aralkoxycarbonyl group, c. an aryl group, wherein the aryl group may be substituted with a hydroxyl group, a $C_{1-6}$ alkoxy group or an aralkoxy group, or d. a $C_{1-6}$ alkyl group, wherein the $C_{1-6}$ alkyl group may be substituted with a substituent selected from the following group Ca:

[Group Ca]

a hydroxyl group, an aralkoxy group,

—COO$R^{b23}$, wherein $R^{b23}$ represents a hydrogen atom, a $C_{1-6}$ alkyl group or an aralkyl group, —N($R^{b21}$)($R^{b22}$), wherein $R^{b21}$ are the same as above, and an aryl group, wherein the aryl may be substituted with a substituent selected from a hydroxyl group, a $C_{1-6}$ alkoxy group, wherein the $C_{1-6}$ alkoxy group may be substituted with a hydroxyl group, an aralkoxy group, —N($R^{b21}$)($R^{b22}$) and an aralkoxycarbonylamino group, wherein $R^{b21}$ and $R^{b22}$ are the same as above, and (4) $R^{b3}$ and $R^{b4}$ may be the same or different and each represent a. a hydrogen atom, b. a $C_{1-6}$ alkyl group, wherein the $C_{1-6}$ alkyl group may be substituted with a substituent selected from a hydroxyl group, a carboxy group, a $C_{1-6}$ alkoxycarbonyl group, a carbamoyl group, a $C_{1-6}$ alkylcarbamoyl group and a di-$C_{1-6}$ alkylcarbamoyl group, c. —COO$R^{b41}$, wherein $R^{b41}$ represents a hydrogen atom, a $C_{1-6}$ alkyl group or an aralkyl group, d. —CO$R^{b42}$, wherein $R^{b42}$ represents a $C_{1-6}$ alkyl group, wherein the $C_{1-6}$ alkyl group may be substituted with a substituent selected from a hydroxyl group, a carboxy group, a $C_{1-6}$ alkoxycarbonyl group, an acyl group, an acyloxy group, an amino group and an acylamino group, a $C_{3-8}$ cycloalkyl group, wherein the $C_{3-8}$ cycloalkyl group may be substituted with a hydroxyl group, a 5- or 6-membered aromatic heterocyclic group having 1 to 4 hetero atoms, wherein the heterocyclic group may be substituted with a $C_{1-6}$ alkyl group, or an aryl group, wherein the aryl group may be substituted with a hydroxyl group, e. —CO—N($R^{b43}$)($R^{b44}$), wherein $R^{b43}$ and $R^{b44}$ may be the same or different and each represent a hydrogen atom, a $C_{1-6}$ alkyl group or an acyl group, or f. —SO$_2$—$R^{b45}$ wherein $R^{b45}$ represents a $C_{1-6}$ alkyl group;

$R^c$ represents —C(=N—$R^{c1}$)—$R^{c2}$, wherein (1) $R^{c1}$ represents a. a hydroxyl group, b. a $C_{1-6}$ alkoxy group, wherein the $C_{1-6}$ alkyl group in the $C_{1-6}$ alkoxy group may be substituted with a hydroxyl group or a $C_{1-6}$ alkoxy group, or c. an acyloxy group, and (2) $R^{c2}$ represents a $C_{1-6}$ alkyl group or an amino group;

$R^d$ represents —C(=O)—$R^{d1}$, wherein $R^{d1}$ represents (1) a hydrogen atom, (2) a $C_{1-6}$ alkyl group, wherein the $C_{1-6}$ alkyl group may be substituted with a hydroxyl group, a carboxy group or a $C_{1-6}$ alkoxycarbonyl group, (3) a hydroxyl group, (4) a $C_{1-6}$ alkoxy group, and (5) —N($R^{d11}$)($R^{d12}$)

wherein $R^{d11}$ and $R^{d12}$ may be the same or different and each represent a substituent selected from the following group Da:

[Group Da]

a. a hydrogen atom, b. a $C_{1-6}$ alkoxy group, c. a $C_{3-8}$ cycloalkyl group, wherein the cycloalkyl group may be substituted with a hydroxyl group, and d. a $C_{1-6}$ alkyl group, wherein the $C_{1-6}$ alkyl group may be substituted with a hydroxyl group, a carboxy group, a $C_{1-6}$ alkoxycarbonyl group or an amino group, or $R^{d1}$ and $R^{d12}$ together with the adjacent nitrogen atom may form a 5- or 6-membered saturated heterocyclic group which has one or more nitrogen atoms, wherein the saturated heterocyclic group may be substituted with a $C_{1-6}$ alkyl groups, wherein the alkyl group may be substituted with a carboxy group, or a carboxy group; $R^e$ represents the following Ring A:

wherein Ring A represents a 5- or 6-membered saturated heterocyclic group having 1 or 2 hetero atoms, a 5- or 6-membered aromatic heterocyclic group having 1 to 4 hetero atoms, a 9- to 12-membered condensed aromatic heterocyclic group having 1 or 2 hetero atoms which may be partially saturated a $C_{3-8}$ cycloalkyl group or a $C_{7-11}$ spiroheterocycloalkyl group having 1 or 2 hetero atoms);

which may be substituted with a substituent respectively selected from the following group Ea:

[Group Ea]

a. —$OR^{e1}$, wherein $R^{e1}$ represents a hydrogen atom, a $C_{1-6}$ alkyl group, the $C_{1-6}$ alkyl group may be substituted with a carboxy group or —CON($R^{e11}$)($R^{e12}$), wherein $R^{e11}$ and $R^{e12}$ may be the same or different and each represent a hydrogen atom or a $C_{1-6}$ alkyl group, an acyl group, a carbamoyl group or an aralkyl group, b. —$COOR^{e2}$, wherein $R^{e2}$ represents a hydrogen atom or a $C_{1-6}$ alkyl group, c. —CO—N($R^{e41}$)($R^{e42}$)

wherein $R^{e41}$ and $R^{e42}$ may be the same or different and each represent a hydrogen atom, a $C_{1-6}$ alkyl group, wherein the $C_{1-6}$ alkyl group may be substituted with a substituent selected from a hydroxyl group, a $C_{1-6}$ alkoxy group, an amino group, a $C_{1-6}$ alkylamino group, a di-$C_{1-6}$ alkylamino group, a halogen atom, a carboxy group, a carbamoyl group, a $C_{1-6}$ alkylcarbamoyl group, a di-$C_{1-6}$ alkylcarbamoyl group or a 5- or 6-membered saturated heterocyclic group or aromatic heterocyclic group having 1 or 2 hetero atoms, a hydroxyl group, a $C_{1-6}$ alkoxy group, a $C_{5-6}$ cycloalkyl group, wherein the $C_{5-6}$ cycloalkyl group may be substituted with a hydroxyl group or a $C_{1-6}$ alkyl group, wherein the $C_{1-6}$ alkyl group may be substituted with a hydroxyl group, or a $C_{1-6}$ alkylsulfonyl group, d. —$COR^{e3}$, wherein $R^{e3}$ represents a hydrogen atom, a $C_{1-6}$ alkyl group, wherein the $C_{1-6}$ alkyl group may be substituted with a substituent selected from a hydroxyl group, a carboxy group, a $C_{1-6}$ alkoxycarbonyl group and a $C_{1-6}$ alkylsulfonyl group, a 5- or 6-membered saturated heterocyclic group or aromatic heterocyclic group having 1 or 2 hetero atoms, wherein the saturated heterocyclic group or aromatic heterocyclic group may be substituted with a hydroxyl group, an oxo group, a carboxy group, a $C_{1-6}$ alkoxy group, wherein the $C_{1-6}$ alkoxy group may be substituted with a carbamoyl group, a carbamoyl group, wherein the carbamoyl group may be substituted with a hydroxyl group, an acyl group, acyloxy group, an amino group, an acylamino group, wherein the acylamino group may be substituted with a hydroxyl group or carbamoyl group, a $C_{1-6}$ alkylamino group, a di-$C_{1-6}$ alkylamino group, a $C_{1-6}$ alkylsulfonylamino group, a 5- or 6-membered saturated heterocyclic group or aromatic heterocyclic group and a $C_{1-6}$ alkyl group, wherein the $C_{1-6}$ alkyl group may be substituted with a substituent selected from a hydroxyl group, a $C_{1-6}$ alkoxy group, wherein the $C_{1-6}$ alkoxy group may be substituted with a carbamoyl group, an acylamino group and a carbamoyl group, or a $C_{5-6}$ cycloalkyl group or aryl group, wherein the $C_{5-6}$ cycloalkyl group or aryl group may be substituted with a hydroxyl group, an oxo group, a $C_{1-6}$ alkoxy group, a carbamoyl group, an acylamino group, an oximino group or an acyloxy group, e. an oxo group, f. —N($R^{e51}$)($R^{e52}$)

wherein $R^{e51}$ and $R^{e52}$ may be the same or different and each represent a hydrogen atom, a $C_{1-6}$ alkylsulfonyl group, a $C_{1-6}$ alkyl group, wherein the $C_{1-6}$ alkyl group may be substituted with a substituent selected from a hydroxyl group, a $C_{1-6}$ alkoxy group and a carbamoyl group, an acyl group, wherein the acyl group may be substituted with a hydroxyl group or a $C_{1-6}$ alkoxy group, —CON($R^{e11}$)($R^{e12}$) or, wherein $R^{e11}$ and $R^{e12}$ represent the same as above, —COR$^{e511}$, wherein $R^{e511}$ represents a 5- or 6-membered saturated heterocyclic group containing at least one nitrogen atom, a $C_{1-6}$ alkyl group, wherein the $C_{1-6}$ alkyl group may be substituted with a hydroxyl group, or a $C_{5-6}$ cycloalkyl group, wherein the cycloalkyl group may be substituted with a hydroxyl group, g. a $C_{1-6}$ alkyl group, wherein the $C_{1-6}$ alkyl group may be substituted with a substituent selected from the following group Eb:

[Group Eb]

a hydroxyl group, a $C_{1-6}$ alkoxy group, wherein a $C_{1-6}$ alkyl group in the $C_{1-6}$ alkoxy group may be substituted with a carboxy group or —CO—N($R^{e11}$)($R^{e12}$), wherein $R^{e11}$ and $R^{e112}$ represnt the same as above, —COOR$^{e2}$, wherein $R^{e2}$ represents the same as above, —N($R^{e51}$)($R^{e52}$)

wherein $R^{e51}$ and $R^{e52}$ represent the same as above,

—CO—N($R^{e51}$)($R^{e52}$), wherein $R^{e51}$ and $R^{e52}$ represent the same as above, a halogen atom, and a 5- or 6-membered saturated heterocyclic group having 1 or 2 hetero atoms, wherein the saturated heterocyclic group may be substituted with a hydroxyl group or a $C_{1-6}$ alkyl group, h. —(CH$_2$)$_n$N($R^{e61}$)—(CH$_2$)$_m$—CO($R^{e62}$), wherein n and m represent an integer of 0 or 1 to 4, and n+m is 1 to 6, $R^{e61}$ represents a hydrogen atom or a $C_{1-6}$ alkyl group and $R^{e62}$ is a $C_{1-6}$ alkyl group, wherein the $C_{1-6}$ alkyl group may be substituted with a hydroxyl group, a $C_{1-6}$ alkoxy group, an amino group, a $C_{1-6}$ alkylamino group or a di-$C_{1-6}$ alkylamino group, i. a hydroxyimino group, j. a $C_{1-6}$ alkylsulfonyl group, k. a cyano group, l. a 5- or 6-membered saturated heterocyclic group (which may be partially unsaturated) containing 1 or 2 hetero atoms selected from a nitrogen atom and an oxygen atom or a 5- or 6-membered aromatic heterocyclic group containing 1 to 4 hetero atoms selected from a nitrogen atom and an oxygen atom, wherein the saturated heterocyclic group and aromatic heterocyclic group may be substituted with an oxo group or a $C_{1-6}$ alkyl group, m. an aminosulfonyl group and n. a $C_{1-6}$ alkylidene group, wherein the $C_{1-6}$ alkylidene group may be substituted with a halogen atom or a carboxy group;

$R^f$ is a $C_{1-6}$ alkyl group or a $C_{2-6}$ alkenyl group, wherein these $C_{1-6}$ alkyl group and $C_{2-6}$ alkenyl group may be substituted with a substituent selected from the following group Fa:

[Group Fa]

a. a $C_{1-6}$ alkoxy group, wherein the $C_{1-6}$ alkyl group in the alkoxy group may be substituted with a carboxy group, a $C_{1-6}$ alkoxycarbonyl group or —CON($R^{f21}$)($R^{f22}$), wherein $R^{f21}$ and $R^{f22}$ may be the same or different and each represent a hydrogen atom, an acyl group, wherein the acyl group may be substituted with a hydroxyl group or a carboxy group, a $C_{1-6}$ alkoxycarbonyl group, —O—COOR$^{f1}$, wherein $R^{f1}$ is a hydrogen atom or a $C_{1-6}$ alkyl group, a $C_{1-6}$ alkyl group, wherein the $C_{1-6}$ alkyl group may be substituted with a hydroxyl group, a carboxy group, a $C_{1-6}$ alkoxycarbonyl group, a carbamoyl group, a $C_{1-6}$ alkylsulfonyl group or a carbamoyl group, b. —COOR$^{f1}$, wherein $R^{f1}$ is a hydrogen atom or a $C_{1-6}$ alkyl group, c. —N($R^{f21}$)($R^{f22}$)

wherein $R^{f21}$ and $R^{f22}$ represnt the same as above, d. —CON($R^{f21}$)($R^{f22}$), wherein $R^{f21}$ and $R^{f22}$ represent the same as above, e. —N($R^{f23}$)CON($R^{f21}$)($R^{f22}$)

wherein $R^{f23}$ represents a hydrogen atom or a $C_{1-6}$ alkyl group, and $R^{21}$ and $R^{f22}$ represnt the same as above, f. an acyl group and g. a halogen atom;

$R^g$ represents a substituent having Ring B represented by the following formula (II):

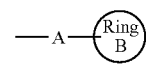

(II)

wherein A represents a linker selected from the following group Ga:

[Group Ga]

—(CH$_2$) k—,

—(CH$_2$)$_k$—NR$^{g1}$—(CH$_2$)$_j$—

—(CH$_2$)$_k$—(CO)NR$^{g1}$(CH$_2$)$_j$—,

—(CH$_2$)$_k$—NR$^{g1}$(CO)—(CH$_2$)$_j$—,

—(CH$_2$)$_k$—(CO)—(CH$_2$)$_j$—,

—(CO)—,

—(CH$_2$)$_k$—O—(CH$_2$)$_j$—,

—(CH$_2$)$_k$—S—(CH$_2$)$_j$—,

—(CH$_2$)$_k$—O—(CO)—(CH$_2$)$_j$—,

—(CO)NR$^{g1}$—, and

—(CH$_2$)$_k$—O—(CH$_2$)$_j$(CO)—(CH$_2$)$_g$—, wherein k, j and g may be the same or different and represnt an integer from 0 to 4 but k and j, or k and g are not 0 at the same time, $R^{g1}$ represents a hydrogen atom, a hydroxyl group, a $C_{1-6}$ alkoxy group, an acyl group, wherein the acyl group may be substituted with a hydroxyl group or a carboxy group, a C$_{3-8}$ cycloalkyl group, wherein the cycloalkyl group may be substituted with a C$_{1-6}$ alkyl group, wherein the alkyl group may be substituted with a carboxy group, an aralkyl group or a C$_{1-6}$ alkyl group, wherein the alkyl group may be substituted with a hydroxyl group, —N(R$^{g41}$)(R$^{42}$) or —CON(R$^{g41}$)(R$^{g42}$)

wherein R$^{g41}$ and R$^{g42}$ may be the same or different and represent a hydrogen atom, an acyl group, wherein the acyl group may be substituted with a hydroxyl group, an aralkyl group, C$_{1-6}$ alkylsulfonyl group or, a C$_{1-6}$ alkyl group, wherein the C$_{1-6}$ alkyl group may be substituted with a hydroxyl group, a carboxy group, a C$_{1-6}$ alkoxycarbonyl group, —N(R$^{g51}$)(R$^{g52}$) or —CO—N(R$^{g51}$)(R$^{g52}$)

wherein R$^{g51}$ and R$^{g52}$ may be the same or different and represent a hydrogen atom, an acyl group, wherein the acyl group may be substituted with a hydroxyl group, a C$_{1-6}$ alkyl group, wherein the C$_{1-6}$ alkyl group may be substituted with a hydroxyl group, a carboxy group, acylamino group, a C$_{1-6}$ alkoxycarbonyl group or a halogen atom, a C$_{1-6}$ alkoxycarbonyl group, a C$_{1-6}$ alkylsulfonyl group or a C$_{3-8}$ cycloalkyl group, wherein the cycloalkyl group may be substituted with a hydroxy group or a C$_{1-6}$ alkoxy group, or R$^{g51}$ and R$^{g52}$ together with the adjacent nitrogen atom may form a 5- or 6-membered saturated heterocyclic group which has one or more nitrogen atoms, wherein the saturated heterocyclic group may be substituted with a hydroxyl group or a C$_{1-6}$ alkoxy group, Ring B represents a ring selected from the following group Ha:

[Group Ha]

an aryl group, a C$_{3-8}$ cycloalkyl group, a 5- to 7-membered saturated heterocyclic group containing one or more nitrogen atoms, a 5- or 6-membered aromatic heterocyclic group containing at least one hetero atoms, and an 8- to 11-membered condensed aromatic heterocyclic group containing at least one hetero atoms, and the Ring B may be substituted with a substituent selected from follows group Ia:

[Group Ia]

a. —OR$^{g2}$, wherein R$^{g2}$ represents a hydrogen atom, a C$_{1-6}$ alkyl group or an aralkyl group, b. —COOR$^{g3}$, wherein R$^{g3}$ represents a hydrogen atom, a C$_{1-6}$ alkyl group or an aralkyl group, wherein the alkyl group may be substituted with a hydroxyl group, c. —N(R$^{g41}$)(R$^{g42}$)

wherein R$^{g41}$ and R$^{g42}$ represnt the same as above, d. —CO—R$^{g53}$, wherein R$^{g53}$ represents a C$_{1-6}$ alkyl group, wherein the alkyl group may be substituted with a hydroxyl group, a carboxy group or an acylamino group, a C$_{3-8}$ cycloalkyl group, wherein the cycloalkyl group may be substituted with a hydroxyl group, a C$_{1-6}$ alkoxy group or oxo group, a 5- or 6-membered saturated heterocyclic group containing at least one hetero atoms, wherein the saturated heterocyclic group may be substituted with a hydroxyl group, a C$_{1-6}$ alkyl group or an oxo group, an aryl group, wherein the aryl may be substituted with a hydroxyl group, a 5- or 6-membered aromatic heterocyclic group containing at least one hetero atoms, an aralkyl group or a 5- or 6-membered saturated heterocyclic group containing 1 or 2 hetero atoms, e. a C$_{1-6}$ alkyl group, wherein the C$_{1-6}$ alkyl group which may be substituted with a hydroxyl group, a C$_{1-6}$ alkoxy group, an aralkoxy group, a carboxy group, a C$_{1-6}$ alkoxycarbonyl group, —CO—R$^{53}$, wherein R$^{g53}$ represents the same as above, —N(R$^{g51}$)(R$^{g52}$) or —CO—N(R$^{g51}$)(R$^{g52}$), wherein R$^{g51}$ and R$^{g52}$ represent the same as above, f. —CO—N(R$^{g51}$)(R$^{g52}$)

wherein R$^{g51}$ and R$^{g52}$ represent the same as above, g. a C$_{1-6}$ alkylsulfonyl group, h. an oxo group, i. an aryl group, wherein the aryl group may be substituted with a hydroxyl group, j. an aralkyl group and k. a halogen atom; and R$^h$ represents —N(R$^{h1}$)(R$^{h2}$)

wherein R$^{h1}$ represents (1) a hydrogen atom, (2) a C$_{1-6}$ alkyl group, wherein the C$_{1-6}$ alkyl group may be substituted with a hydroxyl group, a C$_{1-6}$ alkoxy group, —N(R$^{g51}$)(R$^{g52}$), —CO—N(R$^{g51}$)(R$^{g52}$), wherein R$^{g51}$ and R$^{g52}$ represent the same as above, a C$_{1-6}$ alkylsulfonyl group or a halogen atom, (3) a C$_{2-6}$ alkenyl group, (4) a C$_{3-8}$ cycloalkyl group, wherein the cycloalkyl group may be substituted with a hydroxyl group or a C$_{1-6}$ alkoxy group, or (5) an aralkyl group, R$^{h2}$ represents (1) a C$_{1-6}$ alkyl group, wherein the C$_{1-6}$ alkyl group may be substituted with a substituent selected from the following group Ja:

[Group Ja]

a hydroxyl group, a C$_{1-6}$ alkoxy group, a carboxy group, an aromatic carbocyclic group, wherein the aromatic carbocyclic group may be substituted with a hydroxyl group, a $C_{1-6}$ alkyl group, wherein the alkyl group may be substituted with a carboxy group, a halogen atom, a $C_{1-6}$ alkoxy group, a carboxy group, a $C_{1-6}$ alkoxycarbonyl group, $C_{2-6}$ alkenyl group, wherein the $C_{2-6}$ alkenyl group may be substituted with a carboxy group, a $C_{3-8}$ cycloalkyl group, wherein the cycloalkyl group may be substituted with a carboxy group or an aralkoxy group, a 5- or 6-membered aromatic heterocyclic group containing 1 or 2 hetero atoms, wherein the aromatic heterocyclic group may be substituted with a carboxy group, a 5- or 6-membered saturated heterocyclic group containing 1 or 2 hetero atoms, —N($R^{g51}$)($R^{g52}$)

wherein $R^{g51}$ and $R^{g52}$ represent the same as above,

—CON($R^{g51}$)($R^{g52}$), wherein $R^{g51}$ and $R^{g52}$ represent the same as above, —COR$^{g53}$ wherein $g^{53}$ represents the same as above, and —COOR$^{g3}$, wherein $R^{g3}$ represents the same as above, (2) an acyl group, wherein the acyl group may be substituted with a hydroxyl group, (3) a $C_{1-6}$ alkoxycarbonyl group, (4) a $C_{2-6}$ alkenyl group, wherein the alkenyl group may be substituted with a carboxy group or a halogen atom, (5) a $C_{3-8}$ cycloalkyl group, wherein the cycloalkyl group may be substituted with a hydroxyl group, —COOR$^{g3}$, wherein $R^{g3}$ represents the same as above, —COR$^{g53}$, wherein $R^{g53}$ represents the same as above, —CONR$^{g51}R^{g52}$, wherein $R^{g51}$ and $R^{g52}$ each represent the same as above, or a $C_{1-6}$ alkyl group, wherein the alkyl group may be substituted with a carboxy group, (6) a 5- or 6-membered saturated heterocyclic group containing 1 or 2 hetero atoms, wherein the saturated heterocyclic group may be substituted with —COR$^{g53}$, wherein $R^{g53}$ represents the same as above, —COOR$^{g3}$ wherein $R^{g3}$ represents the same as above, —COOR$^{g51}R^{g52}$, wherein $R^{g51}$ and $R^{g52}$ each represent the same as above or a $C_{1-6}$ alkylsulfonyl group, or (7) an aromatic carbocyclic group, wherein the aromatic carbocyclic group may be substituted with a carboxy group, a $C_{1-6}$ alkyl group, wherein the alkyl group may be substituted with a carboxy group, or a $C_{2-6}$ alkenyl group, wherein the alkenyl group may be substituted with a carboxy group, or a pharmaceutically acceptable salt thereof.

2. The aminopyridine compound or a pharmaceutically acceptable salt thereof according to the above-described 1, wherein Z is a nitrogen atom.

3. The aminopyridine compound or a pharmaceutically acceptable salt thereof according to the above-described 2, wherein the aminopyridine compound according to the above-described 1 is an aminopyridine compound represented by the following general formula (Ia-1):

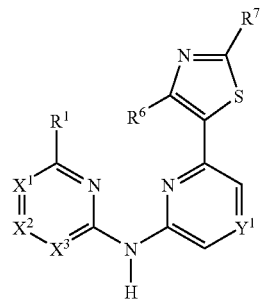

(Ia-1)

wherein $X^1$ represents (1) —C($R^2$)=;

$X^2$ represents (1) —C($R^3$)= or (2) a nitrogen atom;

$X^3$ represents (1) —C($R^4$)= or (2) a nitrogen atom;

$Y^1$ represents (1) —CH= or (2) a nitrogen atom;

$R^1$ represents (1) a hydrogen atom or (2) a $C_{1-6}$ alkyl group;

$R^2$ represents (1) a hydrogen atom, (2) a halogen atom or (3) a $C_{1-6}$ alkyl group;

$R^3$ represents (1) a hydrogen atom, (2) a halogen atom, (3) a $C_{1-6}$ alkoxy group, wherein $C_{1-6}$ alkyl group in the $C_{1-6}$ alkoxy group may be substituted with a substituent selected from the following group Aa-1:

[Group Aa-1]

a. a hydroxyl group, b. a $C_{1-6}$ alkoxy group, c. —N($R^{31}$)($R^{32}$), wherein $R^{31}$ and $R^{32}$ are a hydrogen atom or a $C_{1-6}$ alkyl group, d. a halogen atom, (4) an aralkoxy group, (5) an acyl group, (6) a saturated heterocyclic group or an aromatic heterocyclic group, wherein the heterocyclic group may be substituted with a $C_{1-6}$ alkyl group, and the saturated heterocyclic group may partially have a double bond, (7) a $C_{1-6}$ alkyl group, wherein the $C_{1-6}$ alkyl group may be substituted with a substituent selected from the following group Ab-1:

[Group Ab-1]

a. a hydroxyl group, b. —COOR$^{33}$, wherein R$^{33}$ is a hydrogen atom or a $C_{1-6}$ alkyl group, c. —CO—N(R$^{31}$)(R$^{32}$), wherein R$^{31}$ and R$^{32}$ represent the same as above, and d. a halogen atom, or (8) a cyano group, or R$^3$ together with R$^2$ may form —C=C—C=C—;

R$^4$ represents (1) a hydrogen atom or (2) a $C_{1-6}$ alkyl group;

R$^6$ represents (1) a hydrogen atom, (2) a $C_{1-6}$ alkyl group, wherein the $C_{1-6}$ alkyl group may be substituted with a hydroxyl group or a $C_{1-6}$ alkoxy group, (3) —COOR$^{61}$, wherein R$^{61}$ is a hydrogen atom or a $C_{1-6}$ alkyl group, (4) —N(R$^{62}$)(R$^{63}$)

wherein R$^{62}$ and R$^{63}$ may be the same or different and each represent a hydrogen atom, a $C_{1-6}$ alkyl group, a $C_{1-6}$ alkoxy group or an acyl group, (5) —CO—N(R$^{62}$)(R$^{63}$), wherein R$^{62}$ and R$^{63}$ are the same as above, or (6) an acyl group; and R$^7$ represent the same as in the above described 1.

4. The aminopyridine compound or a pharmaceutically acceptable salt thereof according to the above-described 1 to 3, wherein the aminopyridine compound according to the above-described 1 to 3 is an aminopyridine compound represented by the following general formula (Ia-2):

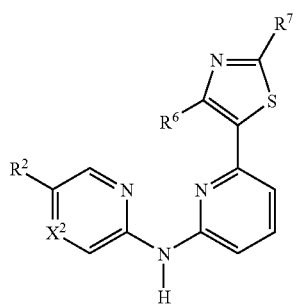

(Ia-2)

wherein

X$^2$ represents (1) =C(R$^3$)— or (2) a nitrogen atom;

R$^2$ represents (1) a hydrogen atom or (2) a halogen atom;

R$^3$ represents (1) a hydrogen atom, (2) a halogen atom, (3) a $C_{1-6}$ alkoxy group, wherein the $C_{1-6}$ alkyl group in the $C_{1-6}$ alkoxy group may be substituted with a substituent selected from the following group Aa-2:

[Group Aa-2]

a. a hydroxyl group and b. a halogen atom, (4) an acyl group, (5) a saturated heterocyclic group or an aromatic heterocyclic group, wherein the heterocyclic group may be substituted with a $C_{1-6}$ alkyl group, and the saturated heterocyclic group may partially have a double bond, (6) a $C_{1-6}$ alkyl group which may be substituted with a substituent selected from the following group Ab-2:

[Group Ab-2]

a. a hydroxyl group and b. a halogen atom or (7) a cyano group, or

R$^3$ together with R$^2$ may form —C=C—C=C—;

R$^6$ is (1) a hydrogen atom or (2) a $C_{1-6}$ alkyl group, wherein the $C_{1-6}$ alkyl group may be substituted with a hydroxyl group or a $C_{1-6}$ alkoxy group;

R$^7$ is a hydrogen atom, or the following R$^a$, R$^b$, R$^c$, R$^d$, R$^e$, R$^f$, R$^g$ or R$^h$;

R$^a$ represents —C$_p$H$_{2(p-1)}$(R$^{a1}$)(R$^{a2}$)—O—R$^{a3}$, wherein (1) p represents an integer from 1 to 6, (2) R$^{a1}$ represents a hydrogen atom, (3) R$^{a2}$ represents a $C_{1-6}$ alkyl group, wherein the $C_{1-6}$ alkyl group may be substituted with a hydroxyl group, a carboxy group, an acyloxy group, a $C_{1-6}$ alkylamino group or a di-$C_{1-6}$ alkylamino group, an aralkyl group, wherein the aralkyl group may be substituted with a hydroxyl group, a carboxy group or an acyloxy group, or an aryl group, (4) R$^{a3}$ is a hydrogen atom, an acyl group or —(CO)N(R$^{a31}$)(R$^{a32}$), wherein R$^{a31}$ and R$^{a32}$ may be the same or different and are a hydrogen atom or a $C_{1-6}$ alkyl group;

R$^b$ represents —C$_p$H$_{2(p-1)}$(R$^{b1}$)(R$^{b2}$)—N—(R$^{b3}$)(R$^{b4}$)

wherein (1) p is an integer from 1 to 6, (2) R$^{b1}$ is a hydrogen atom, (3) $R^{b2}$ is a. an aralkyl group, wherein the aralkyl group may be substituted with a hydroxyl group, a $C_{1-6}$ alkoxy group which may be substituted with a hydroxyl group, aralkoxy group or —N($R^{b21}$)($R^{b22}$), wherein $R^{b21}$ and $R^{b22}$ are a hydrogen atom, a $C_{1-6}$ alkyl group, an acyl group or an aralkoxy carbonyl group, b. an aryl group, wherein the aryl group may be substituted with a hydroxyl group or an aralkoxy group, or c. a $C_{1-6}$ alkyl group, wherein the $C_{1-6}$ alkyl group may be substituted with a hydroxyl group, a carboxy group, an aralkoxy group, an aralkoxycarbonyl group, an amino group, an acyl group or an aralkyl carbonyl group, (4) $R^{b3}$ is a hydrogen atom or a $C_{1-6}$ alkyl group, (5) $R^{b4}$ represents a. a hydrogen atom, b. a $C_{1-6}$ alkyl group, wherein the $C_{1-6}$ alkyl group may be substituted with a carboxy group or a $C_{1-6}$ alkoxycarbonyl group, c. —COR$^{b32}$, wherein $R^{b32}$ is a $C_{1-6}$ alkyl group, wherein the $C_{1-6}$ alkyl group may be substituted with a hydroxyl group, an acyl group, a carboxy group, a $C_{1-6}$ alkoxycarbonyl group or acyloxy group, or d. —CON($R^{b321}$)($R^{b322}$)

wherein $R^{b321}$ and $R^{b322}$ are a hydrogen atom or a $C_{1-6}$ alkyl group;

$R^c$ is —C(=N—$R^{c1}$)—$R^{c2}$, wherein (1) $R^{c1}$ represents a. a hydroxyl group, b. a $C_{1-6}$ alkoxy group, wherein the $C_{1-6}$ alkyl group in the $C_{1-6}$ alkoxy group may be substituted with a hydroxyl group, or c. an acyloxy group, (2) $R^{c2}$ is a $C_{1-6}$ alkyl group;

$R^d$ is —C(=O)—$R^{d1}$ wherein $R^{d1}$ represents (1) a $C_{1-6}$ alkyl group, wherein the $C_{1-6}$ alkyl group may be substituted with a hydroxyl group, a carboxy group or a $C_{1-6}$ alkoxycarbonyl group, (2) a $C_{1-6}$ alkoxy group, (3) a $C_{3-8}$ cycloalkyl group, wherein the $C_{3-8}$ cycloalkyl group may be substituted with a hydroxyl group, (4) —N($R^{d11}$)($R^{d12}$)

wherein $R^{d11}$ and $R^{d12}$ may be the same or different and are each a hydrogen atom, a $C_{1-6}$ alkoxy group, or a $C_{1-6}$ alkyl group, wherein the $C_{1-6}$ alkyl group may be substituted with a hydroxyl group, a carboxy group or a $C_{1-6}$ alkoxycarbonyl group;

$R^e$ represents a 5- or 6-membered saturated heterocyclic group having 1 or 2 hetero atoms, a 5- or 6-membered aromatic heterocyclic group having 1 to 4 hetero atoms, a 9- to 12-membered condensed aromatic heterocyclic group which may be partially saturated having 1 or 2 hetero atoms, a $C_{3-8}$ cycloalkyl group or a $C_{7-11}$ spiroheterocycloalkyl group having 1 or 2 hetero atoms, and may be each substituted with a substituent selected from the following group Ea-1:

[Group Ea-1]

a. —OR$^{e1}$, wherein $R^{e1}$ represents a hydrogen atom, $C_{1-6}$ alkyl group, wherein the $C_{1-6}$ alkyl group may be substituted with a carboxy group or —CON($R^{e11}$)($R^{e12}$), wherein $R^{e11}$ and $R^{e12}$ may be the same or different and each represent a hydrogen atom or a $C_{1-6}$ alkyl group, an acyl group, a carbamoyl group or an aralkyl group, b. —COOR$^{e2}$, wherein $R^{e2}$ is a hydrogen atom or a $C_{1-6}$ alkyl group, c. —CO—N($R^{e41}$)($R^{e42}$)

wherein $R^{e41}$ and $R^{e42}$ may be the same or different and each represent a hydrogen atom, a $C_{1-6}$ alkyl group, wherein the $C_{1-6}$ alkyl group may be substituted with a substituent selected from a hydroxyl group, a $C_{1-6}$ alkoxy group, a di-$C_{1-6}$ alkylamino group, a carboxy group, a halogen atom, a $C_{1-6}$ alkylcarbamoyl group and a 5- or 6-membered saturated heterocyclic group or an aromatic heterocyclic group having 1 or 2 hetero atoms, a hydroxyl group, a $C_{1-6}$ alkoxy group, an acyl group, wherein the acyl group may be substituted with a hydroxyl group, a $C_{3-8}$ cycloalkyl group, wherein the $C_{3-8}$ cycloalkyl group may be substituted with a hydroxyl group, or, a $C_{1-6}$ alkylsulfonyl group, d. —COR$^{e3}$, wherein $R^{e3}$ is a hydrogen atom, a $C_{1-6}$ alkyl group, wherein a $C_{1-6}$ alkyl group may be substituted with a hydroxy group, a carboxy group or a $C_{1-6}$ alkylsulfonyl group, a 5- or 6-membered saturated heterocyclic group having 1 or 2 hetero atoms wherein the saturated heterocyclic group may be substituted with a hydroxyl group, a carboxy group, a $C_{1-6}$ alkyl group, an acyl group, a $C_{1-6}$ alkoxy group, a carbamoyl group, —N($R^{e41}$)($R^{e42}$), wherein $R^{e41}$ and $R^{e42}$ represnt the same as above, an acylamino group or an oxo group, a $C_{3-8}$ cycloalkyl group, wherein the $C_{3-8}$ cycloalkyl group may be substituted with a hydroxyl group, an aromatic hydrocarbon group, wherein the aromatic hydrocarbon group may be substituted with a hydroxyl group, or a 5- or 6-membered aromatic heterocyclic group having 1 or 2 hetero atoms, e. an oxo group, f. —N($R^{e51}$)($R^{e52}$)

wherein $R^{e51}$ and $R^{e52}$ may be the same or different and each represent
- a hydrogen atom,
- a $C_{1-6}$ alkylsulfonyl group,
- a $C_{1-6}$ alkyl group, wherein the $C_{1-6}$ alkyl group may be substituted with a hydroxyl group,
- an acyl group, wherein the acyl group may be substituted with a hydroxyl group, or
- —$COR^{e511}$, wherein $R^{e511}$ represents a 5- or 6-membered saturated heterocyclic group containing at least one nitrogen atom or a $C_{3-8}$ cycloalkyl group, wherein the $C_{3-8}$ cycloalkyl group may be substituted with a hydroxyl group, g. a $C_{1-6}$ alkyl group, wherein the $C_{1-6}$ alkyl group may be substituted with a substituent selected from the following group Eb-1:

[Group Eb-1]
- a hydroxyl group,
- a $C_{1-6}$ alkoxy group, wherein the $C_{1-6}$ alkyl group in the $C_{1-6}$ alkoxy group may be substituted with a carboxy group or —CO—$N(R^{e11})(R^{e12})$, wherein $R^{e11}$ and $R^{e112}$ represnt the same as above,
- —$COOR^{e2}$, wherein $R^{e2}$ represents the same as above,
$N(R^{e51})(R^{e52})$ wherein $R^{e51}$ and $R^{e52}$ represnt the same as above,
—CO—$N(R^{e51})(R^{e52})$ wherein $R^{e51}$ and $R^{e52}$ represnt the same as above,
- a halogen atom and
- a 5- or 6-membered saturated heterocyclic group having 1 or 2 hetero atoms, h. a hydroxyimino group, i. a $C_{1-6}$ alkylsulfonyl group, j. a cyano group, k. a 5- or 6-membered saturated heterocyclic group containing 1 or 2 hetero atoms selected from a nitrogen atom and an oxygen atom (which may be partially unsaturated and may be substituted with an oxo group or a $C_{1-6}$ alkyl group) or an aromatic heterocyclic group containing 1 to 4 hetero atoms selected from a nitrogen atom and an oxygen atom, l. an aminosulfonyl group and m. a $C_{1-6}$ alkylidene group, wherein the $C_{1-6}$ alkylidene group may be substituted with a halogen atom or a carboxy group;

$R^f$ is a $C_{1-6}$ alkyl group, wherein the $C_{1-6}$ alkyl group may be substituted with a substituent selected from the following group Fa-1:

[Group Fa-1]
a. a $C_{1-6}$ alkoxy group, wherein $C_{1-6}$ alkyl group in the alkoxy group may be substituted with a carboxy group $C_{1-6}$ alkoxycarbonyl group or —$CON(R^{f21})(R^{f22})$, wherein $R^{f21}$ and $R^{f22}$ may be the same or different and each represent
- a hydrogen atom,
- an acyl group, wherein the acyl group may be substituted with a hydroxyl group or a carboxy group,
- a $C_{1-6}$ alkoxycarbonyl group,
- —O—$COOR^{f1}$ wherein $R^{f1}$ is a hydrogen atom or a $C_{1-6}$ alkyl group,
- a $C_{1-6}$ alkyl group, wherein the $C_{1-6}$ alkyl group may be substituted with a hydroxyl group, a carboxy group, a $C_{1-6}$ alkoxycarbonyl group or a carbamoyl group,
- a $C_{1-6}$ alkylsulfonyl group or,
- a carbamoyl group, b. —$COOR^{f1}$, wherein $R^{f1}$ represents the same as above, c. —$N(R^{f21})(R^{f22})$ wherein $R^{f21}$ and $R^{f22}$ represnt the same as above, d. —$CON(R^{f21})(R^{f22})$, wherein $R^{f21}$ and $R^{f22}$ represnt the same as above, e. an acyl group and f. a halogen atom;

$R^g$ represents a substituent having Ring B' represented by the following formula (IIa):

(IIa)

wherein A' is a linker selected from the following group Ga-1:

[Group Ga-1]
- —$(CH_2)_k$—,
- —$(CH_2)_k$—$NR^{g1}$—$(CH_2)_j$—,
- —$(CH_2)_k$—O—(CO)$NR^{g1}$—$(CH_2)_j$—,
- —$(CH_2)_k$—$NR^{g1}$(CO)—$(CH_2)_j$—,
- —$(CH_2)_k$—$NR^{g1}$—$(CH_2)_j$—,
- —$(CH_2)_k$—(CO)—$(CH_2)_j$—,
- —(CO)—,
- —$(CH_2)_k$—O—$(CH_2)_j$—,
- —$(CH_2)_k$—S—$(CH_2)_j$—,
- —$(CH_2)_k$—O—(CO)—$(CH_2)_j$—, and
- —$(CH_2)_k$—$(CH_2)_j$(CO)—$(CH_2)_g$—.

wherein k, j and g may be the same or different and represnt an integer from 0 to 4 but k and j, or k and g are not 0 at the same time, $R^{g1}$ is
- a hydrogen atom,
- an acyl group, wherein the acyl group may be substituted with a carboxy group or a hydroxyl group, or
- a $C_{1-6}$ alkyl group, wherein the alkyl group may be substituted with a carboxy group, Ring B' is a ring selected from the following group Ha-1:

[Group Ha-1]
- an aryl group,
- a $C_{3-8}$ cycloalkyl group,
- a 5- to 7-membered saturated heterocyclic group having at least one nitrogen atom, wherein the saturated heterocyclic ring may form a condensed ring with a phenyl group, and
- a 5- or 6-membered aromatic heterocyclic group containing 1 or 2 hetero atoms, and the Ring B' may be substituted with a substituent selected from follows group Ia-1:

[Group Ia-1]

a. —$OR^{g2}$, wherein $R^{g2}$ represents
a hydrogen atom,
a $C_{1-6}$ alkyl group or
an aralkyl group, b. —$COOR^{g3}$, wherein $R^{g3}$ represents
a hydrogen atom or
a $C_{1-6}$ alkyl group, wherein the alkyl group may be substituted with a hydroxyl group, c. —$N(R^{g41})(R^{g42})$ wherein $R^{g41}$ and $R^{g42}$ represnt the same as above, d. —$CO$—$R^{g53}$, wherein $R^{g53}$ represents
a $C_{1-6}$ alkyl group, wherein the alkyl group may be substituted with a hydroxyl group, a carboxy group or an acylamino group,
a $C_{3-8}$ cycloalkyl group, wherein the cycloalkyl group may be substituted with a hydroxyl group, a $C_{1-6}$ alkoxy group or an oxo group,
an aryl group, wherein the aryl group may be substituted with a hydroxyl group,
a 5- or 6-membered saturated heterocyclic group containing 1 or 2 hetero atoms, wherein the saturated heterocyclic group may be substituted with a hydroxyl group, a $C_{1-6}$ alkyl group or an oxo group,
an aralkyl group or
a 5- or 6-membered aromatic heterocyclic group containing 1 or 2 hetero atoms, e. a $C_{1-6}$ alkyl group, wherein the $C_{1-6}$ alkyl group may be substituted with a hydroxyl group, a carboxy group or —$CO$—$R^{g53}$, wherein $R^{g53}$ represents the same as above, f. —$CO$—$N(R^{g51})(R^{g52})$ wherein $R^{g51}$ and $R^{g52}$ may be the same or different and are
a hydrogen atom,
an acyl group, wherein the acyl group may be substituted with a hydroxyl group,
a $C_{1-6}$ alkyl group, wherein the $C_{1-6}$ alkyl group may be substituted with a hydroxyl group, a carboxy group, an acylamino group, a $C_{1-6}$ alkoxycarbonyl group or a halogen atom,
a $C_{1-6}$ alkylsulfonyl group,
a $C_{1-6}$ alkoxycarbonyl group,
a carbamoyl group or
a $C_{3-8}$ cycloalkyl group, wherein the cycloalkyl group may be substituted with a hydroxyl group or a $C_{1-6}$ alkoxy group, g. a $C_{1-6}$ alkylsulfonyl group, h. an oxo group and i. a halogen atom; and $R^h$ is —$N(R^{h1})(R^{h2})$ wherein $R^{h1}$ is (1) a hydrogen atom, (2) a $C_{1-6}$ alkyl group, wherein the $C_{1-6}$ alkyl group may be substituted with a hydroxyl group, a $C_{1-6}$ alkoxy group, —$N(R^{g51})(R^{g52})$, —$CO$—$N(R^{g51})(R^{g52})$ a $C_{1-6}$ alkylsulfonyl or a halogen atom, wherein $R^{g51}$ and $R^{g52}$ represnt the same as above, (3) a $C_{2-6}$ alkenyl group, (4) a $C_{3-8}$ cycloalkyl group, wherein the cycloalkyl group may be substituted with a hydroxyl group or a $C_{1-6}$ alkoxy group, or (5) an aralkyl group, $R^{h2}$ is (1) a $C_{1-6}$ alkyl group, wherein the $C_{1-6}$ alkyl group may be substituted with a substituent selected from the following group Ja-1:

[Group Ja-1]
a hydroxyl group,
a $C_{1-6}$ alkoxy group,
a carboxy group,
an aromatic carbocyclic group, wherein the aromatic carbocyclic group may be substituted with a hydroxyl group, a $C_{1-6}$ alkyl group, wherein the alkyl group may be substituted with a carboxy group, a halogen atom, a $C_{1-6}$ alkoxy group, a carboxy group, a $C_{1-6}$ alkoxycarbonyl group, $C_{2-6}$ alkenyl group, wherein the $C_{2-6}$ alkenyl group may be substituted with a carboxy group,
a $C_{3-8}$ cycloalkyl group, wherein the cycloalkyl group may be substituted with a carboxy group or an aralkoxy group,
a 5- or 6-membered aromatic heterocyclic group containing 1 or 2 hetero atoms, wherein the aromatic heterocyclic group may be substituted with a carboxy group,
a 5- or 6-membered saturated heterocyclic group containing 1 or 2 hetero atoms,
—$N(R^{g51})(R^{g52})$ and
—$CON(R^{g51})(R^{g52})$ wherein $R^{g51}$ and $R^{g52}$ represent the same as above, (2) an acyl group, wherein the acyl group may be substituted with a hydroxyl group, (3) a $C_{2-6}$ alkenyl group, wherein the alkenyl group may be substituted with a carboxy group or a halogen atom, (4) a $C_{3-8}$ cycloalkyl group, wherein the cycloalkyl group may be substituted with a hydroxyl group, —$COOR^{g3}$, wherein $R^{g3}$ represents the same as above, —$COR^{g53}$, wherein $R^{g53}$ represents the same as above, —$CONR^{g51}R^{g52}$, wherein $R^{g51}$ and $R^{g52}$ each represent the same as above, or a $C_{1-6}$ alkyl group, wherein the alkyl group may be substituted with a carboxy group, (5) a 5- or 6-membered saturated heterocyclic group containing 1 or 2 hetero atoms, wherein the saturated heterocyclic group may be substituted with —$COR^{g53}$ wherein $R^{g53}$ represents the same as above, —$COOR^{g3}$, wherein $R^{g3}$ represents the same as above, —$CONR^{g51}R^{g52}$, wherein $R^{g51}$ and $R^{g52}$ each represent the same as above, or a $C_{1-6}$ alkylsulfonyl group, or (6) an aromatic carbocyclic group, wherein the aromatic carbocyclic group may be substituted with a carboxy group, $C_{1-6}$ alkyl group, wherein the alkyl group may be substituted with a carboxy group, or a $C_{2-6}$ alkenyl group, wherein the alkenyl group may be substituted with a carboxy group.

5. The aminopyridine compound or a pharmaceutically acceptable salt thereof according to the above-described 4, wherein $R^2$ is a hydrogen atom, $R^3$ is a $C_{1-6}$ alkyl group, wherein the $C_{1-6}$ alkyl group may be substituted with a hydroxyl group or a halogen atom, $R^6$ is a hydrogen atom, and $R^7$ is $R^e$, $R^g$ or $R^h$.

6. The aminopyridine compound or a pharmaceutically acceptable salt thereof according to the above-described 5, wherein $R^7$ is $R^e$, and $R^e$ is (1) a 5- or 6-membered saturated heterocyclic group containing 1 or 2 hetero atoms, wherein the saturated heterocyclic group may be substituted with a $C_{1-6}$ alkyl group, wherein the alkyl group may be substituted with a carboxy group, —$COR^{e3}$, wherein $R^{e3}$ is a 5- or 6-membered saturated heterocyclic group having 1 or 2 hetero atoms, wherein the 5- or 6-membered saturated heterocyclic group may be substituted with a hydroxyl group, or —CO—$N(R^{e41})(R^{e42})$, wherein $R^{e41}$ and $R^{e42}$ may be the same or different and each represent a hydrogen atom or a $C_{1-6}$ alkyl group, or (2) a $C_{3-8}$ cycloalkyl group, wherein the cycloalkyl group may be substituted with a $C_{1-6}$ alkyl group, wherein the alkyl group may be substituted with a carboxy group, —$COR^{e3}$, wherein $R^{e3}$ is a 5- or 6-membered saturated heterocyclic group having 1 or 2 hetero atoms, wherein the 5- or 6-membered saturated heterocyclic group may be substituted with a hydroxyl group, or —CO—$N(R^{e41})(R^{e42})$, wherein $R^{e41}$ and $R^{e42}$ may be the same or different and each represent a hydrogen atom or a $C_{1-6}$ alkyl group.

7. The aminopyridine compound or a pharmaceutically acceptable salt thereof according to the above-described 6, wherein $R^e$ is (1) a 5- or 6-membered saturated heterocyclic group having 1 or 2 hetero atoms represented by the following Ring L, wherein the saturated heterocyclic group may be substituted with 1 or 2 identical or different substituents selected from a $C_{1-6}$ alkyl group, wherein the alkyl group may be substituted with a carboxy group, —$COR^{e3}$, wherein $R^{e3}$ is a 5- or 6-membered saturated heterocyclic group having 1 or 2 hetero atoms, wherein the 5- or 6-membered saturated heterocyclic group may be substituted with a hydroxyl group, or —CO—$N(R^{e41})(R^{e42})$, wherein $R^{e41}$ and $R^{e42}$ may be the same or different and each represent a hydrogen atom or a $C_{1-6}$ alkyl group,

wherein Ring L is a 5- or 6-membered saturated heterocyclic group having 1 or 2 hetero atoms, or (2) a 5- or 6-membered cycloalkyl group, wherein the cycloalkyl group may be substituted with 1 or 2 identical or different substituents selected from a $C_{1-6}$ alkyl group, wherein the alkyl group may be substituted with a carboxy group, —$COR^{e3}$, wherein $R^{e3}$ is a 5- or 6-membered saturated heterocyclic group having 1 or 2 hetero atoms, wherein the 5- or 6-membered saturated heterocyclic group may be substituted with a hydroxyl group, or —CO—$N(R^{e41})(R^{e42})$ wherein $R^{e4}1$ and $R^{e42}$ may be the same or different and each represent a hydrogen atom or a $C_{1-6}$ alkyl group.

8. The aminopyridine compound or a pharmaceutically acceptable salt thereof according to the above-described 5, wherein $R^h$ is —$N(R^{h1})(R^{h2})$ and the $R^{h1}$ is a $C_{1-6}$ alkyl group, the $R^{h2}$ is a $C_{3-8}$ cycloalkyl group, wherein the cycloalkyl group is —$COOR^{g3}$, wherein $R^{g3}$ is a hydrogen atom or a $C_{1-6}$ alkyl group, wherein the alkyl group may be substituted with a hydroxyl group.

9. The aminopyridine compound or a pharmaceutically acceptable salt thereof according to the above-described 1, wherein the aminopyridine compound is selected from the following compound group.
(001) 1-methyl-4-{5-[6-(4-methylpyridin-2-ylamino)pyridin-2-yl]thiazol-2-yl}piperazin-2-one,
(002) 1-{5-[6-(4-methylpyridin-2-ylamino)pyridin-2-yl]thiazol-2-yl}piperidine-4-carboxylic acid,
(003) 1-{5-[6-(4-methylpyridin-2-ylamino)pyridin-2-yl]thiazol-2-yl}piperidine-4-carboxamide,
(004) N-methyl-1-{5-[6-(4-methylpyridin-2-ylamino)pyridin-2-yl]thiazol-2-yl}piperidine-4-carboxamide,
(005) N-(2-hydroxyethyl)-1-{5-[6-(4-methylpyridin-2-ylamino)pyridin-2-yl]thiazol-2-yl}piperidine-4-carboxamide,
(006) trans-4-{5-[6-(4-methylpyridin-2-ylamino)pyridin-2-yl]thiazol-2-yl}cyclohexanecarboxylic acid methyl ester,
(007) trans-4-{5-[6-(4-methylpyridin-2-ylamino)pyridin-2-yl]thiazol-2-yl}cyclohexanecarboxylic acid,
(008) (4-hydroxypiperidin-1-yl)-(trans-4-{5-[6-(4-methylpyridin-2-ylamino)pyridin-2-yl]thiazol-2-yl}cyclohexyl)methanone,
(009) N—((S)-1-{5-[6-(4-methylpyridin-2-ylamino)pyridin-2-yl]thiazol-2-yl}ethyl)amine,
(010) N—((S)-1-{5-[6-(4-methylpyridin-2-ylamino)pyridin-2-yl]thiazol-2-yl}ethyl)acetamide,
(011) (S)-3-methyl-4-{5-[6-(4-methylpyridin-2-ylamino)pyridin-2-yl]thiazol-2-yl}oxazolidin-2-one,
(012) (S)-2,2-dimethyl-4-{5-[6-(4-methylpyridin-2-ylamino)pyridin-2-yl]thiazol-2-yl}oxazolidine-3-carboxylic acid tert-butyl ester,
(013) (S)-2-amino-2-{5-[6-(4-methylpyridin-2-ylamino)pyridin-2-yl]thiazol-2-yl}ethanol,
(014) (S)-4-{5-[6-(4-methylpyridin-2-ylamino)pyridin-2-yl]thiazol-2-yl}oxazolidin-2-one,
(015) (1-{5-[6-(4-methylpyridin-2-ylamino)pyridin-2-yl]thiazol-2-yl}piperidin-4-yl)acetic acid,
(016) trans-4-[(N-methyl-N-{5-[6-(4-methylpyridin-2-ylamino)pyridin-2-yl]thiazol-2-yl}amino)methyl]cyclohexanecarboxylic acid,
(017) 3-(1-{5-[6-(4-methylpyridin-2-ylamino)pyridin-2-yl]thiazol-2-yl}piperidin-4-yl)propionic acid,
(018) 2-methyl-2-(1-{5-[6-(4-methylpyridin-2-ylamino)pyridin-2-yl]thiazol-2-yl}piperidin-4-yl)propionic acid,
(019) N-{4-methyl-5-[6-(4-methylpyridin-2-ylamino)pyridin-2-yl]thiazol-2-yl}propionamide,
(020) N-{4-methyl-5-[6-(4-methylpyridin-2-ylamino)pyridin-2-yl]thiazol-2-yl}acetamide,
(021) N-{4-methyl-5-[6-(4-methylpyridin-2-ylamino)pyrazin-2-yl]thiazol-2-yl}acetamide,
(022) acetic acid(S)-1-{5-[6-(4-methylpyridin-2-ylamino)pyridin-2-yl]thiazol-2-yl}ethyl ester,
(023) (S)-1-{5-[6-(4-methylpyridin-2-ylamino)pyridin-2-yl]thiazol-2-yl}ethanol,
(024) 1-{5-[6-(4-methylpyridin-2-ylamino)pyridin-2-yl]thiazol-2-yl}ethanone,
(025) 5-[6-(4-methylpyridin-2-ylamino)pyridin-2-yl]thiazole-2-carboxylic acid ethyl ester,
(026) 1-{5-[6-(4-methylpyridin-2-ylamino)pyridin-2-yl]thiazol-2-yl}ethanone oxime,
(027) (S)-5-{5-[6-(4-methylpyridin-2-ylamino)pyridin-2-yl]dihydrofuran-2-one,
(028) 1-{5-[6-(4-methylpyridin-2-ylamino)pyridin-2-yl]thiazol-2-yl}ethanone O-(2-hydroxyethyl)oxime,
(029) N-methoxy-N-methyl-5-[6-(4-methylpyridin-2-ylamino)pyridin-2-yl]thiazole-2-carboxamide, (030) N-methyl-5-[6-(4-methylpyridin-2-ylamino)pyridin-2-yl]thiazole-2-carboxamide,
(031) N-methyl-N—((S)-1-{5-[6-(4-methylpyridin-2-ylamino)pyridin-2-yl]thiazol-2-yl}ethyl)acetamide,
(032) (S)-5-{5-[6-(4-methylpyridin-2-ylamino)pyridin-2-yl]thiazol-2-yl}pyrrolidin-2-one,
(033) 5-{5-[6-(4-methylpyridin-2-ylamino)pyridin-2-yl]thiazol-2-yl}pentanoic acid,
(034) 5-{5-[6-(4-methylpyridin-2-ylamino)pyridin-2-yl]thiazol-2-yl}pentan-1-ol,
(035) 5-{5-[6-(4-methylpyridin-2-ylamino)pyridin-2-yl]thiazol-2-yl}pentanamide,
(036) 4-{5-[6-(4-methylpyridin-2-ylamino)pyridin-2-yl]thiazol-2-yl}cyclohexanol,
(037) 4-{5-[6-(4-methylpyridin-2-ylamino)pyridin-2-yl]thiazol-2-yl}cyclohexanone oxime,
(038) N-{6-[2-((S)-1-aminoethyl)thiazol-5-yl]pyridin-2-yl}-N-([4,4']bipyridinyl-2-yl)amine,
(039) N—((S)-1-{5-[6-([4,4']bipyridinyl-2-ylamino)pyridin-2-yl]thiazol-2-yl}ethyl)acetamide,
(040) N—((S)-1-{5-[6-(4-chloropyridin-2-ylamino)pyridin-2-yl]thiazol-2-yl}ethyl)acetamide,
(041) (S)-2-methyl-1-{5-[6-(4-methylpyridin-2-ylamino)pyridin-2-yl]thiazol-2-yl}propan-1-ol,
(042) N—((S)-1-{5-[6-(isoquinolin-3-ylamino)pyridin-2-yl]thiazol-2-yl}ethyl)acetamide,
(043) (4-methylpyridin-2-yl)-[6-(2-piperidin-4-ylthiazol-5-yl)pyridin-2-yl]amine,
(044) trans-4-{5-[6-(4-methylpyridin-2-ylamino)pyridin-2-yl]thiazol-2-yl}cyclohexanecarboxamide,
(045) 5-{5-[6-(4-methylpyridin-2-ylamino)pyridin-2-yl]thiazol-2-yl}pentylamine,
(046) 4-{5-[6-(4-methylpyridin-2-ylamino)pyridin-2-yl]thiazol-2-yl}butan-1-ol,
(047) 4-(2-{5-[6-(4-methylpyridin-2-ylamino)pyridin-2-yl]thiazol-2-yl}ethyl)phenol,
(048) 2-hydroxy-N—(S)-1-{5-[6-(4-methylpyridin-2-ylamino)pyridin-2-yl]thiazol-2-yl}ethyl)acetamide,
(049) 3-({5-[6-(4-methylpyridin-2-ylamino)pyridin-2-yl]thiazole-2-carbonyl}amino)propionic acid,
(050) 4-(2-{5-[6-(4-methylpyridin-2-ylamino)pyridin-2-yl]thiazol-2-yl}ethyl)benzoic acid,
(051) 1-{5-[6-(4-methylpyridin-2-ylamino)pyridin-2-yl]thiazol-2-ylmethyl}piperidin-4-ol,
(052) 3,3-dimethyl-4-{5-[6-(4-methylpyridin-2-ylamino)pyridin-2-yl]thiazol-2-yl}butan-1-ol,
(053) [4-(2-{5-[6-(4-methylpyridin-2-ylamino)pyridin-2-yl]thiazol-2-yl}ethyl)phenyl]methanol,
(054) N—((R)-(4-hydroxyphenyl)-{5-[6-(4-methylpyridin-2-ylamino)pyridin-2-yl]thiazol-2-yl}methyl)acetamide,
(055) N-(2-hydroxyethyl)-4-(2-{5-[6-(4-methylpyridin-2-ylamino)pyridin-2-yl]thiazol-2-yl}ethyl)benzamide,
(056) 4-(2-{5-[6-(4-methylpyridin-2-ylamino)pyridin-2-yl]thiazol-2-yl}ethyl)cyclohexanone,
(057) 4-(2-{5-[6-(4-methylpyridin-2-ylamino)pyridin-2-yl]thiazol-2-yl}ethyl)cyclohexanol,
(058) ((3R,4S)-3,4-dihydroxypyrrolidin-1-yl)-(trans-4-{5-[6-(4-methylpyridin-2-ylamino)pyridin-2-yl]thiazol-2-yl}cyclohexyl)methanone,
(059) (trans-4-{5-[6-(4-methylpyridin-2-ylamino)pyridin-2-yl]thiazol-2-yl}cyclohexyl)-(piperazin-1-yl)methanone,
(060) 4-{5-[6-(4-methylpyridin-2-ylamino)pyridin-2-yl]thiazol-2-yl}piperidine-1-carboxamide,
(061) 2-hydroxy-1-(4-{5-[6-(4-methylpyridin-2-ylamino)pyridin-2-yl]thiazol-2-yl}piperidin-1-yl)ethanone,
(062) trans-4-{5-[6-(4-methoxypyridin-2-ylamino)pyridin-2-yl]thiazol-2-yl}cyclohexanecarboxylic acid,
(063) 3-(4-{5-[6-(4-methylpyridin-2-ylamino)pyridin-2-yl]thiazol-2-yl}piperidin-1-yl)-3-oxopropionic acid,
(064) N-(4-methylpyridin-2-yl)-N-{6-[2-(piperazin-1-ylmethyl)thiazol-5-yl]pyridin-2-yl}amine,
(065) 1-{5-[6-(4-methylpyridin-2-ylamino)pyridin-2-yl]thiazol-2-ylmethyl}piperidin-4-ylamine,
(066) N-{5-[6-(4-methylpyridin-2-ylamino)pyridin-2-yl]thiazol-2-ylmethyl}methanesulfonamide,
(067) N-(trans-4-{5-[6-(4-methylpyridin-2-ylamino)pyridin-2-yl]thiazol-2-yl}cyclohexyl)acetamide,
(068) trans-4-{5-[6-(4-chloropyridin-2-ylamino)pyridin-2-yl]thiazol-2-yl}cyclohexanecarboxylic acid,
(069) 2-{5-[6-(4-methylpyridin-2-ylamino)pyridin-2-yl]thiazol-2-yl}ethanol,
(070) (trans-4-{5-[6-(4-methylpyridin-2-ylamino)pyridin-2-yl]thiazol-2-yl}cyclohexyl)methanol,
(071) trans-4-{5-[6-(isoquinolin-3-ylamino)pyridin-2-yl]thiazol-2-yl}cyclohexanecarboxylic acid,
(072) trans-4-{5-[6-(4-methylpyridin-2-ylamino)pyridin-2-yl]thiazol-2-yl}cyclohexylmethylamine,
(073) ((3R,4S)-3,4-dihydroxypyrrolidin-1-yl)-[4-(2-{5-[6-(4-methylpyridin-2-ylamino)pyridin-2-yl]thiazol-2-yl}ethyl)phenyl]methanone,
(074) N-(trans-4-{5-[6-(4-methylpyridin-2-ylamino)pyridin-2-yl]thiazol-2-yl}cyclohexylmethyl)acetamide,
(075) N-(trans-4-{5-[6-(4-methylpyridin-2-ylamino)pyridin-2-yl]thiazol-2-yl}cyclohexylmethyl)methanesulfonamide,
(076) 2-hydroxy-N-(trans-4-{5-[6-(4-methylpyridin-2-ylamino)pyridin-2-yl]thiazol-2-yl}cyclohexylmethyl)acetamide,
(077) 2-hydroxy-N-[4-(2-{5-[6-(4-methylpyridin-2-ylamino)pyridin-2-yl]thiazol-2-yl}ethyl)phenyl]acetamide,
(078) ((3R,4S)-3,4-dihydroxypiperidin-1-yl)-(trans-4-{5-[6-(4-methylpyridin-2-ylamino)pyridin-2-yl]thiazol-2-yl}cyclohexyl)methanone,
(079) ((R)-3-hydroxypyrrolidin-1-yl)-(trans-4-{5-[6-(4-methylpyridin-2-ylamino)pyridin-2-yl]thiazol-2-yl}cyclohexyl)metanone,
(080) (4-{5-[6-(4-methylpyridin-2-ylamino)pyridin-2-yl]thiazol-2-ylmethyl}phenyl)methanol,
(081) N-(4-methylpyridin-2-yl)-N-[6-(2-pyridin-3-ylmethylthiazol-5-yl)pyridin-2-yl]amine,
(082) N-(4-methylpyridin-2-yl)-N-{6-[2-(2-piperidin-4-ylethyl)thiazol-5-yl]pyridin-2-yl}amine,
(083) N-(6-{2-[2-(1-methanesulfonylpiperidin-4-yl)ethyl]thiazol-5-yl}pyridin-2-yl)-N-(4-methylpyridin-2-yl)amine,
(084) 2-hydroxy-1-[4-(2-{5-[6-(4-methylpyridin-2-ylamino)pyridin-2-yl]thiazol-2-yl}ethyl)piperidin-1-yl]ethanone,
(085) N-(2-hydroxyethyl)-trans-4-{5-[6-(4-methylpyridin-2-ylamino)pyridin-2-yl]thiazol-2-yl}cyclohexanecarboxamide,
(086) N-(2-morpholin-4-ylethyl)-trans-4-{5-[6-(4-methylpyridin-2-ylamino)pyridin-2-yl]thiazol-2-yl}cyclohexanecarboxamide,
(087) [3-(2-{5-[6-(4-methylpyridin-2-ylamino)pyridin-2-yl]thiazol-2-yl}ethyl)phenyl]methanol,
(088) (3-hydroxypyrrolidin-1-yl)-(trans-4-{5-[6-(4-methylpyridin-2-ylamino)pyridin-2-yl]thiazol-2-yl}cyclohexyl)methanone,
(089) 4-(trans-4-{5-[6-(4-methylpyridin-2-ylamino)pyridin-2-yl]thiazol-2-yl}cyclohexanecarbonyl)piperazin-2-one, (090) ((R)-2-hydroxymethylpyrrolidin-1-yl)-(trans-4-{5-[6-(4-methylpyridin-2-ylamino)pyridin-2-yl]thiazol-2-yl}cyclohexyl)metanone,
(091) (4-aminopiperidin-1-yl)-(trans-4-{5-[6-(4-methylpyridin-2-ylamino)pyridin-2-yl]thiazol-2-yl}cyclohexyl)methanone,
(092) [4-(2-{5-[6-(4-methylpyridin-2-ylamino)pyridin-2-yl]thiazol-2-yl}ethyl)piperidin-1-yl]-(piperidin-4-yl)metanone,
(093) (trans-4-{5-[6-(4-chloropyridin-2-ylamino)pyridin-2-yl]thiazol-2-yl}cyclohexyl)-(4-hydroxypiperidin-1-yl)metanone,
(094) N-(4-hydroxypiperidin-1-yl)-(trans-4-{5-[6-(4-methylpyridin-2-ylamino)pyridin-2-yl]thiazol-2-yl}cyclohexanecarboxamide,
(095) N—[(R)-2-hydroxy-1-(3H-imidazol-4-ylmethyl)ethyl]-trans-4-{5-[6-(4-methylpyridin-2-ylamino)pyridin-2-yl]thiazol-2-yl}cyclohexanecarboxamide,
(096) N—[(S)-2-hydroxy-1-(3H-imidazol-4-ylmethyl)ethyl]-trans-4-{5-[6-(4-methylpyridin-2-ylamino)pyridin-2-yl]thiazol-2-yl}cyclohexanecarboxamide,
(097) N-(2-dimethylaminoethyl)-trans-4-{5-[6-(4-methylpyridin-2-ylamino)pyridin-2-yl]thiazol-2-yl}cyclohexanecarboxamide,
(098) (3-aminopyrrolidin-1-yl)-(trans-4-{5-[6-(4-methylpyridin-2-ylamino)pyridin-2-yl]thiazol-2-yl}cyclohexyl)methanone,
(099) N-[1-(trans-4-{5-[6-(4-methylpyridin-2-ylamino)pyridin-2-yl]thiazol-2-yl}cyclohexanecarbonyl)pyrrolidin-3-yl]methanesulfonamide,
(100) (3R,4S)-1-(trans-4-{5-[6-(4-methylpyridin-2-ylamino)pyridin-2-yl]thiazol-2-yl}cyclohexylmethyl)pyrrolidin-3,4-diol,
(101) trans-4-{5-[6-(4-methylpyridin-2-ylamino)pyridin-2-yl]thiazol-2-yl}cyclohexanecarbonitrile,
(102) cis-4-{5-[6-(4-methylpyridin-2-ylamino)pyridin-2-yl]thiazol-2-yl}cyclohexanecarbonitrile,
(103) (S)-5-{5-[6-(4-methoxypyridin-2-ylamino)pyridin-2-yl]thiazol-2-yl}pyrrolidin-2-one,
(104) (S)-1-{5-[6-(4-methoxypyridin-2-ylamino)pyridin-2-yl]thiazol-2-yl}ethanol,
(105) (S)-1-(5-{6-[4-(2-hydroxyethyl)pyridin-2-ylamino]pyridin-2-yl}thiazol-2-yl)ethanol,
(106) (S)-1-{5-[6-(4-chloropyridin-2-ylamino)pyridin-2-yl]thiazol-2-yl}ethanol,
(107) (S)-5-{5-[6-(4-chloropyridin-2-ylamino)pyridin-2-yl]thiazol-2-yl}pyrrolidin-2-one,
(108) 3-(trans-4-{5-[6-(4-methylpyridin-2-ylamino)pyridin-2-yl]thiazol-2-yl}cyclohexyl)-4H-[1,2,4]oxazol-5-one,
(109) N-(4-methylpyridin-2-yl)-N-(6-{2-[4-(1H-tetrazol-5-yl)cyclohexyl]thiazol-5-yl}pyridin-2-yl)amine,
(110) (S)-5-(5-{6-[4-(2-hydroxyethyl)pyridin-2-ylamino]pyridin-2-yl}thiazol-2-yl)pyrrolidin-2-one,
(111) N-(1,1-dimethyl-2-{5-[6-(4-methylpyridin-2-ylamino)pyridin-2-yl]thiazol-2-yl}ethyl)acetamide,
(112) (S)-1-(5-{6-[4-(2-methyl-[1,3]dioxolan-2-yl)pyridin-2-ylamino]pyridin-2-yl}thiazol-2-yl)ethanol,
(113) N-methyl-trans-4-{5-[6-(4-methylpyridin-2-ylamino)pyridin-2-yl]thiazol-2-yl}cyclohexanecarboxamide,
(114) N-(1,1-dimethyl-2-{5-[6-(4-methylpyridin-2-ylamino)pyridin-2-yl]thiazol-2-yl}ethyl)methanesulfonamide,
(115) trans-4-{5-[6-(4-chloropyridin-2-ylamino)pyridin-2-yl]thiazol-2-yl}cyclohexanecarboxamide,
(116) trans-4-{5-[6-(4-methoxypyridin-2-ylamino)pyridin-2-yl]thiazol-2-yl}cyclohexanecarboxamide,
(117) 4-{5-[6-(4-methylpyridin-2-ylamino)pyridin-2-yl]thiazol-2-ylmethyl}cyclohexanol,
(118) (S)-1-(5-{6-[4-(2-hydroxyethoxy)pyridin-2-ylamino]pyridin-2-yl}thiazol-2-yl)ethanol,
(119) dimethylcarbamic acid(S)-1-{5-[6-(4-methylpyridin-2-ylamino)pyridin-2-yl]thiazol-2-yl}ethyl ester,
(120) 4-{5-[6-(4-methylpyridin-2-ylamino)pyridin-2-yl]thiazol-2-ylmethyl}piperazin-2-one,
(121) 4-(2-hydroxy-2-{5-[6-(4-methylpyridin-2-ylamino)pyridin-2-yl]thiazol-2-yl}ethyl)phenol,
(122) 4-(2-{5-[6-(4-methylpyridin-2-ylamino)pyridin-2-yl]thiazol-2-ylmethoxy}acetyl)piperazin-2-one,
(123) N—((R)-(4-hydroxyphenyl)-{5-[6-(4-methylpyridin-2-ylamino)pyridin-2-yl]thiazol-2-yl}methyl)-N-methylacetamide,
(124) 4-{5-[6-(4-methylpyridin-2-ylamino)pyridin-2-yl]thiazol-2-ylmethyl}piperazin-2,6-dione,
(125) (S)-5-{5-[6-(4-methylpyridin-2-ylamino)pyridin-2-yl]thiazol-2-yl}oxazolidin-2-one,
(126) 4-{5-[6-(4-methylpyridin-2-ylamino)pyridin-2-yl]thiazol-2-ylmethyl}piperazin-2-one,
(127) N-(4-methylpyridin-2-yl)-N-[6-(2-morpholin-4-ylthiazol-5-yl)pyridin-2-yl]amine,
(128) 1-(4-{5-[6-(4-methylpyridin-2-ylamino)pyridin-2-yl]thiazol-2-yl}piperazin-1-yl)ethanone,
(129) 4-{5-[6-(4-methylpyridin-2-ylamino)pyridin-2-yl]thiazol-2-yl}piperazine-1-sulfonamide,
(130) N-(4-methoxypyridin-2-yl)-N-{6-[2-(morpholin-4-yl)thiazol-5-yl]pyridin-2-yl}amine,
(131) (3R,4S)-1-{5-[6-(4-methylpyridin-2-ylamino)pyridin-2-yl]thiazol-2-yl}pyrrolidine-3,4-diol,
(132) N-methyl-N-{5-[6-(4-methylpyridin-2-ylamino)pyridin-2-yl]thiazol-2-yl}acetamide,
(133) N-[6-(4-methyl-2-morpholin-4-ylthiazol-5-yl)pyridin-2-yl]-N-(4-methylpyridin-2-yl)amine,
(134) N-methyl-N-{5-[6-(4-methylpyridin-2-ylamino)pyridin-2-yl]thiazol-2-yl}amine,
(135) N-methyl-4-{5-[6-(4-methylpyridin-2-ylamino)pyridin-2-yl]thiazol-2-yl}piperazine-1-carboxamide,
(136) 1-{4-methyl-5-[6-(4-methylpyridin-2-ylamino)pyridin-2-yl]thiazol-2-yl}piperidine-4-carboxamide,
(137) N-{6-[2-(4-methoxypiperidin-1-yl)thiazol-5-yl]pyridin-2-yl}-N-(4-methylpyridin-2-yl)amine,
(138) N-{6-[2-(4-methylpiperazin-1-yl)thiazol-5-yl]pyridin-2-yl}-N-(4-methylpyridin-2-yl)amine,
(139) 1-{5-[6-(4-methylpyridin-2-ylamino)pyridin-2-yl]thiazol-2-yl}piperidin-4-ol,
(140) N-methyl-1-{5-[6-(4-methoxypyridin-2-ylamino)pyridin-2-yl]thiazol-2-yl}piperidine-4-carboxamide,
(141) 4-{4-methyl-5-[6-(4-methylpyridin-2-ylamino)pyridin-2-yl]thiazol-2-yl}piperazine-1-carbaldehyde,
(142) 4-{5-[6-(4-methylpyridin-2-ylamino)pyridin-2-yl]thiazol-2-yl}piperazine-4-carboxylic methl ester,
(143) 2-hydroxy-1-(4-{5-[6-(4-methylpyridin-2-ylamino)pyridin-2-yl]thiazol-2-yl}piperazin-1-yl)ethanone,
(144) 1-(4-{5-[6-(4-methylpyridin-2-ylamino)pyridin-2-yl]thiazol-2-yl}piperazin-1-yl)propan-1-one,
(145) N,N-dimethyl-4-{5-[6-(4-methylpyridin-2-ylamino)pyridin-2-yl]thiazol-2-yl}piperazine-1-carboxamide,
(146) 1-(4-{5-[6-(4-methoxypyridin-2-ylamino)pyridin-2-yl]thiazol-2-yl}piperazin-1-yl)ethanone,
(147) 1-(4-{5-[6-(4-chloropyridin-2-ylamino)pyridin-2-yl]thiazol-2-yl}piperazin-1-yl)ethanone,
(148) 4-(methyl-{5-[6-(4-methylpyridin-2-ylamino)pyridin-2-yl]thiazol-2-yl}amino)cyclohexanecarboxylic acid, (149) 4-(N-methyl-N-{5-[6-(4-methylpyridin-2-ylamino)pyridin-2-yl]thiazol-2-yl}amino)cyclohexanecarboxamide,
(150) 3-(1-{5-[6-(4-methylpyridin-2-ylamino)pyridin-2-yl]thiazol-2-yl}piperidin-4-yl)-4H-[1,2,4]oxadiazole-5-one,
(151) N-methyl-N-{5-[6-(4-methylpyridin-2-ylamino)pyridin-2-yl]thiazol-2-yl}-N-piperidin-4-ylamine,
(152) 4-(1-{5-[6-(4-methylpyridin-2-ylamino)pyridin-2-yl]thiazol-2-yl}piperidine-4-carbonyl)piperazin-2-one,
(153) N-(2,2-dimethoxyethyl)-N-methyl-N-{5-[6-(4-methylpyridin-2-ylamino)pyridin-2-yl]thiazol-2-yl}amine,
(154) 1-[4-(N-methyl-N-{5-[6-(4-methylpyridin-2-ylamino)pyridin-2-yl]thiazol-2-yl}amino)piperidin-1-yl]ethanone,
(155) 2-hydroxy-1-[4-(N-methyl-N-{5-[6-(4-methylpyridin-2-ylamino)pyridin-2-yl]thiazol-2-yl}amino)piperidin-1-yl]ethanone,
(156) N-methyl-4-(N'-methyl-N'-{5-[6-(4-methylpyridin-2-ylamino)pyridin-2-yl]thiazol-2-yl}amino)piperidine-1-carboxamide,
(157) N-{2-[4-(N'-methyl-N'-{5-[6-(4-methylpyridin-2-ylamino)pyridin-2-yl]thiazol-2-yl}amino)piperidin-1-yl]-2-oxoethyl}acetamide,
(158) (4-{5-[6-(4-methylpyridin-2-ylamino)pyridin-2-yl]thiazol-2-yl}-2-oxopiperazin-1-yl)acetic acid,
(159) 2-(4-{5-[6-(4-methylpyridin-2-ylamino)pyridin-2-yl]thiazol-2-yl}-2-oxopiperazin-1-yl)acetamide,
(160) N-methyl-2-(4-{5-[6-(4-methylpyridin-2-ylamino)pyridin-2-yl]thiazol-2-yl}-2-oxopiperazin-1-yl)acetamide,
(161) N-(2-hydroxyethyl)-2-(4-{5-[6-(4-methylpyridin-2-ylamino)pyridin-2-yl]thiazol-2-yl}-2-oxopiperazin-1-yl)acetamide,
(162) N-methyl-N-methylcarbamoylmethyl-1-{5-[6-(4-methylpyridin-2-ylamino)pyridin-2-yl]thiazol-2-yl}piperidine-4-carboxamide,
(163) N-methyl-N-{5-[6-(4-methylpyridin-2-ylamino)pyridin-2-yl]thiazol-2-yl}-N-tetrahydropyran-4-ylamine,
(164) 4-[(N-methyl-N-{5-[6-(4-methylpyridin-2-ylamino)pyridin-2-yl]thiazol-2-yl}amino)methyl]phenol,
(165) N—((R)-1-{5-[6-(4-methylpyridin-2-ylamino)pyridin-2-yl]thiazol-2-yl}pyrrolidin-3-yl)acetamide,
(166) (R)-1-{5-[6-(4-methylpyridin-2-ylamino)pyridin-2-yl]thiazol-2-yl}pyrrolidin-3-ylamine,
(167) 1-{5-[6-(4-methylpyridin-2-ylamino)pyridin-2-yl]thiazol-2-yl}piperidine-3-carboxylic acid,
(168) 2-hydroxy-N—((R)-1-{5-[6-(4-methylpyridin-2-ylamino)pyridin-2-yl]thiazol-2-yl}pyrrolidin-3-yl)acetamide,
(169) 1-{5-[6-(4-methylpyridin-2-ylamino)pyridin-2-yl]thiazol-2-yl}piperidine-3-carboxamide,
(170) N-methyl-1-{5-[6-(4-methylpyridin-2-ylamino)pyridin-2-yl]thiazol-2-yl}piperidine-3-carboxamide,
(171) N-(2-hydroxyethyl)-1-{5-[6-(4-methylpyridin-2-ylamino)pyridin-2-yl]thiazol-2-yl}piperidine-3-carboxamide,
(172) (R)-1-{5-[6-(4-methylpyridin-2-ylamino)pyridin-2-yl]thiazol-2-yl}pyrrolidin-3-ol,
(173) trans-4-(N-methyl-N-{5-[6-(4-methylpyridin-2-ylamino)pyridin-2-yl]thiazol-2-yl}amino)cyclohexanol,
(174) N-{6-[2-(3-methoxymethylpiperidin-1-yl)thiazol-5-yl]pyridin-2-yl}-N-(4-methylpyridin-2-yl)amine,
(175) 2-hydroxy-N-(1-{5-[6-(4-methylpyridin-2-ylamino)pyridin-2-yl]thiazol-2-yl}piperidin-4-yl)acetamide,
(176) 2-hydroxy-N-methyl-N-(1-{5-[6-(4-methylpyridin-2-ylamino)pyridin-2-yl]thiazol-2-yl}piperidin-4-yl)acetamide,
(177) N-(1-{5-[6-(4-methylpyridin-2-ylamino)pyridin-2-yl]thiazol-2-yl}piperidin-4-yl)methanesulfonamide,
(178) N-methyl-N-(1-{5-[6-(4-methylpyridin-2-ylamino)pyridin-2-yl]thiazol-2-yl}piperidin-4-yl)methanesulfonamide,
(179) 2-hydroxy-N-(1-{5-[6-(4-methylpyridin-2-ylamino)pyridin-2-yl]thiazol-2-yl}piperidin-4-ylmethyl)acetamide,
(180) N-(1-{5-[6-(4-methylpyridin-2-ylamino)pyridin-2-yl]thiazol-2-yl}piperidin-4-ylmethyl)acetamide,
(181) N-methyl-(S)-1-{5-[6-(4-methylpyridin-2-ylamino)pyridin-2-yl]thiazol-2-yl}pyrrolidine-2-carboxamide,
(182) N—((R)-1-{5-[6-(4-methylpyridin-2-ylamino)pyridin-2-yl]thiazol-2-yl}pyrrolidin-3-yl)methanesulfonamide,
(183) N-{6-[2-((R)-3-methoxypyrrolidin-1-yl)thiazol-5-yl]pyridin-2-yl}-N-(4-methylpyridin-2-yl)amine,
(184) N-methyl-4-(N'-methyl-N'-{5-[6-(4-methylpyridin-2-ylamino)pyridin-2-yl]thiazol-2-yl}amino)cyclohexanecarboxamide,
(185) N-(2-hydroxyethyl)-4-(N'-methyl-N'-{5-[6-(4-methylpyridin-2-ylamino)pyridin-2-yl]thiazol-2-yl}amino)cyclohexanecarboxamide,
(186) N-(2-acetylaminoethyl)-4-(N'-methyl-N'-{5-[6-(4-methylpyridin-2-ylamino)pyridin-2-yl]thiazol-2-yl}amino)cyclohexanecarboxamide,
(187) (1-{5-[6-(4-methylpyridin-2-ylamino)pyridin-2-yl]thiazol-2-yl}piperidin-3-ylmethoxy)acetic acid,
(188) (1-{5-[6-(4-methylpyridin-2-ylamino)pyridin-2-yl]thiazol-2-yl}piperidin-3-yl)methanol,
(189) 2-(1-{5-[6-(4-methylpyridin-2-ylamino)pyridin-2-yl]thiazol-2-yl}piperidin-3-ylmethoxy)acetamide,
(190) 4-methyl-1-{5-[6-(4-methylpyridin-2-ylamino)pyridin-2-yl]thiazol-2-yl}piperidine-4-carboxamide,
(191) N-methyl-4-methyl-1-{5-[6-(4-methylpyridin-2-ylamino)pyridin-2-yl]thiazol-2-yl}piperidine-4-carboxamide,
(192) N-methyl-2-(1-{5-[6-(4-methylpyridin-2-ylamino)pyridin-2-yl]thiazol-2-yl}piperidin-3-ylmethoxy)acetamide,
(193) N-(2-hydroxyethyl)-4-methyl-1-{5-[6-(4-methylpyridin-2-ylamino)pyridin-2-yl]thiazol-2-yl}-piperidine-4-carboxamide,
(194) 2-(1-{5-[6-(4-methylpyridin-2-ylamino)pyridin-2-yl]thiazol-2-yl}piperidin-4-yl)acetamide,
(195) N-methyl-2-(1-{5-[6-(4-methylpyridin-2-ylamino)pyridin-2-yl]thiazol-2-yl}piperidin-4-yl)acetamide,
(196) N-(2-hydroxyethyl)-2-(1-{5-[6-(4-methylpyridin-2-ylamino)pyridin-2-yl]thiazol-2-yl}piperidin-4-yl)acetamide,
(197) N,N-diallyl-N-{5-[6-(4-methylpyridin-2-ylamino)pyridin-2-yl]thiazol-2-yl}amine,
(198) N-[2-(N'-methyl-N'-{5-[6-(4-methylpyridin-2-ylamino)pyridin-2-yl]thiazol-2-yl}amino)ethyl]acetamide,
(199) 2-hydroxy-N-[2-(N'-methyl-{5-[6-(4-methylpyridin-2-ylamino)pyridin-2-yl]thiazol-2-yl}amino)ethyl]acetamide,
(200) N-(4-methanesulfonylpiperidin-1-yl)-N-methyl-N-{5-[6-(4-methylpyridin-2-ylamino)pyridin-2-yl]thiazol-2-yl}amine,
(201) N,N-dimethyl-4-(N'-methyl-N'-{5-[6-(4-methylpyridin-2-ylamino)pyridin-2-yl]thiazol-2-yl}amino)piperidine-1-carboxamide,
(202) (4-hydroxyphenyl)-[4-(N-methyl-N-{5-[6-(4-methylpyridin-2-ylamino)pyridin-2-yl]thiazol-2-yl}amino)piperidin-1-yl]methanone,
(203) 1-(4-{5-[6-(4-methylpyridin-2-ylamino)pyridin-2-yl]thiazol-2-ylamino}piperidin-1-yl)ethanone, (204) 1-[4-(N-isopropyl-N-{5-[6-(4-methylpyridin-2-ylamino)pyridin-2-yl]thiazol-2-yl}amino)piperidin-1-yl]ethanone,
(205) N-methyl-2-((R)-1-{5-[6-(4-methylpyridin-2-ylamino)pyridin-2-yl]thiazol-2-yl}pyrrolidin-3-yloxy)acetamide,
(206) 1-{5-[6-(4-methoxypyridin-2-ylamino)pyridin-2-yl]thiazol-2-yl}piperidine-4-carboxamide,
(207) 1-{5-[6-(4-chloropyridin-2-ylamino)pyridin-2-yl]thiazol-2-yl}piperidine-4-carboxamide,
(208) 2-(N-methyl-N-{5-[6-(4-methylpyridin-2-ylamino)pyridin-2-yl]thiazol-2-yl}amino)ethanol,
(209) N-(2-methoxyethyl)-N-methyl-N-{5-[6-(4-methylpyridin-2-ylamino)pyridin-2-yl]thiazol-2-yl}amine,
(210) N-[2-(N'-(1-acetylpiperidin-4-yl)-N'-{5-[6-(4-methylpyridin-2-ylamino)pyridin-2-yl]thiazol-2-yl}amino)ethyl]methanesulfonamide,
(211) 1-[4-(N-(2-hydroxyethyl)-N-{5-[6-(4-methylpyridin-2-ylamino)pyridin-2-yl]thiazol-2-yl}amino)piperidin-1-yl]ethanone,
(212) 1-[4-(N-(2-methoxyethyl)-N-{5-[6-(4-methylpyridin-2-ylamino)pyridin-2-yl]thiazol-2-yl}amino)piperidin-1-yl]ethanone,
(213) (S)-1-{5-[6-(4-methylpyridin-2-ylamino)pyridin-2-yl]thiazol-2-yl}pyrrolidine-2-carboxamide,
(214) N-methyl-(S)-1-{5-[6-(4-methylpyridin-2-ylamino)pyridin-2-yl]thiazol-2-yl}pyrrolidine-2-carboxamide,
(215) N-(2,2,2-trifluoroethyl)-(S)-1-{5-[6-(4-methylpyridin-2-ylamino)pyridin-2-yl]thiazol-2-yl}pyrrolidine-2-carboxamide,
(216) (R)-1-{5-[6-(4-methylpyridin-2-ylamino)pyridin-2-yl]thiazol-2-yl}piperidine-3-carboxylic acid,
(217) ((R)-1-{5-[6-(4-methylpyridin-2-ylamino)pyridin-2-yl]thiazol-2-yl}piperidin-3-yl)methanol,
(218) (R)-1-{5-[6-(4-methylpyridin-2-ylamino)pyridin-2-yl]thiazol-2-yl}piperidine-3-carboxamide,
(219) 1-[4-(N-ethyl-N-{5-[6-(4-methylpyridin-2-ylamino)
(220) pyridin-2-yl]thiazol-2-yl}amino)piperidin-1-yl]ethanone,
(221) 1-{4-[N-{5-[6-(4-methylpyridin-2-ylamino)pyridin-2-yl]thiazol-2-yl}-N-(2,2,2-trifluoroethyl)amino]piperidin-1-yl}ethanone,
(222) 1-[4-(N-{5-[6-(4-chloropyridin-2-ylamino)pyridin-2-yl]thiazol-2-yl}-N-methylamino)piperidin-1-yl]ethanone,
(223) 1-[4-(N-{5-[6-(4-chloropyridin-2-ylamino)pyridin-2-yl]thiazol-2-yl}-N-methylamino)piperidin-1-yl]-2-hydroxyethanone,
(224) (R)-1-{5-[6-(4-methoxypyridin-2-ylamino)pyridin-2-yl]thiazol-2-yl}pyrrolidin-3-ol,
(225) (R)-1-{5-[6-(4-chloropyridin-2-ylamino)pyridin-2-yl]thiazol-2-yl}pyrrolidin-3-ol,
(226) 4-methyl-1-{5-[6-(4-methylpyridin-2-ylamino)pyridin-2-yl]thiazol-2-yl}piperidine-4-carboxylic acid,
(227) (S)-1-{5-[6-(4-methoxypyridin-2-ylamino)pyridin-2-yl]thiazol-2-yl}pyrrolidine-2-carboxamide,
(228) (S)-1-{5-[6-(4-chloropyridin-2-ylamino)pyridin-2-yl]thiazol-2-yl}pyrrolidine-2-carboxamide,
(229) 1-{5-[6-(4-acetylpyridin-2-ylamino)pyridin-2-yl]thiazol-2-yl}piperidine-4-carboxamide,
(230) 2-(N-(2-hydroxyethyl)-N-{5-[6-(4-methylpyridin-2-ylamino)pyridin-2-yl]thiazol-2-yl}amino)ethanol,
(231) 2-[N-{5-[6-(4-chloropyridin-2-ylamino)pyridin-2-yl]thiazol-2-yl}-N-(2-hydroxyethyl)amino]ethanol,
(232) (R)-1-{5-[6-(4-chloropyridin-2-ylamino)pyridin-2-yl]thiazol-2-yl}piperidine-3-carboxylic acid,
(233) 1-(5-{6-[4-(1-hydroxyethyl)pyridin-2-ylamino]pyridin-2-yl}thiazol-2-yl)piperidine-4-carboxamide,
(234) (R)-1-(5-{6-[4-(2-methyl-[1,3]dioxolan-2-yl)pyridin-2-ylamino]pyridin-2-yl}thiazol-2-yl)pyrrolidin-3-ol,
(235) 1-(2-{6-[2-((R)-3-hydroxypyrrolidin-1-yl)thiazol-5-yl]pyridin-2-ylamino}pyridin-4-yl)ethanone,
(236) 4-(4-{5-[6-(4-methylpyridin-2-ylamino)pyridin-2-yl]thiazol-2-yl}piperazin-1-yl)-4-oxobutyric acid,
(237) N-hydroxy-(R)-1-{5-[6-(4-chloropyridin-2-ylamino)pyridin-2-yl]thiazol-2-yl}piperidine-3-carboxamide,
(238) 4-[4-(N-methyl-N-{5-[6-(4-methylpyridin-2-ylamino)pyridin-2-yl]thiazol-2-yl}amino)piperidin-1-yl]-4-oxobutyric acid,
(239) (R)-1-(5-{6-[4-(1-hydroxyethyl)pyridin-2-ylamino]pyridin-2-yl}thiazol-2-yl)pyrrolidin-3-ol,
(240) 2-(N-methyl-N-{5-[6-(4-methylpyridin-2-ylamino)pyridin-2-yl]thiazol-2-yl}amino)acetamide,
(241) (R)-1-(5-{6-[4-(2-methyl-[1,3]dioxolan-2-yl)pyridin-2-ylamino]pyridin-2-yl}thiazol-2-yl)piperidine-3-carboxylic acid,
(242) (R)-1-{5-[6-(4-acetylpyridin-2-ylamino)pyridin-2-yl]thiazol-2-yl}piperidine-3-carboxylic acid,
(243) (S)-1-{5-[6-(4-acetylpyridin-2-ylamino)pyridin-2-yl]thiazol-2-yl}pyrrolidine-2-carboxamide,
(244) (1-{5-[6-(4-chloropyridin-2-ylamino)pyridin-2-yl]thiazol-2-yl}pyrrolidin-3-yl)methanol,
(245) 1-[(R)-3-(N-methyl-N-{5-[6-(4-methylpyridin-2-ylamino)pyridin-2-yl]thiazol-2-yl}amino)pyrrolidin-1-yl]ethanone,
(246) (S)-1-{5-[6-(4-acetylpyridin-2-ylamino)pyridin-2-yl]thiazol-2-yl}pyrrolidine-2-carboxylic acid,
(247) (R)-1-(5-{6-[4-(2-methyl-[1,3]dioxolan-2-yl)pyridin-2-ylamino]pyridin-2-yl}thiazol-2-yl)piperidine-3-carboxamide,
(248) ((S)-1-{5-[6-(4-methylpyridin-2-ylamino)pyridin-2-yl]thiazol-2-yl}piperidin-3-yl)acetic acid,
(249) (S)-3-methyl-2-[2-(N-methyl-N-{5-[6-(4-methylpyridin-2-ylamino)pyridin-2-yl]thiazol-2-yl}amino)acetylamino]butyric acid,
(250) 3-[2-(N-methyl-N-{5-[6-(4-methylpyridin-2-ylamino)pyridin-2-yl]thiazol-2-yl}amino)acetylamino]propionic acid,
(251) [2-(N-methyl-N-{5-[6-(4-methylpyridin-2-ylamino)pyridin-2-yl]thiazol-2-yl}amino)acetylamino]acetic acid,
(252) [1-(5-{6-[4-(2-methyl-[1,3]dioxolan-2-yl)pyridin-2-ylamino]pyridin-2-yl}thiazol-2-yl)piperidin-4-yl]acetic acid,
(253) (1-{5-[6-(pyridin-2-ylamino)pyridin-2-yl]thiazol-2-yl}piperidin-4-yl)acetic acid,
(254) 4-[(N-methyl-N-{5-[6-(4-methylpyridin-2-ylamino)pyridin-2-yl]thiazol-2-yl}amino)methyl]benzoic acid,
(255) ((R)-1-{5-[6-(4-methylpyridin-2-ylamino)pyridin-2-yl]thiazol-2-yl}pyrrolidin-3-yloxy)acetic acid,
(256) 1-{5-[6-(4-methylpyridin-2-ylamino)pyridin-2-yl]thiazol-2-yl}pyrrolidine-3-carboxylic acid,
(257) (R)-1-(5-{6-[4-(2-hydroxyethyl)pyridin-2-ylamino]pyridin-2-yl}thiazol-2-yl)pyrrolidin-3-ol,
(258) 4-(N-methyl-N-{5-[6-(4-methylpyridin-2-ylamino)pyridin-2-yl]thiazol-2-yl}amino)benzoic acid,
(259) (2S,4R)-4-(N-methyl-N-{5-[6-(4-methylpyridin-2-ylamino)pyridin-2-yl]thiazol-2-yl}amino)pyrrolidine-2-carboxylic acid,
(260) {N-methyl-N-[2-(N'-methyl-N'-{5-[6-(4-methylpyridin-2-ylamino)pyridin-2-yl]thiazol-2-yl}amino)acetyl]amino}acetic acid,
(261) 2-{5-[6-(4-methylpyridin-2-ylamino)pyridin-2-yl]thiazol-2-yl}-1,2,3,4-tetrahydroisoquinoline-5-carboxylic acid, (262) 3-[(N-methyl-N-{5-[6-(4-methylpyridin-2-ylamino)pyridin-2-yl]thiazol-2-yl}amino)methyl]benzoic acid,
(263) {4-[(N-methyl-N-{5-[6-(4-methylpyridin-2-ylamino)pyridin-2-yl]thiazol-2-yl}amino)methyl]phenyl}acetic acid,
(264) (1-{5-[6-(4-methylpyridin-2-ylamino)pyridin-2-yl]thiazol-2-yl}pyrrolidin-3-yl)acetic acid,
(265) (4-{5-[6-(4-methylpyridin-2-ylamino)pyridin-2-yl]thiazol-2-yl}piperazin-1-yl)acetic acid,
(266) N-(4-methylpyridin-2-yl)-N-(6-{2-[(R)-3-(1H-tetrazol-5-yl)piperidin-1-yl]thiazol-5-yl}pyridin-2-yl)amine,
(267) cis-4-(N-methyl-N-{5-[6-(4-methylpyridin-2-ylamino)pyridin-2-yl]thiazol-2-yl}amino)cyclohexanecarboxylic acid,
(268) trans-4-(N-methyl-N-{5-[6-(4-methylpyridin-2-ylamino)pyridin-2-yl]thiazol-2-yl}amino)cyclohexanecarboxylic acid,
(269) 4-[2-(N-methyl-N-{5-[6-(4-methylpyridin-2-ylamino)pyridin-2-yl]thiazol-2-yl}amino)ethyl]benzoic acid,
(270) (1-{5-[6-(4-methylpyridin-2-ylamino)pyridin-2-yl]thiazol-2-yl}piperidin-4-yloxy)acetic acid,
(271) (4-{5-[6-(4-methylpyridin-2-ylamino)pyridin-2-yl]thiazol-2-yl}cyclohexyl)acetic acid,
(272) 4-{[N-methyl-N-(5-{6-[4-(2-methyl-[1,3]dioxolan-2-yl)pyridin-2-ylamino]pyridin-2-yl}thiazol-2-yl)amino]methyl}benzoic acid,
(273) 4-[(N-dimethylcarbamoylmethyl-N-{5-[6-(4-methylpyridin-2-ylamino)pyridin-2-yl]thiazol-2-yl}amino)methyl]benzoic acid,
(274) cis-4-(N-carbamoylmethyl-N-{5-[6-(4-methylpyridin-2-ylamino)pyridin-2-yl]thiazol-2-yl}amino)cyclohexanecarboxylic acid,
(275) trans-4-[(N-carbamoylmethyl-N-{5-[6-(4-methylpyridin-2-ylamino)pyridin-2-yl]thiazol-2-yl]amino)methyl}cyclohexanecarboxylic acid,
(276) 5-[(N-methyl-N-{5-[6-(4-methylpyridin-2-ylamino)pyridin-2-yl]thiazol-2-yl}amino)methyl]thiophene-2-carboxylic acid,
(277) 3-chloro-4-[(N-methyl-N-{5-[6-(4-methylpyridin-2-ylamino)pyridin-2-yl]thiazol-2-yl}amino)methyl]benzoic acid,
(278) 4-{5-[6-(4-methylpyridin-2-ylamino)pyridin-2-yl]thiazol-2-ylmethoxy}benzoic acid,
(279) 3-methoxy-4-[(N-methyl-N-{5-[6-(4-methylpyridin-2-ylamino)pyridin-2-yl]thiazol-2-yl}amino)methyl]benzoic acid,
(280) 2-{5-[6-(4-methylpyridin-2-ylamino)pyridin-2-yl]thiazol-2-yl}-1,2,3,4-tetrahydroisoquinoline-6-carboxylic acid,
(281) 2-[(N-methyl-N-{5-[6-(4-methylpyridin-2-ylamino)pyridin-2-yl]thiazol-2-yl}amino)methyl]thiazole-4-carboxylic acid,
(282) [trans-4-(N-methyl-N-{5-[6-(4-methylpyridin-2-ylamino)pyridin-2-yl]thiazol-2-yl}amino)cyclohexyl]acetic acid,
(283) [cis-4-(N-methyl-N-{5-[6-(4-methylpyridin-2-ylamino)pyridin-2-yl]thiazol-2-yl}amino)cyclohexyl]acetic acid,
(284) 4-(2-{5-[6-(4-methylpyridin-2-ylamino)pyridin-2-yl]thiazol-2-yl}ethyl)cyclohexanecarboxylic acid,
(285) (4-methyl-1-{5-[6-(4-methylpyridin-2-ylamino)pyridin-2-yl]thiazol-2-yl}piperidin-4-yl)acetic acid,
(286) 4-{5-[6-(4-methylpyridin-2-ylamino)pyridin-2-yl]thiazol-2-yl}-3,4-dihydro-2H-benzo[1,4]oxazine-8-carboxylic acid,
(287) {5-[6-(4-methylpyridin-2-ylamino)pyridin-2-yl]thiazol-2-ylmethoxy}acetic acid,
(288) 4-[1-methyl-1-(N-methyl-N-{5-[6-(4-methylpyridin-2-ylamino)pyridin-2-yl]thiazol-2-yl}amino)ethyl]benzoic acid,
(289) [4-(N-methyl-N-{5-[6-(4-methylpyridin-2-ylamino)pyridin-2-yl]thiazol-2-yl}amino)phenyl]acetic acid,
(290) (1-{5-[6-(4-chloropyridin-2-ylamino)pyridin-2-yl]thiazol-2-yl}piperidin-4-yl)acetic acid,
(291) trans-4-[(N-benzyl-N-{5-[6-(4-methylpyridin-2-ylamino)pyridin-2-yl]thiazol-2-yl}amino)methyl]cyclohexanecarboxylic acid,
(292) [trans-4-(N-benzyl-N-{5-[6-(4-methylpyridin-2-ylamino)pyridin-2-yl]thiazol-2-yl}amino)cyclohexyl]acetic acid,
(293) trans-4-[(N-isopropyl-N-{5-[6-(4-methylpyridin-2-ylamino)pyridin-2-yl]thiazol-2-yl}amino)methyl]cyclohexanecarboxylic acid,
(294) 1-{5-[6-(4-methylpyridin-2-ylamino)pyridin-2-yl]thiazol-2-yl}-1,2,3,4-tetrahydroquinoline-5-carboxylic acid,
(295) fluoro-(1-{5-[6-(4-methylpyridin-2-ylamino)pyridin-2-yl]thiazol-2-yl}piperidin-4-ylidene)acetic acid,
(296) 5-(N-methyl-N-{5-[6-(4-methylpyridin-2-ylamino)pyridin-2-yl]thiazol-2-yl}amino)pentanoic acid,
(297) N-[2-(1-{5-[6-(4-methylpyridin-2-ylamino)pyridin-2-yl]thiazol-2-yl}piperidin-4-yl)acetyl]methanesulfonamide,
(298) 4-(N-methyl-N-{5-[6-(4-methylpyridin-2-ylamino)pyridin-2-yl]thiazol-2-yl}amino)butyric acid,
(299) (1-{5-[6-(4-trifluoromethylpyridin-2-ylamino)pyridin-2-yl]thiazol-2-yl}piperidin-4-yl)acetic acid,
(300) (1-{5-[6-(5-chloropyridin-2-ylamino)pyridin-2-yl]thiazol-2-yl}piperidin-4-yl)acetic acid,
(301) (1-{5-[6-(4-methoxypyridin-2-ylamino)pyridin-2-yl]thiazol-2-yl}piperidin-4-yl)acetic acid,
(302) trans-4-(N-methyl-N-{5-[6-(4-trifluoromethylpyridin-2-ylamino)pyridin-2-yl]thiazol-2-yl}amino)cyclohexanecarboxylic acid,
(303) 3-[4-(N-methyl-N-{5-[6-(4-methylpyridin-2-ylamino)pyridin-2-yl]thiazol-2-yl}amino)phenyl]propionic acid,
(304) (E)-6-(N-methyl-N-{5-[6-(4-methylpyridin-2-ylamino)pyridin-2-yl]thiazol-2-yl}amino)hex-2-enoic acid,
(305) (2-{5-[6-(4-methylpyridin-2-ylamino)pyridin-2-yl]thiazol-2-yl}-1,2,3,4-tetrahydroisoquinolin-6-yl)acetic acid,
(306) 3-(2-{5-[6-(4-methylpyridin-2-ylamino)pyridin-2-yl]thiazol-2-yl}-1,2,3,4-tetrahydroisoquinolin-5-yl)propionic acid,
(307) 5-(N-isopropyl-N-{5-[6-(4-methylpyridin-2-ylamino)pyridin-2-yl]thiazol-2-yl}amino)pentanoic acid,
(308) 5-{5-[6-(4-methylpyridin-2-ylamino)pyridin-2-yl]thiazol-2-ylamino}pentanoic acid,
(309) 6-(N-methyl-N-{5-[6-(4-methylpyridin-2-ylamino)pyridin-2-yl]thiazol-2-yl}amino)hexanoic acid,
(310) (Z)-2-fluoro-6-(N-methyl-N-{5-[6-(4-methylpyridin-2-ylamino)pyridin-2-yl]thiazol-2-yl}amino)hex-2-enoic acid,
(311) (8-{5-[6-(4-trifluoromethylpyridin-2-ylamino)pyridin-2-yl]thiazol-2-yl}-8-azabicyclo[3.2.1]oct-3-yl)acetic acid,
(312) (8-{5-[6-(4-methylpyridin-2-ylamino)pyridin-2-yl]thiazol-2-yl}-8-azabicyclo[3.2.1]oct-3-yl)acetic acid,
(313) (1-{5-[6-(4-cyanopyridin-2-ylamino)pyridin-2-yl]thiazol-2-yl}piperidin-4-yl)acetic acid,
(314) {4-((N-methyl-N-{5-[6-(4-trifluoromethylpyridin-2-ylamino)pyridin-2-yl]thiazol-2-yl}amino)methyl]phenyl}acetic acid, (315) 2-(1-{5-[6-(4-methylpyridin-2-ylamino)pyridin-2-yl]thiazol-2-yl}piperidin-4-yl)propionic acid,
(316) (1-{5-[6-(4-methylpyridin-2-ylamino)pyridin-2-yl]thiazol-2-yl}piperidin-4-yl)acetic acid,
(317) 4-(1-methyl-1-(N-methyl-N-{5-[6-(4-trifluoromethylpyridin-2-ylamino)pyridin-2-yl]thiazol-2-yl}amino)ethyl]benzoic acid,
(318) 3-methyl-6-(N-methyl-N-{5-[6-(4-trifluoromethylpyridin-2-ylamino)pyridin-2-yl]thiazol-2-yl}amino)hex-2-enoic acid,
(319) 3-methyl-6-(N-methyl-N-{5-[6-(4-methylpyridin-2-ylamino)pyridin-2-yl]thiazol-2-yl}amino)hex-2-enoic acid,
(320) (E)-6-(N-methyl-N-{5-[6-(4-trifluoromethylpyridin-2-ylamino)pyridin-2-yl]thiazol-2-yl}amino)hex-2-enoic acid,
(321) N-(2-hydroxyethyl)-(S)-1-{5-[6-(4-methylpyridin-2-ylamino)pyridin-2-yl]thiazol-2-yl}pyrrolidine-2-carboxamide,
(322) 2-(N-isopropyl-N-{5-[6-(4-methylpyridin-2-ylamino)pyridin-2-yl]thiazol-2-yl}amino)acetamide,
(323) 3-methyl-2-(N-methyl-N-{5-[6-(4-methylpyridin-2-ylamino)pyridin-2-yl]thiazol-2-yl}amino)butylamide,
(324) 2-(1-{5-[6-(4-methylpyridin-2-ylamino)pyridin-2-yl]thiazol-2-yl}piperidin-4-yl)ethanol,
(325) 5-(N-isopropyl-N-{5-[6-(4-methylpyridin-2-ylamino)pyridin-2-yl]thiazol-2-yl}amino)pentan-1-ol,
(326) (1-{5-[6-(pyrazin-2-ylamino)pyridin-2-yl]thiazol-2-yl}piperidin-4-yl)acetic acid,
(327) [1-(5-{6-[4-(2-hydroxyethyl)pyridin-2-ylamino]pyridin-2-yl}thiazol-2-yl)piperidin-4-yl]acetic acid,
(328) fluoro-(1-{5-[6-(4-methylpyridin-2-ylamino)pyridin-2-yl]thiazol-2-yl}piperidin-4-yl)acetic acid,
(329) 1-{5-[6-(4-methylpyridin-2-ylamino)pyridin-2-yl]thiazol-2-ylmethyl}piperidine-4-carboxamide,
(330) (1-{5-[6-(4-ethylpyridin-2-ylamino)pyridin-2-yl]thiazol-2-yl}piperidin-4-yl)acetic acid,
(331) N-isopropyl-N-{5-[6-(4-methylpyridin-2-ylamino)pyridin-2-yl]thiazol-2-yl}amine,
(332) N-{5-[6-(4-methylpyridin-2-ylamino)pyridin-2-yl]thiazol-2-yl}-N-(2-morpholin-4-ylethyl)amine,
(333) 2-(N-methyl-N-{5-[6-(4-methylpyridin-2-ylamino)pyridin-2-yl]thiazol-2-ylmethyl}amino)acetamide,
(334) 2-(1-{5-[6-(4-methylpyridin-2-ylamino)pyridin-2-yl]thiazol-2-yl}piperidin-4-yl)butyric acid,
(335) trans-4-[(N-methyl-N-{5-[6-(pyridin-2-ylamino)pyridin-2-yl]thiazol-2-yl}amino)methyl]cyclohexanecarboxylic acid,
(336) [1-(5-{6-[4-(2,2,2-trifluoroethoxy)pyridin-2-ylamino]pyridin-2-yl}thiazol-2-yl)piperidin-4-yl]acetic acid,
(337) 2-methyl-1-(N-methyl-N-{5-[6-(4-methylpyridin-2-ylamino)pyridin-2-yl]thiazol-2-yl}amino)propan-2-ol,
(338) 3-(1-{5-[6-(4-methylpyridin-2-ylamino)pyridin-2-yl]thiazol-2-yl}piperidin-3-yl)propionic acid,
(339) N-(2-hydroxyethyl)-4-(N'-methyl-N'-{5-[6-(4-methylpyridin-2-ylamino)pyridin-2-yl]thiazol-2-yl}amino)piperidine-1-carboxamide,
(340) 2-methyl-2-(1-{5-[6-(pyrazin-2-ylamino)pyridin-2-yl]thiazol-2-yl}piperidin-4-yl)propionic acid,
(341) 4-[(N-acetyl-N-{5-[6-(4-methylpyridin-2-ylamino)pyridin-2-yl]thiazol-2-ylmethyl}amino)methyl]benzoic acid,
(342) (1-{5-[6-(4-tert-butylpyridin-2-ylamino)pyridin-2-yl]thiazol-2-yl}piperidin-4-yl)acetic acid,
(343) (1-{5-[6-(4-isopropylpyridin-2-ylamino)pyridin-2-yl]thiazol-2-yl}piperidin-4-yl)acetic acid,
(344) 2-ylamino)pyridin-2-yl]thiazol-2-yl}-6-azaspiro[2.5]octane-1-carboxylic acid,
(345) 2-[1-(5-{6-[4-(2-hydroxyethyl)pyridin-2-ylamino]pyridin-2-yl}thiazol-2-yl)piperidin-4-yl]-2-methylpropionic acid,
(346) 2-methyl-2-(1-{5-[6-(pyridin-2-ylamino)pyridin-2-yl]thiazol-2-yl}piperidin-4-yl)propionic acid,
(347) fluoro-(1-{5-[6-(pyrazin-2-ylamino)pyridin-2-yl]thiazol-2-yl}piperidin-4-yl)acetic acid,
(348) fluoro-(1-{5-[6-(pyridin-2-ylamino)pyridin-2-yl]thiazol-2-yl}piperidin-4-yl)acetic acid,
(349) [1-(5-{6-[4-(1-hydroxy-1-methylethyl)pyridin-2-ylamino]pyridin-2-yl}thiazol-2-yl)piperidin-4-yl]acetic acid,
(350) 2-methyl-2-(1-{5-[6-(4-methylpyridin-2-ylamino)pyridin-2-yl]thiazol-2-yl}piperidin-4-yl)propionic acid,
(351) 5-(1-{5-[6-(4-methylpyridin-2-ylamino)pyridin-2-yl]thiazol-2-yl}piperidin-3-yl)pentanoic acid, and
(352) 2-methyl-2-(N-methyl-N-{5-[6-(4-methylpyridin-2-ylamino)pyridin-2-ylmethyl}amino)propionamide.

10. The aminopyridine compound or a pharmaceutically acceptable salt thereof according to the above-described 9, wherein the aminopyridine compound is selected from the following compound group:

(01) (S)-1-{5-[6-(4-methylpyridin-2-ylamino)pyridin-2-yl]thiazol-2-yl}pyrrolidine-2-carboxamide,
(02) cis-4-(N-methyl-N-{5-[6-(4-methylpyridin-2-ylamino)pyridin-2-yl]thiazol-2-yl}amino)cyclohexanecarboxylic acid,
(03) (1-{5-[6-(pyridin-2-ylamino)pyridin-2-yl]thiazol-2-yl}piperidin-4-yl)acetic acid and
(04) (4-methyl-1-{5-[6-(4-methylpyridin-2-ylamino)pyridin-2-yl]thiazol-2-yl}piperidin-4-yl)acetic acid.

11. The aminopyridine compound or a pharmaceutically acceptable salt thereof according to the above-described 10, wherein the aminopyridine compound is (S)-1-{5-[6-(4-methylpyridin-2-ylamino)pyridin-2-yl]thiazol-2-yl}pyrrolidine-2-carboxamide.

12. The aminopyridine compound or a pharmaceutically acceptable salt thereof according to the above-described 10, wherein the aminopyridine compound is (1-{5-[6-(pyridin-2-ylamino)pyridin-2-yl)thiazol-2-yl}piperidin-4-yl)acetic acid.

13. The aminopyridine compound or a pharmaceutically acceptable salt thereof according to the above-described 10 wherein the aminopyridine compound is (4-methyl-1-{5-[6-(4-methylpyridin-2-ylamino)pyridin-2-yl]thiazol-2-yl}piperidin-4-yl)acetic acid.

14. The aminopyridine compound or a pharmaceutically acceptable salt thereof according to the above-described 1 wherein the aminopyridine compound is cis-4-(N-methyl-N-{5-[6-(4-methylpyridin-2-ylamino)pyridin-2-yl]thiazol-2-yl}amino)cyclohexanecarboxylic acid.

15. The aminopyridine compound or a pharmaceutically acceptable salt thereof according to the above-described 1, wherein Z is a carbon atom.

16. The aminopyridine compound or a pharmaceutically acceptable salt thereof according to the above-described 15, wherein the aminopyridine compound according to the above-described 1 is an aminopyridine compound represented by the following general formula (Ib-1):

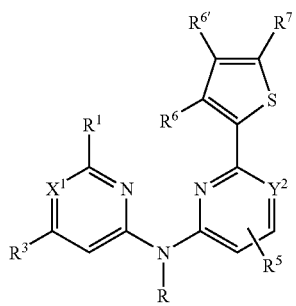
(Ib-1)

wherein $X^1$ is (1) —CH= or (2) a nitrogen atom;

$Y^2$ is (1) —CH= or (2) a nitrogen atom;

R is (1) a hydrogen atom, (2) a $C_{1-6}$ alkyl group or (3) an acyl group;

$R^1$ is (1) a hydrogen atom or (2) a halogen atom;

$R^3$ is (1) a hydrogen atom, (2) a halogen atom, (3) —N($R^{31}$)($R^{32}$)

wherein $R^{31}$ and $R^{32}$ are a hydrogen atom or a $C_{1-6}$ alkyl group, (4) a $C_{1-6}$ alkoxy group, wherein the $C_{1-6}$ alkyl group in the $C_{1-6}$ alkoxy group may be substituted with a substituent selected from the following group Aa-3:

[Group Aa-3]

a. a hydroxyl group and b. —N($R^{31}$)($R^{32}$), wherein $R^{31}$ and $R^{32}$ are the same as above, (5) an acyl group, (6) a saturated heterocyclic group or an aromatic heterocyclic group, wherein the heterocyclic group may be substituted with a $C_{1-6}$ alkyl group, and the saturated heterocyclic group may partially have a double bond, (7) a $C_{1-6}$ alkyl group, wherein the $C_{1-6}$ alkyl group may be substituted with a substituent selected from the following group Ab-3:

[group Ab-3]

a. a hydroxyl group, b. —COOR$^{33}$, wherein $R^{33}$ is a hydrogen atom or a $C_{1-6}$ alkyl group, and c. —CO—N($R^{31}$)($R^{32}$), wherein $R^{31}$ and $R^{32}$ are the same as above, or (8) —COOR$^{33}$, wherein $R^{33}$ is the same as the above;

$R^5$ is (1) a hydrogen atom, (2) a $C_{1-6}$ alkyl group or (3) —COOR$^{51}$, wherein $R^{51}$ is a hydrogen atom or a $C_{1-6}$ alkyl group;

$R^6$ and $R^{6'}$ may be the same or different and each represent (1) a hydrogen atom, (2) a $C_{1-6}$ alkyl group or (3) an acyl group; and $R^7$ represnt the same as in the above-described 1.

17. The aminopyridine compound or a pharmaceutically acceptable salt thereof according to the above-described 16, wherein the aminopyridine compound is an aminopyridine compound represented by the following general formula (Ib-2):

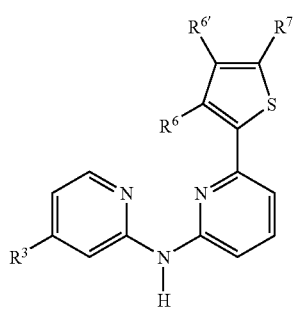
(Ib-2)

wherein $R^3$ is (1) a halogen atom, (2) —N($R^{31}$)($R^{32}$)

wherein $R^{31}$ and $R^{32}$ are hydrogen atom or a $C_{1-6}$ alkyl groups, (3) a $C_{1-6}$ alkoxy group, wherein the $C_{1-6}$ alkyl group in the $C_{1-6}$ alkoxy group may be substituted with a substituent selected from the following group Aa-3:

[Group Aa-4]

a. a hydroxyl group and b. —N($R^{31}$)($R^{32}$), wherein $R^{31}$ and $R^{32}$ are the same as above, (4) an acyl group, (5) a saturated heterocyclic group, wherein the heterocyclic group partially have a double bond and may be substituted with a $C_{1-6}$ alkyl group, (6) a $C_{1-6}$ alkyl group which may be substituted with a substituent selected from the following group Ab-4:

[Group Ab-4]

a. a hydroxyl group, b. —COOR$^{33}$, wherein $R^{33}$ is a hydrogen atom or a $C_{1-6}$ alkyl group, and c. —CO—N($R^{31}$)($R^{32}$)

wherein $R^{31}$ and $R^{32}$ are the same as above, or (7) —COOR$^{33}$, wherein R$^{33}$ is the same as the above;

R$^5$ is (1) a hydrogen atom, (2) a C$_{1-6}$ alkyl group or (3) —COOR$^{51}$, wherein R$^{51}$ is a hydrogen atom or a C$_{1-6}$ alkyl group;

R$^6$ and R$^{6'}$ may be the same or different and each represent (1) a hydrogen atom, (2) a C$_{1-6}$ alkyl group which may be substituted with a hydroxyl group or a C$_{1-6}$ alkyl group which may be substituted with a C$_{1-6}$ alkoxy group or (3) an acyl group;

R$^7$ is a hydrogen atom, a halogen atom, a nitro group, a cyano group, or the following R$^a$, R$^b$, R$^c$, R$^d$, R$^e$, R$^f$, R$^g$ or R$^h$;

R$^a$ is —C$_p$H$_{2(p-1)}$(R$^{a1}$)(R$^{a2}$)—O—R$^{a3}$, wherein (1) p is an integer from 1 to 6, (2) R$^{a1}$ is a hydrogen atom, (3) R$^{a2}$ is a C$_{1-6}$ alkyl group, wherein the C$_{1-6}$ alkyl group may be substituted with a hydroxyl group, a halogen atom, a carboxy group, and (4) R$^{a3}$ is a hydrogen atom or an acyl group;

R$^b$ is —C$_p$H$_{2(p-1)}$(R$^{b1}$)(R$^{b2}$)—N—(R$^{b3}$)(R$^{b4}$)

wherein (1) p is an integer from 1 to 6, (2) R$^{b1}$ is a hydrogen atom, (3) R$^{b2}$ is a C$_{1-6}$ alkyl group, (4) R$^{b3}$ is a hydrogen atom or a C$_{1-6}$ alkyl group, and (5) R$^{b4}$ is a. a hydrogen atom or b. —CO R$^{b42}$, wherein R$^{b42}$ is a C$_{1-6}$ alkyl group;

R$^c$ is —C(=N—R$^{c1}$)—R$^{c2}$, wherein (1) R$^{c1}$ is a. a hydroxyl group, b. a C$_{1-6}$ alkoxy group, wherein C$_{1-6}$ alkyl group in the C$_{1-6}$ alkoxy group may be substituted with a hydroxyl group or a C$_{1-6}$ alkoxy group, or c. an acyloxy group, and (2) R$^{c2}$ is a C$_{1-6}$ alkyl group or an amino group;

R$^d$ is —C(=O)—R$^{d1}$, wherein R$^{d1}$ is (1) a hydrogen atom, (2) a C$_{1-6}$ alkyl group, wherein the C$_{1-6}$ alkyl group may be substituted with a hydroxyl group, (3) a hydroxyl group, (4) a C$_{1-6}$ alkoxy group, (5) —N(R$^{d11}$)(R$^{d12}$)

wherein R$^{d11}$ and R$^{d12}$ may be the same or different and are a hydrogen atom or a C$_{1-6}$ alkyl group, wherein the C$_{1-6}$ alkyl group may be substituted with an amino group, a carboxy group or a hydroxyl group, or R$^{d11}$ and R$^{d12}$ together with the adjacent nitrogen atom may form a 5- or 6-membered saturated heterocyclic ring, or (6) a C$_{1-6}$ alkoxy group;

R$^e$ is a 5- or 6-membered aromatic heterocyclic group having 1 to 4 hetero atoms, wherein the aromatic heterocyclic group may be substituted with a C$_{1-6}$ alkyl group or an oxo group;

R$^f$ is a C$_{1-6}$ alkyl group or a C$_{2-6}$ alkenyl group, wherein these C$_{1-6}$ alkyl group and C$_{2-6}$ alkenyl group may be substituted with a substituent selected from the following group Fa-2:

[Group Fa-2]

a. —COOH, b. —N(R$^{f21}$)(R$^{f22}$)

wherein R$^{f21}$ and R$^{f22}$ may be the same or different and are a hydrogen atom, an acyl group or a C$_{1-6}$ alkyl group, wherein the C$_{1-6}$ alkyl group may be substituted with a carboxy group, and c. a halogen atom.

R$^g$ is a substituent having Ring B" represented by the following formula (IIb);

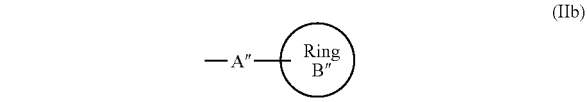

(IIb)

wherein A" is a linker selected from the following group Ga-2:

[Group Ga-2]

—(CH$_2$)$_k$—,
—(CH$_2$)$_k$—NR$^{g1}$(CO)—,
—(CH$_2$)$_k$—NR$^{g1}$—(CH$_2$)$_j$—,
—(CH$_2$)$_k$—O—(CO)—,
—(CH$_2$)$_k$—O—,
—(CO)—NR$^{g1}$—(CH$_2$)$_j$—,
—(CO)— and
—(CO)—NR$^{g1}$—, wherein k and j may be the same or different and represnt an integer from 1 to 4, R$^{g1}$ is a hydrogen atom, an acyl group, wherein the acyl group may be substituted with a hydroxyl group or a carboxy group, or a C$_{1-6}$ alkyl group, wherein the alkyl group may be substituted with —CON(R$^{g41}$)(R$^{g42}$), Ring B" is a ring selected from the following group Ha-2:

[Group Ha-2]
an aromatic hydrocarbon group,
a $C_{3-8}$ cycloalkyl group and
a 5- to 7-membered saturated heterocyclic group containing at least one nitrogen atoms, wherein the saturated heterocyclic ring may form a condensed ring with a phenyl group, and the Ring B" may be substituted with a substituent selected from follows group Ia-2:

[Group Ia-2]

a. —OR (wherein $R^{g2}$ is
a hydrogen atom,
a $C_{1-6}$ alkyl group or
an aralkyl group, and b. —COOR$^{g3}$, wherein $R^{g3}$ is
a hydrogen atom or
a $C_{1-6}$ alkyl group, wherein the alkyl group may be substituted with a hydroxyl group; and $R^h$ is —N($R^{h1}$) ($R^{h2}$)

wherein $R^{h1}$ is a hydrogen atom, and $R^{h2}$ is an acyl group, wherein the acyl group may be substituted with a hydroxyl group, or a $C_{1-6}$ alkoxycarbonyl group.

18. The aminopyridine compound or a pharmaceutically acceptable salt thereof according to the above-described 1, wherein the aminopyridine compound is selected from the following compound group:
(01) 1-{5-[6-(4-methylpyridin-2-ylamino)pyridin-2-yl]thiophen-2-yl}ethanone,
(02) 5-[6-(4-methylpyridin-2-ylamino)pyridin-2-yl]thiophene-2-carbaldehyde,
(03) 1-{5-[6-(4-methylpyridin-2-ylamino)pyridin-2-yl]thiophen-2-yl}ethanol,
(04) acetic acid1-{5-[6-(4-methylpyridin-2-ylamino)pyridin-2-yl]thiophen-2-yl}ethyl ester,
(05) N-{5-[6-(4-methylpyridin-2-ylamino)pyridin-2-yl]thiophen-2-yl}acetamide,
(06) N-methyl-5-[6-(4-methylpyridin-2-ylamino)pyridin-2-yl]thiophene-2-carboxamide,
(07) {5-[6-(4-methylpyridin-2-ylamino)pyridin-2-yl]thiophen-2-yl}methanol,
(08) 1-{5-[6-(4-methylpyridin-2-ylamino)pyridin-2-yl]thiophen-2-yl}ethanone oxime,
(09) 1-{5-[6-(4-methoxypyridin-2-ylamino)pyridin-2-yl]thiophen-2-yl}ethanone,
(10) 5-[6-(4-methylpyridin-2-ylamino)pyridin-2-yl]thiophene-2-carboxamide,
(11) 1-{5-[6-(6-isopropoxypyrimidin-4-ylamino)pyridin-2-yl]thiophen-2-yl}ethanone,
(12) N-{5-[6-(4-methylpyridin-2-ylamino)pyridin-2-yl]thiophen-2-yl}acetamide,
(13) 1-{5-[6-(4-methylpyridin-2-ylamino)pyridin-2-yl]thiophen-2-yl}ethanone 0-(2-hydroxyethyl)oxime,
(14) N-(2-aminoethyl)-5-[6-(4-methylpyridin-2-ylamino)pyridin-2-yl]thiophene-2-carboxamide,
(15) 1-{5-[6-(4-methylpyridin-2-ylamino)pyridin-2-yl]thiophen-2-yl}propan-1-one oxime,
(16) {2-[6-(5-acetylthiophen-2-yl)pyridin-2-ylamino]pyridin-4-yl}acetic acid ethyl ester,
(17) 2-[6-(5-acetylthiophen-2-yl)pyridin-2-ylamino]isonicotinic acid methyl ester,
(18) 1-(5-{6-[4-(2-hydroxyethyl)pyridin-2-ylamino]pyridin-2-yl}thiophen-2-yl)ethanol,
(19) N-hydroxy-5-[6-(4-methylpyridin-2-ylamino)pyridin-2-yl]thiophene-2-carboxyamidine,
(20) 1-(5-{6-[4-(2-hydroxyethoxy)pyridin-2-ylamino]pyridin-2-yl}thiophen-2-yl)ethanone,
(21) 1-{5-[6-(4-chloropyridin-2-ylamino)pyridin-2-yl]thiophen-2-yl}ethanone,
(22) 1-{5-[6-(4-chloropyridin-2-ylamino)pyridin-2-yl]thiophen-2-yl}ethanone oxime,
(23) {5-[6-(4-methylpyridin-2-ylamino)pyridin-2-yl]thiophen-2-yl}piperazin-1-ylmethanone,
(24) 1-(5-{6-[4-(4,4-dimethyl-4,5-dihydrooxazol-2-yl)pyridin-2-ylamino]pyridin-2-yl}thiophen-2-yl)ethanone,
(25) 2,2-difluoro-3-hydroxy-3-{5-[6-(4-methylpyridin-2-ylamino)pyridin-2-yl]thiophen-2-yl}propionic acid,
(26) 4-[({5-[6-(4-methylpyridin-2-ylamino)pyridin-2-yl]thiophen-2-ylmethyl}amino)methyl]benzoic acid,
(27) 4-[(N-acetyl-N-{5-[6-(4-methylpyridin-2-ylamino)pyridin-2-yl]thiophen-2-ylmethyl}amino)methyl]benzoic acid,
(28) trans-4-[(N-acetyl-N-{5-[6-(4-methylpyridin-2-ylamino)pyridin-2-yl]thiophen-2-ylmethyl}amino)methyl]cyclohexanecarboxylic acid,
(29) 3-(N-acetyl-N-{5-[6-(4-methylpyridin-2-ylamino)pyridin-2-yl]thiophen-2-ylmethyl}amino)propionic acid,
(30) 4-[(N-isobutyryl-N-{5-[6-(4-methylpyridin-2-ylamino)pyridin-2-yl]thiophen-2-ylmethyl}amino)methyl]benzoic acid, and
(31) 4-[(N-(2-hydroxyacetyl)-N-{5-[6-(4-methylpyridin-2-ylamino)pyridin-2-yl]thiophen-2-ylmethyl}amino)methyl]benzoic acid.

19. A pharmaceutical composition comprising an aminopyridine compound or a pharmaceutically acceptable salt thereof according to the above-described 1 as an active ingredient.

20. An Syk inhibitor comprising an aminopyridine compound or a pharmaceutically acceptable salt thereof according to the above-described 1 as an active ingredient.

21. A therapeutic and/or prophylactic agent for allergic diseases comprising an aminopyridine compound or a pharmaceutically acceptable salt thereof according to the above-described 1 as an active ingredient.

22. A therapeutic and/or prophylactic agent for bronchial asthma comprising an aminopyridine compound or a pharmaceutically acceptable salt thereof according to the above-described 1 as an active ingredient.

23. A therapeutic and/or prophylactic agent for allergic rhinitis comprising an aminopyridine compound or a pharmaceutically acceptable salt thereof according to the above-described 1 as an active ingredient.

24. A therapeutic and/or prophylactic agent for allergic dermatitis comprising an aminopyridine compound or a pharmaceutically acceptable salt thereof according to the above-described 1 as an active ingredient.

25. A therapeutic and/or prophylactic agent for allergic conjunctivitis comprising an aminopyridine compound or a pharmaceutically acceptable salt thereof according to the above-described 1 as an active ingredient.

26. A therapeutic and/or prophylactic agent for autoimmune diseases comprising an aminopyridine compound or a pharmaceutically acceptable salt thereof according to the above-described 1 as an active ingredient.

27. A therapeutic agent for rheumatoid arthritis comprising an aminopyridine compound or a pharmaceutically acceptable salt thereof according to the above-described 1 as an active ingredient.

28. A therapeutic agent for systemic lupus erythematosus comprising contains an aminopyridine compound or a pharmaceutically acceptable salt thereof according to the above-described 1 as an active ingredient.

29. A therapeutic agent for multiple sclerosis comprising an aminopyridine compound or a pharmaceutically acceptable salt thereof according to the above-described 1 as an active ingredient.

30. A therapeutic agent for malignant tumor comprising an aminopyridine compound or a pharmaceutically acceptable salt thereof according to the above-described 1 as an active ingredient.

31. A therapeutic agent for B-lymphoma and B-cell leukemia comprising an aminopyridine compound or a pharmaceutically acceptable salt thereof according to the above-described 1 as an active ingredient.

32. A therapeutic and/or prophylactic agent for allergic diseases comprising an Syk inhibitor according to the above-described 20 in combination with another anti-allergic agent.

ADVANTAGES OF THE INVENTION

The present invention relates to a novel aminopyridine compound represented by the above general formula (I) or a pharmaceutically acceptable salt thereof and a drug containing the same as an active ingredient.

These compounds of the present invention are useful as active ingredients of pharmaceutical preparation. Since these compounds of the present invention have excellent inhibitory effect against and selectivity for Syk, they are useful as a therapeutic or preventive agent for the diseases in which allergia or inflammatory reaction in which Syk is involved is a main etiologic cause (asthma, nasal catarrh, atopic dermatitis, contact dermatitis, urticarial rash, food allergy, conjunctivitis, spring catarrh, etc.), diseases in which ADCC is involved (autoimmune hemolytic anemia, myasthenia gravis, etc.), thrombus in which platelet aggregation is involved and so on.

BEST MODE FOR CARRYING OUT THE INVENTION

Definition of the terms used in this specification are as follows. The meaning of a term not particularly defined follows a meaning usually used in this field.

A "halogen atom" is a fluorine atom, a chlorine atom, a bromine atom or an iodine atom, and preferably it is a fluorine atom, a chlorine atom or a bromine atom.

A "$C_{1-6}$ alkyl group" represents a linear or branched alkyl group having 1 to 6 carbon atoms and specifically includes a methyl group, an ethyl group, a propyl group, an isopropyl group, a butyl group, an isobutyl group, a sec-butyl group, a tert-butyl group, a pentyl group, an isopentyl group, a tert-pentyl group, a hexyl group, etc. Preferably it is a linear or branched alkyl group having 1 to 4 carbon atoms and specifically it is a methyl group, an ethyl group, a propyl group, an isopropyl group, a butyl group, an isobutyl group, a sec-butyl group, a tert-butyl group, etc.

An "alkylene group" represents an alkylene group which may be branched having 2 to 6 carbon atoms and specifically includes a methylene group, a propylene group, an isopropylene group, a butylene group, a 2-methylpropylene group, etc.

A "$C_{1-6}$ alkoxy group" is an alkyl-oxy group in which the alkyl part thereof is a "$C_{1-6}$ alkyl group" as defined above and specifically includes a methoxy group, an ethoxy group, a propoxy group, an isopropyloxy group, a butoxy group, an isobutyl oxy group, a tert-butyl oxy group, a pentyl oxy group, a hexyloxy group, etc. Preferably it is a "$C_{1-4}$ alkoxy group".

A "$C_{1-6}$ alkoxycarbonyl group" is an alkoxy-carbonyl group in which the alkoxy part thereof is a "$C_{1-6}$ alkoxy group" as defined above and specifically includes a methoxycarbonyl group, an ethoxycarbonyl group, a propoxycarbonyl group, an isopropoxycarbonyl group, a butoxycarbonyl group, an isobutoxycarbonyl group, a s-butoxycarbonyl group, a t-butoxycarbonyl group, a pentyloxycarbonyl group, an iso pentyloxycarbonyl group, a 2-methylbutoxycarbonyl group, a neopentyloxycarbonyl group, a 1-ethylpropoxycarbonyl group, a hexyloxycarbonyl group, a 4-methylpentyloxycarbonyl group, a 3-methylpentyloxycarbonyl group, a 2-methylpentyloxycarbonyl group, a 1-methylpentyloxycarbonyl group, a 3,3-dimethylbutoxycarbonyl group, a 2,2-dimethylbutoxycarbonyl group, a 1,1-dimethylbutoxycarbonyl group, a 1,2-dimethylbutoxycarbonyl group, a 1,3-dimethylbutoxycarbonyl group, a 2,3-dimethylbutoxycarbonyl group or a 2ethylbutoxycarbonyl group, etc. Preferably it is a ($C_{1-4}$ alkoxy)carbonyl group, and more preferably it is a methoxycarbonyl group or an ethoxycarbonyl group.

A "$C_{1-6}$ alkylamino group" represents a group in which one "$C_{1-6}$ alkyl group" as above is linked with an amino group and, for example, includes a methylamino group, an ethylamino group, a propylamino group, an isopropylamino group, a butylamino group, an isobutylamino group, a s-butylamino group, a t-butylamino group, a pentylamino group, an isopentylamino group, a 2-methylbutylamino group, a neopentylamino group, a 1-ethylpropylamino group, a hexylamino group, an isohexylamino group, a 4-methylpentylamino group, a 3-methylpentylamino group, a 2-methylpentylamino group, a 1-methylpentylamino group, a 3,3-dimethylbutylamino group, a 2,2-dimethylbutylamino group, a 1,1-dimethylbutylamino group, a 1,2-dimethylbutylamino group, a 1,3-dimethylbutylamino group, a 2,3-dimethylbutylamino group or a 2-ethylbutylamino group, etc. Preferably it is $C_{1-4}$ alkylamino groups such as a methylamino group, an ethylamino group and a propylamino group.

A "di-$C_{1-6}$ alkylamino group" represents a group in which two "$C_{1-6}$ alkyl groups" as above are linked with an amino group and, for example, includes a di-$C_{1-6}$ alkylamino group such as a dimethylamino group, a diethylamino group, an N-ethyl-N-methylamino group, a dipropylamino group, a dibutylamino group, a dipentylamino group or a dihexylamino group and preferably it is a di-$C_{1-4}$ alkylamino group.

A "$C_{1-6}$ alkylsulfonyl group" represents a group in which a "$C_{1-6}$ alkyl group" as above is linked with a sulfonyl group and, for example, includes a methylsulfonyl group, an ethylsulfonyl group, a propylsulfonyl group, an isopropylsulfonyl group, a butylsulfonyl group, an isobutylsulfonyl group, a s-butylsulfonyl group, a t-butylsulfonyl group, a pentylsulfonyl group, an isopentylsulfonyl group, a 2-methylbutylsulfonyl group, a neopentylsulfonyl group, a 1-ethylpropylsulfonyl group, a hexylsulfonyl group, an isohexylsulfonyl group, a 4-methylpentylsulfonyl group, a 3-methylpentylsulfonyl group, a 2-methylpentylsulfonyl group, a 1-methylpentylsulfonyl group, a 3,3-dimethylbutylsulfonyl group, a 2,2-dimethylbutylsulfonyl group, a 1,1-dimethylbutylsulfonyl group, a 1,2-dimethylbutylsulfonyl group, a 1,3-dimethylbutylsulfonyl group, a 2,3-dimethylbutylsulfonyl group or 2-ethylbutylsulfonyl group, etc. Preferably it is a $C_{1-4}$ alkylsulfonyl group such as a methylsulfonyl group.

A "carbamoyl group" represents a carbamoyl group, a $C_{1-6}$ alkylcarbamoyl group or a di-$C_{1-6}$ alkylcarbamoyl group.

A "$C_{1-6}$ alkylcarbamoyl group represents a group in which one "$C_{1-6}$ alkyl group" as above is linked with a carbamoyl group and, for example, includes an alkylcarbamoyl group such as a methylcarbamoyl group, an ethylcarbamoyl group, a propylcarbamoyl group, an isopropylcarbamoyl group, a butylcarbamoyl group, an isobutylcarbamoyl group, a s-butylcarbamoyl group, a t-butylcarbamoyl group, a pentylcarbamoyl group, an isopentylcarbamoyl group, a 2-methylbutylcarbamoyl group, a neopentylcarbamoyl group, a 1-ethylpropylcarbamoyl group or a hexylcarbamoyl group, and preferably it is a $C_{1-4}$ alkylcarbamoyl group.

A "di-$C_{1-6}$ alkylcarbamoyl group represents a group in which two "$C_{1-6}$ alkyl groups" as above are linked with a carbamoyl group and, for example, includes a dialkylcarbamoyl group such as a dimethylcarbamoyl group, a diethylcarbamoyl group, an N-ethyl-N-methylcarbamoyl group, a dipropylcarbamoyl group, a dibutylcarbamoyl group, a dipentylcarbamoyl group or a dihexylcarbamoyl group, and preferably it is a di-$C_{1-4}$ alkylcarbamoyl group.

A "cycloaliphatic hydrocarbon" represents a saturated or unsaturated $C_{3-8}$ cycloaliphatic hydrocarbon group, for example, a cycloalkyl group, a cycloalkenyl group, a cycloalkadienyl group, etc.

A "$C_{3-8}$ saturated hydrocarbons ring" and a "$C_{3-8}$ cycloalkyl group" have identical meaning and represent a saturated cycloalkyl group having 3 to 8 carbon atoms and, for example, includes a cyclopropyl group, a cyclobutyl group, a cyclopentyl group, a cyclohexyl group, a cycloheptyl group, a cyclooctyl group, a bicyclo[2.2.1]heptyl group, a bicyclo[2.2.2]octyl group, a bicyclo[3.2.1]octyl group, etc. Preferably it is a 5-7 carbon atoms saturated cycloalkyl group, and specifically it is a cyclopentyl group, a cyclohexyl group and a cycloheptyl group.

The above-mentioned "saturated hydrocarbons ring" may contain a double bond in a part thereof, and "cycloalkenyl", etc. is also included by the "saturated hydrocarbons ring".

A "$C_{3-8}$ cycloalkenyl group" is a cycloalkenyl group having 3 to 8 carbon atoms and a cycloalkenyl group containing at least one, preferably 1 or 2 double bonds. Specifically included are a cyclopropenyl group, a cyclobutenyl group, a cyclopentenyl group, a cyclopentadienyl group, a cyclohexenyl group, a 2,4-cyclohexadien-1-yl group, a 2,5-cyclohexadien-1-yl group, a cycloheptenyl group and a cyclooctenyl group, etc. Preferably it is a 5-7 carbon atoms cycloalkenyl group.

A "cycloalkyl $C_{1-6}$ alkyl group" represents a $C_{1-6}$ alkyl group substituted with a "$C_{3-8}$ cycloalkyl group" as above and, preferable examples include a cycloalkyl group having 4 to 13 carbon atoms, for example, a cyclopropylmethyl group, a cyclopropylethyl group, a cyclopentylmethyl group, a cyclopentylethyl group, a cyclohexylmethyl group, a cyclohexylethyl group, etc.

An "aryl group" represents an aromatic hydrocarbocyclic group or an aromatic heterocycle group, but represents an aromatic hydrocarbocyclic group when it is referred to as merely "aryl group". An aromatic hydrocarbon ring can be merely referred to as aromatic carbocyclic ring. An "aromatic hydrocarbocyclic group" represents an aromatic hydrocarbocyclic group having 6 to 14 carbon atoms, and specifically it includes a phenyl group, a naphthyl group, a biphenyl group, an anthryl group, an indenyl group, an azulenyl group, a fluorenyl group, a phenanthryl group, etc. Preferably it is phenyl group, a naphthyl group, a biphenyl group.

An "aromatic aliphatic hydrocarbon group" and an "aralkyl group" have identical meaning and represnt an aliphatic hydrocarbon group having 7 to 14 carbon atoms, and specifically represnt an aralkyl group, an arylalkenyl group, an arylalkynyl group, etc.

An "aralkyl group" represents a $C_{1-6}$ alkyl group substituted with an aryl group as mentioned above, and preferable examples include a $C_{7-10}$ phenylalkyl group such as a benzyl group, a phenethyl group, a 1-phenylethyl group, a 1-phenylpropyl group, a 2-phenylpropyl group, a 3-phenylpropyl group, a phenylbutyl group; a biphenylmethyl group; a $C_{11-13}$ naphthylalkyl group such as an α-naphthylmethyl group, an α-naphthylethyl group, a β-naphthylmethyl group, a β-naphthylethyl group. It may be a $C_{8-10}$ phenylalkenyl group such as a styryl group; a naphthylalkenyl group such as a 2-(2-naphthylvinyl) group.

An "aralkoxy group" represents an aralkoxy group in which the aralkyl part thereof is an aralkyl group as mentioned above and includes, for example, a $C_{7-10}$ phenylalkoxy group such as a benzyloxy group, a phenethyloxy group, a 1-phenylethyloxy group, a 1-phenylpropyloxy group, a 2-phenylpropyloxy group, a 3-phenylpropyloxy group, a phenylbutyloxy group; a biphenylmethyloxy group; a $C_{11-13}$ naphthylalkoxy group such as an α-naphthylmethyloxy group, an α-naphthylethyloxy group, a β-naphthylmethyloxy group, a β-naphthylethyloxy group.

An "aralkoxycarbonylamino group" represents an amino group substituted with an aralkoxycarbonyl group, and the aralkoxy part of the aralkoxycarbonyl group is an aralkoxy group as mentioned above. For example, included are a benzyloxycarbonylamino group, a phenethyloxycarbonylamino group, etc.

A "$C_{2-6}$ alkenyl group" represents an alkenyl group having 2 to 6 carbon atoms, and includes, for example, an ethenyl group, a 1-propenyl group, a 2-propenyl group, a 1-butenyl group, a 2-butenyl group, a 3-butenyl group, a 2-methyl-1-propenyl group, a 1-pentenyl group, a 2-pentenyl group, a 3-pentenyl group, a 4-pentenyl group, a 3-methyl-2-butenyl group, a 1-hexenyl group, a 3-hexenyl group, a 2,4-hexadienyl group, and a 5-hexenyl group. Among these, a $C_{2-6}$ alkenyl, for example, a vinyl group or a propenyl group is particularly preferable.

An "acyl group" represents an aliphatic acyl group, an aromatic acyl group or a heterocyclic acyl group in which a saturated or unsaturated hydrocarbon group or a heterocyclic group is linked with a carbonyl group. In a narrow sense, it represents an acyl group in which an aliphatic hydrocarbon group is linked with a carbonyl group. Specifically, a $C_{1-6}$ alkyl-carbonyl group (for example, an acetyl group, a propionyl group, a butyryl group, an isobutyryl group, a valeryl group, an isovaleryl group, a pivaloyl group, a hexanoyl group); a $C_{2-7}$ alkenyl-carbonyl group (for example, crotonyl group); a $C_{3-8}$ cycloalkyl-carbonyl group (for example, a cyclobutane carbonyl group, a cyclopentane carbonyl group, a cyclohexane carbonyl group, a cycloheptane carbonyl group); a $C_{3-8}$ cycloalkenyl-carbonyl group (for example, a 2-cyclohexenecarbonyl group); a $C_{6-14}$ aryl-carbonyl group (for example, an arylcarbonyl group such as a benzoyl group, an α-naphthoyl group, a β-naphthoyl group, a halogenated arylcarbonyl group such as a 2-bromobenzoyl group, a 4-chlorobenzoyl group, a lower-alkylated arylcarbonyl group such as a 2,4,6-trimethyl benzoyl group, a 4-toluoyl group, a lower-alkoxylated arylcarbonyl group such as a 4-anisoyl group, a nitrated arylcarbonyl group such as a 4-nitrobenzoyl group, a 2-nitrobenzoyl group, an alkoxycarbonylated arylcarbonyl group such as a 2-(methoxycarbonyl)benzoyl group, an arylated arylcarbonyl group such as a 4-phenylbenzoyl group); a $C_{7-14}$ aralkyl-carbonyl group (for example, a benzylcarbonyl group, a phenethylcarbonyl group, phenylpropylcarbonyl group, a phenylbutylcarbonyl group); a $C_{8-13}$ arylalkenyl-carbonyl group (for example, a styrylcarbonyl group); a $C_{8-13}$ arylalkynyl-carbonyl group (for example, a phenylethynyl carbonyl group); an aromatic heterocyclic carbonyl group (for example, a nicotinoyl group, an isonicotinoyl group, a furylcarbonyl group, a thienylcarbonyl group, a pyrimidinylcarbonyl group, a benzofuranylcarbonyl group, a 1H-indazolylcarbonyl group, a quinolylcarbonyl group); a non-aromatic heterocyclic carbonyl groups (for example, a pyrrolidinylcarbonyl group, a piperidinocarbonyl group, a morpholinocarbonyl group, a thiomorpholinocarbonyl group, a piperazinocarbonyl group, a thiazolidinylcarbonyl group, a hexamethyleneiminylcarbonyl group, a tetrahydroisoquinolylcarbonyl group), etc. can be exemplified.

An "acyloxy group" is a group in which an oxygen atom is linked with an "acyl group" as mentioned above and, for example, includes a benzoyloxy group, etc.

An "acylamino group" indicates a group in which an "acyl group" as mentioned above is linked with an amino atom and, for example, it is a linear or branched lower aliphatic acylamino group having 2 to 7 carbon atoms such as an acetylamino group, a propionylamino group, a butyrylamino group, an isobutyrylamino group, a valerylamino group, an isovalerylamino group, a pivaloylamino group, a hexanoylamino group, an acryloylamino group, a methacryloylamino group, a crotonoylamino group.

A "heterocyclic group" or a "heterocycle group" represents a saturated ring (which may have a double bond in its part) or an aromatic ring having 1 to 4 hetero atoms selected from an oxygen atom, a nitrogen atom and a sulfur atom other than a carbon atom as an atom constituting the ring in which the number of ring constituting atoms is 3 to 14. The "heterocyclic group" may be a monocycle or may form a condensed ring with a cycloalkyl ring such as a cyclohexyl ring, an aromatic hydrocarbon ring such as a benzene ring or other heterocyclic ring.

A "5- to 7-membered saturated heterocyclic group" represents a "heterocyclic group" consisting of a 5-membered to 7-membered, preferably 5-membered or 6-membered saturated ring.

A "heterocyclic group" which is a monocycle includes, for example, a pyridyl group, pyrazinyl group, a pyrimidinyl group, a pyridazinyl group, a 1,3,5-triazinyl group, a pyrrolyl group, a pyrazolyl group, an imidazolyl group, a 1,2,4-triazolyl group, a tetrazolyl group, a thienyl group, a furyl group, an oxazolyl group, an isoxazolyl group, a thiazolyl group, an isothiazolyl group, a thiadiazolyl group, a pyrrolinyl group, a pyrrolidinyl group, an imidazolidinyl group, a piperidyl group, a piperazinyl group, a morpholinyl group, a thiomorpholinyl group, a tetrahydropyranyl group, etc.

The "heterocyclic group which is a monocycle" mentioned above may be an "aromatic heterocyclic group" or may be a saturated ring (which may have a double bond in its part). The "saturated heterocyclic group" as used herein represents a so-called heterocyclic group containing no double bond as well as a heterocyclic group having a double in its part. Examples of these "saturated heterocyclic groups" include a pyrrolidinyl group (for example, a 2-pyrrolidinyl group, a 3-pyrrolidinyl group), a pyrrolinyl group (for example, 2-pyrrolin-3-yl), an imidazolyl group (for example, 2-imidazolin-4-yl), a piperidyl group (for example, a 2-piperidyl group, a 3-piperidyl group), a piperazinyl group (for example, 2-piperazinyl group), a morpholinyl group (for example, a 3-morpholinyl group), a tetrahydrofuryl group, a tetrahydrothienyl group, a pyrazolidinyl group, a 1,3-dioxolanyl group, a 1,3-oxathiolanyl group, a oxazolidinyl group, a thiazolidinyl group, a tetrahydropyranyl group, a tetrahydrothiopyranyl group, a dioxanyl group, a morpholinyl group, a thiomorpholinyl group, a 2-oxopyrrolidinyl group, a 2-oxopiperidinyl group, a 4-oxopiperidinyl group, a 2,6-dioxopiperidinyl group, etc.

An "aromatic heterocyclic group (heteroaryl group)" represents a 5- to 7-membered, preferably 5- or 6-membered monocyclic aromatic heterocyclic group or a bicyclic or tricyclic aromatic heterocyclic group in which such a monocycle is condensed with other rings wherein the heterocyclic group contains, for example, 1 to 5, preferably 1 to 4 hetero atoms selected from an oxygen atom, a nitrogen atom and a sulfur atom other than a carbon atom as a ring constituting atom.

Preferable examples of such an "aromatic heterocyclic group" (heteroaryl group) include a furyl group (for example, 2-furyl, 3-furyl), a thienyl group (for example, 2-thienyl, 3-thienyl), a pyridyl group (for example, 2-pyridyl, 3-pyridyl, 4-pyridyl), a pyrimidinyl group (for example, 2-pyrimidinyl, 4-pyrimidinyl, 5-pyrimidinyl, 6-pyrimidinyl), a pyridazinyl group (for example, 3-pyridazinyl, 4-pyridazinyl), a pyrazinyl group (for example, 2-pyrazinyl), a pyrrolyl group (for example, 1-pyrrolyl, 2-pyrrolyl, 3-pyrrolyl), an imidazolyl group (for example, 1-imidazolyl, 2-imidazolyl, 4-imidazolyl, 5-imidazolyl), a pyrazolyl group (for example, 1-pyrazolyl, 3-pyrazolyl, 4-pyrazolyl), an oxazolyl group (for example, 2-oxazolyl, 4-oxazolyl, 5-oxazolyl), an isoxazolyl group, a thiazolyl group (for example, 2-thiazolyl, 4-thiazolyl, 5-thiazolyl), an isothiazolyl group, an oxadiazolyl group (for example, 1,2,4-oxadiazol-5-yl, 1,3,4oxadiazol-2-yl), a thiadiazolyl group (for example, 1,3,4thiadiazol-2-yl), a triazolyl group (for example, 1,2,4-triazol-1-yl, 1,2,4-triazol-3-yl, 1,2,3-triazol-1-yl, 1,2,3-triazol-2-yl, 1,2,3-triazol-4-yl), a tetrazolyl group (for example, tetrazol-1-yl, tetrazol-5-yl), a quinolyl group (for example, 2-quinolyl, 3-quinolyl, 4-quinolyl), quinazolyl group (for example, 2-quinazolyl, 4-quinazolyl), a quinoxalyl group (for example, 2-quinoxalyl), a benzofuryl (for example, 2-benzofuryl, 3-benzofuryl), a benzothienyl group (for example, 2-benzothienyl, 3-benzothienyl), a benzoxazolyl group (for example, 2-benzoxazolyl), a benzothiazolyl group (for example, 2-benzothiazolyl), a benzimidazolyl group (for example, benzimidazol-1-yl, benzimidazol-2-yl), an indolyl group (for example, indol-1-yl, indol-3-yl), a 1H-indazolyl group (for example, 1H-indazol-3-yl), a 1H-pyrrolo[2,3-b]pyrazinyl group (for example, 1H-pyrrolo [2,3-b]pyrazin-2-yl), a 1H-pyrrolopyridinyl group (for example, 1H-pyrrolo[2,3b]pyridin-6-yl), a 1H-imidazopyridinyl group (for example, 1H-imidazo[4,5-b]pyridin-2-yl, 1H-imidazo[4,5-c]pyridin-2-yl), a 1H-imidazopyrazinyl group (for example, 1H-imidazo[4,5-b]pyrazin-2-yl), a triazinyl group, an isoquinolyl group, a benzoxadiazolyl group, a benzothiadiazolyl group, benzotriazolyl group, etc.

A "5- or 6-membered aromatic heterocyclic group or saturated heterocyclic group" specifically includes a pyridyl group, a pyrazinyl group, a pyrimidinyl group, a pyridazinyl group, a 1,3,5-triazinyl group, a pyrrolyl group, a pyrazolyl group, an imidazolyl group, a 1,2,4-triazolyl group, a tetrazolyl group, a thienyl group, a furyl group, an oxazolyl group, an isoxazolyl group, a thiazolyl group, an isothiazolyl group, a thiadiazolyl group, a pyrrolidinyl group, a piperidyl group, a piperazinyl group, etc.

The "condensed heterocyclic group" mentioned above may be partially saturated, and, examples of partial saturated condensed heterocycle include an isochromanyl group (for example, 3-isochromanyl, etc.), an indolinyl group (for example, 2-indolinyl etc.), an isoindolinyl group (for example, 1-isoindolinyl etc.), a 1,2,3,4-tetrahydro-2-quinolyl group, a 1,2,3,4-tetrahydro-3-isoquinolyl group, etc.

Preferable examples of "condensed aromatic heterocyclic group" or "condensed heterocyclic group" include a benzofuranyl group, isobenzofuranyl group, a benzo[b]thienyl group, an indolyl group, an isoindolyl group, a 1H-indazolyl group, a benzimidazolyl group, a benzoxazolyl group, a benzothiazolyl group, a 1H-benzotriazolyl group, a quinolyl group, an isoquinolyl group, a cinnolyl group, a quinazolyl group, a quinoxalinyl group, a phthalazyl group, a naphthyridinyl group, a purinyl group, a pteridinyl group, a carbazolyl group, an α-carbonylyl group, a β-carbonylyl group, an acridinyl group, a phenoxazinyl group, a phenothiazinyl group, a phenazinyl group, a phenoxathiinyl group, a thianthrenyl group, an indolizinyl group, a 5,6,7,8-tetrahydroquinolyl group, a pyrrolo[1,2-b]pyridazinyl group, a pyrazolo[1,5-a]pyridyl group, an imidazo[1,2-a]pyridyl group, an imidazo[1,5-a]pyridyl group, an imidazo[1,2-b]pyridazinyl group, an imidazo[1,2-a]pyrimidinyl group, a 1,2,4triazolo[4,3-a]pyridyl group, a 1,2,4triazolo[4,3-b]pyridazinyl group, etc.

A "heterocycloalkyl group" represents the same as a "saturated heterocyclic group".

A "$C_{7-11}$ spiroheterocycloalkyl group" represents a group in which a heterocycloalkyl group mentioned above forms a spiro link with a $C_{3-8}$ cycloalkyl group mentioned above or a heterocycloalkyl group mentioned above and, for example, includes an azaspiro[2.3]hexyl group, an azaspiro[2.4]heptyl group, an azaspiro[3.4]octyl group, an azaspiro[2.5]octyl group, an azaspiro[3.5]nonyl group, an azaspiro[4.4]nonyl group, an azaspiro[4.5]decanyl group, an azaspiro[5.5]undecanyl group, etc.

A "$C_{1-6}$ alkylidene group" represents a group which is generated by removing two hydrogen atoms from the same carbon atom of an alkane, and the free valency becomes a part of double bond, and includes, for example, methylidyne, ethylidene, propylidene, butylidene, pentylidene, hexylidene, etc.

The definition of each term is as stated above, and particularly preferred is as follows. In addition, substitution may be substituted with the same or different two or more substituents.

$X^1$, $X^2$ and $X^3$ are preferably —CH=, =C($R^3$)— and —CH=, respectively.

As for $Y^1$ and $Y^2$, either one of $Y^1$ and $Y^2R$ is preferably a nitrogen atom, and more preferably both are carbon atoms (—CH=) at the same time.

Preferably R is a hydrogen atom.

$R^3$ is preferably a halogen atom, a hydroxyl group or a $C_{1-6}$ alkyl group (wherein the alkyl group may be substituted with an alkoxycarbonyl group or a $C_{1-6}$ alkoxy group.), and particularly preferably it is a $C_{1-6}$ alkyl group (wherein the alkyl group may be substituted with an alkoxycarbonyl group or a $C_{1-6}$ alkoxy group) and still more preferably it is a methyl group.

Preferably $R^5$ is a hydrogen atom.

$R^6$ and $R^{6'}$ are preferably hydrogen atoms or $C_{1-6}$ alkyl groups, and particularly preferably are hydrogen atoms.

$R^7$ is particularly preferably $R^e$, $R^g$ or $R^h$.

"p" in $R^a$ and $R^b$ is an integer from 1 to 6, and preferably an integer from 1 to 4. Particularly, when p is 1 in $R^a$, $R^{a2}$ is preferably a substituent other than a hydrogen atom, and when p is 2 or more, substituent —O—$R^{a3}$ is preferably linked to the 2-position to 6-position of —$C_pH_{2(p-1)}(R^{b1})(R^{b2})$—.

In the same way, when p is 1 in $R^b$, $R^{b2}$ is preferably a substituent other than a hydrogen atom, and when p is 2 or more, substituent —N—$(R^{b3})(R^{b4})^3$ is preferably linked to the 2-position to 6-position of —$C_pH_{2(p-1)}(R^{b1})(R^{b2})$—.

In $R^a$, preferable $R^{a1}$ is a hydrogen atom and preferable $R^{a2}$ is a $C_{1-6}$ alkyl group, an aralkyl group or an aryl group (wherein these $C_{1-6}$ alkyl group, aralkyl group and aryl group may be substituted with a substituent selected from a hydroxyl group or carboxy group), and preferable $R^{a3}$ is a hydrogen atom, an acyl group, a carbamoyl group represented by —CON($R^{a31}$)($R^{a32}$) or a $C_{1-6}$ alkyl group (wherein the alkyl group may be substituted with a $C_{1-6}$ alkoxycarbonyl group or —CON($R^{a31}$)($R^{a32}$)).

As for $R^{a31}$ and $R^{a32}$, specifically as a 5 or 6 membered saturated heterocyclic group together with the adjacent nitrogen atom and having one or more nitrogen atoms can be exemplified a saturated heterocyclic group as shown below:

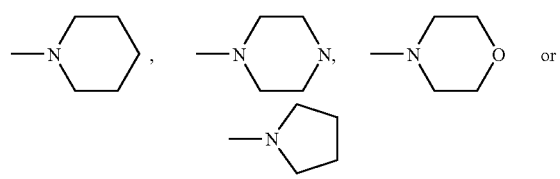

In $R^b$, preferable $R^{b1}$ is a hydrogen atom, and preferable $R^{b2}$ is a phenyl group which may be substituted with a $C_{1-6}$ alkyl group which may be substituted with a substituent selected from Group Ca or a hydroxyl group, and preferable $R^{b3}$ is a hydrogen atom or a $C_{1-6}$ alkyl group, and preferable $R^{b4}$ is a hydrogen atom, an acyl group which may be substituted with a hydroxyl group or a $C_{1-6}$ alkylsulfonyl group.

$R^{c1}$ which is particularly preferable in $R^c$ is a hydroxyl group or a $C_{1-6}$ alkoxy group (wherein the $C_{1-6}$ alkoxy group may be substituted with a hydroxyl group or a $C_{1-6}$ alkoxy group.).

$R^{d1}$ which is preferable in $R^d$ is a $C_{1-6}$ alkyl group, a $C_{1-6}$ alkoxy group or —N($R^{d11}$)($R^{d12}$). In addition, $R^{d11}$ and $R^{d12}$ preferable here are hydrogen atoms, $C_{1-6}$ alkoxy groups or $C_{1-6}$ alkyl groups (wherein the $C_{1-6}$ alkyl group may be substituted with a hydroxyl group or a carboxy group.).

Preferable as Ring A in $R^e$ is the following.

Particularly preferable examples as "5- to 6-membered saturated heterocyclic group having one to two hetero atoms" in $R^e$ include the following saturated heterocyclic groups.

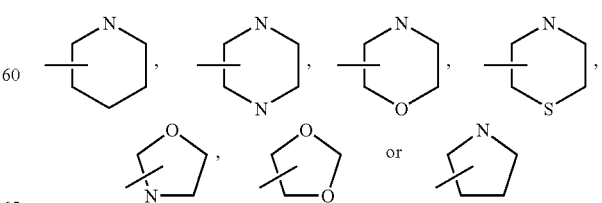

More specifically, the following groups are included.

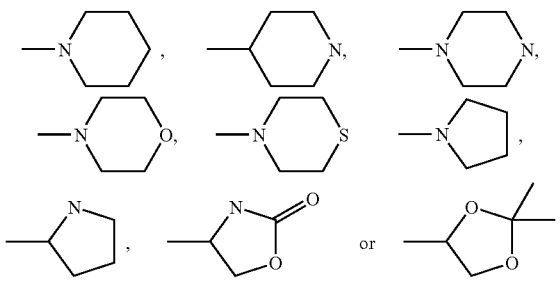

Of these, particularly preferred are the following saturated heterocyclic groups which are directly bonded to the thiazole ring or thiophene ring of the above general formula (I) through a nitrogen atom constituting these saturated heterocyclic rings.

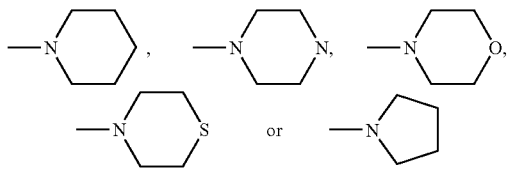

Preferable examples of "5- or 6-membered saturated heterocyclic group having 1 to 4 hetero atoms" in $R^e$ include the following aromatic heterocyclic groups.

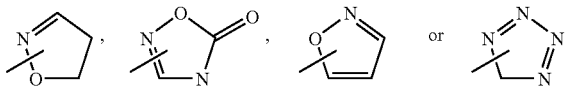

Preferable examples of "9- to 12-membered condensed aromatic heterocyclic group having 1 or 2 hetero atoms which may be partially saturated" in $R^e$ include the following condensed aromatic heterocyclic groups.

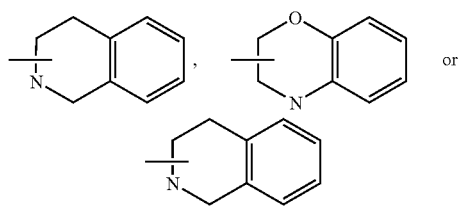

The following condensed ring is also included.

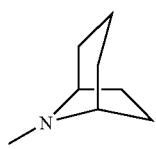

Particularly preferable examples of "$C_{3-8}$ cycloalkyl group" in $R^e$ include the following cycloalkyl group.

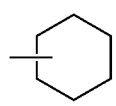

Preferable examples of "$C_{7-11}$ spiro heterocycloalkyl group having 1 or 2 hetero atoms" in $R^e$ include the following spiroheterocycloalkyl group.

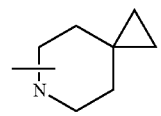

Substituents for Ring A are as shown in group Ea. Preferable substituents for Ring A are as follows.

Examples preferable as —$OR^{e1}$ include:
  a hydroxyl group,
  a $C_{1-6}$ alkyl group, wherein the $C_{1-6}$ alkyl group may be substituted with a carboxy group or —$CON(R^{e11})(R^{e12})$.) (wherein $R^{e11}$ and $R^{e12}$ may be the same or different and each represent a hydrogen atom or a $C_{1-6}$ alkyl group,
  an acyloxy group,
  an aralkoxy group or
  a carbamoyloxy group.

Examples Preferable as —$COOR^{e2}$ Include:
  a carboxy group or
  a $C_{1-6}$ alkoxycarbonyl group.

Examples Preferable as —CO—$N(R^{e41})(R^{e42})$ Include:
—CO—$NO(R^{e41})(R^{e42})$ wherein $R^{e41}$ and $R^{e42}$ may be the same or different and each represent
  a hydrogen atom,
  a $C_{1-6}$ alkyl group, wherein the $C_{1-6}$ alkyl group may be substituted with a substituent selected from a hydroxyl group, a $C_{1-6}$ alkoxy group, an amino group, a $C_{1-6}$ alkylamino group, a di-$C_{1-6}$ alkylamino group, a halogen atom, a carboxy group, a carbamoyl group, a $C_{1-6}$ alkylcarbamoyl group, di-$C_{1-6}$ alkylcarbamoyl group or a 5- or 6-membered saturated heterocyclic group or an aromatic heterocyclic group having 1 or 2 hetero atoms,
  a hydroxyl group,
  a $C_{1-6}$ alkoxy group,
  a $C_{5-6}$ cycloalkyl group, wherein the $C_{5-6}$ cycloalkyl group may be substituted with a hydroxyl group or a $C_{1-6}$ alkyl group, wherein the $C_{1-6}$ alkyl group may be substituted with a hydroxyl group; or
  a $C_{1-6}$ alkylsulfonyl group.

Particularly preferable is a carbamoyl group.

Examples Preferable as —$COR^{e3}$ Include:
—$COR^{e3}$, wherein $R^{e3}$ is
  a $C_{1-6}$ alkyl group, wherein the $C_{1-6}$ alkyl group may be substituted with a substituent selected from a hydroxyl group, a carboxy group, a $C_{1-6}$ alkoxycarbonyl group and $C_{1-6}$ alkylsulfonyl group,
  a 5- or 6-membered saturated heterocyclic group or aromatic heterocyclic group having 1 or 2 hetero atoms, wherein the saturated heterocyclic group and aromatic heterocyclic group may be substituted with a substituent selected from a hydroxyl group, an oxo group, a carboxy group, a $C_{1-6}$ alkoxy group, wherein the $C_{1-6}$ alkoxy group may be substituted with a carbamoyl group, a carbamoyl group, wherein the carbamoyl group may be substituted with a hydroxyl group, an acyl group, an acyloxy group, an amino group, an acylamino group, wherein the acylamino group may be substituted with a hydroxyl group or a carbamoyl group, a $C_{1-6}$ alkylamino group, a di-$C_{1-6}$ alkylamino group, a $C_{1-6}$ alkylsulfonylamino group, a 5- or 6-membered saturated heterocyclic group or aromatic heterocyclic group and a $C_{1-6}$ alkyl group, wherein the $C_{1-6}$ alkyl group may be substituted with a hydroxyl group, a $C_{1-6}$ alkoxy group, wherein the $C_{1-6}$ alkoxy group may be substituted with a carbamoyl group, an acylamino group and a carbamoyl group, or a $C_{5-6}$ cycloalkyl group or aryl group, wherein the $C_{5-6}$ cycloalkyl group and aryl group may be substituted with a hydroxyl group, an oxo group, a $C_{1-6}$ alkoxy group, a carbamoyl group, an acylamino group, an oximino group or an acyloxy group.

Furthermore, preferable examples of "5- or 6-membered saturated heterocyclic group having 1 or 2 hetero atoms" in the above $R^{e3}$ include the following heterocyclic groups.

In addition, preferable examples of "5- or 6-membered aromatic heterocyclic group having 1 or 2 hetero atoms" in the above $R^{e3}$ include the following heterocyclic aromatic group.

In addition, preferable examples as —$COR^{e3}$ in the above $R^{e3}$ include the following.

Examples Preferable as —$N(R^{e51})(R^{e52})$ Include:

—$N(R^{e51})(R^{e52})$ wherein $R^{e51}$ and $R^{e52}$ may be the same or different and each represent
    a hydrogen atom,
    a $C_{1-6}$ alkylsulfonyl group,
    a $C_{1-6}$ alkyl group, wherein the $C_{1-6}$ alkyl group may be substituted with a substituent selected from a hydroxyl group, a $C_{1-6}$ alkoxy group and carbamoyl group,
    —$CON(R^{e11})(R^{e12})$ wherein $R^{e11}$ and $R^{e12}$ are the same as above,
    —$COR^{e511}$, wherein the $R^{e511}$ is a 5- or 6-membered saturated heterocyclic group containing at least one nitrogen atom, a $C_{1-6}$ alkyl group (wherein the $C_{1-6}$ alkyl group may be substituted with a hydroxyl group.) or a $C_{5-6}$ cycloalkyl group, wherein the cycloalkyl group may be substituted with a hydroxyl group.

Examples Preferable as a $C_{1-6}$ alkyl Group Include:

$C_{1-6}$ alkyl groups which may be substituted with
    a hydroxyl group,
    a $C_{1-6}$ alkoxy group, a $C_{1-6}$ alkyl group in the $C_{1-6}$ alkoxy group may be substituted with a carboxy group or —CO—N$(R^{e11})(R^{e12})$ and $R^{e11}$ and $R^{e12}$ are the same as above;
    —$COOR^{e2}$, wherein $R^{e2}$ is the same as above,
    —$N(R^{e51})(R^{e52})$ wherein $R^{e51}$ and $R^{e52}$ are the same as above,
    —CO—$N(R^{e51})(R^{e52})$ wherein $R^{e51}$ and $R^{e52}$ are the same as above,
    a halogen atom or
    a 5- or 6-membered saturated heterocyclic group having 1 or 2 hetero atoms, wherein the saturated heterocyclic group may be substituted with a hydroxyl group or a $C_{1-6}$ alkyl group.

Particularly preferred is a $C_{1-6}$ alkyl group substituted with —$COOR^{e2}$, for example, a carboxymetyl group or an unsubstituted methyl group.

Examples Preferable as a 5- to 6-Membered Saturated Heterocyclic Group (which May be Partially Saturated) Containing 1 or 2 Hetero Atoms Selected from a Nitrogen Atom and an Oxygen Atom or an Aromatic Heterocyclic Group Containing 1 to 4 Hetero Atoms Selected from a Nitrogen Atom and an Oxygen Atom, Wherein the Saturated Heterocyclic Group and Aromatic Heterocyclic Group May be Substituted with an oxo Group or a $C_{1-6}$ alkyl Group, Include:

In addition, substituents preferable for Ring A are an oxo group, a $C_{1-6}$ alkylsulfonyl group and a cyano group.

k and l in linker "A" of $R^g$ are preferably 1 or 2, and k+l is 2 to 4.

In addition, preferable Ring B in $R^g$ is as follows.
Preferable examples of an "aryl group" in $R^g$ include a phenyl group.

Preferable examples of a "$C_{3-8}$ cycloalkyl group" in $R^g$ include the following $C_{3-8}$ cycloalkyl groups:

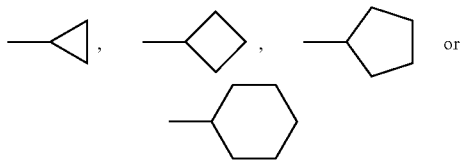

Preferable examples of a "5- to 7-membered saturated heterocyclic group having one or more nitrogen atoms" in $R^g$ include the following saturated heterocyclic groups:

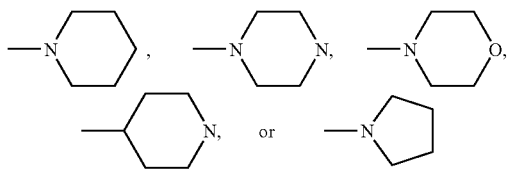

Preferable examples of a "5- to 6-membered aromatic heterocyclic group having at least one hetero atom" in $R^g$ include the following aromatic heterocyclic groups:

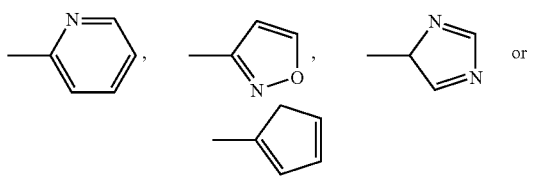

Preferable examples of a "8- to 11-membered condensed aromatic heterocyclic group having at least one hetero atom" in $R^g$ include the following condensed aromatic heterocyclic groups:

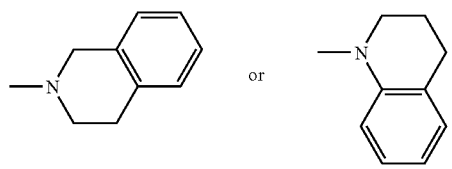

$R^{h1}$ in $R^h$ is preferably a hydrogen atom or a $C_{1-6}$ alkyl group.

In addition, preferable "aromatic carbocyclic ring group", "5- to 6-membered aromatic heterocyclic group having 1 or 2 hetero atoms", "$C_{3-8}$ cycloalkyl group" and "5- to 6-membered saturated heterocyclic group having 1 or 2 hetero atoms" in group Ja of $R^{h2}$ are specifically as follows. Particularly preferred are "$C_{3-8}$ cycloalkyl group".

Preferable examples of an "aromatic carbocyclic group" in group Ja of $R^{h2}$ include a phenyl group.

Preferable examples of a "5- to 6-membered aromatic heterocyclic group having 1 or 2 hetero atoms" in group Ja of $R^{h2}$ include the following aromatic heterocyclic groups:

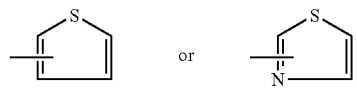

Preferable examples of a "5- to 6-membered saturated heterocyclic group having 1 or 2 hetero atoms" in group Ja of $R^{h2}$ include the following saturated heterocyclic groups.

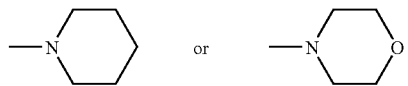

Preferable examples of a "$C_{3-8}$ cycloalkyl group" in (5) of $R^{h2}$ include a cyclohexyl group. Particularly preferred is a cyclohexyl group substituted with a carboxy group.

Preferable examples of a "5- to 6-membered saturated heterocyclic group having 1 or 2 hetero atoms" in (6) of $R^{h2}$ include the following saturated heterocyclic groups:

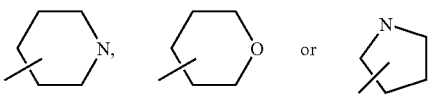

The definition of each term is described as above but among each symbol $X^1$, $X^2$, $X^3$, $Z$, $Y^1$, $Y^2$, $R$, $R^1$, $R^5$, $R^6$, $R^7$ and various substituents defined as the narrower concept thereof in the general formula (I), "preferable $X^1$, $X^2$, $X^3$, $Z$, $Y^1$, $Y^2$, $R$, $R^1$, $R^5$, $R^6$, $R^7$ and various substituents" are those specifically described in the Examples given below (for example, "a methyl group, an ethyl group", "a phenyl group, a naphthyl group") and particularly preferred are $X^1$, $X^2$, $X^3$, $Z$, $Y^1$, $Y^2$, $R$, $R^1$, $R^5$, $R^6$, $R^7$ and various substituents derived from the group of compounds which show particularly high inhibitory activity among them (more than ++).

Preferable examples of a compound of the present invention include the following compounds, wherein the number in the parenthesis represents the compound number mentioned in the Examples:

1-methyl-4-{5-[6-(4-methylpyridin-2-ylamino)pyridin-2-yl]thiazol-2-yl}pyridin-2-one (compound A-1), 1-{5-[6-(4-methylpyridin-2-ylamino)pyridin-2-yl]thiazol-2-yl}piperidine-4-carboxylic acid (compound A-2), 1-{5-[6-(4-methylpyridin-2-ylamino)pyridin-2-yl]thiazol-2-yl}piperidine-4-carboxamide (compound A-3), N-methyl-1-{5-[6-(4-methylpyridin-2-ylamino)pyridin-2-yl]thiazol-2-yl}piperidine-4-carboxamide (compound A-4), N-(2-hydroxyethyl)-1-{5-[6-(4-methylpyridin-2-ylamino)pyridin-2-yl]thiazol-2-yl}piperidine-4-carboxamide (compound A-5), trans-4-{5-[6-(4-methylpyridin-2-ylamino)pyridin-2-yl]thiazol-2-yl}cyclohexanecarboxylic acid methyl ester (compound A-6), trans-4-{5-[6-(4-methylpyridin-2-ylamino)pyridin-2-yl]thiazol-2-yl}cyclohexanecarboxylic acid (compound A-7), (4-hydroxypiperidin-1-yl)-(trans-4-{5-[6-(4-methylpyridin-2-ylamino)pyridin-2-yl]thiazol-2-yl}cyclohexyl)methanone (compound A-8), N—((S)-1-{5-[6-(4-methylpyridin-2-ylamino)pyridin-2-yl]thiazol-2-yl}ethyl)amine (compound A-9), N—((S)-1-{5-[6-(4-methylpyridin-2-ylamino)pyridin-2-yl]thiazol-2-yl}ethyl)acetamide (compound A-10), (S)-3-methyl-4-{5-[6-(4-methylpyridin-2-ylamino)pyridin-2-yl]thiazol-2-yl}oxazolidin-2-one (compound A-11), (S)-2,2-dimethyl-4-{5-[6-(4-methylpyridin-2-ylamino)pyridin-2-yl]thiazol-2-yl}oxazolidine-3-carboxylic acid tert-butyl ester (compound A-12), (S)-2-amino-2-{5-[6-(4-methylpyridin-2-ylamino)pyridin-2-yl]thiazol-2-yl}ethanol (compound A-13), (S)-4-{5-[6-(4-methylpyridin-2-ylamino)pyridin-2-yl]thiazol-2-yl}oxazolidin-2-one (compound A-14),
(1-{5-[6-(4-methylpyridin-2-ylamino)pyridin-2-yl]thiazol-2-yl}piperidin-4-yl)acetic acid dihydrochloride (compound A-15),
trans-4-[(N-methyl-N-{5-[6-(4-methylpyridin-2-ylamino)pyridin-2-yl]thiazol-2-yl}amino)methyl]cyclohexanecarboxylic acid (compound A-16),
3-(1-{5-[6-(4-methylpyridin-2-ylamino)pyridin-2-yl]thiazol-2-yl}piperidin-4-yl)propionic acid (compound A-17),
2-methyl-2-(1-{5-[6-(4-methylpyridin-2-ylamino)pyridin-2-yl]thiazol-2-yl}piperidin-4-yl)propionic acid (compound A-18),
N-{4-methyl-5-[6-(4-methylpyridin-2-ylamino)pyridin-2-yl]thiazol-2-yl}propionamide (compound A-19),
N-{4-methyl-5-[6-(4-methylpyridin-2-ylamino)pyridin-2-yl]thiazol-2-yl}acetamide (compound A-20),
N-{4-methyl-5-[6-(4-methylpyridin-2-ylamino)pyrazin-2-yl]thiazol-2-yl}acetamide (compound A-21),
acetic acid(S)-1-{5-[6-(4-methylpyridin-2-ylamino)pyridin-2-yl]thiazol-2-yl}ethyl ester (compound A-25),
(S)-1-{5-[6-(4-methylpyridin-2-ylamino)pyridin-2-yl]thiazol-2-yl}ethanol (compound A-26),
1-{5-[6-(4-methylpyridin-2-ylamino)pyridin-2-yl]thiazol-2-yl}ethanone (compound A-27),
5-[6-(4-methylpyridin-2-ylamino)pyridin-2-yl]thiazole-2-carboxylic acid ethyl ester (compound A-28),
1-{5-[6-(4-methylpyridin-2-ylamino)pyridin-2-yl]thiazol-2-yl}ethanone oxime (compound A-30),
(S)-5-{5-[6-(4-methylpyridin-2-ylamino)pyridin-2-yl]thiazol-2-yl}dihydrofuran-2-one (compound A-33),
1-{5-[6-(4-methylpyridin-2-ylamino)pyridin-2-yl]thiazol-2-yl}ethanone 0-(2-hydroxyethyl)oxime (compound A-35),
N-methoxy-N-methyl-5-[6-(4-methylpyridin-2-ylamino)pyridin-2-yl]thiazole-2-carboxamide (compound A-46),
N-methyl-5-[6-(4-methylpyridin-2-ylamino)pyridin-2-yl]thiazole-2-carboxamide (compound A-47),
N-methyl-((S)-1-{5-[6-(4-methylpyridin-2-ylamino)pyridin-2-yl]thiazol-2-yl}ethyl)acetamide (compound A-52),
(S)-5-{5-[6-(4-methylpyridin-2-ylamino)pyridin-2-yl]thiazol-2-yl}pyrrolidin-2-one (compound A-55),
5-{5-[6-(4-methylpyridin-2-ylamino)pyridin-2-yl]thiazol-2-yl}pentanoic acid (compound A-69),
5-{5-[6-(4-methylpyridin-2-ylamino)pyridin-2-yl]thiazol-2-yl}pentan-1-ol (compound A-70),
5-{5-[6-(4-methylpyridin-2-ylamino)pyridin-2-yl]thiazol-2-yl}pentanamide (compound A-71),
4-{5-[6-(4-methylpyridin-2-ylamino)pyridin-2-yl]thiazol-2-yl}cyclohexanol (compound A-73),
4-{5-[6-(4-methylpyridin-2-ylamino)pyridin-2-yl]thiazol-2-yl}cyclohexanone oxime (compound A-74),
N-{6-[2-((S)-1-aminoethyl)thiazol-5-yl]pyridin-2-yl}-N-([4,4']bipyridinyl-2-yl)amine (compound A-75),
N—((S)-1-{5-[6-([4,4']bipyridinyl-2-ylamino)pyridin-2-yl]thiazol-2-yl}ethyl)acetamide (compound A-79),
N—((S)-1-{5-[6-(4-chloropyridin-2-ylamino)pyridin-2-yl]thiazol-2-yl}ethyl)acetamide (compound A-81),
(S)-2-methyl-1-{5-[6-(4-methylpyridin-2-ylamino)pyridin-2-yl]thiazol-2-yl}propan-1-ol (compound A-82),
N—((S)-1-{5-[6-(isoquinolin-3-ylamino)pyridin-2-yl]thiazol-2-yl}ethyl)acetamide (compound A-91),
(4-methylpyridin-2-yl)-[6-(2-piperidin-4-ylthiazol-5-yl)pyridin-2-yl]amine (compound A-92),
trans-4-{5-[6-(4-methylpyridin-2-ylamino)pyridin-2-yl]thiazol-2-yl}cyclohexanecarboxamide (compound A-111),
5-{5-[6-(4-methylpyridin-2-ylamino)pyridin-2-yl]thiazol-2-yl}pentylamine (compound A-128),
4-{5-[6-(4-methylpyridin-2-ylamino)pyridin-2-yl]thiazol-2-yl}butan-1-ol (compound A-132),
4-(2-{5-[6-(4-methylpyridin-2-ylamino)pyridin-2-yl]thiazol-2-yl}ethyl)phenol (compound A-135),
2-hydroxy-N—((S)-1-{5-[6-(4-methylpyridin-2-ylamino)pyridin-2-yl]thiazol-2-yl}ethyl)acetamide (compound A-147),
3-({5-[6-(4-methylpyridin-2-ylamino)pyridin-2-yl]thiazole-2-carbonyl}amino)propionic acid (compound A-148),
4-(2-{5-[6-(4-methylpyridin-2-ylamino)pyridin-2-yl]thiazol-2-yl}ethyl)benzoic acid (compound A-151),
1-{5-[6-(4-methylpyridin-2-ylamino)pyridin-2-ylmethyl}piperidin-4-ol (compound A-152),
3,3-dimethyl-4-{5-[6-(4-methylpyridin-2-ylamino)pyridin-2-yl]thiazol-2-yl}butan-1-ol (compound A-158),
[4-(2-{5-[6-(4-methylpyridin-2-ylamino)pyridin-2-yl]thiazol-2-yl}ethyl)phenyl]methanol (compound A-159),
N—((R)-(4-hydroxyphenyl)-{5-[6-(4-methylpyridin-2-ylamino)pyridin-2-yl]thiazol-2-yl}methyl)acetamide (compound A-161),
N-(2-hydroxyethyl)-4-(2-{5-[6-(4-methylpyridin-2-ylamino)pyridin-2-yl]thiazol-2-yl}ethyl)benzamide (compound A-162),
4-(2-{5-[6-(4-methylpyridin-2-ylamino)pyridin-2-yl]thiazol-2-yl}ethyl)cyclohexanone (compound A-172),
4-(2-{5-[6-(4-methylpyridin-2-ylamino)pyridin-2-yl]thiazol-2-yl}ethyl)cyclohexanol (compound A-173),
((3R,4S)-3,4-dihydroxypyrrolidin-1-yl)-(trans-4-{5-[6-(4-methylpyridin-2-ylamino)pyridin-2-yl]thiazol-2-yl}cyclohexyl)methanone (compound A-174),
(trans-4-{5-[6-(4-methylpyridin-2-ylamino)pyridin-2-yl]thiazol-2-yl}cyclohexyl)-(piperazin-1-yl)methanone (compound A-176),
4-{5-[6-(4-methylpyridin-2-ylamino)pyridin-2-yl]thiazol-2-yl}piperidine-1-carboxamide (compound A-182),
2-hydroxy-1-(4-{5-[6-(4-methylpyridin-2-ylamino)pyridin-2-yl]thiazol-2-yl}piperidin-1-yl)ethanone (compound A-187),
trans-4-{5-[6-(4-methoxypyridin-2-ylamino)pyridin-2-yl]thiazol-2-yl}cyclohexanecarboxylic acid (compound A-188),
3-(4-{5-[6-(4-methylpyridin-2-ylamino)pyridin-2-yl]thiazol-2-yl}piperidin-1-yl)-3-oxopropionic acid hydrochloride (compound A-192),
N-(4-methylpyridin-2-yl)-N-{6-[2-(piperazin-1-ylmethyl)thiazol-5-yl]pyridin-2-yl}amine (compound A-194),
1-{5-[6-(4-methylpyridin-2-ylamino)pyridin-2-yl]thiazol-2-ylmethyl}piperidin-4-ylamine (compound A-197),
N-{5-[6-(4-methylpyridin-2-ylamino)pyridin-2-yl]thiazol-2-ylmethyl}methanesulfonamide (compound A-200),
N-(trans-4-{5-[6-(4-methylpyridin-2-ylamino)pyridin-2-yl]thiazol-2-yl}cyclohexyl)acetamide (compound A-202),
trans-4-{5-[6-(4-chloropyridin-2-ylamino)pyridin-2-yl]thiazol-2-yl}cyclohexanecarboxylic acid (compound A-204),
2-{5-[6-(4-methylpyridin-2-ylamino)pyridin-2-yl]thiazol-2-yl}ethanol (compound A-205),
(trans-4-{5-[6-(4-methylpyridin-2-ylamino)pyridin-2-yl]thiazol-2-yl}cyclohexyl)methanol (compound A-211),
trans-4-{5-[6-(isoquinolin-3-ylamino)pyridin-2-yl]thiazol-2-yl}cyclohexanecarboxylic acid (compound A-215),
trans-4-{5-[6-(4-methylpyridin-2-ylamino)pyridin-2-yl]thiazol-2-yl}cyclohexylmethylamine (compound A-219), ((3R,4S)-3,4-dihydroxypyrrolidin-1-yl)-[4-(2-{5-[6-(4-methylpyridin-2-ylamino)pyridin-2-yl]thiazol-2-yl}ethyl)phenyl]methanone (compound A-223), N-(trans-4-{5-[6-(4-methylpyridin-2-ylamino)pyridin-2-yl]thiazol-2-yl}cyclohexylmethyl)acetamide (compound A-228), N-(trans-4-{5-[6-(4-methylpyridin-2-ylamino)pyridin-2-yl]thiazol-2-yl}cyclohexylmethyl)methanesulfonamide (compound A-229), 2-hydroxy-N-(trans-4-{5-[6-(4-methylpyridin-2-ylamino)pyridin-2-yl]thiazol-2-yl}cyclohexylmethyl)acetamide (compound A-235), 2-hydroxy-N-[4-(2-{5-[6-(4-methylpyridin-2-ylamino)pyridin-2-yl]thiazol-2-yl}ethyl)phenyl]acetamide (compound A-237), ((3R,4S)-3,4-dihydroxypiperidin-1-yl)-(trans-4-{5-[6-(4-methylpyridin-2-ylamino)pyridin-2-yl]thiazol-2-yl}cyclohexyl)methanone (compound A-239), ((R)-3-hydroxypyrrolidin-1-yl)-(trans-4-{5-[6-(4-methylpyridin-2-ylamino)pyridin-2-yl]thiazol-2-yl}cyclohexyl)methanone (compound A-241), (4-{5-[6-(4-methylpyridin-2-ylamino)pyridin-2-yl]thiazol-2-ylmethyl}phenyl)methanol (compound A-243), N-(4-methylpyridin-2-yl)-N-[6-(2-pyridin-3-ylmethylthiazol-5-yl)pyridin-2-yl]amine (compound A-248), N-(4-methylpyridin-2-yl)-N-{6-[2-(2-piperidin-4-ylethyl)thiazol-5-yl]pyridin-2-yl}amine (compound A-258), N-(6-{2-[2-(1-methanesulfonylpiperidin-4-yl)ethyl]thiazol-5-yl}pyridin-2-yl)-N-(4-methylpyridin-2-yl)amine (compound A-260), 2-hydroxy-1-[4-(2-{5-[6-(4-methylpyridin-2-ylamino)pyridin-2-yl]thiazol-2-yl}ethyl)piperidin-1-yl]ethanone (compound A-263), N-(2-hydroxyethyl)-trans-4-{5-[6-(4-methylpyridin-2-ylamino)pyridin-2-yl]thiazol-2-yl}cyclohexanecarboxamide (compound A-267), N-(2-morpholin-4-ylethyl)-trans-4-{5-[6-(4-methylpyridin-2-ylamino)pyridin-2-yl]thiazol-2-yl}cyclohexanecarboxamide (compound A-268),

[3-(2-{5-[6-(4-methylpyridin-2-ylamino)pyridin-2-yl]thiazol-2-yl}ethyl)phenyl]methanol (compound A-277), (3-hydroxypyrrolidin-1-yl)-(trans-4-{5-[6-(4-methylpyridin-2-ylamino)pyridin-2-yl]thiazol-2-yl}cyclohexyl)methanone (compound A-282), 4-(trans-4-{5-[6-(4-methylpyridin-2-ylamino)pyridin-2-yl]thiazol-2-yl}cyclohexanecarbonyl)piperazin-2-one (compound A-283), ((R)-2-hydroxymethylpyrrolidin-1-yl)-(trans-4-{5-[6-(4-methylpyridin-2-ylamino)pyridin-2-yl]thiazol-2-yl}cyclohexyl)methanone (compound A-286), (4-aminopiperidin-1-yl)-(trans-4-{5-[6-(4-methylpyridin-2-ylamino)pyridin-2-yl]thiazol-2-yl}cyclohexyl)methanone (compound A-290),

[4-(2-{5-[6-(4-methylpyridin-2-ylamino)pyridin-2-yl]thiazol-2-yl}ethyl)piperidin-1-yl]-(piperidin-4-yl)methanone (compound A-295), (trans-4-{5-[6-(4-chloropyridin-2-ylamino)pyridin-2-yl]thiazol-2-yl}cyclohexyl)-(4-hydroxypiperidin-1-yl)methanone (compound A-297), N-(4-hydroxypiperidin-1-yl)-trans-4-{5-[6-(4-methylpyridin-2-ylamino)pyridin-2-yl]thiazol-2-yl}cyclohexanecarboxamide (compound A-298), N—[(R)-2-hydroxy-1-(3H-imidazol-4-ylmethyl)ethyl]-trans-4-{5-[6-(4-methylpyridin-2-ylamino)pyridin-2-yl]thiazol-2-yl}cyclohexanecarboxamide (compound A-303), N—[(S)-2-hydroxy-1-(3H-imidazol-4-ylmethyl)ethyl]-trans-4-{5-[6-(4-methylpyridin-2-ylamino)pyridin-2-yl]thiazol-2-yl}cyclohexanecarboxamide (compound A-304), N-(2-dimethylaminoethyl)-trans-4-{5-[6-(4-methylpyridin-2-ylamino)pyridin-2-yl]thiazol-2-yl}cyclohexanecarboxamide (compound A-309), (3-aminopyrrolidin-1-yl)-(trans-4-{5-[6-(4-methylpyridin-2-ylamino)pyridin-2-yl]thiazol-2-yl}cyclohexyl)methanone trihydrochloride (compound A-311), N-[1-(trans-4-{5-[6-(4-methylpyridin-2-ylamino)pyridin-2-yl]thiazol-2-yl}cyclohexanecarbonyl)pyrrolidin-3-yl]methanesulfonamide (compound A-312), (3R,4S)-1-(trans-4-{5-[6-(4-methylpyridin-2-ylamino)pyridin-2-yl]thiazol-2-yl}cyclohexylmethyl)pyrrolidin-3,4-diol (compound A-314), trans-4-{5-[6-(4-methylpyridin-2-ylamino)pyridin-2-yl]thiazol-2-yl}cyclohexanecarbonitrile (compound A-316), cis-4-{5-[6-(4-methylpyridin-2-ylamino)pyridin-2-yl]thiazol-2-yl}cyclohexanecarbonitrile (compound A-317), (S)-5-{5-[6-(4-methoxypyridin-2-ylamino)pyridin-2-yl]thiazol-2-yl}pyrrolidin-2-one (compound A-319), (S)-1-{5-[6-(4-methoxypyridin-2-ylamino)pyridin-2-yl]thiazol-2-yl}ethanol (compound A-320), (S)-1-(5-{6-[4-(2-hydroxyethyl)pyridin-2-ylamino]pyridin-2-yl}thiazol-2-yl)ethanol (compound A-321), (S)-1-{5-[6-(4-chloropyridin-2-ylamino)pyridin-2-yl]thiazol-2-yl}ethanol (compound A-322), (S)-5-{5-[6-(4-chloropyridin-2-ylamino)pyridin-2-yl]thiazol-2-yl}pyrrolidin-2-one (compound A-323), 3-(trans-4-{5-[6-(4-methylpyridin-2-ylamino)pyridin-2-yl]thiazol-2-yl}cyclohexyl)-4H-[1,2,4]oxazol-5-one (compound A-325), N-(4-methylpyridin-2-yl)-N-(6-{2-[4-(1H-tetrazol-5-yl)cyclohexyl]thiazol-5-yl}pyridin-2-yl)amine (compound A-326), (S)-5-(5-{6-[4-(2-hydroxyethyl)pyridin-2-ylamino]pyridin-2-yl}thiazol-2-yl)pyrrolidin-2-one (compound A-330), N-(1,1-dimethyl-2-{5-[6-(4-methylpyridin-2-ylamino)pyridin-2-yl]thiazol-2-yl}ethyl)acetamide (compound A-334), (S)-1-(5-{6-[4-(2-methyl-[1,3]dioxolan-2-yl)pyridin-2-ylamino]pyridin-2-yl}thiazol-2-yl)ethanol (compound A-335), N-methyl-trans-4-{5-[6-(4-methylpyridin-2-ylamino)pyridin-2-yl]thiazol-2-yl}cyclohexanecarboxamide (compound A-336), N-(1,1-dimethyl-2-{5-[6-(4-methylpyridin-2-ylamino)pyridin-2-yl]-thiazol-2-yl}ethyl)methanesulfonamide (compound A-337), trans-4-{5-[6-(4-chloropyridin-2-ylamino)pyridin-2-yl]thiazol-2-yl}cyclohexanecarboxamide (compound A-338), trans-4-{5-[6-(4-methoxypyridin-2-ylamino)pyridin-2-yl]thiazol-2-yl}cyclohexanecarboxamide (compound A-339), 4-{5-[6-(4-methylpyridin-2-ylamino)pyridin-2-yl]thiazol-2-ylmethyl}cyclohexanol (compound A-341), (S)-1-(5-{6-[4-(2-hydroxyethoxy)pyridin-2-ylamino]pyridin-2-yl}thiazol-2-yl)ethanol (compound A-344), dimethylcarbamic acid(S)-1-{5-[6-(4-methylpyridin-2-ylamino)pyridin-2-yl]thiazol-2-yl}ethyl ester (compound A-345), potassium carbonate 4-{5-[6-(4-methylpyridin-2-ylamino)pyridin-2-ylthiazol-2-ylmethyl}piperazin-2-one (compound A-351), 4-(2-hydroxy-2-{5-[6-(4-methylpyridin-2-ylamino)pyridin-2-yl]thiazol-2-yl}ethyl)phenol (compound A-362), 4-(2-{5-[6-(4-methylpyridin-2-ylamino)pyridin-2-yl]thiazol-2-ylmethoxy}acetyl)piperazin-2-one (compound A-370), N—((R)-(4-hydroxyphenyl)-{5-[6-(4-methylpyridin-2-ylamino)pyridin-2-yl]thiazol-2-yl}methyl)-N-methylacetamide (compound A-372), 4-{5-[6-(4-methylpyridin-2-ylamino)pyridin-2-yl]thiazol-2-ylmethyl}piperazine-2,6-dione (compound A-383), (S)-5-{5-[6-(4-methylpyridin-2-ylamino)pyridin-2-yl]thiazol-2-yl}oxazolidin-2-one (compound A-409), 4-{5-[6-(4-methylpyridin-2-ylamino)pyridin-2-yl]thiazol-2-ylmethyl}piperazin-2-one (compound A-416), N-(4-methylpyridin-2-yl)-N-[6-(2-morpholin-4-ylthiazol-5-yl)pyridin-2-yl]amine (compound A-417), 1-(4-{5-[6-(4-methylpyridin-2-ylamino)pyridin-2-yl]thiazol-2-yl}piperazin-1-yl)ethanone (compound A-419), 4-{5-[6-(4-methylpyridin-2-ylamino)pyridin-2-yl]thiazol-2-yl}piperazine-1-sulfonamide (compound A-421), N-(4-methoxypyridin-2-yl)-N-{6-[2-(morpholin-4-yl)thiazol-5-yl]pyridin-2-yl}amine (compound A-422), (3R,4S)-1-{5-[6-(4-methylpyridin-2-ylamino)pyridin-2-yl]thiazol-2-yl}pyrrolidine-3,4-diol (compound A-423), N-methyl-N-{5-[6-(4-methylpyridin-2-ylamino)pyridin-2-yl]thiazol-2-yl}acetamide (compound A-424), N-[6-(4-methyl-2-morpholin-4-ylthiazol-5-yl)pyridin-2-yl]-N-(4-methylpyridin-2-yl)amine (compound A-425), N-methyl-N-{5-[6-(4-methylpyridin-2-ylamino)pyridin-2-yl]thiazol-2-yl}amine (compound A-426), N-methyl-4-{5-[6-(4-methylpyridin-2-ylamino)pyridin-2-yl]thiazol-2-yl}piperazine-1-carboxamide (compound A-427), 1-{4-methyl-5-[6-(4-methylpyridin-2-ylamino)pyridin-2-yl]thiazol-2-yl}piperidine-4-carboxamide (compound A-429), N-{6-[2-(4-methoxypiperidin-1-yl)thiazol-5-yl]pyridin-2-yl}-N-(4-methylpyridin-2-yl)amine (compound A-431), N-{6-[2-(4-methylpiperazin-1-yl)thiazol-5-yl]pyridin-2-yl}-N-(4-methylpyridin-2-yl)amine (compound A-432), 1-{5-[6-(4-methylpyridin-2-ylamino)pyridin-2-yl]thiazol-2-yl}piperidin-4-ol (compound A-433), N-methyl-1-{5-[6-(4-methoxypyridin-2-ylamino)pyridin-2-yl]thiazol-2-yl}piperidine-4-carboxamide (compound A-436), 4-{4-methyl-5-[6-(4-methylpyridin-2-ylamino)pyridin-2-yl]thiazol-2-yl}piperazine-1-carbaldehyde (compound A-437), methyl 4-{5-[6-(4-methylpyridin-2-ylamino)pyridin-2-yl]thiazol-2-yl}piperazine-1-carboxylic acid methyl ester (compound A-438), 2-hydroxy-1-(4-{5-[6-(4-methylpyridin-2-ylamino)pyridin-2-yl]thiazol-2-yl}piperazin-1-yl)ethanone (compound A-439), 1-(4-{5-[6-(4-methylpyridin-2-ylamino)pyridin-2-yl]piperazin-1-yl)propan-1-one (compound A-440), N,N-dimethyl-4-{5-[6-(4-methylpyridin-2-ylamino)pyridin-2-yl]thiazol-2-yl}piperazine-1-carboxamide (compound A-441), 1-(4-{5-[6-(4-methoxypyridin-2-ylamino)pyridin-2-yl]thiazol-2-yl}piperazin-1-yl)ethanone (compound A-442), 1-(4-{5-[6-(4-chloropyridin-2-ylamino)pyridin-2-yl]thiazol-2-yl}piperazin-1-yl)ethanone (compound A-443), 4-(methyl-{5-[6-(4-methylpyridin-2-ylamino)pyridin-2-yl]thiazol-2-yl}amino)cyclohexanecarboxylic acid (compound A-444), 4-(N-methyl-N-{5-[6-(4-methylpyridin-2-ylamino)pyridin-2-yl]thiazol-2-yl}amino)cyclohexanecarboxamide (compound A-446), 3-(1-{5-[6-(4-methylpyridin-2-ylamino)pyridin-2-yl]thiazol-2-yl}piperidin-4-yl)-4H-[1,2,4]oxadiazole-5-one (compound A-450), N-methyl-N-{5-[6-(4-methylpyridin-2-ylamino)pyridin-2-yl]thiazol-2-yl}-N-piperidin-4-ylamine (compound A-452), 4-(1-{5-[6-(4-methylpyridin-2-ylamino)pyridin-2-yl]thiazol-2-yl}piperidine-4-carbonyl)piperazin-2-one (compound A-453), N-(2,2-dimethoxyethyl)-N-methyl-N-{5-[6-(4-methylpyridin-2-ylamino)pyridin-2-yl]thiazol-2-yl}amine (compound A-457), 1-[4-(N-methyl-N-{5-[6-(4-methylpyridin-2-ylamino)pyridin-2-yl]thiazol-2-yl}amino)piperidin-1-yl]ethanone (compound A-458), 2-hydroxy-1-[4-(N-methyl-N-{5-[6-(4-methylpyridin-2-ylamino)pyridin-2-yl]thiazol-2-yl}amino)piperidin-1-yl]ethanone (compound A-459), N-methyl-4-(N'-methyl-N'-{5-[6-(4-methylpyridin-2-ylamino)pyridin-2-yl]thiazol-2-yl}amino)piperidine-1-carboxamide (compound A-460), N-{2-[4-(N'-methyl-N'-{5-[6-(4-methylpyridin-2-ylamino)pyridin-2-yl]thiazol-2-yl}amino)piperidin-1-yl]-2-oxoethyl}acetamide (compound A-461), (4-{5-[6-(4-methylpyridin-2-ylamino)pyridin-2-yl]thiazol-2-yl}-2-oxopiperazin-1-yl)acetic acid dihydrochloride (compound A-464), 2-(4-{5-[6-(4-methylpyridin-2-ylamino)pyridin-2-yl]thiazol-2-yl}-2-oxopiperazin-1-yl)acetamide (compound A-465), N-methyl-2-(4-{5-[6-(4-methylpyridin-2-ylamino)pyridin-2-yl]thiazol-2-yl}-2-oxopiperazin-1-yl)acetamide (compound A-466), N-(2-hydroxyethyl)-2-(4-{5-[6-(4-methylpyridin-2-ylamino)pyridin-2-yl]thiazol-2-yl}-2-oxopiperazin-1-yl)acetamide (compound A-468), N-methyl-N-methylcarbamoylmethyl-1-{5-[6-(4-methylpyridin-2-ylamino)pyridin-2-yl]thiazol-2-yl}piperidine-4-carboxamide (compound A-469), N-methyl-N-{5-[6-(4-methylpyridin-2-ylamino)pyridin-2-yl]thiazol-2-yl}-N-tetrahydropyran-4-ylamine (compound A-470), 4-[(N-methyl-N-{5-[6-(4-methylpyridin-2-ylamino)pyridin-2-yl]thiazol-2-yl}amino)methyl]phenol (compound A-471), N—((R)-1-{5-[6-(4-methylpyridin-2-ylamino)pyridin-2-yl]thiazol-2-yl}pyrrolidin-3-yl)acetamide (compound A-472), (R)-1-{5-[6-(4-methylpyridin-2-ylamino)pyridin-2-yl]thiazol-2-yl}pyrrolidin-3-ylamine (compound A-473), 1-{5-[6-(4-methylpyridin-2-ylamino)pyridin-2-yl]thiazol-2-yl}piperidine-3-carboxylic acid (compound A-474), 2-hydroxy-N—((R)-1-{5-[6-(4-methylpyridin-2-ylamino)pyridin-2-yl]thiazol-2-yl}pyrrolidin-3-yl)acetamide (compound A-475), 1-{5-[6-(4-methylpyridin-2-ylamino)pyridin-2-yl]thiazol-2-yl}piperidine-3-carboxamide (compound A-476), N-methyl-1-{5-[6-(4-methylpyridin-2-ylamino)pyridin-2-yl]thiazol-2-yl}piperidine-3-carboxamide (compound A-477), N-(2-hydroxyethyl)-1-{5-[6-(4-methylpyridin-2-ylamino)pyridin-2-yl]thiazol-2-yl}piperidine-3-carboxamide (compound A-478), (R)-1-{5-[6-(4-methylpyridin-2-ylamino)pyridin-2-yl]thiazol-2-yl}pyrrolidin-3-ol (compound A-479), trans-4-(N-methyl-N-{5-[6-(4-methylpyridin-2-ylamino)pyridin-2-yl]thiazol-2-yl}amino)cyclohexanol (compound A-480), N-{6-[2-(3-methoxymethylpiperidin-1-yl)thiazol-5-yl]pyridin-2-yl}-N-(4-methylpyridin-2-yl)amine (compound A-481), 2-hydroxy-N-(1-{5-[6-(4-methylpyridin-2-ylamino)pyridin-2-yl]thiazol-2-yl}piperidin-4-yl)acetamide (compound A-482), 2-hydroxy-N-methyl-N-(1-{5-[6-(4-methylpyridin-2-ylamino)pyridin-2-yl]thiazol-2-yl}piperidin-4-yl)acetamide (compound A-483), N-(1-{5-[6-(4-methylpyridin-2-ylamino)pyridin-2-yl]thiazol-2-yl}piperidin-4-yl)methanesulfonamide (compound A-484), N-methyl-N-(1-{5-[6-(4-methylpyridin-2-ylamino)pyridin-2-yl]thiazol-2-yl}piperidin-4-yl)methanesulfonamide (compound A-485), 2-hydroxy-N-(1-{5-[6-(4-methylpyridin-2-ylamino)pyridin-2-yl]thiazol-2-yl}piperidin-4-ylmethyl)acetamide (compound A-486), N-(1-{5-[6-(4-methylpyridin-2-ylamino)pyridin-2-yl]thiazol-2-yl}piperidin-4-ylmethyl)acetamide (compound A-487), N-methyl-(S)-1-{5-[6-(4-methylpyridin-2-ylamino)pyridin-2-yl]thiazol-2-yl}pyrrolidine-2-carboxamide dihydrochloride (compound A-488), N—((R)-1-{5-[6-(4-methylpyridin-2-ylamino)pyridin-2-yl]thiazol-2-yl}pyrrolidin-3-yl)methanesulfonamide (compound A-489), N-{6-[2-((R)-3-methoxypyrrolidin-1-yl)thiazol-5-yl]pyridin-2-yl}-N-(4-methylpyridin-2-yl)amine (compound A-490), N-methyl-4-(N'-methyl-N'-{5-[6-(4-methylpyridin-2-ylamino)pyridin-2-yl]thiazol-2-yl}amino)cyclohexanecarboxamide (compound A-492), N-(2-hydroxyethyl)-4-(N'-methyl-N'-{5-[6-(4-methylpyridin-2-ylamino)pyridin-2-yl]thiazol-2-yl}amino)cyclohexanecarboxamide (compound A-493), N-(2-acetylaminoethyl)-4-(N'-methyl-N'-{5-[6-(4-methylpyridin-2-ylamino)pyridin-2-yl]thiazol-2-yl}amino)cyclohexanecarboxamide (compound A-494), (1-{5-[6-(4-methylpyridin-2-ylamino)pyridin-2-yl]thiazol-2-yl}piperidin-3-ylmethoxy)acetic acid dihydrochloride (compound A-497), (1-{5-[6-(4-methylpyridin-2-ylamino)pyridin-2-yl]thiazol-2-yl}piperidin-3-yl)methanol (compound A-498), 2-(1-{5-[6-(4-methylpyridin-2-ylamino)pyridin-2-yl]thiazol-2-yl}piperidin-3-ylmethoxy)acetamide (compound A-499), 4-methyl-1-{5-[6-(4-methylpyridin-2-ylamino)pyridin-2-yl]thiazol-2-yl}piperidine-4-carboxamide (compound A-500), N-methyl-4-methyl-1-{5-[6-(4-methylpyridin-2-ylamino)pyridin-2-yl]thiazol-2-yl}piperidine-4-carboxamide (compound A-501), N-methyl-2-(1-{5-[6-(4-methylpyridin-2-ylamino)pyridin-2-yl]thiazol-2-yl}piperidin-3-ylmethoxy)acetamide (compound A-502), N-(2-hydroxyethyl)-4-methyl-1-{5-[6-(4-methylpyridin-2-ylamino)pyridin-2-yl]thiazol-2-yl}-piperidine-4-carboxamide (compound A-503), 2-(1-{5-[6-(4-methylpyridin-2-ylamino)pyridin-2-yl]thiazol-2-yl}piperidin-4-yl)acetamide (compound A-504), N-methyl-2-(1-{5-[6-(4-methylpyridin-2-ylamino)pyridin-2-yl]thiazol-2-yl}piperidin-4-yl)acetamide (compound A-505), N-(2-hydroxyethyl)-2-(1-{5-[6-(4-methylpyridin-2-ylamino)pyridin-2-yl]thiazol-2-yl}piperidin-4-yl)acetamide (compound A-506), N,N-diallyl-N-{5-[6-(4-methylpyridin-2-ylamino)pyridin-2-yl]thiazol-2-yl}amine (compound A-507), N-[2-(N'-methyl-N'-{5-[6-(4-methylpyridin-2-ylamino)pyridin-2-yl]thiazol-2-yl}amino)ethyl]acetamide (compound A-508), 2-hydroxy-N-[2-(N'-methyl-{5-[6-(4-methylpyridin-2-ylamino)pyridin-2-yl]thiazol-2-yl}amino)ethyl]acetamide (compound A-509), N-(4-methanesulfonylpiperidin-1-yl)-N-methyl-N-{5-[6-(4-methylpyridin-2-ylamino)pyridin-2-yl]thiazol-2-yl}amine (compound A-510), N,N-dimethyl-4-(N'-methyl-N'-{5-[6-(4-methylpyridin-2-ylamino)pyridin-2-yl]thiazol-2-yl}amino)piperidine-1-carboxamide (compound A-511), (4-hydroxyphenyl)-[4-(N-methyl-N-{5-[6-(4-methylpyridin-2-ylamino)pyridin-2-yl]thiazol-2-yl}amino)piperidin-1-yl]methanone (compound A-513), 1-(4-{5-[6-(4-methylpyridin-2-ylamino)pyridin-2-yl]thiazol-2-ylamino}piperidin-1-yl)ethanone (compound A-514), 1-[4-(N-isopropyl-N-{5-[6-(4-methylpyridin-2-ylamino)pyridin-2-yl]thiazol-2-yl}amino)piperidin-1-yl]ethanone (compound A-515), N-methyl-2-((R)-1-{5-[6-(4-methylpyridin-2-ylamino)pyridin-2-yl]thiazol-2-yl}pyrrolidin-3-yloxy)acetamide (compound A-516), 1-{5-[6-(4-methoxypyridin-2-ylamino)pyridin-2-yl]thiazol-2-yl}piperidine-4-carboxamide (compound A-517), 1-{5-[6-(4-chloropyridin-2-ylamino)pyridin-2-yl]thiazol-2-yl}piperidine-4-carboxamide (compound A-518), 2-(N-methyl-N-{5-[6-(4-methylpyridin-2-ylamino)pyridin-2-yl]thiazol-2-yl}amino)ethanol (compound A-519), N-(2-methoxyethyl)-N-methyl-N-{5-[6-(4-methylpyridin-2-ylamino)pyridin-2-yl]thiazol-2-yl}amine (compound A-520), N-[2-(N'-(1-acetylpiperidin-4-yl)-N'-{5-[6-(4-methylpyridin-2-ylamino)pyridin-2-yl]thiazol-2-yl}amino)ethyl]methanesulfonamide (compound A-524), 1-[4-(N-(2-hydroxyethyl)-N-{5-[6-(4-methylpyridin-2-ylamino)pyridin-2-yl]thiazol-2-yl}amino)piperidin-1-yl]ethanone (compound A-525), 1-[4-(N-(2-methoxyethyl)-N-{5-[6-(4-methylpyridin-2-ylamino)pyridin-2-yl]thiazol-2-yl}amino)piperidin-1-yl]ethanone (compound A-526), (S)-1-{5-[6-(4-methylpyridin-2-ylamino)pyridin-2-yl]thiazol-2-yl}pyrrolidine-2-carboxamide (compound A-528), N-methyl-(S)-1-{5-[6-(4-methylpyridin-2-ylamino)pyridin-2-yl]thiazol-2-yl}pyrrolidine-2-carboxamide (compound A-529), N-(2,2,2-trifluoroethyl)-(S)-1-{5-[6-(4-methylpyridin-2-ylamino)pyridin-2-yl]thiazol-2-yl}pyrrolidine-2-carboxamide (compound A-530), (R)-1-{5-[6-(4-methylpyridin-2-ylamino)pyridin-2-yl]thiazol-2-yl}piperidine-3-carboxylic acid (compound A-531), ((R)-1-{5-[6-(4-methylpyridin-2-ylamino)pyridin-2-yl]thiazol-2-yl}piperidin-3-yl)methanol (compound A-532), (R)-1-{5-[6-(4-methylpyridin-2-ylamino)pyridin-2-yl]thiazol-2-yl}piperidine-3-carboxamide (compound A-533), 1-[4-(N-ethyl-N-{5-[6-(4-methylpyridin-2-ylamino)pyridin-2-yl]thiazol-2-yl}amino)piperidin-1-yl]ethanone (compound A-534), 1-{4-[N-{5-[6-(4-methylpyridin-2-ylamino)pyridin-2-yl]thiazol-2-yl}-N-(2,2,2-trifluoroethyl)amino]piperidin-1-yl}ethanone (compound A-535), 1-[4-(N-{5-[6-(4-chloropyridin-2-ylamino)pyridin-2-yl]thiazol-2-yl}-N-methylamino)piperidin-1-yl]ethanone (compound A-536), 1-[4-(N-{5-[6-(4-chloropyridin-2-ylamino)pyridin-2-yl]thiazol-2-yl}-N-methylamino)piperidin-1-yl]-2-hydroxy-ethanone (compound A-537), (R)-1-{5-[6-(4-methoxypyridin-2-ylamino)pyridin-2-yl]thiazol-2-yl}pyrrolidin-3-ol (compound A-538), (R)-1-{5-[6-(4-chloropyridin-2-ylamino)pyridin-2-yl]thiazol-2-yl}pyrrolidin-3-ol (compound A-539), 4-methyl-1-{5-[6-(4-methylpyridin-2-ylamino)pyridin-2-yl]thiazol-2-yl}piperidine-4-carboxylic acid (compound A-540), (S)-1-{5-[6-(4-methoxypyridin-2-ylamino)pyridin-2-yl]thiazol-2-yl}pyrrolidine-2-carboxamide (compound A-541), (S)-1-{5-[6-(4-chloropyridin-2-ylamino)pyridin-2-yl]thiazol-2-yl}pyrrolidine-2-carboxamide (compound A-542), 1-{5-[6-(4-acetylpyridin-2-ylamino)pyridin-2-yl]thiazol-2-yl}piperidine-4-carboxamide (compound A-543), 2-(N-(2-hydroxyethyl)-N-{5-[6-(4-methylpyridin-2-ylamino)pyridin-2-yl]thiazol-2-yl}amino)ethanol (compound A-544), 2-[N-{5-[6-(4-chloropyridin-2-ylamino)pyridin-2-yl]thiazol-2-yl}-N-(2-hydroxyethyl)amino]ethanol (compound A-545), (R)-1-{5-[6-(4-chloropyridin-2-ylamino)pyridin-2-yl]thiazol-2-yl}piperidine-3-carboxylic acid (compound A-546), 1-(5-{6-[4-(1-hydroxyethyl)pyridin-2-ylamino]pyridin-2-yl}thiazol-2-yl)piperidine-4-carboxamide (compound A-547), (R)-1-(5-{6-[4-(2-methyl-[1,3]dioxolan-2-yl)pyridin-2-ylamino]pyridin-2-yl}thiazol-2-yl)pyrrolidin-3-ol (compound A-548), 1-(2-{6-[2-((R)-3-hydroxypyrrolidin-1-yl)thiazol-5-yl]pyridin-2-ylamino}pyridin-4-yl)ethanone (compound A-549), 4-(4-{5-[6-(4-methylpyridin-2-ylamino)pyridin-2-yl]thiazol-2-yl}piperazin-1-yl)-4-oxobutyric acid (compound A-551), N-hydroxy-(R)-1-{5-[6-(4-chloropyridin-2-ylamino)pyridin-2-yl]thiazol-2-yl}piperidine-3-carboxamide (compound A-552), 4-[4-(N-methyl-N-{5-[6-(4-methylpyridin-2-ylamino)pyridin-2-yl]thiazol-2-yl}amino)piperidin-1-yl]-4-oxobutyric acid (compound A-553), (R)-1-(5-{6-[4-(1-hydroxyethyl)pyridin-2-ylamino]pyridin-2-yl}thiazol-2-yl)pyrrolidin-3-ol (compound A-554), 2-(N-methyl-N-{5-[6-(4-methylpyridin-2-ylamino)pyridin-2-yl]thiazol-2-yl}amino)acetamide (compound A-556), (R)-1-{5-(6-[4-(2-methyl-[1,3]dioxolan-2-yl)pyridin-2-ylamino]pyridin-2-yl}thiazol-2-yl)piperidine-3-carboxylic acid (compound A-558), (R)-1-{5-[6-(4-acetylpyridin-2-ylamino)pyridin-2-yl]thiazol-2-yl}piperidine-3-carboxylic acid (compound A-560), (S)-1-{5-[6-(4-acetylpyridin-2-ylamino)pyridin-2-yl]thiazol-2-yl}pyrrolidine-2-carboxamide (compound A-561), (1-{5-[6-(4-chloropyridin-2-ylamino)pyridin-2-yl]thiazol-2-yl}pyrrolidin-3-yl)methanol (compound A-562), 1-[(R)-3-(N-methyl-N-{5-[6-(4-methylpyridin-2-ylamino)pyridin-2-yl]thiazol-2-yl}amino)pyrrolidin-1-yl]ethanone (compound A-563), (S)-1-{5-[6-(4-acetylpyridin-2-ylamino)pyridin-2-yl]thiazol-2-yl}pyrrolidine-2-carboxylic acid dihydrochloride (compound A-564), (R)-1-(5-{6-[4-(2-methyl-[1,3]dioxolan-2-yl)pyridin-2-ylamino]pyridin-2-yl}thiazol-2-yl)piperidine-3-carboxamide (compound A-565), ((S)-1-{5-[6-(4-methylpyridin-2-ylamino)pyridin-2-yl]thiazol-2-yl}piperidin-3-yl)acetic acid (compound A-567), (S)-3-methyl-2-[2-(N-methyl-N-{5-[6-(4-methylpyridin-2-ylamino)pyridin-2-yl]thiazol-2-yl}amino)acetylamino]butyric acid dihydrochloride (compound A-568), 3-[2-(N-methyl-N-{5-[6-(4-methylpyridin-2-ylamino)pyridin-2-yl]thiazol-2-yl}amino)acetylamino]propionic acid dihydrochloride (compound A-570),

[2-(N-methyl-N-{5-[6-(4-methylpyridin-2-ylamino)pyridin-2-yl]thiazol-2-yl}amino)acetylamino]acetic acid dihydrochloride (compound A-571),

[1-(5-{6-[4-(2-methyl-[1,3]dioxolan-2-yl)pyridin-2-ylamino]pyridin-2-yl}thiazol-2-yl)piperidin-4-yl]acetic acid dihydrochloride (compound A-572), (1-{5-[6-(pyridin-2-ylamino)pyridin-2-yl]thiazol-2-yl}piperidin-4-yl)acetic acid dihydrochloride (compound A-573), 4-[(N-methyl-N-{5-[6-(4-methylpyridin-2-ylamino)pyridin-2-yl]thiazol-2-yl}amino)methyl]benzoic acid dihydrochloride (compound A-574), ((R)-1-{5-[6-(4-methylpyridin-2-ylamino)pyridin-2-yl]thiazol-2-yl}pyrrolidin-3-yloxy)acetic acid dihydrochloride (compound A-575), 1-{5-[6-(4-methylpyridin-2-ylamino)pyridin-2-yl]thiazol-2-yl}pyrrolidine-3-carboxylic acid dihydrochloride (compound A-576), (R)-1-(5-{6-[4-(2-hydroxyethyl)pyridin-2-ylamino]pyridin-2-yl}thiazol-2-yl)pyrrolidin-3-ol dihydrochloride (compound A-577), 4-(N-methyl-N-{5-[6-(4-methylpyridin-2-ylamino)pyridin-2-yl]thiazol-2-yl}amino)benzoic acid (compound A-578), (2S,4R)-4-(N-methyl-N-{5-[6-(4-methylpyridin-2-ylamino)pyridin-2-yl]thiazol-2-yl}amino)pyrrolidine-2-carboxylic acid (compound A-579), {N-methyl-N-[2-(N'-methyl-N'-{5-[6-(4-methylpyridin-2-ylamino)pyridin-2-yl]thiazol-2-yl}amino)acetyl]amino}acetic acid dihydrochloride (compound A-580), 2-{5-[6-(4-methylpyridin-2-ylamino)pyridin-2-yl]thiazol-2-yl}-1,2,3,4-tetrahydroisoquinoline-5-carboxylic acid (compound A-582), 3-[(N-methyl-N-{5-[6-(4-methylpyridin-2-ylamino)pyridin-2-yl]thiazol-2-yl}amino)methyl]benzoic acid dihydrochloride (compound A-586), {4-[(N-methyl-N-{5-[6-(4-methylpyridin-2-ylamino)pyridin-2-yl]thiazol-2-yl}amino)methyl]phenyl}acetic acid dihydrochloride (compound A-587), (1-{5-[6-(4-methylpyridin-2-ylamino)pyridin-2-yl]thiazol-2-yl}pyrrolidin-3-yl)acetic acid (compound A-588), (4-{5-[6-(4-methylpyridin-2-ylamino)pyridin-2-yl]thiazol-2-yl}piperazin-1-yl)acetic acid dihydrochloride (compound A-589), N-(4-methylpyridin-2-yl)-N-(6-{2-[(R)-3-(1H-tetrazol-5-yl)piperidin-1-yl]thiazol-5-yl}pyridin-2-yl)amine (compound A-590), cis-4-(N-methyl-N-{5-[6-(4-methylpyridin-2-ylamino)pyridin-2-yl]thiazol-2-yl}amino)cyclohexanecarboxylic acid (compound A-591), trans-4-(N-methyl-N-{5-[6-(4-methylpyridin-2-ylamino)pyridin-2-yl]thiazol-2-yl}amino)cyclohexanecarboxylic acid (compound A-592), 4-[2-(N-methyl-N-{5-[6-(4-methylpyridin-2-ylamino)pyridin-2-yl]thiazol-2-yl}amino)ethyl]benzoic acid dihydrochloride (compound A-593), (1-{5-[6-(4-methylpyridin-2-ylamino)pyridin-2-yl]thiazol-2-yl}piperidin-4-yloxy)acetic acid dihydrochloride (compound A-594), (4-{5-[6-(4-methylpyridin-2-ylamino)pyridin-2-yl]thiazol-2-yl}cyclohexyl)acetic acid hydrochloride (compound A-595), 4-{[N-methyl-N-(5-{6-[4-(2-methyl-[1,3]dioxolan-2-yl)pyridin-2-ylamino]pyridin-2-yl}thiazol-2-yl)amino]methyl}benzoic acid (compound A-596), 4-[(N-dimethylcarbamoylmethyl-N-{5-[6-(4-methylpyridin-2-ylamino)pyridin-2-yl]thiazol-2-yl}amino)methyl]benzoic acid dihydrochloride (compound A-597), cis-4-(N-carbamoylmethyl-N-{5-[6-(4-methylpyridin-2-ylamino)pyridin-2-yl]thiazol-2-yl}amino)cyclohexanecarboxylic acid (compound A-598), trans-4-[(N-carbamoylmethyl-N-{5-[6-(4-methylpyridin-2-ylamino)pyridin-2-yl]thiazol-2-yl}amino)methyl]cyclohexanecarboxylic acid (compound A-599), 5-[(N-methyl-N-{5-[6-(4-methylpyridin-2-ylamino)pyridin-2-yl]thiazol-2-yl}amino)methyl]thiophene-2-carboxylic acid (compound A-603), 3-chloro-4-[(N-methyl-N-{5-[6-(4-methylpyridin-2-ylamino)pyridin-2-yl]thiazol-2-yl}amino)methyl]benzoic acid dihydrochloride (compound A-604), 4-{5-[6-(4-methylpyridin-2-ylamino)pyridin-2-yl]thiazol-2-ylmethoxy}benzoic acid (compound A-605), 3-methoxy-4-[(N-methyl-N-{5-[6-(4-methylpyridin-2-ylamino)pyridin-2-yl]thiazol-2-yl}amino)methyl]benzoic acid dihydrochloride (compound A-606), 2-{5-[6-(4-methylpyridin-2-ylamino)pyridin-2-yl]thiazol-2-yl}-1,2,3,4-tetrahydroisoquinoline-6-carboxylic acid (compound A-607), 2-[(N-methyl-N-{5-[6-(4-methylpyridin-2-ylamino)pyridin-2-yl]thiazol-2-yl}amino)methyl]thiazole-4-carboxylic acid (compound A-609),

[trans-4-(N-methyl-N-{5-[6-(4-methylpyridin-2-ylamino)pyridin-2-yl]thiazol-2-yl}amino)cyclohexyl]acetic acid (compound A-610),

[cis-4-(N-methyl-N-{5-[6-(4-methylpyridin-2-ylamino)pyridin-2-yl]thiazol-2-yl}amino)cyclohexyl]acetic acid (compound A-611), 4-(2-{5-[6-(4-methylpyridin-2-ylamino)pyridin-2-yl]thiazol-2-yl}ethyl)cyclohexanecarboxylic acid (compound A-612), (4-methyl-1-{5-[6-(4-methylpyridin-2-ylamino)pyridin-2-yl]thiazol-2-yl}piperidin-4-yl)acetic acid dihydrochloride (compound A-613), 4-{5-[6-(4-methylpyridin-2-ylamino)pyridin-2-yl]thiazol-2-yl}-3,4-dihydro-2H-benzo[1,4]oxazine-8-carboxylic acid (compound A-614), {5-[6-(4-methylpyridin-2-ylamino)pyridin-2-ylmethoxy}acetic acid hydrochloride (compound A-615), 4-[1-methyl-1-(N-methyl-N-{5-[6-(4-methylpyridin-2-ylamino)pyridin-2-yl]thiazol-2-yl}amino)ethyl]benzoic acid dihydrochloride (compound A-616),

[4-(N-methyl-N-{5-[6-(4-methylpyridin-2-ylamino)pyridin-2-yl]thiazol-2-yl}amino)phenyl]acetic acid dihydrochloride (compound A-617), (1-{5-[6-(4-chloropyridin-2-ylamino)pyridin-2-yl]thiazol-2-yl}piperidin-4-yl)acetic acid dihydrochloride (compound A-620), trans-4-[(N-benzyl-N-{5-[6-(4-methylpyridin-2-ylamino)pyridin-2-yl]thiazol-2-yl}amino)methyl]cyclohexanecarboxylic acid (compound A-622),

[trans-4-(N-benzyl-N-{5-[6-(4-methylpyridin-2-ylamino)pyridin-2-yl]thiazol-2-yl}amino)cyclohexyl]acetic acid (compound A-624), trans-4-[(N-isopropyl-N-{5-[6-(4-methylpyridin-2-ylamino)pyridin-2-yl]thiazol-2-yl}amino)methyl]cyclohexanecarboxylic acid (compound A-626), 1-{5-[6-(4-methylpyridin-2-ylamino)pyridin-2-yl]thiazol-2-yl}-1,2,3,4-tetrahydroquinoline-5-carboxylic acid (compound A-627), fluoro-(1-{5-[6-(4-methylpyridin-2-ylamino)pyridin-2-yl]thiazol-2-yl}piperidin-4-ylidene)acetic acid (compound A-631), 5-(N-methyl-N-{5-[6-(4-methylpyridin-2-ylamino)pyridin-2-yl]thiazol-2-yl}amino)pentanoic acid (compound A-632), N-[2-(1-{5-[6-(4-methylpyridin-2-ylamino)pyridin-2-yl]thiazol-2-yl}piperidin-4-yl)acetyl]methanesulfonamide (compound A-633), 4-(N-methyl-N-{5-[6-(4-methylpyridin-2-ylamino)pyridin-2-yl]thiazol-2-yl}amino)butyric acid dihydrochloride (compound A-634), (1-{5-[6-(4-trifluoromethylpyridin-2-ylamino)pyridin-2-yl]thiazol-2-yl}piperidin-4-yl)acetic acid dihydrochloride (compound A-635), (1-{5-[6-(5-chloropyridin-2-ylamino)pyridin-2-yl]thiazol-2-yl}piperidin-4-yl)acetic acid dihydrochloride (compound A-636), (1-{5-[6-(4-methoxypyridin-2-ylamino)pyridin-2-yl]thiazol-2-yl}piperidin-4-yl)acetic acid dihydrochloride (compound A-637), trans-4-(N-methyl-N-{5-[6-(4-trifluoromethylpyridin-2-ylamino)pyridin-2-yl]thiazol-2-yl}amino)cyclohexanecarboxylic acid (compound A-638), 3-[4-(N-methyl-N-{5-[6-(4-methylpyridin-2-ylamino)pyridin-2-yl]thiazol-2-yl}amino)phenyl]propionic acid (compound A-639), (E)-6-(N-methyl-N-{5-[6-(4-methylpyridin-2-ylamino)pyridin-2-yl]thiazol-2-yl}amino)hex-2-enoic acid dihydrochloride (compound A-640), (2-{5-[6-(4-methylpyridin-2-ylamino)pyridin-2-yl]thiazol-2-yl}-1,2,3,4-tetrahydroisoquinolin-6-yl)acetic acid (compound A-641), 3-(2-{5-[6-(4-methylpyridin-2-ylamino)pyridin-2-yl]thiazol-2-yl}-1,2,3,4-tetrahydroisoquinolin-5-yl)propionic acid (compound A-642), 5-(N-isopropyl-N-{5-[6-(4-methylpyridin-2-ylamino)pyridin-2-yl]thiazol-2-yl}amino)pentanoic acid (compound A-643), 5-{5-[6-(4-methylpyridin-2-ylamino)pyridin-2-yl]thiazol-2-ylamino}pentanoic acid (compound A-644), 6-(N-methyl-N-{5-[6-(4-methylpyridin-2-ylamino)pyridin-2-yl]thiazol-2-yl}amino)hexanoic acid dihydrochloride (compound A-645), (Z)-2-fluoro-6-(N-methyl-N-{5-[6-(4-methylpyridin-2-ylamino)pyridin-2-yl]thiazol-2-yl}amino)hex-2-enoic acid dihydrochloride (compound A-647), (8-{5-[6-(4-trifluoromethylpyridin-2-ylamino)pyridin-2-yl]thiazol-2-yl}-8-azabicyclo[3.2.1]oct-3-yl)acetic acid (compound A-648), (8-{5-[6-(4-methylpyridin-2-ylamino)pyridin-2-yl]thiazol-2-yl}-8-azabicyclo[3.2.1]oct-3-yl)acetic acid (compound A-649), (1-{5-[6-(4-cyanopyridin-2-ylamino)pyridin-2-yl]thiazol-2-yl}piperidin-4-yl)acetic acid dihydrochloride (compound A-650), {4-[(N-methyl-N-{5-[6-(4-trifluoromethylpyridin-2-ylamino)pyridin-2-yl]thiazol-2-yl}amino)methyl]phenyl}acetic acid (compound A-651), 2-(1-{5-[6-(4-methylpyridin-2-ylamino)pyridin-2-yl]thiazol-2-yl}piperidin-4-yl)propionic acid (compound A-652), (1-{5-[6-(4-methylpyridin-2-ylamino)pyridin-2-yl]thiazol-2-yl}piperidin-4-yl)acetic acid (compound A-653), 4-[1-methyl-1-(N-methyl-N-{5-[6-(4-trifluoromethylpyridin-2-ylamino)pyridin-2-yl]thiazol-2-yl}amino)ethyl]benzoic acid (compound A-654),
3-methyl-6-(N-methyl-N-{5-[6-(4-trifluoromethylpyridin-2-ylamino)pyridin-2-yl]thiazol-2-yl}amino)hex-2-enoic acid dihydrochloride (compound A-655),
3-methyl-6-(N-methyl-N-{5-[6-(4-methylpyridin-2-ylamino)pyridin-2-yl]thiazol-2-yl}amino)hex-2-enoic acid dihydrochloride (compound A-656),
(E)-6-(N-methyl-N-{5-[6-(4-trifluoromethylpyridin-2-ylamino)pyridin-2-yl]thiazol-2-yl}amino)hex-2-enoic acid dihydrochloride (compound A-657),
N-(2-hydroxyethyl)-(S)-1-{5-[6-(4-methylpyridin-2-ylamino)pyridin-2-yl]thiazol-2-yl}pyrrolidine-2-carboxamide (compound A-658),
2-(N-isopropyl-N-{5-[6-(4-methylpyridin-2-ylamino)pyridin-2-yl]thiazol-2-yl}amino)acetamide (compound A-663),
3-methyl-2-(N-methyl-N-{5-[6-(4-methylpyridin-2-ylamino)pyridin-2-yl]thiazol-2-yl}amino)butylamide (compound A-668),
2-(1-{5-[6-(4-methylpyridin-2-ylamino)pyridin-2-yl]thiazol-2-yl}piperidin-4-yl)ethanol (compound A-677),
5-(N-isopropyl-N-{5-[6-(4-methylpyridin-2-ylamino)pyridin-2-yl]thiazol-2-yl}amino)pentan-1-ol (compound A-678),
(1-{5-[6-(pyrazin-2-ylamino)pyridin-2-yl]thiazol-2-yl}piperidin-4-yl)acetic acid (compound A-680),
[1-(5-{6-[4-(2-hydroxyethyl)pyridin-2-ylamino]pyridin-2-yl}thiazol-2-yl)piperidin-4-yl]acetic acid dihydrochloride (compound A-681),
fluoro-(1-{5-[6-(4-methylpyridin-2-ylamino)pyridin-2-yl]thiazol-2-yl}piperidin-4-yl)acetic acid (compound A-684),
1-{5-[6-(4-methylpyridin-2-ylamino)pyridin-2-yl]thiazol-2-ylmethyl}piperidine-4-carboxamide (compound A-685),
(1-{5-[6-(4-ethylpyridin-2-ylamino)pyridin-2-yl]thiazol-2-yl}piperidin-4-yl)acetic acid dihydrochloride (compound A-692),
N-isopropyl-N-{5-[6-(4-methylpyridin-2-ylamino)pyridin-2-yl]thiazol-2-yl}amine (compound A-693),
N-{5-[6-(4-methylpyridin-2-ylamino)pyridin-2-yl]thiazol-2-yl}-N-(2-morpholin-4-ylethyl)amine (compound A-695),
2-(N-methyl-N-{5-[6-(4-methylpyridin-2-ylamino)pyridin-2-yl]thiazol-2-ylmethyl}amino)acetamide (compound A-697),
2-(1-{5-[6-(4-methylpyridin-2-ylamino)pyridin-2-yl]thiazol-2-yl}piperidin-4-yl)butyric acid (compound A-698),
trans-4-[(N-methyl-N-{5-[6-(pyridin-2-ylamino)pyridin-2-yl]thiazol-2-yl}amino)methyl]cyclohexanecarboxylic acid dihydrochloride (compound A-699),
[1-(5-{6-[4-(2,2,2-trifluoroethoxy)pyridin-2-ylamino]pyridin-2-yl}thiazol-2-yl)piperidin-4-yl]acetic acid dihydrochloride (compound A-700),
2-methyl-1-(N-methyl-N-{5-[6-(4-methylpyridin-2-ylamino)pyridin-2-yl]thiazol-2-yl}amino)propan-2-ol (compound A-702),
3-(1-{5-[6-(4-methylpyridin-2-ylamino)pyridin-2-yl]thiazol-2-yl}piperidin-3-yl)propionic acid (compound A-704),
N-(2-hydroxyethyl)-4-(N'-methyl-N'-{5-[6-(4-methylpyridin-2-ylamino)pyridin-2-yl]thiazol-2-yl}amino)piperidine-1-carboxamide (compound A-705),
2-methyl-2-(1-{5-[6-(pyrazin-2-ylamino)pyridin-2-yl]thiazol-2-yl}piperidin-4-yl)propionic acid dihydrochloride (compound A-707),
4-[(N-acetyl-N-{5-[6-(4-methylpyridin-2-ylamino)pyridin-2-yl]thiazol-2-ylmethyl}amino)methyl]benzoic acid (compound A-709),
(1-{5-[6-(4-tert-butylpyridin-2-ylamino)pyridin-2-yl]thiazol-2-yl}piperidin-4-yl)acetic acid dihydrochloride (compound A-710),
(1-{5-[6-(4-isopropylpyridin-2-ylamino)pyridin-2-yl]thiazol-2-yl}piperidin-4-yl)acetic acid dihydrochloride (compound A-711),
6-{5-[6-(4-methylpyridin-2-ylamino)pyridin-2-yl]thiazol-2-yl}-6-azaspiro[2.5]octane-1-carboxylic acid (compound A-712),
2-[1-(5-{6-[4-(2-hydroxyethyl)pyridin-2-ylamino]pyridin-2-yl}thiazol-2-yl)piperidin-4-yl]-2-methylpropionic acid (compound A-713),
2-methyl-2-(1-{5-[6-(pyridin-2-ylamino)pyridin-2-yl]thiazol-2-yl}piperidin-4-yl)propionic acid (compound A-714),
fluoro-(1-{5-[6-(pyrazin-2-ylamino)pyridin-2-yl]thiazol-2-yl}piperidin-4-yl)acetic acid dihydrochloride (compound A-715),
fluoro-(1-{5-[6-(pyridin-2-ylamino)pyridin-2-yl]thiazol-2-yl}piperidin-4-yl)acetic acid dihydrochloride (compound A-716),
[1-(5-{6-[4-(1-hydroxy-1-methylethyl)pyridin-2-ylamino]pyridin-2-yl}thiazol-2-yl)piperidin-4-yl]acetic acid dihydrochloride (compound A-717),
2-methyl-2-(1-{5-[6-(4-methylpyridin-2-ylamino)pyridin-2-yl]thiazol-2-yl}piperidin-4-yl)propionic acid dihydrochloride (compound A-718),
5-(1-{5-[6-(4-methylpyridin-2-ylamino)pyridin-2-yl]thiazol-2-yl}piperidin-3-yl)pentanoic acid dihydrochloride (compound A-719),
2-methyl-2-(N-methyl-N-{5-[6-(4-methylpyridin-2-ylamino)pyridin-2-yl]thiazol-2-ylmethyl}amino)propionamide (compound A-720),
1-{5-[6-(4-methylpyridin-2-ylamino)pyridin-2-yl]thiophen-2-yl}ethanone (compound B-1),
5-[6-(4-methylpyridin-2-ylamino)pyridin-2-yl]thiophene-2-carbaldehyde (compound B-2),
1-{5-[6-(4-methylpyridin-2-ylamino)pyridin-2-yl]thiophen-2-yl}ethanol (compound B-3),
acetic acid 1-{5-[6-(4-methylpyridin-2-ylamino)pyridin-2-yl]thiophen-2-yl}ethyl ester (compound B-4),
N-{5-[6-(4-methylpyridin-2-ylamino)pyridin-2-yl]thiophen-2-yl}acetamide (compound B-10),
N-methyl-5-[6-(4-methylpyridin-2-ylamino)pyridin-2-yl]thiophene-2-carboxamide (compound B-11),
{5-[6-(4-methylpyridin-2-ylamino)pyridin-2-yl]thiophen-2-yl}methanol (compound B-12),
1-{5-[6-(4-methylpyridin-2-ylamino)pyridin-2-yl]thiophen-2-yl}ethanone oxime (compound B-15),
1-{5-[6-(4-methoxypyridin-2-ylamino)pyridin-2-yl]thiophen-2-yl}ethanone (compound B-17),
5-[6-(4-methylpyridin-2-ylamino)pyridin-2-yl]thiophene-2-carboxamide (compound B-23),
1-{5-[6-(6-isopropoxypyrimidin-4-ylamino)pyridin-2-yl]thiophen-2-yl}ethanone (compound B-30),
N-{5-[6-(4-methylpyridin-2-ylamino)pyridin-2-yl]thiophen-2-yl}acetamide (compound B-31),
1-{5-[6-(4-methylpyridin-2-ylamino)pyridin-2-yl]thiophen-2-yl}ethanone O-(2-hydroxyethyl)oxime (compound B-38),
N-(2-aminoethyl)-5-[6-(4-methylpyridin-2-ylamino)pyridin-2-yl]thiophene-2-carboxamide (compound B-43),
1-{5-[6-(4-methylpyridin-2-ylamino)pyridin-2-yl]thiophen-2-yl}propan-1-one oxime (compound B-51), {2-[6-(5-acetylthiophen-2-yl)pyridin-2-ylamino]pyridin-4-yl}acetic acid ethyl ester (compound B-52), 2-[6-(5-acetylthiophen-2-yl)pyridin-2-ylamino]isonicotinic acid methyl ester (compound B-53), 1-(5-{6-[4-(2-hydroxyethyl)pyridin-2-ylamino]pyridin-2-yl}thiophen-2-yl)ethanol (compound B-55), N-hydroxy-5-[6-(4-methylpyridin-2-ylamino)pyridin-2-yl]thiophene-2-carboxyamidine (compound B-60), 1-(5-{6-[4-(2-hydroxyethoxy)pyridin-2-ylamino]pyridin-2-yl}thiophen-2-yl)ethanone (compound B-73), 1-{5-[6-(4-chloropyridin-2-ylamino)pyridin-2-yl]thiophen-2-yl}ethanone (compound B-74), 1-{5-[6-(4-chloropyridin-2-ylamino)pyridin-2-yl]thiophen-2-yl}ethanone oxime (compound B-75), {5-[6-(4-methylpyridin-2-ylamino)pyridin-2-yl]thiophen-2-yl}piperazin-1-ylmethanone (compound B-84), 1-(5-{6-[4-(4,4-dimethyl-4,5-dihydrooxazol-2-yl)pyridin-2-ylamino]pyridin-2-yl}thiophen-2-yl)ethanone (compound B-87), 2,2-difluoro-3-hydroxy-3-{5-[6-(4-methylpyridin-2-ylamino)pyridin-2-yl]thiophen-2-yl}propionic acid (compound B-109), 4-[({5-[6-(4-methylpyridin-2-ylamino)pyridin-2-yl]thiophen-2-ylmethyl}amino)methyl]benzoic acid (compound B-116), 4-[(N-acetyl-N-{5-[6-(4-methylpyridin-2-ylamino)pyridin-2-yl]thiophen-2-ylmethyl}amino)methyl]benzoic acid (compound B-119), trans-4-[(N-acetyl-N-{5-[6-(4-methylpyridin-2-ylamino)pyridin-2-yl]thiophen-2-ylmethyl}amino)methyl]cyclohexanecarboxylic acid (compound B-120), 3-(N-acetyl-N-{5-[6-(4-methylpyridin-2-ylamino)pyridin-2-yl]thiophen-2-ylmethyl}amino)propionic acid hydrochloride (compound B-124), 4-[(N-isobutyryl-N-{5-[6-(4-methylpyridin-2-ylamino)pyridin-2-yl]thiophen-2-ylmethyl}amino)methyl]benzoic acid (compound B-127) and 4-[(N-(2-hydroxyacetyl)-N-{5-[6-(4-methylpyridin-2-ylamino)pyridin-2-yl]thiophen-2-ylmethyl}amino)methyl]benzoic acid (compound B-128).

As for the salt of a compound represented by formula (I), pharmacologically acceptable salts are preferable, and examples thereof include a salt with an inorganic base, a salt with an organic base, a salt with an inorganic acid, a salt with an organic acid, a salt with a basic or acidic amino acid, etc.

Preferable examples of a salt with an inorganic base include, for example, a salt with an alkaline metal such as sodium, potassium, a salt with an alkaline earth metal such as calcium, magnesium as well as salts with aluminium, ammonium, etc.

Preferable examples of a salt with an organic base include, for example, salts with trimethylamine, triethylamine, pyridine, picoline, ethanolamine, diethanolamine, triethanolamine, dicyclohexylamine, N,N-dibenzylethylenediamine, etc.

Preferable examples of a salt with an inorganic acid include, for example, salts with hydrochloric acid, hydrobromic acid, nitric acid, sulfuric acid, phosphoric acid, etc.

Preferable examples of a salt with an organic acid include, for example, salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.

Preferable examples of a salt with a basic amino acid include, for example, salts with arginine, lysin, ornithine, and, preferable examples of a salt with an acidic amino acid include, for example, salts with aspartic acid, glutamic acid, etc.

The compound of the present invention has excellent Syk inhibitory effect and is useful as a therapeutic agent for allergic diseases or a therapeutic agent for autoimmune diseases.

When the compound of the present invention is used as a drug for allergic diseases, particularly a drug for bronchial asthma, a drug for allergic rhinitis, a drug for allergic dermatitis and a drug for allergic conjunctivitis, or a drug for autoimmune diseases, a drug for rheumatoid arthritis, a drug for systemic lupus erythematosus, a drug for multiple sclerosis, a drug for malignant tumor, a drug for B-lymphoma, B-cell leukemia; usually it is administered systemically or locally, orally or parenterally.

More specifically, the compound (I) of the present invention or a salt thereof can be combined with a pharmaceutically acceptable carrier and administered orally or parenterally as a solid preparation such as tablet, capsule, granule and powder; or a liquid preparation such as syrup and injection.

The administration may be in any form of oral administration by tablet, pill, capsule, granule, powder, liquid, etc. or parenteral administration by injection such as intravenous infusion, intramuscular injection, suppository or percutaneous preparation. The parenteral administration includes intravenous, intramuscular, subcutaneous administration, administration into a tissue, intranosal, intracutaneous injection, drip infusion, intracerebral, intracerebral, intrarectal, intravaginal, intraabdominal interperitoneal, etc.

As the solid composition for oral administration according to the present invention, tablet, powder, granule, etc. are used. In such a solid composition, one or more active substance is mixed with at least one inert diluent, for example, lactose, mannitol, glucose, hydroxypropylcellulose, microcrystalline cellulose, starch, polyvinylpyrrolidone, magnesium aluminometasilicate, etc. The composition may contain additives in addition to the inert diluent, for example, a lubricant such as magnesium stearate, a disintegrating agent such as calcium carboxymethylcellulose, a stabilizer such as lactose, a solubilizing agent such as glutamic acid or aspartic acid according to a conventional method. Tablet or pill may be coated with a coating of sucrose, gelatine, hydroxypropylcellulose, hydroxypropyl methylcellulose, hydroxypropyl methylcellulose phthalate, macrosol, titanium dioxide, talc, or gastric or enteric film as required.

The liquid composition for oral administration includes pharmaceutically acceptable emulsion, liquid drug, suspension, syrup, and elixir, and may contain a commonly used inert solvent, for example, purified water and ethanol. This composition may contain auxiliary agents such as solubilizing agent, humecant, suspending agent, sweetener, corrective, flavor and preservative in addition to the inert solvent.

The injection for parenteral administration can be produced by dissolving, suspending or emulsifying a predetermined amount of an active agent in an aqueous solvent (for example, distilled water for injection, physiologic saline, Ringer's solution, etc.) or an oily solvent (for example, vegetable oil such as olive oil, sesame oil, cotton oil, corn oil, propylene glycol, etc.) together with a dispersing agent (for example, polysorbate 80, polyoxyethylene hydrogenated castor oil 60, polyethylene glycol, carboxymetyl-cellulose, sodium alginate, etc.), preservative (for example, methylparaben, propylparaben, benzyl alcohol, chlorobutanol, phenol, etc.), isotonizing agent (for example, sodium chloride, glycerine, D-mannitol, D-sorbitol, glucose, etc.), etc.

At this time, additives such as a solubilizer (for example, sodium salicylate, sodium acetate, etc.), a stabilizer (for example, human serum albumin, etc.) and a soothing agent (for example, benzyl alcohol, etc.) may be optionally used.

Further, preservative, anti oxidant, coloring agent, flavoring agent, sweetening agent, absorbing agent, hydrating agent and other additives may be contained as required.

As a pharmaceutically acceptable carrier, various organic or an inorganic support materials conventionally used as pharmaceutical materials can be mentioned. An excipient, lubricant, binder, disintegrating agent are appropriately added to a solid preparation, and a solvent, solubilizer, suspending agent, isotonizing agent, buffer, soothing agent are appropriately added to a liquid preparation. In addition, pharmaceutical additives such as a preservative, anti oxidant, coloring agent, sweetening agent, absorbing agents, hydrating agent, etc. may be used as required according to a conventional method.

Preferable examples of an excipient include lactose, corn starch, saccharose, D-mannitol, D-sorbitol, starch, dextrin, crystal cellulose, low-substituted hydroxypropylcellulose, sodium carboxymethylcellulose, gum arabic, glucose, silicon dioxide, etc.

Preferable examples of an anti oxidant include, for example, a sulfite salt, ascorbic acid, etc.

Preferable examples of a disintegrating agent include, for example, carboxymetylcellulose, carboxymetylcellulose calcium, sodium carboxymethyl starch, sodium croscarmellose, crospovidone, low-substituted hydroxypropylcellulose, hydroxypropyl starch, etc.

Preferable examples of a binder include, for example, hydroxypropylcellulose, hydroxypropyl methylcellulose, polyvinylpyrrolidone, crystal cellulose, saccharose, powdered gum arabic, etc. Preferably binder is hydroxypropylcellulose or polyvinylpyrrolidone. Polyvinylpyrrolidone is preferable inter alia when the active ingredient used in the present invention is metformin hydrochloride.

Preferable examples of a lubricant include, for example, magnesium stearate, calcium stearate, talc, colloidal silica, etc.

Preferable examples of an isotonizing agent include, for example, glucose, D-sorbitol, sodium chloride, glycerine, D-mannitol, etc.

Preferable examples of a pH adjusting agent include, for example, citrate, phosphate, carbonate, tartrate, fumarate, acetate, amino acid salt, etc.

Preferable examples of a solubilizer include, for example, polyethylene glycol, propylene glycol, D-mannitol, benzyl benzoate, ethanol, tris-aminomethane, cholesterol, triethanolamine, sodium carbonate, sodium citrate, etc.

As a preferable example of a solvent, for example, injection solvent, alcohol, propylene glycol, macrogol, sesame oil, corn oil, olive oil etc. can be used.

As a preferable example of a suspending agent, for example, a surfactant such as stearyl triethanolamine, sodium lauryl sulfate, laurylaminopropionic acid, commercial lecithin, benzalkonium chloride, benzethonium chloride, glyceryl monostearate; hydrophilic macromolecule such as polyvinyl alcohol, polyvinylpyrrolidone, sodium carboxymethylcellulose, methyl cellulose, hydroxymethylcellulose, hydroxyethylcellulose, hydroxypropylcellulose, for example, can be exemplified.

Preferable examples of a soothing agent include, for example, benzyl alcohol, etc.

Preferable examples of a buffer include, for example, buffers such as phosphate, acetate, carbonate, citrate, etc.

Preferable examples of a preservative include, for example, p-oxybenzoic acid esters, chlorobutanol, benzyl alcohol, phenethyl alcohol, dehydroacetic acid, sorbic acid, etc.

Dosage of the compound of the present invention varies depending on the subject of administration, route of administration, target disease, condition, etc. but when, for example, it is orally administered to an adult allergia patient (about 60 kg in weight), a single dose is usually about 0.005 to 50 mg/kg body weight, preferably 0.01 to 5 mg/kg body weight for dose, and more preferably it is 0.025 to 2 mg/kg body weight, and it is preferable that this quantity is administered once or several times a day.

In the case of oral administration, it is usually suitable that the dosage per day is from about 0.01 mg/kg to 10 g/kg per body weight, preferably 0.1 mg/kg to 1 g/kg and this is administered at once or divided into 2 to 4 times a day. When it is intravenous is administered, dosage per day is suitably from about 0.01 mg/kg to 1 g/kg per body weight and it is administered at once or divided into plural times a day. The dosage is appropriately determined in consideration of condition, age, sex, etc. in each case.

The pharmaceutical composition, Syk inhibitor, drug for allergic diseases, drug for bronchial asthma, drug for allergic rhinitis, drug for allergic dermatitis, drug for allergic conjunctivitis, drug for autoimmune diseases, drug for rheumatoid arthritis, drug for systemic lupus erythematosus, drug for multiple sclerosis, drug for malignant tumor, drug for B-lymphoma, B-cell leukemia containing a compound represented by the general formula (I) of the present invention can be used together with other antiallergic therapeutic and/or preventive agent.

In this case, the drug of the present invention and other antiallergic drug may be formed as one combined drug or separate pharmaceutical preparations respectively containing a suitable amount of each dosage or optionally may be a kit. When it is formed as separate pharmaceutical preparations, each preparation may be taken at the same time or and taken with an interval of time.

As an antiallergic drug, an inhibitor of chemical transmitter releaser, histamine antagonist, thromboxane synthesis inhibitor, TH2 cytokine inhibitor, leukotriene antagonist, etc. are known, but antiallergic drug which can be used in combination with the drug of the present invention is not particularly limited and can be used in an appropriate combination. For example, as an inhibitor of chemical transmitter releaser, sodium cromoglycate, emedastine fumarate, suplatast tosylate, epinastin hydrochloride, etc., as a histamine antagonist, clemastine fumarate, d-chlorpheniramine maleate, cyproheptadine hydrochloride, promethazine hydrochloride, homochlorcyclizine hydrochloride, mequitazine, diphenhydramine hydrochloride, ebastin, cetirizine hydrochloride, olopatadine hydrochloride, fexofenadine hydrochloride, etc., as a thromboxane synthesis inhibitor, ozagrel hydrochloride, etc., as a leukotriene antagonist, pranlukast hydrate, zafirlukast, etc. can be used.

Next, processes for producing a compound represented by the general formula (I) of the present invention are specifically described. However, the present invention should not be limited to these processes. The production of the compound of the present invention may be appropriately performed from the part which is easy to perform. In addition, when there is a reactive functional group, protection or deprotection may be appropriately performed in each step, and a reagent other than the exemplified reagents can be used appropriately to promote the progress of the reaction.

Any compound obtained in each step can be isolated and purified by a conventional method, but the compound may optionally be subjected to the following step without isolation and purification.

As a method used for isolation and purification when they are performed, a conventional method such as distillation, crystallization, recrystallization, silica gel column chromatography, thin layer chromatography, preparative HPLC can be appropriately selected or performed in combination.

In the case where a compound in which $R^7$ is a nucleophile substituent is desired, it can be produced following the following production process.

Production Example 1

Process Chart 1

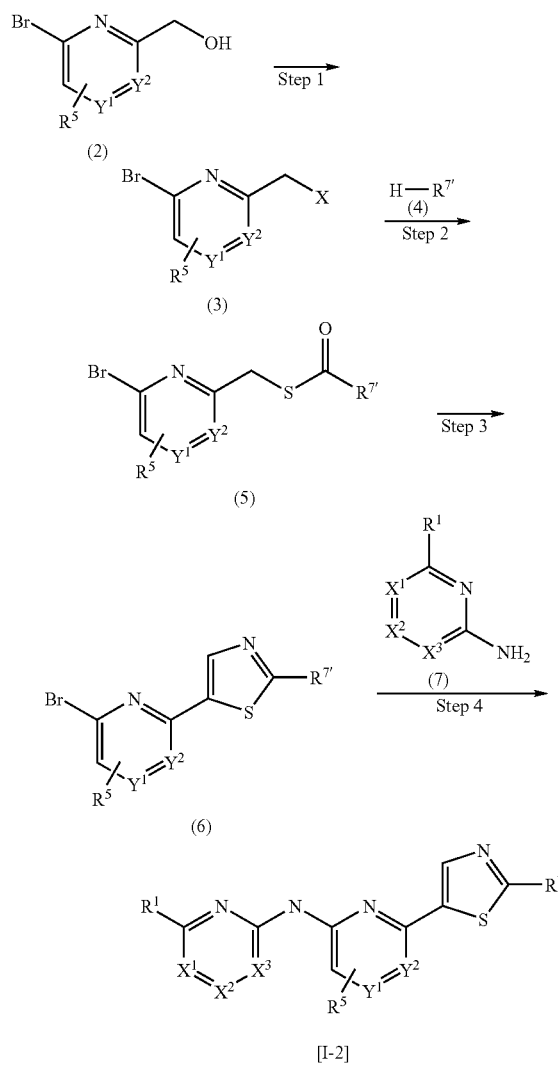

(wherein X represents a leaving group such as a halogen atom, and $R^{7'}$ represents a nucleophile substituent among $R^7$, and each other symbol represents the same meaning as above.)

Step 1

Compound (3) is obtained by subjecting compound (2) to halogenation using a halogenating agent such as thionyl chloride, oxalyl chloride in a solvent such as dichloromethane, 1,2-dichloroethane, chloroform, carbon tetrachloride, acetonitrile, toluene or to a reaction using a leaving group inducing reagent such as methanesulfonyl chloride, p-toluenesulfonyl chloride, trifluoromethane sulfonic acid anhydride in the presence of a base such as triethylamine, N,N-diisopropylethylamine and pyridine.

Step 2

Compound (5) is obtained by converting compound (4) to a thiourea using 9-fluorenylmethoxycarbonylisothiocyanate, piperidine in a solvent such as ethanol, isopropanol, ethyl acetate, tetrahydrofuran, N,N-dimethylformamide, dimethylsulfoxide, chloroform, acetonitrile, ethylene glycol dimethylether, 1,4-dioxane followed by the reaction with compound (3).

Step 3

Compound (6) is obtained by subjecting compound (5) to a reaction in acetic anhydride solvent in the presence of formic acid or to a reaction using N,N-dimethylformamide dimethylacetal, N,N-dimethylformamide diethyl acetal, etc. in a solvent such as methanol, ethanol, isopropanol, tetrahydrofuran, acetonitrile, toluene in the presence of a base such as triethylamine, N,N-diisopropylethylamine, pyridine.

Step 4

A compound represented by the general formula [1-2] is obtained by reacting compound (6) obtained in Step 3 with compound (8) in a solvent such as toluene, benzene, 1,4-dioxane, tetrahydrofuran, dichloro-methane, 1,2-dichloroethane, chloroform, carbon tetrachloride, ethylene glycol dimethylether, 1-methyl-2-pyrrolidinone, N,N-dimethylformamide, N,N-dimethylacetamide in the presence of a base such as 2,2'-bis(diphenylphosphino)-1,1-binaphthyl, palladium acetate and cesium carbonate, potassium carbonate, potassium phosphate.

Production Example 2

Process Chart 2

(Each symbol in the chart represents the same meaning as above respectively.)

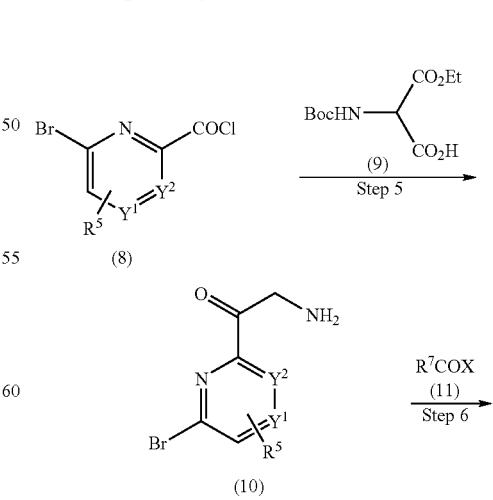

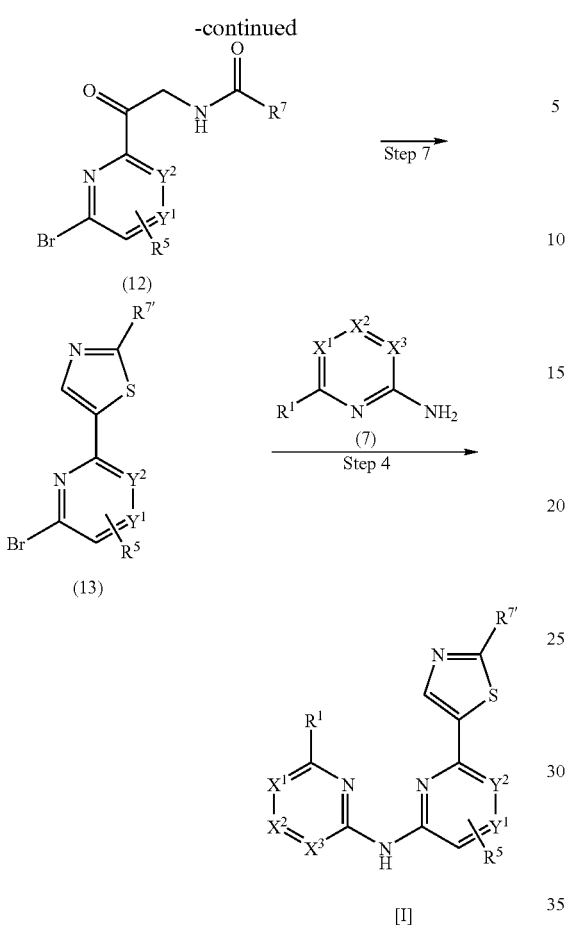

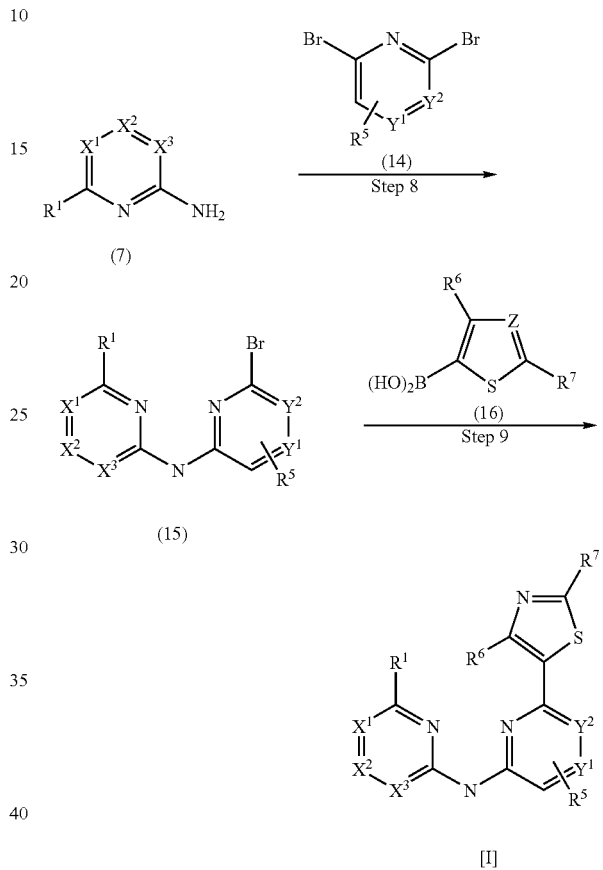

roform, carbon tetrachloride. A compound represented by the general formula [I] is obtained by performing a method of the above Step 4 after that.

Production Example 3

Process Chart 3

Step 5

Compound (10) is obtained by reacting a nicotinic acid chloride compound (8) and malonic acid compound (9) in a solvent such as acetonitrile, tetrahydrofuran, 1,4-dioxane, N,N-dimethylformamide in the presence of magnesium chloride and a base such as triethylamine and N,N-diisopropylethylamine following a method described in Organic Letters, 5 (18), 3233-3236, (2003) and further performing decarboxylation and deprotection of the tert-butoxycarbonyl group using a concentrated hydrochloric acid at the same time.

Step 6

Compound (12) is obtained by reacting compound (10) with compound (11) in a solvent such as acetonitrile, tetrahydrofuran, 1,4-dioxane, N,N-dimethylformamide, dichloromethane, 1,2-dichloroethane, chloroform, carbon tetrachloride. In this reaction, bases such as pyridine, triethylamine, N,N-diisopropylethylamine may be used depending on the case. When compound (11) is a carboxlic acid compound, compound (12) may be obtained by performing a reaction using a condensing agent such as dicyclohexylcarbodiimide, 1-ethyl-3-(3-dimethylaminopropyl)carbodiimide, diisopropylcarbodiimide, diphenylphosphoryl azide, 2-ethoxy-1-ethoxycarbonyl-1,2-dihydroquinoline (EEDQ).

Step 7

Compound (13) is obtained by reacting Compound (12) using a Lawesson reagent in a solvent such as tetrahydrofuran, 1,4-dioxane, dichloromethane, 1,2-dichloroethane, chlo- Step 8

Compound (15) can be obtained by reacting compound (7) and compound (14) according to the method shown in Step 4.

Step 9

Compound [I] can be obtained by reacting compound (15) with compound (16) in a solvent such as dimethoxyethane, diethyl ether, acetone, butanone, dioxane, tetrahydrofuran in the presence of tetrakis(triphenylphosphine)palladium and a base such as sodium hydrogen carbonate, potassium bicarbonate, sodium carbonate, potassium carbonate.

When compound [I] having a "—CONH-bond" in substituent $R^7$ is desired, the desired compound [I] having a "—CONH-bond" can be obtained by subjecting a compound having a "—COOH group" and a compound having a "—NH$_2$ group" to amidation reaction.

In addition, when compound [I] having "—N(-(substituted)$C_{1-6}$ alkyl)-" in substituent $R^7$ is desired, a known alkylation reaction may be performed using a compound having "—NH—".

When compound [I] having a "—CH(OH)—" in substituent $R^7$ is desired, a known Grignard reaction may be performed on a "—CHO" compound.

When an acid addition salt or a base addition salt of a compound represented by the general formula [I] is desired, a well-known method can be used. For example, a compound represented by the general formula [I] is dissolved in water, methanol, ethanol, n-propanol, isopropanol, diethyl ether, tetrahydrofuran, 1,4-dioxane, ethyl acetate, dichloromethane, 1,2-dichloroethane or chloroform or a mixed solvent of these, and a solvent as mentioned above in which a desired acid or a base is dissolved is added and deposited crystal may be just separated by filtration or concentration under reduced pressure may be performed.

When a compound represented by the general formula [I] or an intermediate is a racemate and an optically active substance is desired, they can be separated by a well-known method. As for the separation method, a conventional method such as separation by salt crystallization using optically active 1-phenethylamine, an optically active alkaloid, optically active camphorsulfonic acid, optically active tartaric acid and derivatives thereof, recrystallization, chiral column chromatography, chiral preparative HPLC can be appropriately selected or performed in combination.

The obtained object compound can be separated and purified, if necessary, by a conventional method, for example, recrystallization, reprecipitation or a conventional method usually used for separation and purification of an organic compound, for example, a method using a synthesized adsorbing agent such as adsorption column chromatography, distribution column chromatography, a method using ion exchange chromatography, a method in which normal phase/reversed phase column chromatography methods by silica gel or alkylation silica gel are appropriately combined and elution is performed with a suitable eluent.

The compound represented by the general formula [I] of the present invention and the production process thereof will be specifically described by way of the following Examples. Needless to say, however, the present invention is not limited to these Examples.

Example 1

Preparation of 1-methyl-4-{5-[6-(4-methylpyridin-2-ylamino)pyridin-2-yl]thiazol-2-yl}piperazin-2-one (Compound A-1)

Step 1; Preparation of 2-bromo-6-chloromethylpyridine

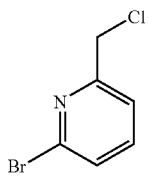

2-Bromo-6-hydroxymethylpyridine (5.00 g, 25.5 mmol) was dissolved in chloroform (30 ml) and thionyl chloride (2.8 ml, 38.3 mmol) was added, and the mixture was stirred at room temperature for 3 hours. After the reaction solution was concentrated, a saturated aqueous sodium bicarbonate was added to the residue and the precipitates were collected by filtration. After washing with water, the precipitates were dried in vacuo to give the title compound (5.20 g, 99%).

Step 2; Preparation of 3-oxopiperazine-1-carbothionic acid amide

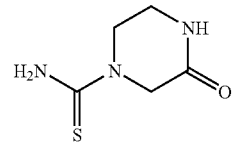

Piperazin-2-one (1.43 g, 14.3 mmol) was dissolved in chloroform (30 ml) and 9-fluorenylmethoxycarbonyl isothiocyanate (4.02 g, 14.3 mmol) was added and the mixture was stirred at room temperature for 2 hours. After the reaction solution was concentrated, diethyl ether was added to the residue and the precipitates were collected by filtration. The obtained precipitates were dissolved in N,N-dimethylformamide (10 ml) and piperidine (10 ml) was added and the mixture was stirred at room temperature for 6 hours. After the reaction solution was concentrated again, diethyl ether was added to the residue and the precipitates were collected by filtration and, after drying in vacuo, the title compound (2.22 g, 98%) was obtained.

Step 3; Preparation of 3-oxopiperazine-1-carboxyimidothionic acid 6-bromopyridin-2-ylmethyl ester

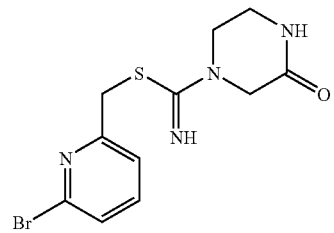

2-Bromo-6-chloromethylpyridine (1.50 g, 7.26 mmol) obtained in Step 1 was dissolved in ethanol (15 ml) and 3-oxopiperazine-1-carbothionic acid amide (1.16 g, 7.29 mmol) obtained in Step 2 was added, and the mixture was heated to reflux for 2 hours. After the reaction solution was cooled to room temperature, the solution obtained by vacuum concentration was neutralized with a saturated aqueous sodium bicarbonate, and the precipitated solid was separated by filtration, washed with water and the title compound (1.67 g, 70%) was obtained.

Step 4; Preparation of 4-[5-(6-bromopyridin-2-yl)thiazol-2-yl]piperazin-2-one

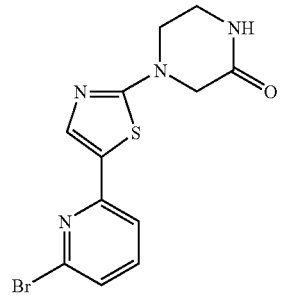

Formic acid (5 ml) and acetic anhydride (10 ml) were added to 3-oxopiperazine-1-carboxyimidothionic acid 6-bromopyridin-2-ylmethyl ester obtained in Step 3 (1.67 g, 5.08 mmol) and the mixture was stirred at room temperature for 12 hours. The crystal precipitated in the process of vacuum concentrating the reaction solution was collected by filtration, washed with water and the title compound (1.37 g, 80%) was obtained.

$^1$H-NMR (400MHz, DMSO-d$_6$) δ: 8.22 (1H, br), 8.01 (1H, s), 7.83 (1H, d, J=7.8 Hz), 7.69 (1H, t, J=7.8 Hz), 7.38 (1H, d, J=7.8 Hz), 4.04 (2H, s), 3.73-3.68 (2H, m), 3.38-3.34 (2H, m)

Step 5; Preparation of 4-[5-(6-bromopyridin-2-yl)thiazol-2-yl]-1-methylpiperazin-2-one

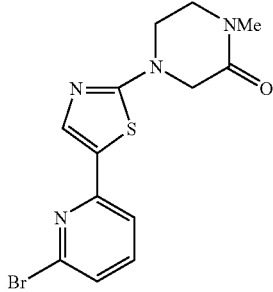

4-[5-(6-bromopyridin-2-yl)thiazol-2-yl]piperazin-2-one obtained in Step 4 (200 mg, 0.59 mmol) was dissolved in tetrahydrofuran (2 ml) and N,N-dimethylformamide (2 ml) and after sodium hydride (60% oily, 26 mg, 0.65 mmol) was added, methyl iodide (39 μl, 0.62 mmol) was added and the mixture was stirred overnight at room temperature. Water was added to the reaction solution and the residue obtained by vacuum concentration was extracted with ethyl acetate and washed with a saturated brine. The organic layer was dried over sodium sulfate and concentrated in vacuo to give the title compound (188 mg, 90%).

Step 6; Preparation of 1-methyl-4-{5-[6-(4-methylpyridin-2-ylamino)pyridin-2-yl]thiazol-2-yl}piperazin-2-one

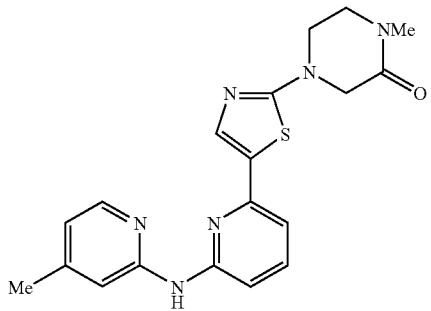

4-[5-(6-bromopyridin-2-yl)thiazol-2-yl]-1-methylpiperazin-2-one obtained in Step 5 (188 mg, 0.53 mmol) was dissolved in toluene (5 ml), and after 2-amino-4-methylpyridine (58 mg, 0.53 mmol) was added, 2,2'-bis(diphenylphosphino)-1,1'-binaphthyl (66 mg, 0.11 mmol), palladium acetate (18 mg, 0.08 mmol) and cesium carbonate (260 mg, 0.80 mmol) were added and the mixture was stirred overnight at 100° C. Water was added to the reaction solution and extracted with ethyl acetate and the organic layer was washed with a saturated saline solution. The organic layer was dried over sodium sulfate and after vacuum concentration, the residue was washed with methanol and the title compound (77 mg, 38%) was obtained.

$^1$H-NMR (400MHz, DMSO-d$_6$) δ: 8.09 (1H, d, J=4.8 Hz), 7.92 (1H, br), 7.89 (1H, s), 7.60 (1H, dd, J=8.4, 7.6 Hz), 7.26 (1H, d, J=8.4 Hz), 7.26 (1H, d, J=7.6 Hz), 6.75 (1H, brd, J=4.8 Hz), 4.07 (2H, s), 3.80-3.77 (2H, m), 3.52-3.50 (2H, m), 2.92(3H, s), 2.34(3H, s)

Example 2

Preparation of 1-{5-[6-(4-methylpyridin-2-ylamino)pyridin-2-yl]thiazol-2-yl}piperidine-4-carboxylic acid (Compound A-2)

(1) Preparation of 1-{5-[6-(4-methylpyridin-2-ylamino)pyridin-2-yl]thiazol-2-yl}piperidine-4-carboxylic acid ethyl ester Step 1; Preparation of 1-thiocarbamoylpiperidine-4-carboxylic acid ethyl ester

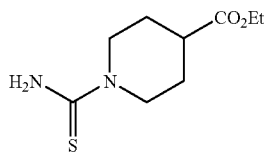

9-Fluorenylmethoxycarbonyl isothiocyanate (5.90 g, 21.0 mmol) was dissolved in chloroform (20 ml) and a chloroform (10 ml) solution of piperidine-4-carboxylic acid ethyl ester (3.30 g, 21.0 mmol) was added and the mixture was stirred at room temperature for 1 hour. The reaction solution was concentrated in vacuo, and the residue obtained by adding diethyl ether was collected by filtration. This was dissolved in N,N-dimethylformamide (20 ml) and piperidine (20 ml) was added and the mixture was stirred at room temperature for 1 hour. After the reaction solution was washed with ethyl acetate and the organic layer was washed with a saturated bline and dried over sodium sulfate, the residue obtained by vacuum concentration was purified by silica gel chromatography (n-hexane:ethyl acetate), and the title compound (4.34 g, 100%) was obtained.

Step 2; Preparation of 1-[5-(6-bromopyridin-2-yl)thiazol-2-yl]piperidine-4-carboxylic acid ethyl ester

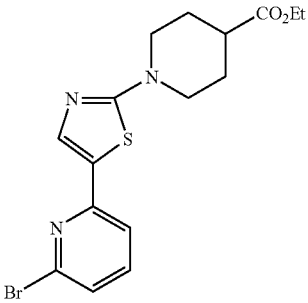

2-Bromo-6-chloromethylpyridine obtained in Step 1 of Example 1 (2.90 g, 14.0 mmol) was dissolved in ethanol (30 ml) and 1-thiocarbamoylpiperidine-4-carboxylic acid ethyl ester (3.00 g, 13.9 mmol) obtained in Step 1 was added, and the mixture was heated to reflux for 2 hours. The reaction solution was cooled to room temperature, dimethylormamide dimethylacetal (2.8 ml, 21.1 mmol) and triethylamine (5.9 ml, 42.3 mmol) were added, and the mixture was heated at reflux for 1 hour. After concentration, water was added and the reaction solution was extracted with ethyl acetate and washed with a saturated brine. The organic layer was dried over magnesium sulfate and the residue obtained by vacuum concentration was purified by silica gel chromatography (n-hexane:ethyl acetate=50:50 to 0:100) and the title compound (3.60 g, 65%) was obtained.

¹H-NMR (400 MHz, DMSO-d₆) δ: 7.92 (1H, s), 7.77 (1H, d, J=7.8 Hz), 7.64 (1H, t, J=7.8 Hz), 7.32 (1H, d, J=7.8 Hz), 4.05 (2H, q, J=7.2 Hz), 3.94-3.85 (2H, m), 3.22-3.12 (2H, m), 2.67-2.57 (2H, m), 1.94-1.86 (1H, m), 1.65-1.53 (2H, m), 1.16(3H, t, J=7.2 Hz).

Step 3; Preparation of ethyl 1-{5-[6-(4-methylpyridin-2-ylamino)pyridin-2-yl]thiazol-2-yl}piperidine-4-carboxylate

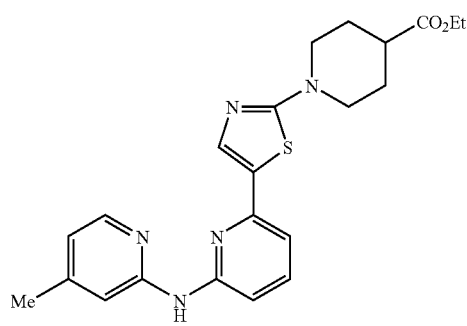

rac-2,2'-bis(diphenylphosphino)-1,1'-binaphthyl (434 mg, 0.70 mmol) and palladium acetate (117 mg, 0.52 mmol) was dissolve in toluene (15 ml), and after 2-amino-4-picoline (395 mg, 3.65 mmol) and a toluene (15 ml) solution of ethyl 1-[5-(6-bromopyridin-2-yl)thiazol-2-yl]piperidine-4-carboxylate obtained by Step 2 (1.38 g, 3.48 mmol) were sequentially added, cesium carbonate (1.70 g, 5.22 mmol) was added and the mixture was stirred at 100° C. overnight. Water was added to the reaction solution and extracted with ethyl acetate and washed with a saturated brine. The organic layer was dried over anhydrous sodium sulfate and the residue obtained by vacuum concentration was purified by silica gel chromatography (n-hexane:ethyl acetate=1:1 to 1:10) and the title compound (817 mg, 55%) was obtained.

¹H-NMR (400 MHz, DMSO-d₆) δ: 9.53(S1H, s), 8.08 (1H, d, J=5.2 Hz), 7.92 (1H, s), 7.83 (1H, s), 7.58 (1H, dd, J=8.0, 7.6 Hz), 7.23 (2H, dd, J=9.6, 7.6 Hz), 6.75-6.74 (1H, m), 4.09 (2H, q, J=6.9 Hz), 3.94-3.87 (2H, m), 3.24-3.164 (2H, m), 2.69-2.61 (1H, m), 2.33(3H, s), 1.99-1.93 (2H, m), 1.71-1.60 (2H, m), 1.20(3H, t, J=7.2 Hz)

(2) Preparation of 1-{5-[6-(4-methylpyridin-2-ylamino)pyridin-2-yl]thiazol-2-yl}piperidine-4-carboxylic acid (Compound A-2)

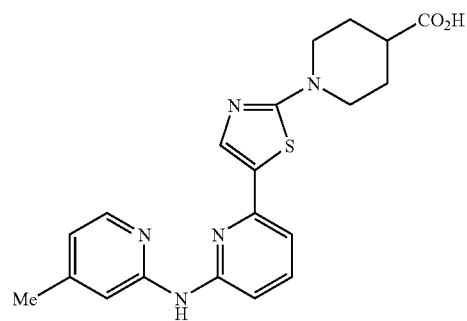

Ethyl 1-{5-[6-(4-methylpyridin-2-ylamino)pyridin-2-yl]thiazol-2-yl}piperidine-4-carboxylate obtained in the above (1) (817 mg, 1.93 mmol) was dissolved in a mixed solvent of tetrahydrofuran (4 ml), methanol (4 ml) and water (2 ml) and lithium hydroxide monohydrate (202 mg, 4.81 mmol) was added and the mixture was stirred at 50° C. for 5 hours. The concentrate obtained by vacuum concentration was neutralized with 0.1N hydrochloric acid, and the precipitated solid was collected by filtration and washed with water and title compound (721 mg) was obtained.

¹H-NMR (400M Hz, DMSO-d₆) δ: 12.34 (1H, brs), 9.53 (1H, s), 8.08 (1H, d, J=5.2 Hz), 7.92 (1H, s), 7.83 (1H, s), 7.58 (1H, dd, J=4.0, 8.0 Hz), 7.23 (2H, dd, J=11.6, 8.0 Hz), 6.75-6.73 (1H, m), 3.92-3.86 (2H, m), 3.23-3.15 (2H, m), 2.58-2.52 (1H, m), 2.33(3H, s), 1.99-1.90 (2H, m), 1.69-1.58 (2H, m)

MS: 396.2(M⁺+1)

Example 3

Preparation of 1-{5-[6-(4-methylpyridin-2-ylamino)pyridin-2-yl]thiazol-2-yl}piperidine-4-carboxamide (Compound A-3)

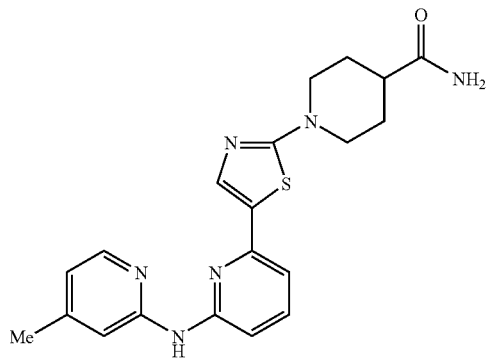

1-{5-[6-(4-methylpyridin-2-ylamino)pyridin-2-yl]thiazol-2-yl} piperidine-4-carboxylic acid (100 mg, 0.25 mmol) obtained in Example 2 was dissolved in N,N-dimethylformamide (2 ml) and benzotriazolyloxy trispyrrolidino phosphonium hexafluorophosphate (263 mg, 0.50 mmol), diisopropylethylamine (0.18 ml, 1.03 mmol) and ammonium chloride (41 mg, 0.77 mmol) were added and the mixture was stirred at room temperature for 1 hour. A saturated aqueous sodium bicarbonate was added to the reaction solution and the precipitated solid was collected by filtration and washed with water and title compound (89 mg, 89%) was obtained.

¹H-NMR (400M Hz, DMSO-d₆) δ: 9.53 (1H, s), 8.08 (1H, d, J=5.2 Hz), 7.93 (1H, s), 7.83 (1H, s), 7.58 (1H, t, J=8.0 Hz), 7.32 (1H, brs), 7.23 (2H, t, J=8.0 Hz), 6.83 (1H, brs), 6.74 (1H, d, J=5.2 Hz), 3.99-3.92 (2H, m), 3.17-3.08 (2H, m), 2.43-2.34 (1H, m), 2.33(3H, s), 1.86-1.78 (2H, m), 1.67-1.57 (2H, m)

MS: 395.2(M⁺+1)

Example 4

Preparation of N-Methyl-1-{5-[6-(4-methylpyridin-2-ylamino)methyl-1-pyridin-2-yl]thiazol-2-yl}piperidine-4-carboxamide (Compound A-4)

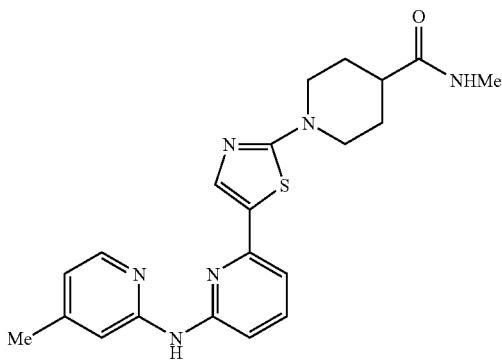

1-{5-[6-(4-methylpyridin-2-ylamino)pyridin-2-yl]thiazol-2-yl}piperidine-4-carboxylic acid (200 mg, 0.51 mmol) obtained in Example 2 was dissolved in N,N-dimethylformamide (5 ml), methylamine hydrochloride (68 mg, 1.00 mmol), benzotriazolyloxy trispyrrolidino phosphonium hexafluorophosphate (520 mg, 1.00 mmol) and triethylamine (0.28 ml, 2.01 mmol) were added and the mixture was stirred overnight at room temperature. Water was added to the reaction solution and the precipitated solid was collected by filtration and washed with water and title compound (160 mg, 78%) was obtained.

$^1$H-NMR (400M Hz, DMSO-$d_6$) δ: 9.53 (1H, s), 8.08 (1H, d, J=5.1 Hz), 7.93 (1H, s), 7.82 (1H, s), 7.79 (1H, q, J=4.5 Hz), 7.58 (1H, t, J=8.0 Hz), 7.23 (2H, t, J=8.0 Hz), 6.74 (1H, d, J=5.1 Hz), 4.01-3.92 (2H, m), 3.18-3.07 (2H, m), 2.57(3H, d, J=4.5 Hz), 2.44-2.35 (1H, m), 2.32(3H, s), 1.83-1.75 (2H, m), 1.70-1.57 (2H, m)

MS: 409.2(M$^+$+1)

Example 5

Preparation of N-(2-hydroxyethyl)-1-{5-[6-(4-methylpyridin-2-ylamino)pyridin-2-yl]thiazol-2-yl}piperidine-4-carboxamide (Compound A-5)

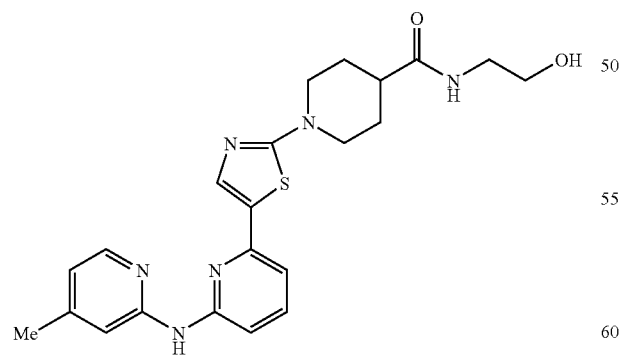

In the same way as in Example 4 wherein 2-hydroxyethylamine (61 mg, 1.00 mmol) was used in substitution for methylamine hydrochloride, title compound (70 mg, 32%) was obtained from 1-{5-[6-(4-methylpyridin-2-ylamino)pyridin-2-yl]thiazol-2-yl}piperidine-4-carboxylic acid (200 mg, 0.50 mmol) obtained in Example 2.

$^1$H-NMR (400M Hz, DMSO-$d_6$) δ: 9.53 (1H, s), 8.08 (1H, d, J=5.1 Hz), 7.93 (1H, s), 7.82-7.86 (2H, m), 7.58 (1H, t, J=8.0 Hz), 7.23 (2H, t, J=8.0 Hz), 6.74 (1H, d, J=5.1 Hz), 4.64 (1H, t, J=5.7 Hz), 4.01-3.92 (2H, m), 3.43-3.35 (2H, m) 3.16-3.06(4H, m), 2.47-2.38 (1H, m), 2.33(3H, s), 1.83-1.58 (4H, m).

MS: 439.2(M$^+$+1)

Example 6

Preparation of trans-4-{5-[6-(4-methylpyridin-2-ylamino)pyridin-2-yl]thiazol-2-yl}cyclohexanecarboxylic acid methyl ester (Compound A-6)

Step 1; Preparation of 2-amino-1-(6-bromopyridin-2-yl)ethanone hydrochloride

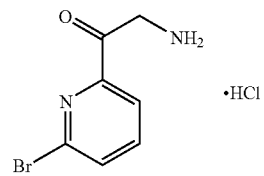

Magnesium chloride (21.30 g, 224 mmol) and triethylamine (62 ml, 446 mmol) were sequentially added to a suspension of 2-tert-butoxycarbonylamidomalonic acid monoethyl ester (50.30 g, 203 mmol) in acetonitrile (300 ml) under Ar atmosphere while ice-cooled and the mixture was stirred for 1 hour. Subsequently, a solution of 6-bromopyridine-2-carbonyl chloride (37.40 g, 170 mmol) in acetonitrile (150 ml) was added dropwise at the same temperature for 3 hours, and the mixture was stirred for 1 hour. After the reaction solution was concentrated, ethyl acetate (300 ml) was added and insolubles were filtrated. The filtrate was washed with 10% aqueous citric acid, a saturated brine and dried over magnesium sulfate and an oily substance was obtained after vacuum concentration. Concentrated hydrochloric acid (200 ml) was added to an ethanol (200 ml) solution of the obtained oily substance and heated at reflux for 6 hours. After concentrated to driness under reduced pressure, the residue was washed with a mixed solvent of ethanol-isopropyl ether (1:3), collected by filtration, dried in vacuo and the title compound (25.40 g, 50%) was obtained.

$^1$H-NMR (400M Hz, DMSO-$d_6$) δ: 8.42-8.31(3H, m), 8.16 (1H, t, J=7.8 Hz), 8.07 (1H, dd, J=7.8, 1.2 Hz), 7.92 (1H, dd, J=7.8, 1.2 Hz), 4.58 (2H, brs)

Step 2; Preparation of trans-4-[2-(6-bromopyridin-2-yl)-2-oxoethylcarbamoyl]cyclohexanecarboxylic acid methyl ester

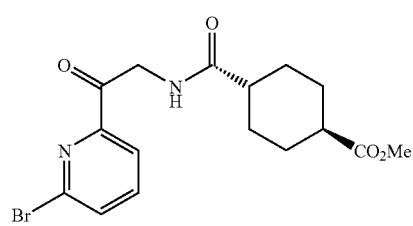

To a suspension of 2-amino-1-(6-bromopyridin-2-yl)ethanone hydrochloride (10.00 g, 39.8 mmol) obtained in Step 1, trans-4-chlorocarbonylcyclohexanecarboxylic acid methyl ester (9.00 g, 44.0 mmol) in acetonitrile (200 ml), a solution of triethylamine (13.9 ml, 100 mmol) in acetonitrile (60 ml) was added dropwise while ice-cooled for 2 hours. After the reaction solution was concentrated, water was added and extracted with ethyl acetate. The organic layer was sequentially washed with 10% aqueous citric acid, a saturated aqueous sodium bicarbonate, a saturated brine and dried over magnesium sulfate. After concentrated, the residue was purified by flash chromatography on silica gel (n-hexane:ethyl acetate=1:2) and the title compound (7.38 g, 48%) was obtained.

Step 3; Preparation of trans-4-[5-(6-bromopyridin-2-yl)thiazol-2-yl]cyclohexanecarboxylic acid methyl ester

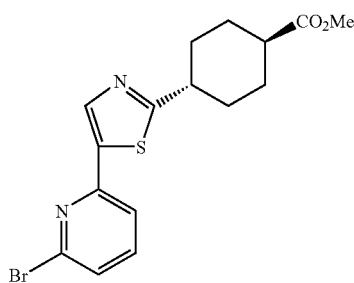

A solution of trans-4-[2-(6-bromopyridin-2-yl)-2-oxoethylcarbamoyl]cyclohexanecarboxylic acid methyl ester (7.38 g, 19.3 mmol) obtained in Step 2 and a Lawesson reagent (8.20 g, 20.3 mmol) in tetrahydrofuran (120 ml) was heated at reflux for 2 hours in an Ar stream. After the reaction solution was concentrated, a saturated aqueous sodium bicarbonate was added and extracted with ethyl acetate. The organic layer was washed with a saturated sodium bicarbonate aqueous solution and dried over magnesium sulfate, and after concentrated, the residue was purified by flash chromatography on silica gel (n-hexane:ethyl acetate=1:1) and the title compound (6.1 g) was obtained.

$^1$H-NMR (400M Hz, DMSO-$d_6$) δ: 8.41 (1H, s), 7.96 (1H, dd, J=7.6, 1.2 Hz), 7.92 (1H, t, J=7.6 Hz), 7.43 (1H, dd, J=7.6, 1.2 Hz), 3.62(3H, s), 2.97-3.05 (1H, m), 2.45-2.37 (1H, m), 2.19-2.12 (2H, m), 2.05-1.98 (2H, m), 1.63-1.46(4H, m)

Step 4; Preparation of trans-4-{5-[6-(4-methylpyridin-2-ylamino)pyridin-2-yl]thiazol-2-yl}cyclohexanecarboxylic acid methyl ester

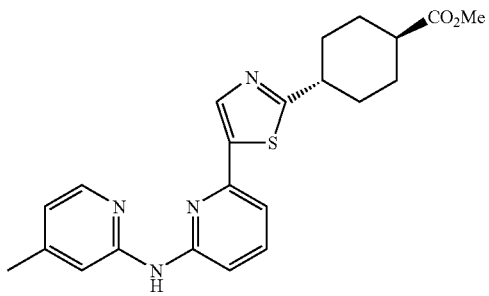

A suspension of trans-4-[5-(6-bromopyridin-2-yl)thiazol-2-yl]cyclohexanecarboxylic acid methyl ester (1.80 g, 4.72 mmol) obtained in Step 3,2-amino-4-picoline (613 mg, 5.66 mmol), palladium acetate (159 mg, 0.71 mmol), rac-2,2'-bis (diphenylphosphino)-1,1'-binaphthyl (529 mg, 0.85 mmol), cesium carbonate (2.00 g, 6.14 mmol) in toluene (100 ml) were heated and stirred at 90° C. in an Ar stream for 7 hours. Water was added to the reaction solution and extracted with a mixed solvent of ethyl acetate-tetrahydrofuran. After the organic layer was washed with a saturated brine and dried over magnesium sulfate; the residue obtained by vacuum concentration was purified by flash chromatography on silica gel (n-hexane:ethyl acetate=1:2) and subsequently washed with a mixed solvent of n-hexane-ethyl acetate and the title compound (1.60 g, 83%) was obtained.

$^1$H-NMR (400M Hz, DMSO-$d_6$) δ: 9.67 (1H, brs), 8.30 (1H, s), 8.10 (1H, dd, J=5.2, 0.8 Hz), 7.92 (1H, br), 7.68 (1H, dd, J=8.0, 7.6 Hz), 7.40 (1H, brd, J=8.0 Hz), 7.40 (1H, brd, J=7.6 Hz), 6.78-6.76 (1H, m), 3.62(3H, s), 3.05-2.97 (1H, m), 2.45-2.38 (1H, m), 2.35(3H, s), 2.21-2.15 (2H, m), 2.05-1.99 (2H, m), 1.64-1.48(4H, m)

Example 7

Preparation of trans-4-{5-[6-(4-methylpyridin-2-ylamino)pyridin-2-yl]thiazol-2-yl}cyclohexanecarboxylic acid (Compound A-7)

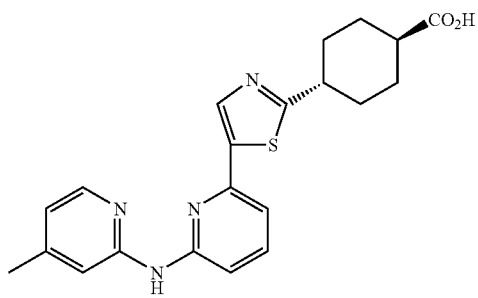

A solution of trans-4-{5-[6-(4-methylpyridin-2-ylamino)pyridin-2-yl]thiazol-2-yl}cyclohexanecarboxylic acid methyl ester (1.50 g, 3.67 mmol) obtained in the above Example 6, lithium hydroxide monohydrate (770 mg, 18.4 mmol) in a mixture of methanol (40 ml), tetrahydrofuran (40 ml), and water (20 ml) were stirred at room temperature for 15 hours. After the reaction solution was concentrated, the concentrate was neutralized with 2N hydrochloric acid (9.2 ml, 18.4 mmol), and the precipitate were collected and washed with water and ethyl acetate. After subjected to drying in vacuo, the title compound (1.41 g, 97%) was obtained.

$^1$H-NMR (400M Hz, DMSO-$d_6$) δ: 12.14 (1H, br), 9.67 (1H, brs), 8.30 (1H, s), 8.10 (1H, d, J=4.8 Hz), 7.93 (1H, br), 7.68 (1H, t, J=8.0 Hz), 7.41 (1H, d, J=8.0 Hz), 7.39 (1H, d, J=8.0 Hz), 6.77 (1H, brd, J=4.8 Hz), 3.04-1.95 (1H, m), 2.35(3H, s), 2.33-2.25 (1H, m), 2.21-2.15 (2H, m), 2.05-1.99 (2H, m), 1.62-1.45(4H, m)

Example 8

Preparation of (4-hydroxynineridino)-(trans-4-{5-[6-(4-methylpyridin-2-ylamino)pyridin-2-yl]thiazol-2-yl}cyclohexyl)methanone (Compound A-8)

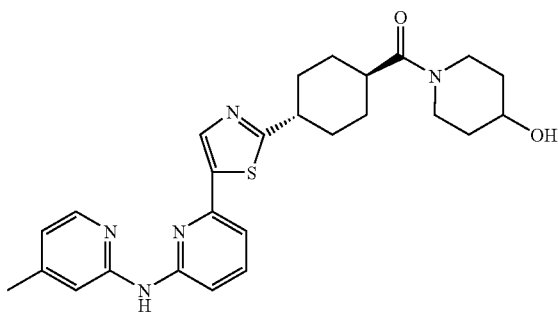

To a suspension of trans-4-{5-[6-(4-methylpyridin-2-ylamino)pyridin-2-yl]thiazol-2-yl}cyclohexanecarboxylic acid (504 mg, 1.28 mmol) obtained in Example 7 and 4-hydroxypiperidine (130 mg, 1.29 mmol) in dimethylformamide (4 ml), triethylamine (4 ml, 2.88 mmol), benzotriazolyloxy trispyrrolidino phosphonium hexafluorophosphate (731 mg, 1.40 mmol) were sequentially added at room temperature, and the mixture was stirred for 1 hour. After the reaction solution was concentrated, saturated aqueous sodium bicarbonate and water were added, and the precipitate were collected and washed with water and subjected to drying in vacuo, the title compound (585 mg, 96%) was obtained.

$^1$H-NMR (400M Hz, DMSO-$d_6$) δ: 9.67 (1H, brs), 8.30 (1H, s), 8.10 (1H, d, J=5.2 Hz), 7.92 (1H, br), 7.69 (1H, dd, J=8.4, 7.6 Hz), 7.41 (1H, d, J=8.4 Hz), 7.39 (1H, d, J=7.6 Hz), 6.77 (1H, brd, J=5.2 Hz), 4.73 (1H, d, J=4.4 Hz), 3.98-3.90 (1H, m), 3.82-3.74 (1H, m), 3.73-3.66 (1H, m), 3.25-3.16 (1H, m), 3.04-1.94 (2H, m), 2.746-2.66 (1H, m), 2.35(3H, s), 2.20-2.13 (2H, m), 1.81-1.49(8H, m), 1.39-1.16 (2H, m)

MS: 478.2($M^+$+1)

Example 9

Preparation of N—((S)-1-{5-[6-(4-methylpyridin-2-ylamino)pyridin-2-yl}thiazol-2-yl}ethyl)amine (Compound A-9)

Step 1; Preparation of {(S)-1-[2-(6-bromopyridin-2-yl)-2-oxoethylcarbamoyl]ethyl}carbamic acid tert-butyl ester

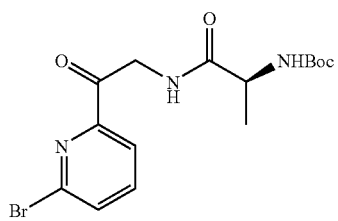

To a suspension of 2-amino-1-(6-bromopyridin-2-yl)ethanone hydrochloride (500 mg, 1.99 mmol) obtained in Step 1 of example 6, (S)-N-tert-butylcarbonylalanine (376 mg, 1.99 mmol), 1-(3-dimethylaminopropyl)-3-ethylcarbodiimide hydrochloride (379 mg, 1.99 mmol), 1-hydroxybenzotriazole monohydrate (305 mg, 1.99 mmol) in acetonitrile (11 ml), a solution of triethylamine (0.7 ml) in acetonitrile (4 ml) was added dropwise while ice-cooled for 15 minutes. After the mixture was stirred at the same temperature for 1 hour, water was added and extracted with ethyl acetate. After the organic layer was washed with water, a saturated brine, dried over magnesium sulfate, the residue obtained by vacuum concentration was purified by flash chromatography on silica gel (n-hexane:ethyl acetate=2:1) and the title compound (456 mg, 59%) was obtained.

Step 2; Preparation of {(S)-1-[5-(6-bromopyridin-2-yl)thiazol-2-yl]ethyl}carbamic acid tert-butyl ester;

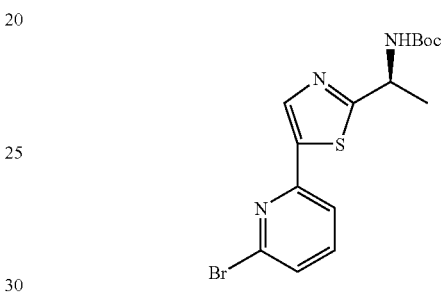

The title compound (282 mg, 71%) was obtained in a similar process as in Step 3 of Example 6 using {(S)-1-[2-(6-bromopyridin-2-yl)-2-oxoethylcarbamoyl]ethyl}carbamic acid tert-butyl ester (400 mg, 1.04 mmol) and a Lawesson reagent (419 mg, 1.04 mmol).

Step 3; Preparation of ((S)-1-{5-[6-(4-methylpyridin-2-ylamino)pyridin-2-yl}thiazol-2-yl}ethyl)carbamic acid tert-butyl ester;

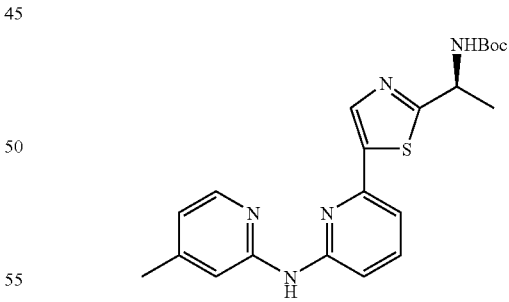

The title compound (234 mg, 87%) was obtained in a similar process as in Step 4 of Example 7 using {(S)-1-[5-(6-bromopyridin-2-yl)thiazol-2-yl]ethyl}carbamic acid tert-butyl ester (250 mg, 0.65 mmol) obtained in Step 2, 2-amino-4-picoline (92 mg, 0.85 mmol), palladium acetate (15 mg, 0.07 mmol), rac-2,2'-bis(diphenylphosphino)-1,1'-binaphthyl (49 mg, 0.08 mmol) and cesium carbonate (276 mg, 0.85 mmol).

Step 4; Preparation of N—((S)-1-{5-[6-(4-methylpyridin-2-ylamino)pyridin-2-yl)thiazol-2-yl}ethyl)amine;

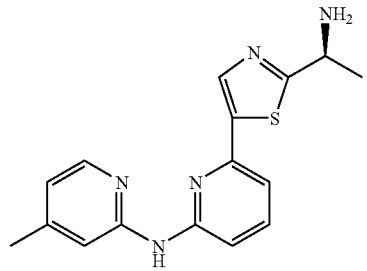

To a solution of (S)-1-({5-[6-(4-methylpyridin-2-ylamino)pyridin-2-yl]thiazol-2-yl}ethyl)carbamic acid tert-butyl ester (200 mg, 0.49 mmol) obtained in Step 3 in chloroform (5 ml), trifluoroacetic acid (5 ml) was added and the mixture was stirred at room temperature for 2 hours. The reaction solution was concentrated and a saturated aqueous sodium bicarbonate was added and extracted with a mixed solution of ethyl acetate-tetrahydrofuran. The organic layer was washed with a saturated brine and dried over magnesium sulfate. The obtained residue was washed with diisoprpyl ether and dried in vacuuo and the title compound (102 mg, 67%) was obtained.

Example 10

Preparation of N—((S)-1-{5-[6-(4-methylpyridin-2-ylamino)pyridin-2-yl]thiazol-2-yl}ethyl)acetamide (Compound A-10)

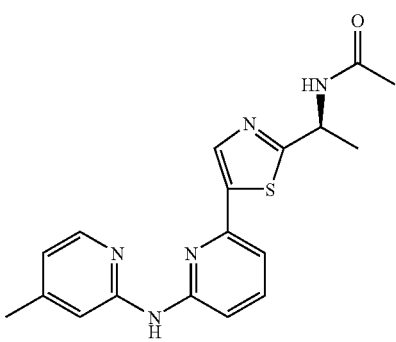

Acetic anhydride (0.02 ml, 0.24 mmol) was added to a solution of N—((S)-1-{5-[6-(4-methyllpyridin-2-ylamino)pyridin-2-yl]thiazol-2-yl}ethyl)amine (50 mg, 0.16 mmol) obtained in Example 9 in pyridine (3 ml) and the mixture was stirred at room temperature for 2 hours. The reaction solution was concentrated and extracted with a mixed solution of ethyl acetate-tetrahydrofuran. The organic layer was washed with a saturated brine and dried over magnesium sulfate. The obtained residue was washed with diisoprpyl ether and dried in vacuo and the title compound (43 mg, 76%) was obtained.
$^1$H-NMR (400M Hz, DMSO-$d_6$) δ: 9.68 (1H, s), 8.71 (1H, d, J=7.6 Hz), 8.30 (1H, s), 8.09 (1H, d, J=4.8 Hz), 7.97 (1H, brs), 7.67 (1H, dd, J=8.4, 7.6 Hz), 7.40 (1H, d, J=7.2 Hz), 7.34 (1H, d, J=8.4 Hz), 6.77 (1H, d, J=5.2 Hz), 5.19-5.12 (1H, m), 2.35(3H, s), 1.92(3H, s), 1.51(3H, d, J=7.2 Hz)
MS: 354.1(M$^+$+1)

Example 11

Preparation of (S)-3-methyl-4-{5-[6-(4-methylpyridin-2-ylamino)pyridin-2-yl]thiazol-2-yl}oxazolidin-2-one (Compound A-11)

Step 1; Preparation of (S)-4-[2-(6-bromopyridin-2-yl)]-2-oxoethylcarbamoyl-2,2-dimethyloxazolidine-3-carboxylic acid tert-butyl ester;

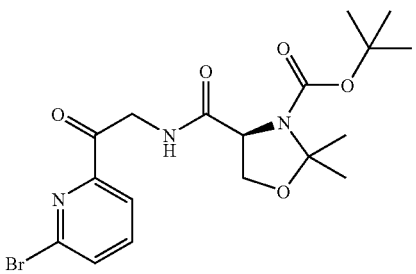

To a suspension of (S)-2,2-dimethyloxazolidine-3,4-dicarboxylic acid-3-tert-butyl ester-4-lithium salt (12.00 g, 47.7 mmol), 1-hydroxybenzotriazole monohydrate (7.30 g, 47.7 mmol), 1-(3-dimethylaminopropyl)-3-ethylcarbodiimide hydrochloride (9.20 g, 47.7 mmol), 2-amino-1-(6-bromopyridin-2-yl)ethanone hydrochloride (10.00 g, 39.7 mmol) obtained in Step 1 of Example 6 acetonitrile (150 ml) was added while ice-cooled and the mixture was stirred for 3 hours. After the reaction solution was concentrated, water was added and extracted with ethyl acetate. The organic layer was sequentially washed with 10% aqueous citric acid, a saturated aqueous sodium bicarbonate, a saturated brine and dried over magnesium sulfate and after that concentrated and dried in vacuo and the title compound (13.70 g, 78%) was obtained.

Step 2; Preparation of (S)-4-[5-(6-bromopyridin-2-yl)-5-thiazol-2-yl]-2,2-dimethyloxazolidine-3-carboxylic acid tert-butyl ester;

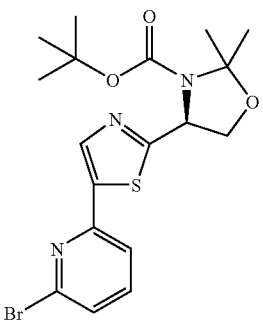

The title compound (10.50 g, 77%) was obtained in a similar process as in Step 3 of Example 6 using (S)-4-[2-(6-bromopyridin-2-yl)-2-oxoethylcarbamoyl-2,2-dimethyloxazolidine-3-carboxylic acid tert-butyl ester (13.70 g, 31.0 mmol) obtained in Step 1, a Lawesson reagent (12.50 g, 31.0 mmol).

Step 3; Preparation of (S)-2-amino-2-[5-(6-bromopyridin-2-yl)thiazol-2-yl]ethanol dihydrochloride;

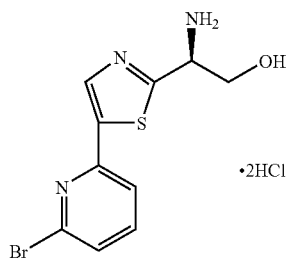

To a solution of (S)-4-[5-(6-bromopyridin-2-yl)thiazol-2-yl]-2,2-dimethyloxazolidine-3-carboxylic acid tert-butyl ester (5.00 g, 11.4 mmol) obtained in Step 2 in tetrahydrofuran (30 ml) was added 4N hydrogen chloride-ethyl acetate solution (30 ml) and heated to reflux at 90° C. for 2 hours. After the reaction solution was cooled, it was concentrated and washed with ethyl ether and dried, and the title compound (3.57 g) was obtained.

$^1$H-NMR (400M Hz, DMSO-$d_6$) δ: 8.91-8.77 (2H, m), 8.62 (1H, s), 8.07 (1H, d, J=8.0 Hz), 7.98 (1H, t, J=8.0 Hz), 7.50 (1H, d, J=8.0 Hz), 6.12-5.85(3H, m), 4.82-4.74 (1H, m), 3.90 (2H, d, J=5.6 Hz)

Step 4; Preparation of (S)-4-[5-(6-bromopyridin-2-yl)thiazol-2-yl]oxazolidin-2-one;

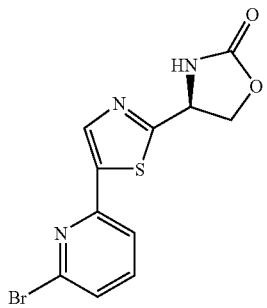

To a solution of (S)-2-amino-2-[5-(6-bromopyridin-2-yl)thiazol-2-yl]ethanol dihydrochloride (1.00 g, 2.68 mmol) obtained in Step 3, triethylamine (3.7 ml, 2.68 mmol) in chloroform (15 ml), a solution of triphosgene (278 mg, 0.94 mmol) in chloroform (5 ml) was added dropwise while cooled to −78° C., and the mixture was stirred at the same temperature for 2 hours. The reaction solution was warmed to room temperature and water was added and it was extracted with ethyl acetate. After washed with a saturated brine, the organic layer was dried over magnesium sulfate. After concentrated, the residue was purified by flash chromatography on silica gel (chloroform:methanol:ethyl acetate=15:1:1) and the title compound (712 mg, 82%) was obtained.

$^1$H-NMR (400M Hz, DMSO-$d_6$) δ: 8.66 (1H, brs), 8.54 (1H, s), 8.03 (1H, dd, J=8.0, 0.8 Hz), 7.96 (1H, t, J=7.8 Hz), 7.48 (1H, dd, J=8.0, 0.8 Hz), 5.31 (1H, ddd, J=8.6, 4.8, 1.2 Hz), 4.74 (1H, t, J=8.6 Hz), 4.36 (1H, dd, J=8.6, 4.8 Hz)

Step 5; Preparation of (S)-4-[5-(6-bromopyridin-2-yl)thiazol-2-yl]-3-methyloxazolidin-2-one

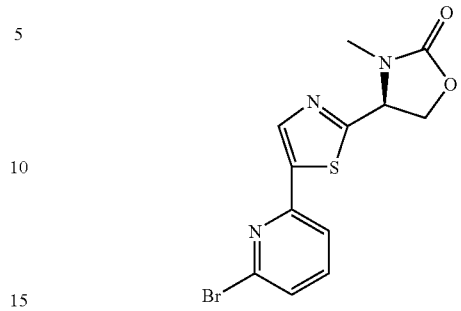

(S)-4-[5-(6-bromopyridin-2-yl)thiazol-2-yl]oxazolidin-2-one (488 mg, 1.50 mmol) obtained in Step 4 and sodium hydride (60% oily, 72 mg, 1.80 mmol) were suspended in tetrahydrofuran (5 ml) and dimethylformamide (5 ml) in an Ar stream and methyl iodide (0.1 ml, 1.65 mmol) was added while ice-cooled and stirred at room temperature for 12 hours. After the reaction solution was concentrated, water was added and it was extracted with ethyl acetate. After the organic layer was washed with a saturated brine and dried over magnesium sulfate, it was concentrated and the residue was purified by flash chromatography on silica gel (chloroform:methanol=20:1) and the title compound (205 mg, 40%) was obtained.

$^1$H-NMR (400M Hz, DMSO-$d_6$) δ: 8.59 (1H, s), 8.05 (1H, d, J=7.8 Hz), 7.97 (1H, t, J=7.8 Hz), 7.49 (1H, d, J=7.8 Hz), 5.29 (1H, dd, J=9.0, 5.6 Hz), 4.68 (1H, t, J=9.0 Hz), 4.32 (1H, dd, J=9.0, 5.6 Hz), 2.76(3H, s)

Step 6; Preparation of (S)-3-methyl-4-{5-[(6-(4-methylpyridin-2-ylamino)pyridin-2-yl]thiazol-2-yl}oxazolidin-2-one (Compound A-11);

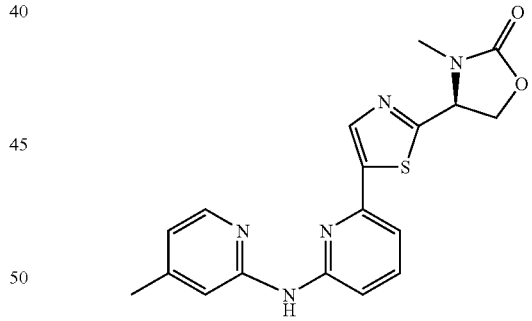

The title compound (132 mg, 60%) was obtained in a similar process as in Step 4 of Example 7 using (S)-4-[5-(6-bromopyridin-2-yl)thiazol-2-yl]-3-methyloxazolidin-2-one (205 mg, 0.60 mmol) obtained in Step 5,2-amino-4-picoline (72 mg, 0.66 mmol), palladium acetate (20 mg, 0.09 mmol), rac-2,2'-bis(diphenylphosphino)-1,1'-binaphthyl (75 mg, 0.12 mmol) and cesium carbonate (295 mg, 0.90 mmol).

$^1$H-NMR (400M Hz, DMSO-$d_6$) δ: 9.71 (1H, brs), 8.47 (1H, s), 8.11 (1H, d, J=4.8 Hz), 7.90 (1H, brs), 7.73 (1H, t, J=8.0 Hz), 7.48 (1H, d, J=8.0 Hz), 7.44 (1H, d, J=8.0 Hz), 6.78 (1H, d, J=4.8 Hz), 5.28 (1H, dd, J=8.8, 4.8 Hz), 4.69 (1H, t, J=8.8 Hz), 4.33 (1H, dd, J=8.8, 4.8 Hz), 2.79(3H, s), 2.34 (3H, s)

MS: 368.1(M$^+$+1)

Example 12

Preparation of (S)-2,2-dimethyl-4-{5-[6-(4-meth1ylpyridin-2-ylamino)pyridin-2-yl]thiazol-2-yl}oxazolidine-3-carboxylic acid tert-butyl ester (Compound A-12)

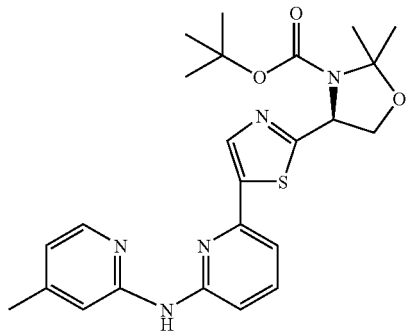

The title compound (1.91 g, 90%) was obtained in a similar process as in Step 4 of Example 6 using (S)-4-[5-(6-bromopyridin-2-yl)-5-thiazol-2-yl]-2,2-dimethyloxazolidine-3-carboxylic acid tert-butyl ester (2.00 g, 4.54 mmol) obtained in Step 2 of example 11, 2-amino-4-picoline (540 mg, 5.00 mmol), palladium acetate (153 mg, 0.68 mmol), rac-2,2'-bis(diphenylphosphino)-1,1'-binaphthyl (565 mg, 0.91 mmol) and cesium carbonate (2.22 g, 6.80 mmol).

Example 13

Preparation of (S)-2-amino-2-{5-[6-(4-methylpyridin-2-ylamino)pyridin-2-yl]thiazol-2-yl}ethanol (Compound A-13)

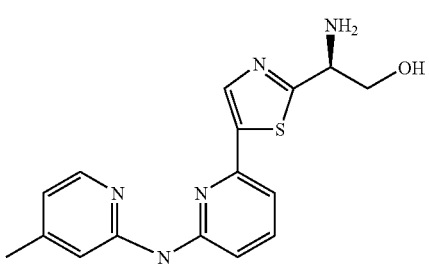

To a solution of (S)-2,2-dimethyl-4-{5-[6-(4-methylpyridin-2-ylamino)pyridin-2-yl]thiazol-2-yl}oxazolidine-3-carboxylic acid tert-butyl ester (1.90 g, 4.06 mmol) obtained in Example 12 in tetrahydrofuran (10 ml), 4N hydrogen chloride-ethyl acetate solution (10 ml) was added and stirred at 60° C. for 5 hours. After the reaction solution was concentrated, it was neutralized with a saturated aqeous sodium bicarbonate, and extracted with ethyl acetate. After the organic layer was washed with a saturated brine and dried over magnesium sulfate, it was concentrated and the residue was purified by flash chromatography on silica gel (chloroform:methanol=20:1) and the title compound (588 mg, 44%) was obtained.

$^1$H-NMR (400M Hz, DMSO-d$_6$) δ: 9.65 (1H, brs), 8.30 (1H, s), 8.10 (1H, d, J=4.8 Hz), 7.98 (1H, brs), 7.67 (1H, t, J=7.8 Hz), 7.39-7.37 (2H, m), 6.77 (1H, d, J=4.8 Hz), 5.01 (1H, t, J=5.8 Hz), 4.16 (1H, dd, J=6.8, 4.4 Hz), 3.77-3.72 (1H, m), 3.56-3.50 (1H, m), 2.35(3H, s)

MS: 328.1(M$^+$+1)

Example 14

Preparation of (S)-4-{5-[6-(4-methylpyridin-2-ylamino)pyridin-2-yl]thiazol-2-yl}oxazolidin-2-one (Compound A-14)

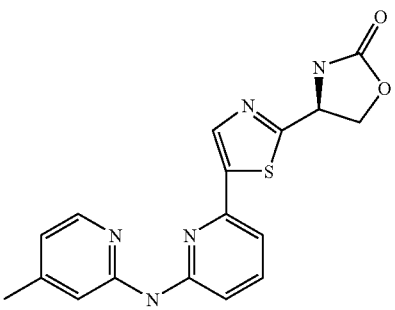

To a solution of (S)-2-amino-2-{5-[6-(4-methylpyridin-2-ylamino)pyridin-2-yl]thiazol-2-yl}ethanol (220 mg, 0.67 mmol) obtained in Example 13, triethylamine (0.93 ml, 0.67 mmol) in chloroform (5 ml), triphosgene (70 mg, 0.24 mmol) was added while cooled to −78° C., and the mixture was stirred at the same temperature for 3 hours. The reaction solution was warmed to room temperature and water was added and it was extracted with ethyl acetate. After washed with a saturated saline solution, the organic layer was dried over magnesium sulfate. After concentrated, the residue was washed with ethanol and the title compound (41 mg, 17%) was obtained.

$^1$H-NMR (400M Hz, DMSO-d$_6$) δ: 9.70 (1H, brs), 8.66 (1H, br), 8.43 (1H, s), 8.1 (1H, d, J=5.2 Hz), 7.89 (1H, brs), 7.72 (1H, t, J=8.0 Hz), 7.46 (1H, d, J=8.0 Hz), 7.44 (1H, d, J=8.0 Hz), 6.78 (1H, brd, J=5.2 Hz), 5.28 (1H, ddd, J=8.8, 4.4, 1.2 Hz), 4.73 (1H, t, J=8.8 Hz), 4.35 (1H, dd, J=8.8, 4.4 Hz), 2.34(3H, s)

MS: 354.1(M$^+$+1)

Example 15

Preparation of (1-{5-[6-(4-methylpyridin-2-ylamino)pyridin-2-yl]thiazol-2-yl}piperidin-4-yl)acetic acid dihydrochloride (Compound A-15)

Step 1;

Preparation of (1-thiocarbamoylpiperidin-4-yl)acetic acid tert-butyl ester

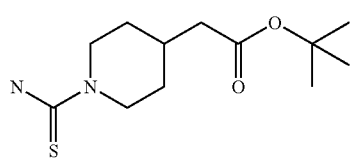

A solution of piperidin-4-ylacetic acid tert-butyl ester (10.72 g, 50.0 mmol) in chloroform (100 ml) was added to a solution of 9-fluorenylmethoxycarbonyl isothiocyanate (14.07 g, 50.0 mmol) in chloroform (100 ml) and the mixture was stirred at room temperature for 1 hour. Then, piperidine (80 ml) was added and the mixture was stirred at room temperature for 30 minutes. After the reaction solution was concentrated, water was added, and it was extracted with ethyl acetate and washed with a saturated brine. The organic layer was dried over magnesium sulfate and the residue obtained by vacuum concentration was washed with isopropyl ether and the title compound was obtained (11.35 g, 98%).

Step 2; Preparation of 1-[5-(6-bromopyridin-2-yl) thiazol-2-yl]piperidin-4-yl}acetic acid tert-butyl ester

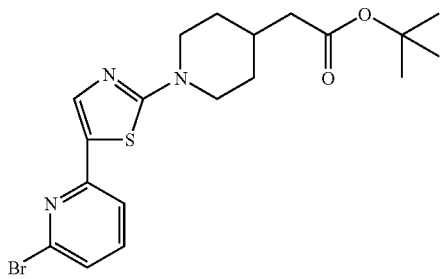

(1-Thiocarbamoylpiperidin-4-yl)acetic acid tert-butyl ester (11.95 g, 46.3 mmol) obtained in Step 1 was added to a solution of 2-bromo-6-chloromethylpyridine (9.55 g, 6.3 mmol) obtained in Step 1 of Example 1 in ethanol (100 ml), and the mixture was heated at reflux overnight. The reaction solution was cooled to room temperature; dimethylformamide dimethylacetal (added 9.3 ml, 69.4 mmol) and triethylamine (19 ml, 139 mmol) were added and heated at reflux for 2 hours. After the reaction solution was concentrated, water was added, and it was extracted with ethyl acetate and washed with a saturated brine. The organic layer was dried over magnesium sulfate and the residue obtained by vacuum concentration was purified by chromatography on silica gel (n-hexane:ethyl acetate=50:50 to 0:100) and the title compound was obtained (13.09 g, 65%).

$^1$H-NMR (400 MHz, DMSO-$d_6$) δ: 7.95 (1H, s), 7.80 (1H, d, J=7.8 Hz), 7.67 (1H, t, J=7.8 Hz), 7.36 (1H, d, J=7.8 Hz), 4.02-3.95 (2H, m), 3.14-3.08 (2H, m), 2.20 (2H, d, J=7.2 Hz), 2.00-1.89 (1H, m), 1.79-1.72 (2H, m), 1.42 (9H, s), 1.34-1.21 (2H, m).

Step 3; Preparation of (1-{5-[6-(4-methylpyridin-2-ylamino)pyridin-2-yl]thiazol-2-yl}piperidin-4-yl) acetic acid tert-butyl ester

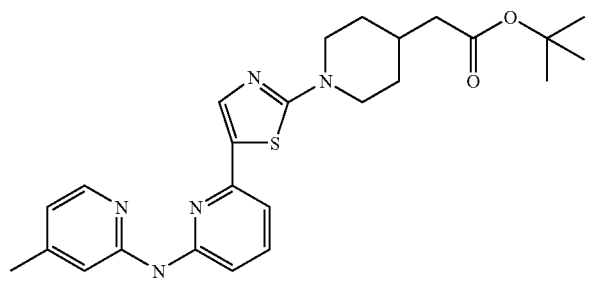

rac-2,2'-bis(diphenylphosphino)-1,1'-binaphthyl (1.85 g, 2.97 mmol) and palladium acetate (500 mg, 2.22 mmol) were suspended in toluene (30 ml), and after 2-amino-4-picoline (1.60 g, 14.8 mmol) and {1-[5-(6-bromopyridin-2-yl)-thiazol-2-yl]piperidin-4-yl}acetic acid tert-butyl ester (6.50 g, 14.8 mmol) obtained in Step 2 were sequentially added, cesium carbonate (7.25 g, 22.2 mmol) was added, and the mixture was stirred overnight at 100° C. Water was added to the reaction solution and extracted with ethyl acetate and washed with a saturated brine. The organic layer was dried over anhydrous sodium sulfate and the residue obtained by vacuum concentration was purified by chromatography on silica gel (n-hexane:ethyl acetate=1:1 to 1:10) and the title compound (4.30 g, 62%) was obtained.

Step 4; Preparation of (1-{5-[6-(4-methylpyridin-2-ylamino)pyridin-2-yl)thiazol-2-yl}piperidin-4-yl) acetic acid dihydrochloride

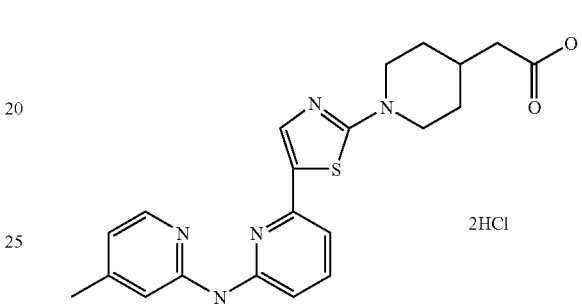

Trifluoroacetic acid (20 ml) was added to a solution of (1-{5-[6-(4-methylpyridin-2-ylamino)pyridin-2-yl]thiazol-2-yl}piperidin-4-yl)acetic acid tert-butyl ester (4.30 g, 9.23 mmol) obtained in Step 3 in chloroform (20 ml) and the solution was stirred overnight at room temperature. Subsequently 4N hydrochloric acid-ethyl acetate solution (20 ml) was added to the concentrate obtained by concentrating the reaction solution in vacuo, and the precipitated solid was collected by filtration, washed with ethyl acetate (20 ml) and the title compound (4.46 g, 100%) was obtained.

$^1$H-NMR (400 MHz, DMSO-$d_6$) δ: 12.23 (1H, br s), 8.45 (1H, d, J=6.4 Hz), 8.07 (1H, s), 7.88 (1H, t, J=7.9 Hz), 7.56 (1H, d, J=7.7 Hz), 7.50 (1H, br s), 7.21 (1H, d, J=6.4 Hz), 7.10 (1H, d, J=8.2 Hz), 4.07-4.04 (2H, m), 3.25-3.15 (2H, m), 2.50 (3H, s), 2.23 (2H, d, J=7.1 Hz), 2.05-1.92 (1H, m), 1.86-1.78 (2H, m), 1.37-1.24 (2H, m). MS: 410.3(M$^+$+1)

Example 16

Preparation of trans-4-[(N-methyl-N-{5-[6-(4-methylpyridin-2-ylamino)pyridin-2-yl]thiazol-2-yl}amino)methyl]cyclohexanecarboxylic acid (Compound A-16)

Step 1; Preparation of trans-4-aminomethylcyclohexanecarboxylic acid methyl ester hydrochloride

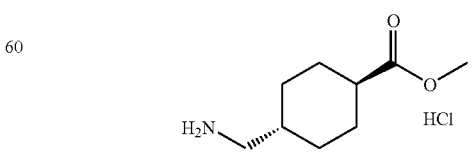

Thionyl chloride (7 ml, 96 mmol) was added to a solution of trans-4-aminomethyl cyclohexanecarboxylic acid (5.00 g, 31.8 mmol) in methanol (50 ml) and the mixture was stirred at room temperature for 16 hours. The reaction solution was concentrated and the obtained solid was washed with diethyl ether (50 ml). Trans-4-aminomethylcyclohexanecarboxylic acid methyl ester hydrochloride (6.49 g, 98%) was obtained by separating by filtration and drying in vacuo.

$^1$H-NMR (400 MHz, DMSO-d$_6$) δ: 8.11-7.78(3H,m), 3.59 (3H, s), 2.69-2.59 (2H, m), 2.31-2.19 (1H, m), 1.96-1.88 (2H, m), 1.85-1.75 (2H, m), 1.59-1.47 (1H, m), 1.36-1.21 (2H, m), 1.05-0.90 (2H, m).

Step 2;

Preparation of trans-4-thiouredide methylcyclohexane carboxylic acid methyl ester

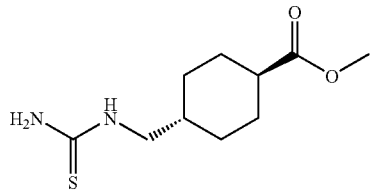

Sodium hydrogen carbonate (1.68 g, 20.0 mmol) was added to a solution of trans-4-aminomethyl cyclohexanecarboxylic acid methyl ester hydrochloride (2.07 g, 10.0 mmol) obtained in Step 1, 9-fluorenylmethoxycarbonyl isothiocyanate (2.81 g, 10.0 mmol) in chloroform (40 ml) while ice-cooled. The reaction solution was stirred at room temperature for 16 hours, piperidine (5 ml, 50 mmol) was added, and the mixture was stirred at room temperature for further 6 hours. Trans-4-thiouredide methylcyclohexane carboxylic acid methyl ester (1.55 g, 67%) was obtained by concentrating the reaction solution in vacuo and purifying the obtained solid by silica gel column chromatography (ethyl acetate).

$^1$H-NMR (400 MHz, DMSO-d$_6$) δ: 7.64-7.52 (1H, m), 6.96-6.76 (2H,m), 3.58 (1H, s), 3.26-3.16 (2H, m), 2.29-2.16 (1H, m), 1.95-1.84 (2H, m), 1.78-1.68 (2H, m), 1.51-1.38 (1H, m), 1.34-1.19 (2H, m), 1.01-0.83 (2H m).

Step 3; Preparation of trans-4-{[5-(6-bromopyridin-2-yl)thiazol-2-ylamino]methyl}cyclohexanecarboxylic acid methyl ester

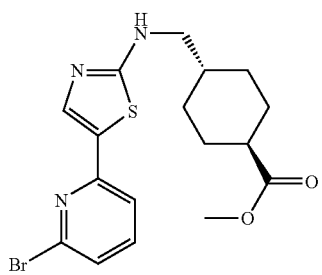

A solution of trans-4-thiouredide methylcyclohexane carboxylic acid methyl ester (1.55 g, 6.73 mmol) obtained in Step 2,2-bromo-6-chloromethylpyridine (1.38 g, 6.73 mmol) obtained in Step 1 of Example 1 in ethanol (15 ml) was stirred under refluxing for 4 hours. After the reaction solution was cooled to room temperature, N,N-dimethylformamide dimethylacetal (0.9 ml, 10 mmol), triethylamine (1.8 ml, 20 mmol) were added and the mixture was stirred under refluxing for 1 hour. The reaction solution was cooled to room temperature and the solid obtained by vacuum concentration was collected by filtration.

trans-4-{[5-(6-bromopyridin-2-yl)thiazol-2-ylamino] methyl}cyclohexanecarboxylic acid methyl ester (2.02 g, 73%) was obtained by sequentially washing with water (10 ml), diethyl ether (10 ml) and drying in vacuo.

$^1$H-NMR (400 MHz, DMSO-d$_6$) δ: 8.15 (1H, t, J=5.7 Hz), 7.83 (1H, s), 7.74 (1H, d, J=7.9 Hz), 7.63 (1H, t, J=7.9 Hz), 7.31 (1H, d, J=7.9 Hz), 3.15-3.06 (2H, m), 2.32-2.19 (1H, m), 1.97-1.87 (2H, m), 1.85-1.76 (2H, m), 1.63-1.49 (1H, m), 1.37-1.23 (2H, m), 1.06-0.93 (2H, m).

Step 4; Preparation of trans-4-({[5-(6-bromopyridin-2-yl]thiazol-2-yl)methylamino}methyl)cyclohexanecarboxylic acid methyl ester

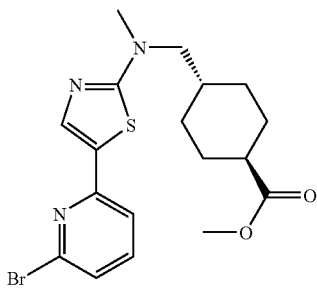

Sodium hydride (53.6 mg, 60% oily, 1.34 mmol) was added to an solution of trans-4-{[5-(6-bromopyridin-2-yl)thiazol-2-ylamino]methyl}cyclohexanecarboxylic acid methyl ester (500 mg, 1.22 mmol) obtained in Step 3 in N,N-dimethylformamide (5 ml), and the mixture was stirred at room temperature for 15 minutes. Methyl iodide (84 µl, 1.34 mmol) was added to the reaction solution and the mixture was stirred at room temperature for 2 hours and extracted by adding ethyl acetate (40 ml) and saturated aqueous ammonium (20 ml). The organic layer was washed with a saturated brine (20 ml×2) and dried over magnesium sulfate. Trans-4-({[5-(6-bromopyridin-2-yl) thiazol-2-yl] methylamino}methyl)cyclohexanecarboxylic acid methyl ester was obtained as a crude product by filtration and vacuum concentration.

$^1$H-NMR (400 MHz, DMSO-d$_6$) δ: 7.92 (1H, s), 7.77 (1H, d, J=7.9 Hz), 7.65 (1H, t, J=7.9 Hz), 7.32 (1H, d, J=7.9 Hz), 3.58(3H, s), 3.39-3.33 (2H, m), 3.10(3H, s), 2.33-2.21 (1H, m), 1.97-1.86 (2H, m), 1.74-1.65 (2H, m), 1.57-1.47 (1H, m), 1.39-1.22 (2H, m), 1.11-0.97 (2H, m).

Step 5; Preparation of trans-4-[(N-methyl-N-{5-[6-(4-methylpyridin-2-ylamino)pyridin-2-yl]thiazol-2-yl}amino)methyl]cyclohexanecarboxylic acid methyl ester

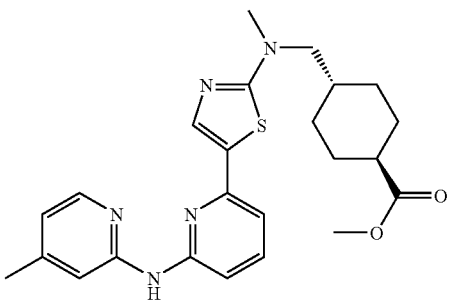

To a solution of trans-4-({[5-(6-bromopyridin-2-yl)thiazol-2-yl]methylamino}methyl)cyclohexanecarboxylic acid methyl ester obtained in Step 4,2-amino-4-picoline (132 mg, 1.22 mmol) in toluene (10 ml), palladium acetate (27 mg, 0.12 mmol), 2,2'-bis(diphenylphosphino)-1,1'-binaphthalene (75 mg, 0.12 mmol), cesium carbonate (596 mg, 1.83 mmol) were added under an Ar atmosphere and the mixture was stirred at 100° C. for 16 hours. After the reaction solution was cooled to room temperature, it was filtrated, concentrated and trans-4-[(methyl{5-[6-(4-methylpyridin-2-ylamino)pyridin-2-yl]thiazol-2-yl}amino]methyl]cyclohexanecarboxylic acid methyl ester (217 mg, 39%) was obtained by purifying the residue by silica gel chromatography (n-hexane:ethyl acetate=1:1).

Step 6; Preparation of trans-4-[(N-methyl-N-{5-[6-(4-methylpyridin-2-ylamino)pyridin-2-yl]thiazol-2-yl}amino]methyl]cyclohexanecarboxylic acid

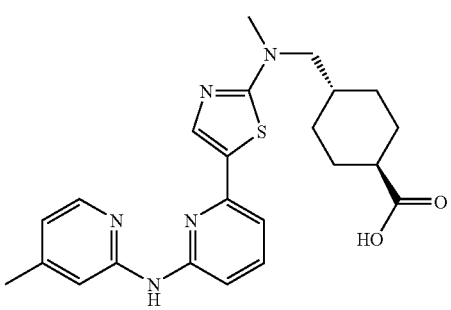

A solution of trans-4-[(N-methyl-N-{5-[6-(4-methylpyridin-2-ylamino)pyridin-2-yl]thiazol-2-yl}amino)methyl]cyclohexanecarboxylic acid methyl ester (217 mg, 0.48 mmol) obtained in Step 5, 1N aqueous sodium hydroxide (2 ml, 2 mmol) in methanol (2 ml) and tetrahydrofuran (2 ml) was stirred at room temperature for 16 hours. The solution was neutralized with 1N hydrochloric acid and extracted with chloroform (50 ml×2). The organic layer was washed with a saturated brine (20 ml) and dried over magnesium sulfate and filtrated and vacuum concentrated. The solid obtained by adding chloroform-diethyl ether (1:1) (10 ml) to the residue was collected by filtration, dried in vacuo and thereby trans-4-[(N-methyl-N-{5-[6-(4-methylpyridin-2-ylamino)pyridin-2-yl]thiazol-2-yl}amino)methyl]cyclohexanecarboxylic acid (190 mg, 90%) was obtained.

$^1$H-NMR (400 MHz, DMSO-$d_6$) δ: 12.04 (1H, s), 9.54 (1H, s), 8.08 (1H, d, J=5.1 Hz), 8.03 (1H, s), 7.79 (1H, s), 7.56 (1H, t, J=7.9 Hz), 7.20 (1H, d, J=7.9 Hz), 7.15 (1H, d, J=7.9 Hz), 6.75 (1H, d, J=5.1 Hz), 3.38-3.29 (2H, m), 3.11 (1H, s), 2.34 (1H, s), 2.19-2.08 (1H, m), 1.97-1.87 (2H, m), 1.77-1.66 (2H, m), 1.57-1.43 (1H, m), 1.36-1.20 (2H, m), 1.10-0.97 (2H, m).

MS 438.2(M+1)

Example 17

Preparation of 3-(1-{5-[6-(4-methyl-pyridin-2-ylamino)pyridin-2-yl]thiazol-2-yl}piperidin-4-yl)propionic acid (Compound A-17)

Step 1;

Preparation of 3-(1-thiocarbamoyl piperidin-4-yl)propionic acid methyl ester

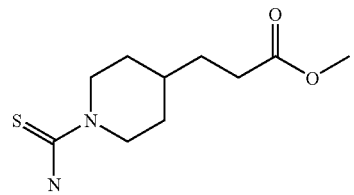

To a solution of 9-fluorenylmethoxycarbonyl-isothiocyanate (4.26 g, 15.2 mmol) in chloroform (40 ml), a solution of (3-piperidin-4-yl)methylpropionic acid methyl ester hydrochloride (2.62 g, 12.6 mol) in chloroform (10 ml) and sodium hydrogen carbonate (6.40 g, 75.8 mmol) were added and the mixture was stirred overnight at room temperature. After the reaction solution was filtered to remove insolubles, chloroform (20 ml) and piperidine (20 ml) were added and the mixture was stirred at room temperature for 1 hour. Water was added to the reaction solution and extracted with ethyl acetate. After the organic layer was washed with a saturated brine and dried over sodium sulfate, the residue obtained by vacuum concentration was purified by silica gel chromatography (n-hexane:ethyl acetate) and the title compound (2.10 g, 63%) was obtained.

Step 2; Preparation of 3-{1-[5-(6-bromopyridin-2-yl)-thiazol-2-yl]piperidin-4-yl}propionic acid methyl ester

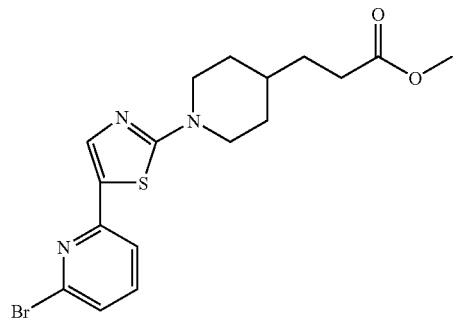

To an solution of 2-bromo-6-chloromethylpyridine (1.88 g, 1.11 mmol) obtained in Step 1 of Example 1 in ethanol (20 ml), 3-(1-thiocarbamoylpiperidin-4-yl)propionic acid methyl ester (2.10 g, 9.12 mmol) obtained in Step 1 was added and the mixture was heated at reflux overnight. The reaction solution was cooled to room temperature, dimethylformamide dimethylacetal (1.8 ml, 14 mmol) and triethylamine (3.8 ml, 27 mmol) were added, and heated at reflux for 1 hour. After the reaction solution was concentrated, water was added, and it was extracted with ethyl acetate and washed with a saturated brine. The organic layer was dried over magnesium sulfate and the residue obtained by vacuum concentration was purified by chromatography on silica gel (n-hexane:ethyl acetate=50:50 to 0:100) and the title compound (748 mg, 20%) was obtained.

$^1$H-NMR (400 MHz, DMSO-$d_6$) δ: 7.95 (1H, s), 7.80 (1H, dd, J=7.9, 0.7 Hz), 7.67 (1H, t, J=7.8 Hz), 7.36 (1H, dd, J=7.7, 0.7 Hz), 4.00-3.97 (2H, m), 3.61 (3H, s), 3.11-3.02 (2H, m), 2.37 (2H, t, J=7.4 Hz), 1.79-1.72 (2H, m), 1.57-1.49 (3H, m), 1.26-1.13 (2H, m).

Step 3; Preparation of 3-(1-{5-[6(4-methyl-pyridin-2-ylamino)pyridin-2-yl]thiazol-2-yl}piperidin-4-yl) propionic acid methyl ester

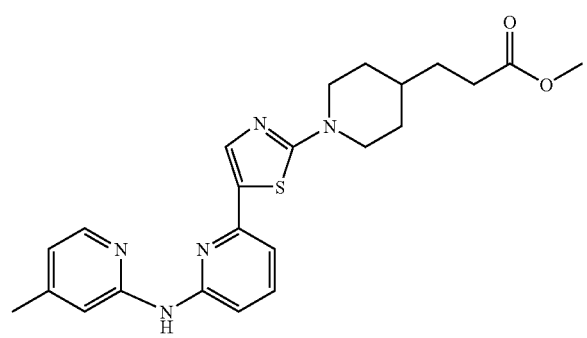

rac-2,2'-bis(diphenylphosphino)-1,1'-binaphthyl (91 mg, 0.15 mmol) and palladium acetate (25 mg, 0.11 mmol) were suspended in toluene (7 ml), and after 2-amino-4-picoline (79 mg, 0.73 mmol) and 3-{1-[5-(6-bromopyridin-2-yl)-thiazol-2-yl]piperidin-4-yl}propionic acid methyl ester (300 mg, 0.73 mmol) obtained in Step 2 were sequentially added, cesium carbonate (357 mg, 1.1 mmol) was added, and the mixture was stirred overnight at 100° C. Water was added to the reaction solution and the solution was extracted with ethyl acetate and washed with a saturated brine. The organic layer was dried over anhydrous sodium sulfate and the residue obtained by vacuum concentration was purified by chromatography on silica gel (n-hexane:ethyl acetate=1:1 to 1:10) and the title compound (250 mg, 55%) was obtained.

$^1$H-NMR (400 MHz, DMSO-$d_6$) δ: 9.55 (1H, br s), 8.09 (1H, d, J=5.1 Hz), 7.96-7.93 (1H, m), 7.83 (1H, s), 7.58 (1H, t, J=8.0 Hz), 7.23 (2H, t, J=7.3 Hz), 6.77-6.74 (1H, m), 3.99-3.92 (2H, m), 3.61 (3H, s), 3.11-3.02 (2H, m), 2.38 (2H, t, J=7.3 Hz), 2.34 (3H, s), 1.81-1.74 (2H, m), 1.57-1.49 (3H, m), 1.29-1.15 (2H, m).

Step 4; Preparation of 3-(1-{5-[6-(4-methyl-pyridin-2-ylamino)pyridin-2-yl]thiazol-2-yl}piperidin-4-yl) propionic acid

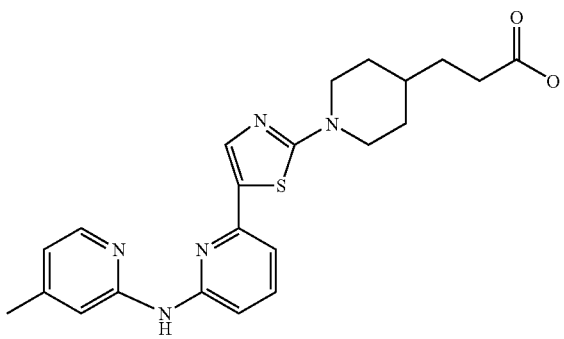

To a mixed solution of 3-(1-{5-[6-(4-methyl-pyridin-2-ylamino)pyridin-2-yl]thiazol-2-yl}piperidine-4-)propionic acid methyl ester (250 mg, 0.57 mmol) obtained in Step 3 in tetrahydrofuran (5 ml) and methanol (5 ml), 4N sodium hydroxide (1.5 ml, 6.0 mmol) was added and the mixture was stirred at room temperature for 12 hours. The concentrate obtained by concentrating the reaction solution in vacuo was neutralized with 0.1N hydrochloric acid, and the precipitated solid was collected by filtration, washed with water and the title compound (142 mg, 59%) was obtained.

$^1$H-NMR (400 MHz, DMSO-$d_6$) δ: 12.07 (1H, br s), 8.24 (1H, d, J=4.6 Hz), 7.91 (1H, s), 7.76-7.66 (2H, m), 7.35 (1H, d, J=7.7 Hz), 7.16 (1H, d, J=8.1 Hz), 6.96-6.90 (1H, m), 4.00 (2H, d, J=13.0 Hz), 3.13-3.03 (2H, m), 2.41 (3H, s), 2.28 (2H, t, J=7.3 Hz), 1.82-1.75 (2H, m), 1.55-1.47 (3H, m), 1.29-1.16 (2H, m).

MS: 424.1(M$^+$+1)

Example 18

Preparation of 2-methyl-2-(1-{5-[6-(4-methylpyridin-2-ylamino)pyridin-2-yl]thiazol-2-yl}piperidin-4-yl)propionic acid (Compound A-18)

Step 1; Preparation of 2-methyl-2-(1-thiocarbamoylpiperidin-4-yl)propionic acid ethyl ester

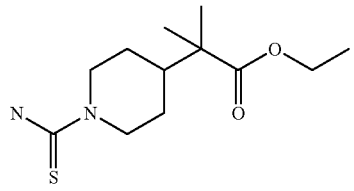

To a solution of 9-fluorenylmethoxycarbonyl-isothiocyanate (2.62 g, 9.32 mmol) in chloroform (20 ml), a solution of 2-methyl-2-piperidin-4-yl-propionic acid ethyl ester hydrochloride (2.27 g, 9.61 mmol) in chloroform (10 ml) and sodium hydrogen carbonate (4.03 g, 48.0 mmol) were added and the mixture was stirred at room temperature. Further, piperidine (30 ml) was added and the mixture was stirred at room temperature for 2 hours. The reaction solution was concentrated in vacuo, and the solid obtained by adding diethyl ether was collected by filtration. The solid was dissolved in N,N-dimethylformamide (20 ml) and piperidine (20 ml) was added and the mixture was stirred at room temperature for 1 hour. Water was added to the reaction solution and the solution was extracted with ethyl acetate. The organic layer was washed with a saturated brine and dried over sodium sulfate, and the residue obtained by vacuum concentration was purified by silica gel chromatography (n-hexane: ethyl acetate) and the title compound (2.4 g, 98%) was obtained.

$^1$H-NMR (400 MHz, DMSO-$d_6$) δ: 7.30 (2H, br s), 4.72-4.57 (2H, m), 4.08 (2H, q, J=7.1 Hz), 2.88-2.77 (2H, m), 1.83-1.72 (1H, m), 1.55-1.46 (2H, m), 1.20-1.09 (2H, m), 1.19 (3H, t, J=7.1 Hz), 1.06 (6H, s).

Step 2; Preparation of 2-{1-[5-(6-bromopyridin-2-yl) thiazol-2-yl]piperidin-4-yl}-2-methylpropionic acid ethyl ester

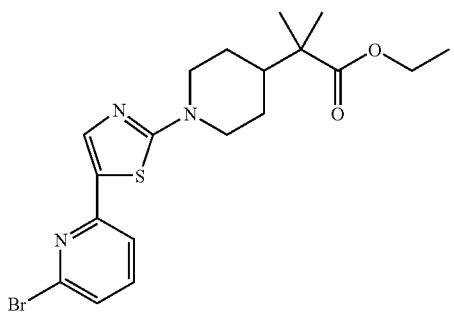

To a solution of 2-bromo-6-chloromethylpyridine (2.14 g, 10.4 mmol) obtained in Step 1 of Example 1 in ethanol (30 ml), 2-methyl-2-(1-thiocarbamoylpiperidin-4-yl)propionic acid ethyl ester (2.44 g, 9.43 mmol) obtained in Step 1 was added and the mixture was heated at reflux for 5 hours. The reaction solution was cooled to room temperature, dimethylformamide dimethylacetal (1.9 ml, 14 mmol) and triethylamine (3.9 ml, 28 mmol) were added, and heated at reflux for 1 hour. After the reaction solution was concentrated, water was added, and the solution was extracted with ethyl acetate and washed with a saturated brine. The organic layer was dried over magnesium sulfate and the residue obtained by vacuum concentration was purified by chromatography on silica gel (n-hexane:ethyl acetate=2:1 to 1:1) and the title compound (2.48 g, 60%) was obtained.

$^1$H-NMR (400 MHz, DMSO-$d_6$) δ: 7.93 (1H, s), 7.78 (1H, d, J=7.8 Hz), 7.66 (1H, t, J=7.8 Hz), 7.34 (1H, d, J=7.8 Hz), 4.08-4.02 (2H, m), 4.08 (2H, q, J=7.1 Hz), 3.08-2.98 (2H, m), 1.86-1.75 (1H, m), 1.66-1.58 (2H, m), 1.37-1.24 (2H, m), 1.18 (3H, t, J=7.1 Hz), 1.08 (6H, s).

Step 3; Preparation of 2-methyl-2-(1-{5-[6-(4-methylpyridin-2-ylamino)pyridin-2-yl]thiazol-2-yl}piperidin-4-yl)propionic acid ethyl ester

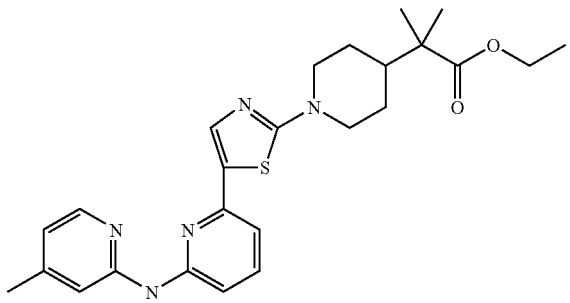

rac-2,2'-bis(diphenylphosphino)-1,1'-binaphthyl (213 mg, 0.34 mmol) and palladium acetate (58 mg, 0.26 mmol) were suspended in toluene (10 ml), and after 2-amino-4-picoline (203 mg, 1.88 mmol) and 2-{1-[5-(6-bromopyridin-2-yl) thiazol-2-yl]piperidin-4-yl}-2-methylpropionic acid ethyl ester (748 mg, 1.71 mmol) obtained in Step 2 were sequentially added, cesium carbonate (1.11 g, 3.41 mmol) was added, and the mixture was stirred overnight at 100° C. Water was added to the reaction solution and extracted with ethyl acetate and washed with a saturated brine. The organic layer was dried over anhydrous sodium sulfate and the residue obtained by vacuum concentration was purified by chromatography on silica gel (n-hexane:ethyl acetate=1:1 to 1:3) and the title compound (697 mg, 88%) was obtained.

$^1$H-NMR (400 MHz, DMSO-$d_6$) δ: 9.53 (1H, brs), 8.09 (1H, d, J=5.1 Hz), 7.95-7.92 (1H, m), 7.82 (1H, s), 7.58 (1H, t, J=8.0 Hz), 7.25 (1H, d, J=8.3 Hz), 7.22 (1H, d, J=7.4 Hz), 6.75 (1H, d, J=5.1 Hz), 4.09 (2H, q, J=7.0 Hz), 4.06-4.01 (2H, m), 3.09-2.99 (2H, m), 2.34 (3H, s), 1.86-1.77 (1H, m), 1.68-1.60 (2H, m), 1.41-1.28 (2H, m), 1.19 (3H, t, J=7.0 Hz), 1.10 (6H, s).

Step 4; Preparation of 2-methyl-2-(1-{5-[6-(4-methylpyridin-2-ylamino)pyridin-2-yl]thiazol-2-yl}piperidin-4-yl)propionic acid:

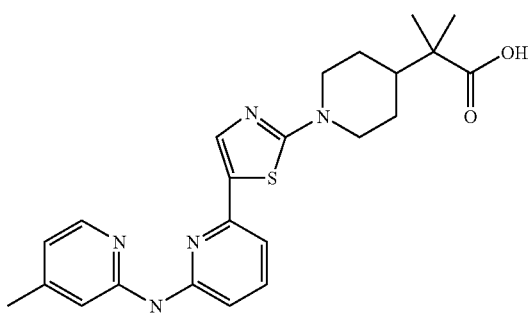

To a mixed solution of 2-methyl-2-(1-{5-[6-(4-methylpyridin-2-ylamino)pyridin-2-yl]thiazol-2-yl}piperidin-4-yl) propionic acid ethyl ester (697 mg, 1.50 mmol) obtained in Step 3 in methanol (5 ml) and tetrahydrofuran (10 ml), 4N aqueous sodium hydroxide (3.7 ml, 15 mmol) was added and the mixture was stirred for 15 hours under refluxing. After concentrated, the reaction solution was neutralized with 1N hydrochloric acid (15 ml, 15 mmol), and the precipitated solid was collected by filtration, washed with water, ethyl acetate, tetrahydrofuran. After dried in vacuo, the title compound (438 mg, 67%) was obtained.

$^1$H-NMR (400 MHz, DMSO-d$_6$) δ: 9.53 (1H, brs), 8.09 (1H, d, J=5.1 Hz), 7.95-7.92 (1H, m), 7.82 (1H, s), 7.58 (1H, t, J=8.0 Hz), 7.25 (1H, d, J=8.0 Hz), 7.22 (1H, d, J=8.0 Hz), 6.75 (1H, d, J=5.1 Hz), 4.07-4.00 (2H, m), 3.09-2.99 (2H, m), 2.34 (3H, S), 1.85-1.75 (1H, m), 1.71-1.64 (2H, m), 1.42-1.28 (2H, m), 1.06 (6H, s).

MS: 438.2(M$^+$+1)

Hereinbelow, other aminopyridine compounds having a thiazole ring were prepared similarly as in the above-mentioned common processes and/or the above Examples. The structures of these compounds have been decided by NMR measurement.

These compounds are shown in the following tables with the inhibitory activity value thereof.

Here, the sign "+++" of IC50(μM) means less than 0.1 μM, and the sign "++" means not less than 0.1 μM and less than 1.0 μM, and the sign "+" means not less than 1.0 μM.

TABLE 1-1

| Chem. Comp. No. | Chemical Compound | M.W. | sykHTRF ave IC50(μM) | human degranulation ave. IC50(μM) |
|---|---|---|---|---|
| A-1 | | 380.47 | ++ | ++ |
| A-2 | | 395.48 | +++ | + |
| A-3 | | 394.50 | +++ | ++ |

TABLE 1-1-continued

| Chem. Comp. No. | Chemical Compound | M.W. | sykHTRF ave IC50(μM) | human degranulation ave. IC50(μM) |
|---|---|---|---|---|
| A-4 | | 408.53 | +++ | + |
| A-5 | | 438.55 | +++ | ++ |

TABLE 1-2

| A-6 | | 408.52 | ++ | ++ |

TABLE 1-2-continued
| A-7 | 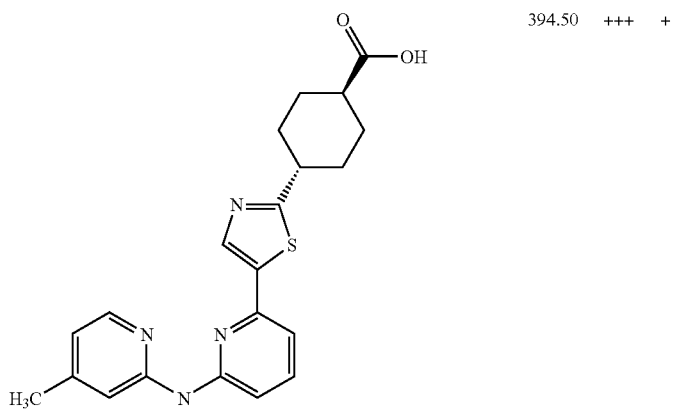 | 394.50 | +++ | + |
| A-8 | 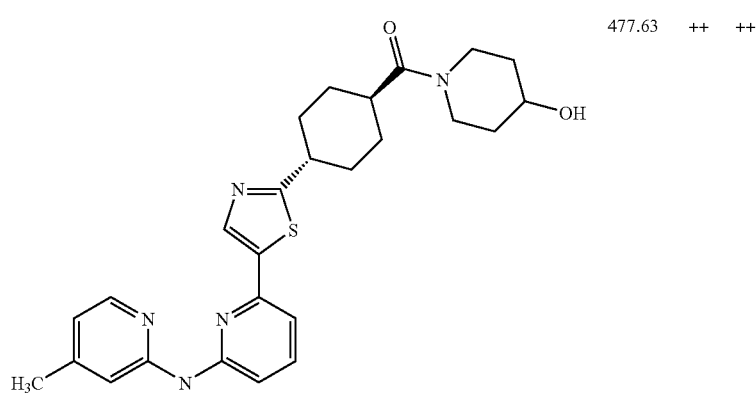 | 477.63 | ++ | ++ |
| A-9 | 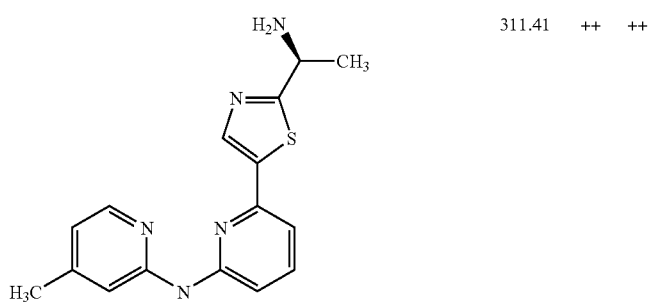 | 311.41 | ++ | ++ |
| A-10 | 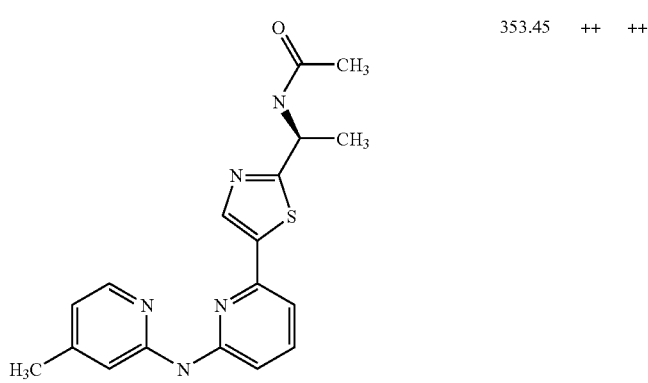 | 353.45 | ++ | ++ |

TABLE 1-2-continued
| A-11 | 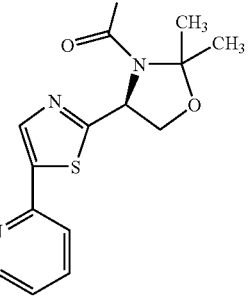 | 367.43 | ++ | ++ |
TABLE 1-3
| A-12 | 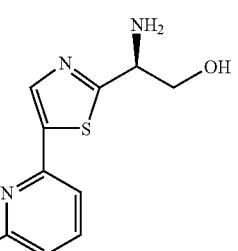 | 467.59 | + | + |
| A-13 | | 327.41 | ++ | ++ |
| A-14 | 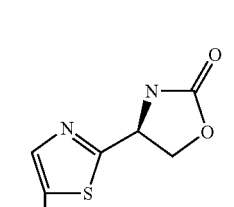 | 353.41 | +++ | ++ |

TABLE 1-3-continued
| ID | Structure | | |
|---|---|---|---|
| A-15 | (structure) | +++ | ++ |
| A-16 | (structure) | +++ | ++ |
| A-17 | (structure) | +++ | ++ |
TABLE 1-4
| ID | Structure | | | |
|---|---|---|---|---|
| A-18 | (structure) | | +++ | |
| A-19 | (structure) | 353.45 | +++ | ++ |

TABLE 1-4-continued

| | | | | |
|---|---|---|---|---|
| A-20 | (structure) | 339.42 | +++ | ++ |
| A-21 | (structure) | 340.41 | +++ | ++ |
| A-22 | (structure) | 356.41 | ++ | + |
| A-23 | (structure) | 325.39 | | ++ |

TABLE 1-5

| | | | | |
|---|---|---|---|---|
| A-24 | (structure) | 268.34 | ++ | + |

TABLE 1-5-continued

| | | | | |
|---|---|---|---|---|
| A-25 | (structure) | 354.43 | +++ | ++ |
| A-26 | (structure) | 312.40 | +++ | ++ |
| A-27 | (structure) | 310.38 | +++ | ++ |
| A-28 | (structure) | 340.41 | +++ | ++ |
| A-29 | (structure) | 355.42 | ++ | ++ |

TABLE 1-6
| | | | | |
|---|---|---|---|---|
| A-30 | 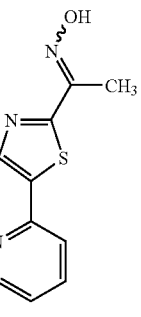 | 325.39 | +++ | ++ |
| A-31 | 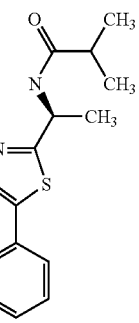 | 381.50 | ++ | ++ |
| A-32 | 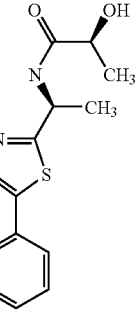 | 383.47 | ++ | ++ |
| A-33 | 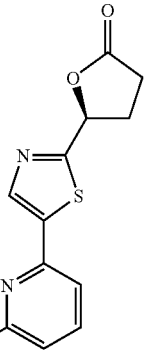 | 352.42 | +++ | ++ |
| A-34 | 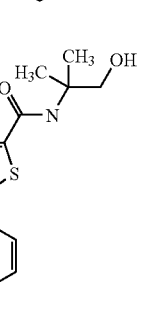 | 383.47 | ++ | + |
TABLE 1-7
| | | | | |
|---|---|---|---|---|
| A-35 | 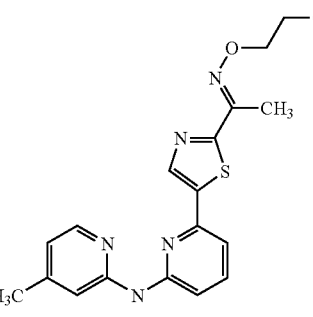 | 369.45 | +++ | ++ |
| A-36 | 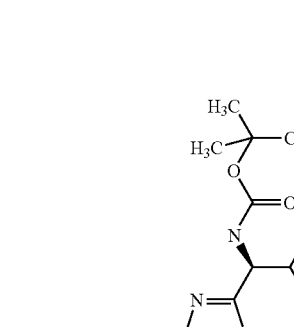 | 439.58 | + | + |
| A-37 | 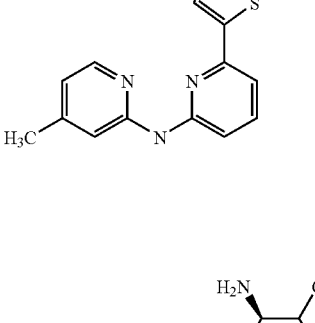 | 339.46 | ++ | + |
| A-38 | 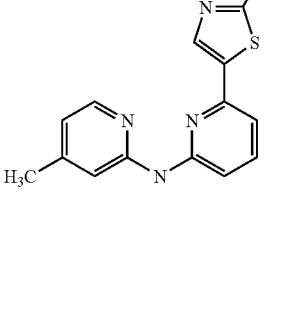 | 381.50 | ++ | ++ |

TABLE 1-8
| | | | | |
|---|---|---|---|---|
| A-39 | 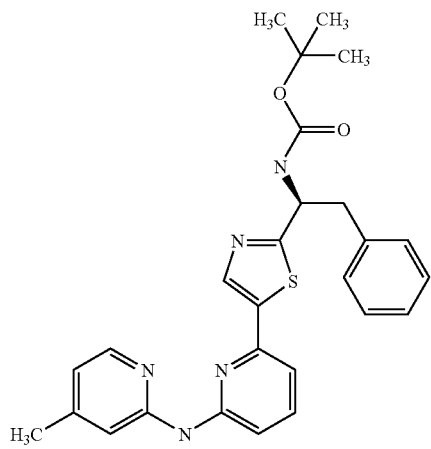 | 487.63 | + | + |
| A-40 | 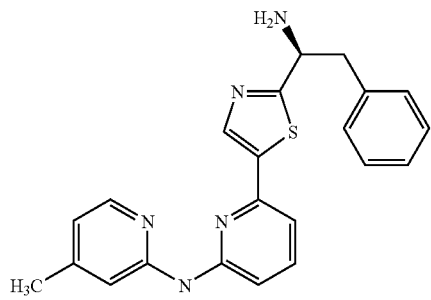 | 387.51 | ++ | + |
| A-41 | 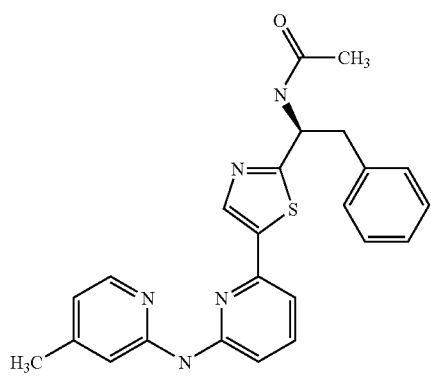 | 429.55 | ++ | + |
| A-42 | 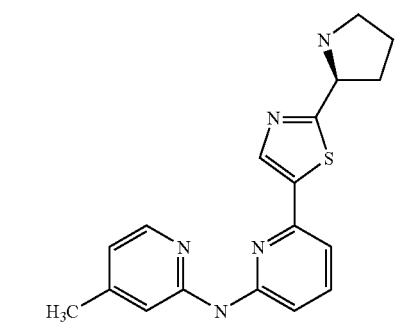 | 337.45 | ++ | + |

TABLE 1-8-continued

| A-43 | (structure) | 517.65 | + | + |

TABLE 1-9

| A-44 | (structure) | 417.53 | + | + |
| A-45 | (structure) | 459.57 | + | + |

TABLE 1-9-continued

| | | | | |
|---|---|---|---|---|
| A-46 | (structure) | 355.42 | +++ | ++ |
| A-47 | (structure) | 325.39 | +++ | ++ |
| A-48 | (structure) | 379.49 | ++ | ++ |

TABLE 1-10

| | | | | |
|---|---|---|---|---|
| A-49 | (structure) | 602.76 | + | + |

TABLE 1-10-continued
| | | | | |
|---|---|---|---|---|
| A-50 | 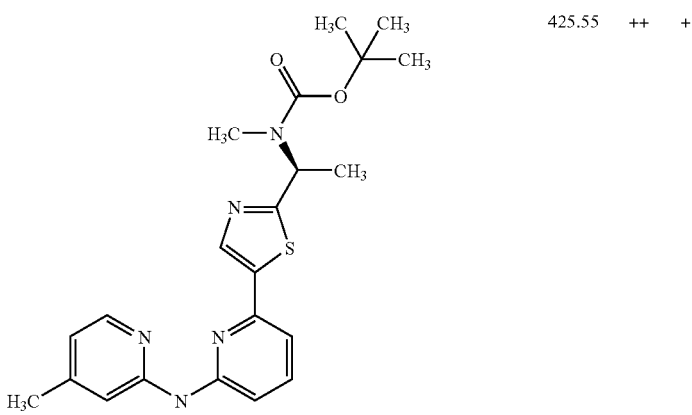 | 425.55 | ++ | + |
| A-51 | 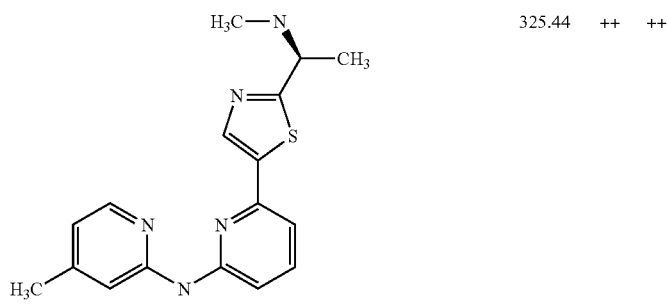 | 325.44 | ++ | ++ |
| A-52 | 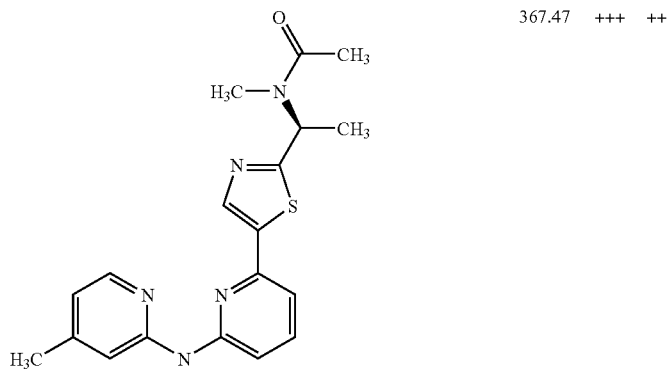 | 367.47 | +++ | ++ |
| A-53 | 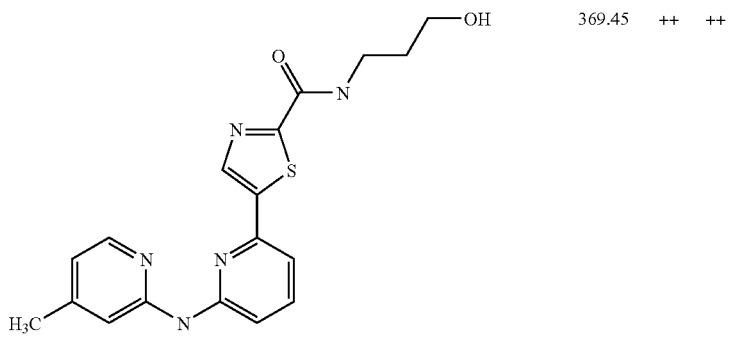 | 369.45 | ++ | ++ |

TABLE 1-11
| A-54 | 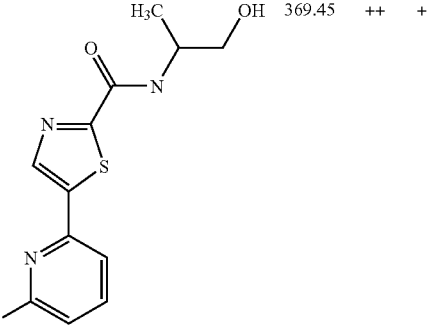 | 369.45 | ++ | + |
| A-55 | 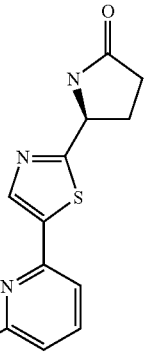 | 351.43 | +++ | ++ |
| A-56 | 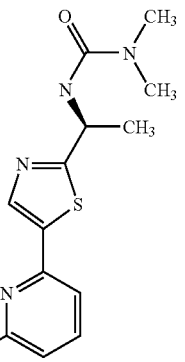 | 382.49 | ++ | ++ |
| A-57 | 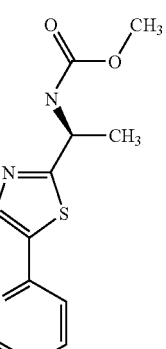 | 369.45 | ++ | ++ |

TABLE 1-11-continued
A-58 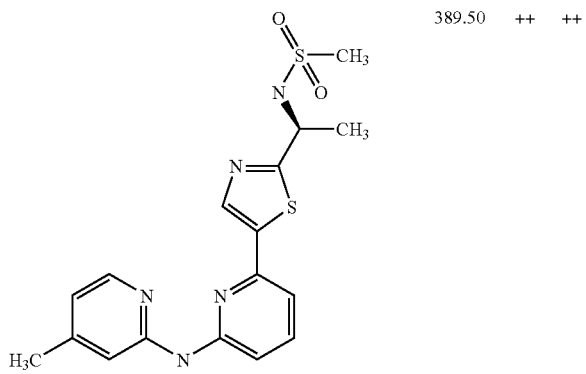 389.50 ++ ++
TABLE 1-12
A-59 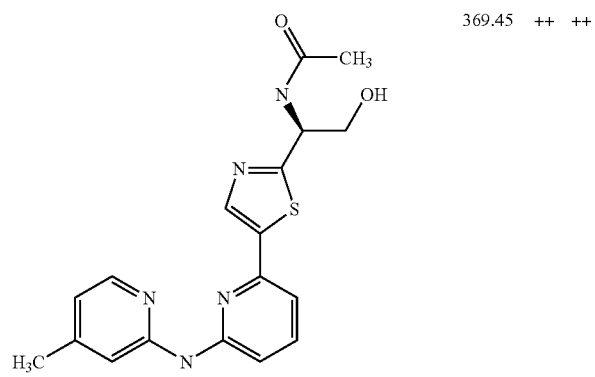 369.45 ++ ++
A-60 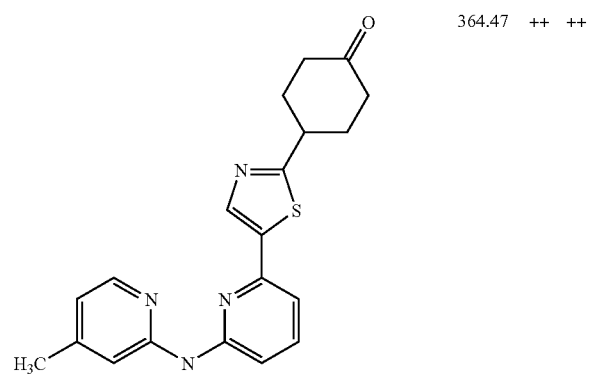 364.47 ++ ++
A-61 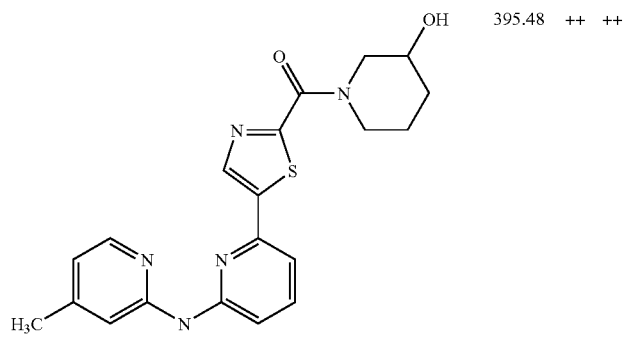 395.48 ++ ++

TABLE 1-12-continued

| | | | | | |
|---|---|---|---|---|---|
| A-62 | (structure) | 397.50 | ++ | + | |
| A-63 | (structure) | 611.24 | ++ | | |

TABLE 1-13

| | | | | |
|---|---|---|---|---|
| A-64 | (structure) | 452.58 | ++ | ++ |
| A-65 | (structure) | 353.49 | ++ | ++ |

TABLE 1-13-continued
| A-66 | 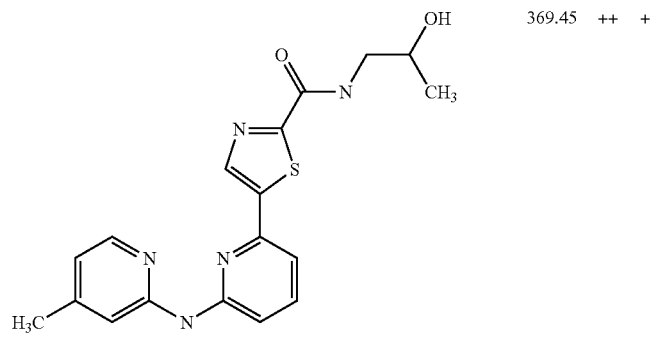 | 369.45 | ++ | + |
| A-67 | 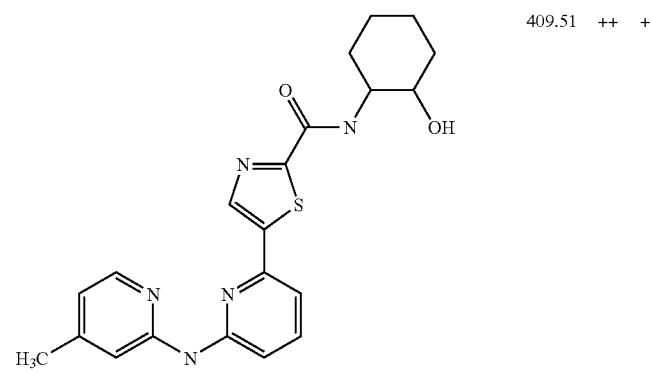 | 409.51 | ++ | + |
| A-68 | 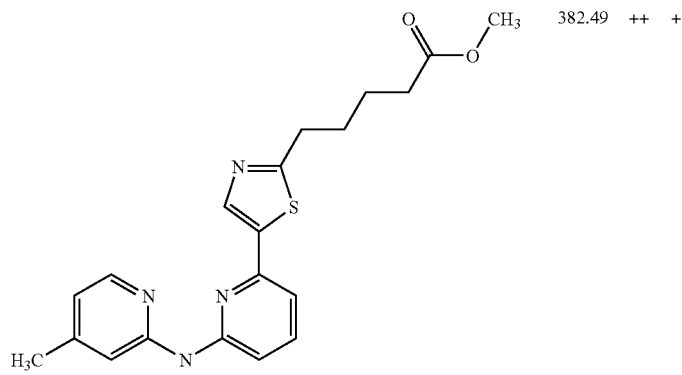 | 382.49 | ++ | + |
TABLE 1-14
| A-69 | 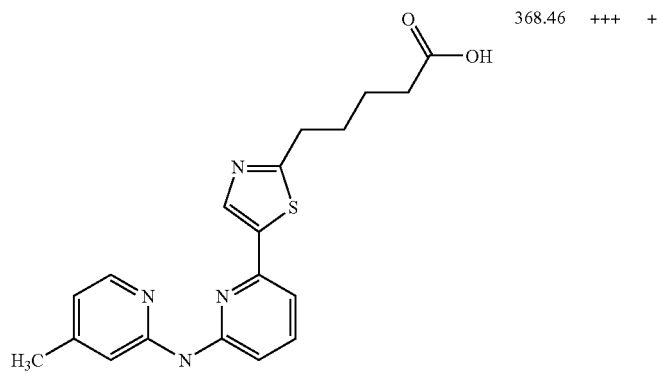 | 368.46 | +++ | + |

TABLE 1-14-continued
| | | | | |
|---|---|---|---|---|
| A-70 |  | 354.48 | +++ | ++ |
| A-71 | 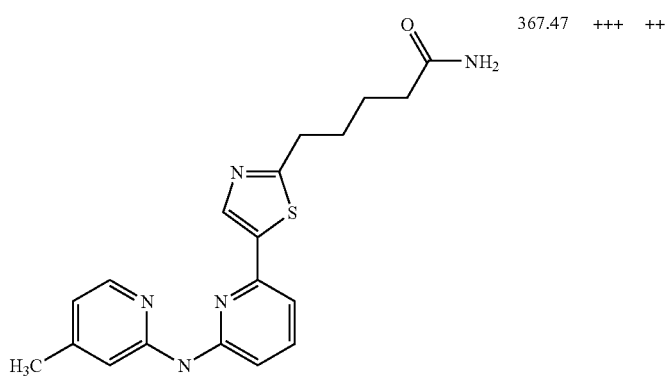 | 367.47 | +++ | ++ |
| A-72 | 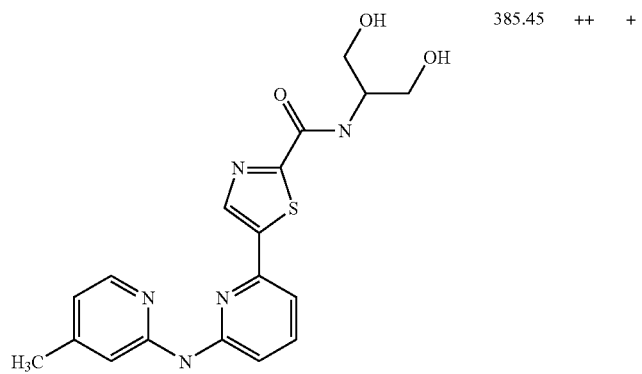 | 385.45 | ++ | + |
| A-73 | 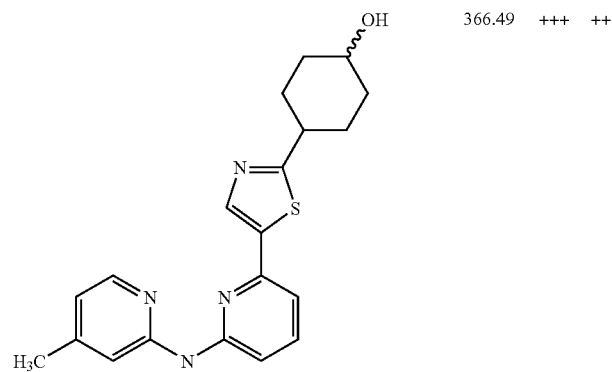 | 366.49 | +++ | ++ |

TABLE 1-15
| A-74 | 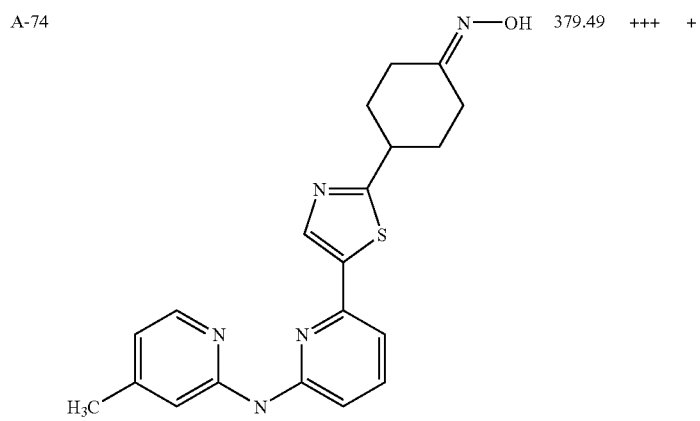 | 379.49 | +++ | + |
| A-75 | 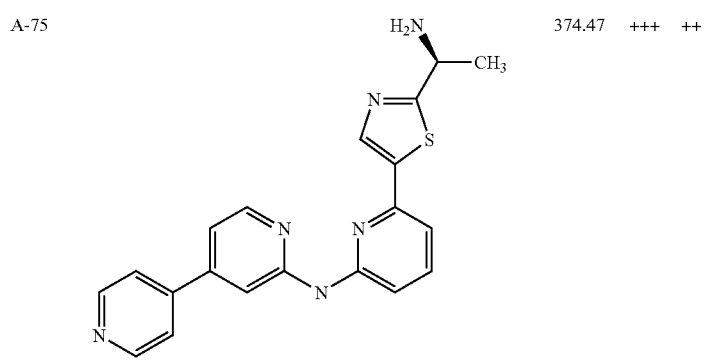 | 374.47 | +++ | ++ |
| A-76 | 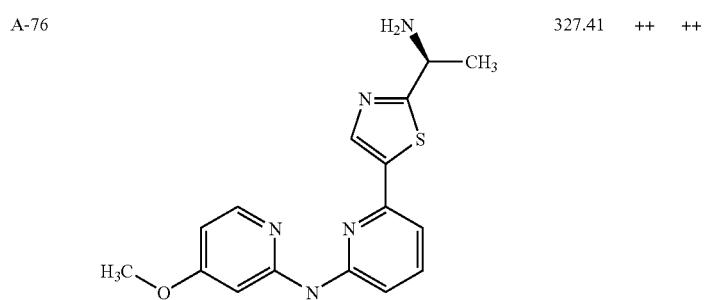 | 327.41 | ++ | ++ |
| A-77 | 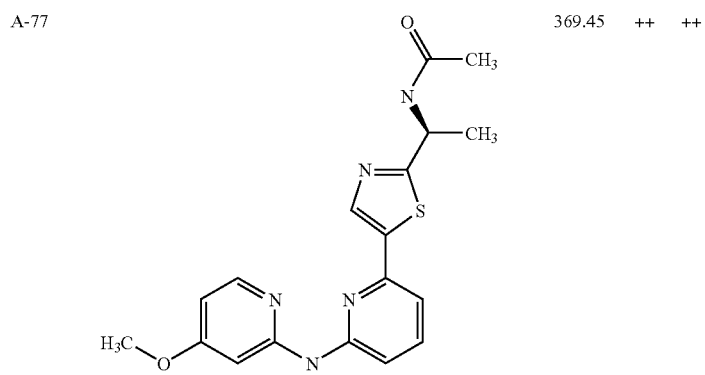 | 369.45 | ++ | ++ |

TABLE 1-15-continued
| A-78 | 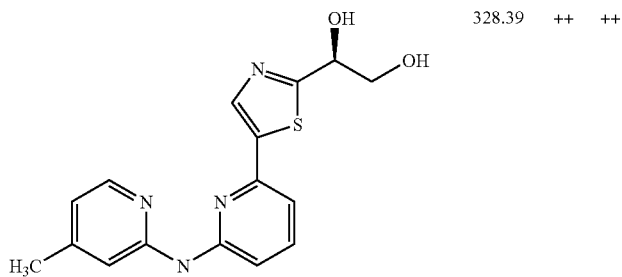 | 328.39 | ++ | ++ |
TABLE 1-16
| A-79 | 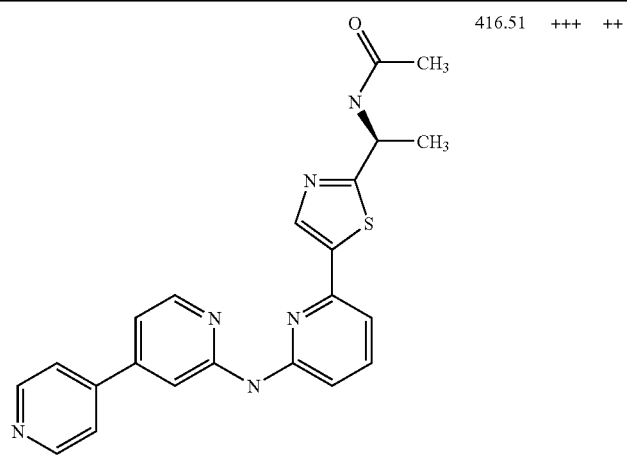 | 416.51 | +++ | ++ |
| A-80 | 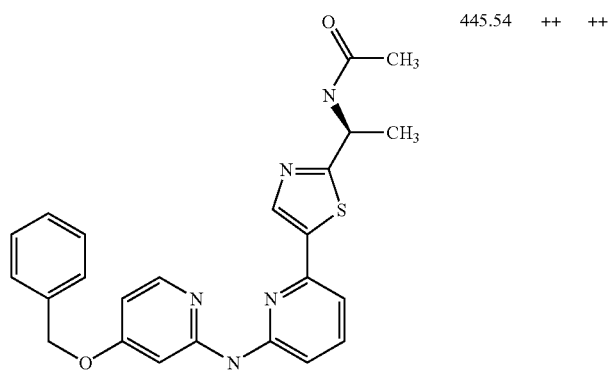 | 445.54 | ++ | ++ |
| A-81 | 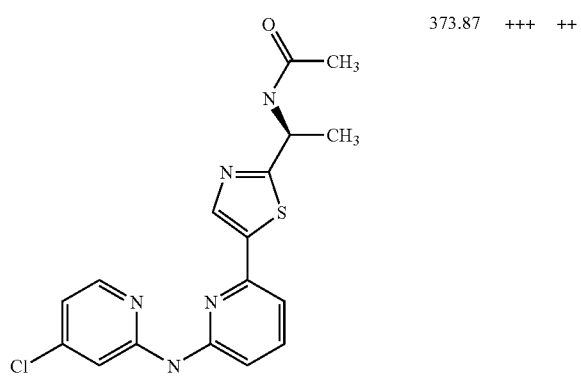 | 373.87 | +++ | ++ |

TABLE 1-16-continued
| A-82 | 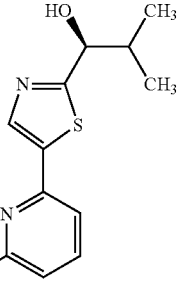 | 340.45 | +++ | ++ |
| A-83 | 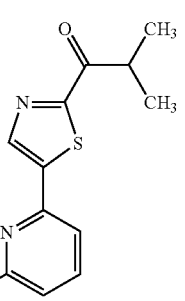 | 338.43 | ++ | + |
TABLE 1-17
| A-84 | 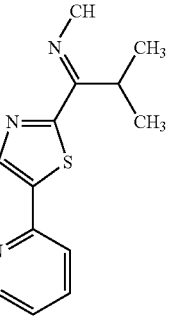 | 353.45 | ++ | ++ |
| A-85 | 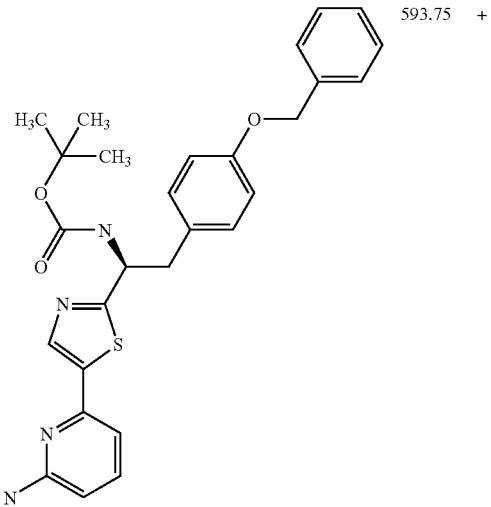 | 593.75 | + | |

TABLE 1-17-continued
A-86 493.63 ++ +
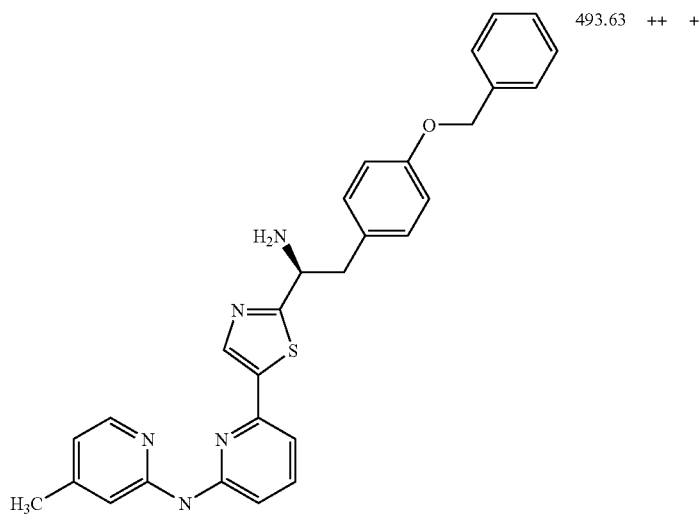
A-87 535.67
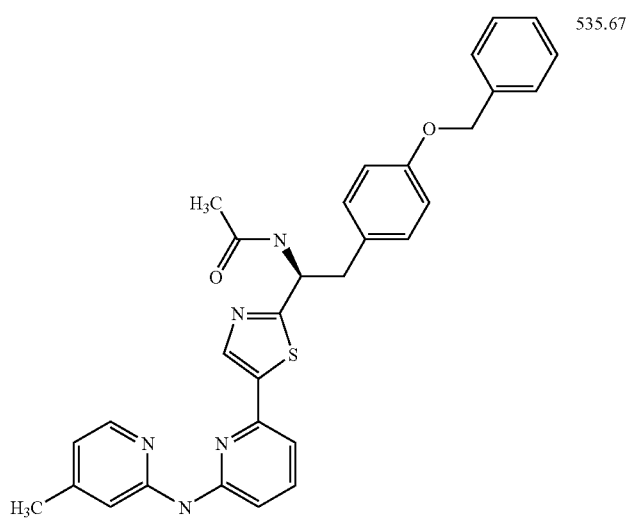
TABLE 1-18
A-88 543.69
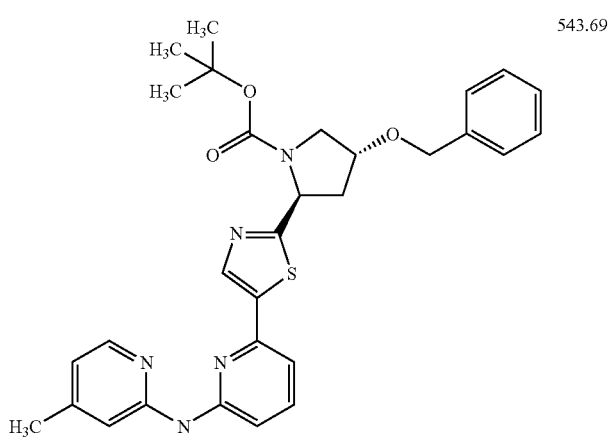

TABLE 1-18-continued
| A-89 | 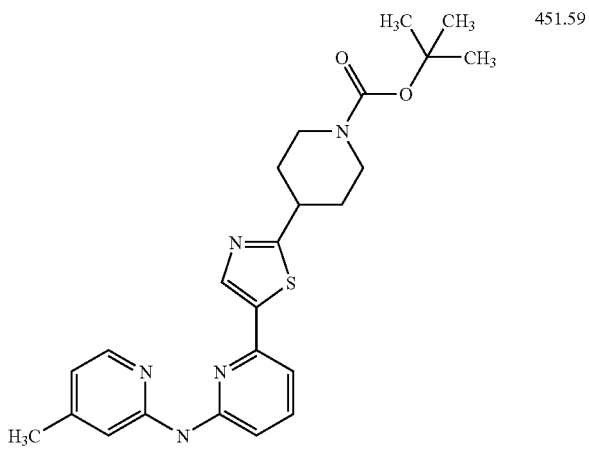 | 451.59 | | |
| A-90 | 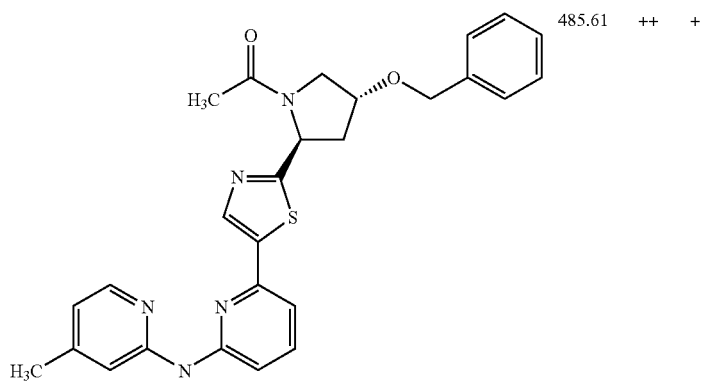 | 485.61 | ++ | + |
| A-91 | 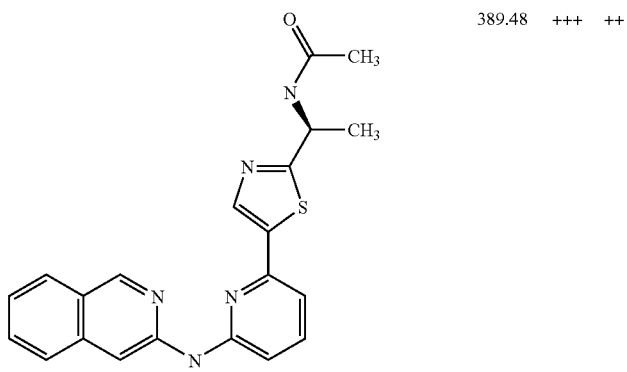 | 389.48 | +++ | ++ |
TABLE 1-19
| A-92 | 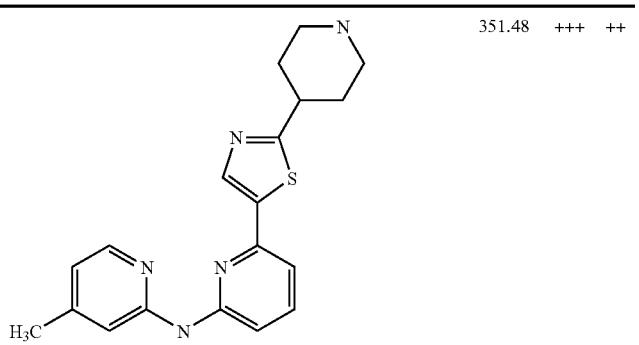 | 351.48 | +++ | ++ |

TABLE 1-19-continued
| | | | | |
|---|---|---|---|---|
| A-93 | 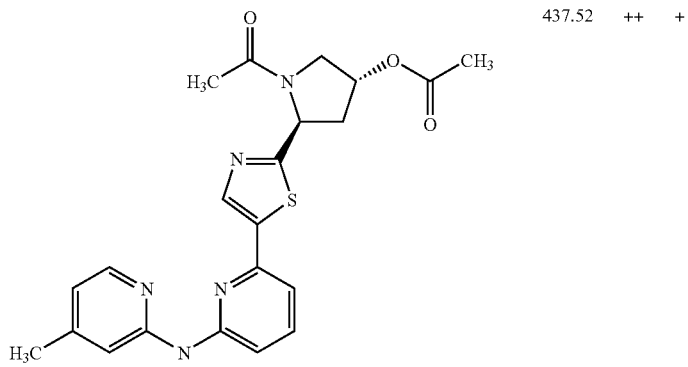 | 437.52 | ++ | + |
| A-94 | 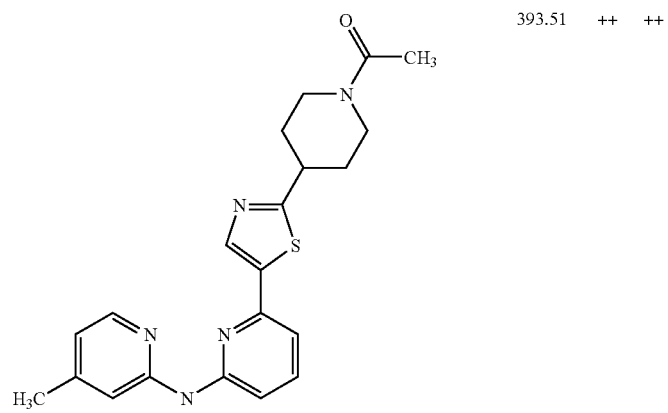 | 393.51 | ++ | ++ |
| A-95 | 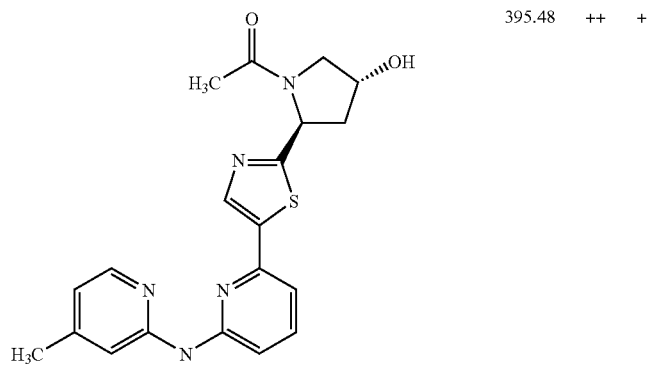 | 395.48 | ++ | + |
| A-96 | 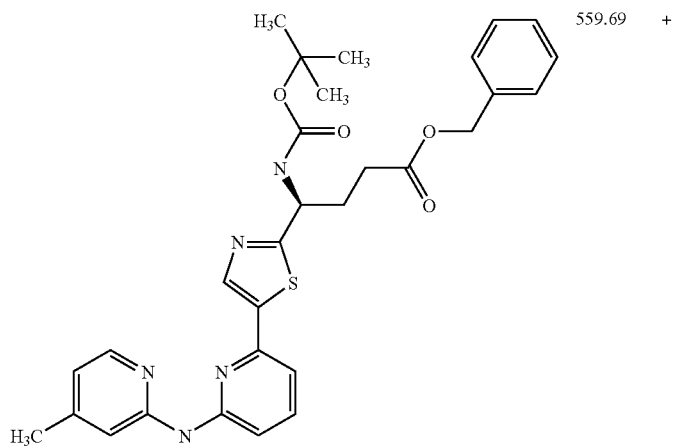 | 559.69 | + | |

TABLE 1-20
A-97 459.57 ++ ++
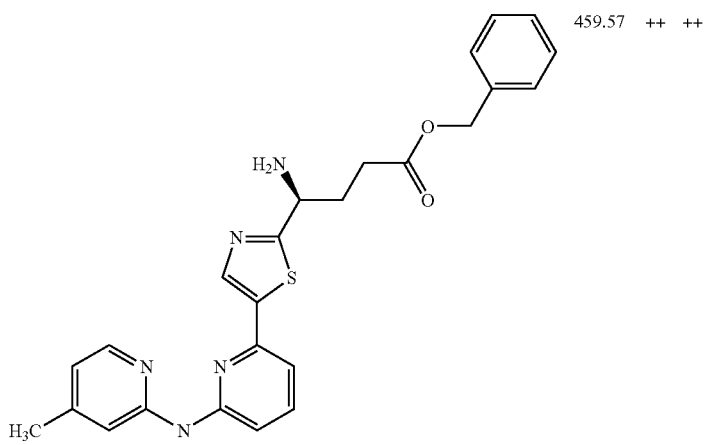
A-98 501.61 ++ +
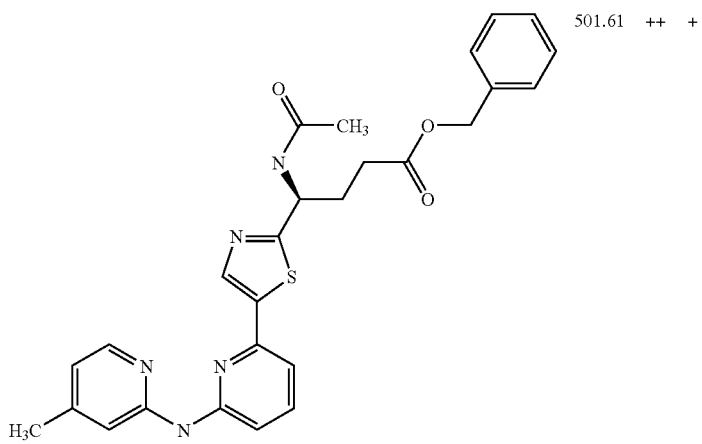
A-99 445.54 ++ ++
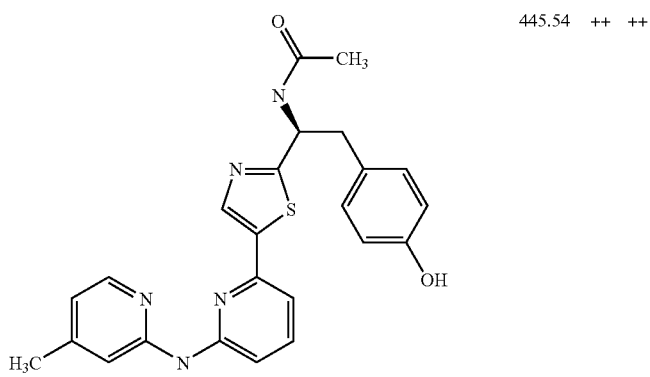

TABLE 1-20-continued

| | | | | |
|---|---|---|---|---|
| A-100 | [structure] | 483.59 | + | |
| A-101 | [structure] | 383.47 | + | + |

TABLE 1-21

| | | | | |
|---|---|---|---|---|
| A-102 | [structure] | 425.51 | + | + |
| A-103 | [structure] | 411.48 | ++ | + |

TABLE 1-21-continued

| | | | | |
|---|---|---|---|---|
| A-104 | [structure] | 325.44 | ++ | + |
| A-105 | [structure] | 367.47 | ++ | + |
| A-106 | [structure] | 369.45 | ++ | + |

TABLE 1-22

| ID | Structure | MW | | |
|---|---|---|---|---|
| A-107 | (3-hydroxy-3-carboxypropyl thiazole, pyridine-NH-methylpyridine) | 370.43 | ++ | + |
| A-108 | (N-acetyl aminoethyl, hydroxymethyl thiazole, pyridine-NH-methylpyridine) | 383.47 | + | + |
| A-109 | (N-acetyl aminoethyl, carboxy thiazole, pyridine-NH-methylpyridine) | 397.46 | + | |

TABLE 1-22-continued

| ID | Structure | MW | | |
|---|---|---|---|---|
| A-110 | (dihydropyrrole-thiazole, pyridine-NH-methylpyridine) | 335.43 | ++ | ++ |
| A-111 | (carboxamide cyclohexyl thiazole, pyridine-NH-methylpyridine) | 393.51 | +++ | ++ |

TABLE 1-23

| ID | Structure | MW | | |
|---|---|---|---|---|
| A-112 | (Boc-amino dimethyl thiazole, pyridine-NH-methylpyridine) | 425.55 | + | + |

TABLE 1-23-continued
| A-113 | 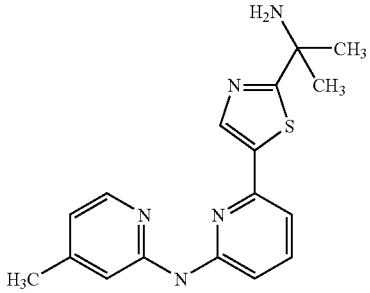 | 325.44 | ++ | ++ |
| A-114 | 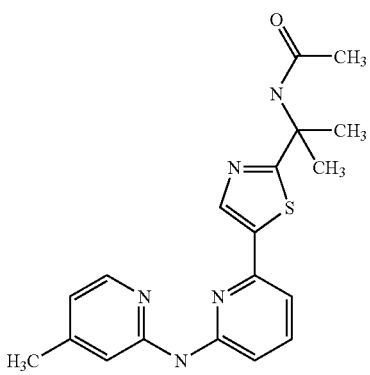 | 367.47 | ++ | + |
| A-115 | 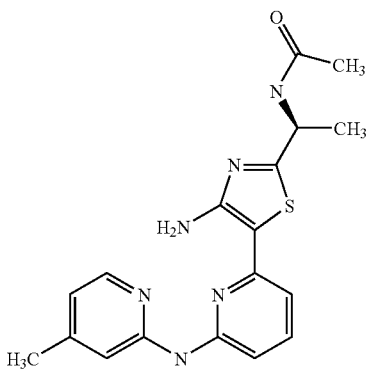 | 368.46 | + | + |
| A-116 | 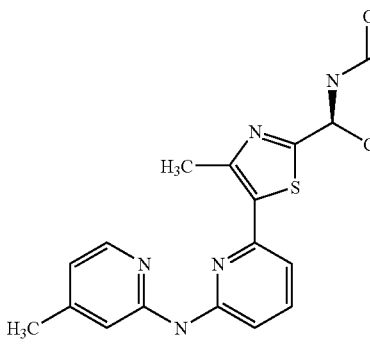 | 425.51 | + | + |

TABLE 1-24
| A-117 | 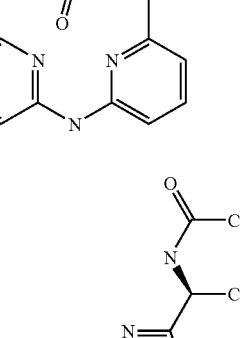 | 396.47 | + | + |
| A-118 | 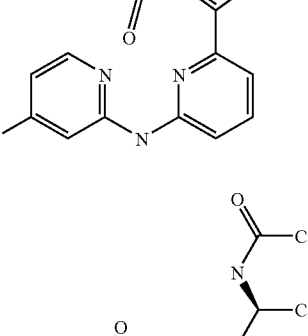 | 410.50 | + | |
| A-119 | 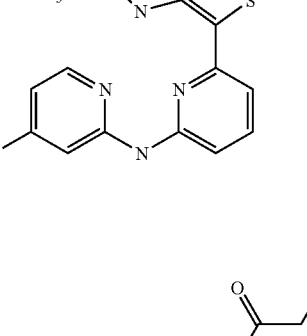 | 410.50 | + | + |
| A-120 | 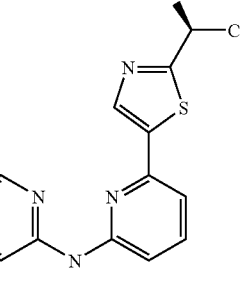 | 439.54 | + | + |

TABLE 1-25
A-121 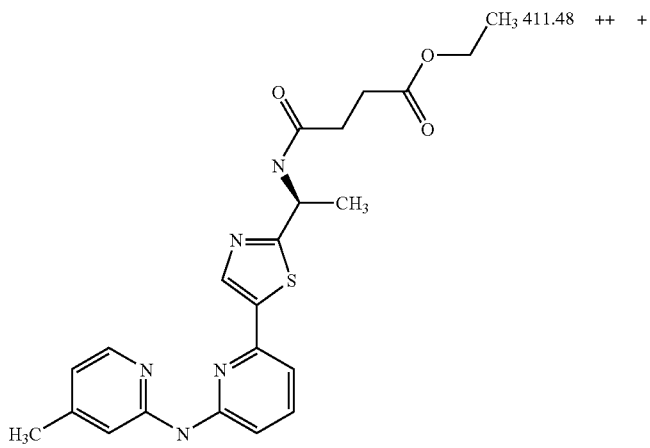 CH₃ 411.48 ++ +
A-122 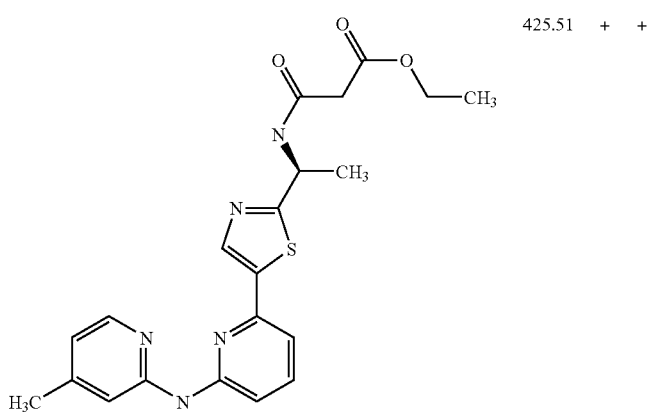 425.51 + +
A-123 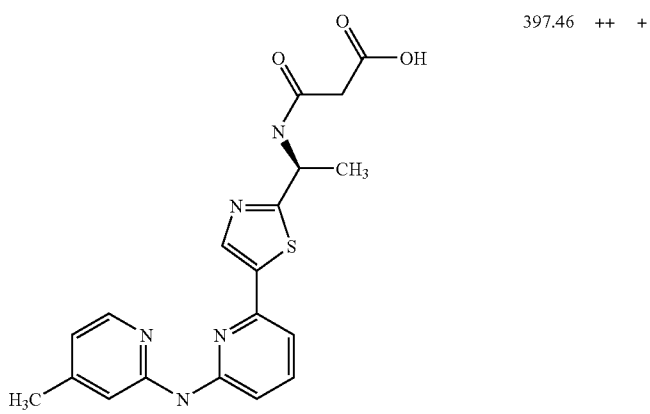 397.46 ++ +
A-124 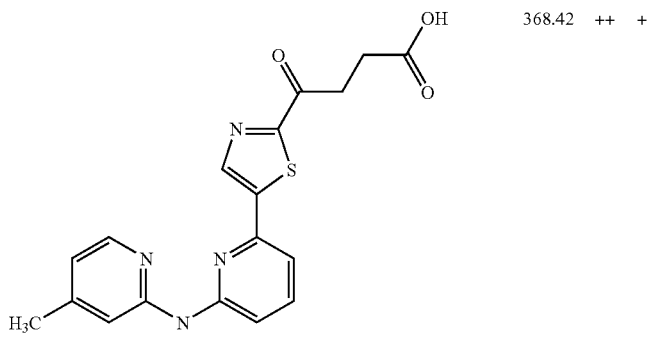 368.42 ++ +

TABLE 1-25-continued
| | | | | |
|---|---|---|---|---|
| A-125 | 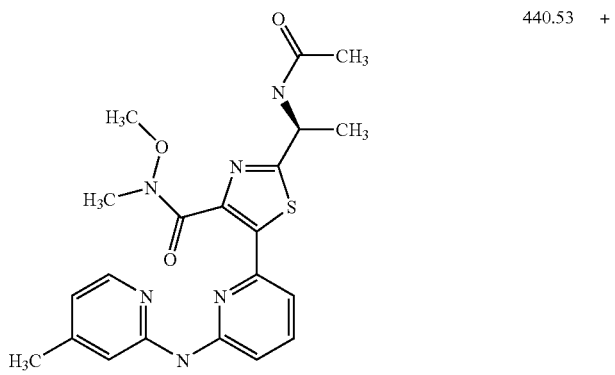 | 440.53 | + | |
TABLE 1-26
| | | | | |
|---|---|---|---|---|
| A-126 | 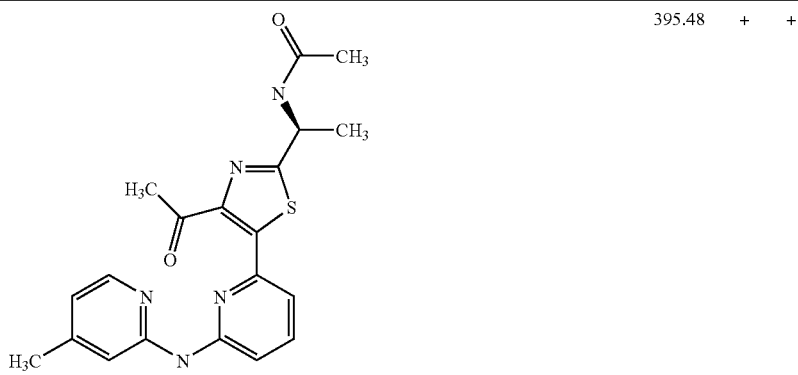 | 395.48 | + | + |
| A-127 | 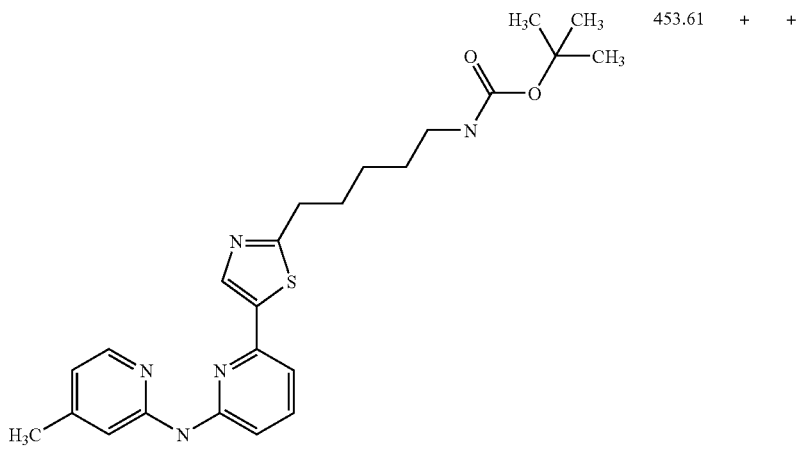 | 453.61 | + | + |
| A-128 | 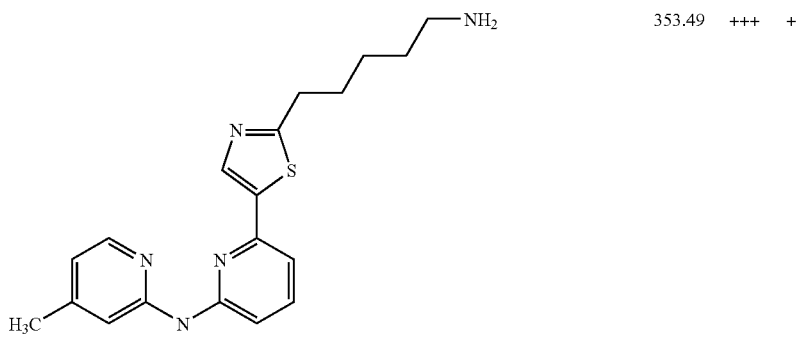 | 353.49 | +++ | + |

TABLE 1-26-continued
| A-129 | 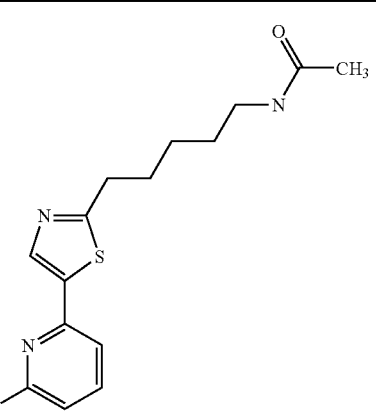 | 395.53 | ++ | + |
| A-130 | 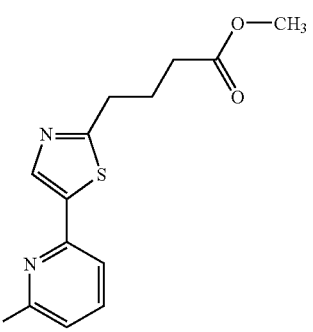 | 368.46 | ++ | + |
TABLE 1-27
| A-131 | 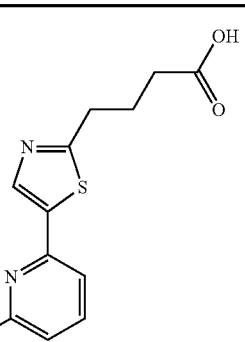 | 354.43 | ++ | + |
| A-132 | 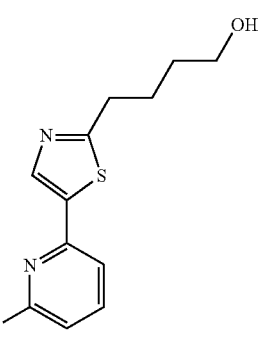 | 340.45 | +++ | ++ |

TABLE 1-27-continued
| A-133 | 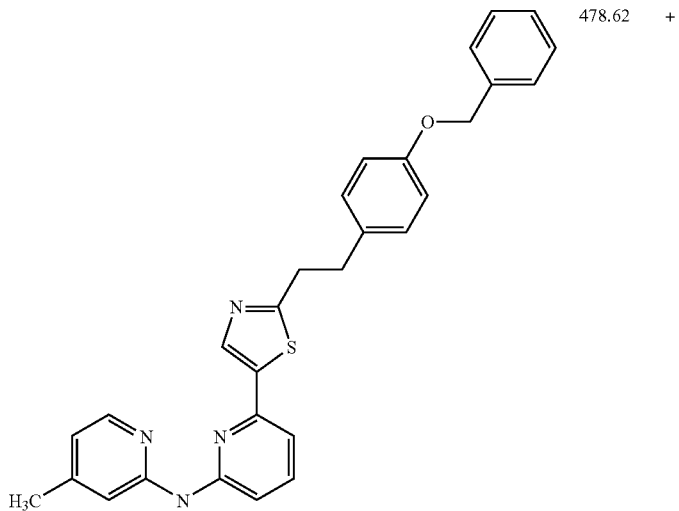 | 478.62 | + | |
| A-134 | 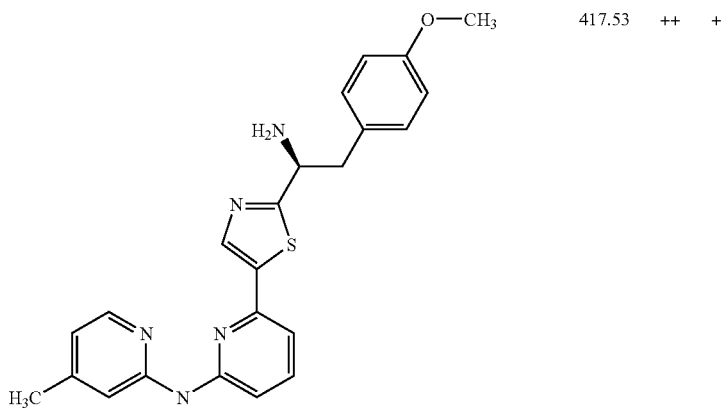 | 417.53 | ++ | + |
| A-135 | 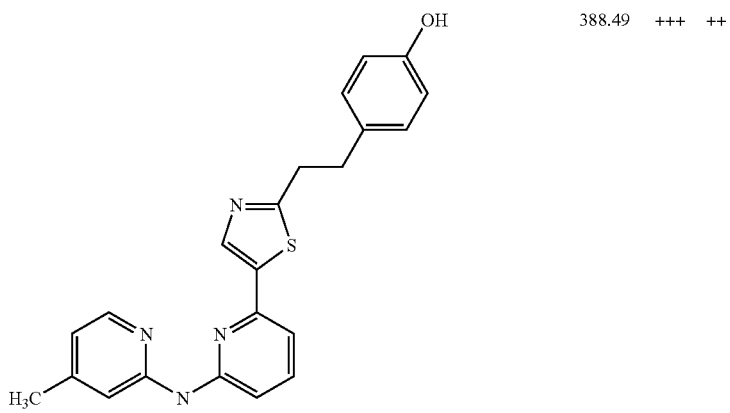 | 388.49 | +++ | ++ |

TABLE 1-28

| | | | |
|---|---|---|---|
| A-136 | | 459.57 | ++ + |
| A-137 | | 402.52 | ++ + |
| A-138 | | 447.56 | ++ + |
| A-139 | | 489.60 | ++ + |

TABLE 1-28-continued
A-140 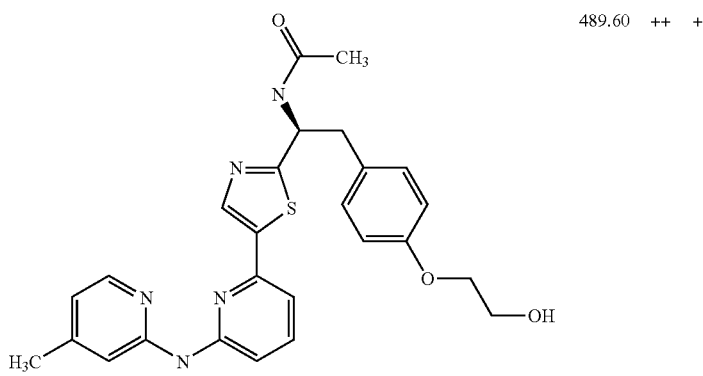 489.60 ++ +
TABLE 1-29
A-141 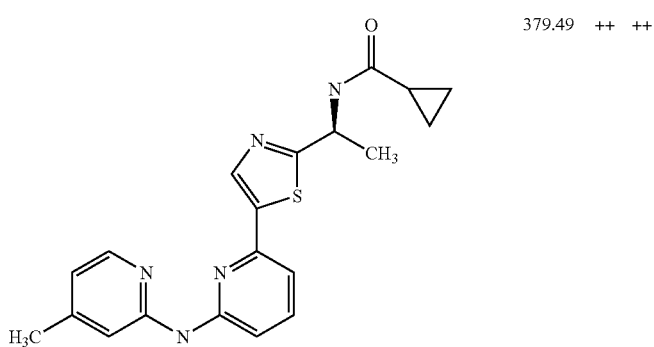 379.49 ++ ++
A-142 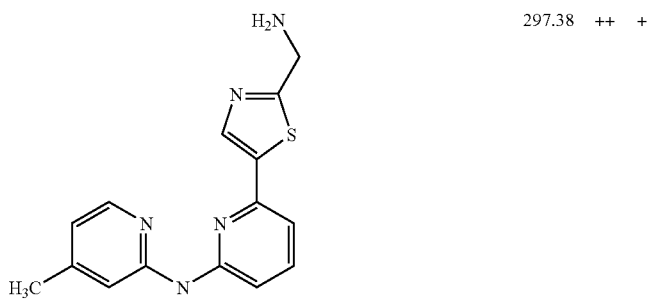 297.38 ++ +
A-143 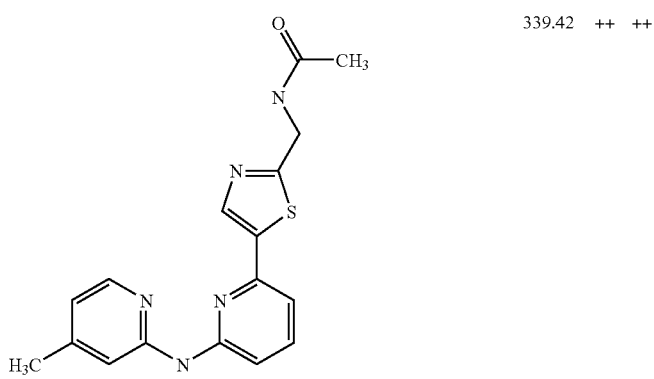 339.42 ++ ++

TABLE 1-29-continued

| A-144 | (structure) | 396.51 | + | + |

| A-145 | (structure) | 368.46 | ++ | + |

TABLE 1-30

| A-146 | (structure) | 411.48 | ++ | ++ |

| A-147 | (structure) | 369.45 | +++ | ++ |

TABLE 1-30-continued
| A-148 | 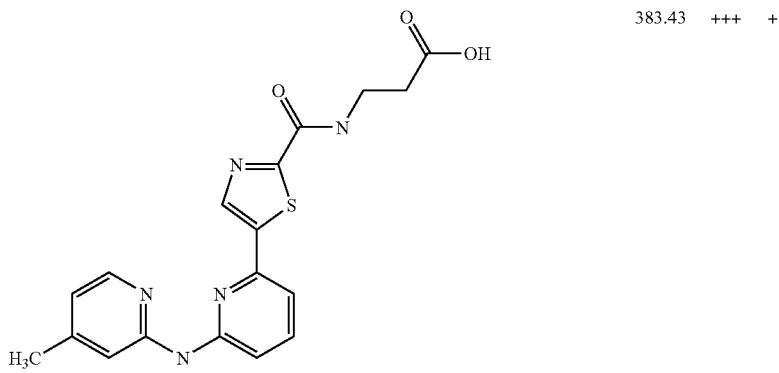 | 383.43 | +++ | + |
| A-149 | 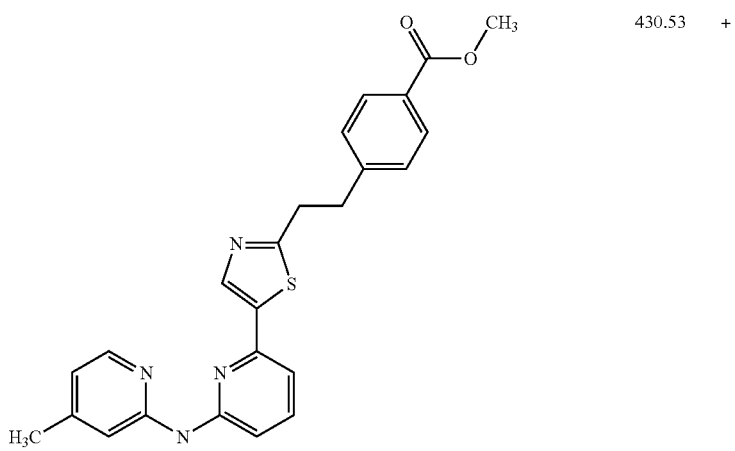 | 430.53 | + | |
| A-150 | 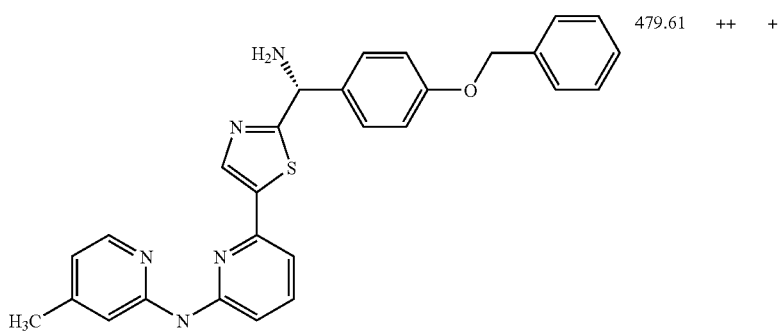 | 479.61 | ++ | + |

TABLE 1-31
A-151 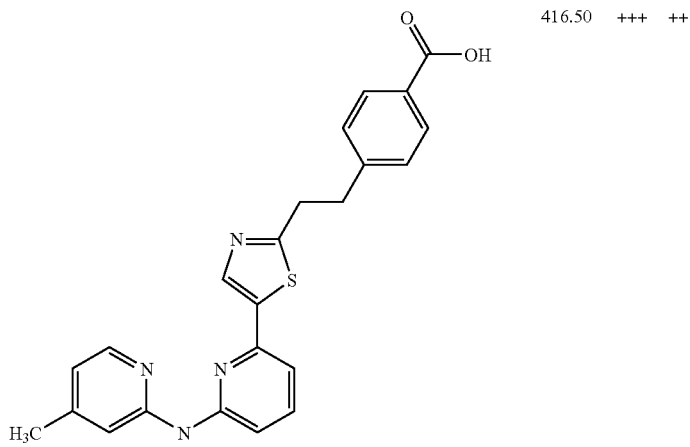 416.50 +++ ++
A-152 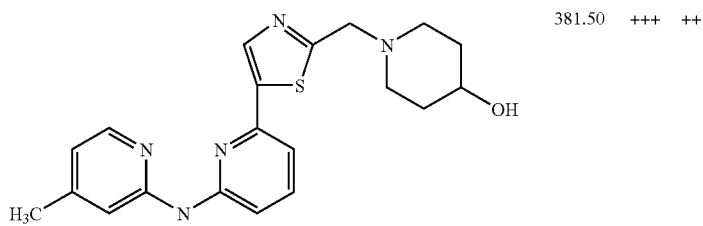 381.50 +++ ++
A-153 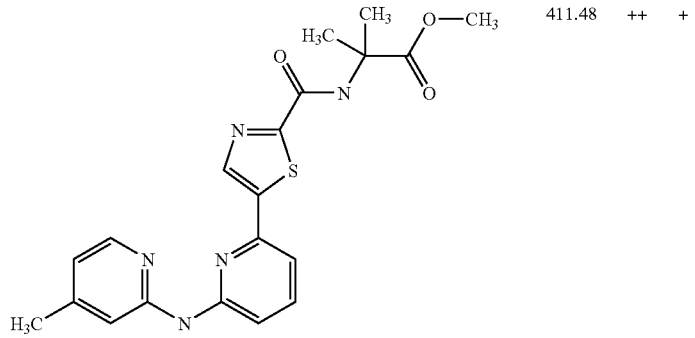 411.48 ++ +
A-154 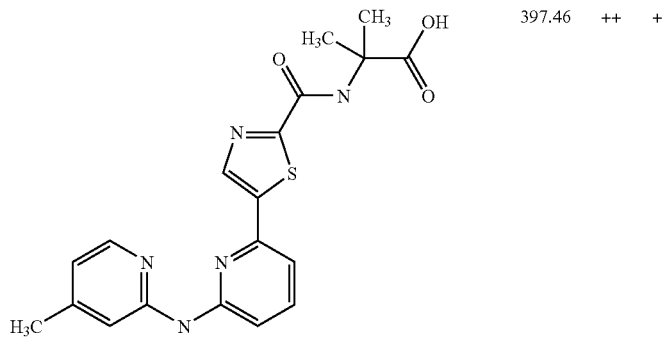 397.46 ++ +

TABLE 1-31-continued
A-155 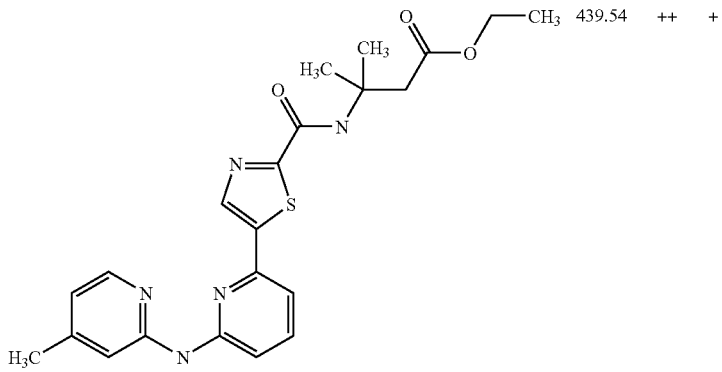 439.54 ++ +
TABLE 1-32
A-156 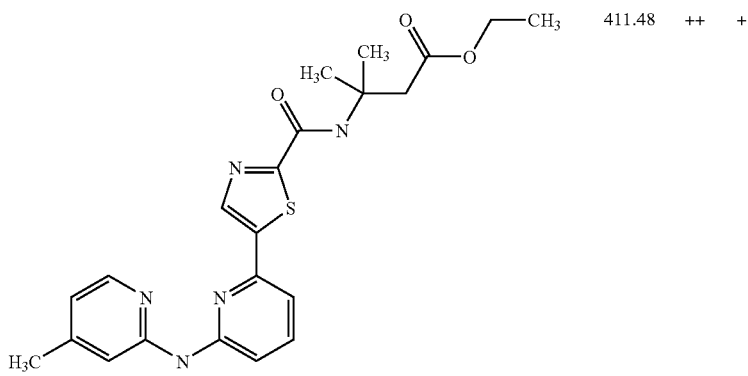 411.48 ++ +
A-157  382.49 ++ +
A-158 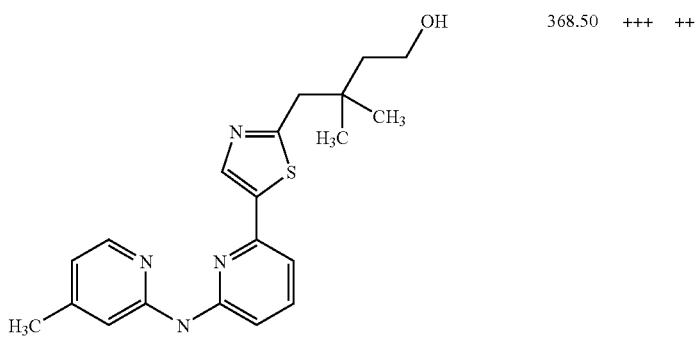 368.50 +++ ++

TABLE 1-32-continued
| | | | | |
|---|---|---|---|---|
| A-159 | 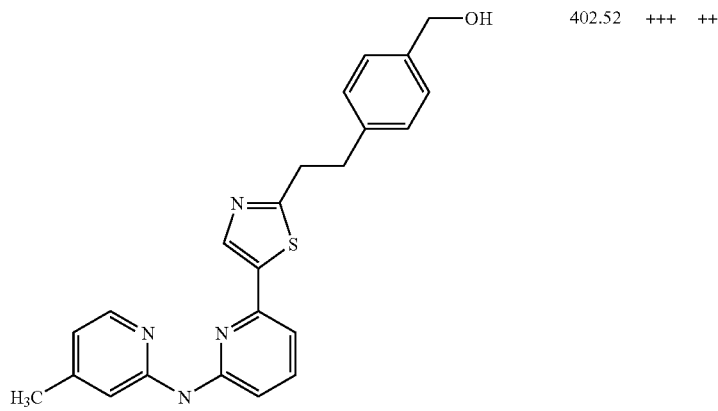 | 402.52 | +++ | ++ |
| A-160 | 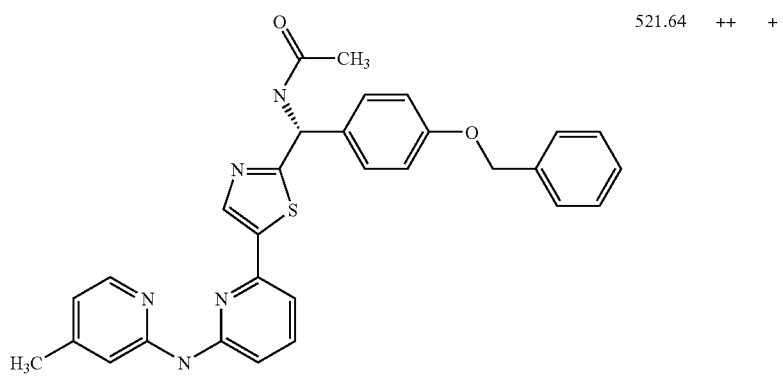 | 521.64 | ++ | + |
TABLE 1-33
| | | | | |
|---|---|---|---|---|
| A-161 | 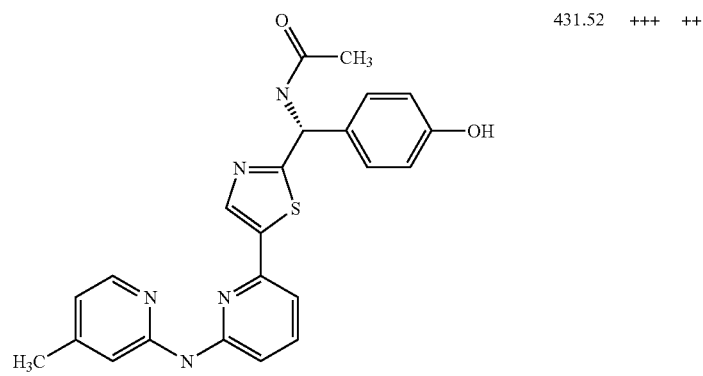 | 431.52 | +++ | ++ |

TABLE 1-33-continued

| ID | Structure | MW | | |
|---|---|---|---|---|
| A-162 | (4-methylpyridin-2-yl)amino-pyridinyl-thiazolyl-CH₂CH₂-C₆H₄-C(=O)NH-CH₂CH₂OH | 459.57 | +++ | ++ |
| A-163 | (4-methylpyridin-2-yl)amino-pyridinyl-thiazolyl-CH₂-NH-CH₂CH₂-C(=O)OCH₃ | 383.47 | ++ | + |
| A-164 | (4-methylpyridin-2-yl)amino-pyridinyl-thiazolyl-CH₂-N(COCH₃)-CH₂CH₂-C(=O)OCH₃ | 425.51 | ++ | + |
| A-165 | (4-methylpyridin-2-yl)amino-pyridinyl-thiazolyl-CH₂-NH-CH₂CH₂-C(=O)OH · 2 ClH | 442.37 | ++ | + |

TABLE 1-34
| A-166 | 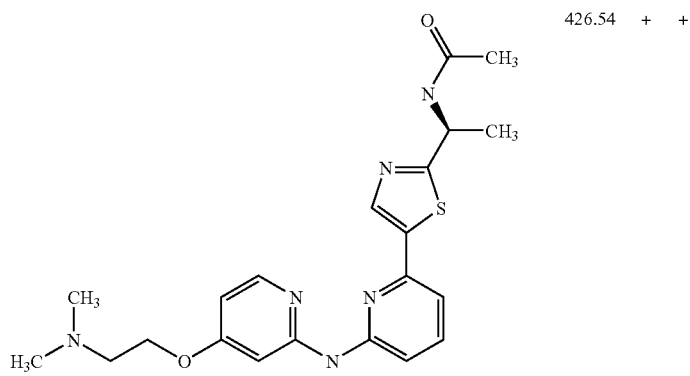 | 426.54 | + | + |
| A-167 | 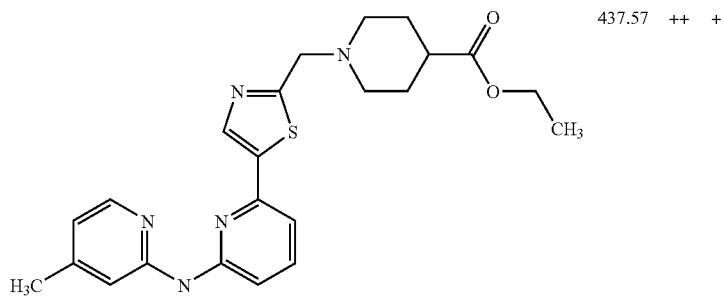 | 437.57 | ++ | + |
| A-168 | 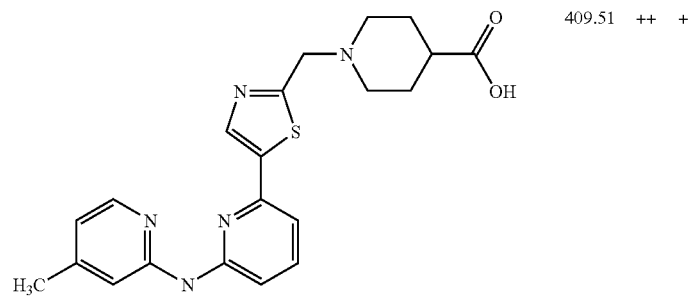 | 409.51 | ++ | + |
| A-169 | 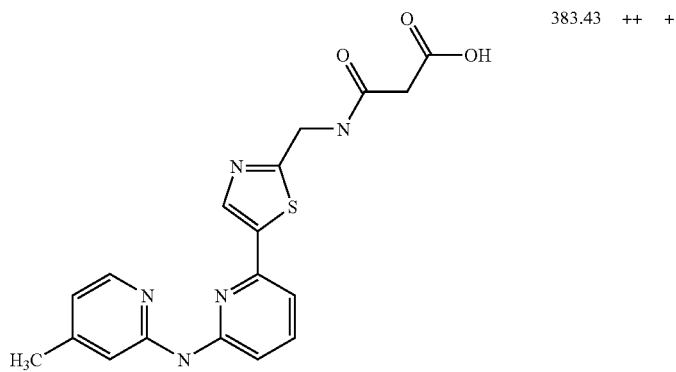 | 383.43 | ++ | + |

TABLE 1-34-continued
A-170     409.51   ++   ++
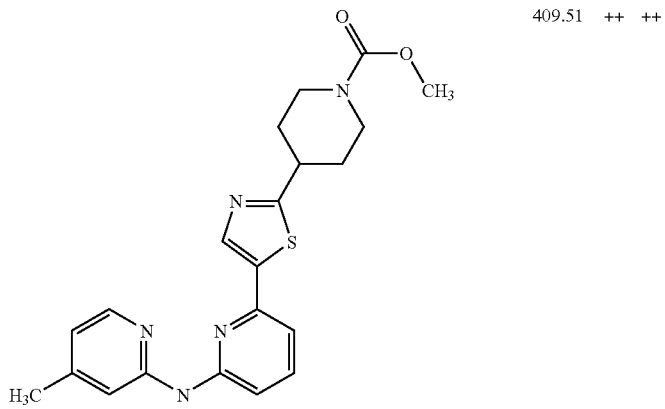
TABLE 1-35
A-171     445.57   ++   +
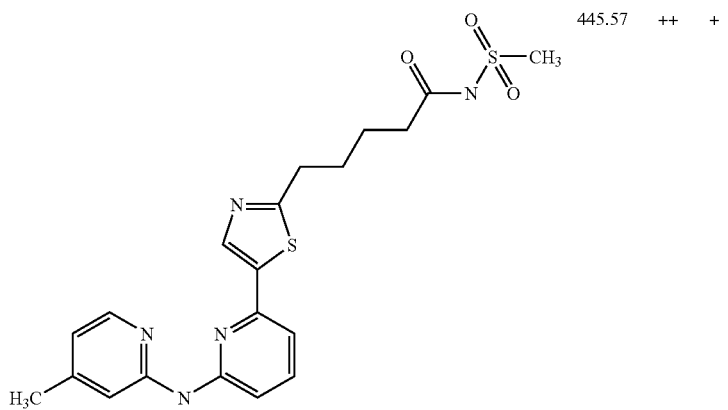
A-172     392.52   +++   ++
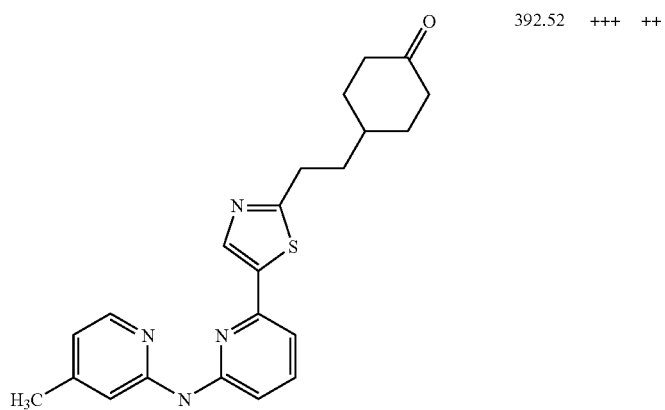

TABLE 1-35-continued
| A-173 | 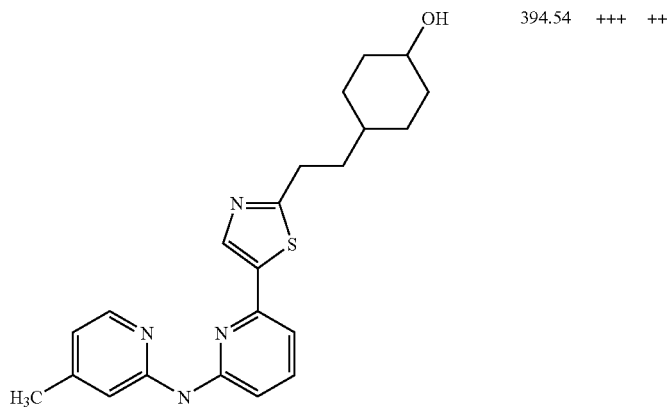 | 394.54 | +++ | ++ |
| A-174 | 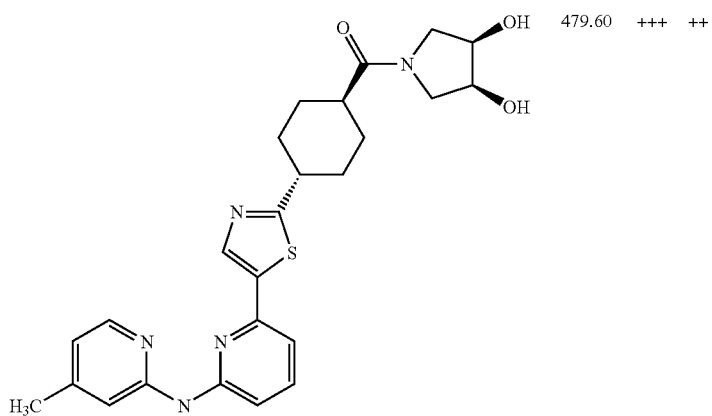 | 479.60 | +++ | ++ |
TABLE 1-36
| A-175 | 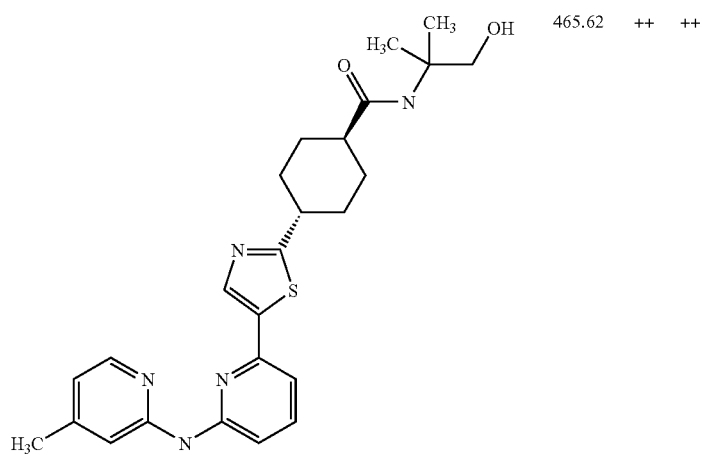 | 465.62 | ++ | ++ |

TABLE 1-36-continued
| A-176 | 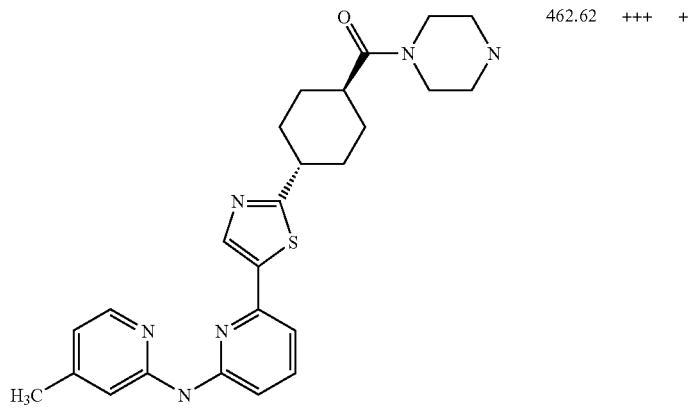 | 462.62 | +++ | + |
| A-177 | 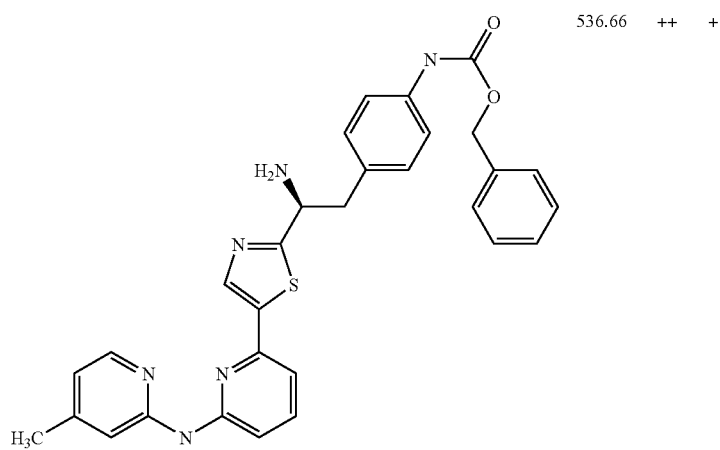 | 536.66 | ++ | + |
| A-178 | 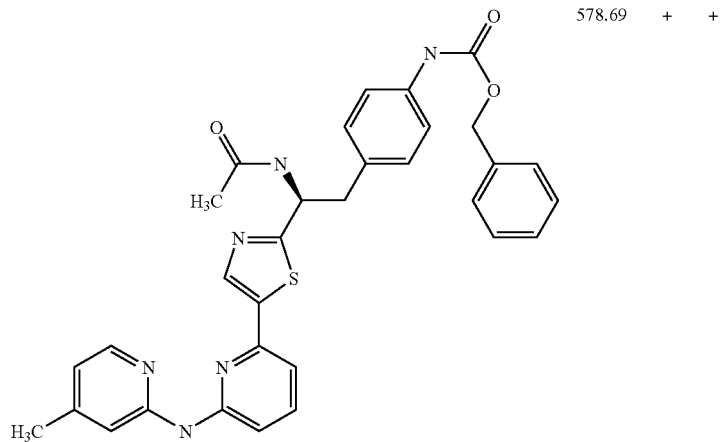 | 578.69 | + | + |

TABLE 1-37
A-179 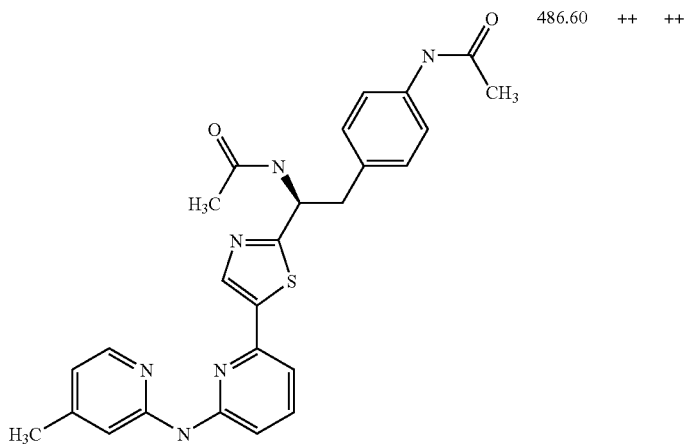 486.60 ++ ++
A-180 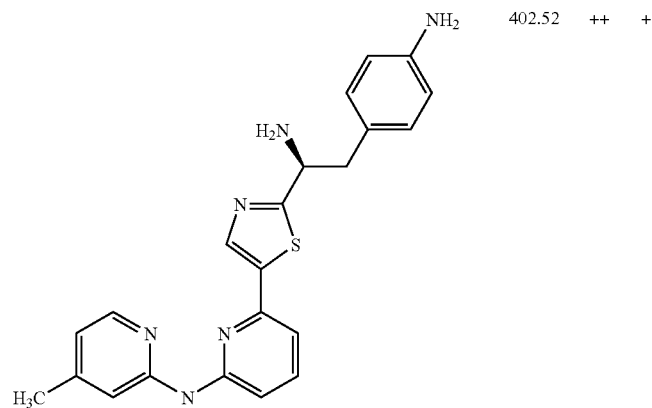 402.52 ++ +
A-181 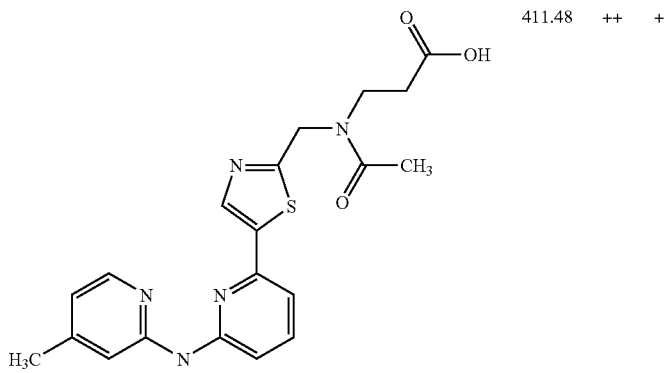 411.48 ++ +
A-182 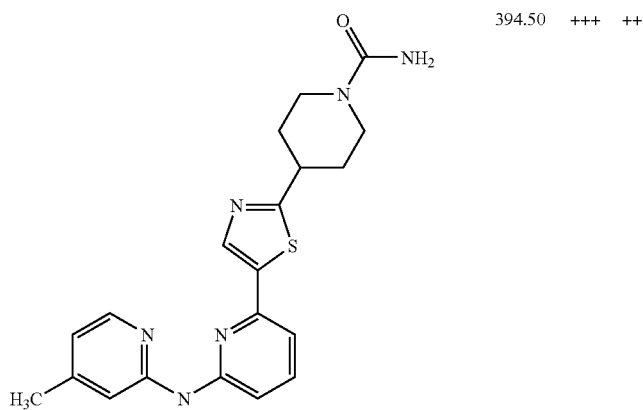 394.50 +++ ++

TABLE 1-37-continued
| A-183 | 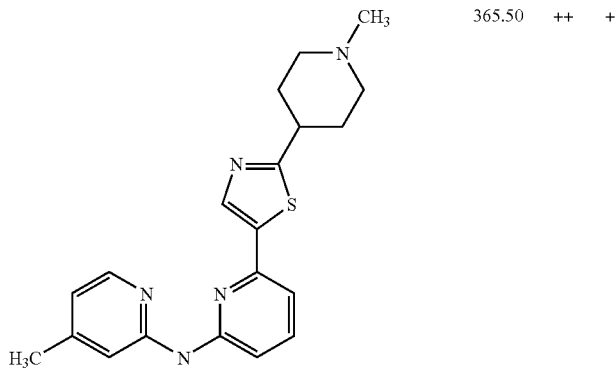 | 365.50 | ++ | + |
TABLE 1-38
| A-184 | 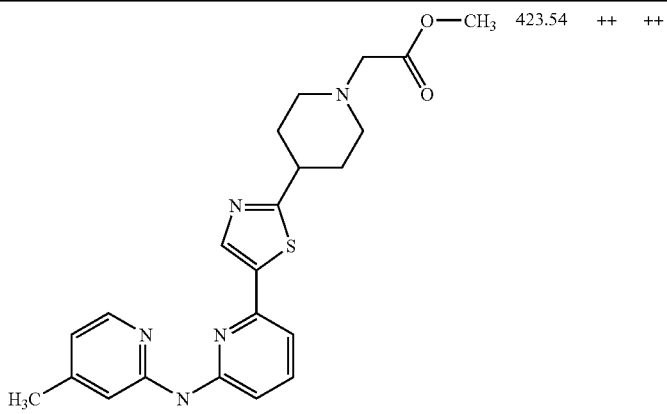 | 423.54 | ++ | ++ |
| A-185 | 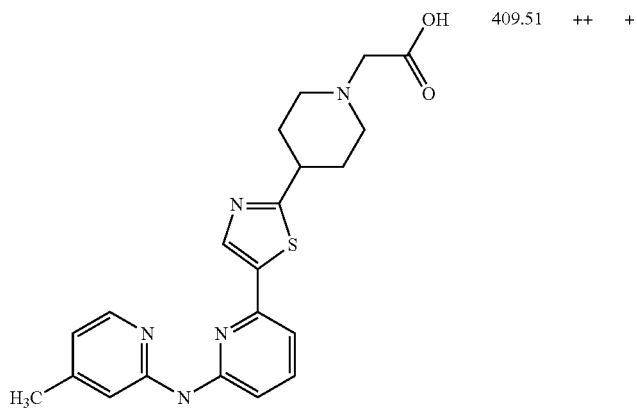 | 409.51 | ++ | + |
| A-186 | 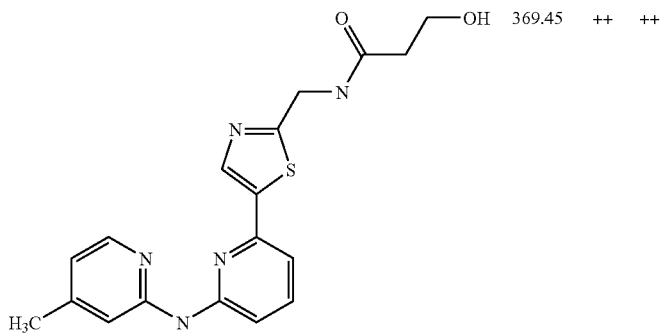 | 369.45 | ++ | ++ |

TABLE 1-38-continued
| A-187 | 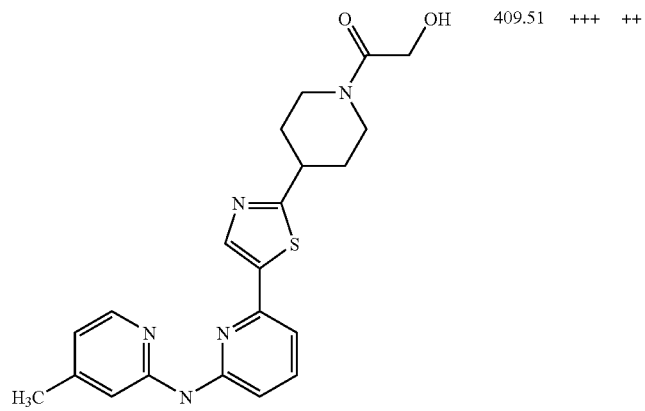 | 409.51 | +++ | ++ |
| A-188 | 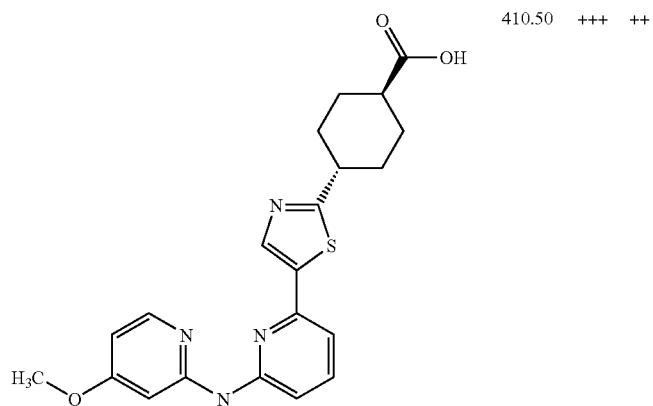 | 410.50 | +++ | ++ |
TABLE 1-39
| A-189 | 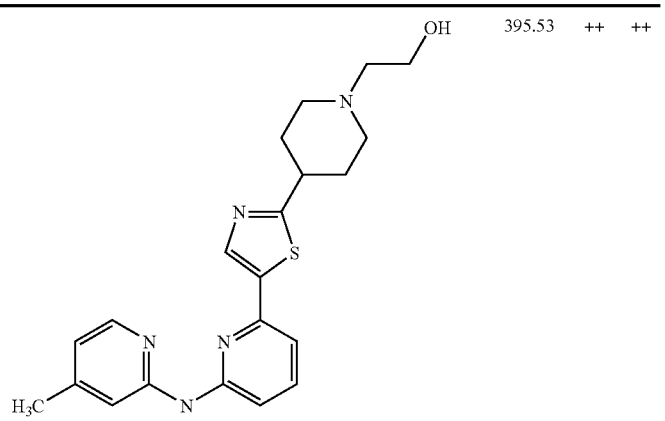 | 395.53 | ++ | ++ |
| A-190 | 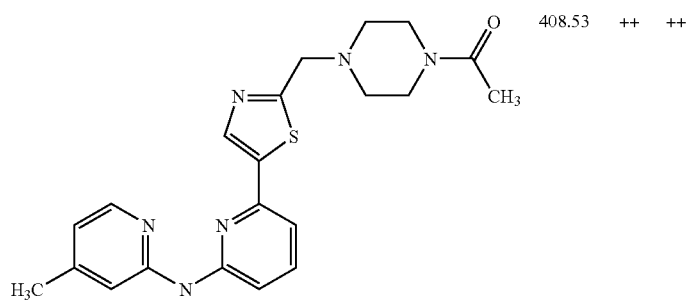 | 408.53 | ++ | ++ |

TABLE 1-39-continued
A-191 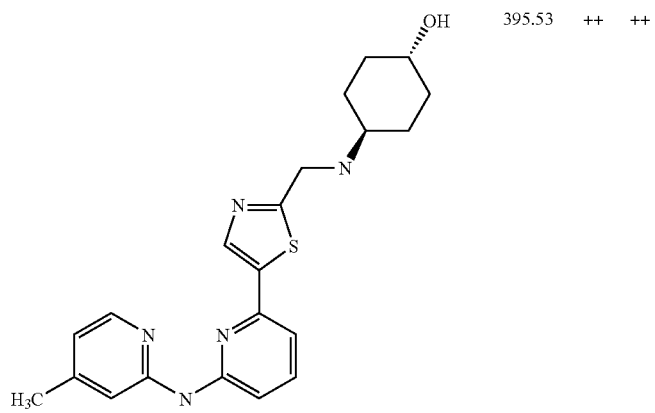 395.53 ++ ++
A-192 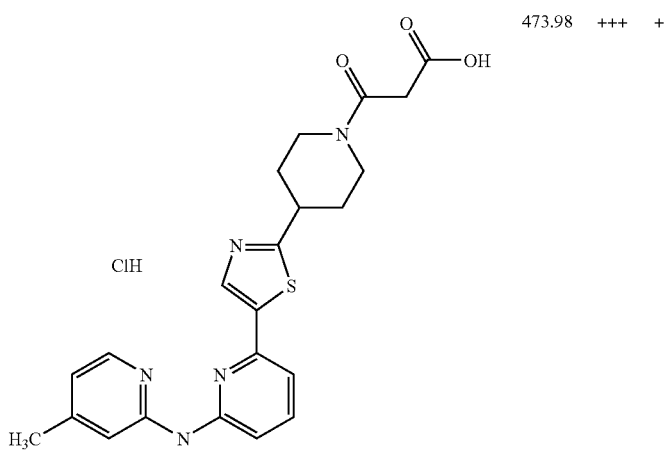 473.98 +++ +
A-193 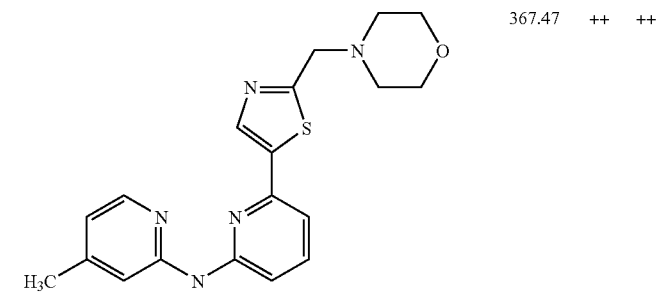 367.47 ++ ++
TABLE 1-40
A-194 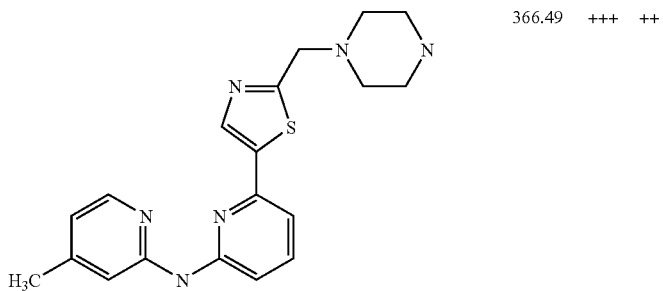 366.49 +++ ++

TABLE 1-40-continued
A-195 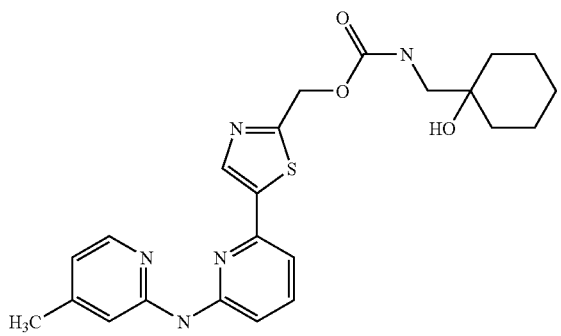 453.56 ++ ++
A-196 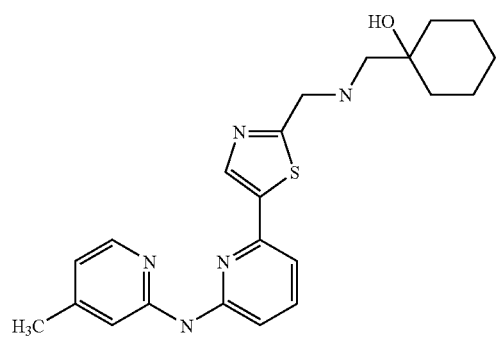 409.56 ++ ++
A-197 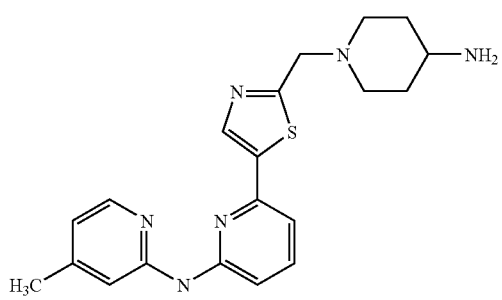 380.52 +++ ++
A-198 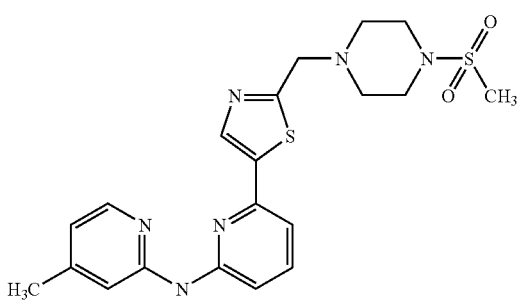 444.58 ++ ++

TABLE 1-41
A-199  425.51  ++  ++
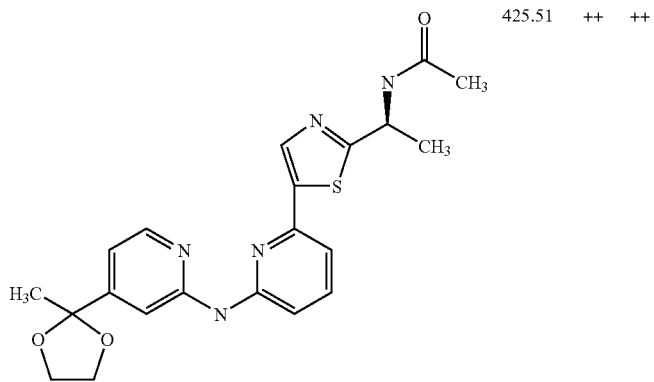
A-200  375.48  +++  ++
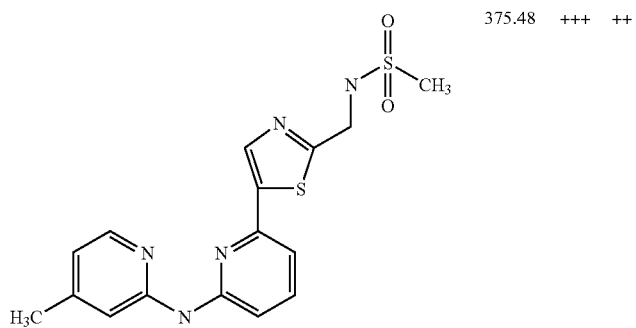
A-201  355.42  ++  ++
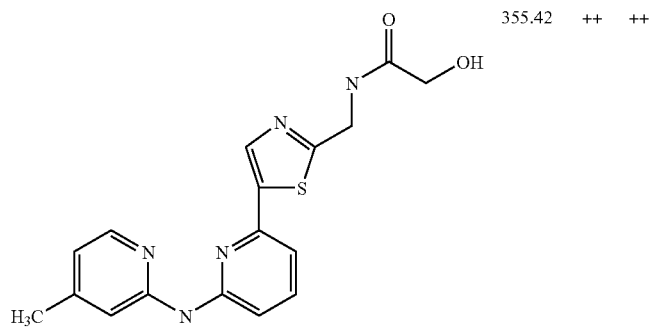
A-202  407.54  +++  +
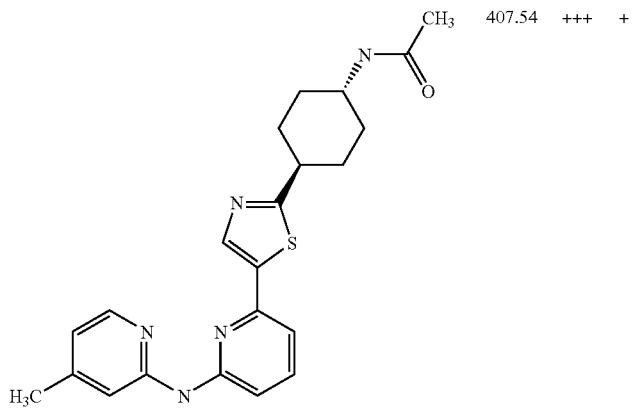

TABLE 1-41-continued

| | | | | |
|---|---|---|---|---|
| A-203 | (structure) | 428.94 | ++ | ++ |

TABLE 1-42

| | | | | |
|---|---|---|---|---|
| A-204 | (structure) | 414.92 | +++ | ++ |
| A-205 | (structure) | 312.40 | +++ | ++ |
| A-206 | (structure) | 481.57 | + | + |

TABLE 1-42-continued
A-207 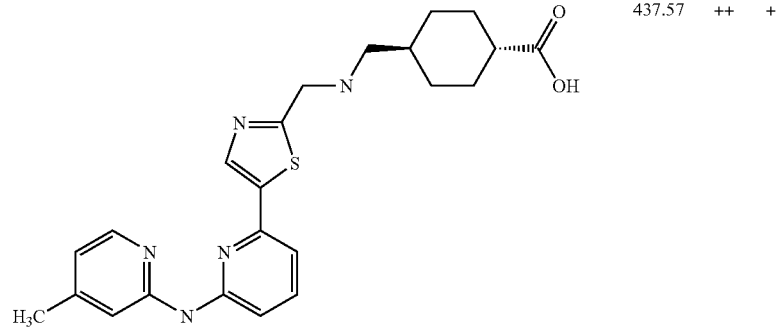 437.57 ++ +
A-208 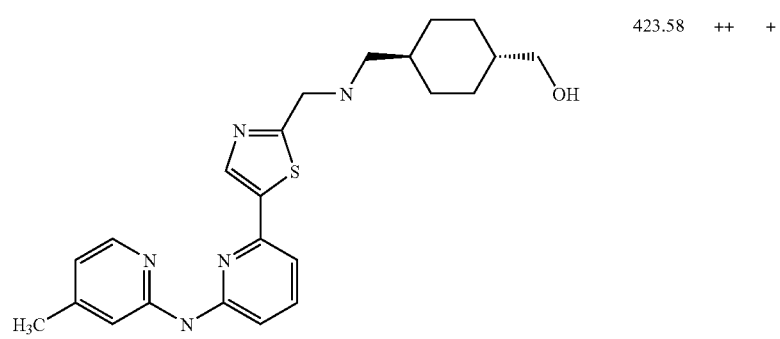 423.58 ++ +
TABLE 1-43
A-209 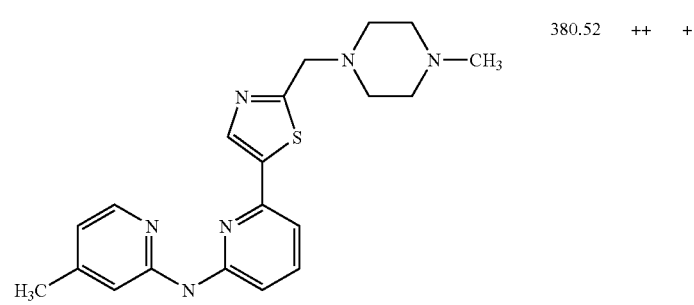 380.52 ++ +
A-210 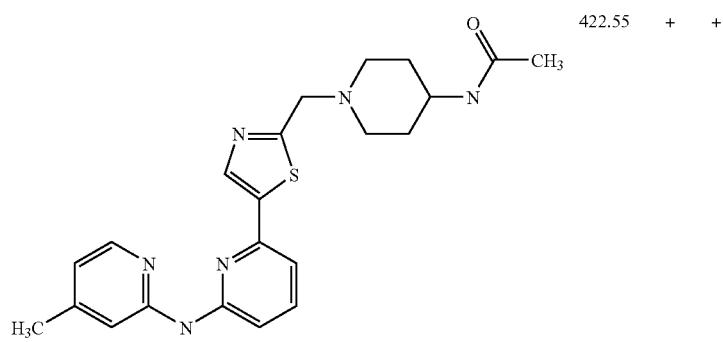 422.55 + +

TABLE 1-43-continued
| A-211 | 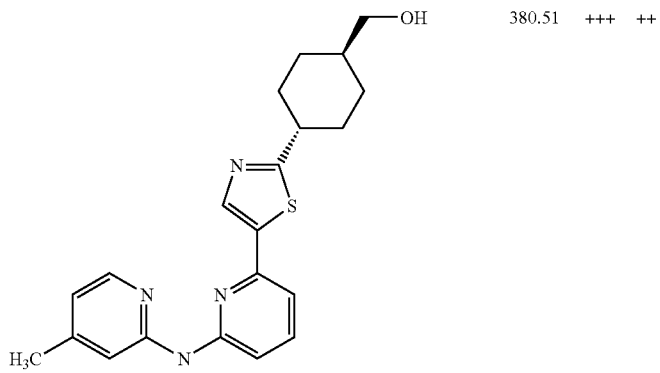 | 380.51 | +++ | ++ |
| A-212 | 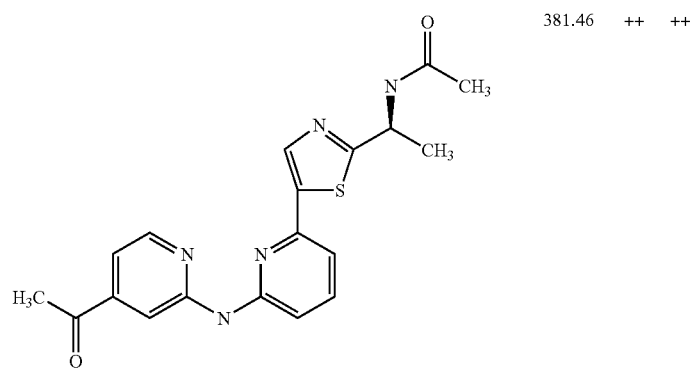 | 381.46 | ++ | ++ |
| A-213 | 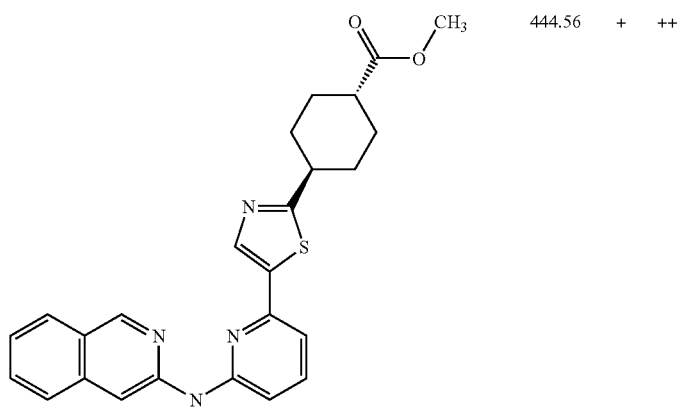 | 444.56 | + | ++ |

TABLE 1-44
A-214 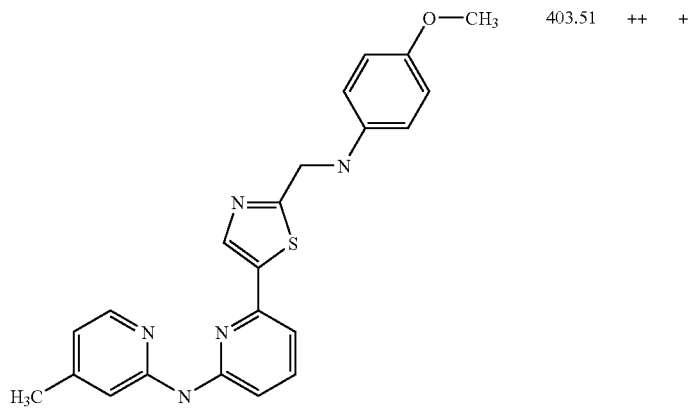 403.51 ++ +
A-215 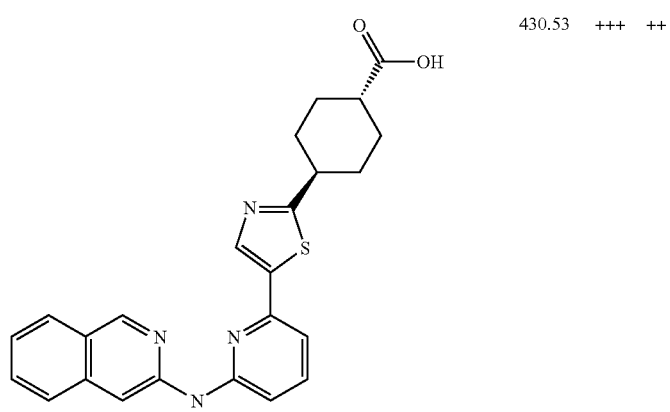 430.53 +++ ++
A-216 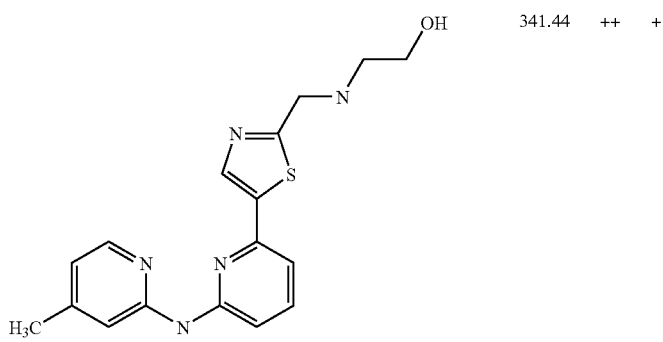 341.44 ++ +
A-217 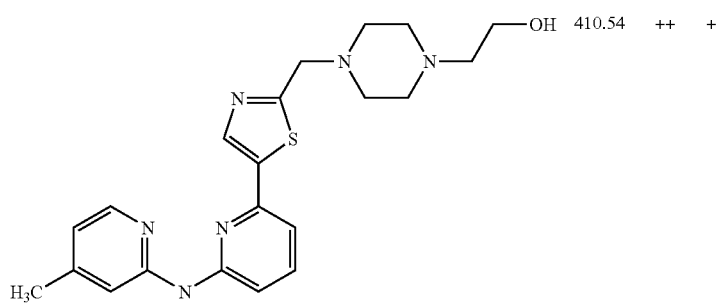 410.54 ++ +

TABLE 1-44-continued
| A-218 | 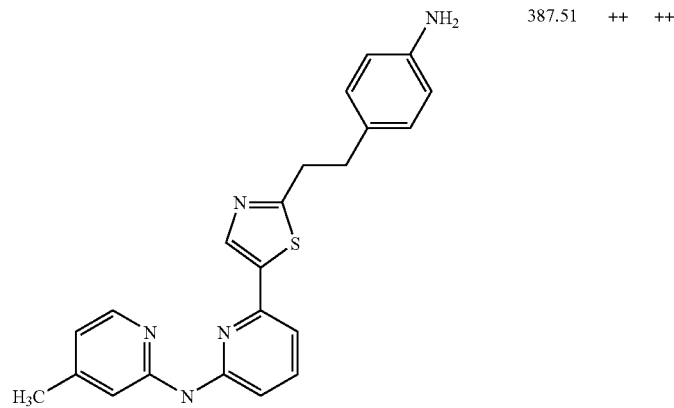 | 387.51 | ++ | ++ |
TABLE 1-45
| A-219 | 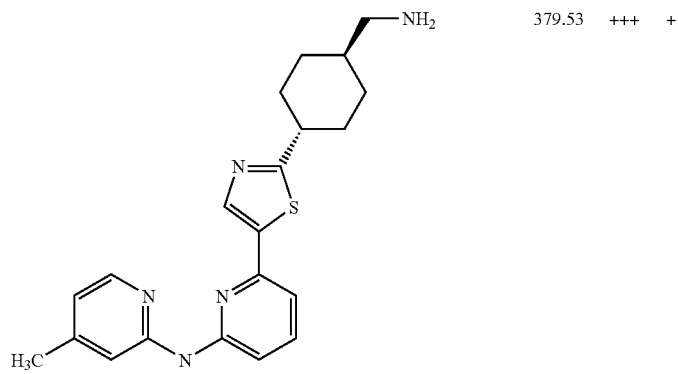 | 379.53 | +++ | + |
| A-220 | 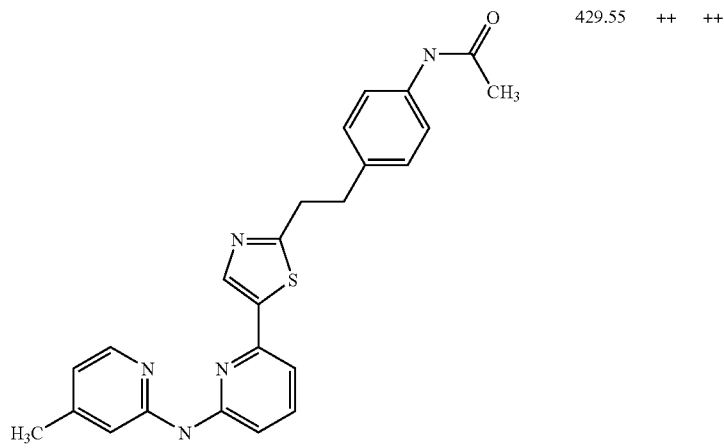 | 429.55 | ++ | ++ |

TABLE 1-45-continued
A-221 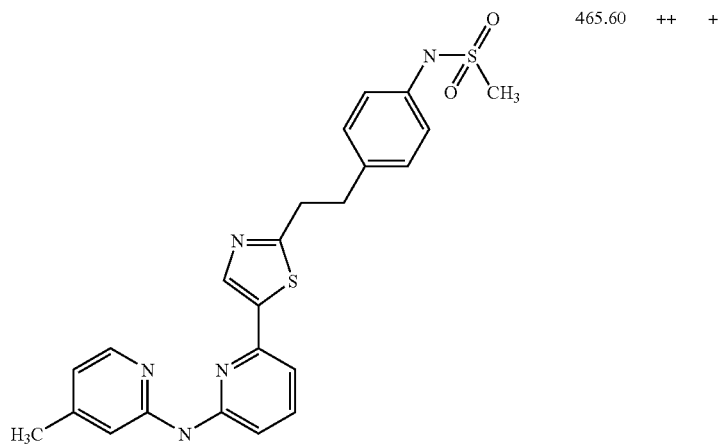 465.60 ++ +
A-222 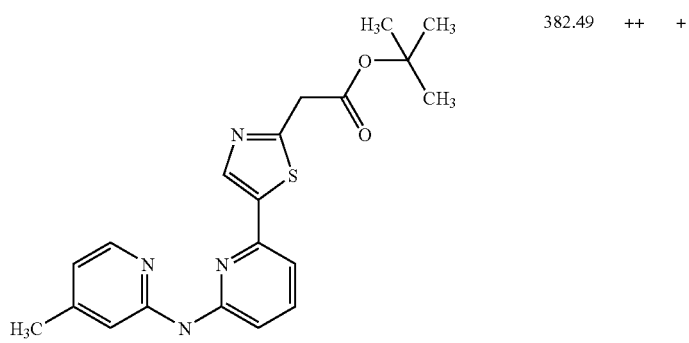 382.49 ++ +
A-223 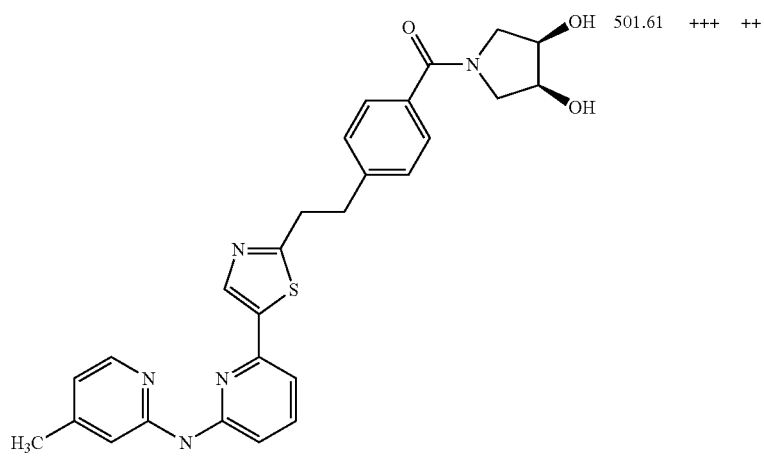 501.61 +++ ++
TABLE 1-46
A-224 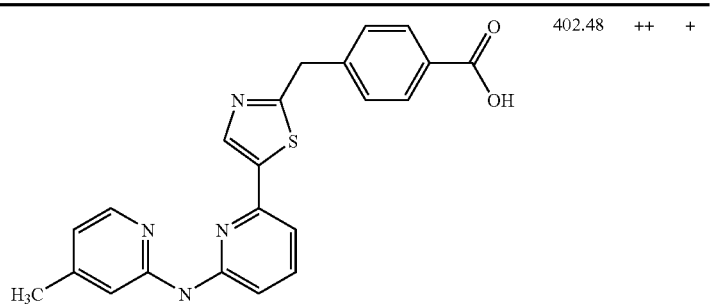 402.48 ++ +

TABLE 1-46-continued
A-225 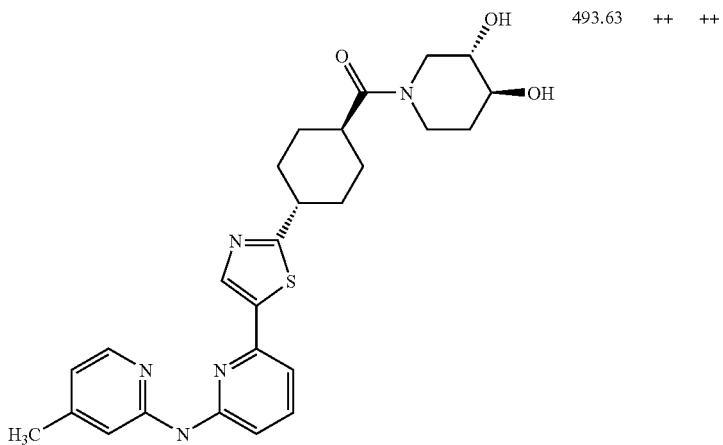 493.63 ++ ++
A-226 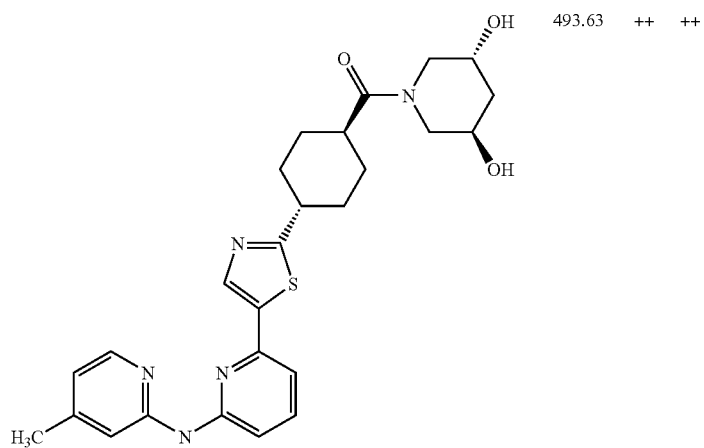 493.63 ++ ++
A-227 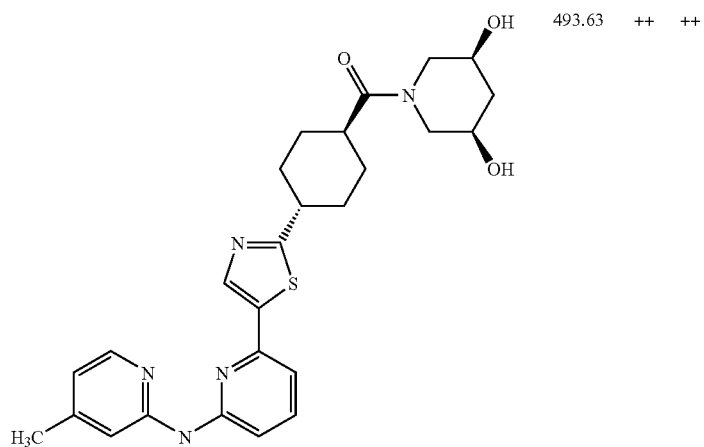 493.63 ++ ++

TABLE 1-46-continued
| | | | | |
|---|---|---|---|---|
| A-228 | 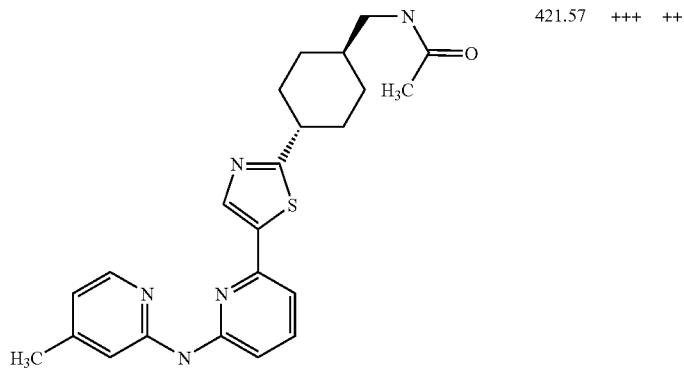 | 421.57 | +++ | ++ |
TABLE 1-47
| | | | | |
|---|---|---|---|---|
| A-229 | 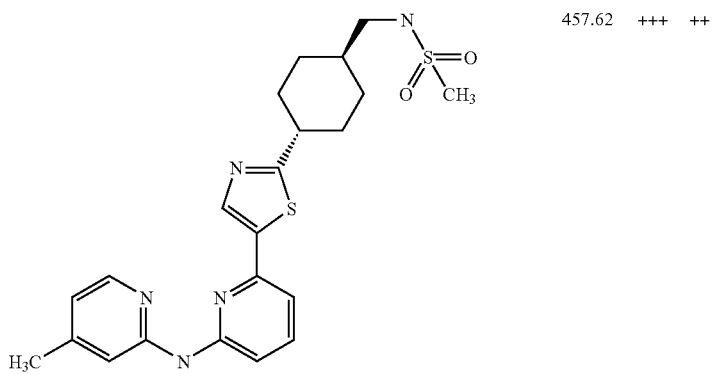 | 457.62 | +++ | ++ |
| A-230 | 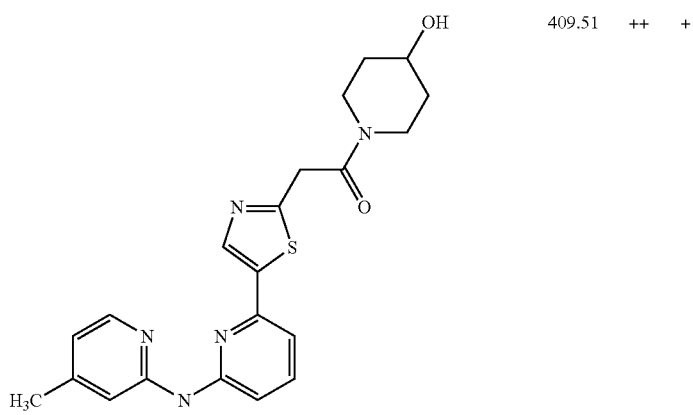 | 409.51 | ++ | + |
| A-231 | 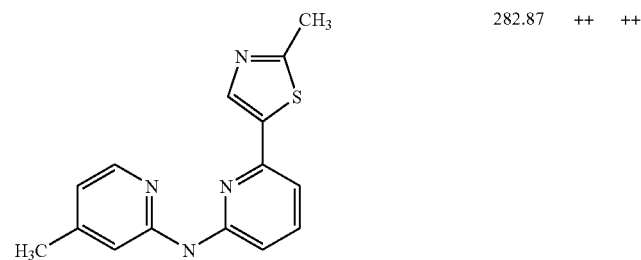 | 282.87 | ++ | ++ |

TABLE 1-47-continued
| A-232 | 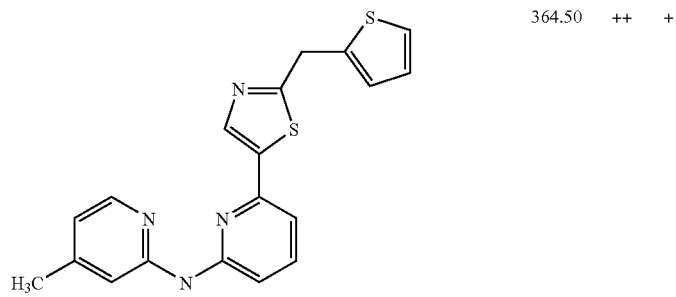 | 364.50 | ++ | + |
| A-233 | 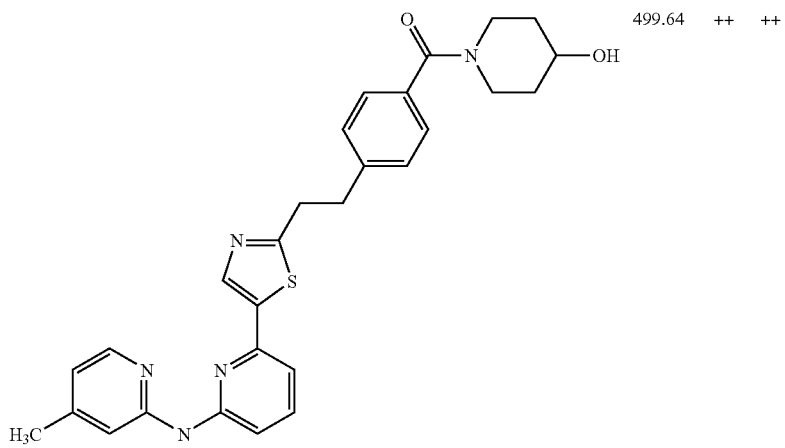 | 499.64 | ++ | ++ |
TABLE 1-48
| A-234 | 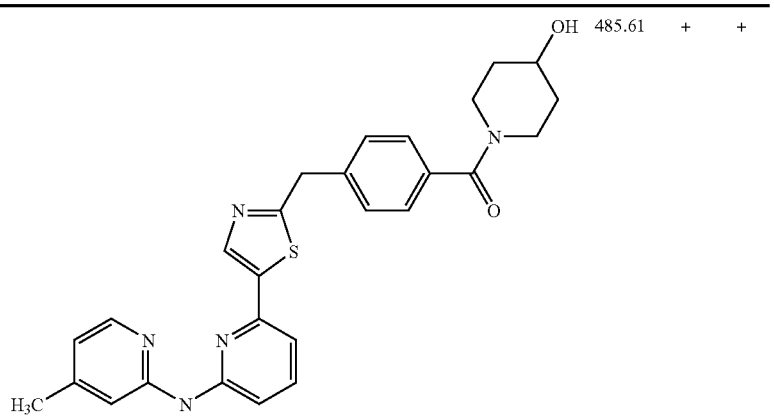 | 485.61 | + | + |
| A-235 | 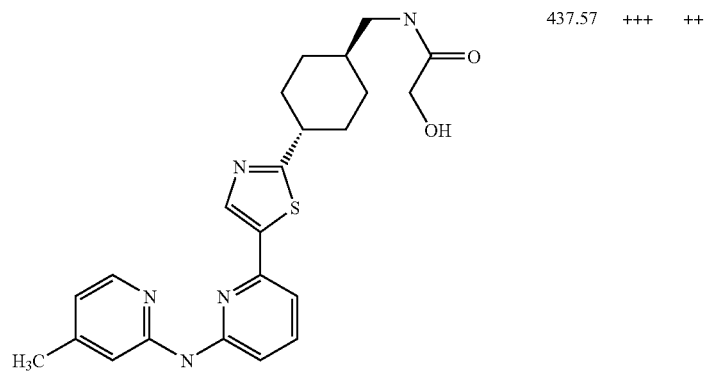 | 437.57 | +++ | ++ |

TABLE 1-48-continued
A-236 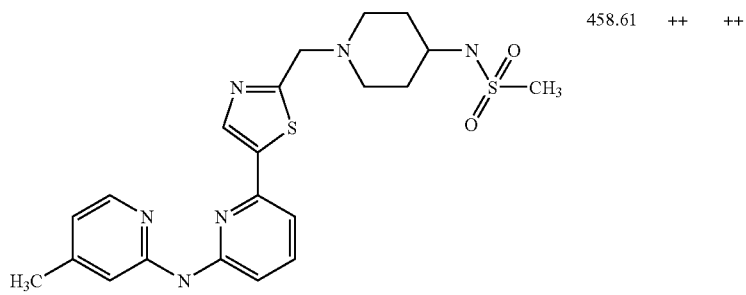 458.61 ++ ++
A-237 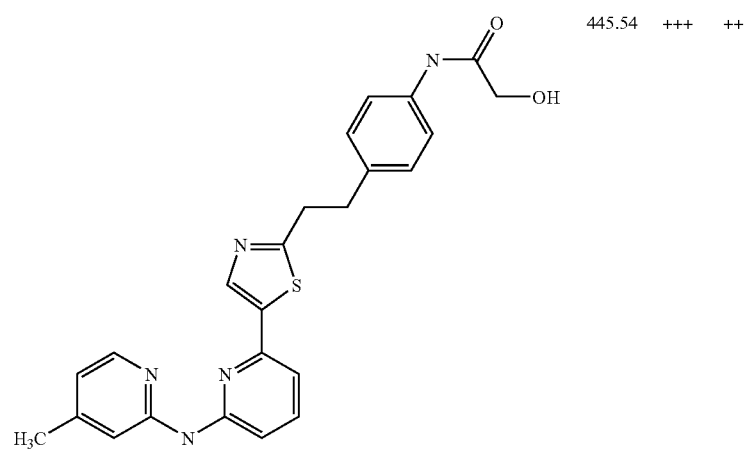 445.54 +++ ++
A-238 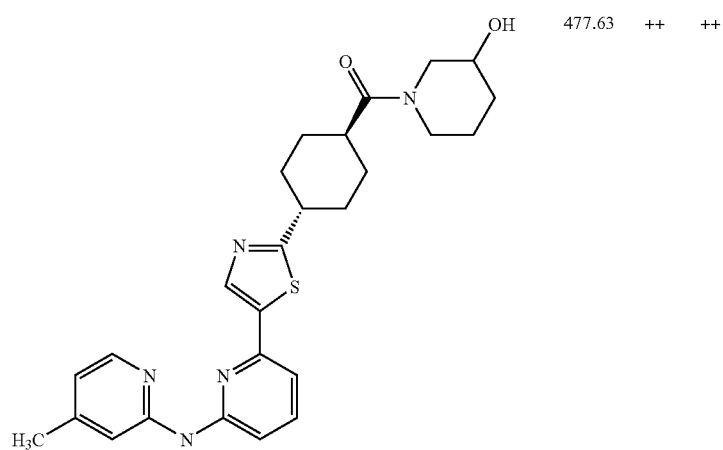 477.63 ++ ++

TABLE 1-49
A-239 493.63 +++ ++
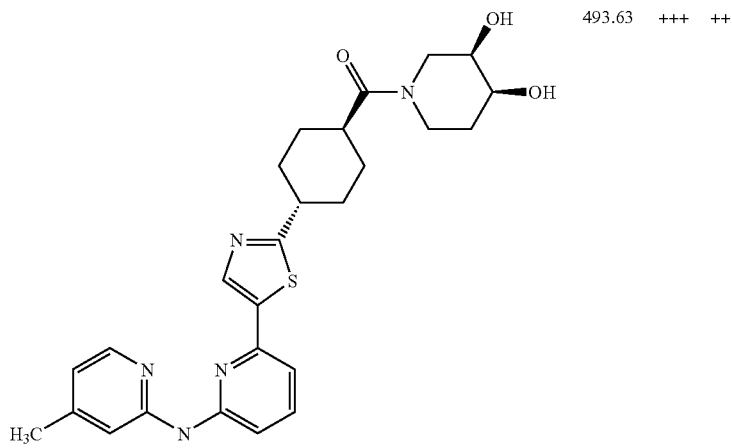
A-240 475.61 ++ +
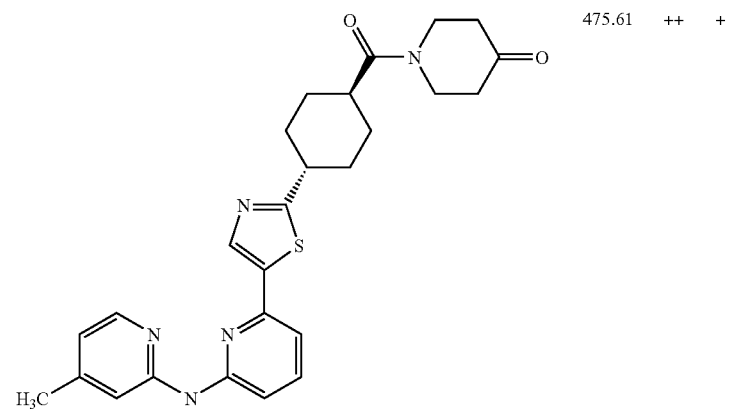
A-241 463.60 +++ +
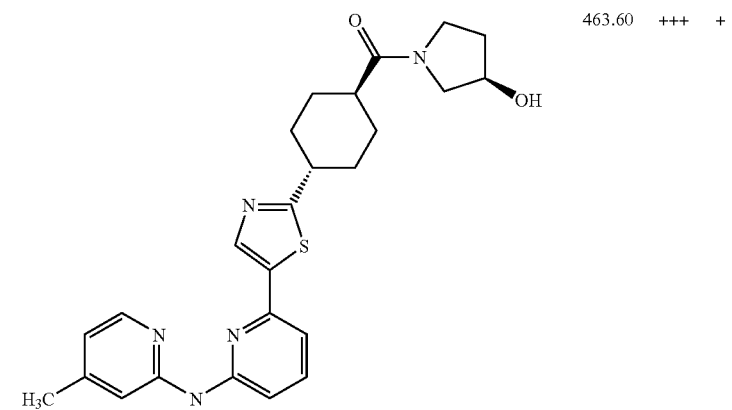

TABLE 1-49-continued
A-242     491.66   ++   ++
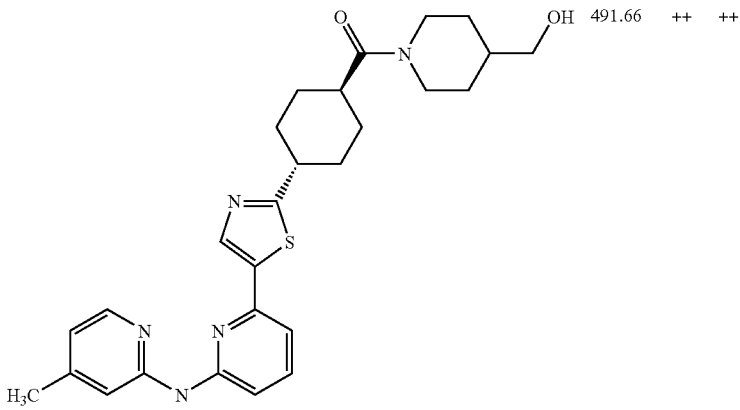
A-243     388.49   +++   ++
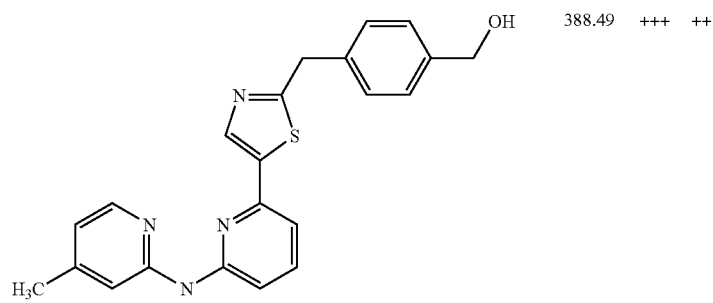
TABLE 1-50
A-244     487.58   ++   ++
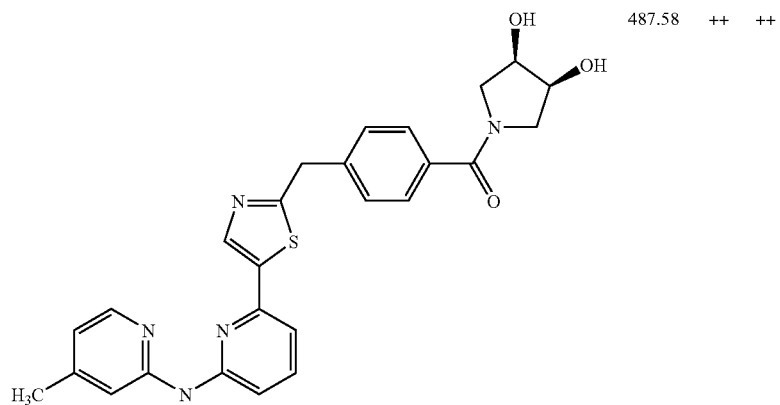
A-245     311.41   ++   ++
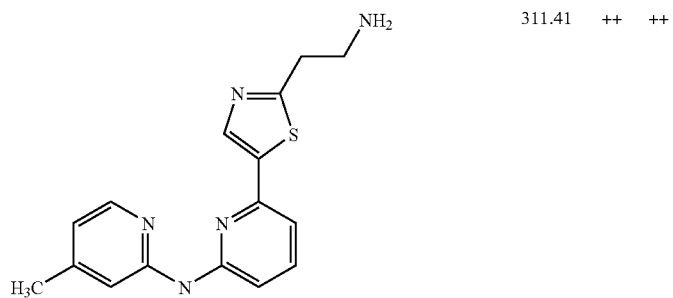

TABLE 1-50-continued
| A-246 | 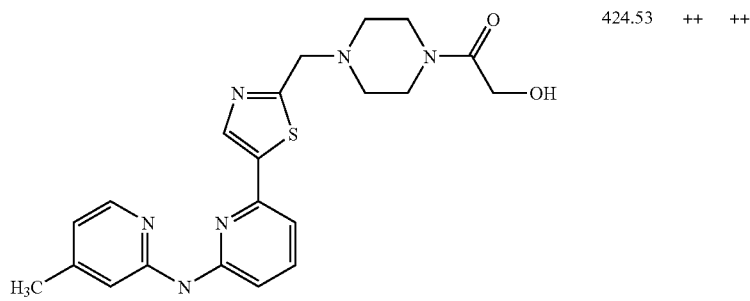 | 424.53 | ++ | ++ |
| A-247 | 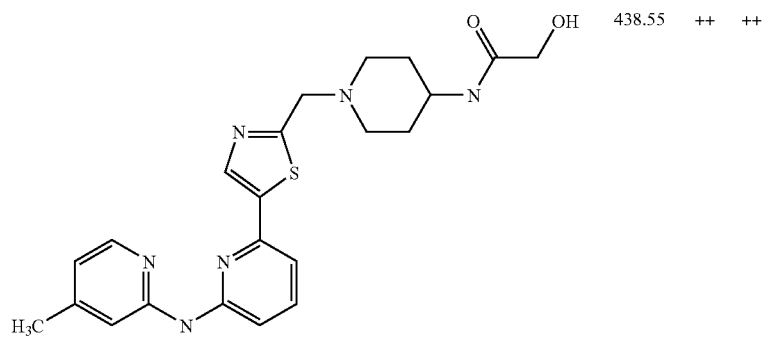 | 438.55 | ++ | ++ |
| A-248 | 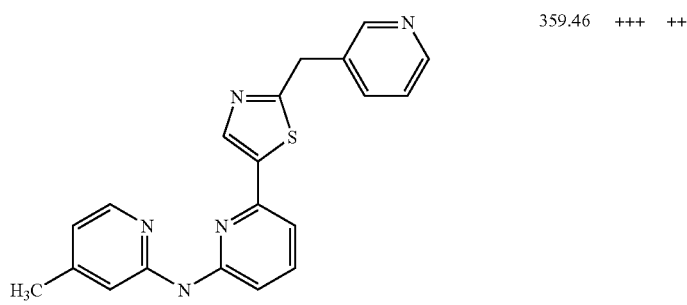 | 359.46 | +++ | ++ |
| A-249 | 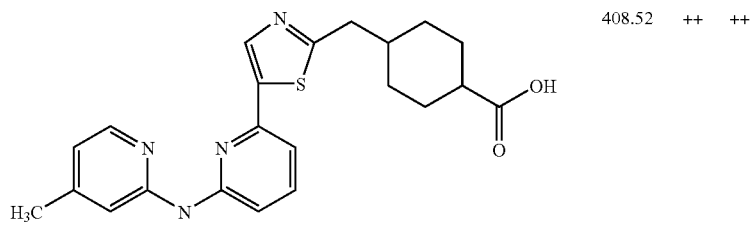 | 408.52 | ++ | ++ |

TABLE 1-51
| | | | | |
|---|---|---|---|---|
| A-250 | 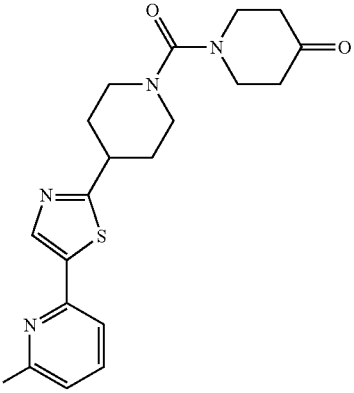 | 476.60 | ++ | ++ |
| A-251 | 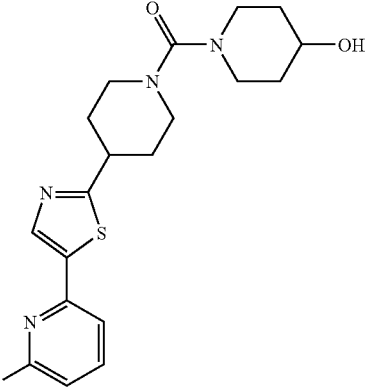 | 478.62 | ++ | ++ |
| A-252 | 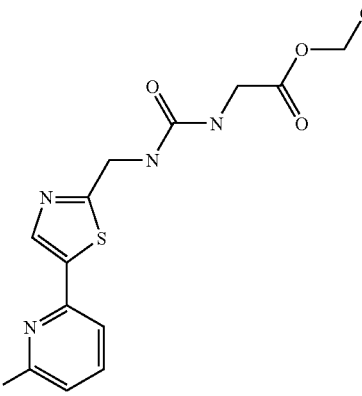 | 426.50 | ++ | ++ |
| A-253 | 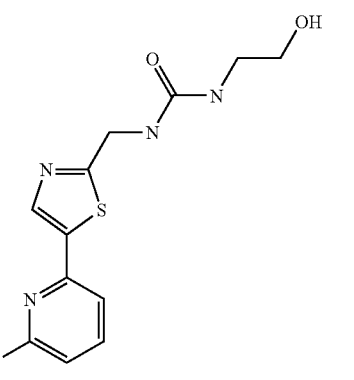 | 384.46 | ++ | ++ |

TABLE 1-51-continued
A-254 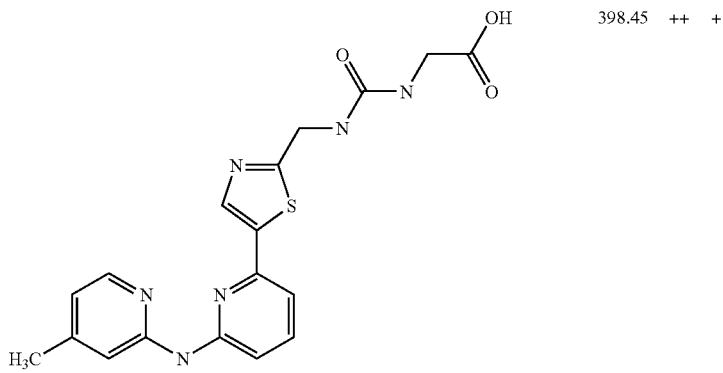 398.45 ++ +
TABLE 1-52
A-255 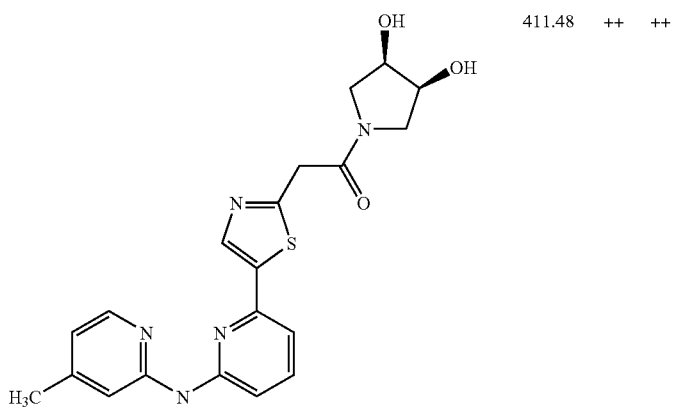 411.48 ++ ++
A-256 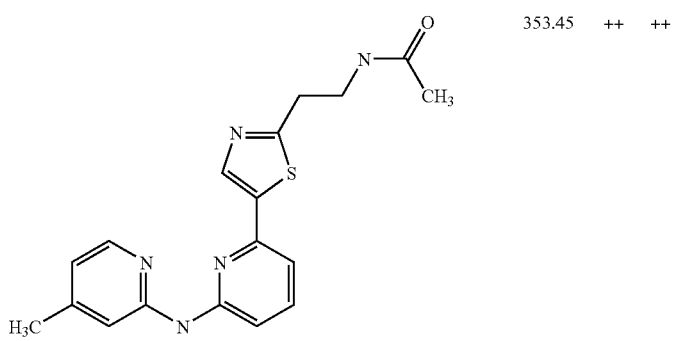 353.45 ++ ++
A-257 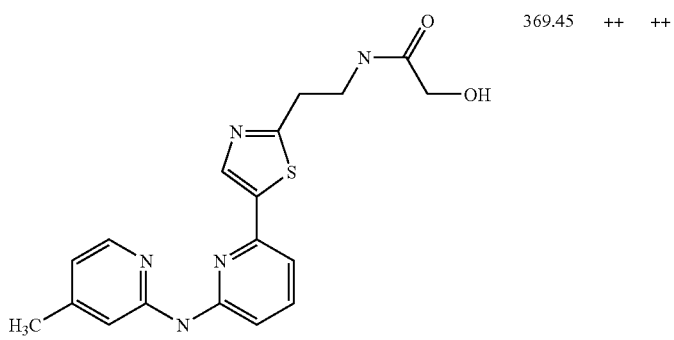 369.45 ++ ++

TABLE 1-52-continued
A-258 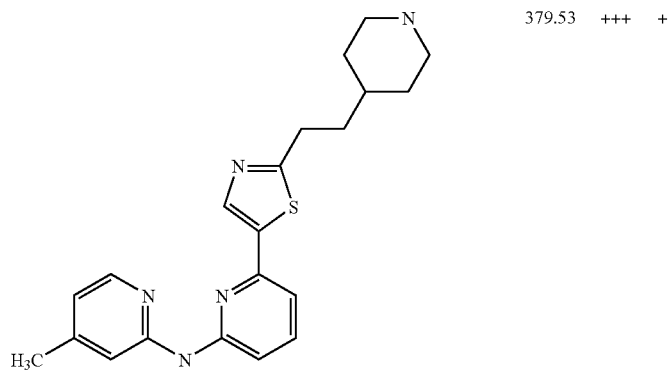 379.53 +++ +
A-259 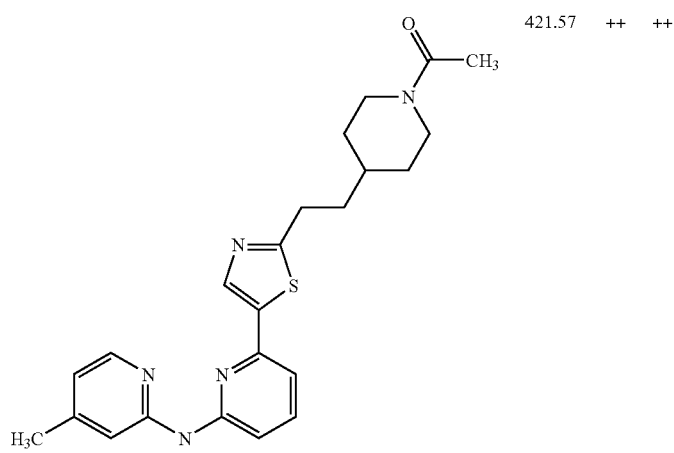 421.57 ++ ++
TABLE 1-53
A-260 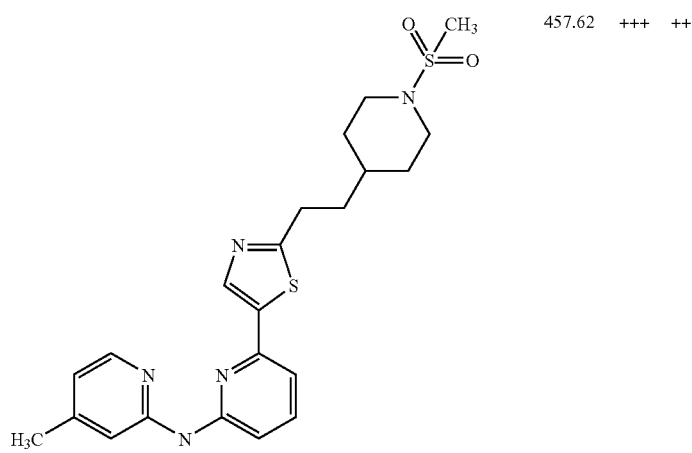 457.62 +++ ++

TABLE 1-53-continued
A-261 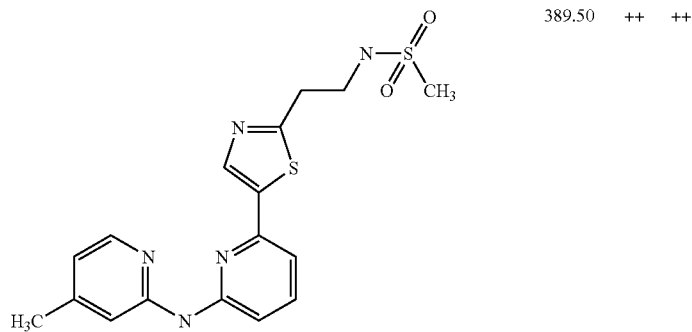 389.50 ++ ++
A-262 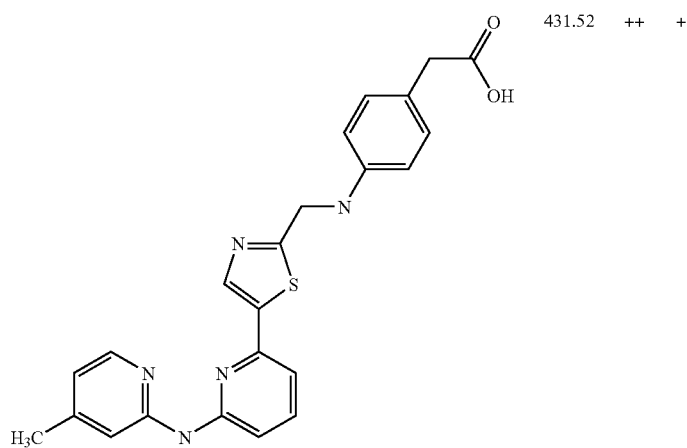 431.52 ++ +
A-263 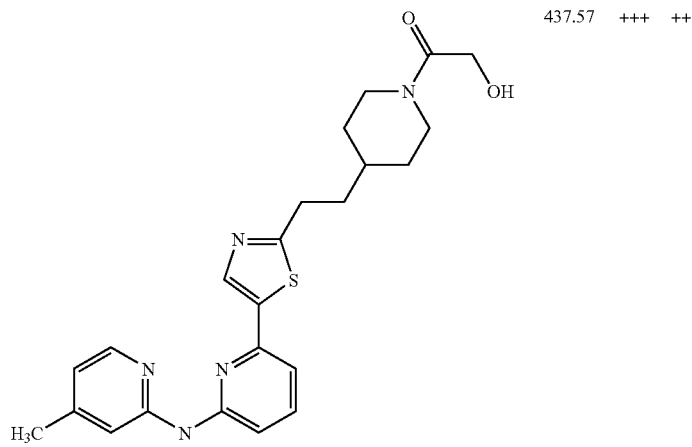 437.57 +++ ++

TABLE 1-54
| | | | | |
|---|---|---|---|---|
| A-264 | 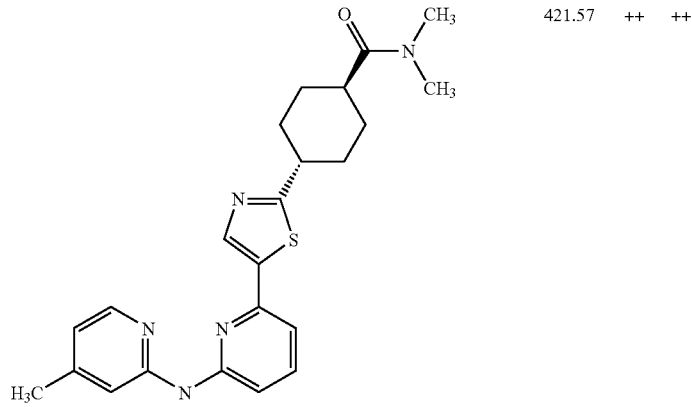 | 421.57 | ++ | ++ |
| A-265 | 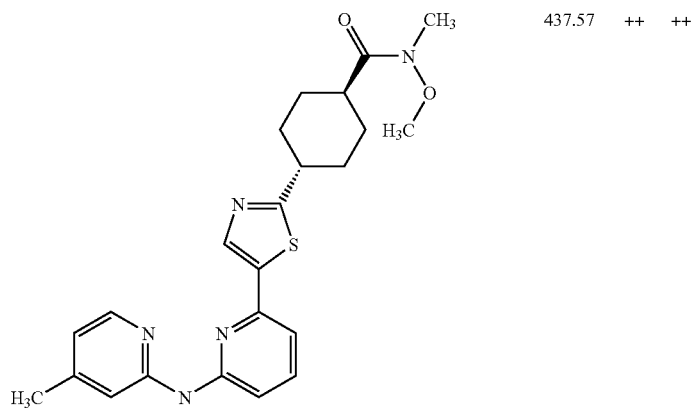 | 437.57 | ++ | ++ |
| A-266 | 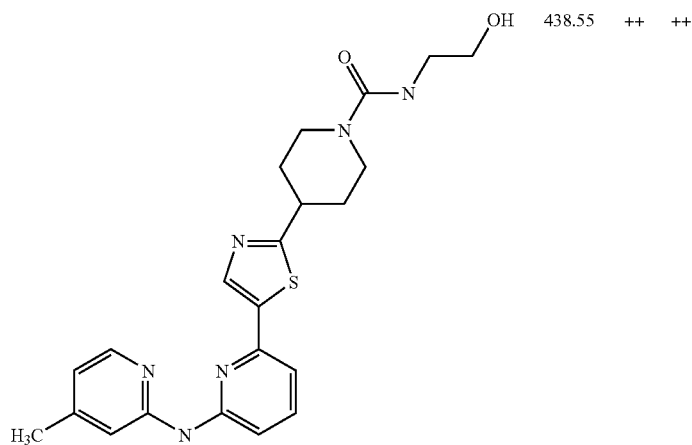 | 438.55 | ++ | ++ |

TABLE 1-54-continued
| A-267 | 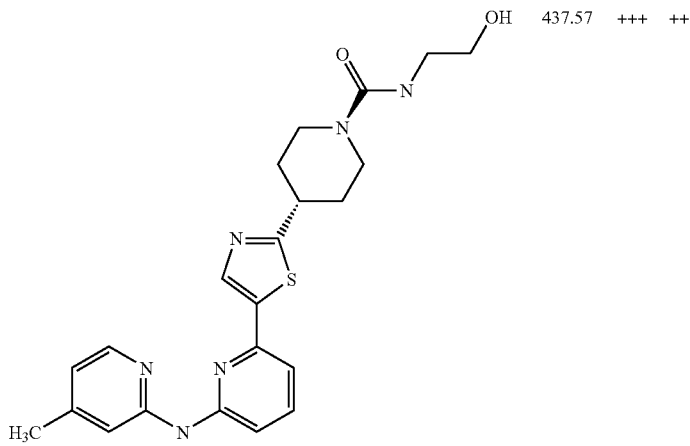 | 437.57 | +++ | ++ |
TABLE 1-55
| A-268 | 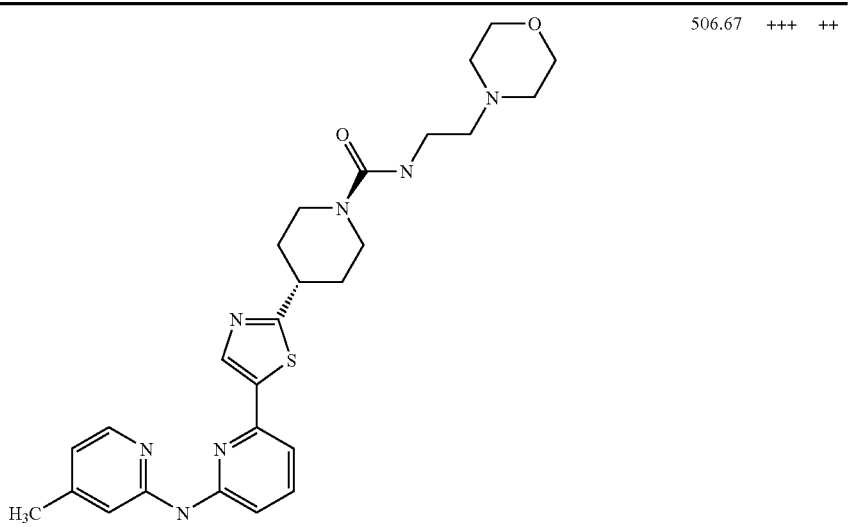 | 506.67 | +++ | ++ |
| A-269 | 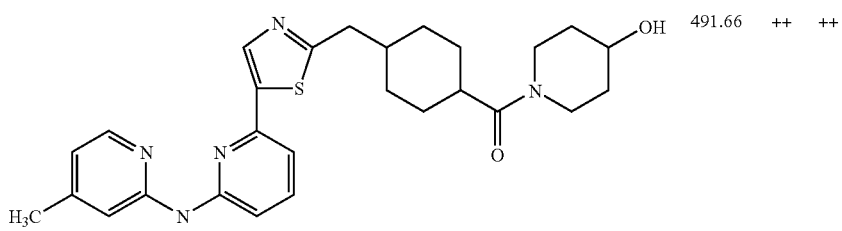 | 491.66 | ++ | ++ |
| A-270 | 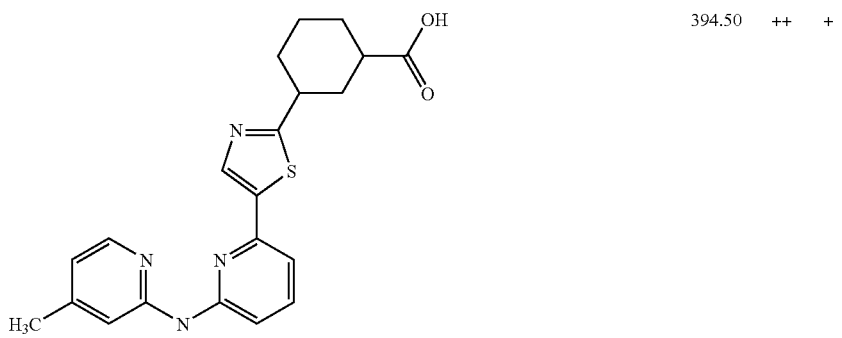 | 394.50 | ++ | + |

TABLE 1-55-continued
| | | | | |
|---|---|---|---|---|
| A-271 | 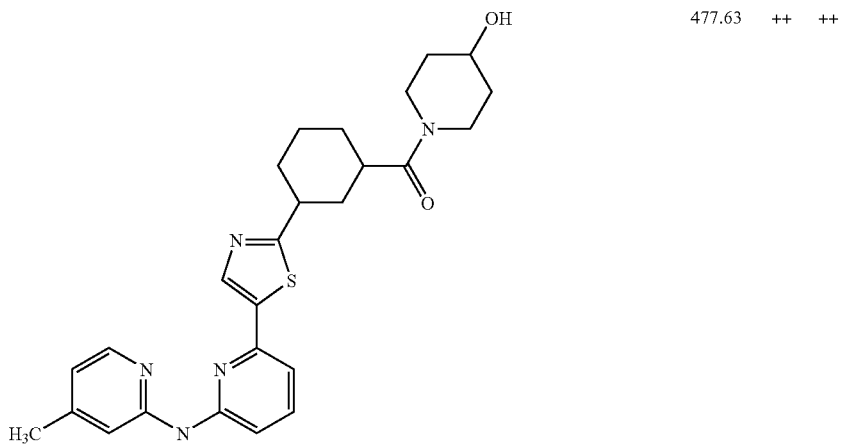 | 477.63 | ++ | ++ |
| A-272 | 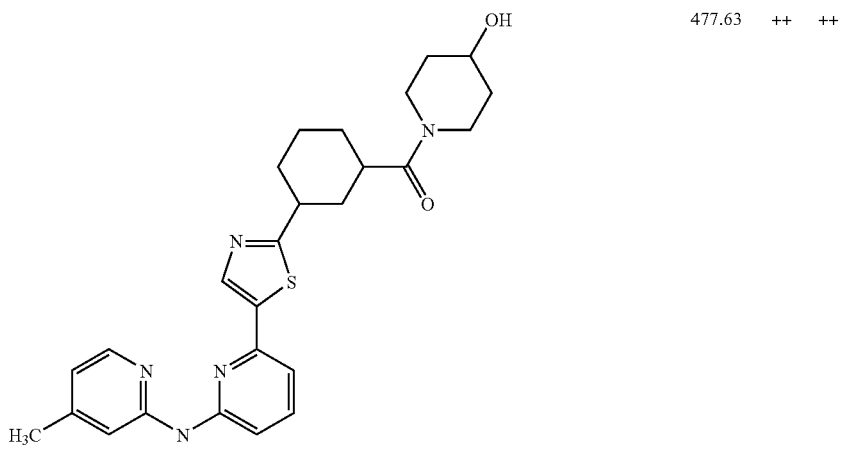 | 477.63 | ++ | ++ |
TABLE 1-56
| | | | | |
|---|---|---|---|---|
| A-273 | 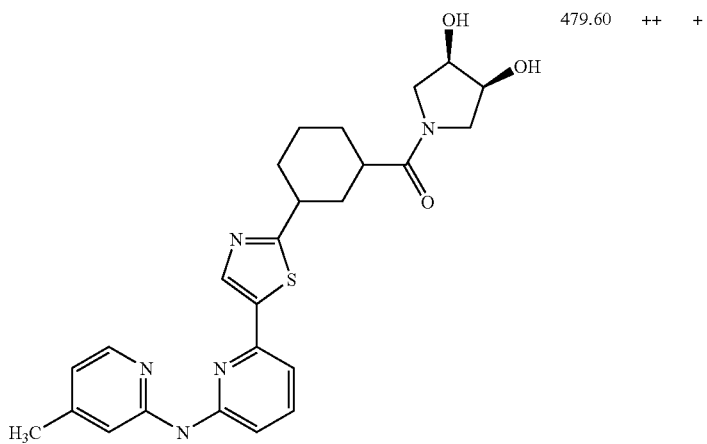 | 479.60 | ++ | + |

TABLE 1-56-continued
| A-274 | 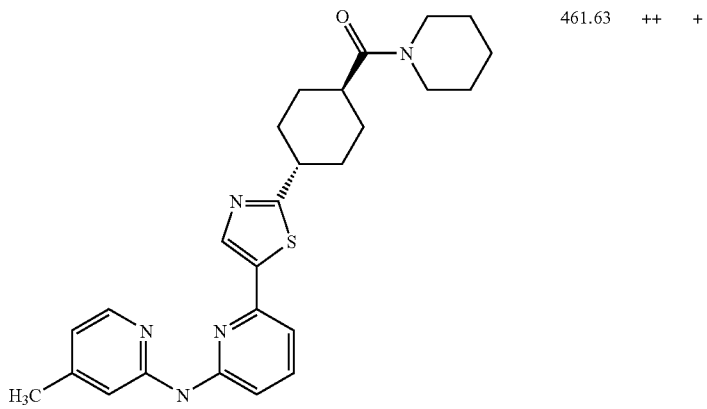 | 461.63 | ++ | + |
| A-275 | 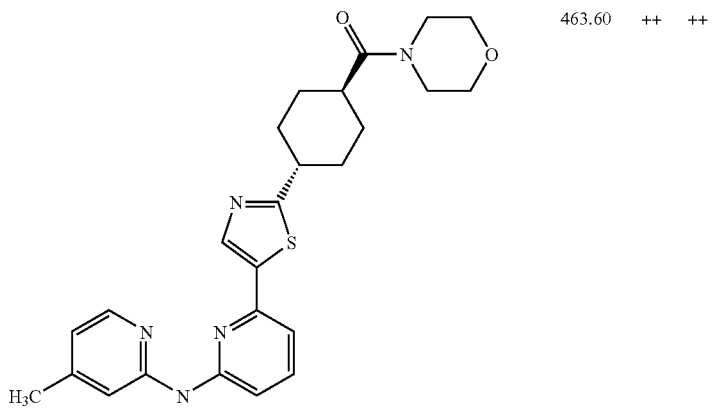 | 463.60 | ++ | ++ |
| A-276 | 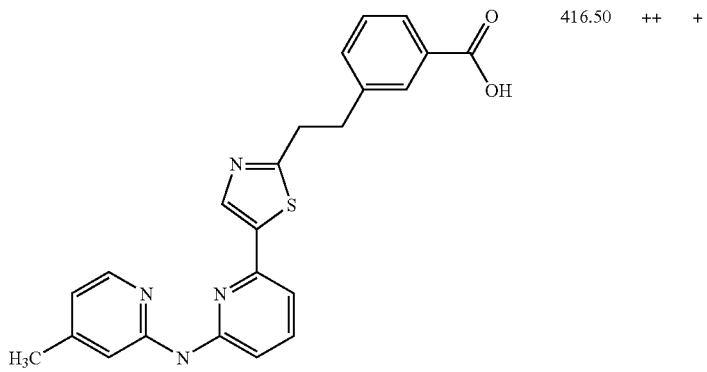 | 416.50 | ++ | + |
| A-277 | 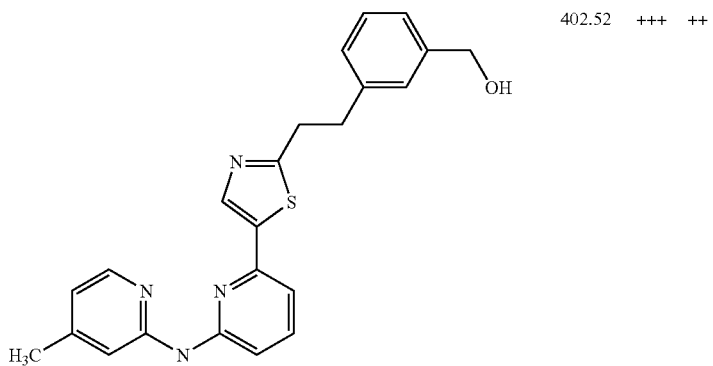 | 402.52 | +++ | ++ |

TABLE 1-57
A-278 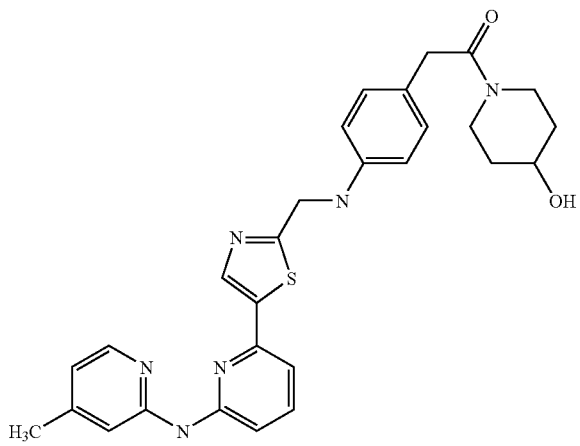 514.65 ++ +
A-279 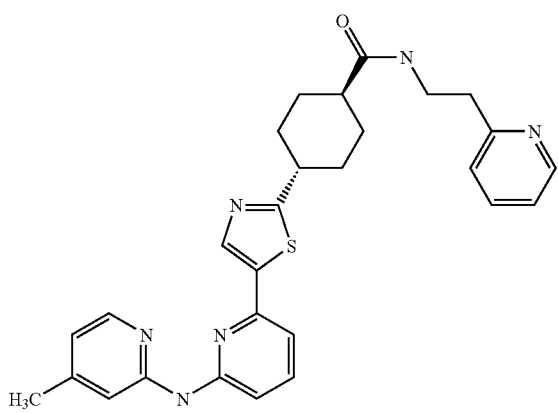 498.65 ++ ++
A-280 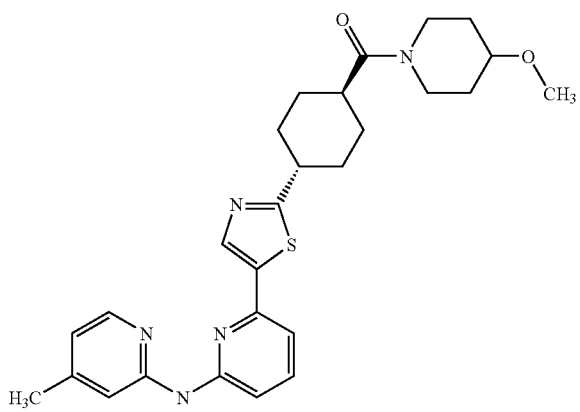 491.66 ++ ++
A-281 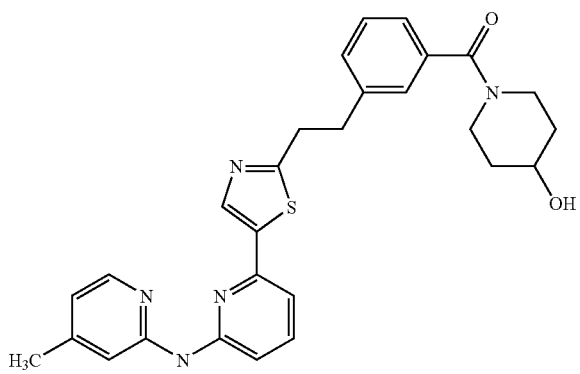 499.64 ++

TABLE 1-57-continued
A-282 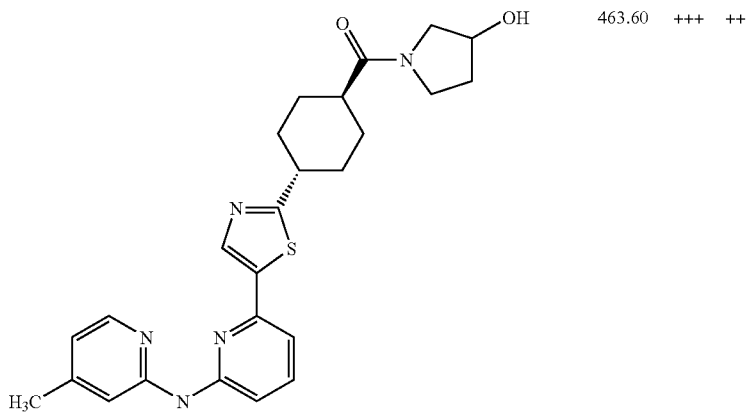 463.60 +++ ++
TABLE 1-58
A-283 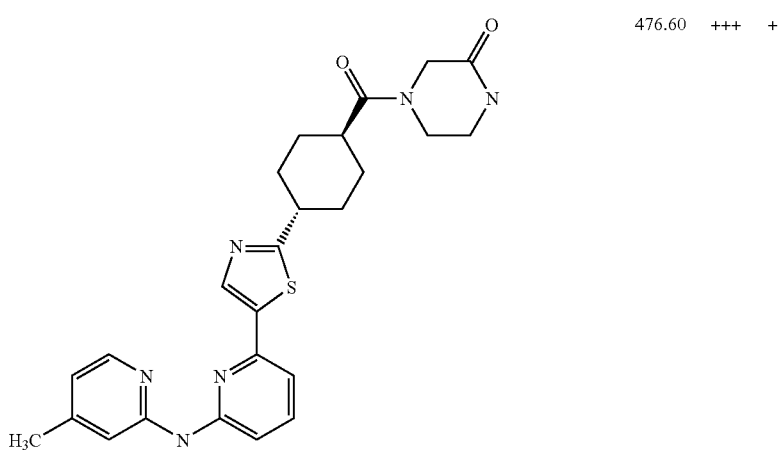 476.60 +++ +
A-284 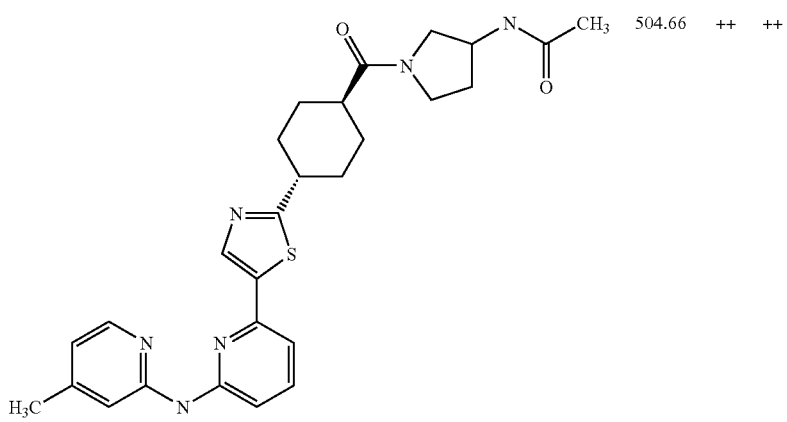 504.66 ++ ++

TABLE 1-58-continued
| | | | | |
|---|---|---|---|---|
| A-285 | 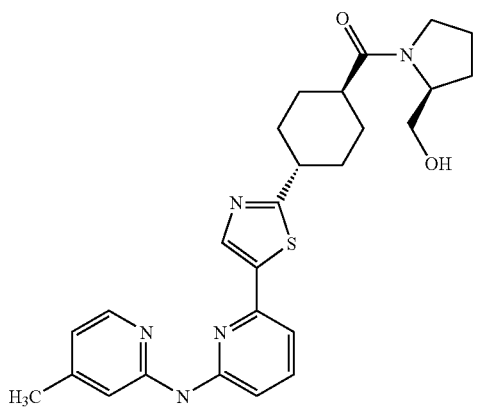 | 477.63 | ++ | ++ |
| A-286 | 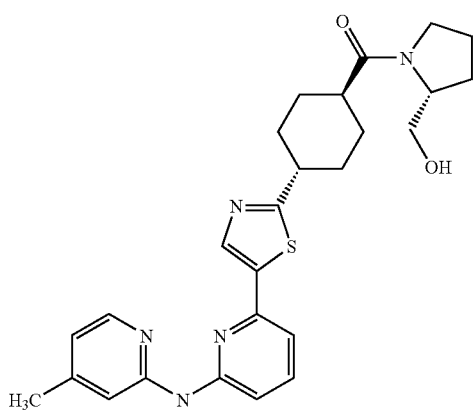 | 477.63 | +++ | ++ |
TABLE 1-59
| | | | | |
|---|---|---|---|---|
| A-287 | 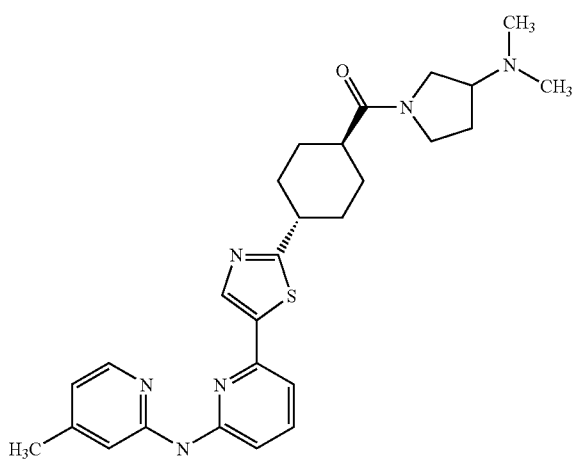 | 490.67 | ++ | ++ |

TABLE 1-59-continued
| A-288 | 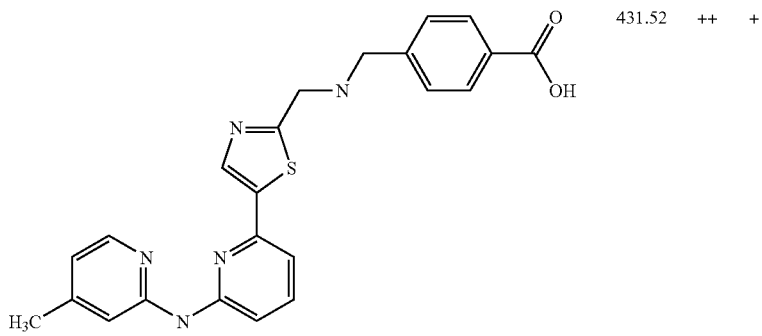 | 431.52 | ++ | + |
| A-289 |  | 504.66 | ++ | + |
| A-290 | 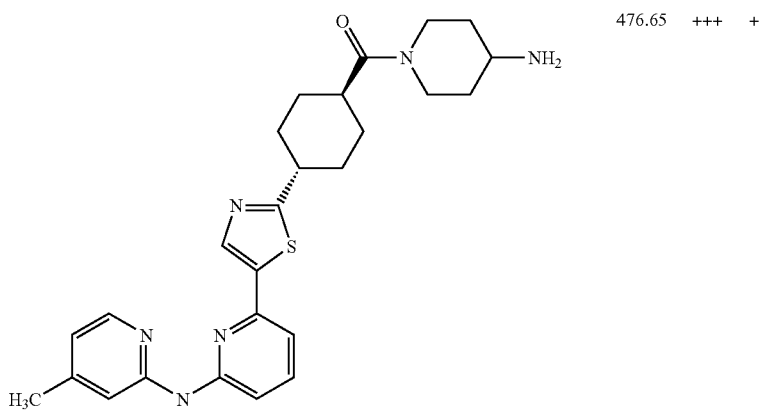 | 476.65 | +++ | + |
| A-291 | 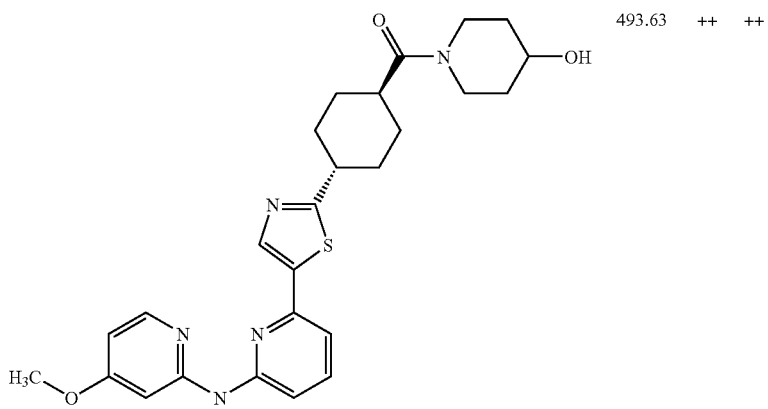 | 493.63 | ++ | ++ |

TABLE 1-60
A-292 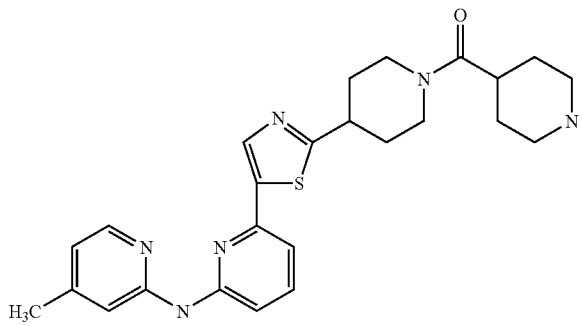 462.62 ++ +
A-293 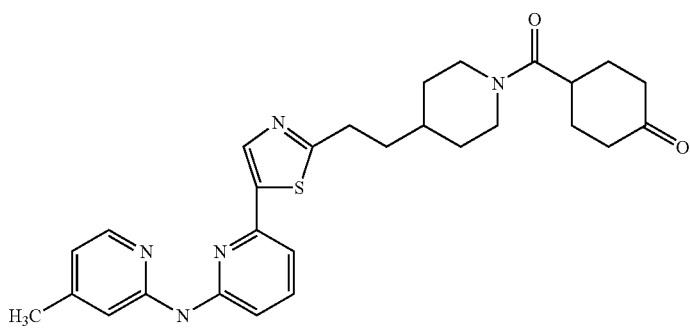 503.67 ++ +
A-294 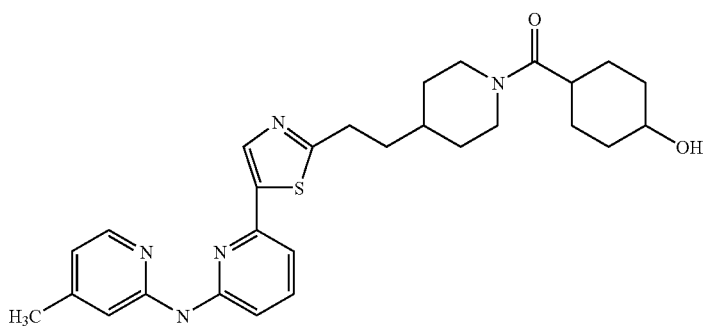 505.68 ++ +
A-295 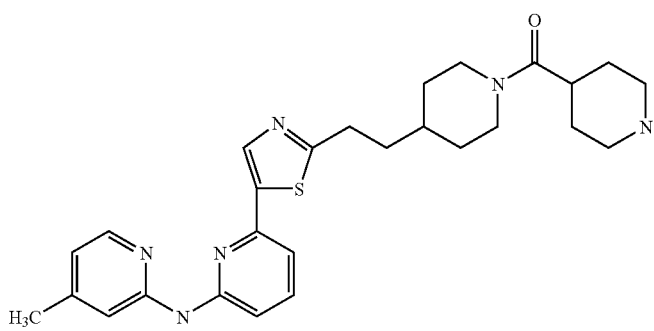 490.67 +++ +

TABLE 1-60-continued
A-296 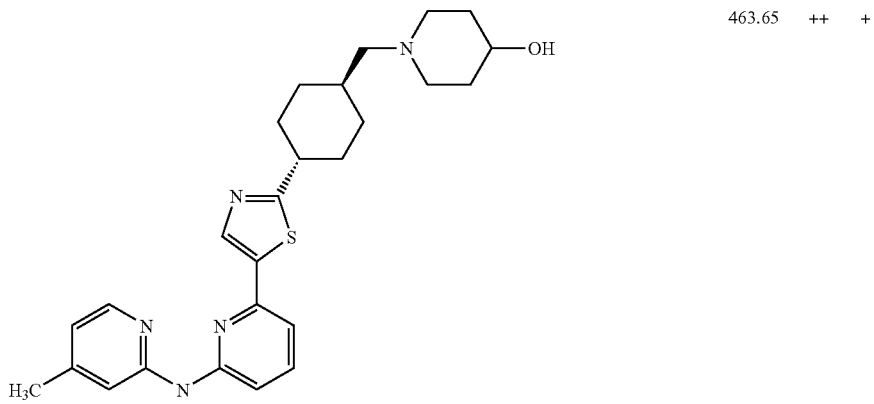 463.65 ++ +
TABLE 1-61
A-297 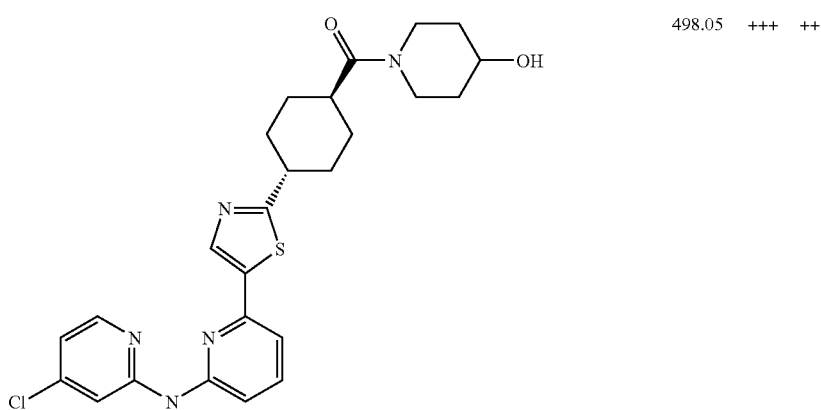 498.05 +++ ++
A-298 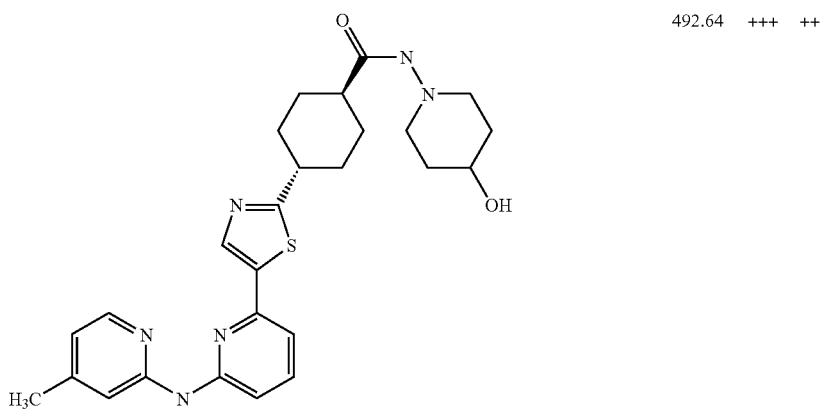 492.64 +++ ++

TABLE 1-61-continued
A-299 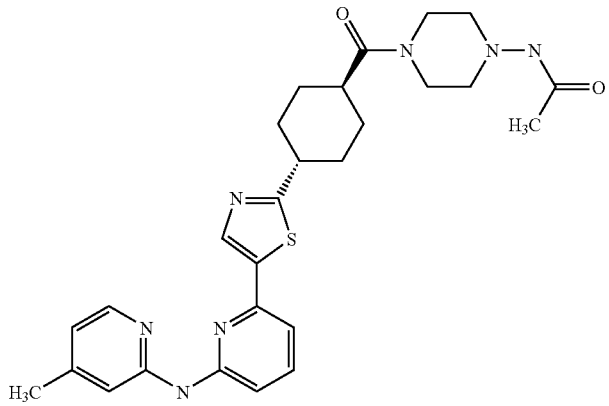 518.68 ++ ++
A-300 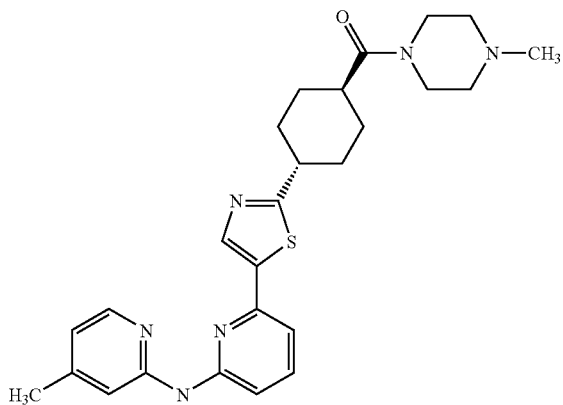 476.65 ++ ++
A-301 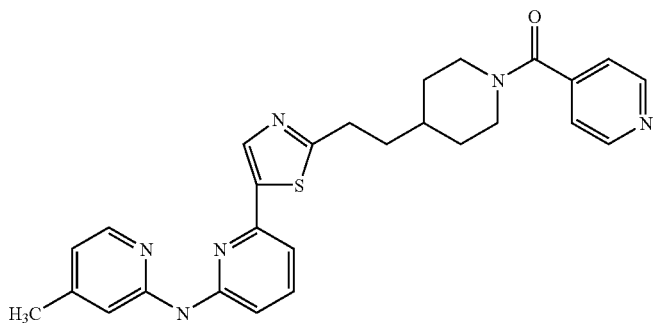 484.63 ++ ++
TABLE 1-62
A-302 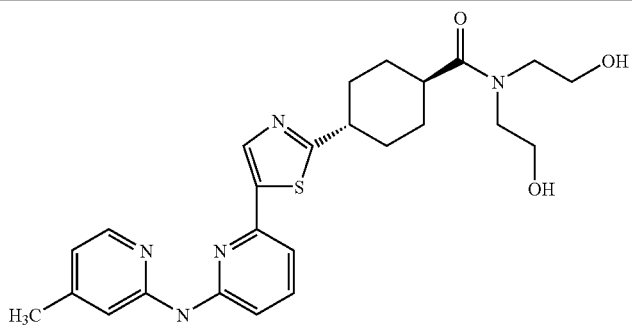 481.62 ++ ++

TABLE 1-62-continued
| A-303 | 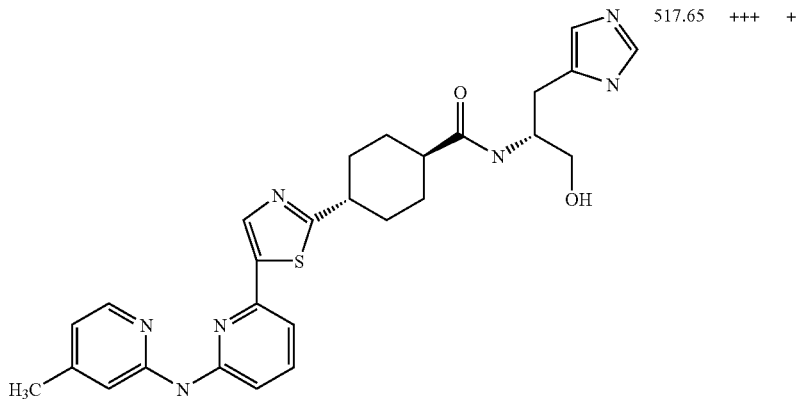 | 517.65 | +++ | + |
| A-304 | 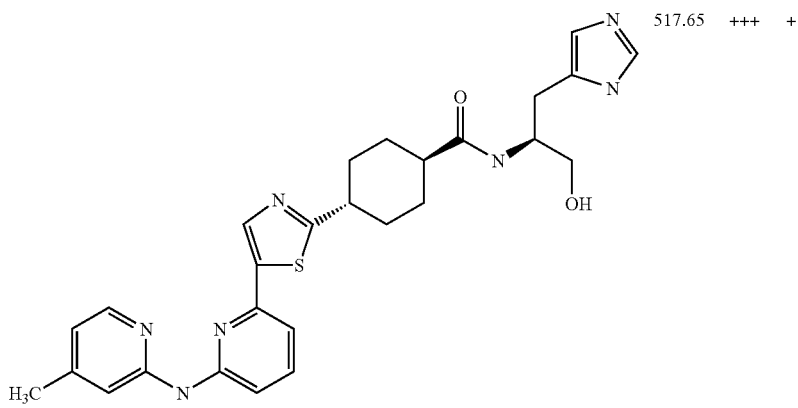 | 517.65 | +++ | + |
| A-305 | 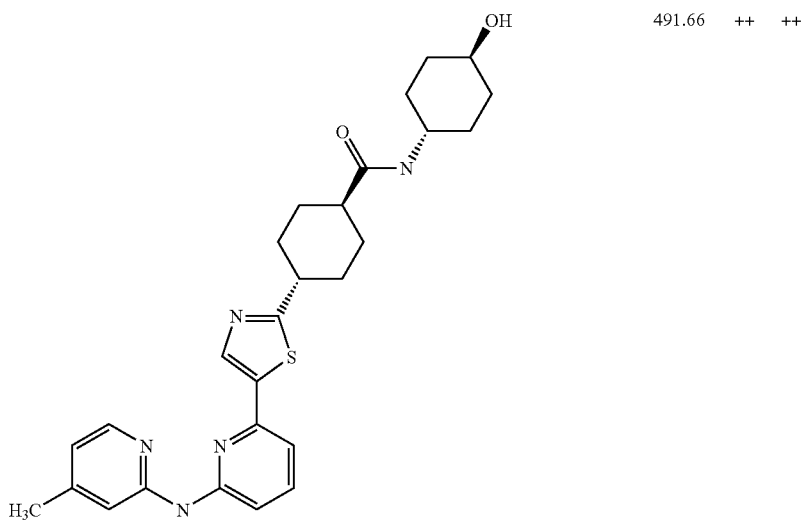 | 491.66 | ++ | ++ |

TABLE 1-62-continued
| A-306 | 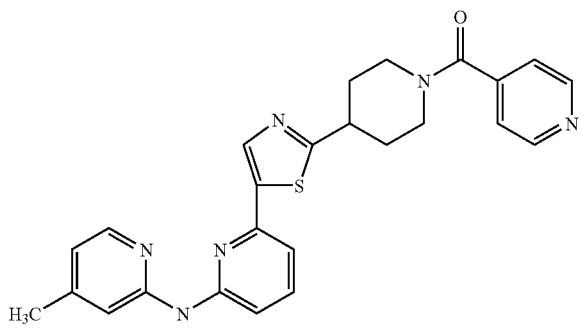 | 456.57 | ++ | ++ |
TABLE 1-63
| A-307 | 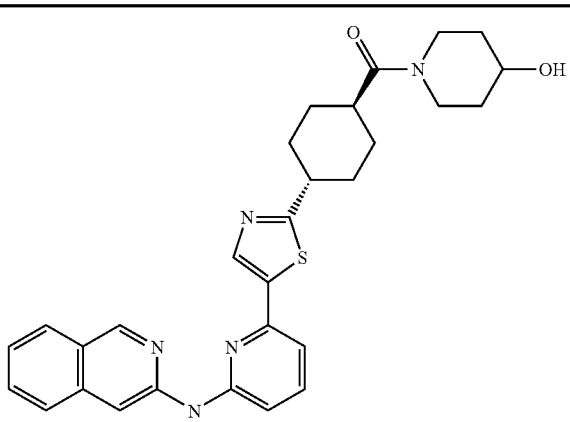 | 513.66 | ++ | ++ |
| A-308 | 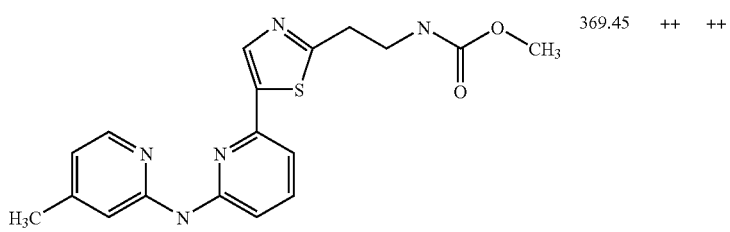 | 369.45 | ++ | ++ |
| A-309 | 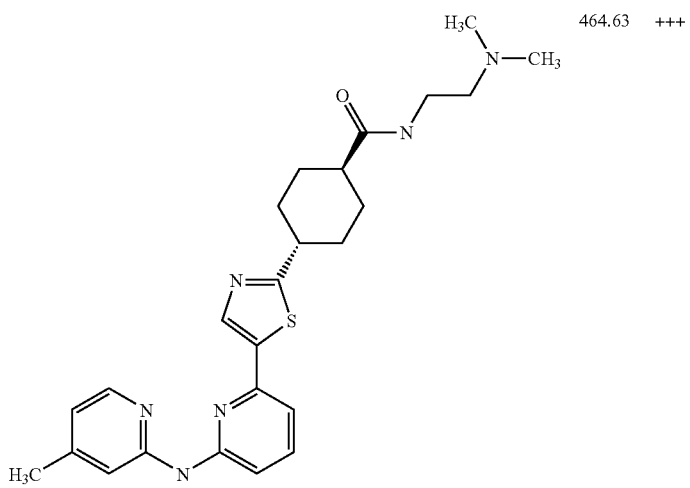 | 464.63 | +++ | ++ |

TABLE 1-63-continued
A-310 491.66 ++ +
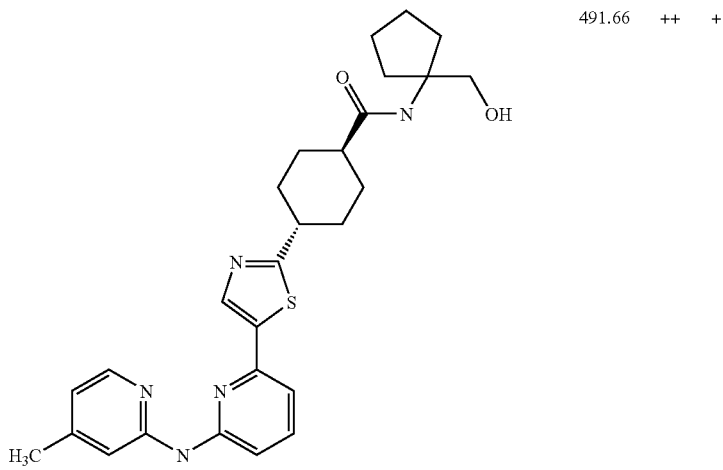
A-311 572.00 +++ ++
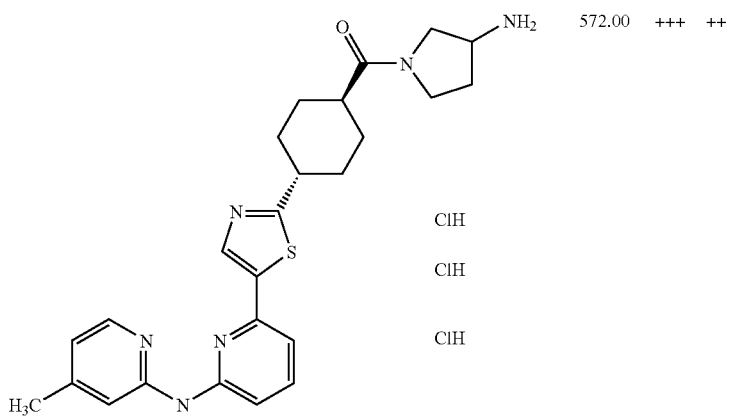
TABLE 1-64
A-312 540.71 +++ ++
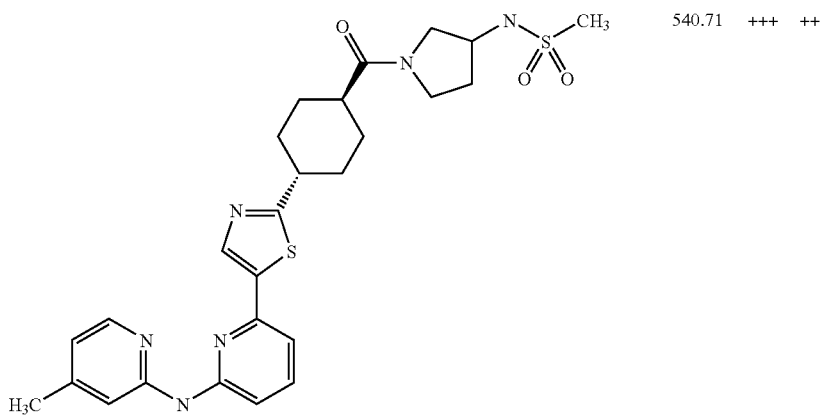

TABLE 1-64-continued
A-313 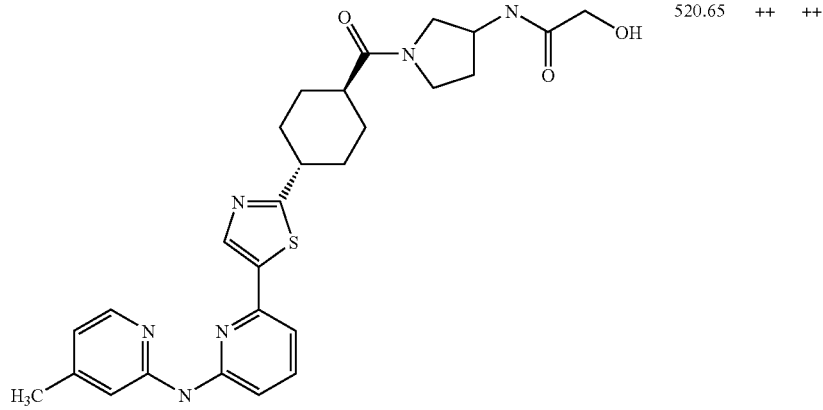 520.65 ++ ++
A-314 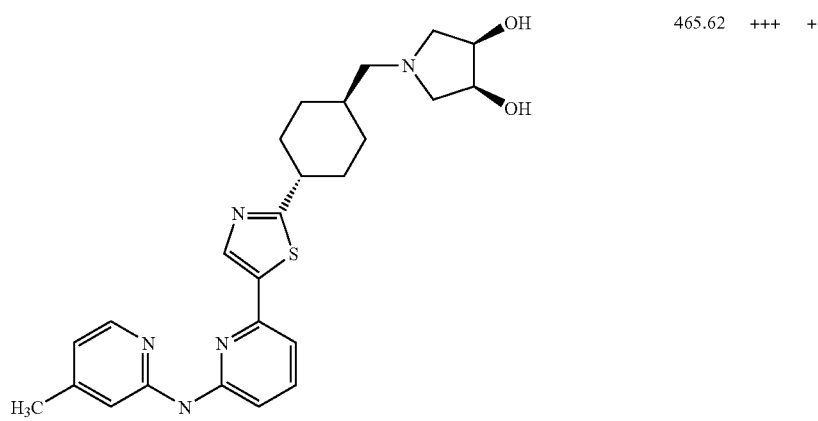 465.62 +++ +
A-315 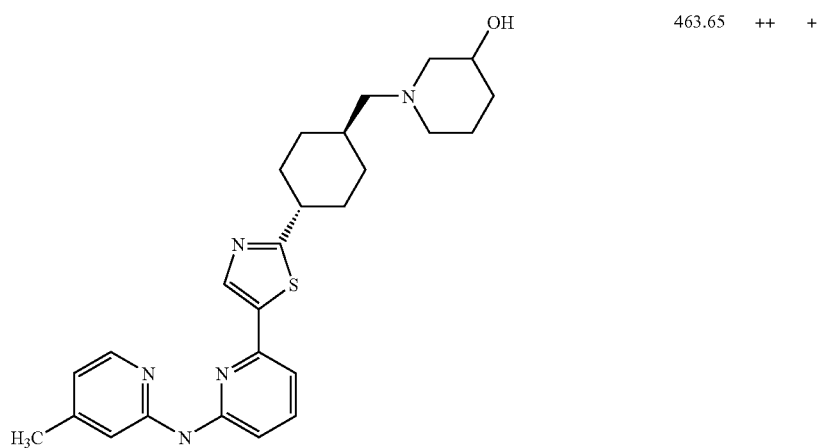 463.65 ++ +

TABLE 1-64-continued
A-316 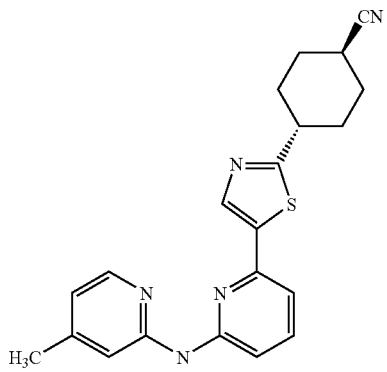 375.50 +++ ++
TABLE 1-65
A-317 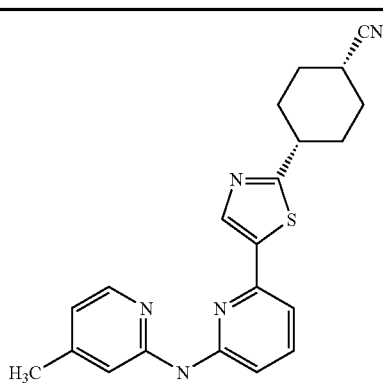 375.50 +++ ++
A-318 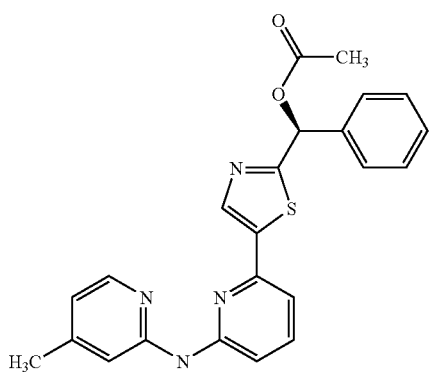 416.50 ++ +
A-319 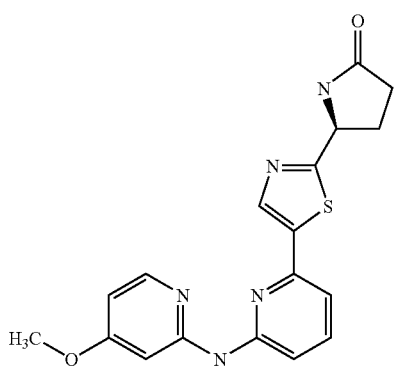 367.43 +++ ++

TABLE 1-65-continued
| A-320 | 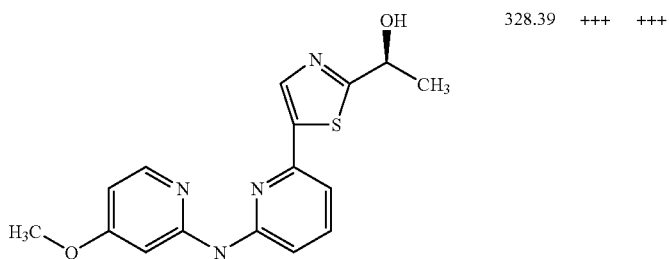 | 328.39 | +++ | +++ |
| A-321 |  | 342.42 | +++ | +++ |
| A-322 | 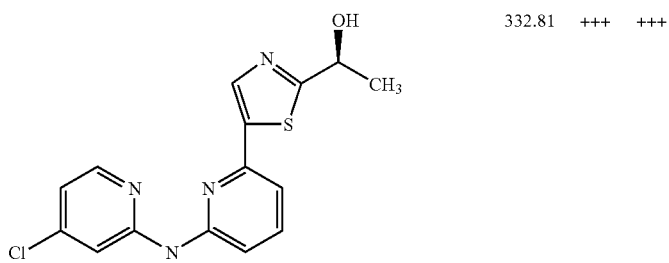 | 332.81 | +++ | +++ |
TABLE 1-66
| A-323 | 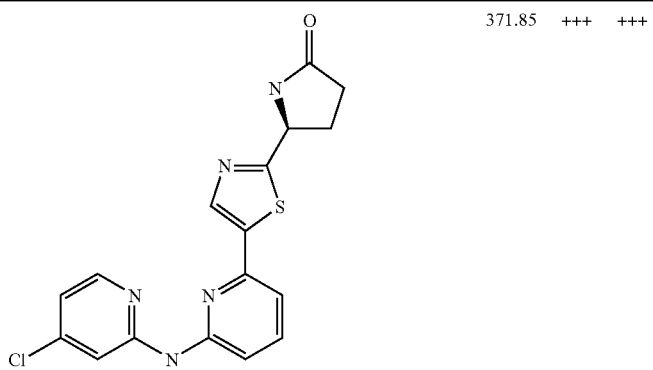 | 371.85 | +++ | +++ |
| A-324 | 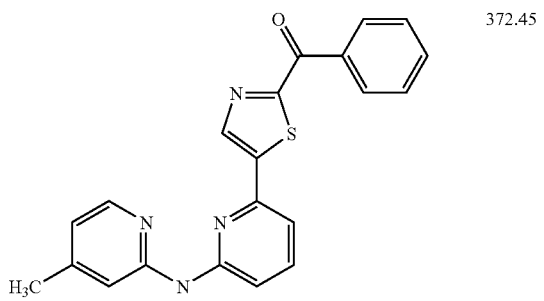 | 372.45 | | |

TABLE 1-66-continued
| | | | | |
|---|---|---|---|---|
| A-325 | 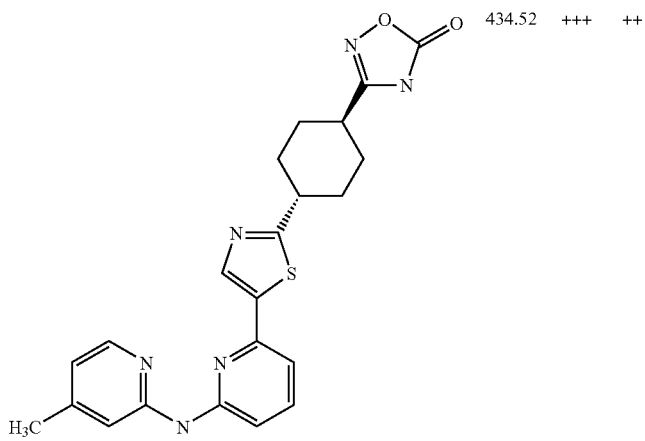 | 434.52 | +++ | ++ |
| A-326 | 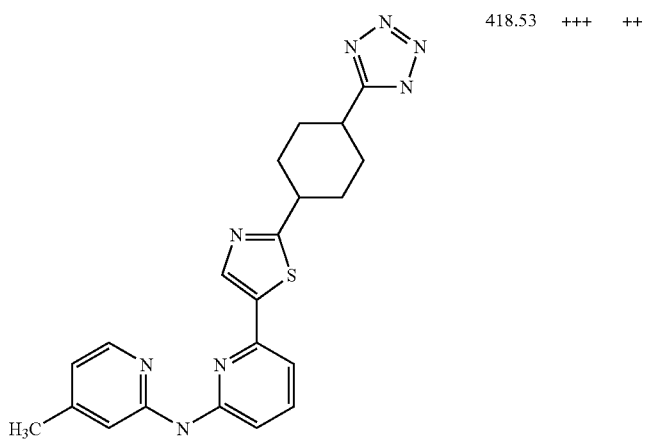 | 418.53 | +++ | ++ |
| A-327 | 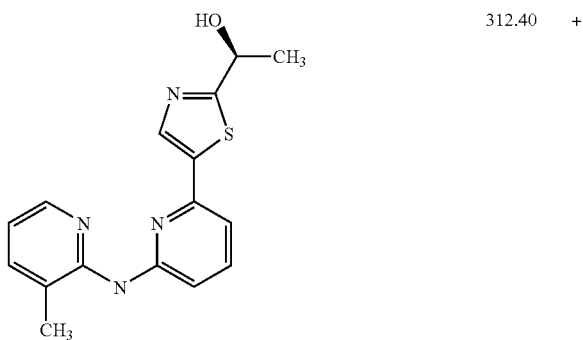 | 312.40 | + | |
TABLE 1-67
| | | | | |
|---|---|---|---|---|
| A-328 | 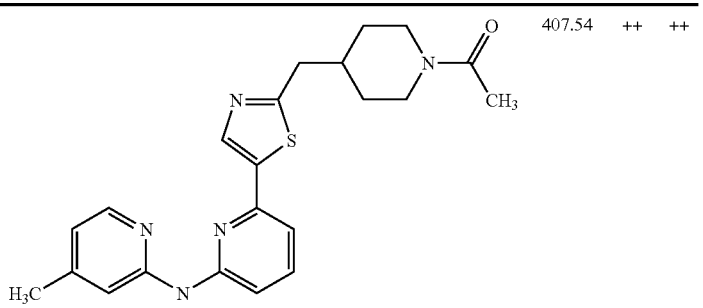 | 407.54 | ++ | ++ |

TABLE 1-67-continued

| ID | Structure | MW | | |
|---|---|---|---|---|
| A-329 | (ethyl 2-(2-((6-(2-((R)-1-acetamidoethyl)thiazol-5-yl)pyridin-2-yl)amino)pyridin-4-yl)acetate) | 425.51 | ++ | |
| A-330 | (2-oxopyrrolidinyl-thiazole-pyridine-pyridine with hydroxyethyl) | 381.46 | +++ | ++ |
| A-331 | (2-(2-((6-(2-((R)-1-acetamidoethyl)thiazol-5-yl)pyridin-2-yl)amino)pyridin-4-yl)acetic acid) | 397.45 | + | + |
| A-332 | (ethyl ester analog with pyrrolidinone-thiazole) | 423.49 | ++ | ++ |

TABLE 1-68

| | | | | |
|---|---|---|---|---|
| A-333 | | 339.46 | ++ | ++ |
| A-334 | | 381.50 | +++ | +++ |
| A-335 | | 384.46 | +++ | ++ |
| A-336 | | 407.54 | +++ | ++ |
| A-337 | | 417.56 | +++ | +++ |

TABLE 1-68-continued
A-338 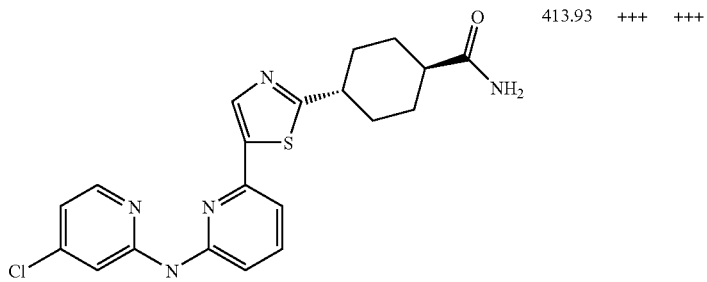 413.93 +++ +++
TABLE 1-69
A-339 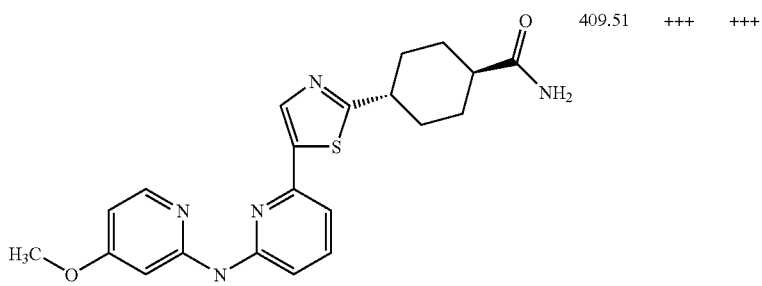 409.51 +++ +++
A-340 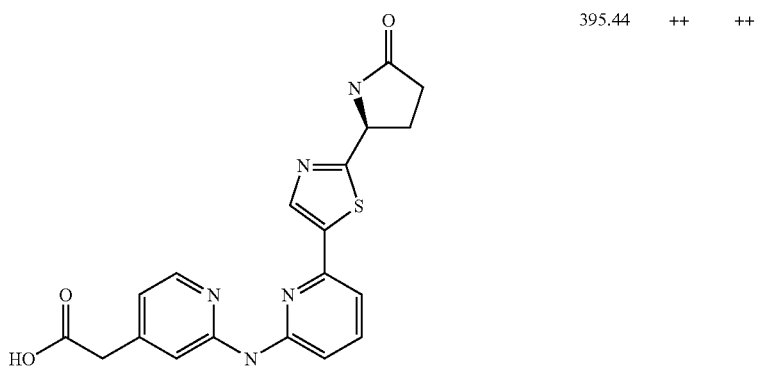 395.44 ++ ++
A-341 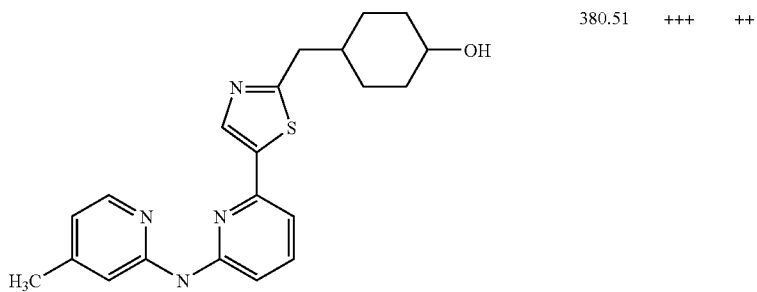 380.51 +++ ++

TABLE 1-69-continued

| A-342 | (structure) | 408.48 | + | + |
| A-343 | (structure) | 397.46 | ++ | ++ |
| A-344 | (structure) | 358.42 | +++ | +++ |

TABLE 1-70

| A-345 | (structure) | 383.48 | +++ | ++ |

TABLE 1-70-continued

| | | | | |
|---|---|---|---|---|
| A-346 | | 411.49 | ++ | ++ |
| A-347 | | 431.52 | ++ | ++ |
| A-348 | | 415.52 | ++ | + |
| A-349 | | 437.57 | ++ | + |

TABLE 1-71
A-350 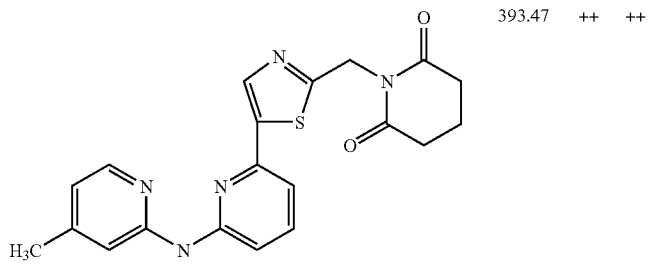 393.47 ++ ++
A-351 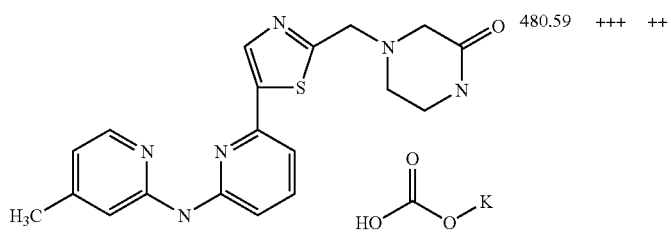 480.59 +++ ++
A-352 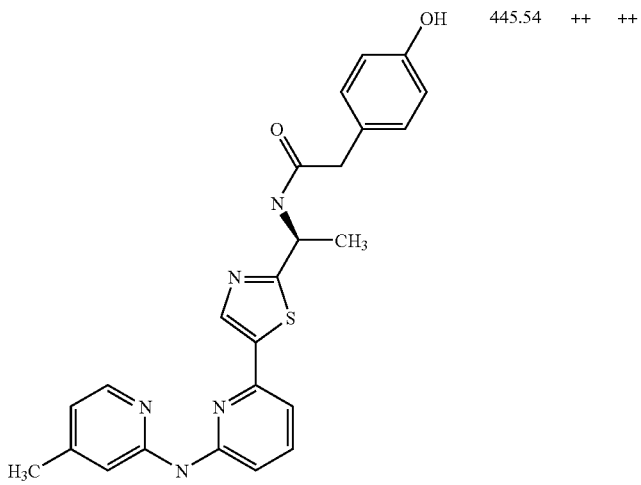 445.54 ++ ++
A-353 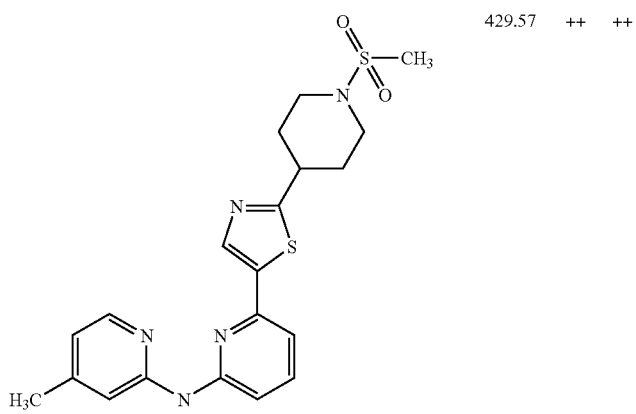 429.57 ++ ++

TABLE 1-71-continued
A-354  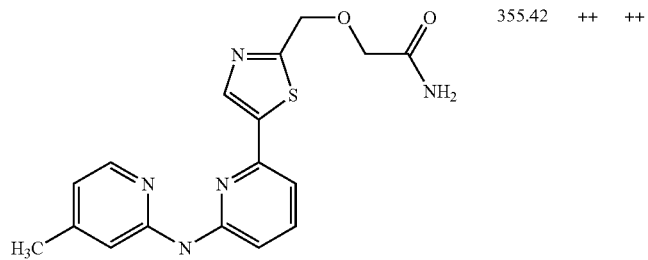  355.42  ++  ++
TABLE 1-72
A-355  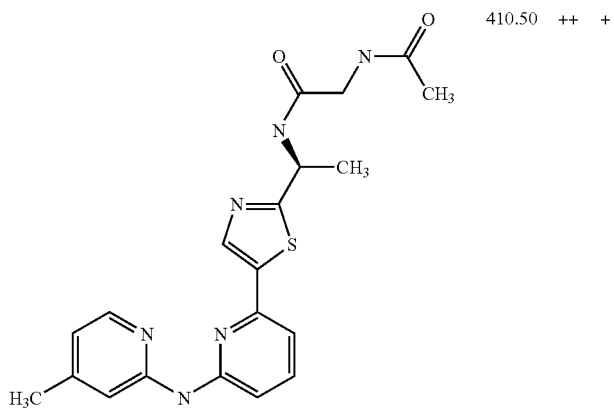  410.50  ++  +
A-356  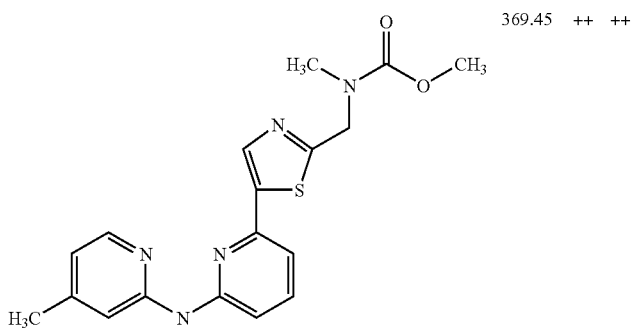  369.45  ++  ++
A-357  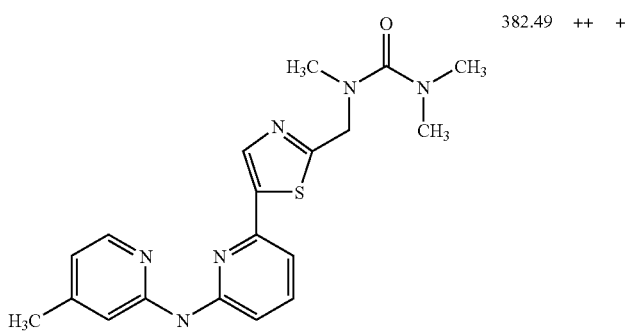  382.49  ++  +

TABLE 1-72-continued
| A-358 | 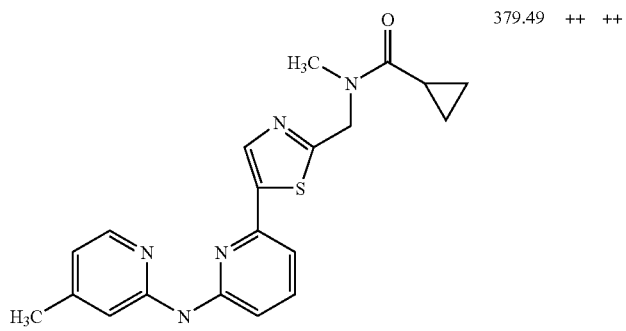 | 379.49 | ++ | ++ |
| A-359 | 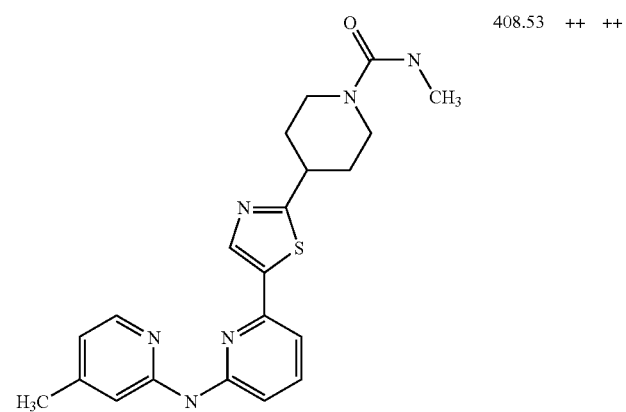 | 408.53 | ++ | ++ |
TABLE 1-73
| A-360 | 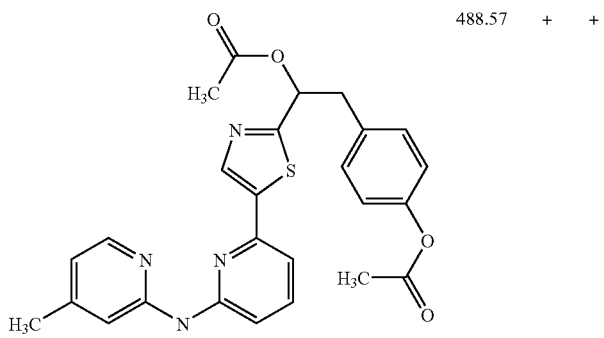 | 488.57 | + | + |
| A-361 | 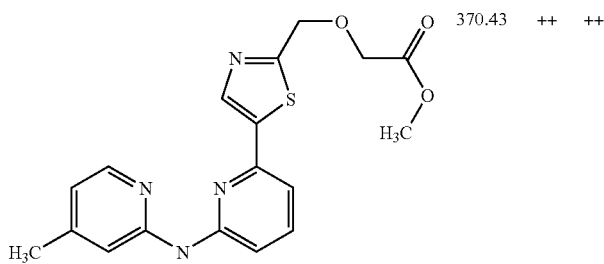 | 370.43 | ++ | ++ |

TABLE 1-73-continued

| A-362 | [structure] | 404.49 | +++ | ++ |
| A-363 | [structure] | 365.46 | ++ | ++ |
| A-364 | [structure] | 379.49 | ++ | ++ |

TABLE 1-74

| A-365 | [structure] | 368.46 | ++ | ++ |

TABLE 1-74-continued
| A-366 | 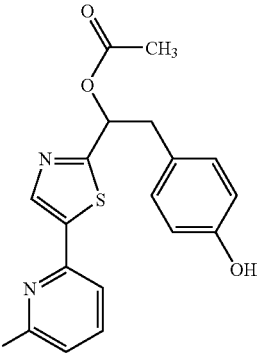 | 446.53 | ++ | ++ |
| A-367 | 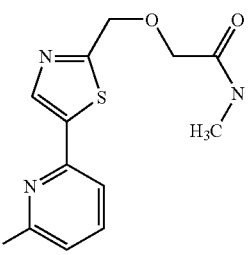 | 369.45 | ++ | ++ |
| A-368 | 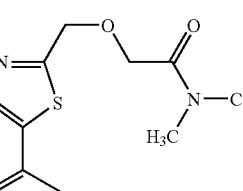 | 383.48 | ++ | ++ |
| A-369 | 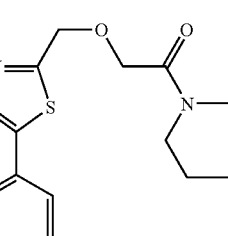 | 439.54 | ++ | + |
| A-370 | 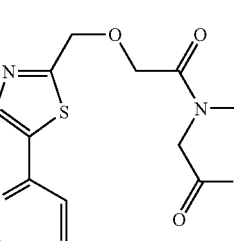 | 438.51 | +++ | ++ |

TABLE 1-75
| | | | | | |
|---|---|---|---|---|---|
| A-371 | 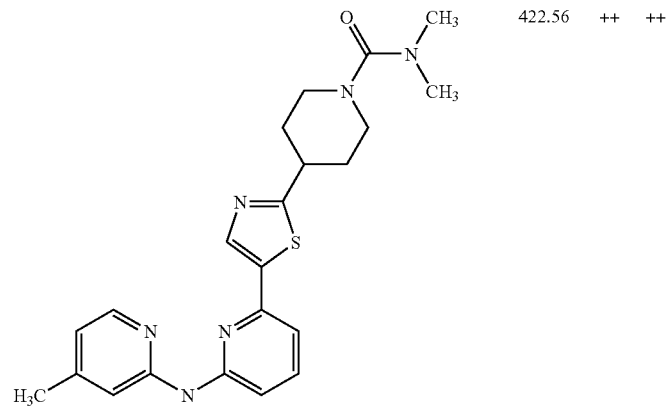 | 422.56 | ++ | ++ | |
| A-372 | 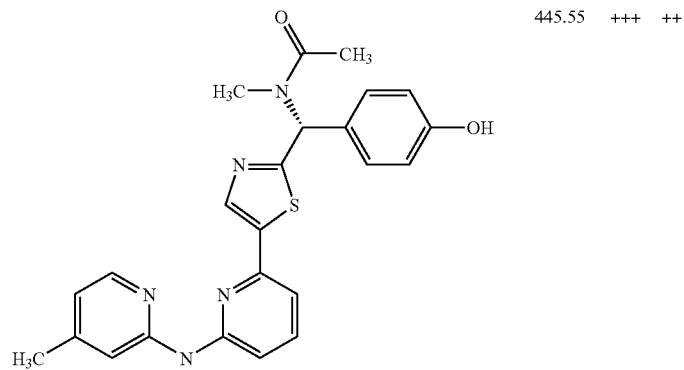 | 445.55 | +++ | ++ | |
| A-373 | 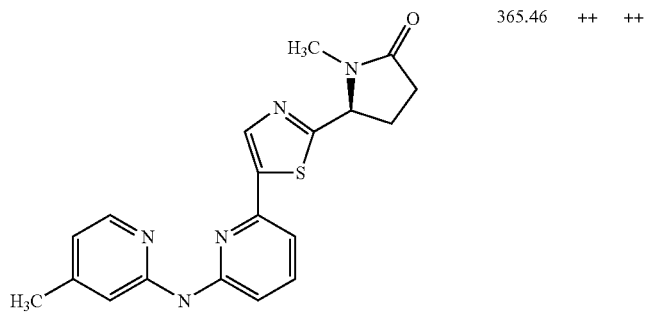 | 365.46 | ++ | ++ | |
| A-374 | 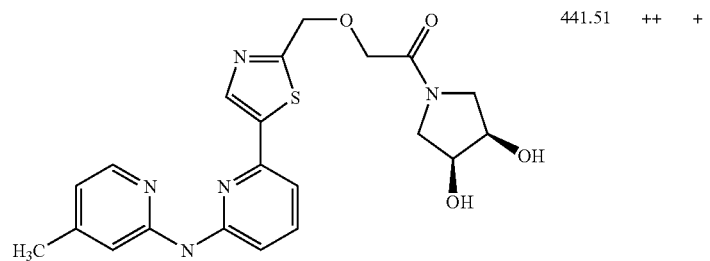 | 441.51 | ++ | + | |

TABLE 1-75-continued

| A-375 | [structure: (S)-2-(dimethylamino)-1-(5-(6-((4-methylpyridin-2-yl)amino)pyridin-2-yl)thiazol-2-yl)ethanol] | 355.46 | ++ | ++ |

TABLE 1-76

| A-376 | [structure: N-methyl-N-((S)-1-(5-(6-((4-methylpyridin-2-yl)amino)pyridin-2-yl)thiazol-2-yl)-2-(4-hydroxyphenyl)ethyl)acetamide] | 459.57 | ++ | ++ |
| A-377 | [structure: 4-(4-(5-(6-((4-methylpyridin-2-yl)amino)pyridin-2-yl)thiazol-2-yl)piperidine-1-carbonyl)phenyl acetate] | 513.62 | ++ | ++ |
| A-378 | [structure: (4-hydroxyphenyl)(4-(5-(6-((4-methylpyridin-2-yl)amino)pyridin-2-yl)thiazol-2-yl)piperidin-1-yl)methanone] | 471.59 | ++ | ++ |

TABLE 1-76-continued
| | | | | |
|---|---|---|---|---|
| A-379 | 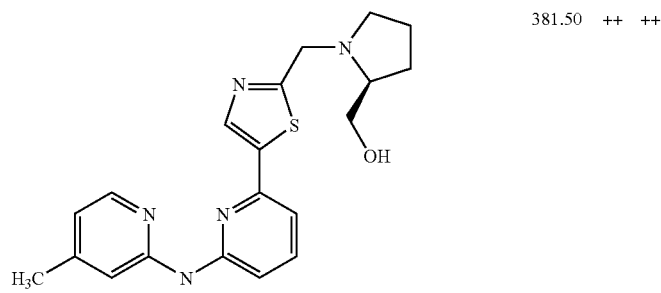 | 381.50 | ++ | ++ |
| A-380 | 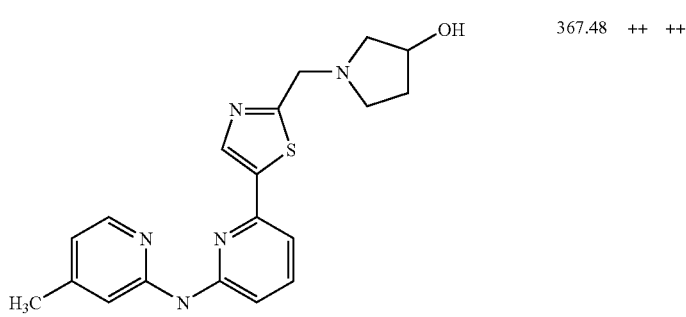 | 367.48 | ++ | ++ |
TABLE 1-77
| | | | | |
|---|---|---|---|---|
| A-381 | 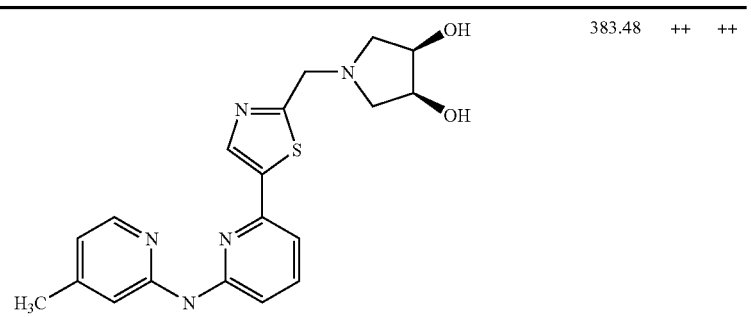 | 383.48 | ++ | ++ |
| A-382 | 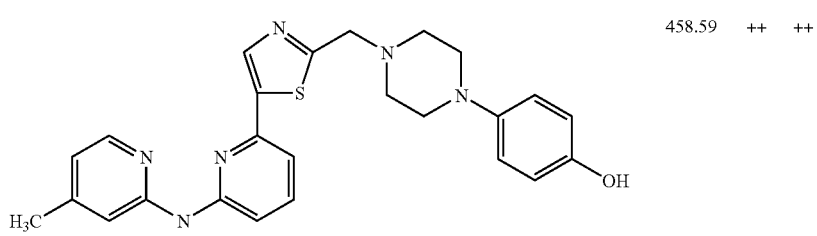 | 458.59 | ++ | ++ |
| A-383 | 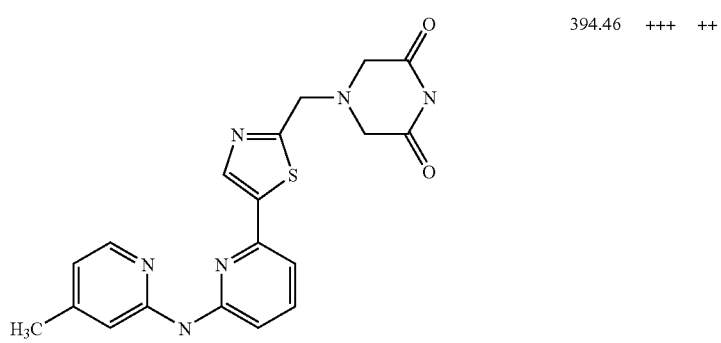 | 394.46 | +++ | ++ |

TABLE 1-77-continued
| A-384 | 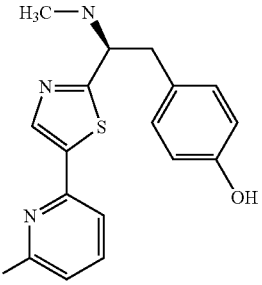 | 417.54 | ++ | ++ |
| A-385 | | 421.52 | ++ | ++ |
| A-386 | | 480.64 | ++ | ++ |
TABLE 1-78
| A-387 | 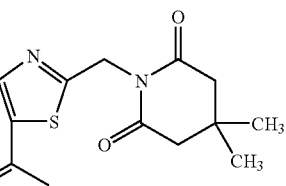 | 395.44 | ++ | ++ |
| A-388 | 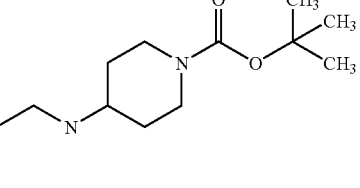 | 452.54 | + | + |

TABLE 1-78-continued
| A-389 | 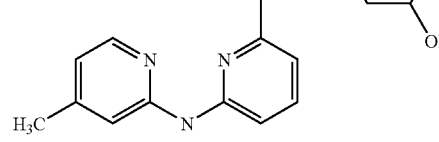 | 403.51 | ++ | |
| A-390 | 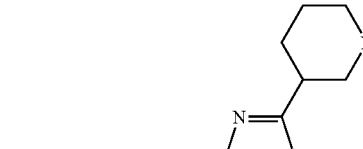 | 351.48 | ++ | ++ |
| A-391 | 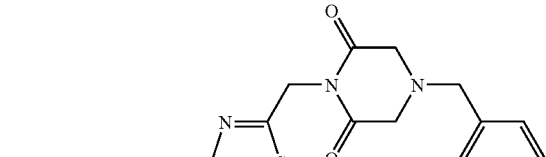 | 484.58 | + | + |
| A-392 | 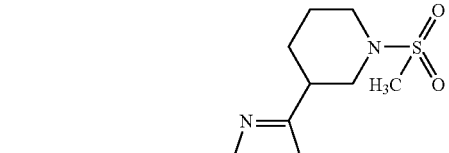 | 429.57 | ++ | ++ |

TABLE 1-79
| A-393 | 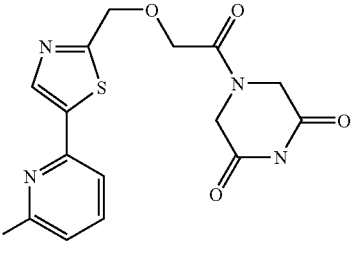 | 452.50 | ++ | + |
| A-394 | 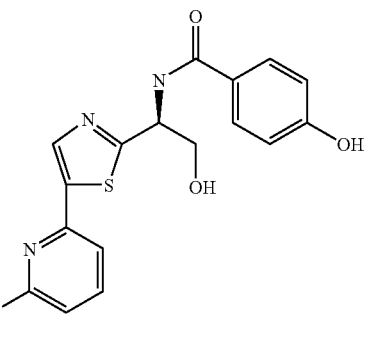 | 447.52 | ++ | ++ |
| A-395 | 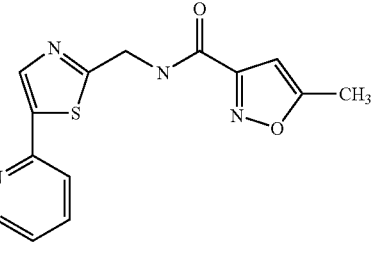 | 406.47 | ++ | + |
| A-396 | 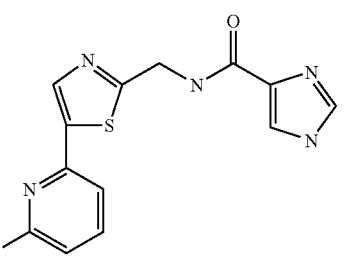 | 391.46 | ++ | + |
| A-397 | 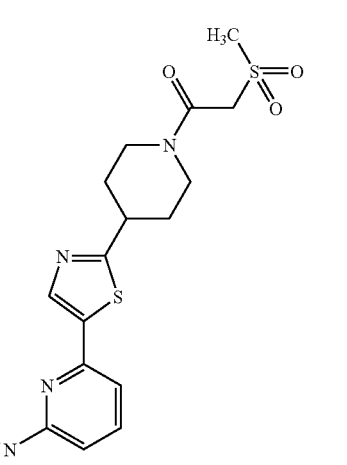 | 471.60 | ++ | ++ |

TABLE 1-80
A-398 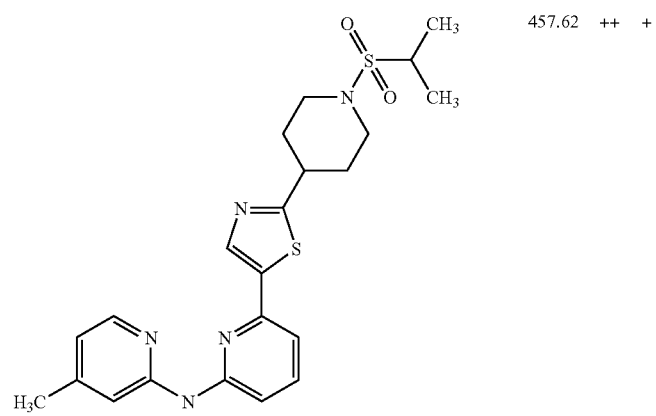 457.62 ++ +
A-399 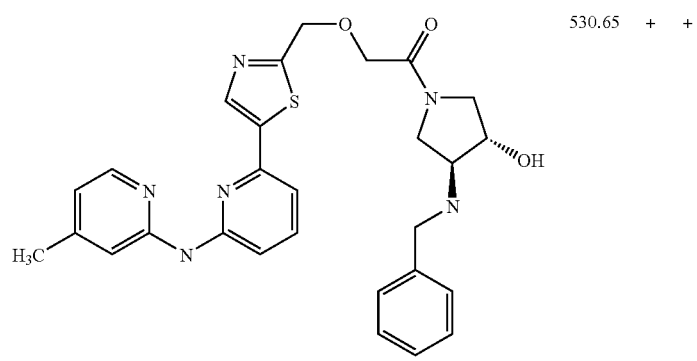 530.65 + +
A-400 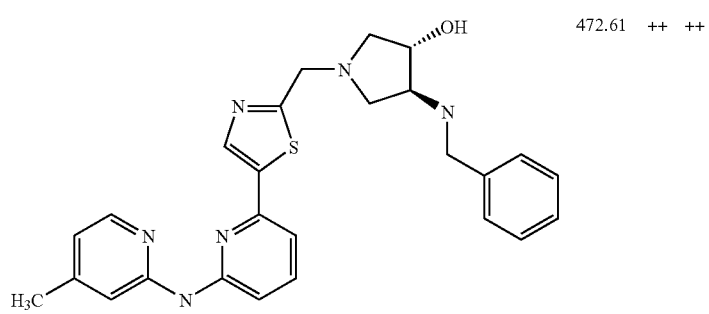 472.61 ++ ++
A-401 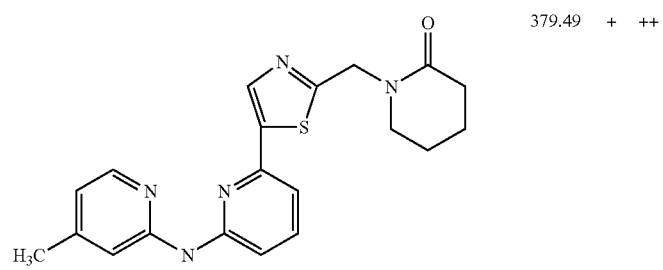 379.49 + ++

TABLE 1-80-continued
| A-402 | 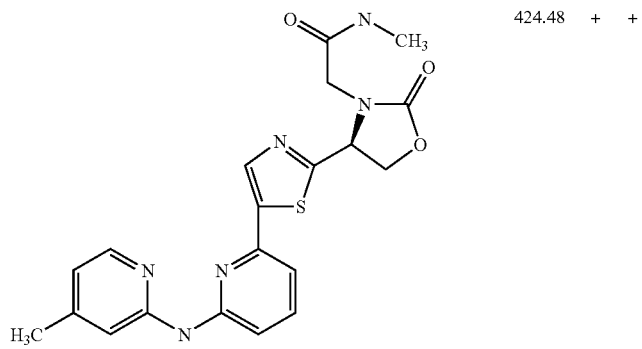 | 424.48 | + | + |
TABLE 1-81
| A-403 | 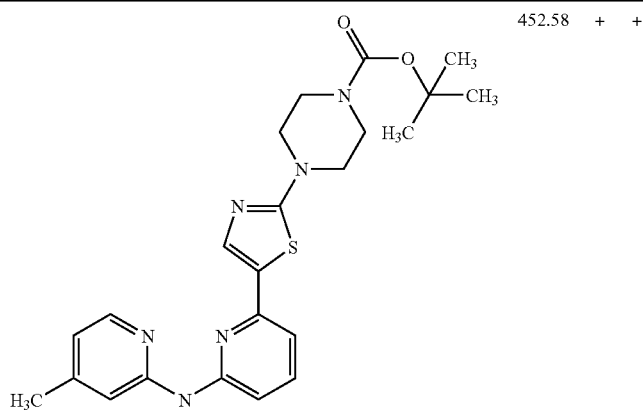 | 452.58 | + | + |
| A-404 | 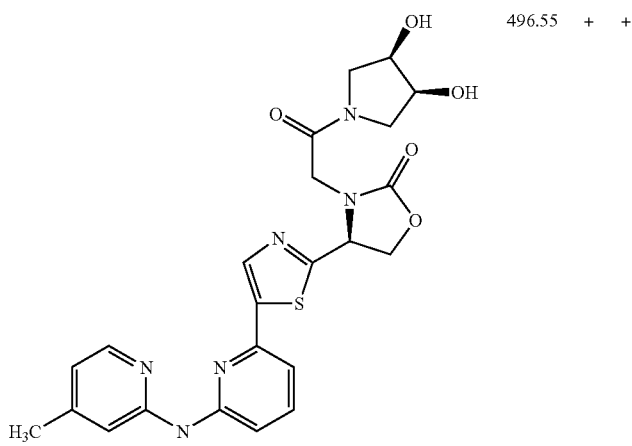 | 496.55 | + | + |
| A-405 | 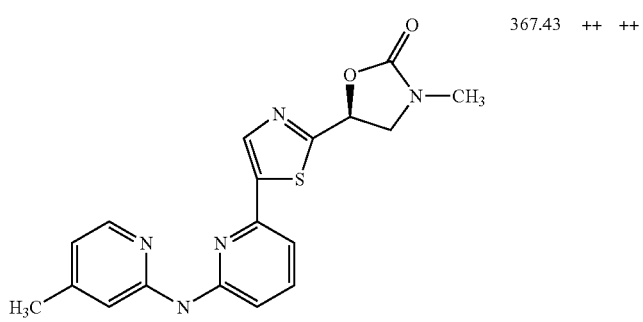 | 367.43 | ++ | ++ |

TABLE 1-81-continued
A-406 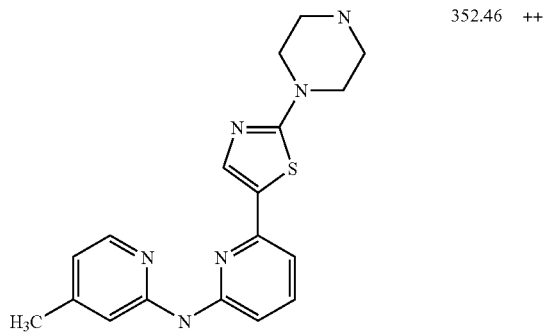 352.46 ++
A-407 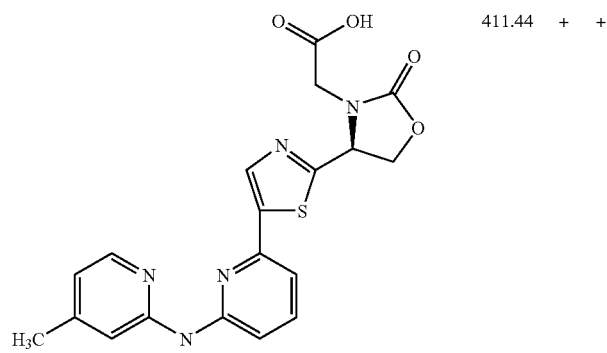 411.44 + +
TABLE 1-82
A-408 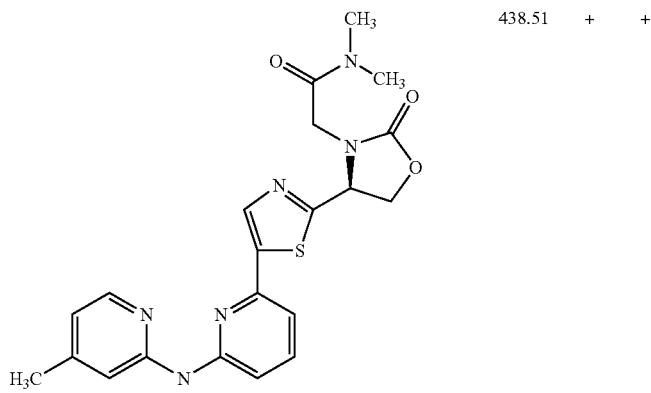 438.51 + +
A-409 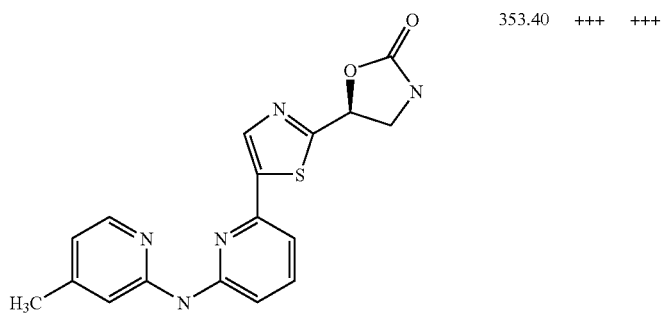 353.40 +++ +++

TABLE 1-82-continued
| A-410 | 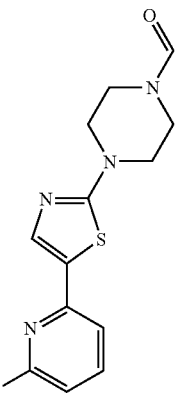 | 380.47 | ++ | +++ |
| A-411 | 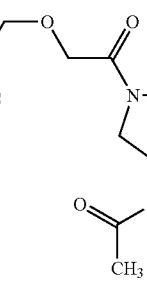 | 482.56 | + | + |
| A-412 | 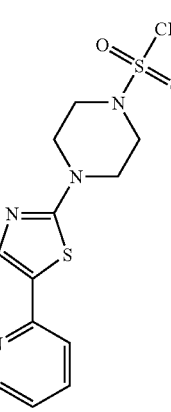 | 430.55 | ++ | ++ |
TABLE 1-83
| A-413 | 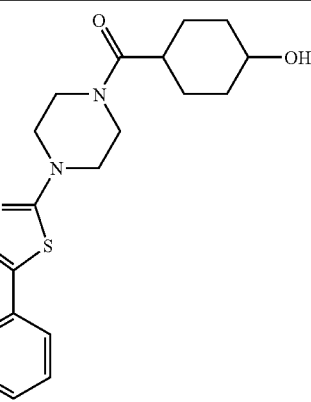 | 478.62 | ++ | ++ |

TABLE 1-83-continued
| | | | | |
|---|---|---|---|---|
| A-414 | 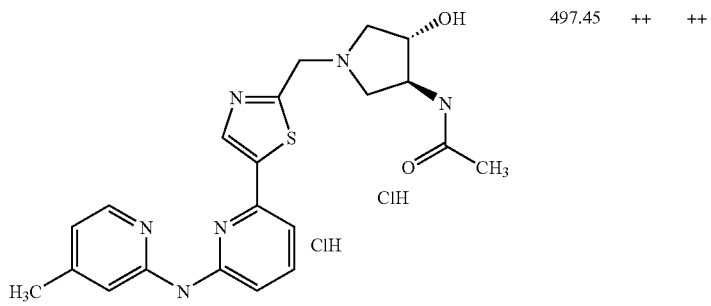 | 497.45 | ++ | ++ |
| A-415 | 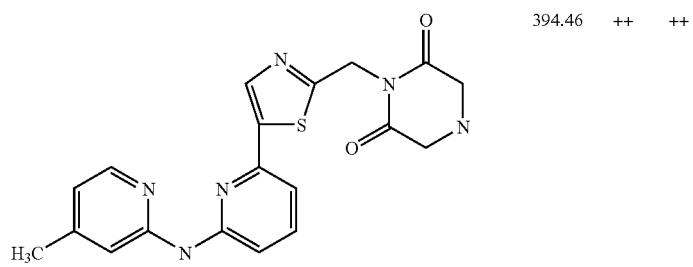 | 394.46 | ++ | ++ |
| A-416 | 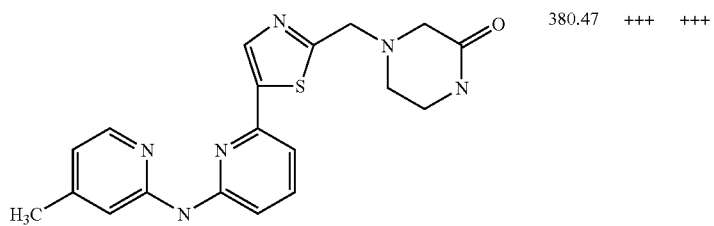 | 380.47 | +++ | +++ |
| A-417 | 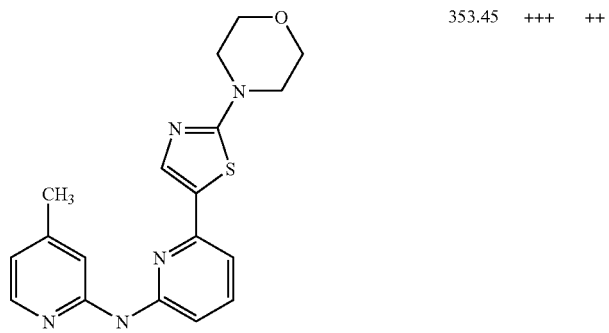 | 353.45 | +++ | ++ |
| A-418 | 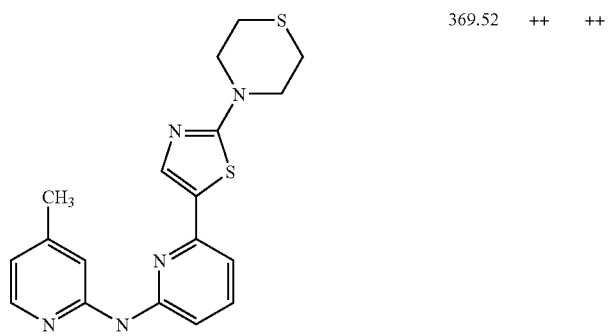 | 369.52 | ++ | ++ |

TABLE 1-84
A-419 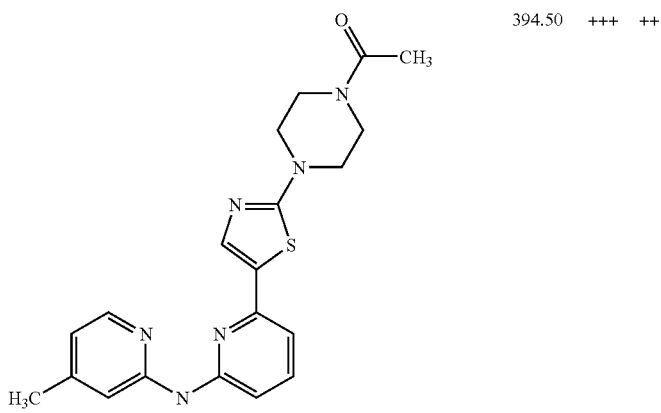 394.50 +++ ++
A-420 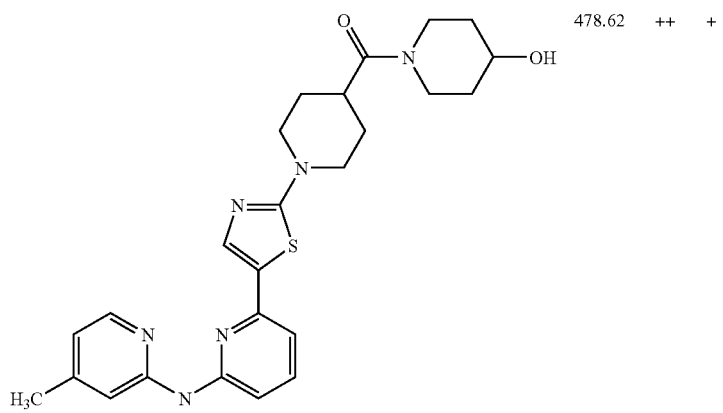 478.62 ++ +
A-421 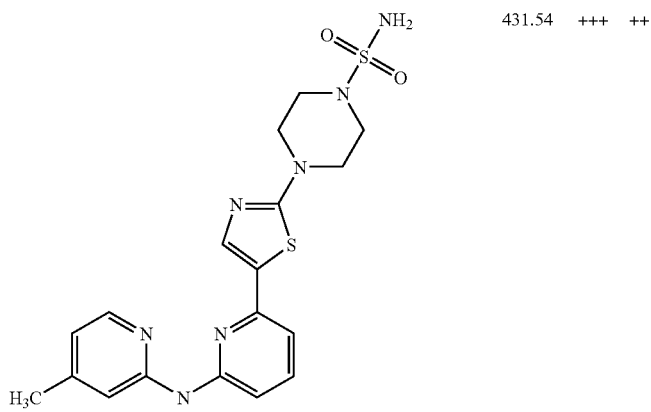 431.54 +++ ++
A-422 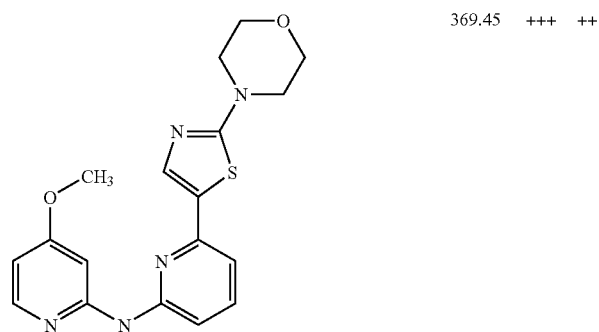 369.45 +++ ++

TABLE 1-84-continued
| A-423 | 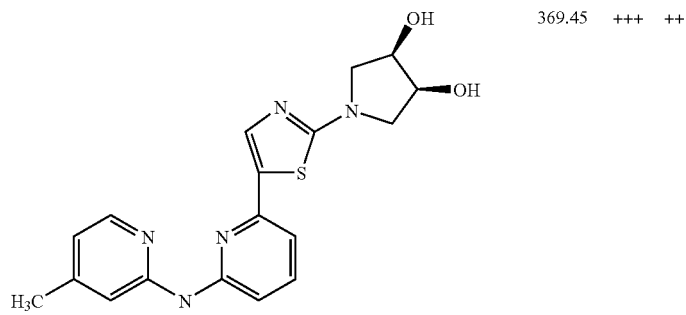 | 369.45 | +++ | ++ |
TABLE 1-85
| A-424 | 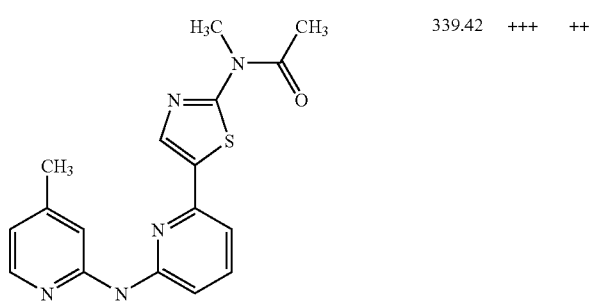 | 339.42 | +++ | ++ |
| A-425 | 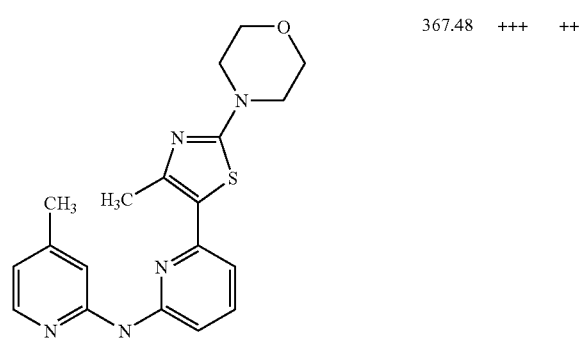 | 367.48 | +++ | ++ |
| A-426 | 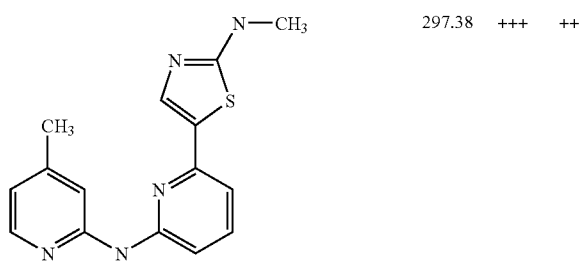 | 297.38 | +++ | ++ |

TABLE 1-85-continued
A-427    409.52   +++   +++
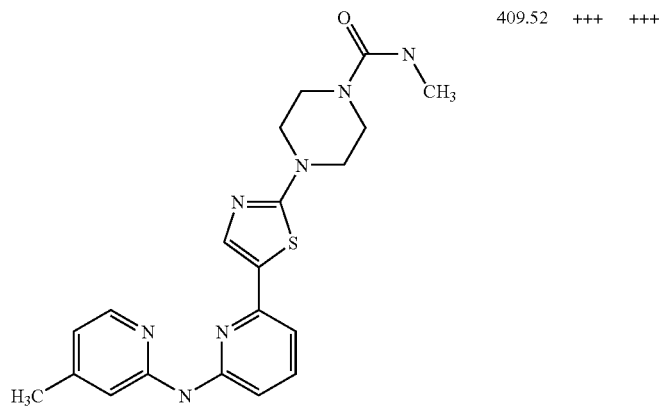
A-428    424.53
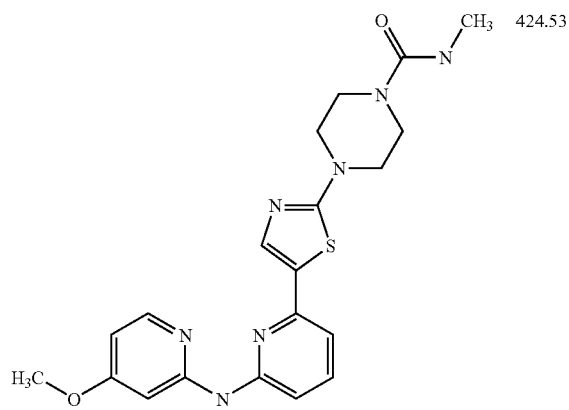
TABLE 1-86
A-429    408.53   +++   +
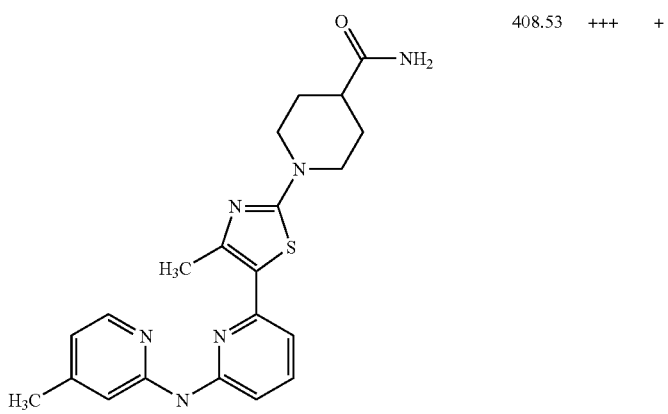

TABLE 1-86-continued
| A-430 | 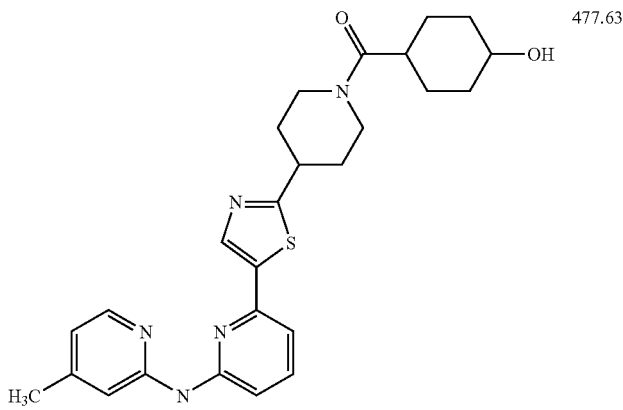 | 477.63 | | |
| A-431 | 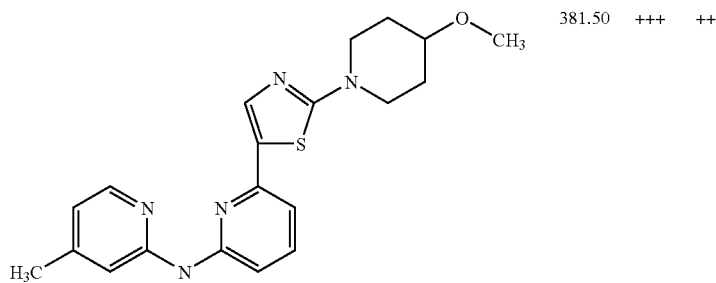 | 381.50 | +++ | ++ |
| A-432 | 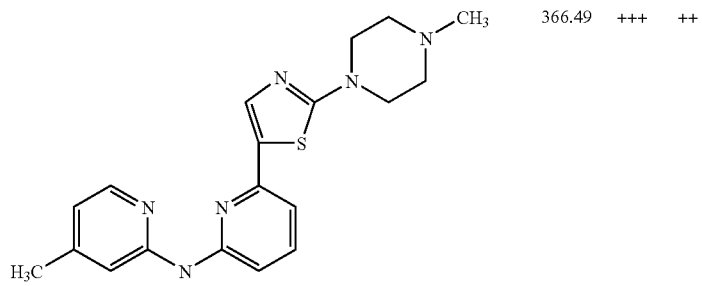 | 366.49 | +++ | ++ |
| A-433 | 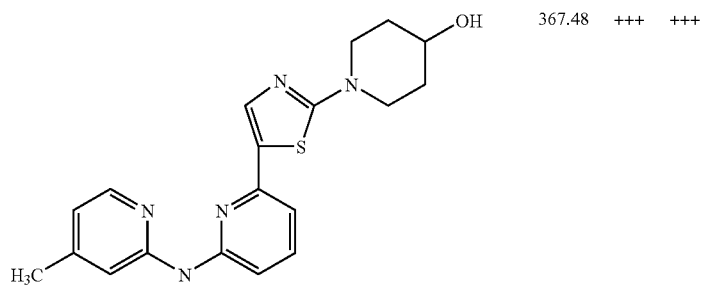 | 367.48 | +++ | +++ |

TABLE 1-87
A-434 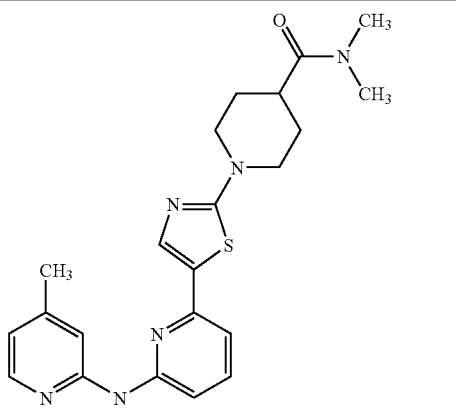 422.55 ++ +
A-435 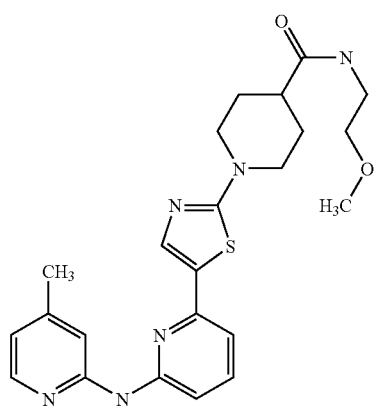 452.58 ++ +
A-436 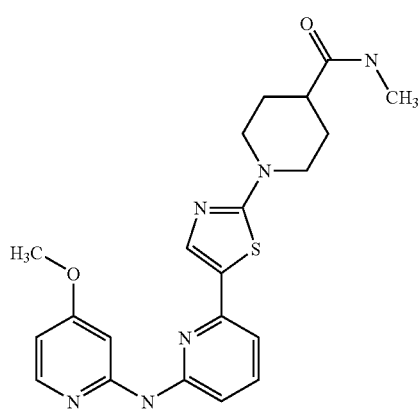 424.53 +++ ++
A-437 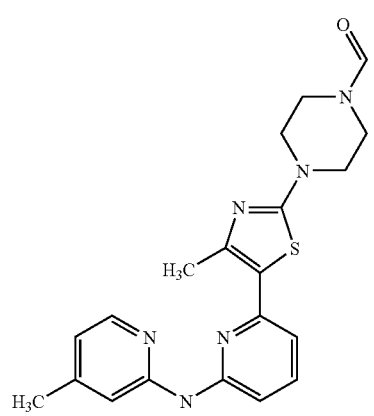 394.50 +++ ++

TABLE 1-87-continued
A-438 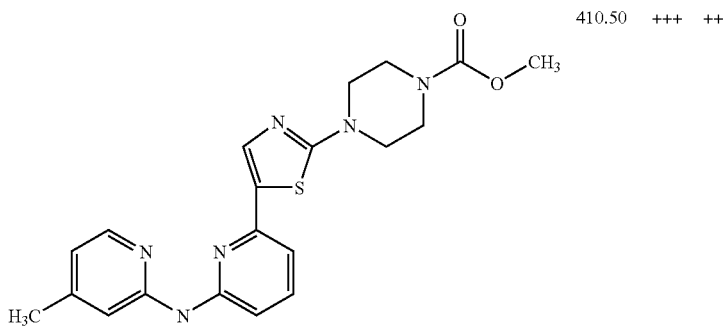 410.50 +++ ++
TABLE 1-88
A-439  410.50 +++ +++
A-440  408.53 +++ ++

TABLE 1-88-continued

| | | | | |
|---|---|---|---|---|
| A-441 | [structure] | 423.54 | +++ | ++ |
| A-442 | [structure] | 410.50 | +++ | ++ |
| A-443 | [structure] | 414.92 | +++ | ++ |

TABLE 1-89

| | | | | |
|---|---|---|---|---|
| A-444 | [structure] | | +++ | ++ |

TABLE 1-89-continued
A-445 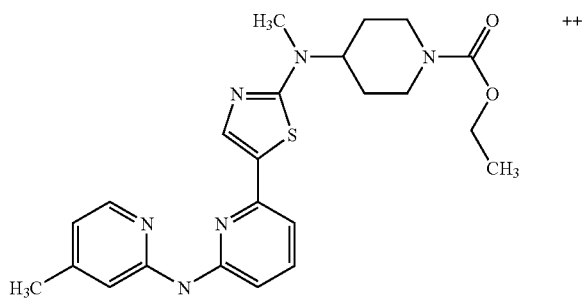 ++
A-446 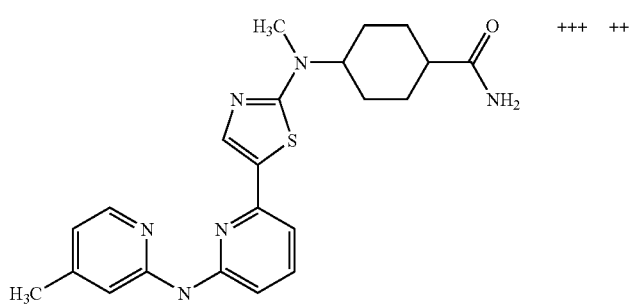 +++ ++
A-447 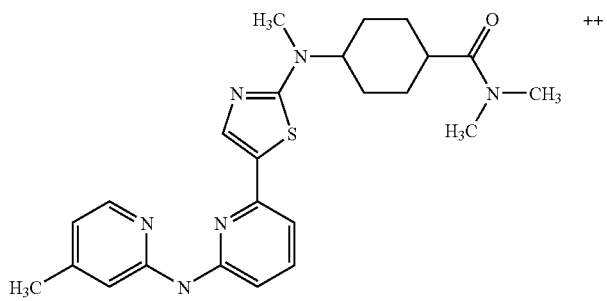 ++
A-448 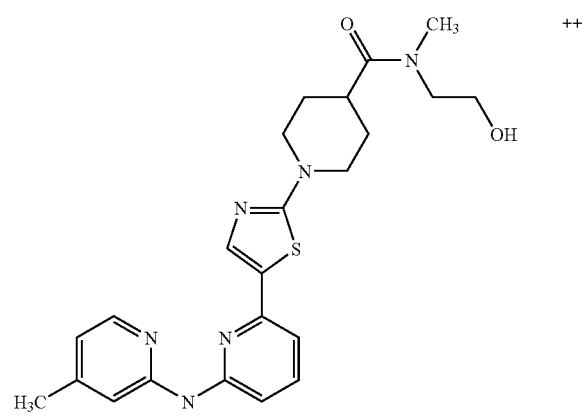 ++

TABLE 1-90
A-449 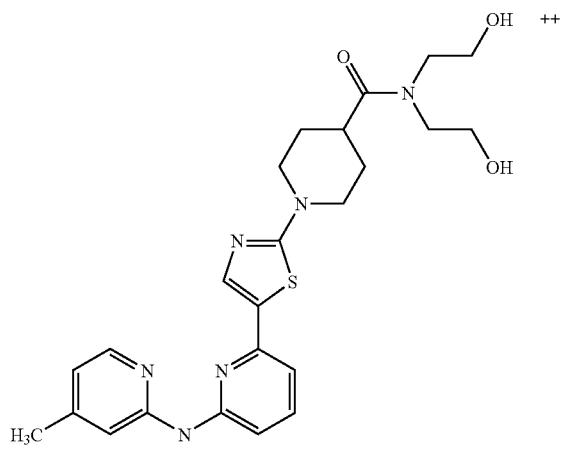 ++
A-450 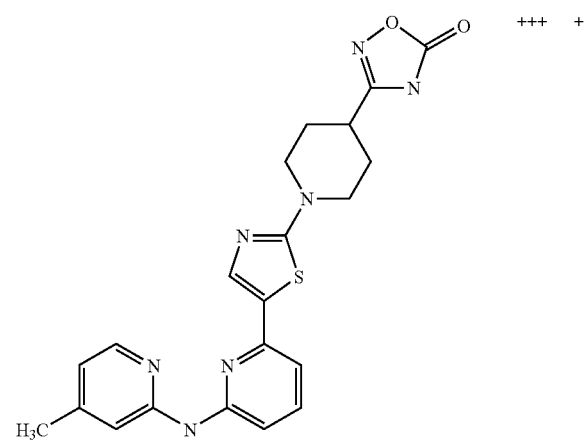 +++ +
A-451 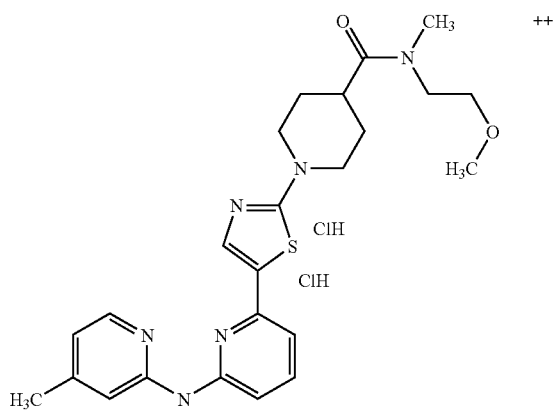 ++
A-452 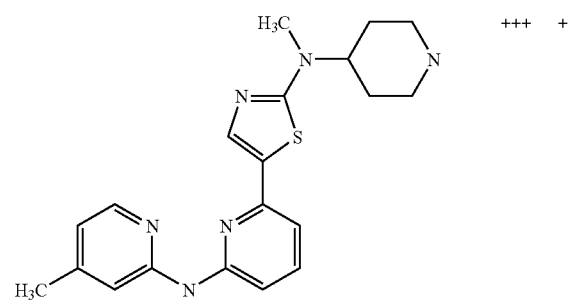 +++ +

TABLE 1-91
A-453 +++
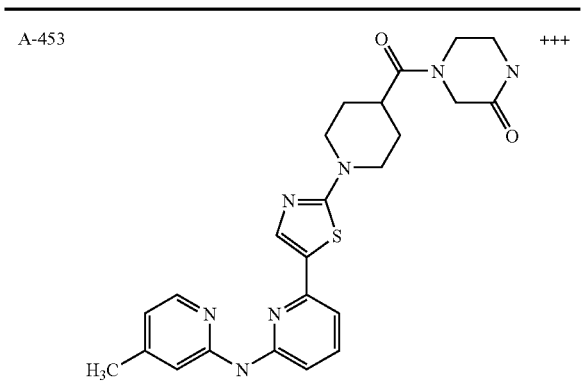
A-454 ++
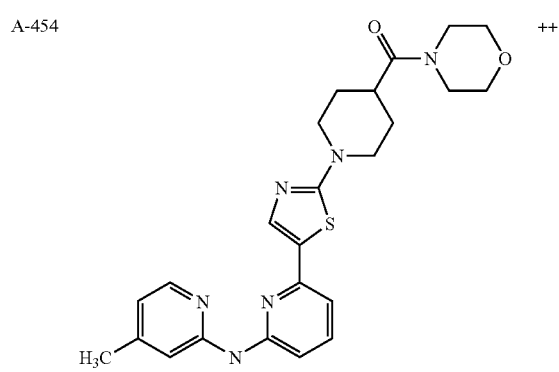
TABLE 1-91-continued
A-455 ++
A-456 ++
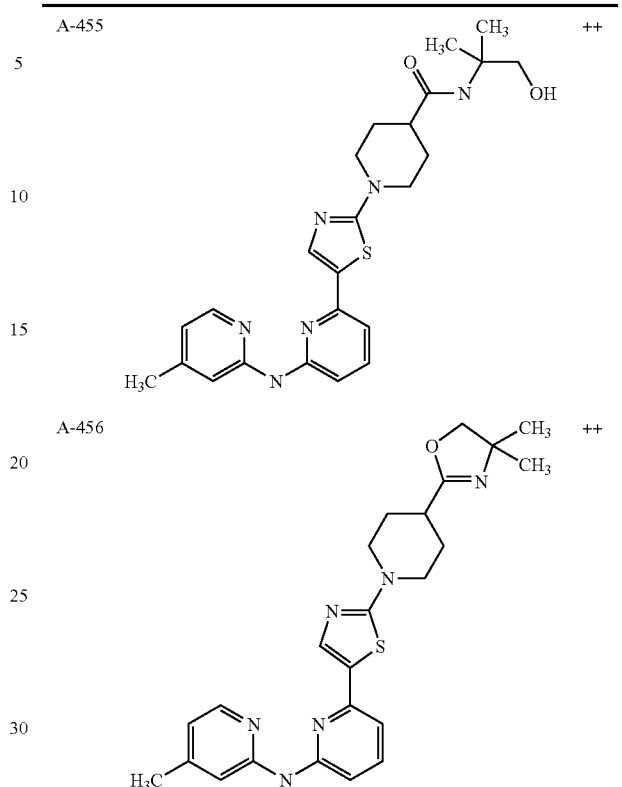
TABLE 1-92
A-457 +++ ++
A-458 +++ ++
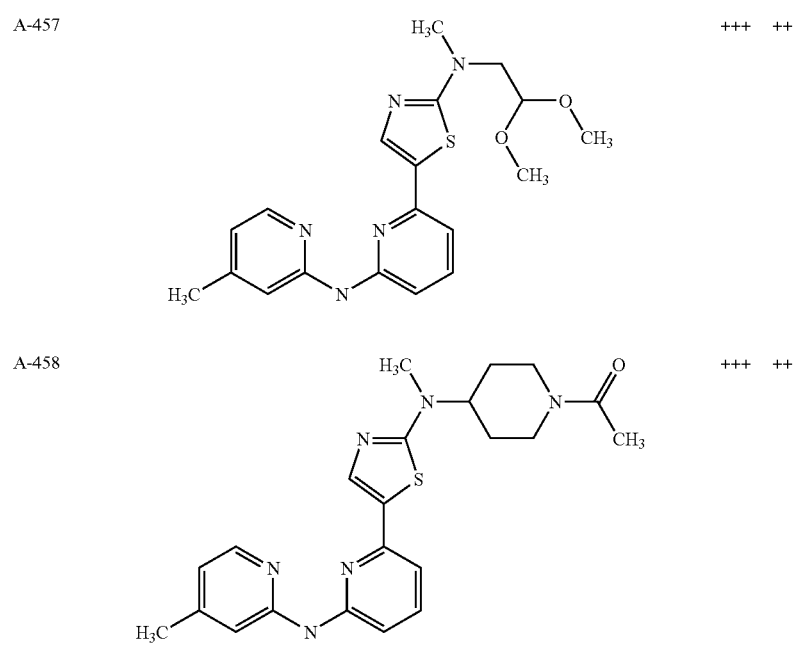

TABLE 1-92-continued
A-459  +++ ++
A-460 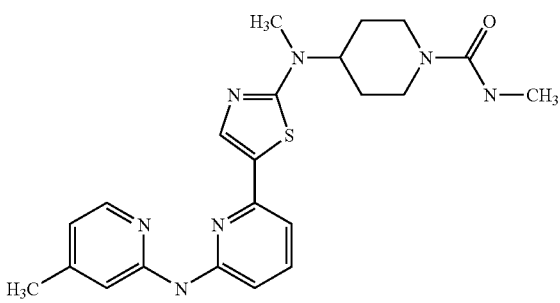 +++ ++
A-461 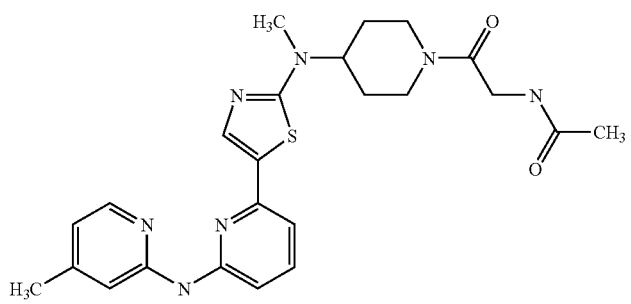 +++ ++
A-462 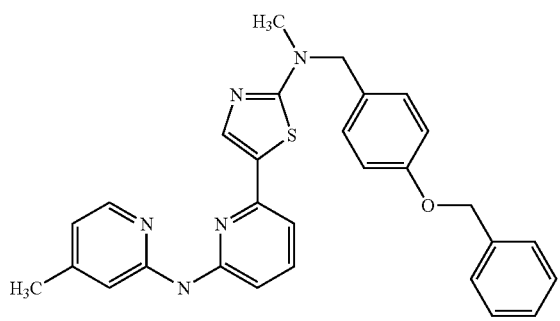 ++

TABLE 1-93
A-463 ++
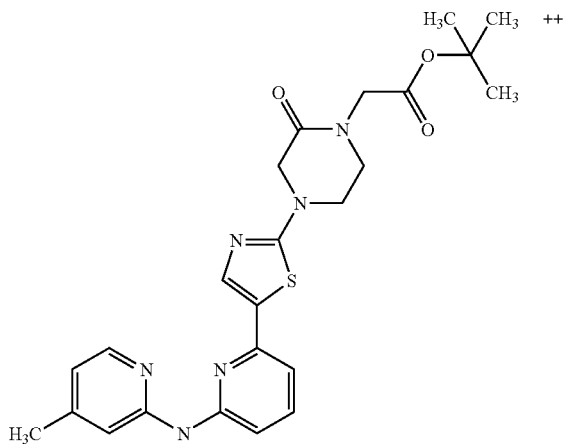
A-464 +++ +
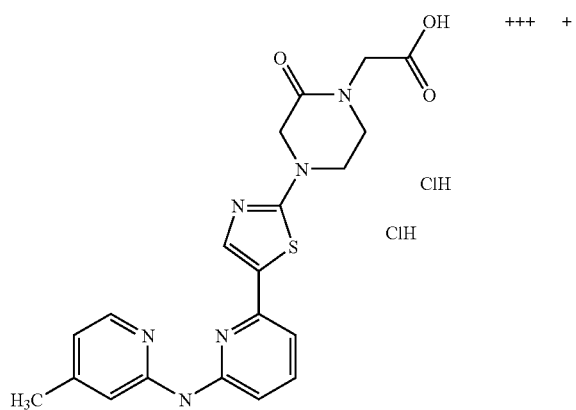
A-465 +++ ++
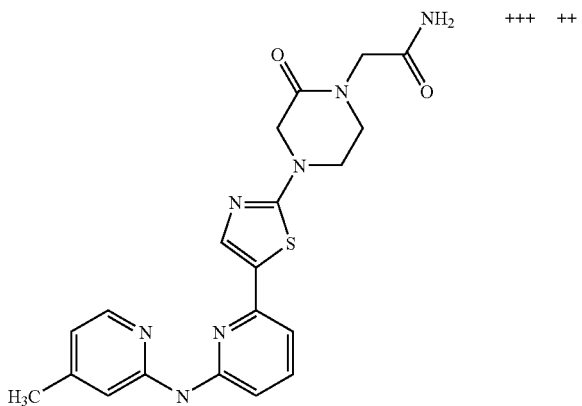

TABLE 1-93-continued
A-466 +++ +
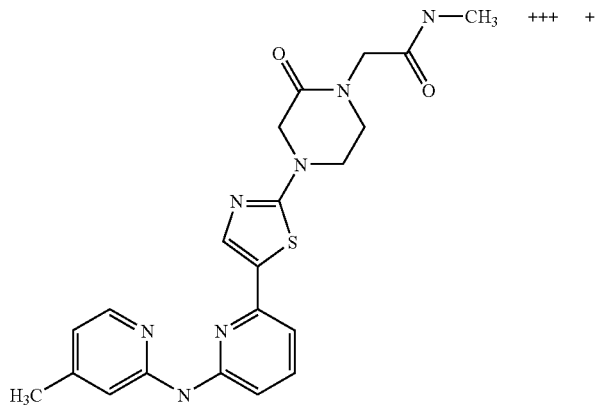
TABLE 1-94
A-467 ++
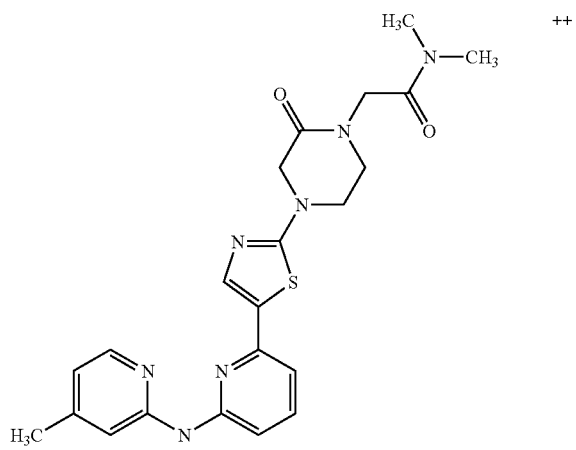
A-468 +++
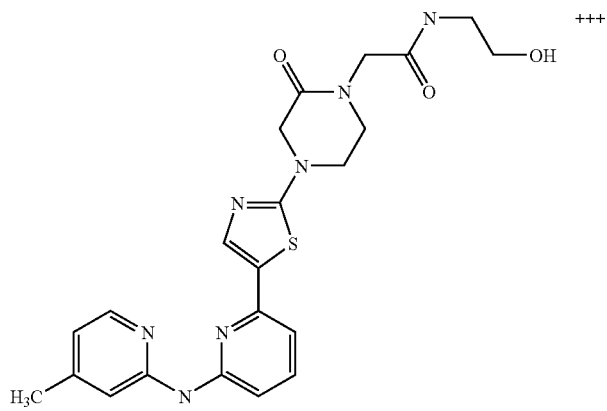

TABLE 1-94-continued
A-469 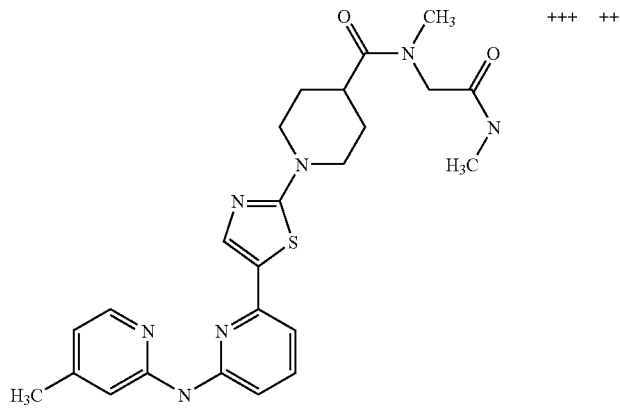 +++ ++
A-470 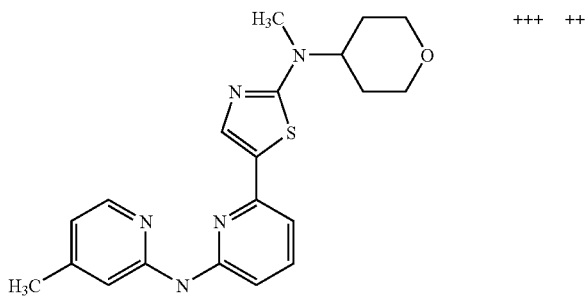 +++ ++
A-471 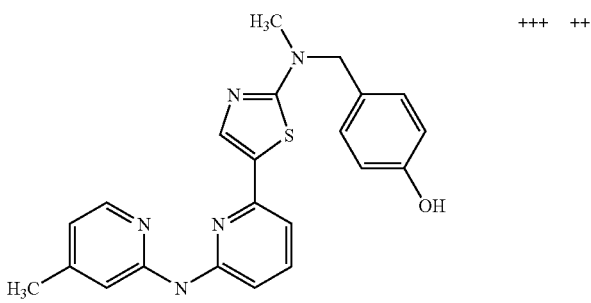 +++ ++
TABLE 1-95
A-472 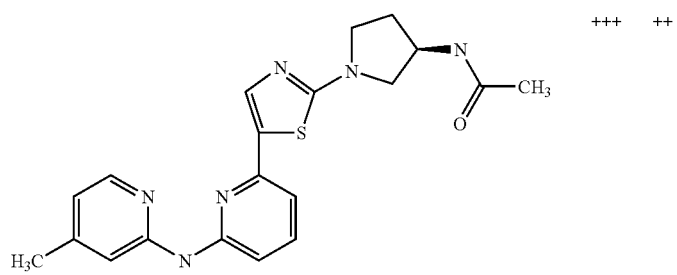 +++ ++

TABLE 1-95-continued
A-473 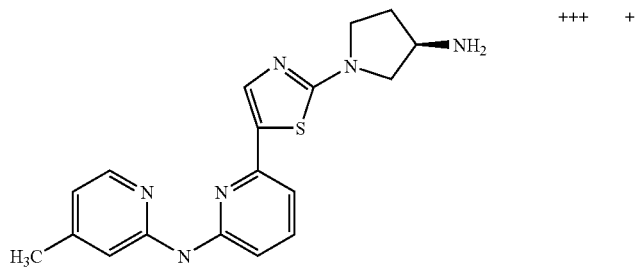 +++ +
A-474 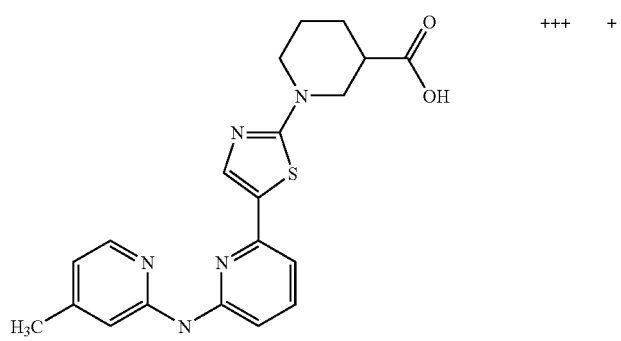 +++ +
A-475 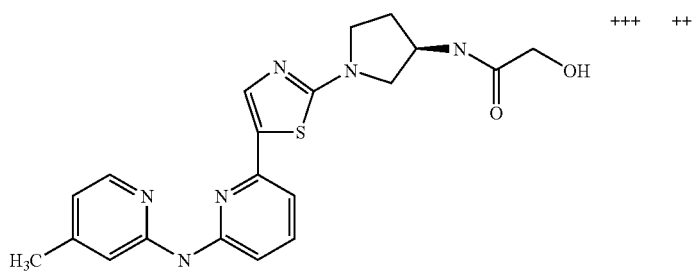 +++ ++
A-476 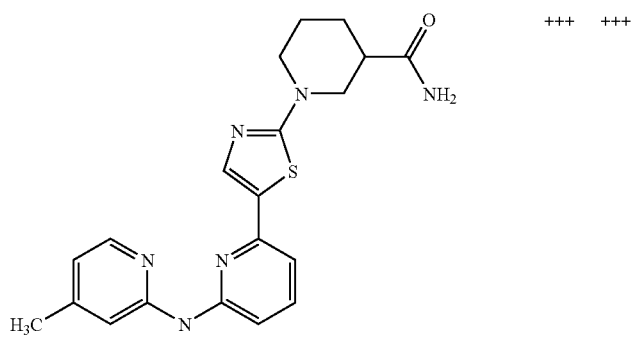 +++ +++

TABLE 1-96
A-477 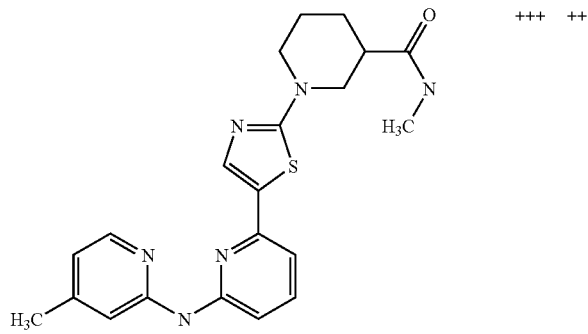 +++ ++
A-478 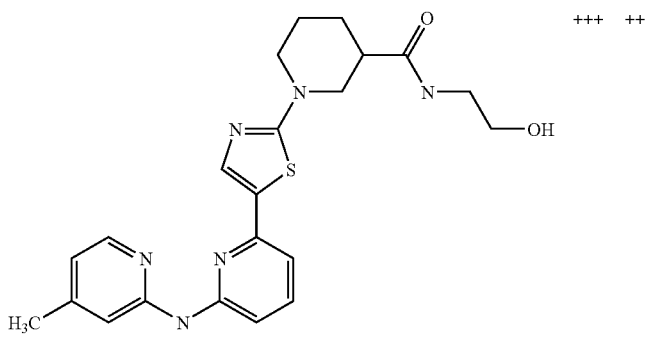 +++ ++
A-479 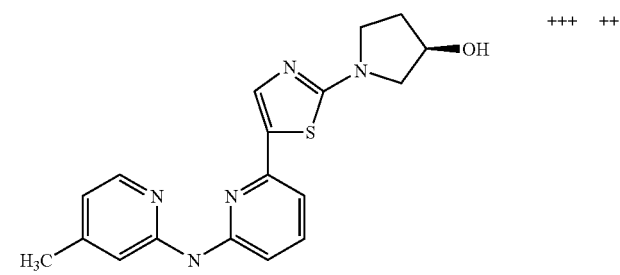 +++ ++
A-480 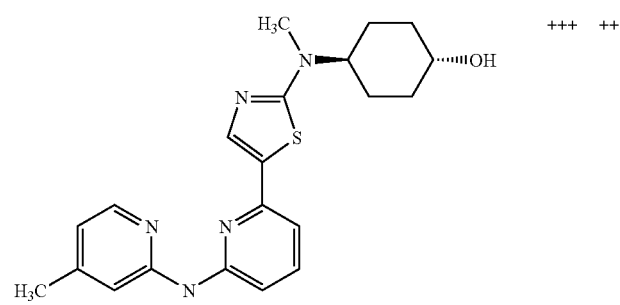 +++ ++
A-481 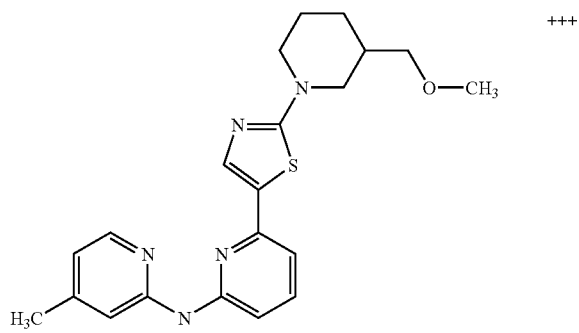 +++

TABLE 1-97
A-482 +++ ++
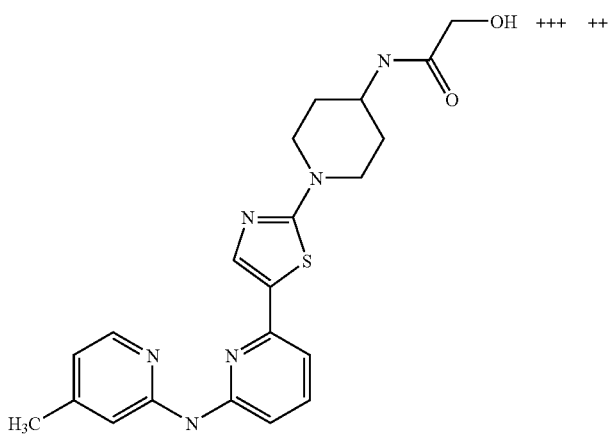
A-483 +++ ++
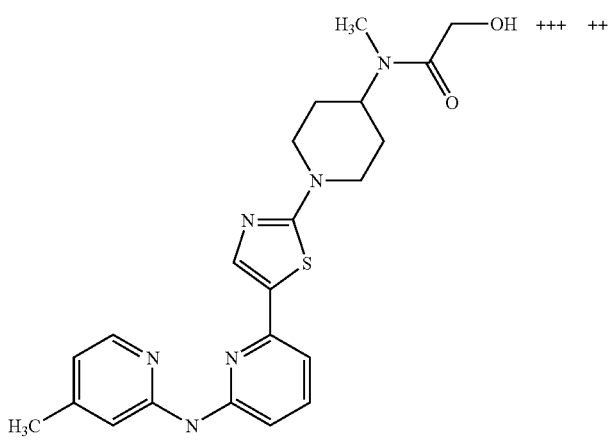
A-484 +++
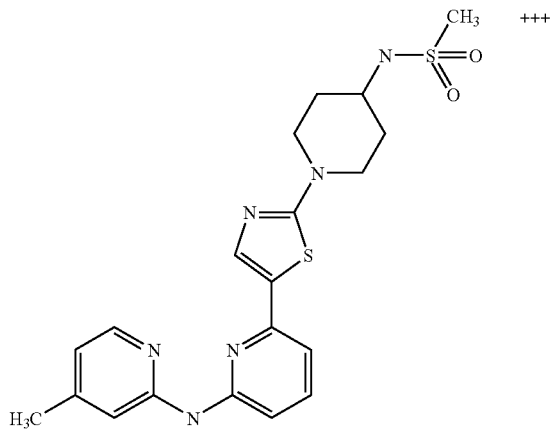

TABLE 1-97-continued
A-485 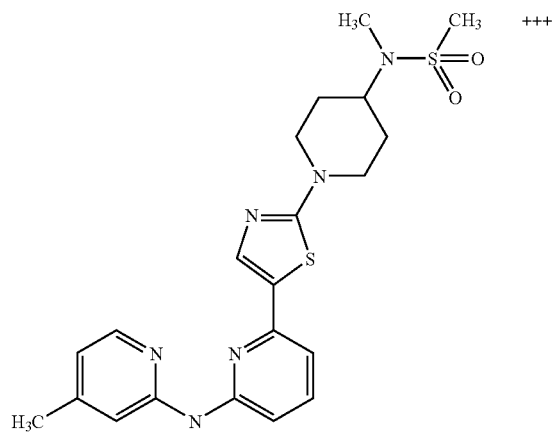 +++
TABLE 1-98
A-486 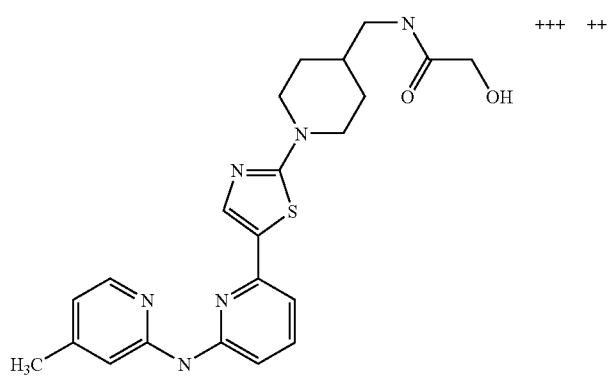 +++ ++
A-487 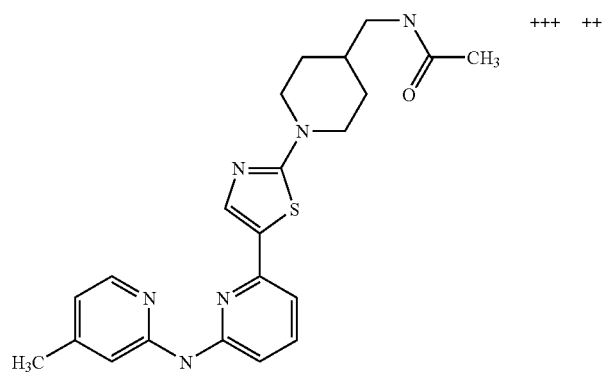 +++ ++
A-488 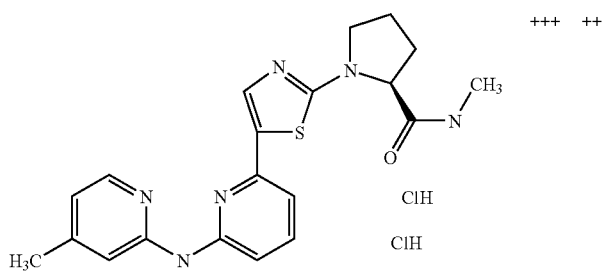 +++ ++

TABLE 1-98-continued
A-489 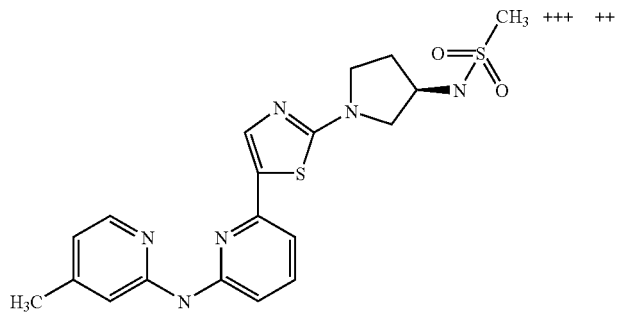 +++ ++
A-490 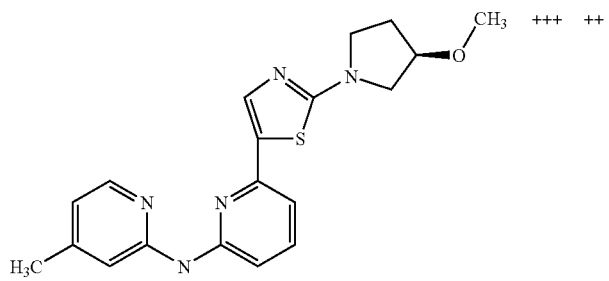 +++ ++
TABLE 1-99
A-491 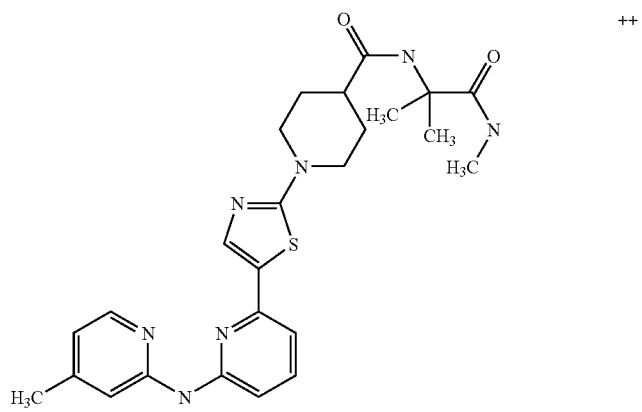 ++
A-492 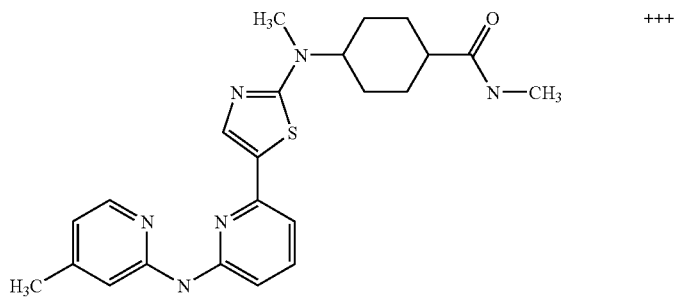 +++

TABLE 1-99-continued
| A-493 |  | +++ |
| A-494 | 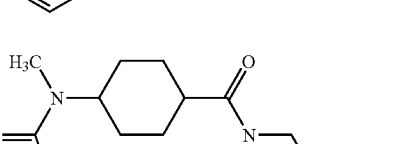 | +++ |
| A-495 |  | ++ |
TABLE 1-100
| A-496 | 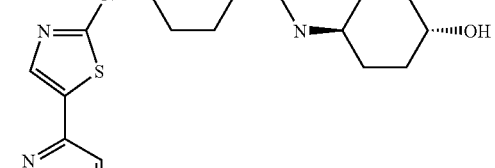 | ++ |
| A-497 | 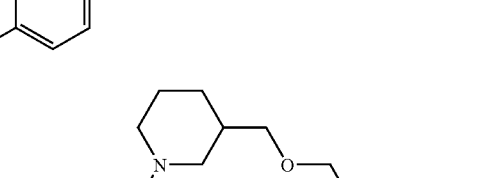 | +++ + |

TABLE 1-100-continued
A-498 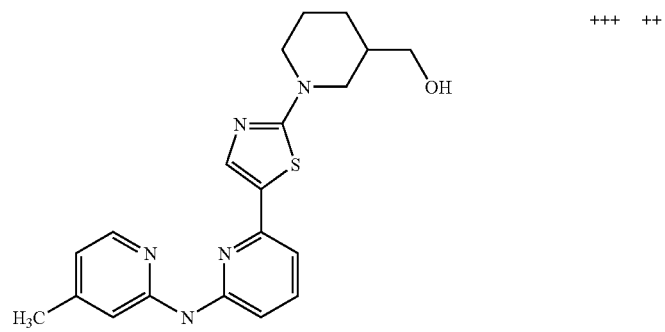 +++ ++
A-499 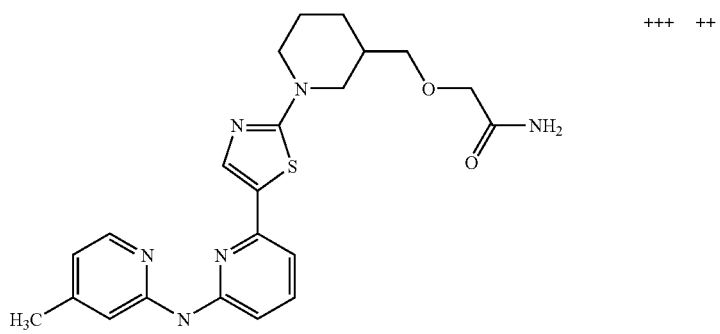 +++ ++
A-500 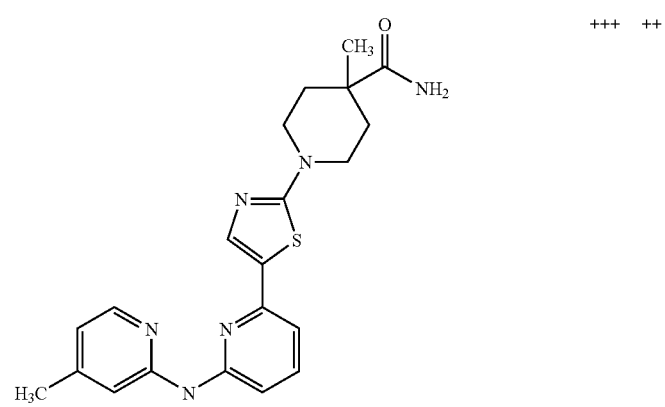 +++ ++
TABLE 1-101
A-501 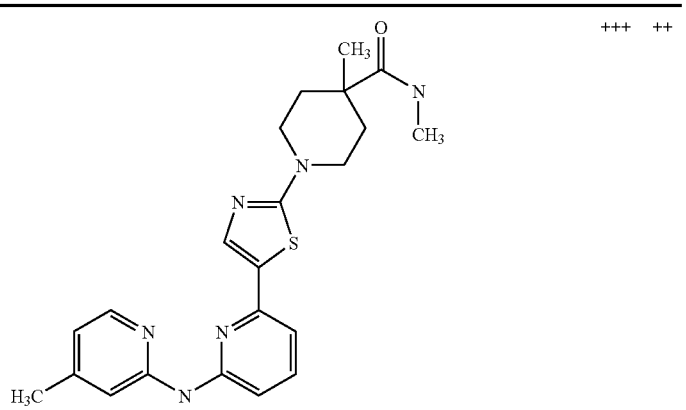 +++ ++

TABLE 1-101-continued
A-502 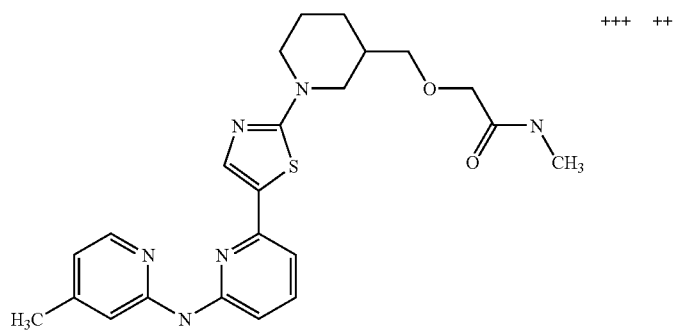 +++ ++
A-503 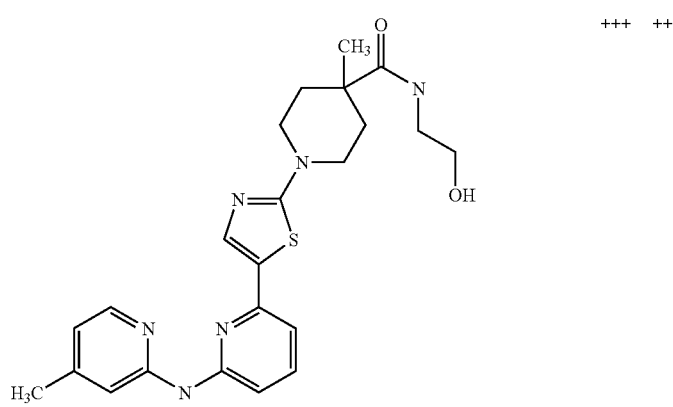 +++ ++
A-504 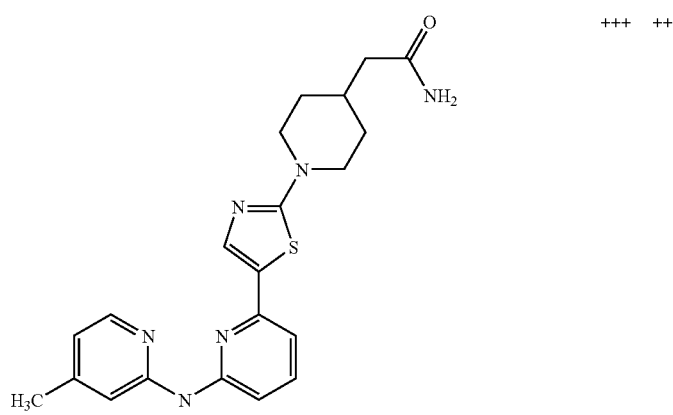 +++ ++

TABLE 1-102
| | | | |
|---|---|---|---|
| A-505 | 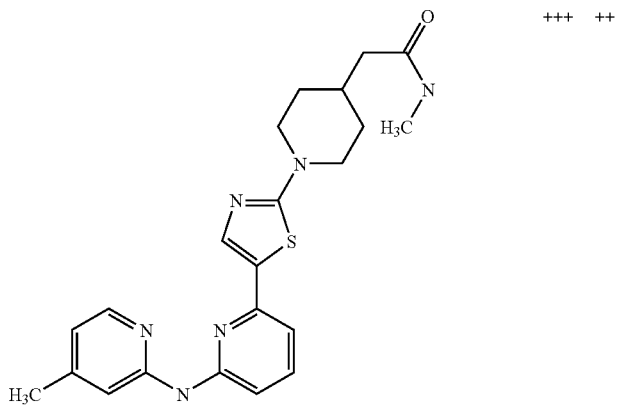 | +++ | ++ |
| A-506 | 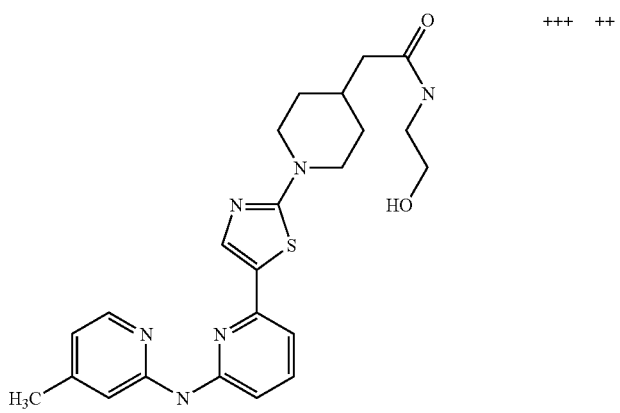 | +++ | ++ |
| A-507 | 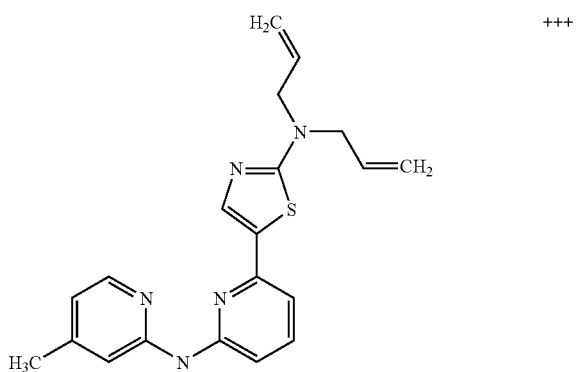 | +++ | |
| A-508 | 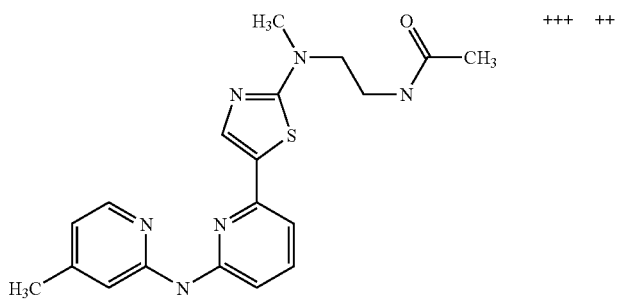 | +++ | ++ |

TABLE 1-103
| | | | |
|---|---|---|---|
| A-509 | 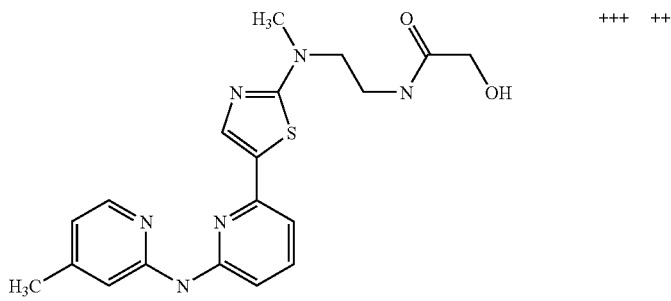 | +++ | ++ |
| A-510 | 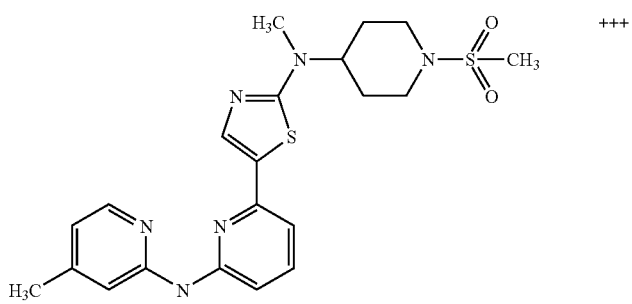 | +++ | |
| A-511 | 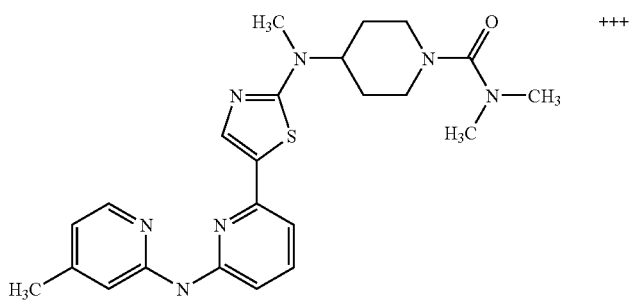 | +++ | |
| A-512 | 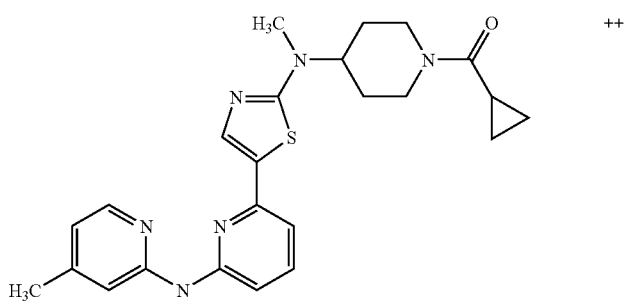 | ++ | |
| A-513 | 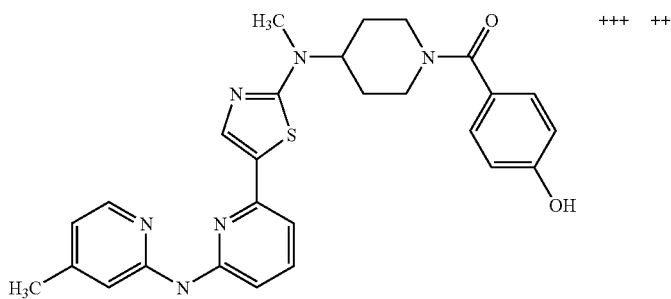 | +++ | ++ |

TABLE 1-104
A-514 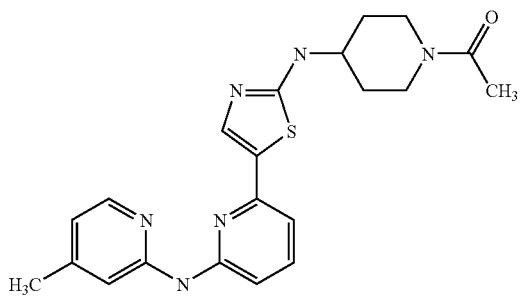 +++ ++
A-515 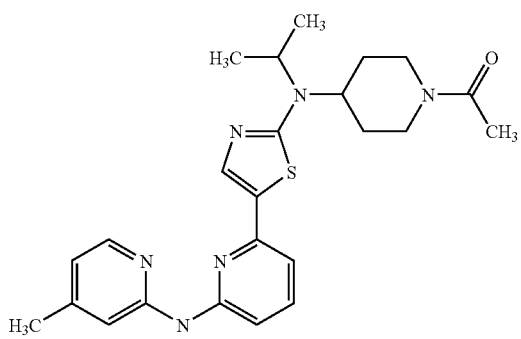 +++ +
A-516 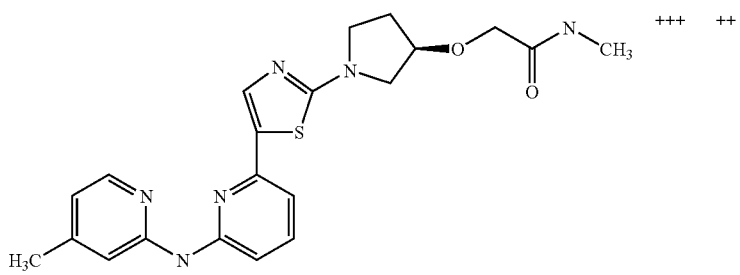 +++ ++
A-517 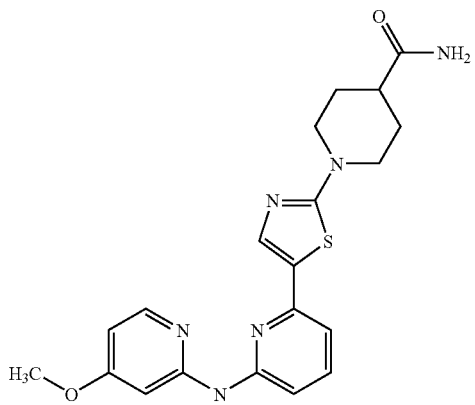 +++ ++

TABLE 1-104-continued
A-518 +++ +++
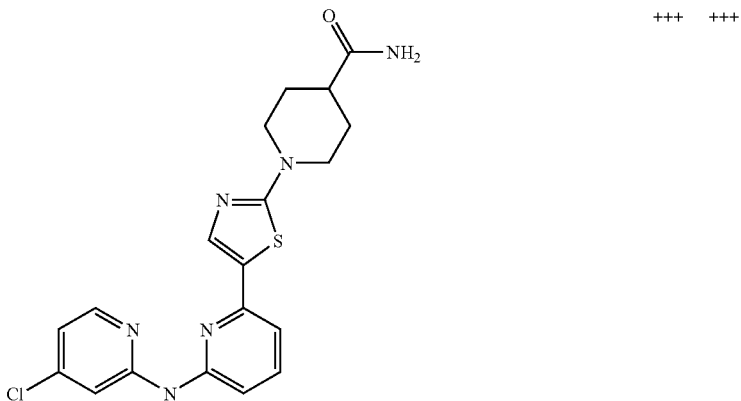
TABLE 1-105
A-519 +++ +++
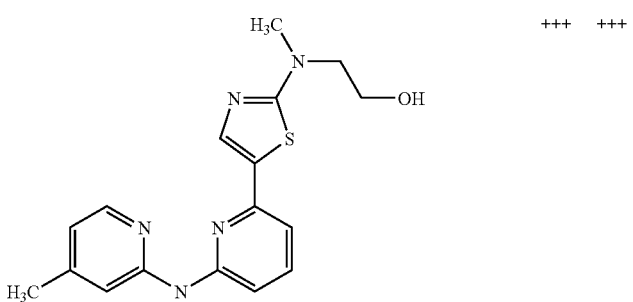
A-520 +++ ++
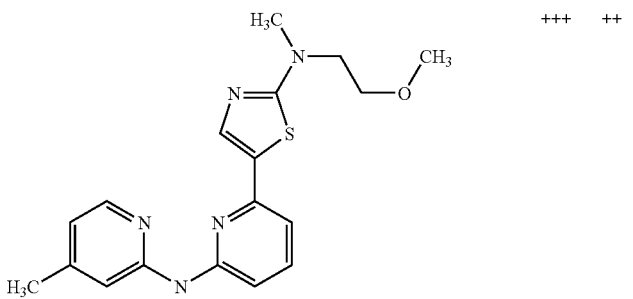
A-521 ++
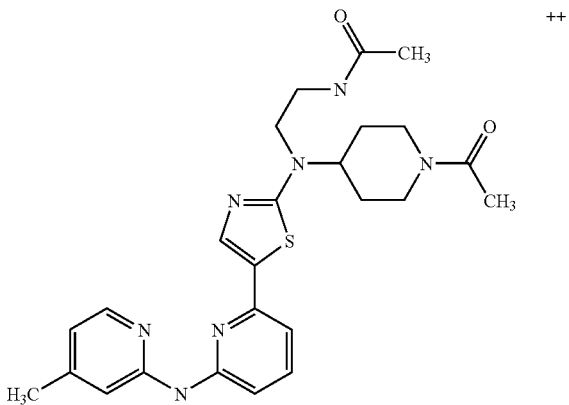

TABLE 1-105-continued
A-522 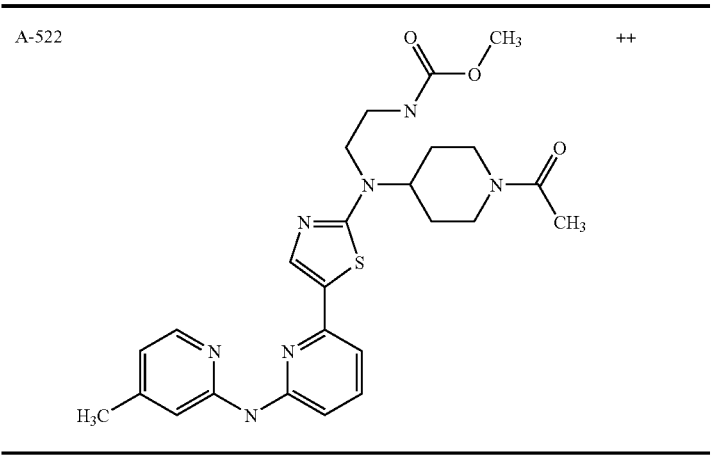 ++
TABLE 1-106
A-523 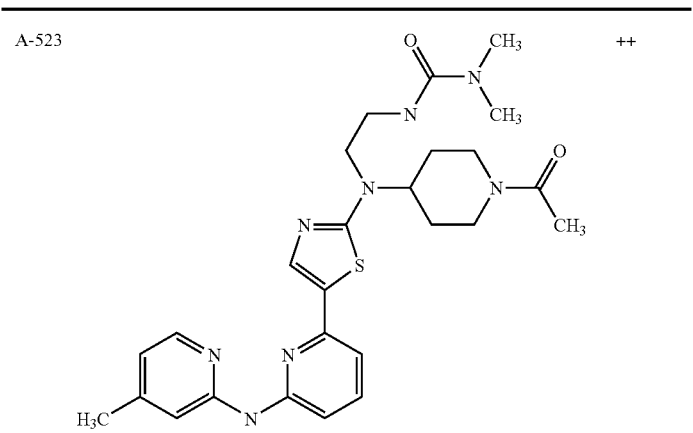 ++
A-524 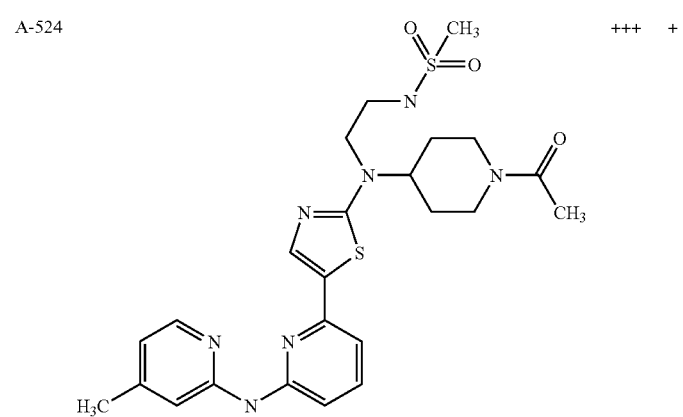 +++ +

TABLE 1-106-continued

| | | | |
|---|---|---|---|
| A-525 | [structure] | +++ | ++ |
| A-526 | [structure] | +++ | ++ |
| A-527 | [structure] | ++ | |

TABLE 1-107

| | | | |
|---|---|---|---|
| A-528 | [structure] | +++ | +++ |
| A-529 | [structure] | +++ | ++ |

TABLE 1-107-continued
A-530 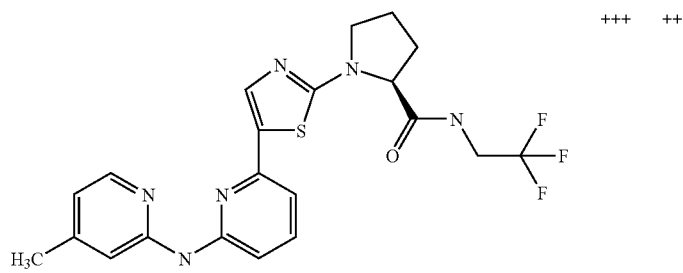 +++ ++
A-531 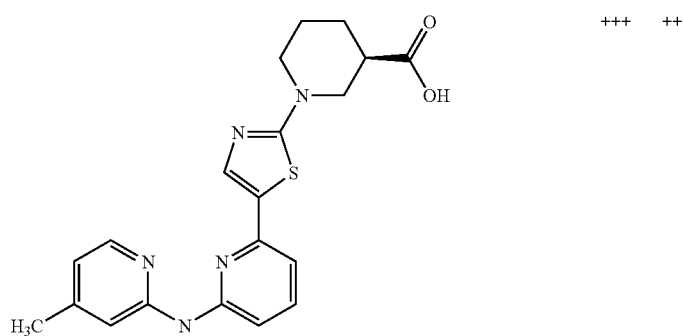 +++ ++
A-532 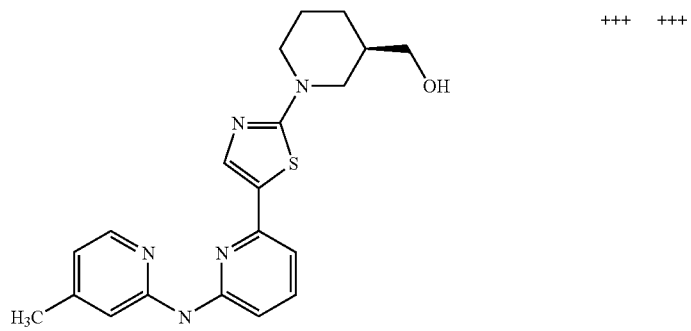 +++ +++
TABLE 1-108
A-533 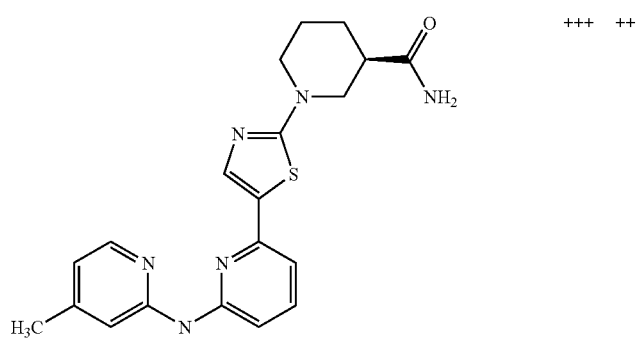 +++ ++

TABLE 1-108-continued
A-534 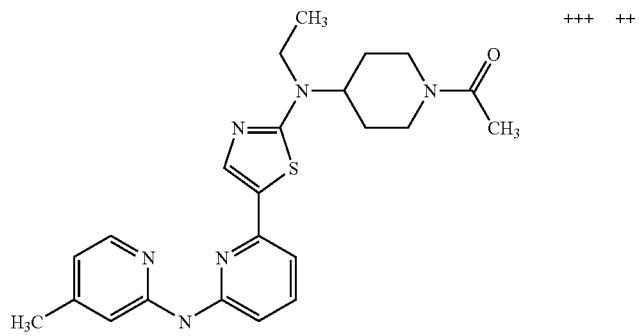 +++ ++
A-535 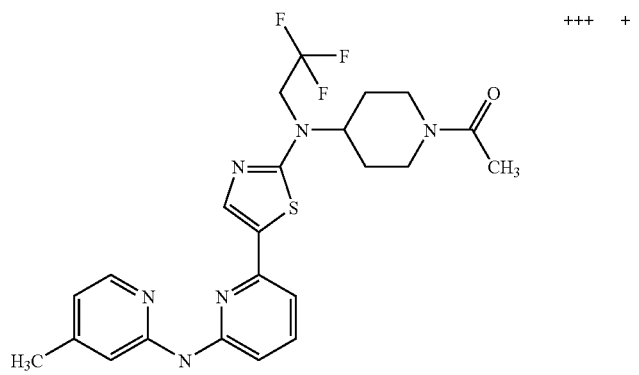 +++ +
A-536 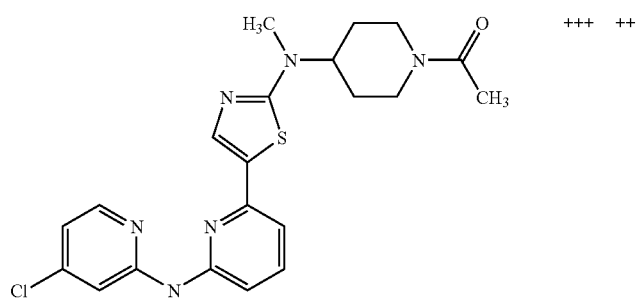 +++ ++
A-537 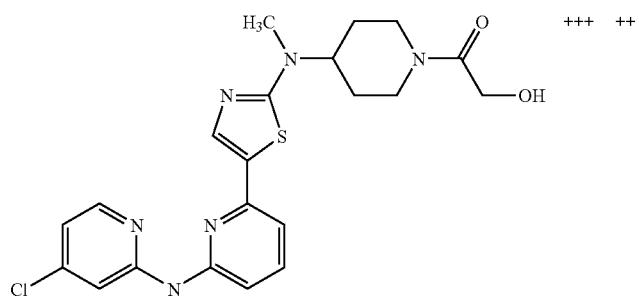 +++ ++

TABLE 1-109

| | | | |
|---|---|---|---|
| A-538 | (structure) | +++ | ++ |
| A-539 | (structure) | +++ | +++ |
| A-540 | (structure) | +++ | ++ |
| A-541 | (structure) | +++ | ++ |
| A-542 | (structure) | +++ | +++ |

TABLE 1-110

| | | | |
|---|---|---|---|
| A-543 | (structure) | +++ | ++ |
| A-544 | (structure) | +++ | +++ |
| A-545 | (structure) | +++ | +++ |
| A-546 | (structure) | +++ | ++ |

TABLE 1-111
| A-547 | 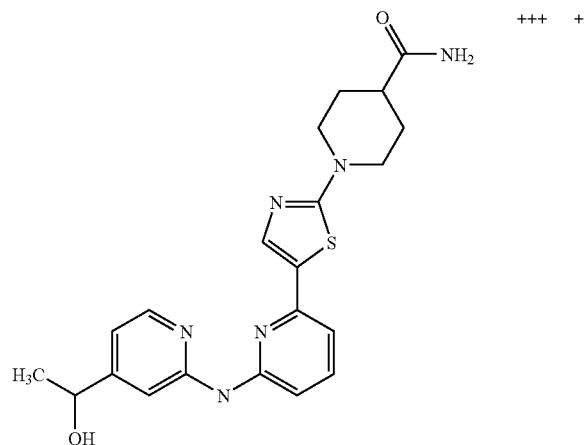 | +++ | + |
| A-548 | 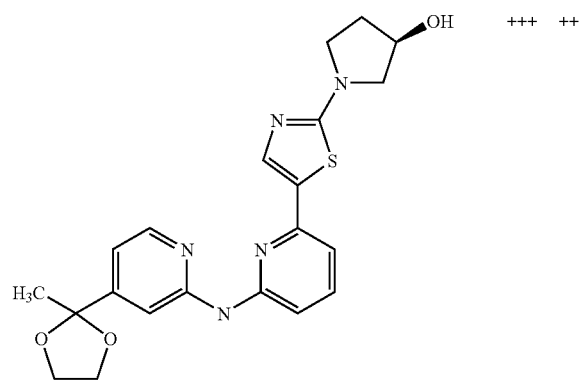 | +++ | ++ |
| A-549 | 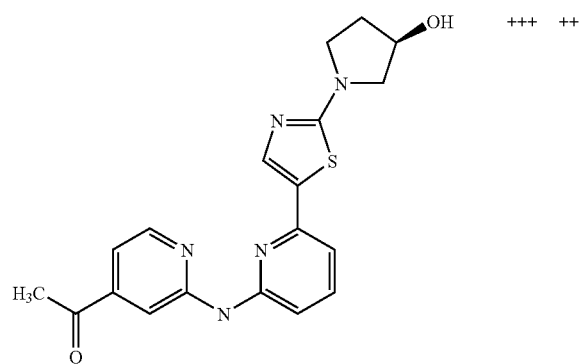 | +++ | ++ |
| A-550 | 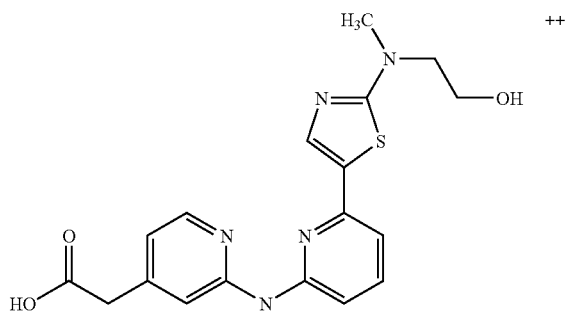 | ++ | |

TABLE 1-112
A-551 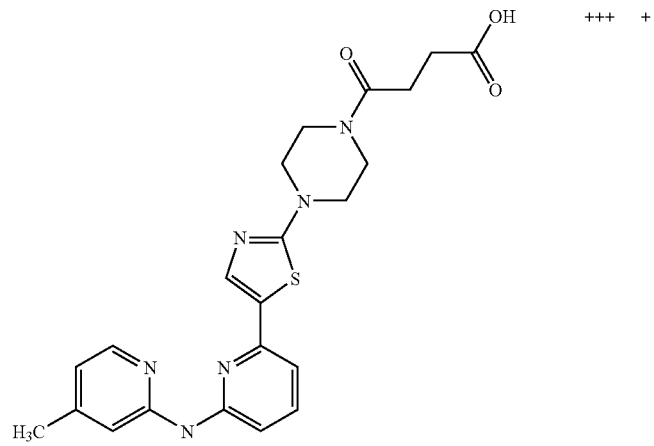 +++ +
A-552 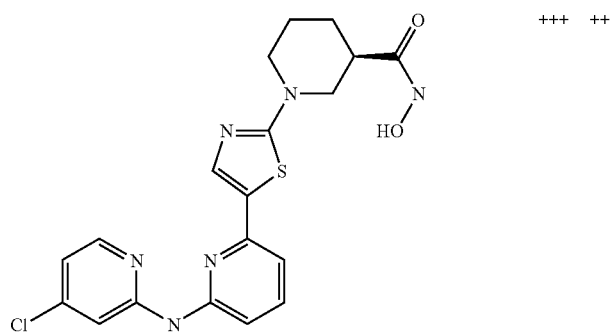 +++ ++
A-553 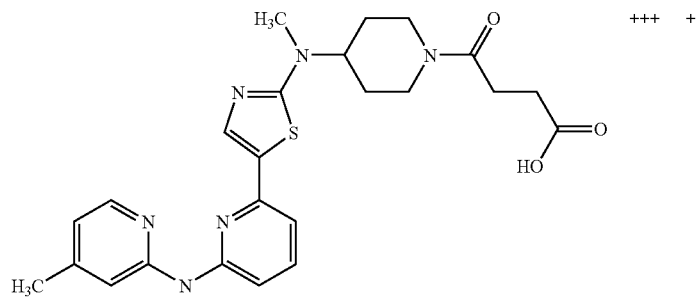 +++ +
A-554 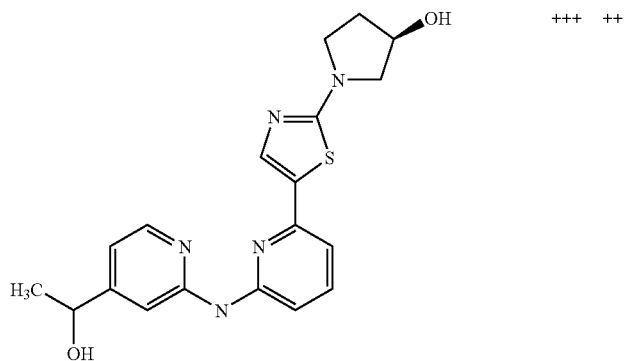 +++ ++

TABLE 1-112-continued
A-555 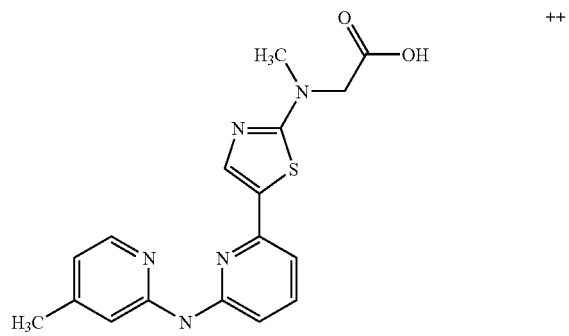 ++
TABLE 1-113
A-556 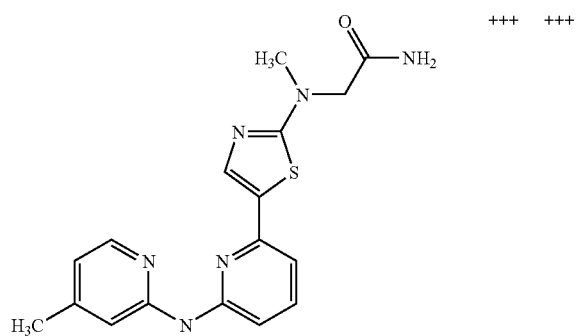 +++ +++
A-557 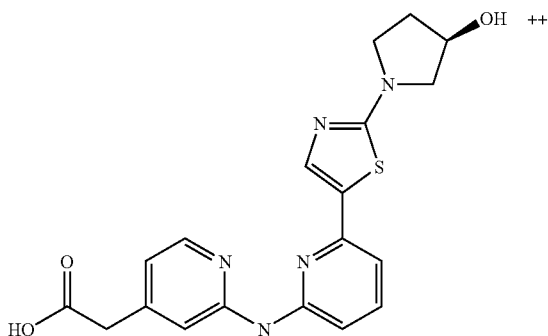 ++
A-558 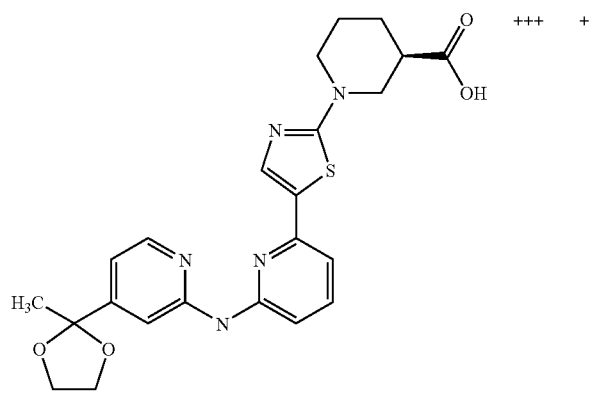 +++ +

TABLE 1-113-continued
A-559 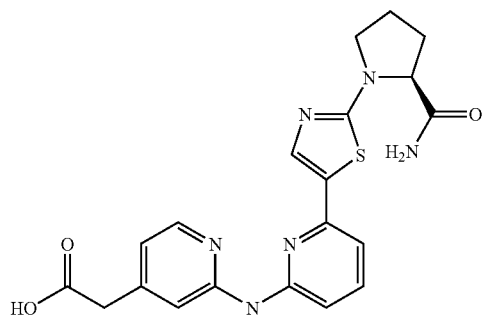 ++
A-560 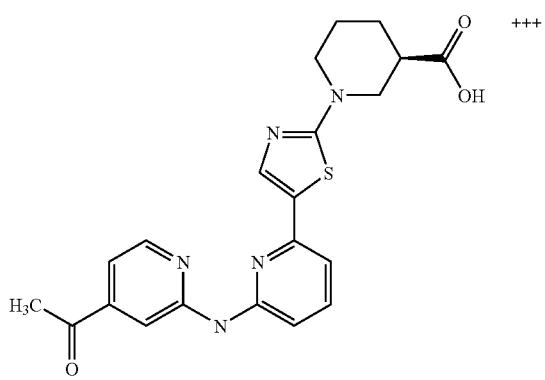 +++ ++
TABLE 1-114
A-561 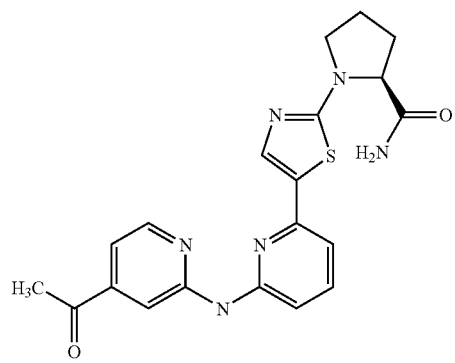 +++ ++
A-562 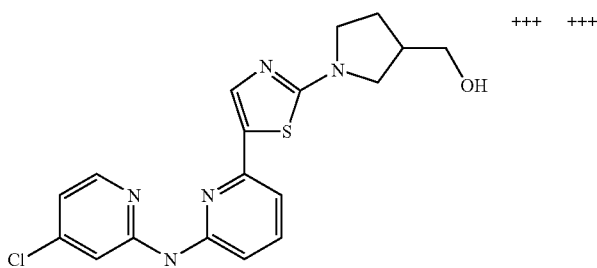 +++ +++

TABLE 1-114-continued

| | | | |
|---|---|---|---|
| A-563 | [structure] | +++ | ++ |
| A-564 | [structure] | +++ | + |
| A-565 | [structure] | +++ | ++ |

TABLE 1-115

| | | | |
|---|---|---|---|
| A-566 | [structure] | | ++ |

TABLE 1-115-continued
A-567 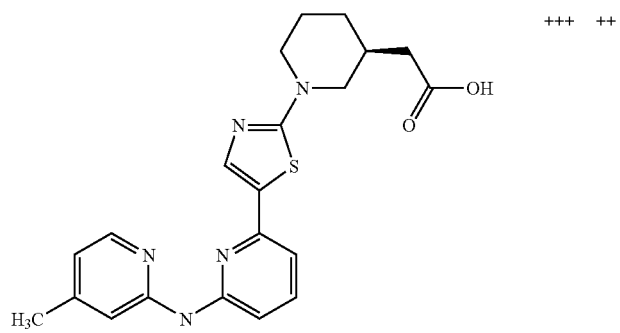 +++ ++
A-568 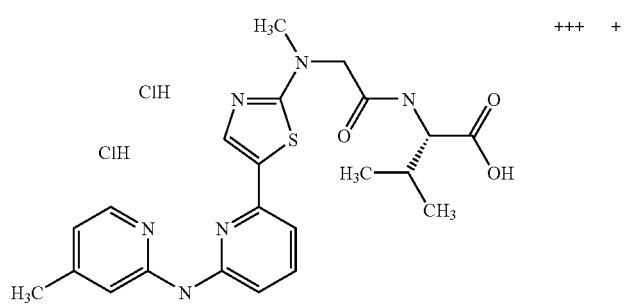 +++ +
A-569 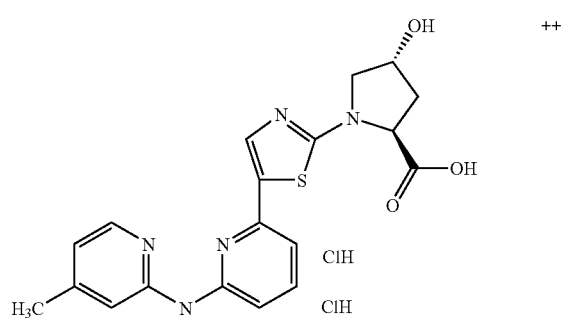 ++
A-570 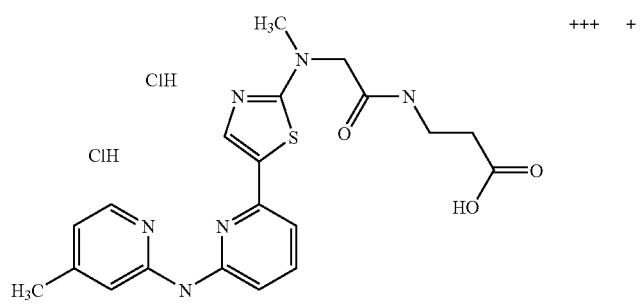 +++ +

TABLE 1-116

| | | | |
|---|---|---|---|
| A-571 | (structure) | +++ | + |
| A-572 | (structure) | +++ | ++ |
| A-573 | (structure) | +++ | + |
| A-574 | (structure) | +++ | ++ |

TABLE 1-116-continued
| A-575 | 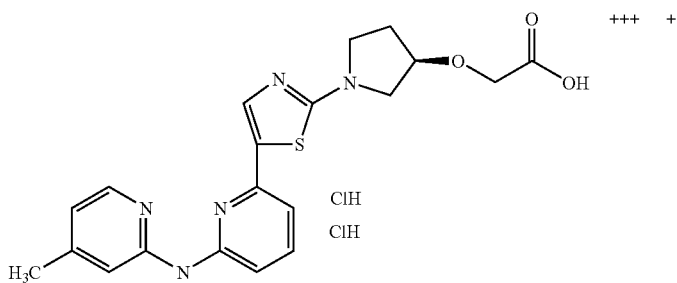 | +++ | + |
TABLE 1-117
| A-576 | 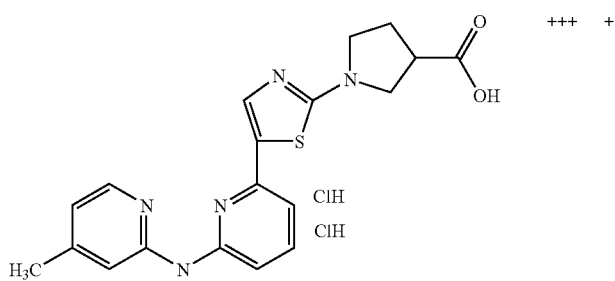 | +++ | + |
| A-577 | 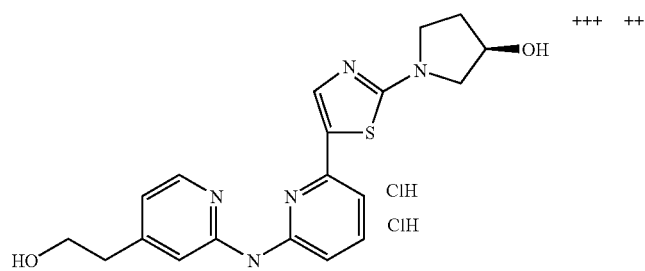 | +++ | ++ |
| A-578 | 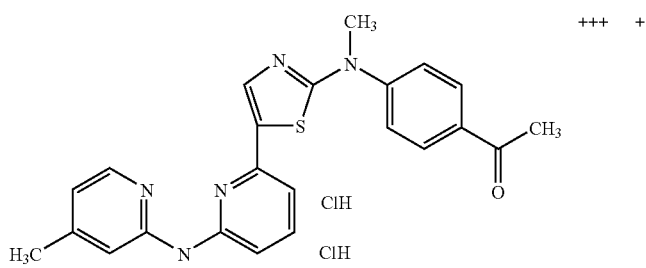 | +++ | + |
| A-579 | 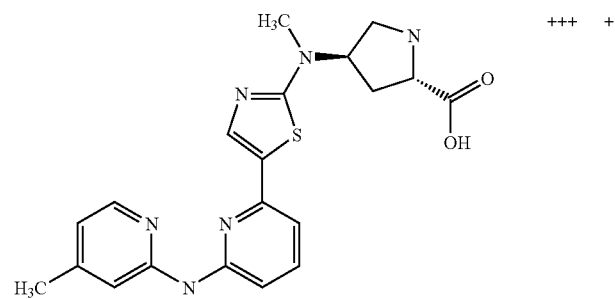 | +++ | + |

TABLE 1-117-continued
A-580 +++ +
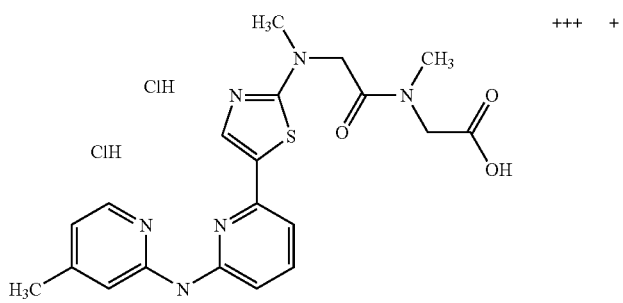
A-581 ++
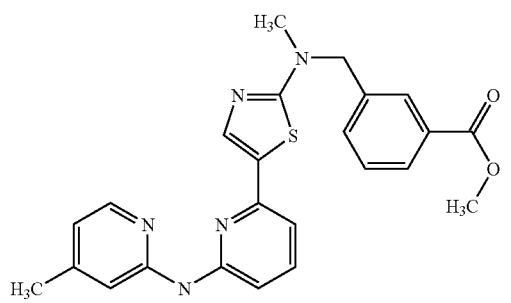
TABLE 1-118
A-582 +++ +
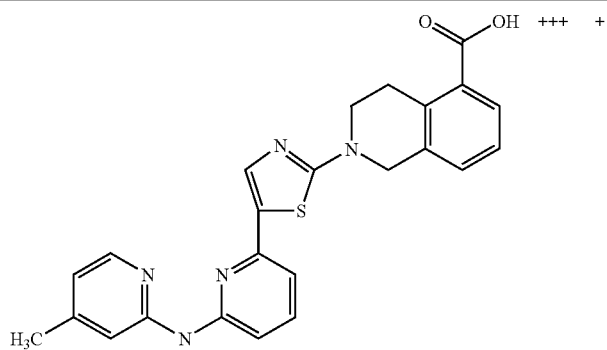
A-583 ++
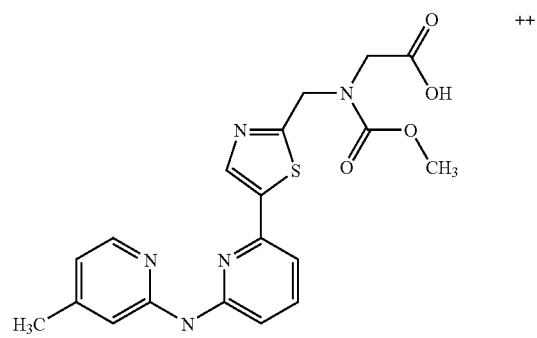

TABLE 1-118-continued
A-584 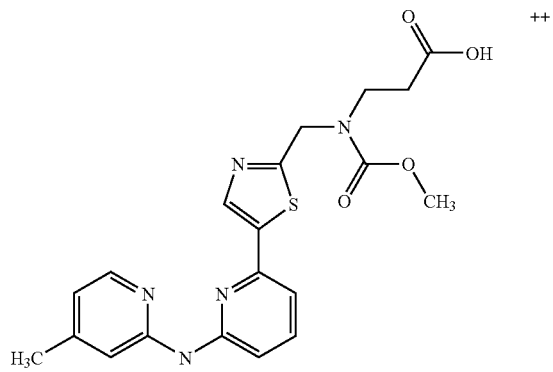 ++
A-585 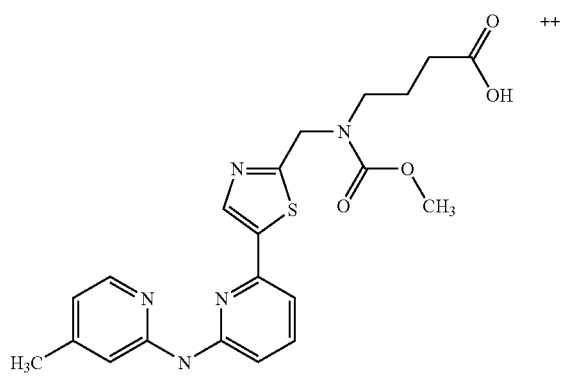 ++
A-586 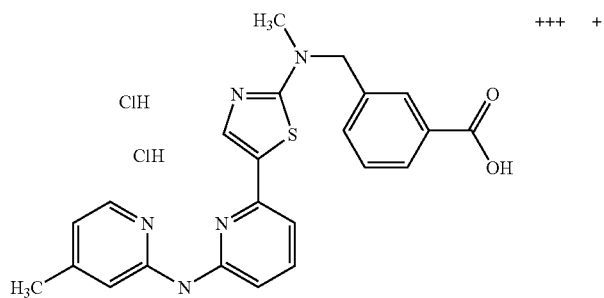 +++ +
TABLE 1-119
A-587 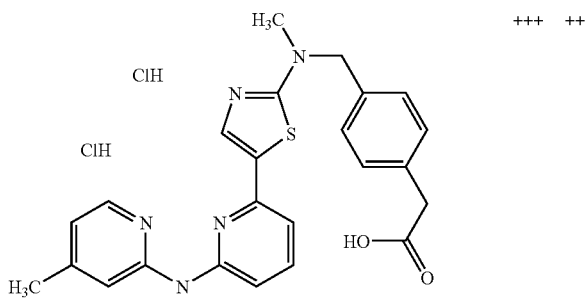 +++ ++

TABLE 1-119-continued
| A-588 | 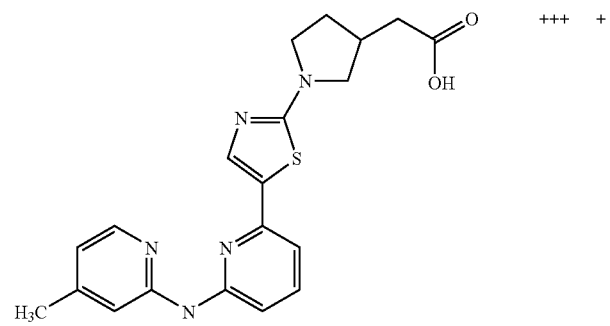 | +++ | + |
| A-589 | 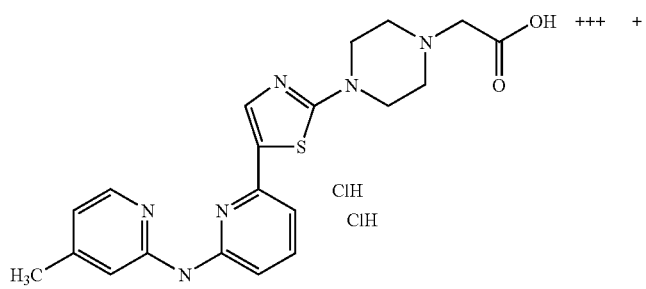 ClH ClH | +++ | + |
| A-590 | 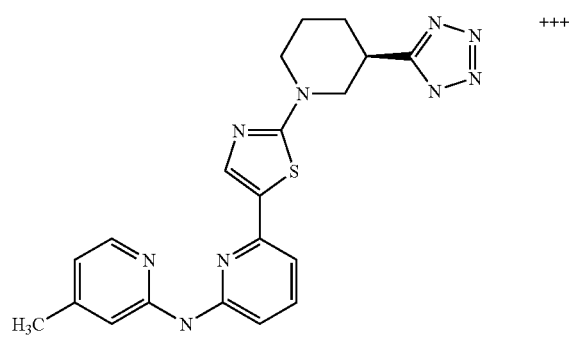 | +++ | |
| A-591 | 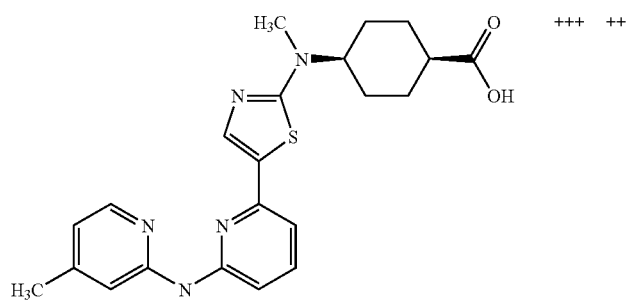 | +++ | ++ |

TABLE 1-120
A-592 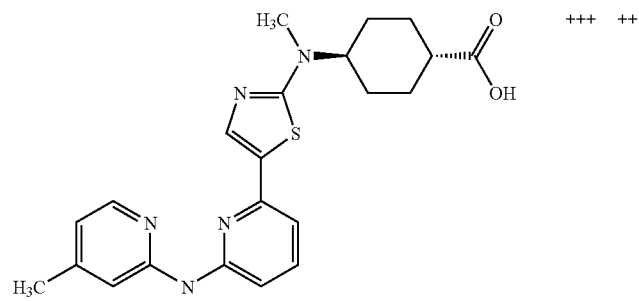 +++ ++
A-593 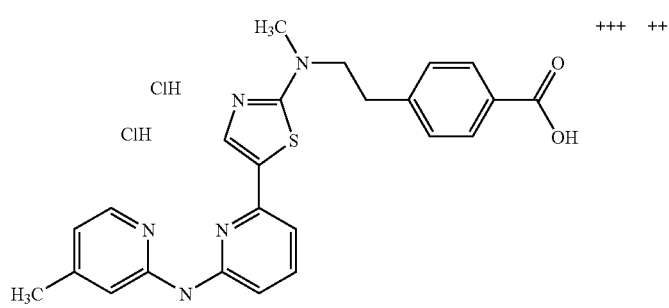 +++ ++
A-594 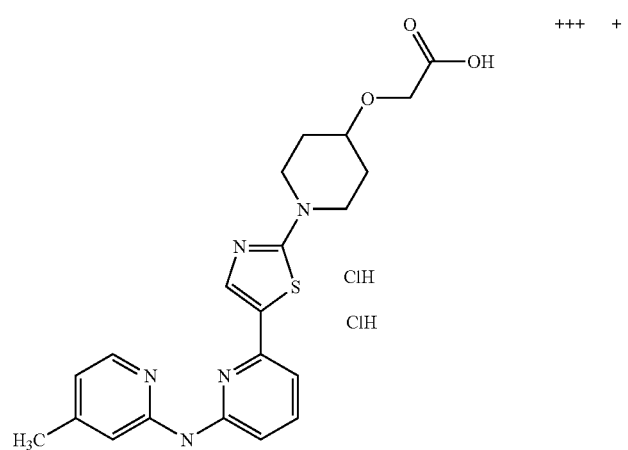 +++ +
A-595 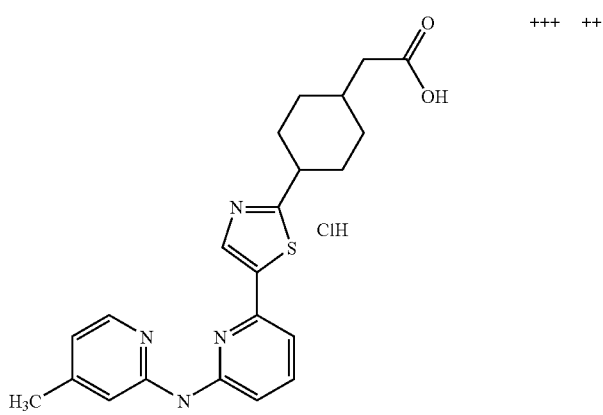 +++ ++

TABLE 1-120-continued
A-596 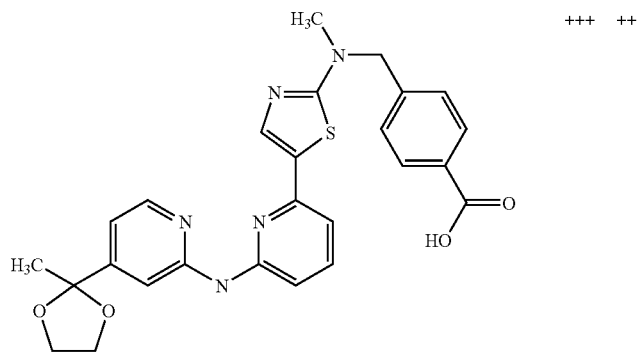 +++ ++
TABLE 1-121
A-597 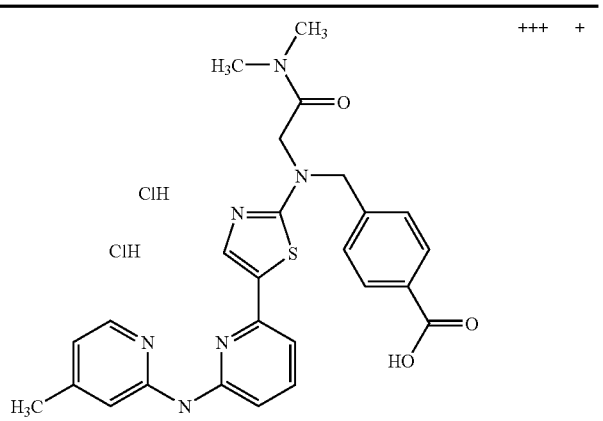 +++ +
A-598 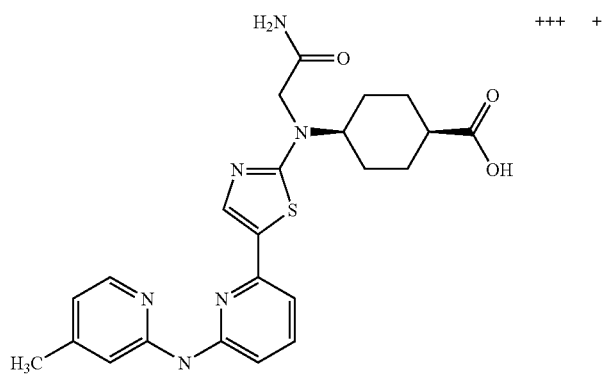 +++ +
A-599 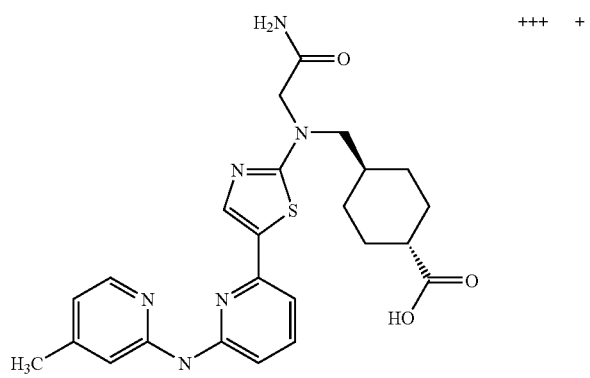 +++ +

TABLE 1-121-continued
| A-600 | 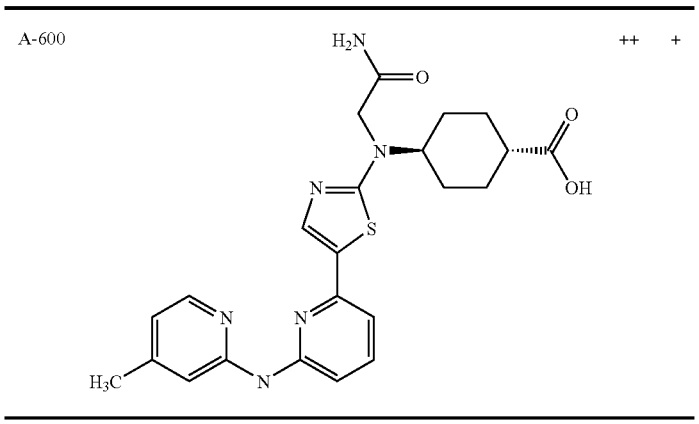 | ++ | + |
TABLE 1-122
| A-601 | 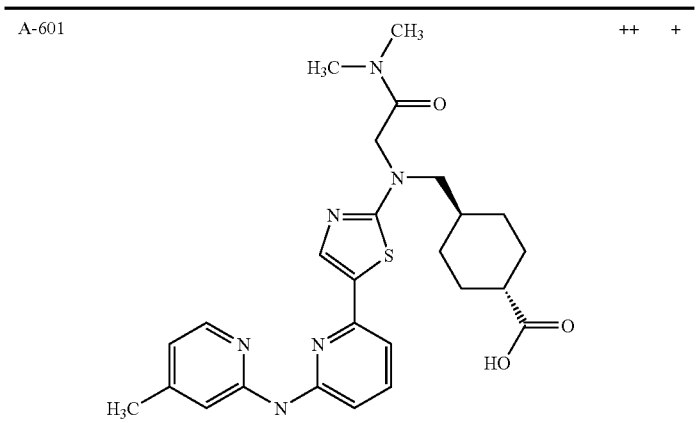 | ++ | + |
| A-602 | 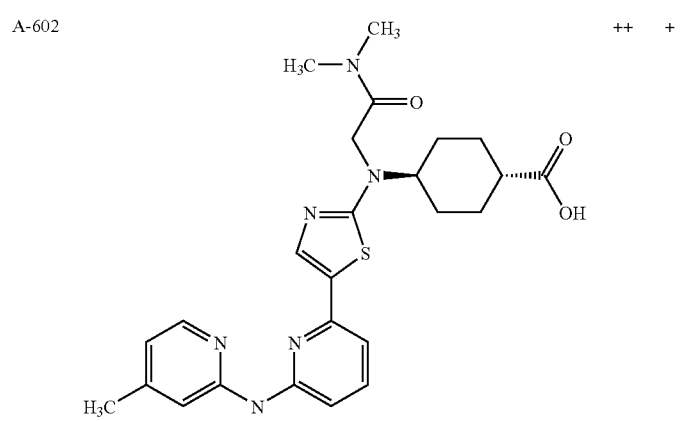 | ++ | + |
| A-603 | 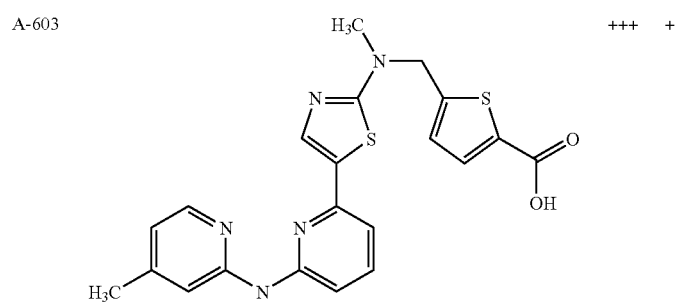 | +++ | + |

TABLE 1-122-continued
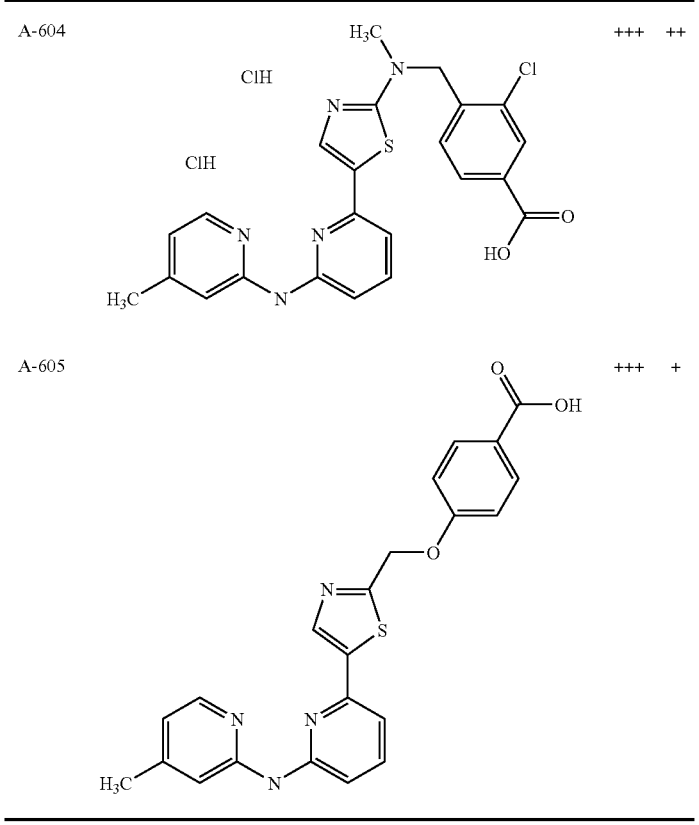
TABLE 1-123
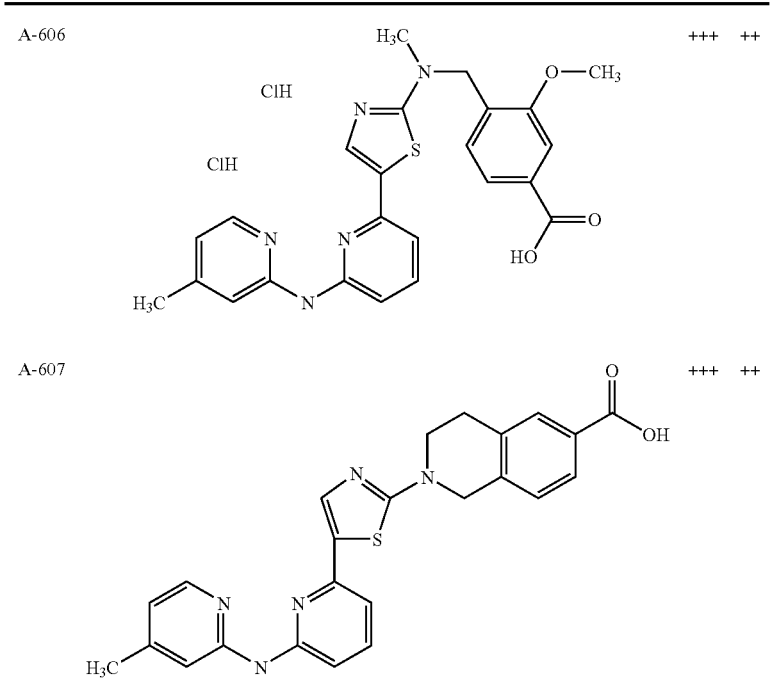

TABLE 1-123-continued
A-608 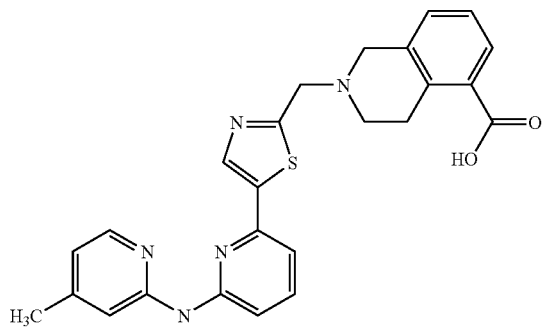 ++
A-609 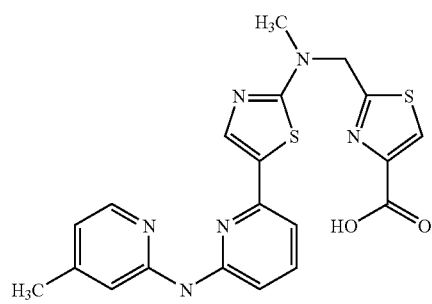 +++ +
A-610 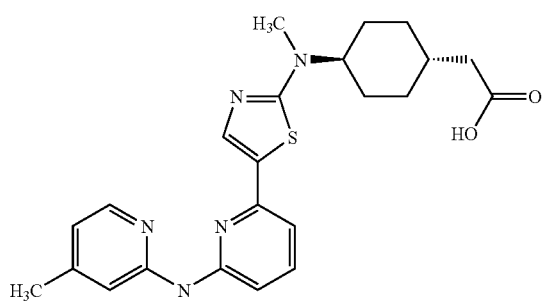 +++ ++
TABLE 1-124
A-611 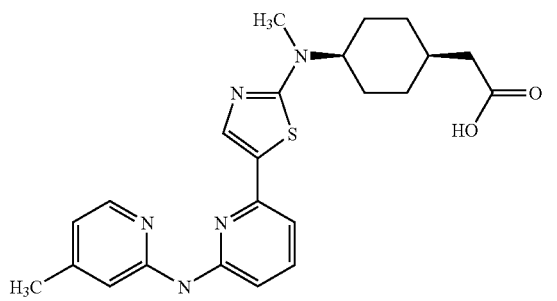 +++ ++

TABLE 1-124-continued
A-612 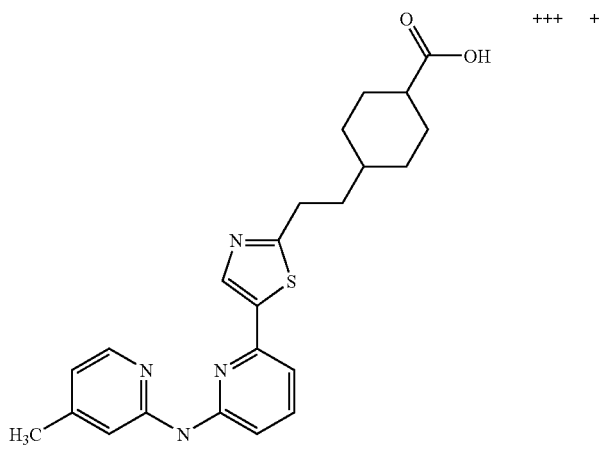 +++ +
A-613 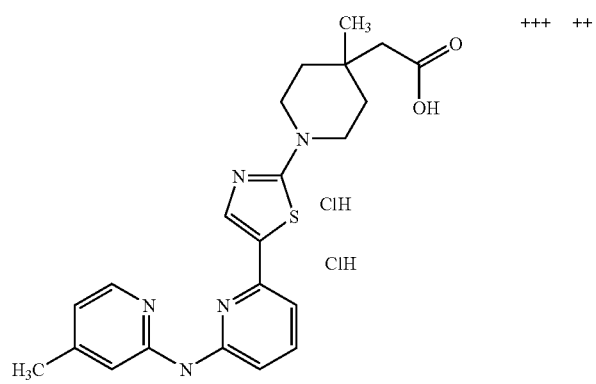 +++ ++
A-614 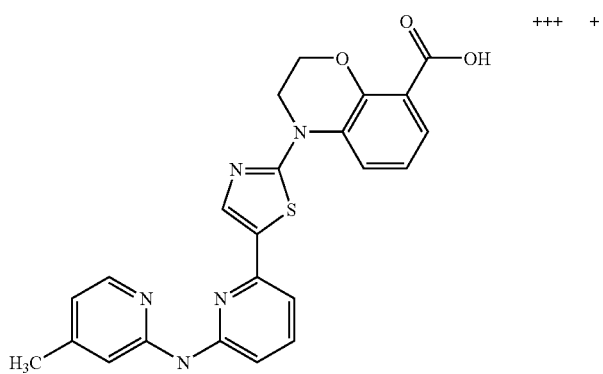 +++ +
A-615 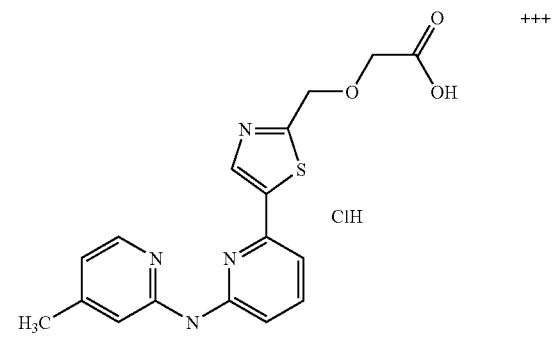 +++

TABLE 1-125
A-616 +++ ++
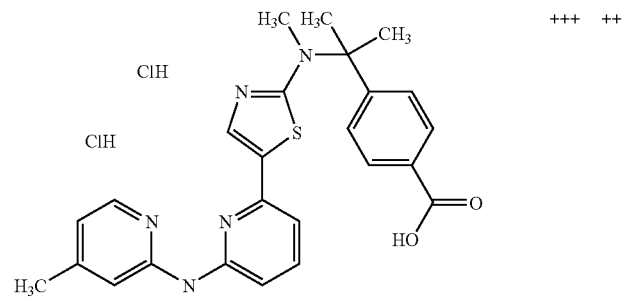
A-617 +++ +
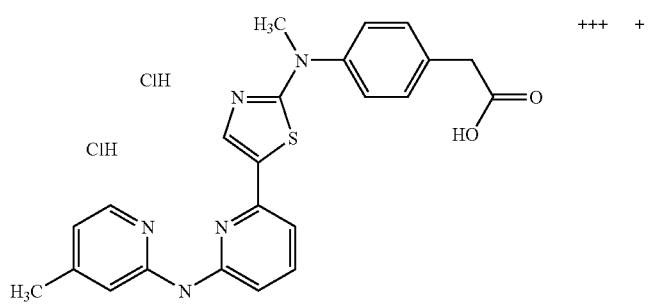
A-618 ++
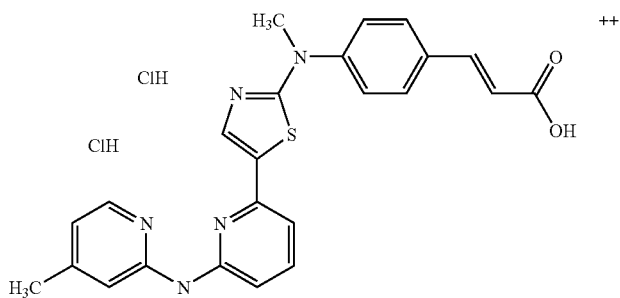
A-619 ++
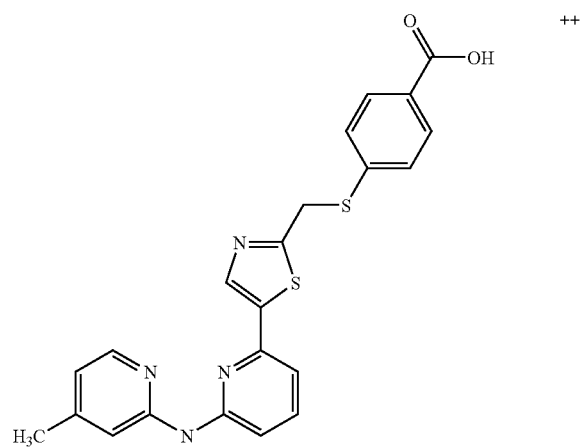

TABLE 1-125-continued
A-620 +++ ++
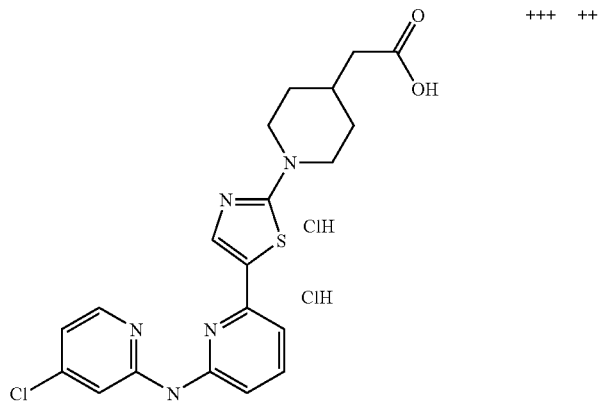
TABLE 1-126
A-621 ++
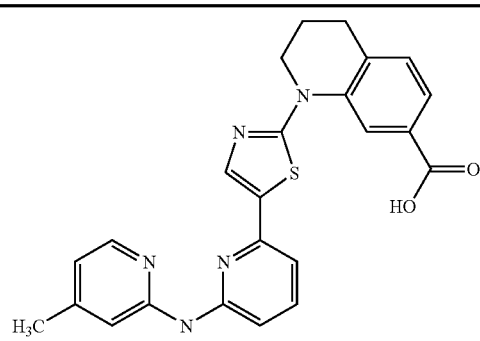
A-622 +++
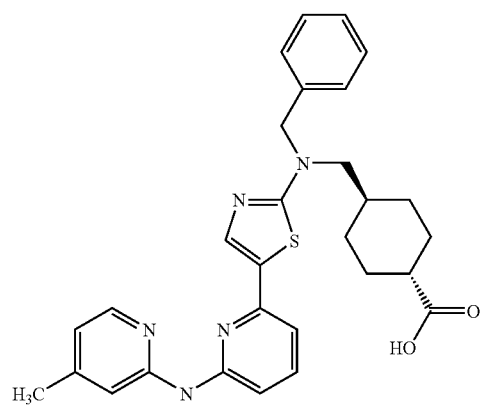
A-623 ++
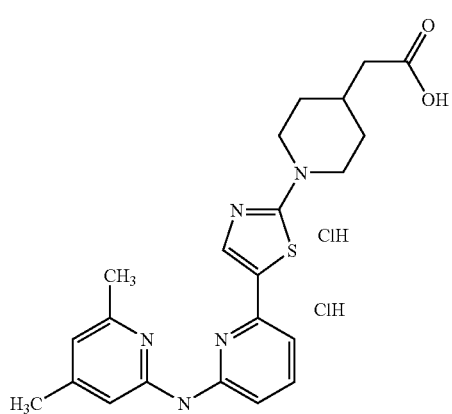

TABLE 1-126-continued
A-624 +++
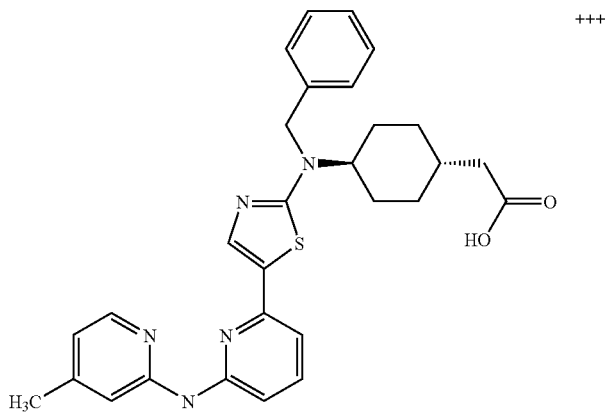
TABLE 1-127
A-625 ++
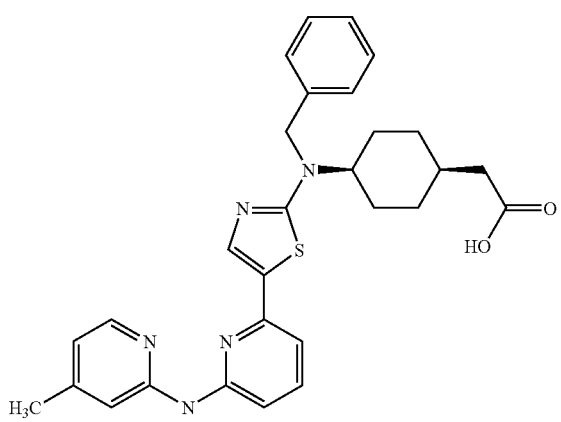
A-626 +++
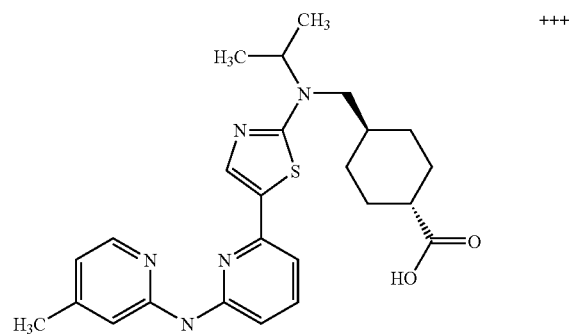

TABLE 1-127-continued
A-627 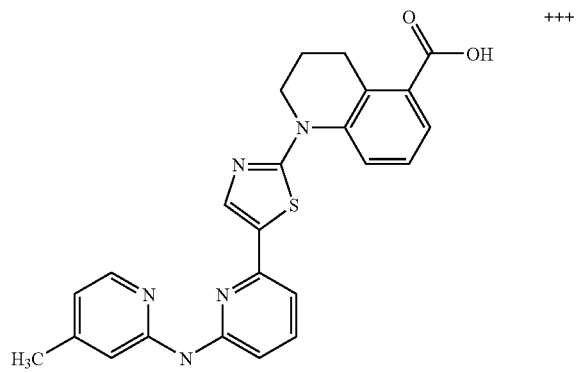 +++
A-628 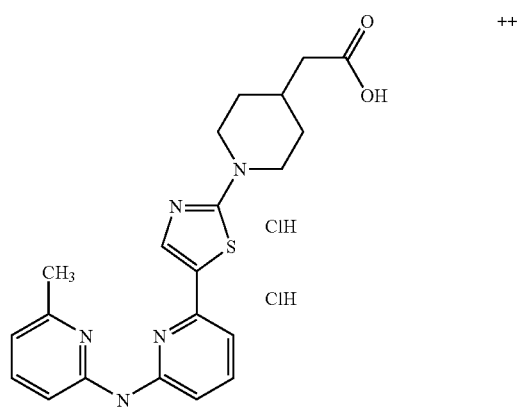 ++
A-629 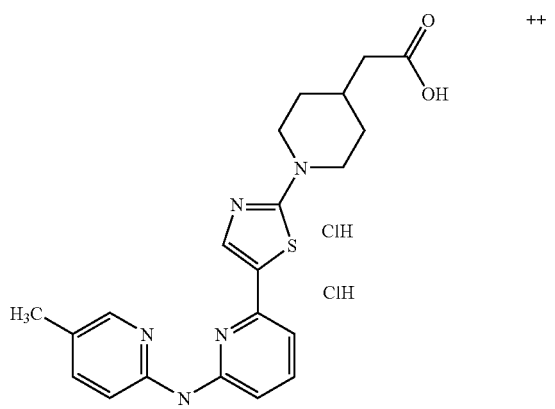 ++

TABLE 1-128
A-630 ++
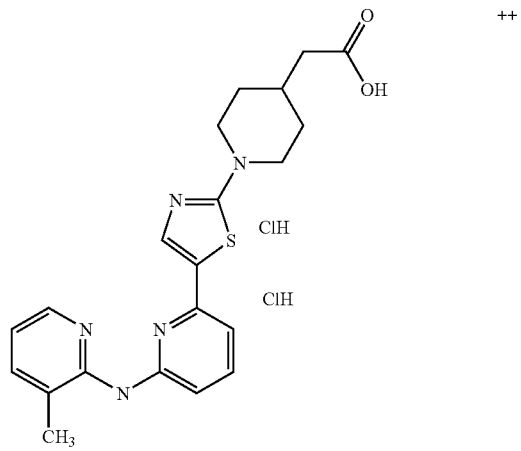
A-631 +++
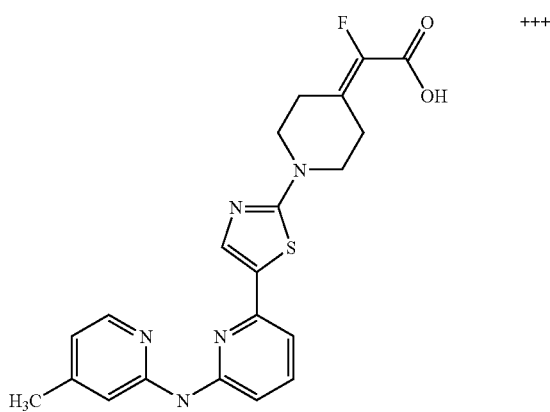
A-632 +++
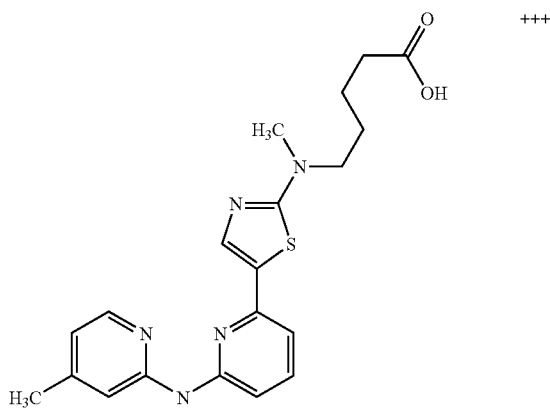

TABLE 1-128-continued
A-633 +++
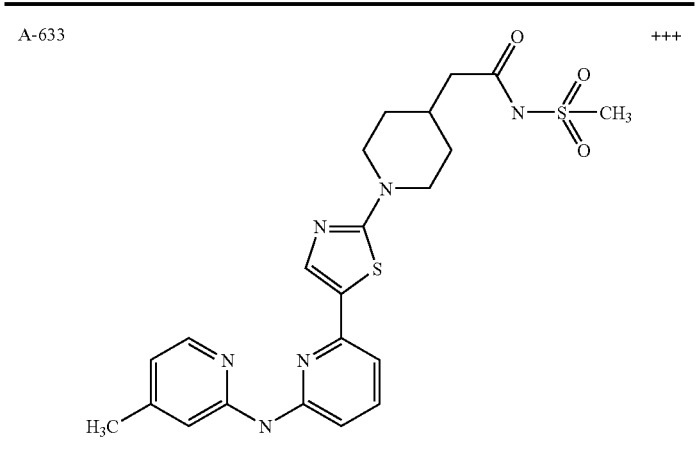
TABLE 1-129
A-634 +++
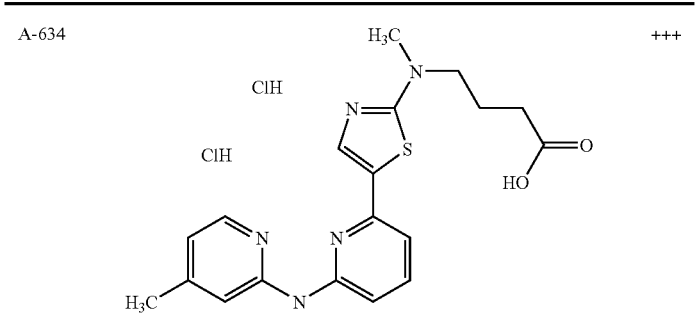
A-635 +++
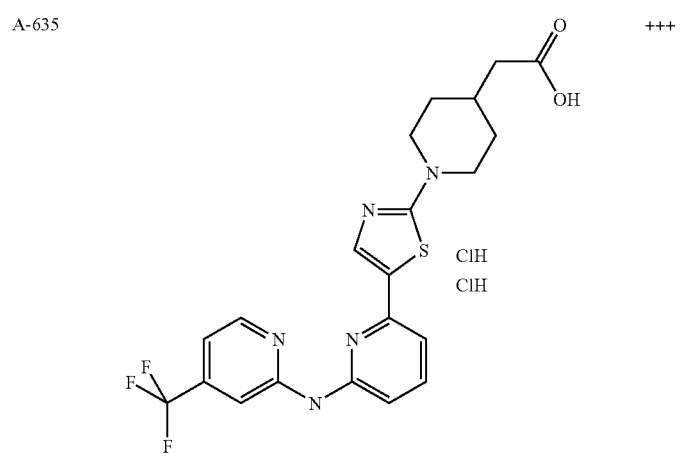

TABLE 1-129-continued
| A-636 | 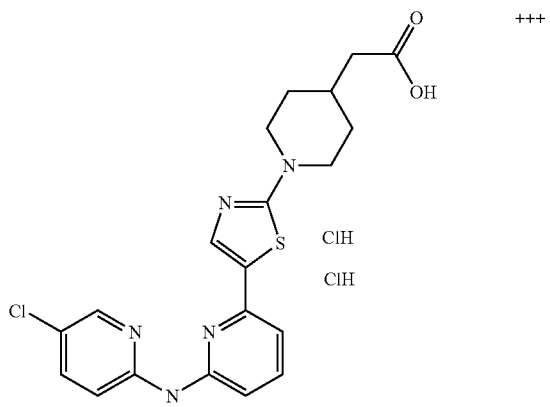 | +++ |
| A-637 | 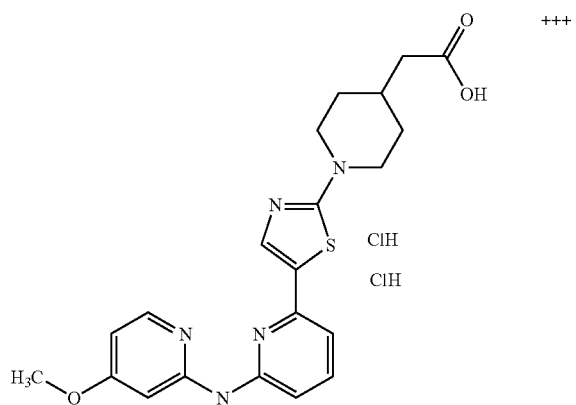 | +++ |
| A-638 | 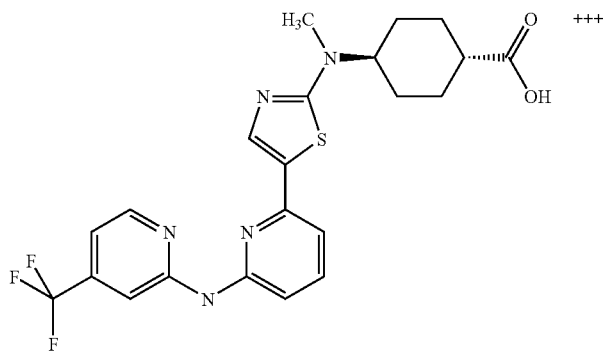 | +++ |
TABLE 1-130
| A-639 | 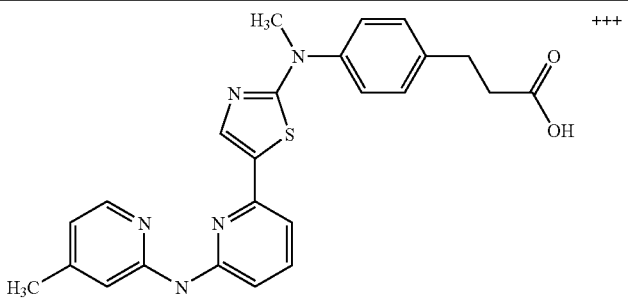 | +++ |

TABLE 1-130-continued
A-640 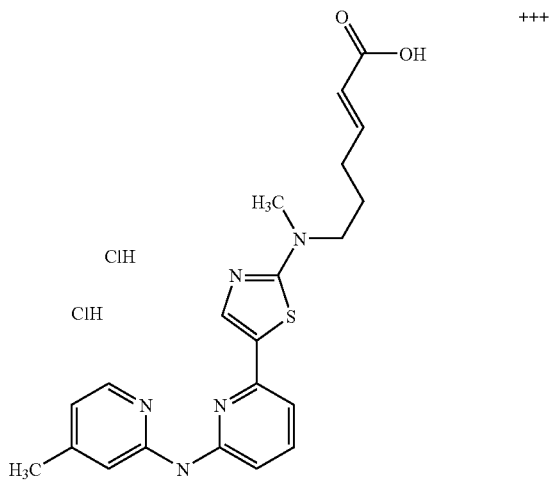 +++
A-641 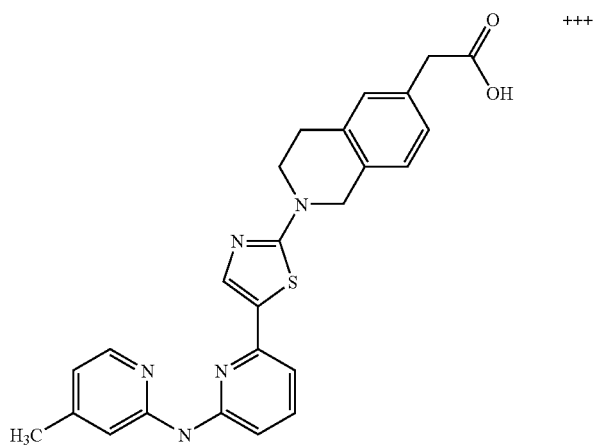 +++
A-642 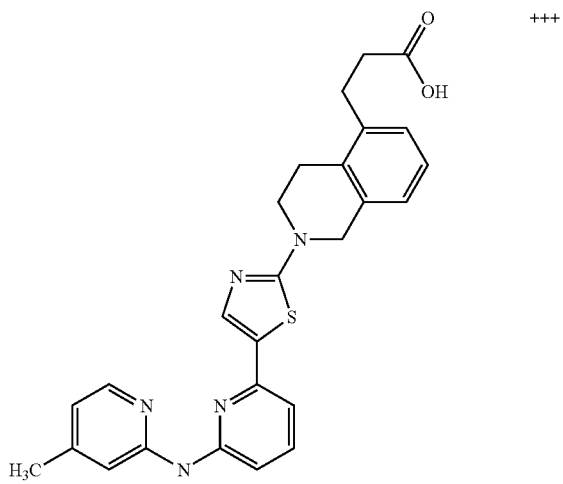 +++

TABLE 1-131
A-643 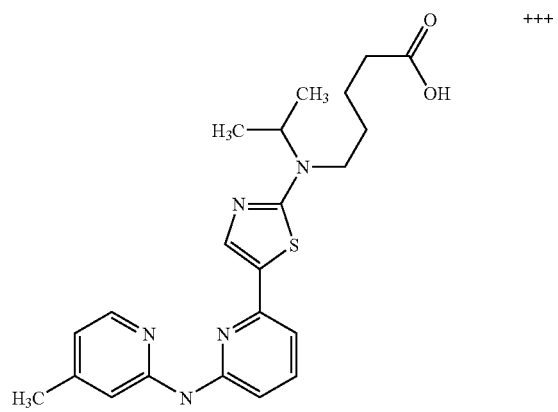 +++
A-644 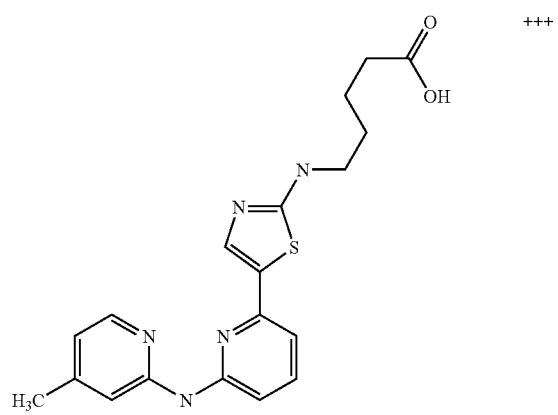 +++
A-645 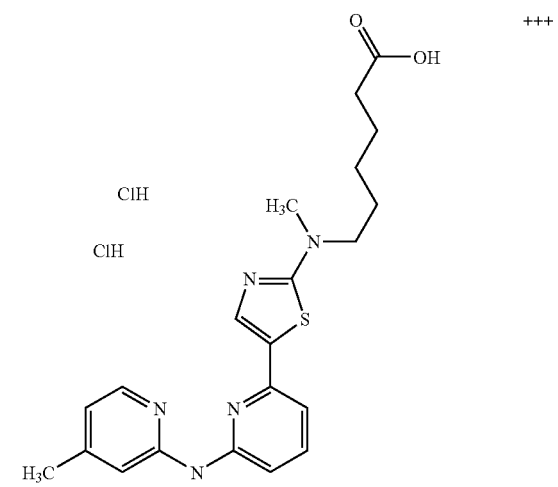 +++
A-646 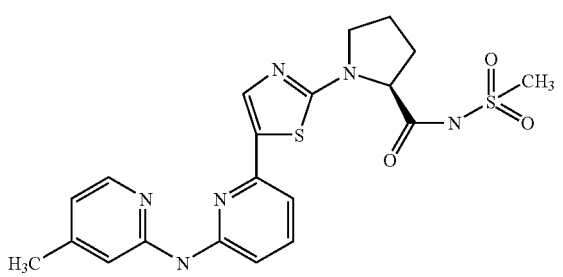 ++

TABLE 1-132
A-647 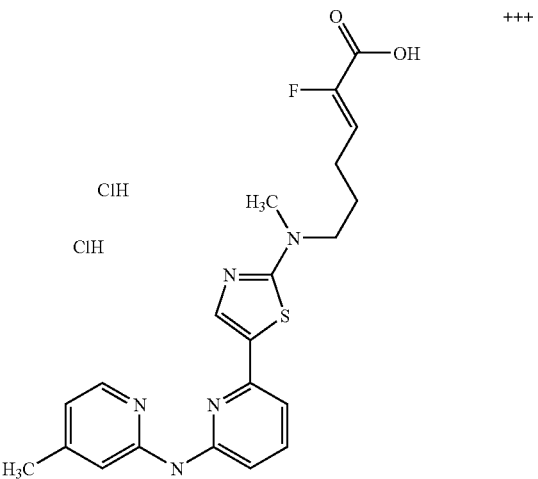 +++
A-648 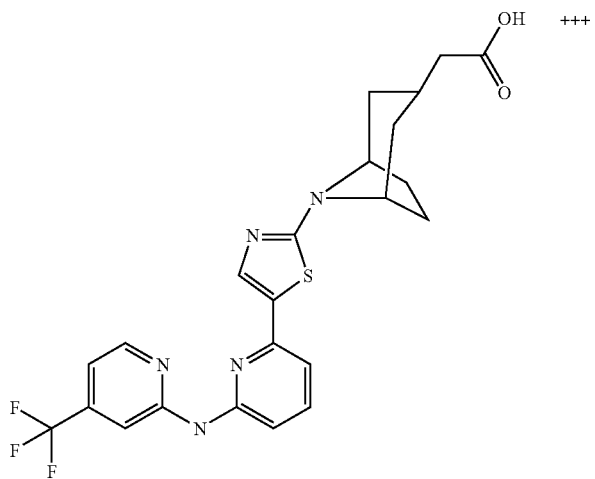 +++
A-649 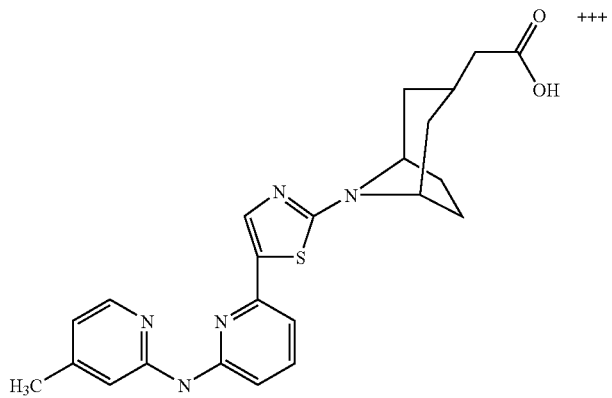 +++

TABLE 1-132-continued
A-650 +++
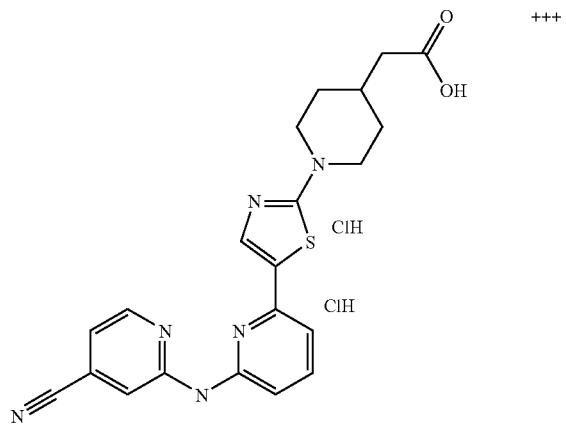
TABLE 1-133
A-651 +++
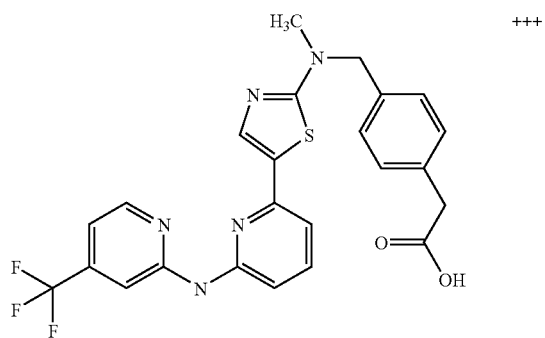
A-652 +++ +++
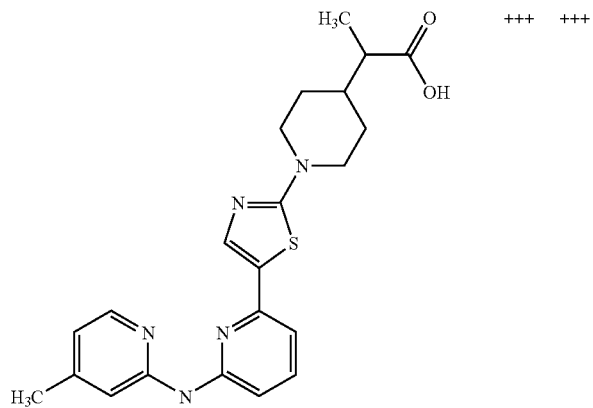

TABLE 1-133-continued
A-653 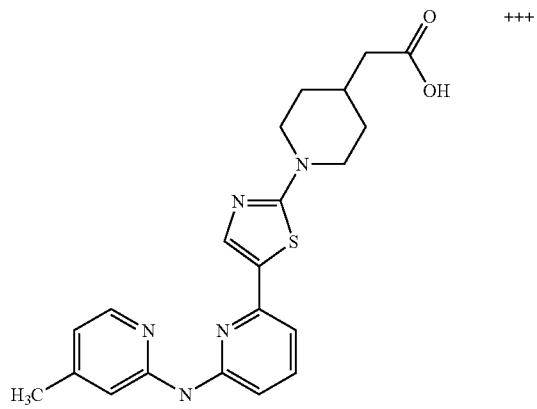 +++
A-654 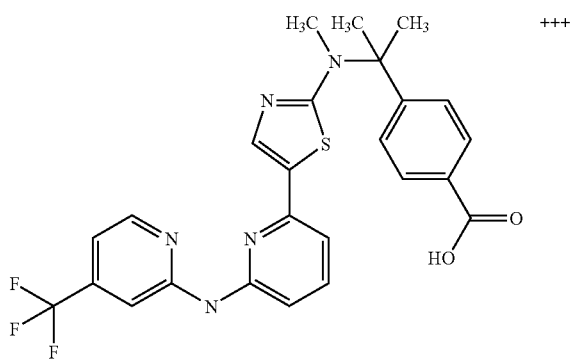 +++
TABLE 1-134
A-655 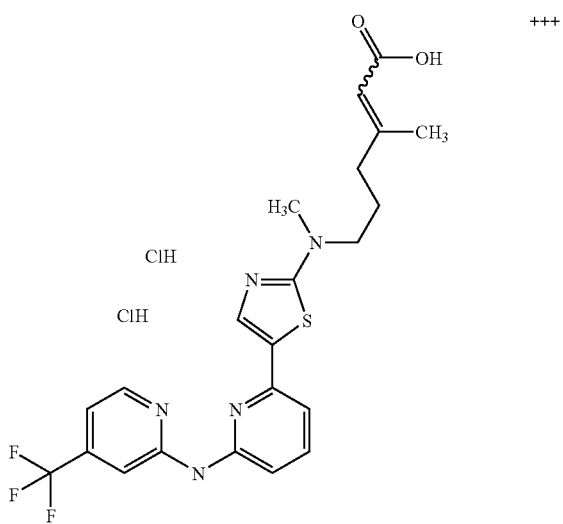 +++

TABLE 1-134-continued
A-656 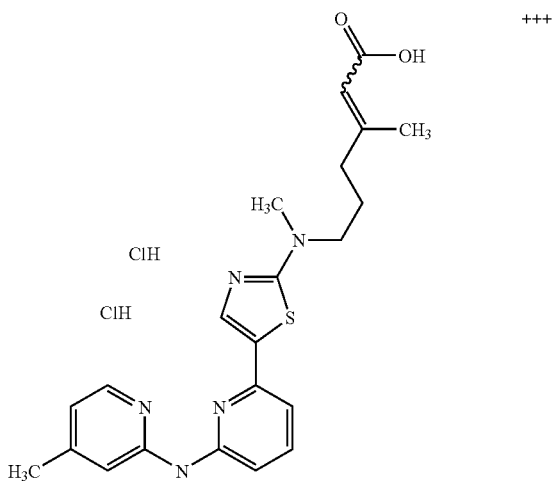 +++
A-657 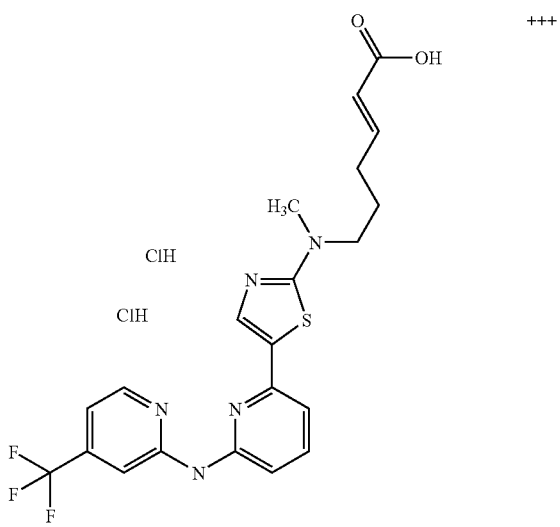 +++
A-658 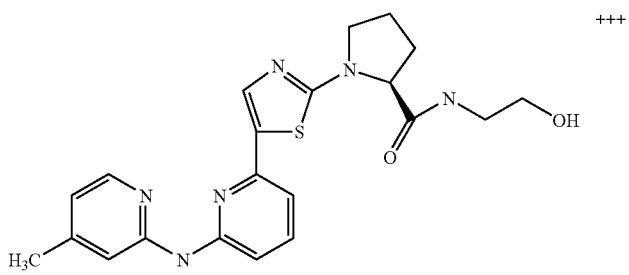 +++
TABLE 1-135
A-659 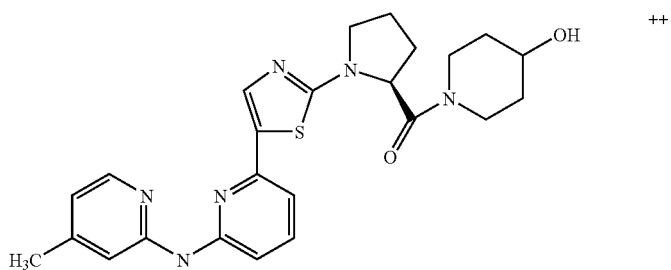 ++

TABLE 1-135-continued
A-660 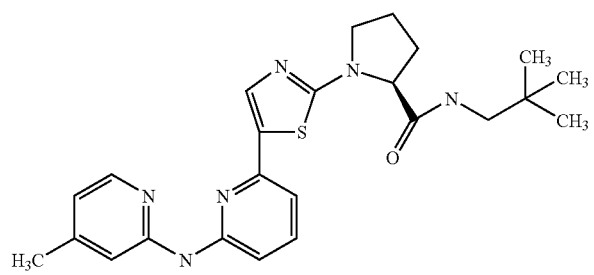 ++
A-661 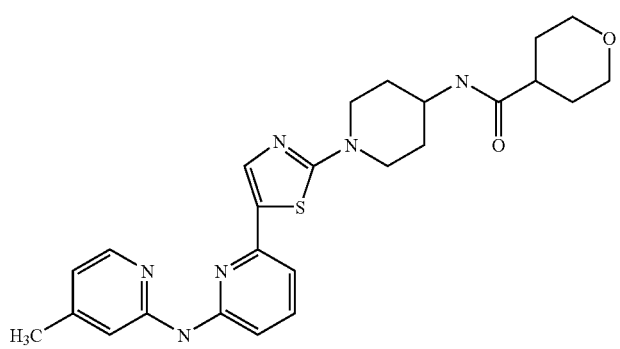 ++
A-662 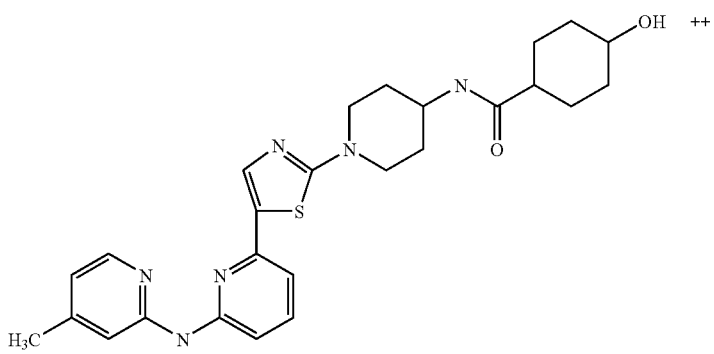 ++
A-663 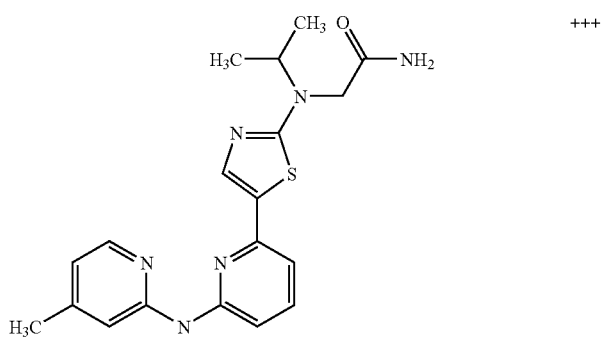 +++
A-664 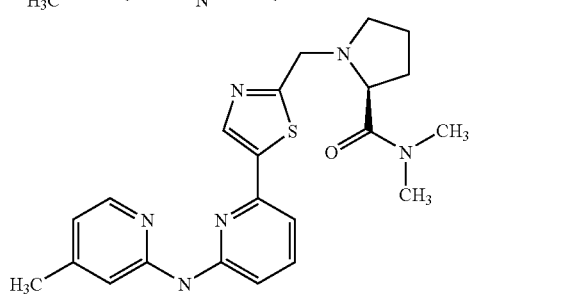 ++

TABLE 1-136
A-665 ++
A-666 ++
A-667 ++
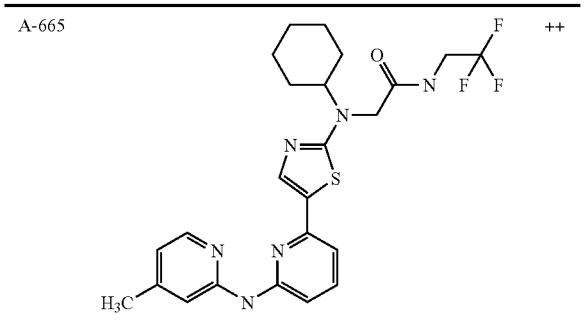
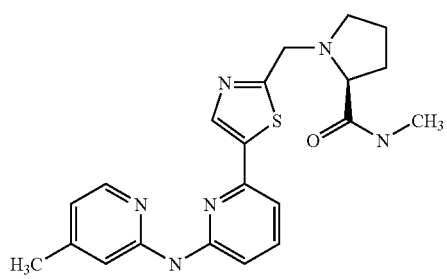
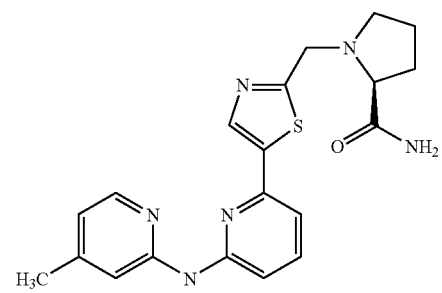
TABLE 1-136-continued
A-668 +++
A-669 ++
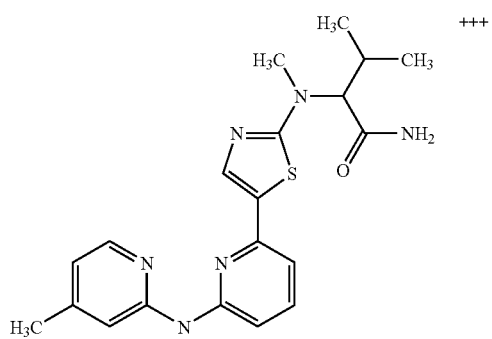
TABLE 1-137
A-670 ++
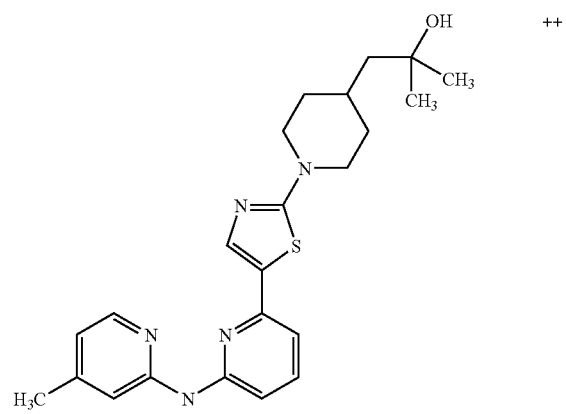

TABLE 1-137-continued
A-671 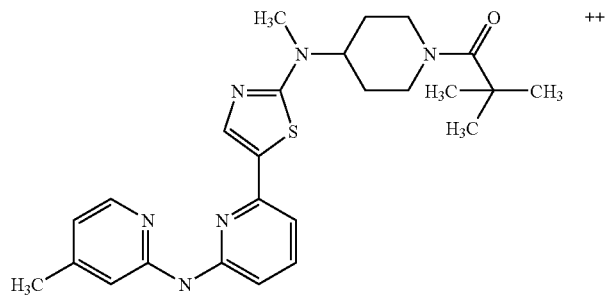 ++
A-672 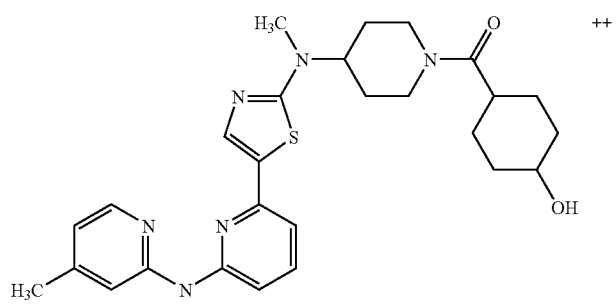 ++
A-673 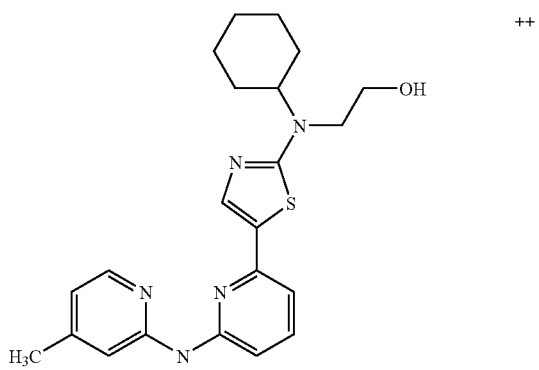 ++
A-674 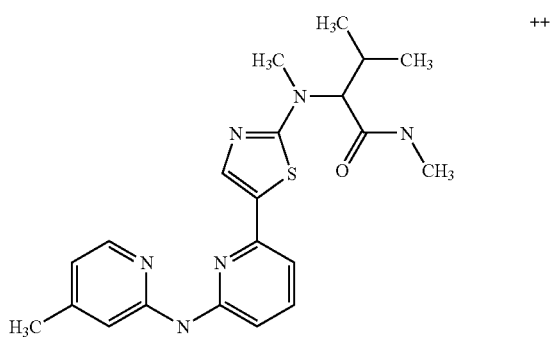 ++

TABLE 1-138
A-675 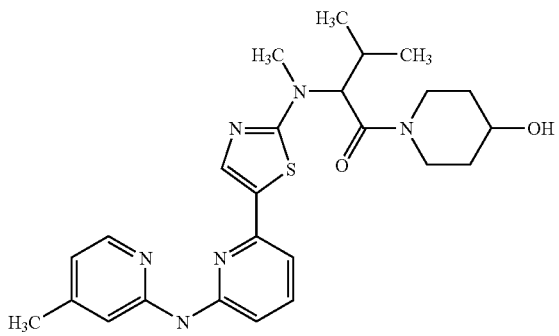 ++
A-676 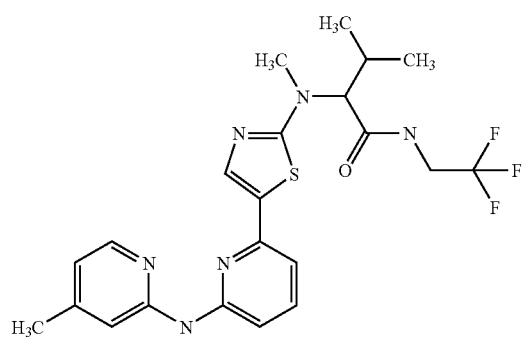 ++
A-677 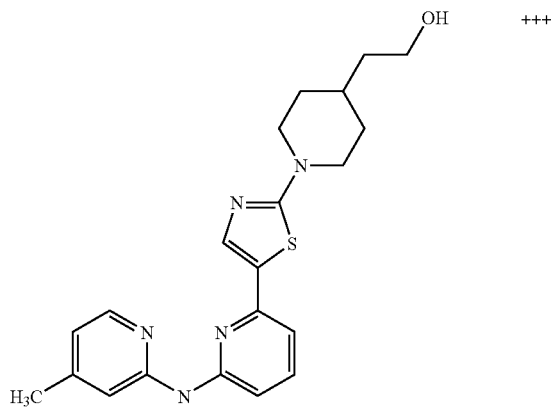 +++
A-678 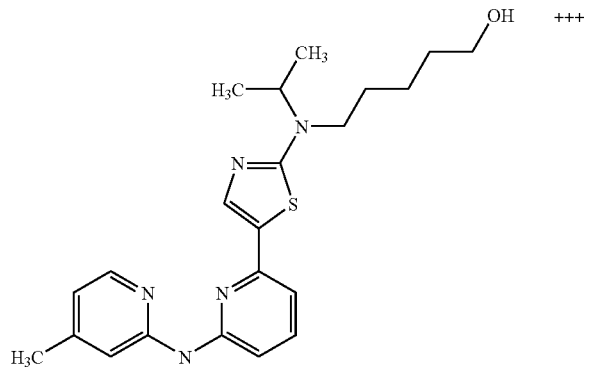 +++

TABLE 1-138-continued

A-679 ++

TABLE 1-139

A-680 +++

A-681 +++

TABLE 1-139-continued

A-682 ++

ClH
ClH

A-683 ++

ClH
ClH

TABLE 1-140
A-684 +++
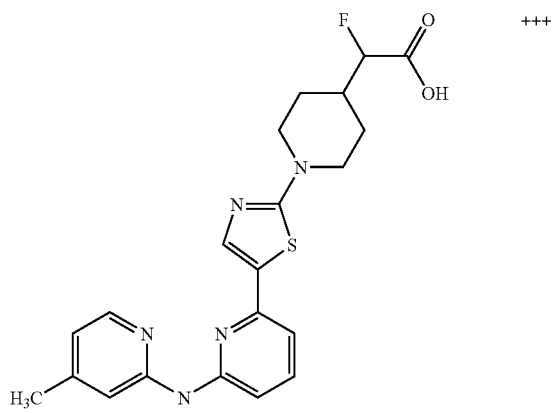
A-685 +++
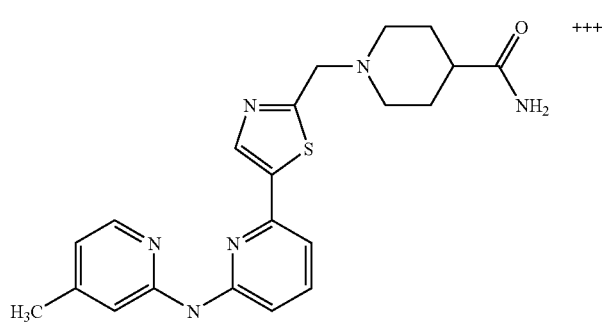
A-686 ++
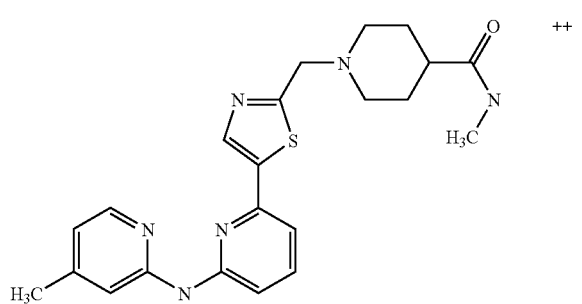
A-687 ++
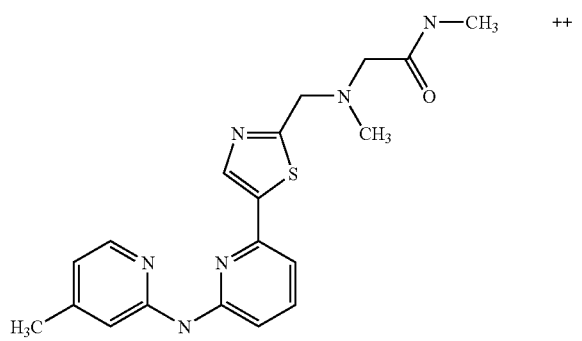

TABLE 1-140-continued
A-688 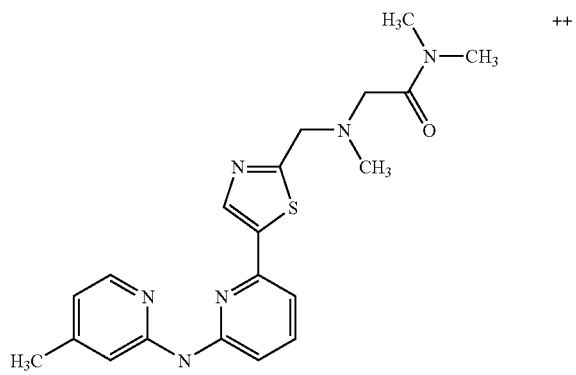 ++
TABLE 1-141
A-689 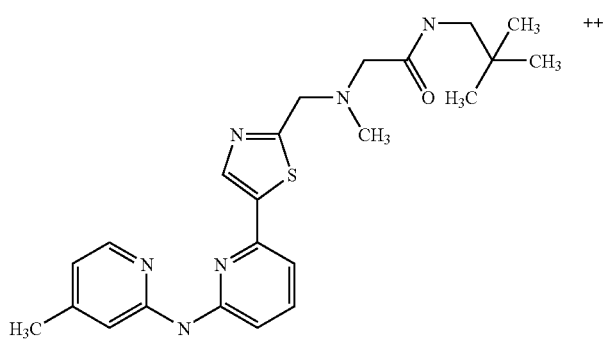 ++
A-690 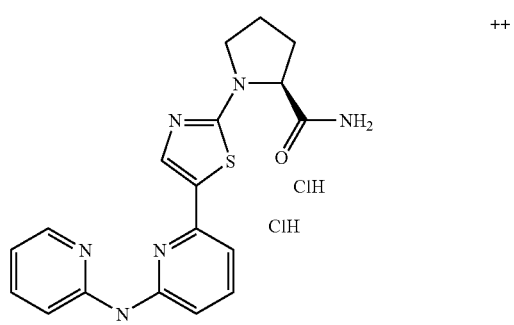 ++
A-691 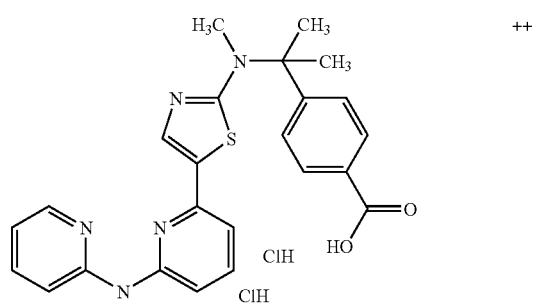 ++

TABLE 1-141-continued
A-692 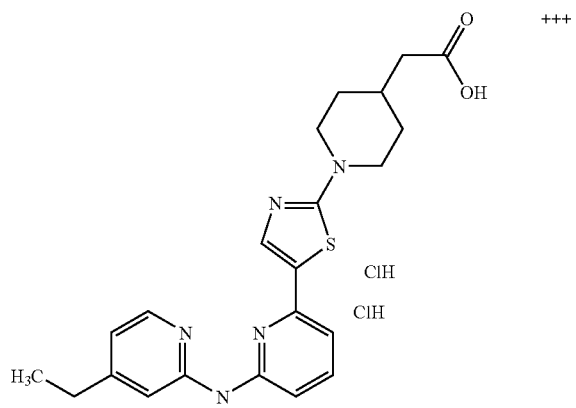 +++
A-693 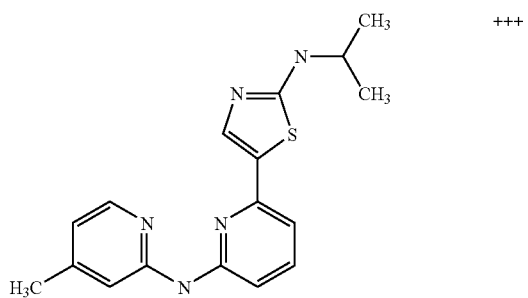 +++
TABLE 1-142
A-694 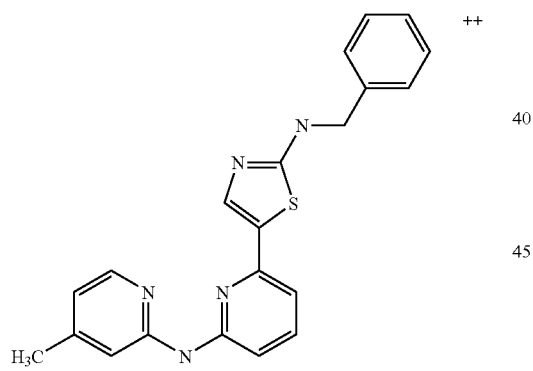 ++
A-695 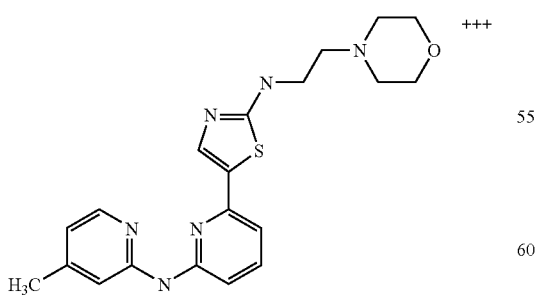 +++
TABLE 1-142-continued
A-696 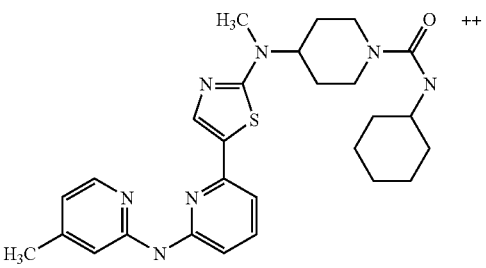 ++
A-697 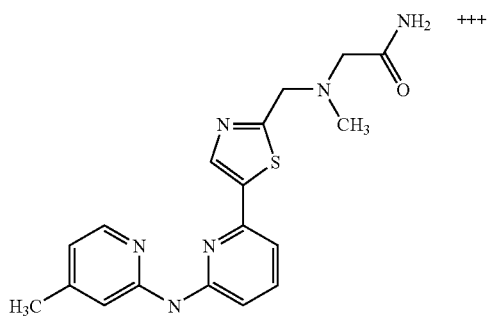 +++

TABLE 1-142-continued
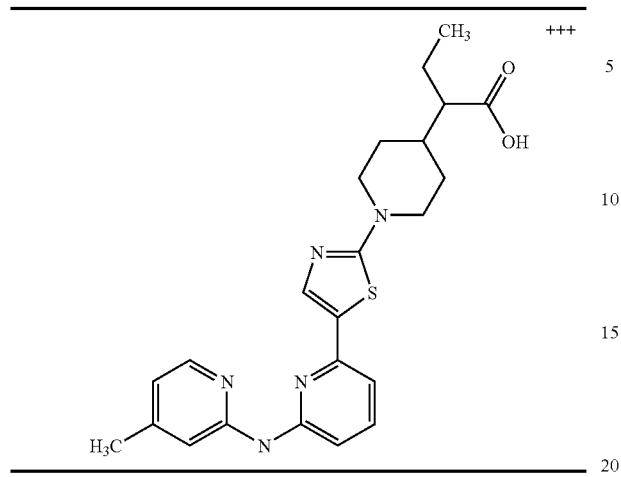
+++
TABLE 1-143
A-699 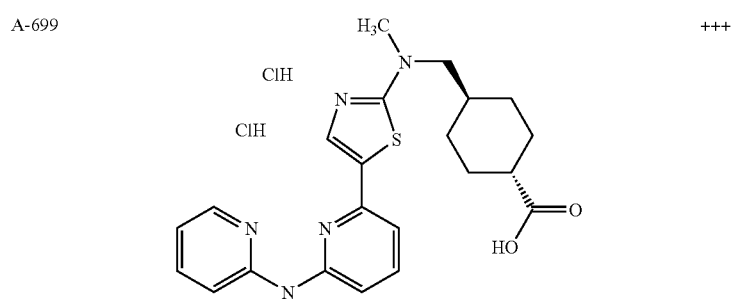 +++
A-700 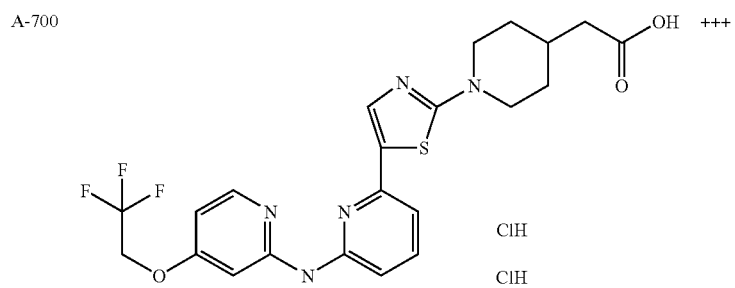 +++
A-701 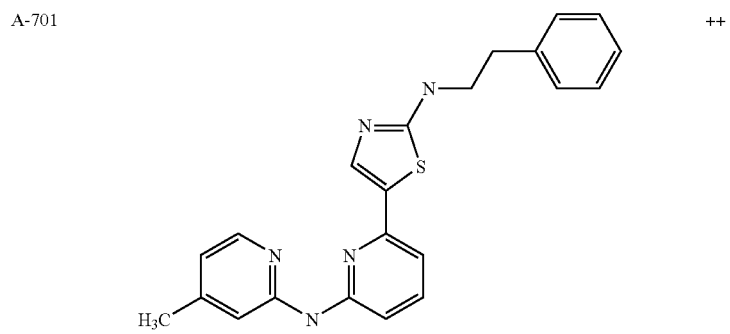 ++

TABLE 1-143-continued
A-702 +++
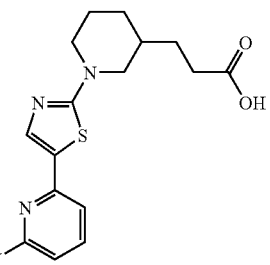
A-703 ++
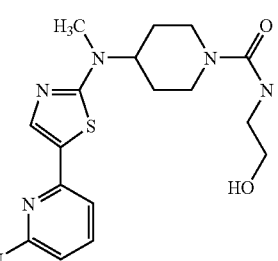
TABLE 1-144
A-704 +++
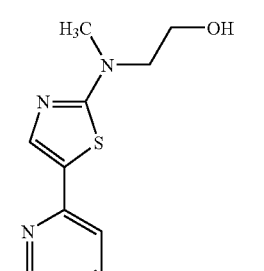
A-705 +++
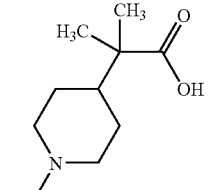
A-706 ++
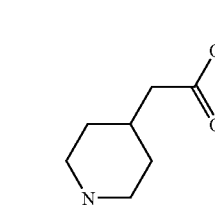
TABLE 1-144-continued
A-707 +++
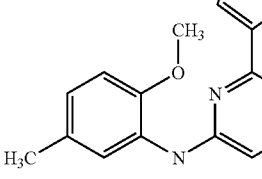
A-708 ++

TABLE 1-145
A-709 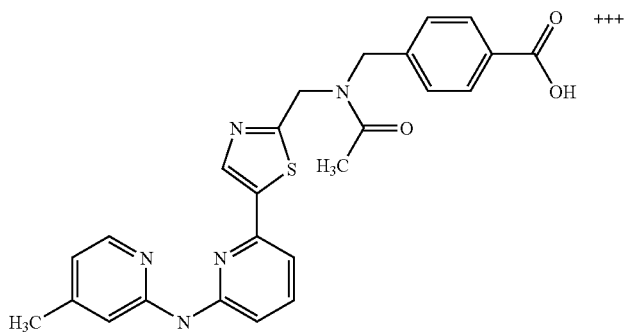 +++
A-710 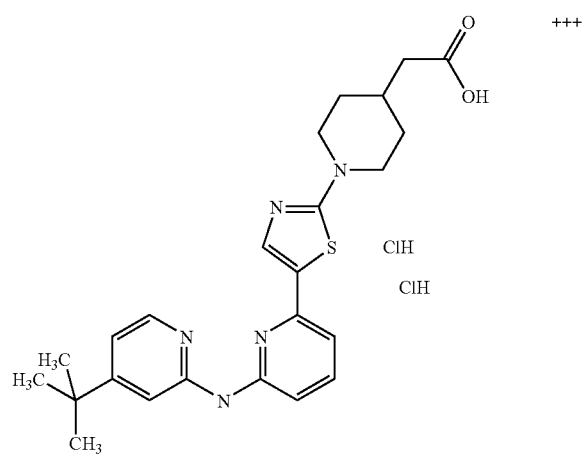 +++
A-711 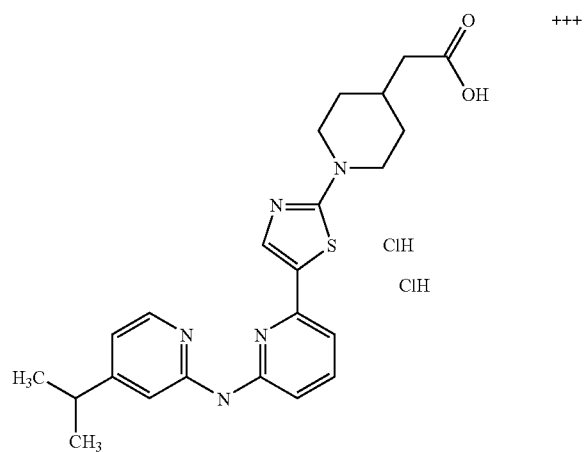 +++
A-712 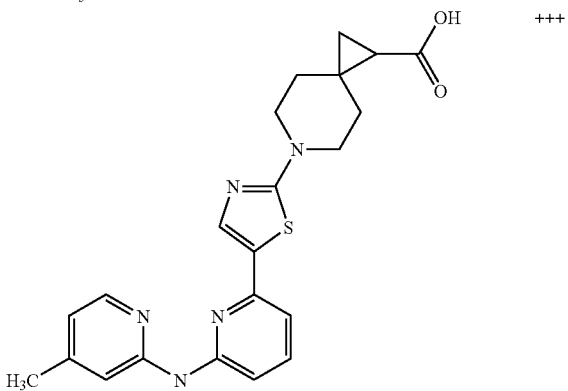 +++

TABLE 1-146
| A-713 | 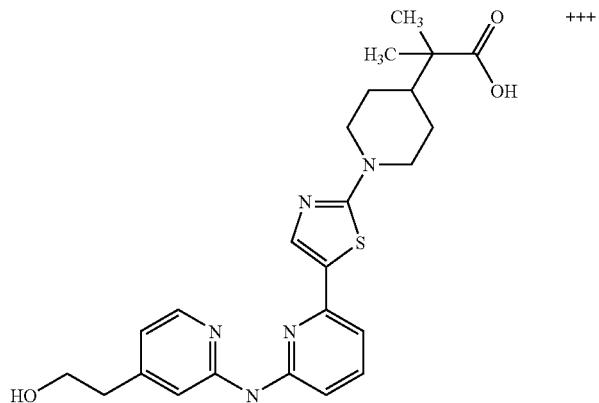 | +++ |
| A-714 | 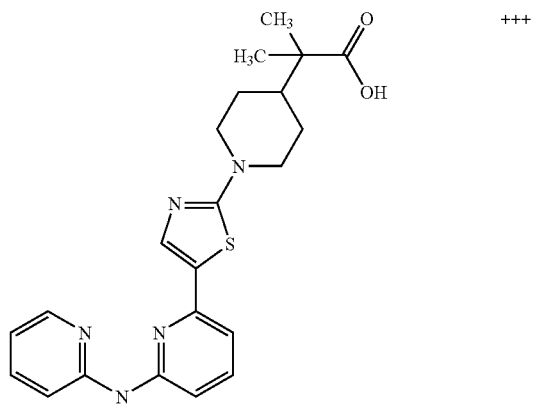 | +++ |
| A-715 | 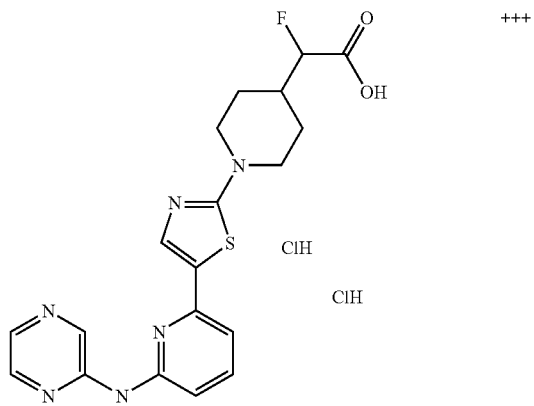 | +++ |
| A-716 | 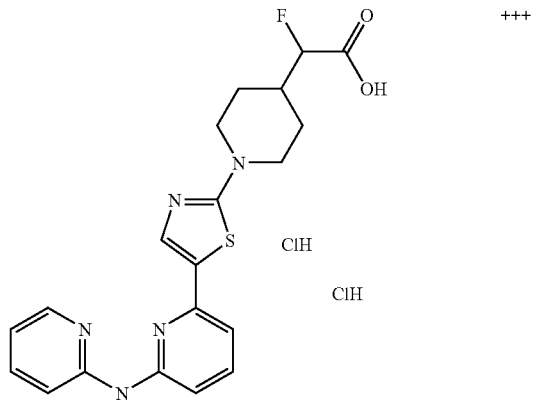 | +++ |

TABLE 1-147
A-717 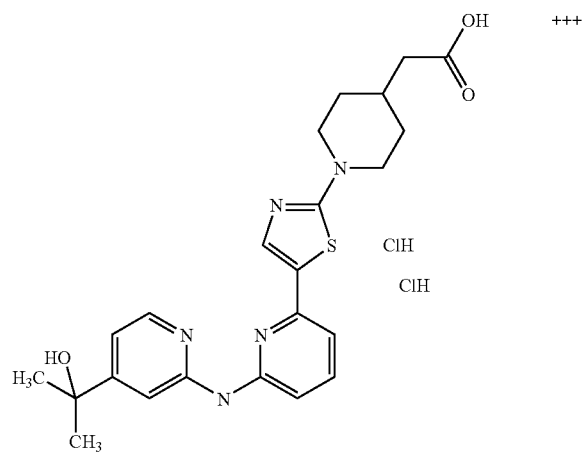 +++
A-718 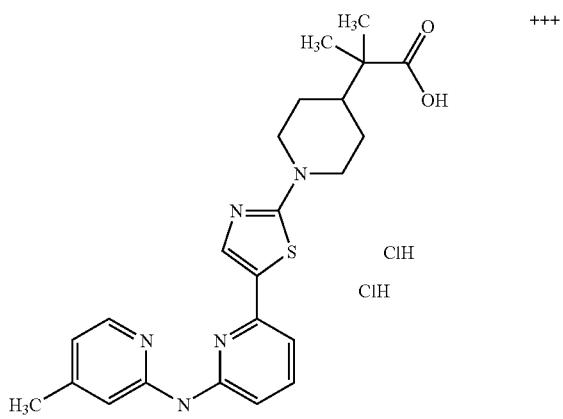 +++
A-719 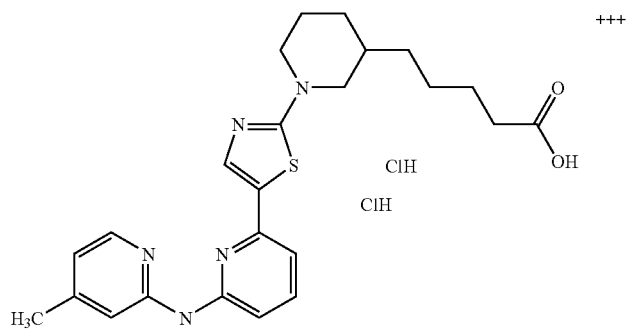 +++
A-720 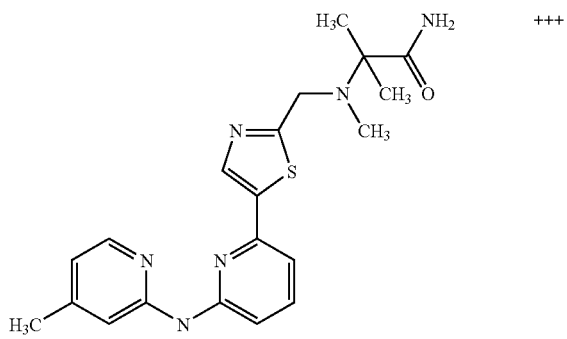 +++

Furthermore, preferable compounds of the present invention also include the following compounds.

TABLE 1-148

| Chem. Comp. No. | Chemical Compound | M.W. | sykHTRF ave IC50(μM) | human degranulation ave. IC50(μM) |
|---|---|---|---|---|
| A-721 | | | | |
| A-722 | | | | |
| A-723 | | | | |
| A-724 | | | | |

TABLE 1-148-continued

| Chem. Comp. No. | Chemical Compound | M.W. | sykHTRF ave IC50(μM) | human degranulation ave. IC50(μM) |
|---|---|---|---|---|
| A-725 | | | | |

TABLE 1-149

A-726

A-727

A-728

TABLE 1-149-continued

A-729

A-730

A-731

TABLE 1-150
A-732 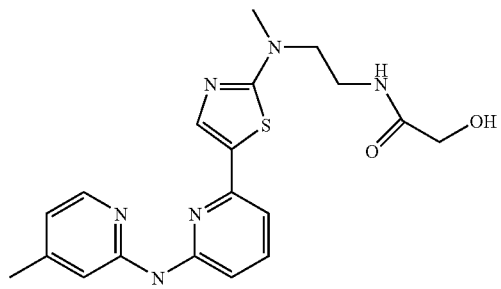
A-733 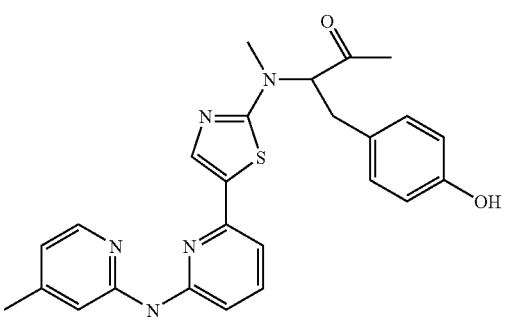
A-734 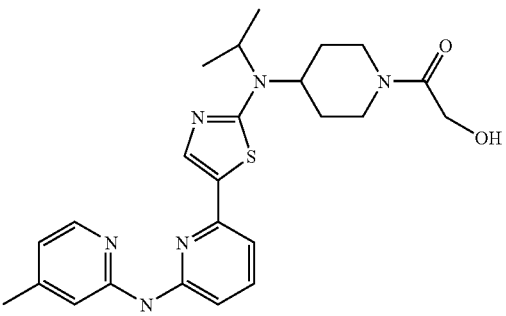
A-735 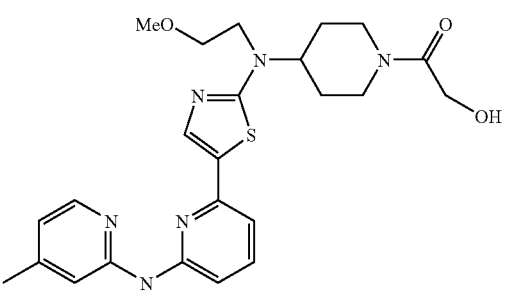
A-736 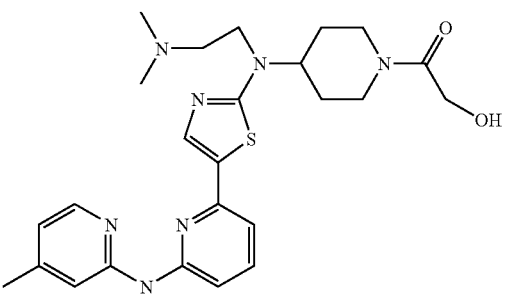
TABLE 1-150-continued
A-737 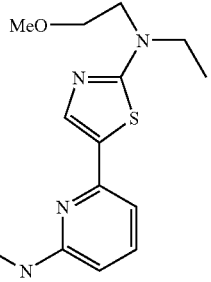
TABLE 1-151
A-738 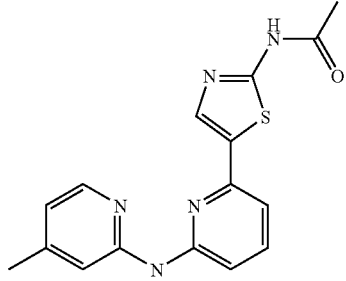
A-739 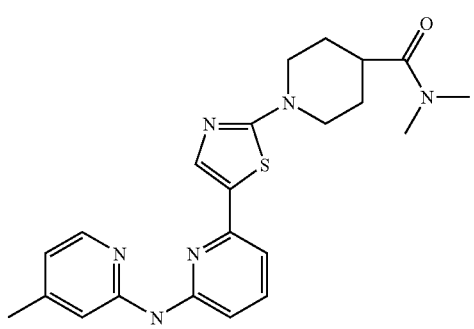
A-740 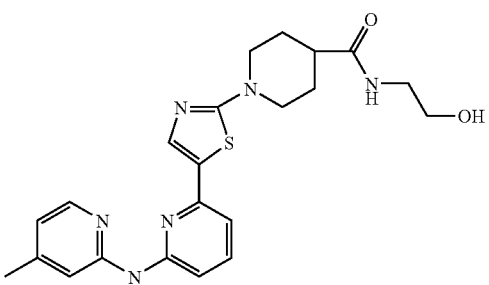
A-741 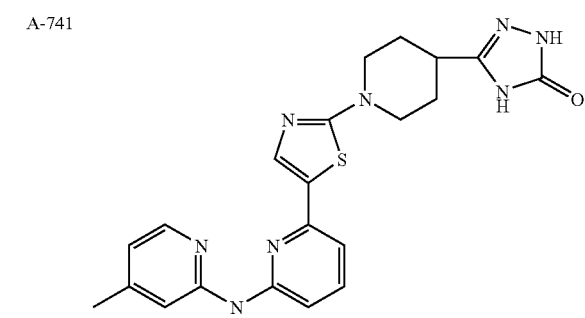

TABLE 1-151-continued
A-742
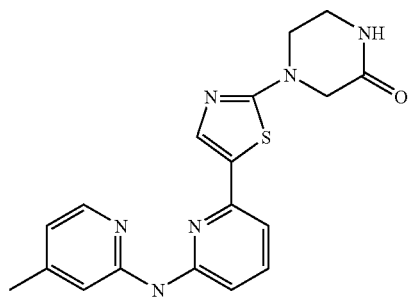
A-743
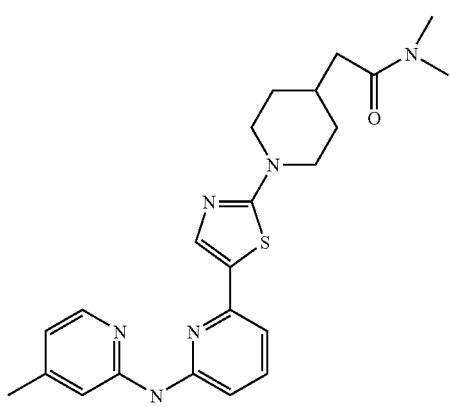
TABLE 1-152
A-744
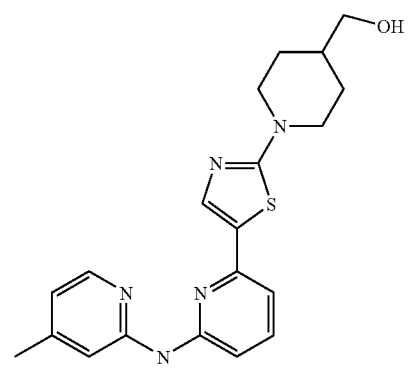
A-745
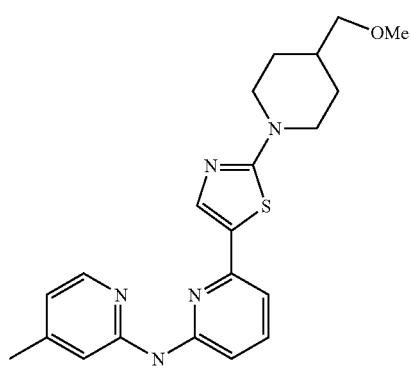
TABLE 1-152-continued
A-746
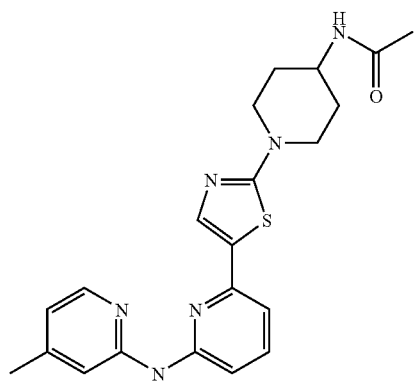
A-747
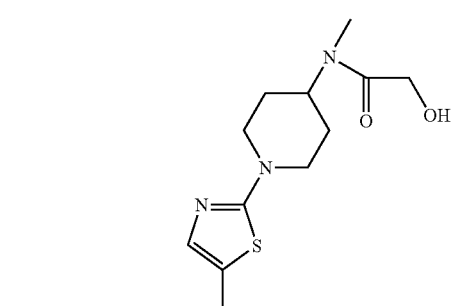
A-748
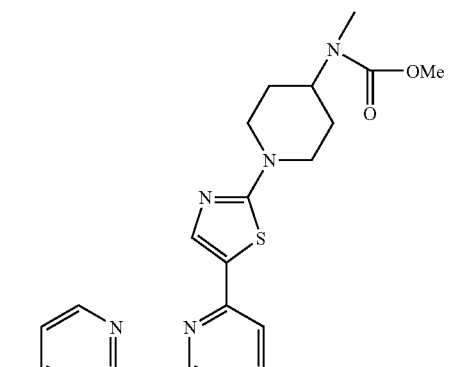
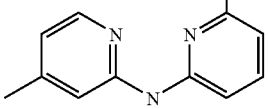

TABLE 1-153
A-749 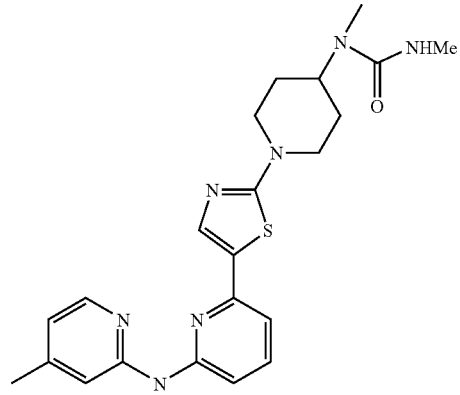
A-750 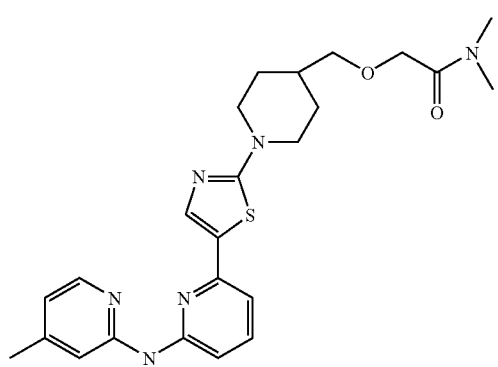
A-751 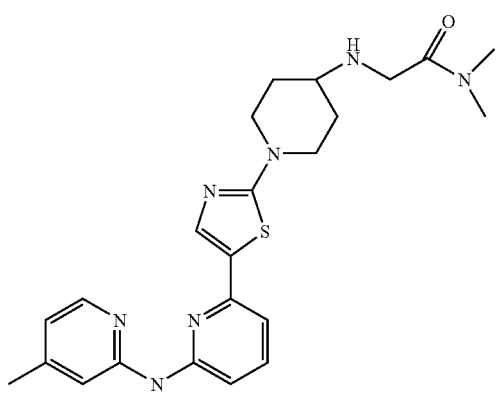
A-752 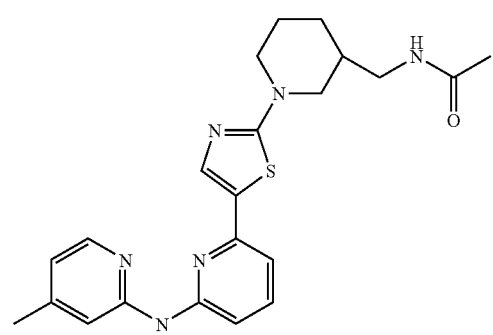
TABLE 1-153-continued
A-753 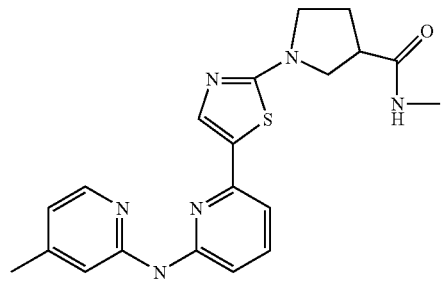
TABLE 1-154
A-754 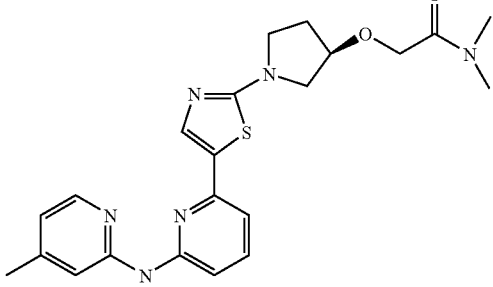
A-755 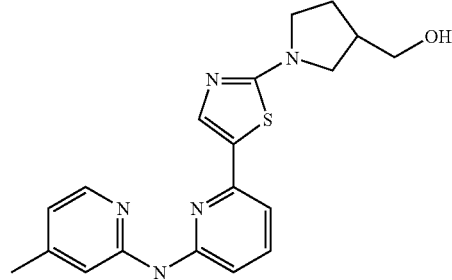
A-756 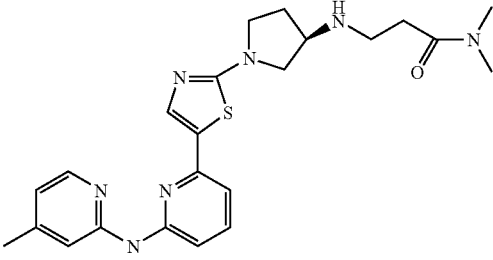
A-757 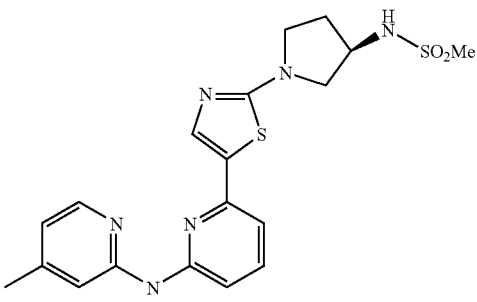

TABLE 1-154-continued

A-758

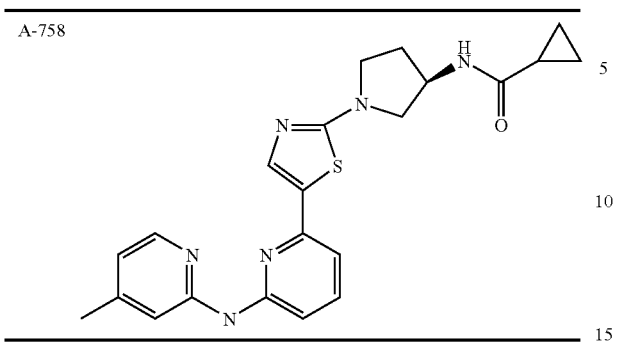

Next, preparation of the compounds of the present invention including thiophene will be described in detail by way of Examples.

Example 19

Preparation of 1-{5-[6-(4-methylpyridin-2-ylamino)pyridin-2-yl]thiophen-2-yl}ethanone (Compound B-1);

Step 1; Preparation of (6-bromopyridin-2-yl)-(4-methylpyridin-2-yl)amine

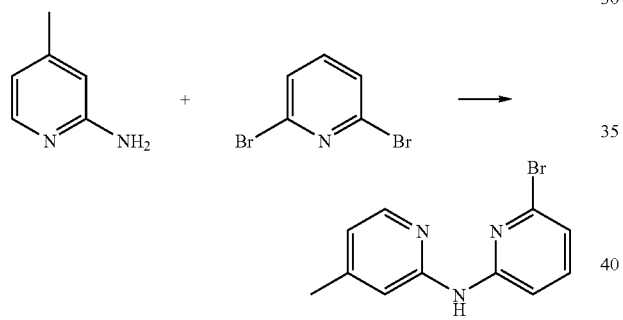

A suspension of 2,6-dibromopyridine (12.5 g), 2-amino-4-picoline (32.8 g, 139 mmol), palladium acetate (2.59 g, 11.6 mmol), rac-2,2'-bis(diphenylphosphino)-1,1'-binaphthyl (8.64 g, 13.9 mmol), sodium tert-butoxide (13.3 g, 139 mmol) in toluene (200 ml) was heated and stirred in an Ar stream at 80° C. for 12 hours. Water was added to the reaction solution and the solution was extracted with ethyl acetate. After the organic layer was washed with a saturated brine and dried over anhydrous magnesium sulfate, the residue obtained by vacuum concentration was purified by flash chromatography on silica gel (n-hexane:ethyl acetate=3:1) and subsequently washed with isopropyl ether and the title compound (15.4 g, 51%) was obtained.

Step 2; Preparation of 1-{5-[6-(4-methylpyridin-2-ylamino)pyridin-2-yl]thiophen-2-yl}ethanone

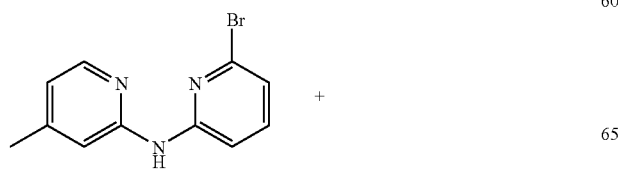

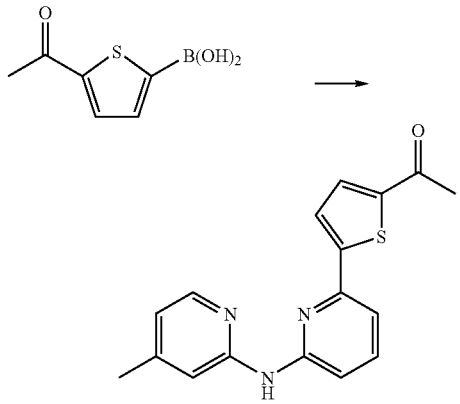

A suspension of (6-bromopyridin-2-yl)-(4-methylpyridin-2-yl)amine (1.00 g, 3.79 mmol), 5-acetylthiophene-2-boronic acid (644 mg, 3.79 mmol), tetrakis triphenylphosphine palladium (440 mg, 0.38 mmol), sodium hydrogen carbonate (480 mg, 5.68 mmol) in dimethoxyethane-water (12 ml) was heated and stirred in an Ar stream at 130° C. for 12 hours. Water was added to the reaction solution and extracted with ethyl acetate. After the organic layer was washed with a saturated brine and dried over anhydrous magnesium sulfate, the residue obtained by concentration in vacuo was washed with tetrahydrofuran-ethyl acetate (1:1), dried, and the title compound (426 mg, 36%) was obtained.

$^1$H-NMR (300 MHz, DMSO-$d_6$): 9.76(bs1H, brs), 8.12 (1H, d, J=4.8 Hz), 8.07 (1H, br), 7.96 (1H, d, J=4.2 Hz), 7.86 (1H, d, J=4.2 Hz), 7.73 (1H, dd, J=8.1, 7.5 Hz), 7.52 (1H, d, J=7.5 Hz), 7.43 (1H, d, J=8.1 Hz), 6.80 (1H, brd, J=4.8 Hz), 2.56(3H, s), 2.36(3H, s).

Example 20

Preparation of 5-[6-(4-methylpyridin-2-ylamino)pyridin-2-yl]thiophene-2-carboxaldehyde (Compound B-2)

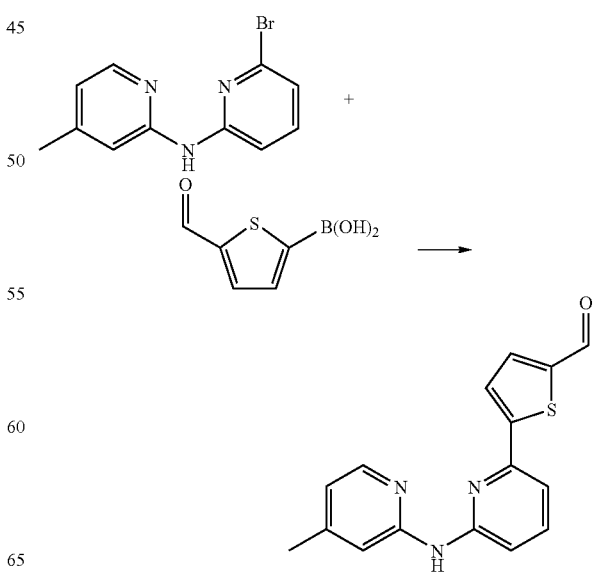

483

The title compound (293 mg, 26%) was obtained in a similar method as in Step 2 of Example 14 using (6-bromopyridin-2-yl)-(4-methylpyridin-2-yl)amine (1.00 g, 3.79 mmol), 5-formylthiophene-2-boronic acid (1.30 g, 8.33 mmol), tetrakistriphenylphosphine palladium (875 mg, 0.76 mmol), sodium hydrogen carbonate (954 mg, 11.4 mmol).

1H-NMR (300 MHz, DMSO-d$_6$): 9.95 (1H, s), 9.80 (1H, s), 8.13 (1H, d, J=5.2 Hz), 8.02-8.10 (2H, m), 7.96 (1H, d, J=3.8 Hz), 7.76 (1H, t, J=7.9 Hz), 7.57 (1H, d, J=7.2 Hz), 7.46 (1H, d, J=8.3 Hz), 6.80 (1H, dd, J=5.2, 0.9 Hz), 2.37(3H, s).

Example 21

Preparation of 1-{5-[6-(4-methylpyridin-2-ylamino) pyridin-2-yl]thiophen-2-yl}ethanol (Compound B-3)

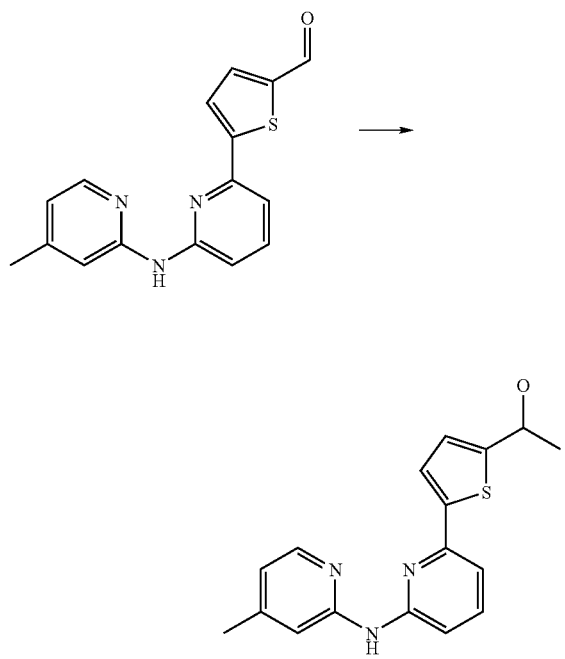

3M-Methylmagnesium bromide ether solution (0.19 ml, 0.57 mmol) was added to a solution of 5-[6-(4-methylpyridin-2-ylamino)pyridin-2-yl]thiophene-2-carboaldehyde (70 mg, 0.24 mmol) in tetrahydrofuran (4 ml) cooled with ice, and after that the mixture was stirred at room temperature for 3 hours in an Ar stream. Water was added to the reaction solution and the solution was extracted with ethyl acetate and the organic layer was washed with a saturated brine and dried over anhydrous magnesium sulfate. Subsequently, the residue obtained by concentration in vacuo was washed with isopropyl ether, dried in vacuo and the title compound (46 mg, 62%) was obtained.

1H-NMR (300 MHz, CDCl$_3$): 8.11 (1H, d, J=7.2 Hz), 7.89 (1H, s), 7.57 (1H, t, J=10.6 Hz), 7.42 (1H, d, J=4.8 Hz), 7.33 (1H, br), 7.19 (1H, d, J=9.2 Hz), 7.12 (1H, d, J=11.2 Hz), 6.99 (1H, dd, J=0.8, 1.2 Hz), 6.73 (1H, d, J=7.2 Hz), 5.15 (1H, q, J=8.5 Hz), 2.41(3H, s), 1.65(3H, d, J=8.8 Hz).

Example 22

Preparation of 1-{5-[6-(4-methylpyridin-2-ylamino) pyridin-2-yl]thiophen-2-yl}ethyl acetate acetic acid ester (Compound B-4);

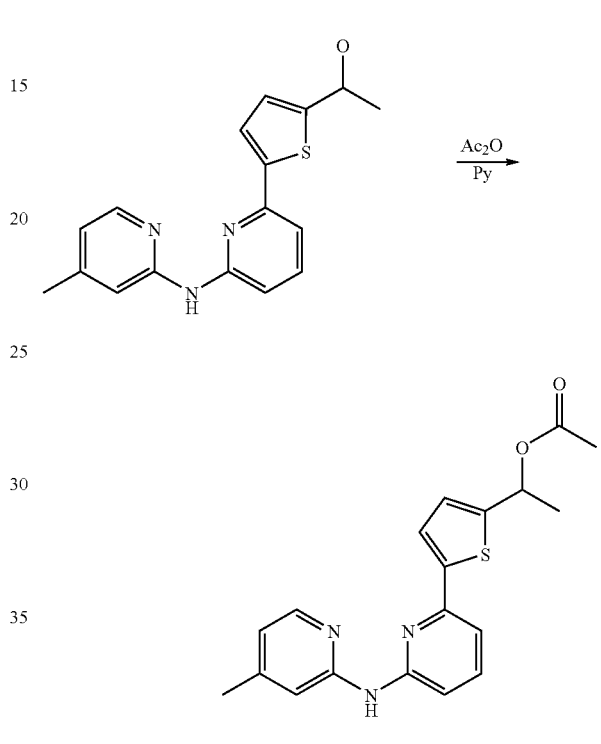

Acetic anhydride (0.02 ml, 0.19 mmol) was added to a solution of 1-{5-[6-(4-methylpyridin-2-ylamino)pyridin-2-yl]thiophen-2-yl}ethanol (40 mg, 0.13 mmol) in pyridine (2 ml) and the solution was stirred at 60° C. for 9 hours. Water was added to the reaction solution and the solution was extracted with ethyl acetate. After the organic layer was washed with a saturated brine and dried over anhydrous magnesium sulfate, the residue obtained by vacuum concentration was purified by flash chromatography on silica gel (n-hexane: ethyl acetate=2:1) and the title compound (10 mg, 22%) was obtained.

Herein below, other aminopyridine compounds having a thiophene ring were prepared similarly as in the above-mentioned common processes and/or the above Examples. The structures of these compounds have been identified by NMR measurement.

These compounds are shown in the following tables with the inhibitory activity value thereof.

Here, the sign "+++" of IC50(·M) means less than 0.1·M, and the sign "++" means not less than 0.1·M and less than 1.0·M, and the sign "+" means not less than 1.0·M.

TABLE 2-1

| Chem. Comp. No. | Chemical Compound | M.W. | sykHTRK ave IC50(mM) | human degranulation ave. IC50(μM) |
|---|---|---|---|---|
| B-1 | | 309.39 | +++ | + |
| B-2 | | 295.36 | +++ | + |
| B-3 | | 311.41 | ++ | ++ |
| B-4 | | 353.44 | ++ | + |
| B-5 | | 281.38 | ++ | + |

TABLE 2-2

| ID | MW | a | b |
|---|---|---|---|
| B-6 | 323.42 | ++ | ++ |
| B-7 | 338.43 | ++ | + |
| B-8 | 338.43 | ++ | + |
| B-9 | 338.43 | ++ | ++ |
| B-10 | 324.41 | +++ | ++ |

TABLE 2-3

| ID | MW | a | b |
|---|---|---|---|
| B-11 | 324.41 | +++ | ++ |
| B-12 | 297.38 | +++ | ++ |
| B-13 | 281.38 | ++ | + |
| B-14 | 324.45 | ++ | ++ |
| B-15 | 324.41 | +++ | ++ |

TABLE 2-4

| | | | | |
|---|---|---|---|---|
| B-16 | [structure with 5-chlorothiophene] | 301.80 | ++ | + |
| B-17 | [structure with 5-acetylthiophene, 4-methoxypyridine] | 325.39 | +++ | ++ |
| B-18 | [structure with methoxyimino-ethyl thiophene] | 338.43 | ++ | + |

TABLE 2-4-continued

| | | | | |
|---|---|---|---|---|
| B-19 | [structure with methyl thiophene-2-carboxylate] | 325.39 | ++ | + |
| B-20 | [structure with thiophene-2-carboxylic acid] | 311.36 | ++ | + |

TABLE 2-5

| | | | | |
|---|---|---|---|---|
| B-21 | [structure with 3-methyl-5-nitrothiophene] | 328.38 | + | + |
| B-22 | [structure with N,N-dimethylthiophene-2-carboxamide] | 338.43 | ++ | + |

TABLE 2-5-continued

| B-23 | [structure] | 310.38 | +++ | + |
| B-24 | [structure] | 354.43 | ++ | ++ |
| B-25 | [structure] | 310.42 | ++ | + |

TABLE 2-6

| B-26 | [structure] | 339.42 | ++ | + |
| B-27 | [structure] | 267.35 | ++ | + |

TABLE 2-6-continued
| | | | | |
|---|---|---|---|---|
| B-28 | 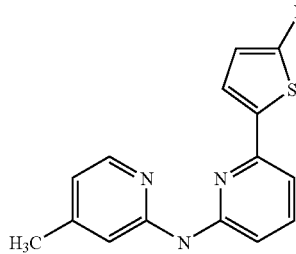 | 312.35 | ++ | + |
| B-29 | 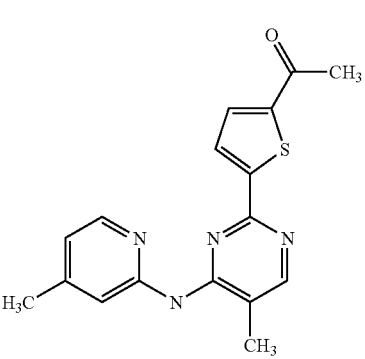 | 324.41 | ++ | + |
| B-30 | 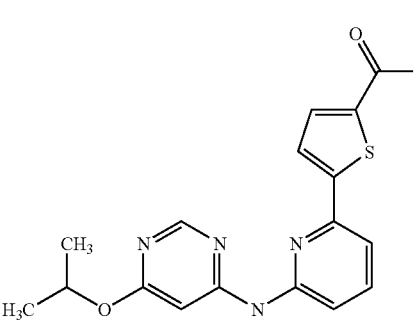 | 354.43 | +++ | + |
TABLE 2-7
| | | | | |
|---|---|---|---|---|
| B-31 | 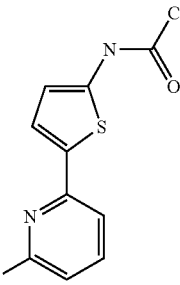 | 324.41 | +++ | ++ |

TABLE 2-7-continued

| B-32 | (structure) | 368.46 | + | + |

| B-33 | (structure) | 383.47 | ++ | + |

| B-34 | (structure) | 382.49 | ++ | + |

TABLE 2-8

| B-35 | (structure) | 354.43 | ++ | ++ |

TABLE 2-8-continued
| B-36 | 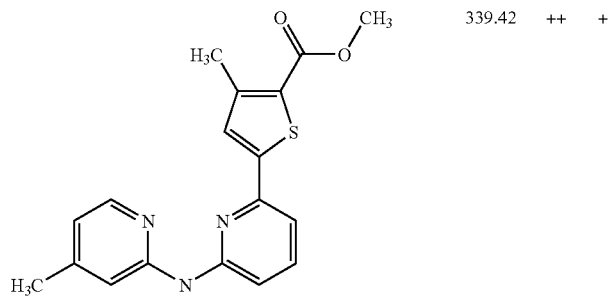 | 339.42 | ++ | + |
| B-37 | 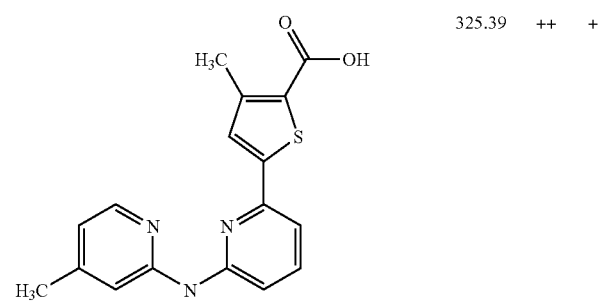 | 325.39 | ++ | + |
| B-38 | 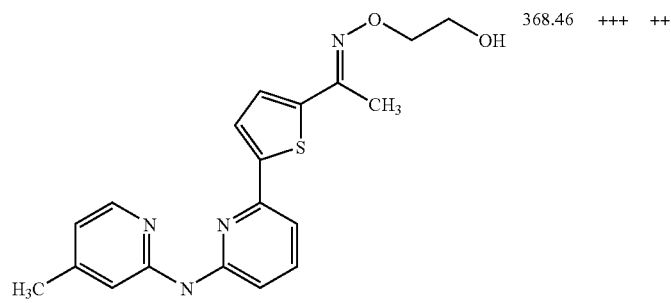 | 368.46 | +++ | ++ |
| B-39 | 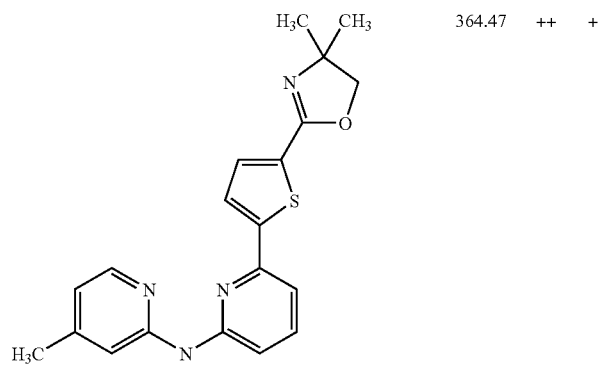 | 364.47 | ++ | + |

TABLE 2-9
| | | | | |
|---|---|---|---|---|
| B-40 | 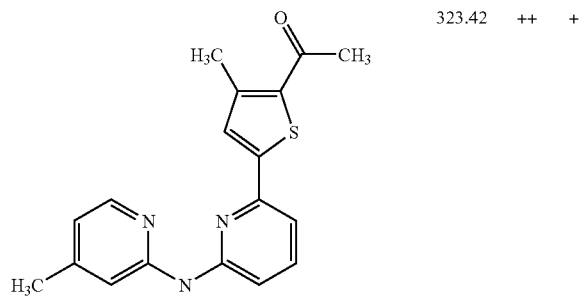 | 323.42 | ++ | + |
| B-41 | 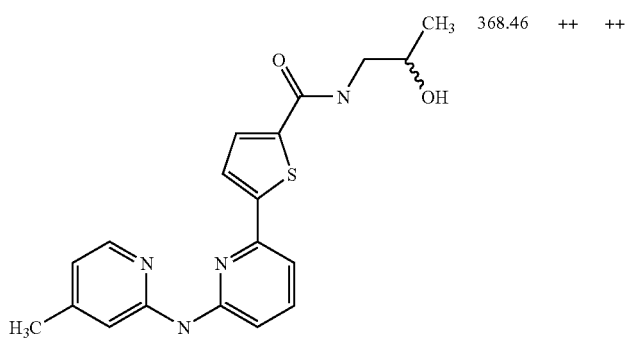 | 368.46 | ++ | ++ |
| B-42 | 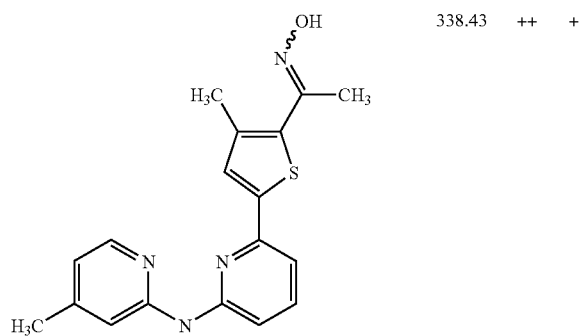 | 338.43 | ++ | + |
| B-43 | 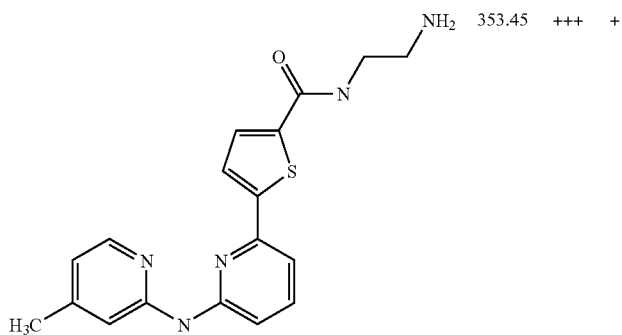 | 353.45 | +++ | + |

TABLE 2-10
| | | | | |
|---|---|---|---|---|
| B-44 | 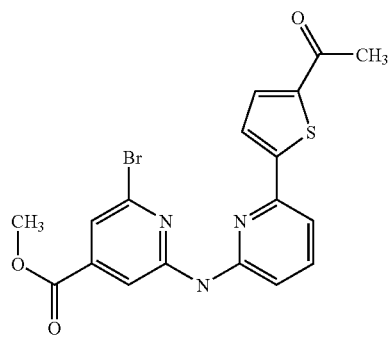 | 432.30 | + | + |
| B-45 | 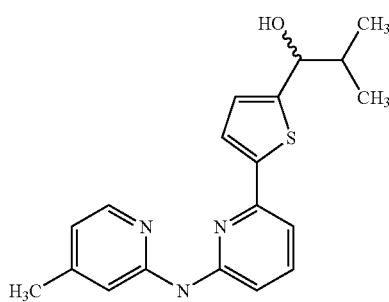 | 339.46 | ++ | + |
| B-46 | 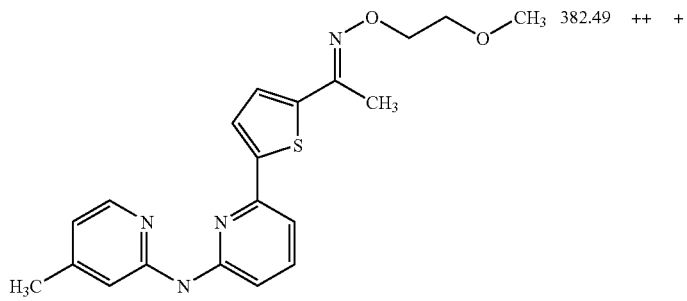 | 382.49 | ++ | + |
| B-47 | 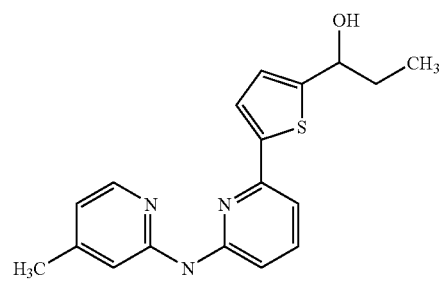 | 325.43 | ++ | ++ |
| B-48 | 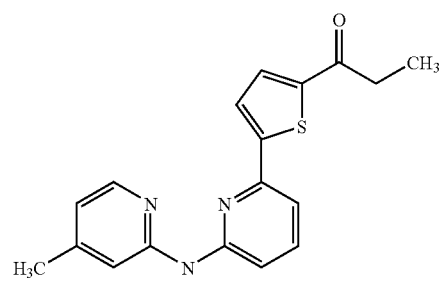 | 323.42 | ++ | + |

TABLE 2-11
| B-49 | 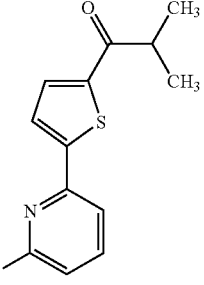 | 337.45 | ++ | + |
| B-50 | 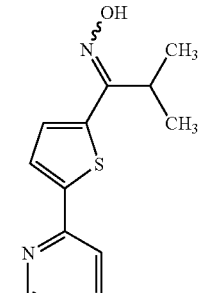 | 352.46 | ++ | + |
| B-51 | 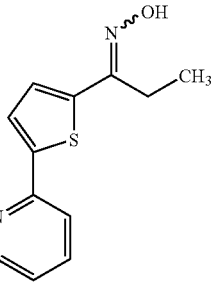 | 338.43 | +++ | + |
| B-52 | 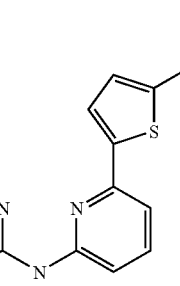 | 381.45 | +++ | + |
| B-53 | 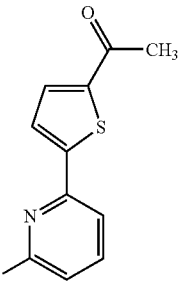 | 353.40 | +++ | + |

TABLE 2-12
| B-54 | 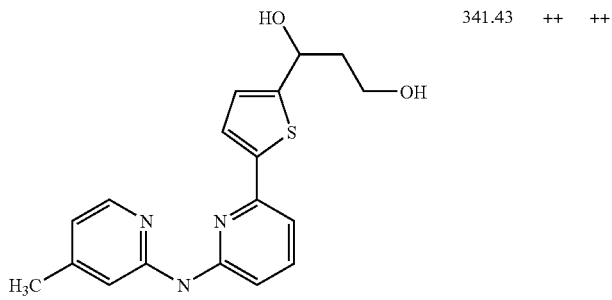 | 341.43 | ++ | ++ |
| B-55 | 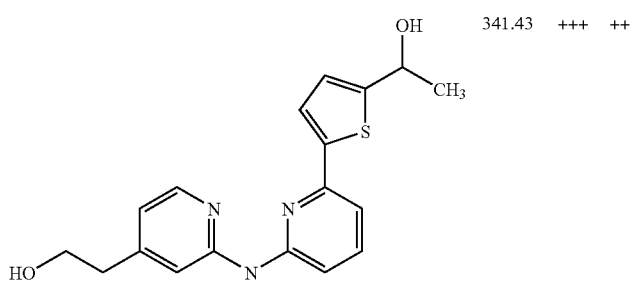 | 341.43 | +++ | ++ |
| B-56 | 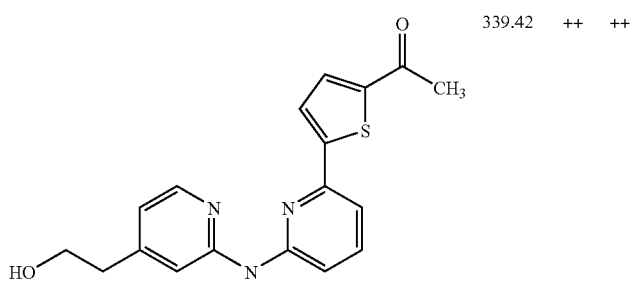 | 339.42 | ++ | ++ |
| B-57 | 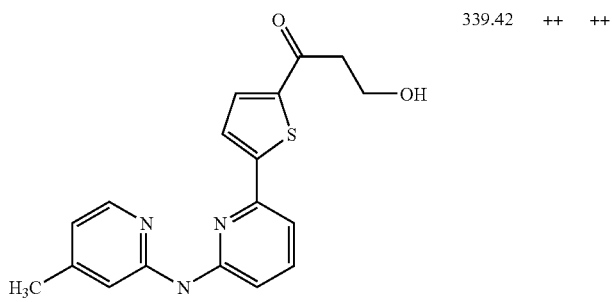 | 339.42 | ++ | ++ |
| B-58 | 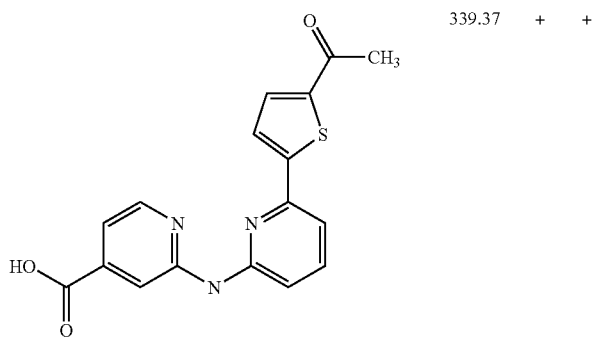 | 339.37 | + | + |

TABLE 2-13

| ID | Structure | MW | a | b |
|---|---|---|---|---|
| B-59 | 4-methylpyridin-2-yl-amino-pyridin-2-yl-thiophene-2-carbonitrile | 292.36 | ++ | + |
| B-60 | N'-hydroxy-thiophene-2-carboxamidine derivative | 325.39 | +++ | ++ |
| B-61 | 1,2,4-oxadiazol-5(4H)-one thiophene derivative | 351.39 | ++ | + |
| B-62 | 1-(thiophen-2-yl)ethanone with nitro-methylpyridinyl-amino-pyridinyl | 354.39 | + | + |
| B-63 | 1-(thiophen-2-yl)ethanone with isopropylamino-pyridinyl-amino-pyridinyl | 352.46 | + | + |

TABLE 2-14

| | | | |
|---|---|---|---|
| B-64 | [structure] | 340.41 | ++ ++ |
| B-65 | [structure] | 338.39 | ++ + |
| B-66 | [structure] | 348.43 | ++ + |

TABLE 2-14-continued

| | | | |
|---|---|---|---|
| B-67 | [structure] | 295.36 | ++ + |
| B-68 | [structure] | 309.39 | ++ + |

TABLE 2-15

| | | | |
|---|---|---|---|
| B-69 | [structure] | 339.42 | ++ ++ |
| B-70 | [structure] | 325.43 | ++ ++ |

TABLE 2-15-continued
| B-71 | 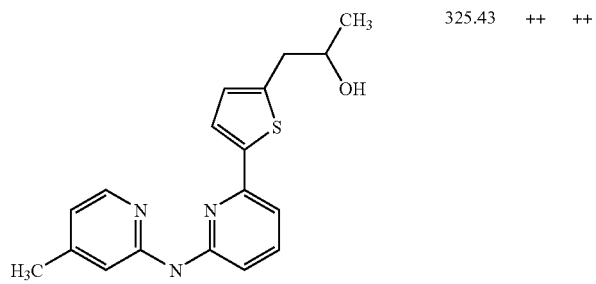 | 325.43 | ++ | ++ |
| B-72 | 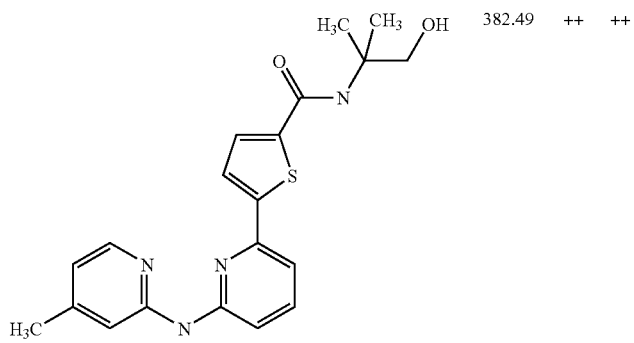 | 382.49 | ++ | ++ |
| B-73 | 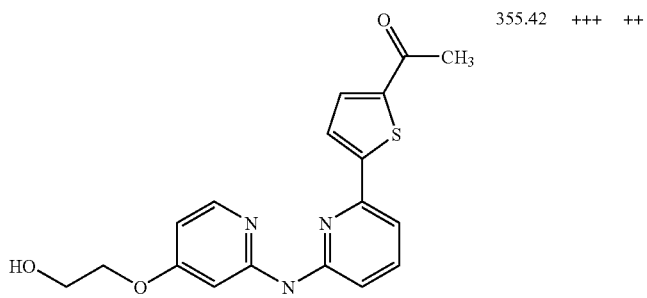 | 355.42 | +++ | ++ |
TABLE 2-16
| B-74 | 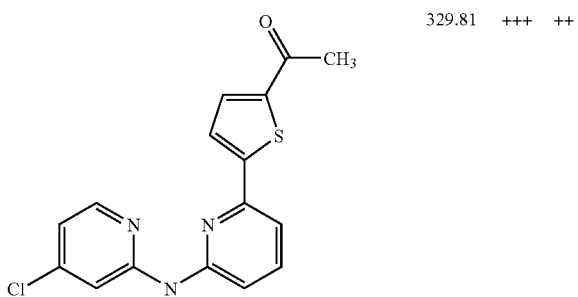 | 329.81 | +++ | ++ |

TABLE 2-16-continued

| ID | Structure | MW | A | B |
|---|---|---|---|---|
| B-75 | 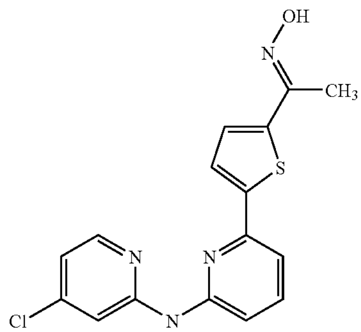 | 344.82 | +++ | ++ |
| B-76 | 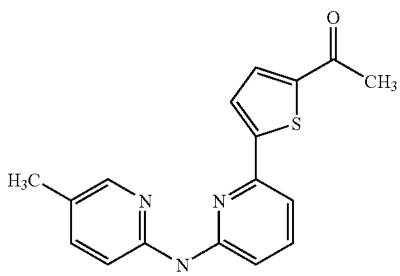 | 309.39 | + | + |
| B-77 | 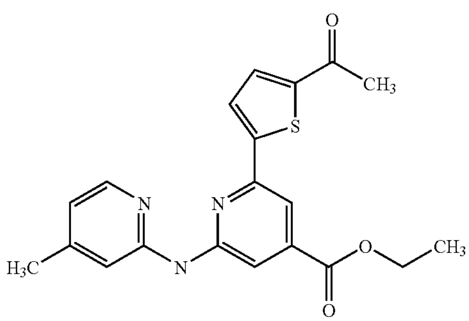 | 381.45 | + | + |
| B-78 | 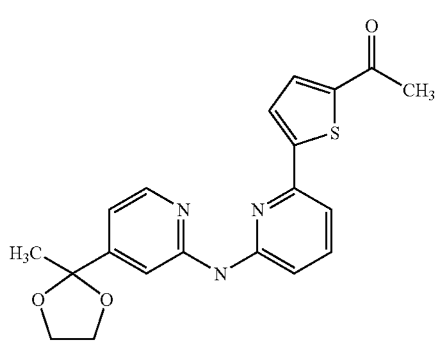 | 381.45 | ++ | ++ |

TABLE 2-17
| | | | | |
|---|---|---|---|---|
| B-79 | 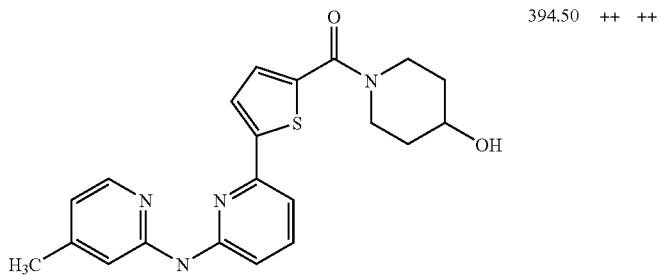 | 394.50 | ++ | ++ |
| B-80 | 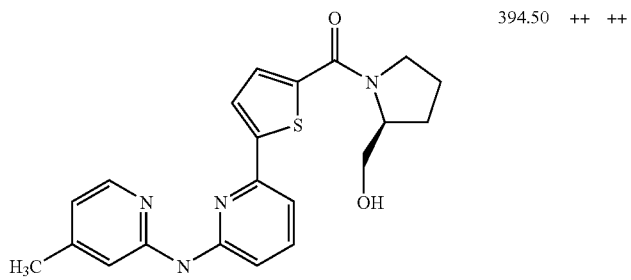 | 394.50 | ++ | ++ |
| B-81 | 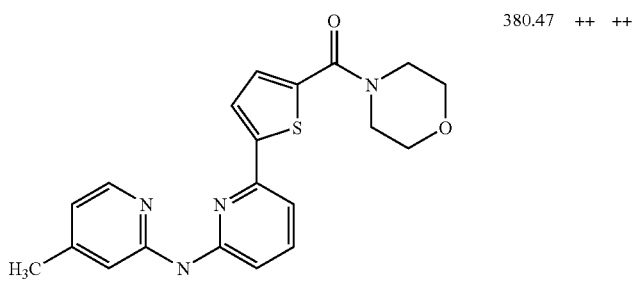 | 380.47 | ++ | ++ |
| B-82 | 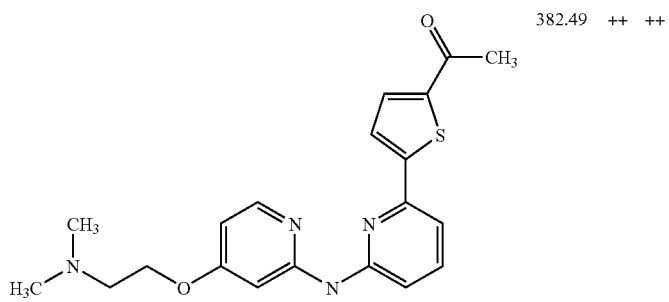 | 382.49 | ++ | ++ |
| B-83 | 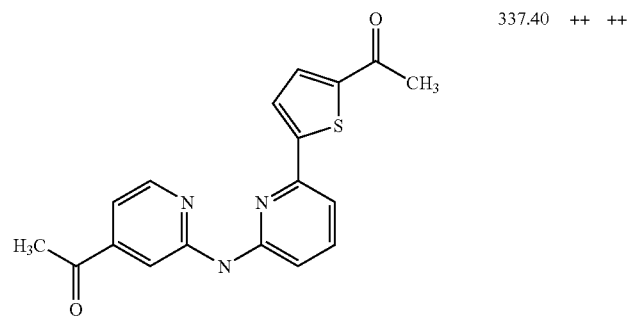 | 337.40 | ++ | ++ |

TABLE 2-18
| B-84 | 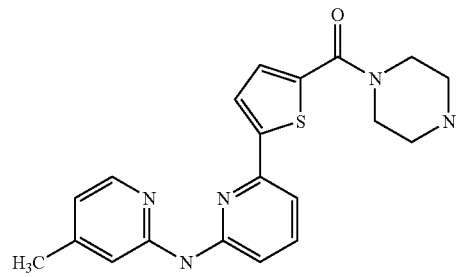 | 379.49 | +++ | ++ |
| B-85 | 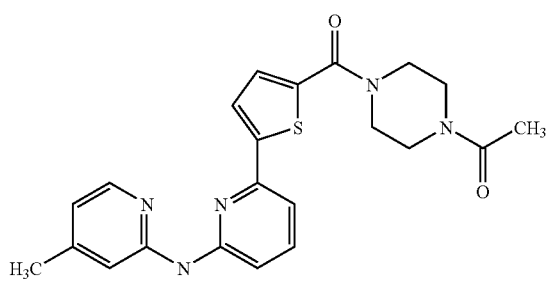 | 421.52 | ++ | ++ |
| B-86 | 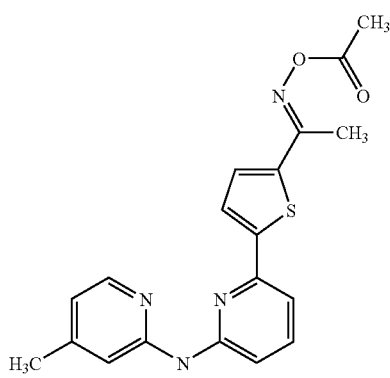 | 366.44 | ++ | ++ |
| B-87 | 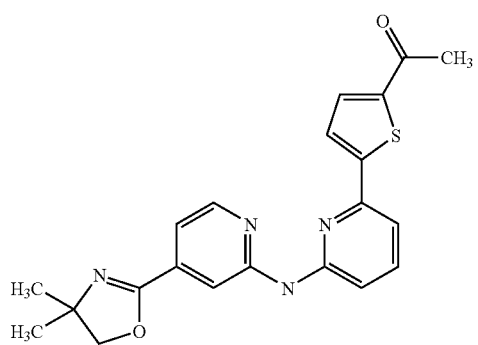 | 392.48 | +++ | ++ |

TABLE 2-19
| B-88 | 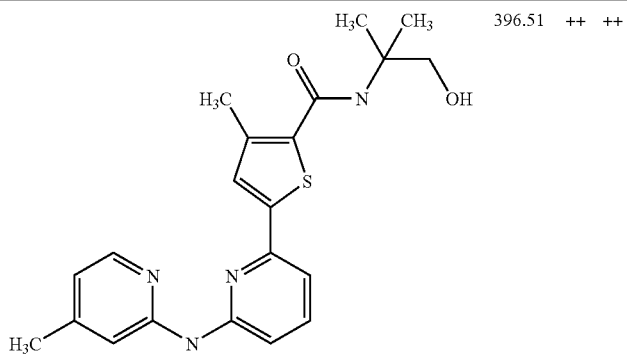 | 396.51 | ++ | ++ |
| B-89 | 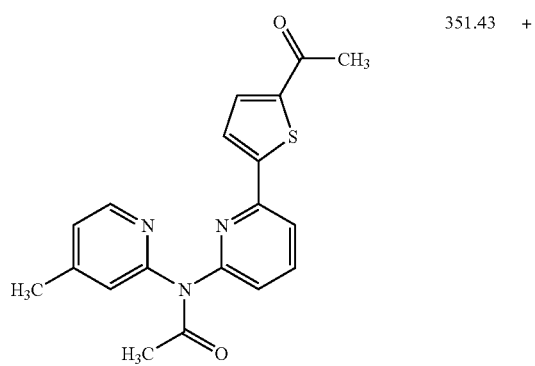 | 351.43 | + | |
| B-90 | 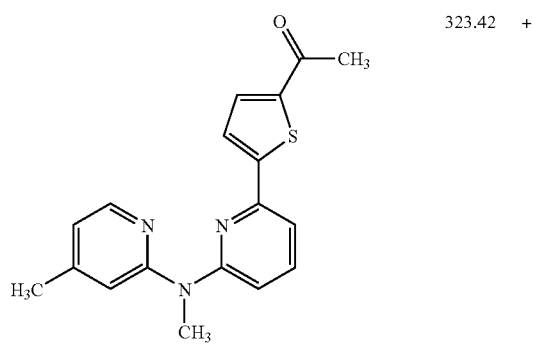 | 323.42 | + | |
| B-91 | 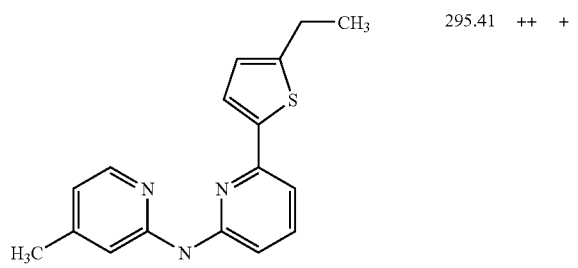 | 295.41 | ++ | + |

TABLE 2-20
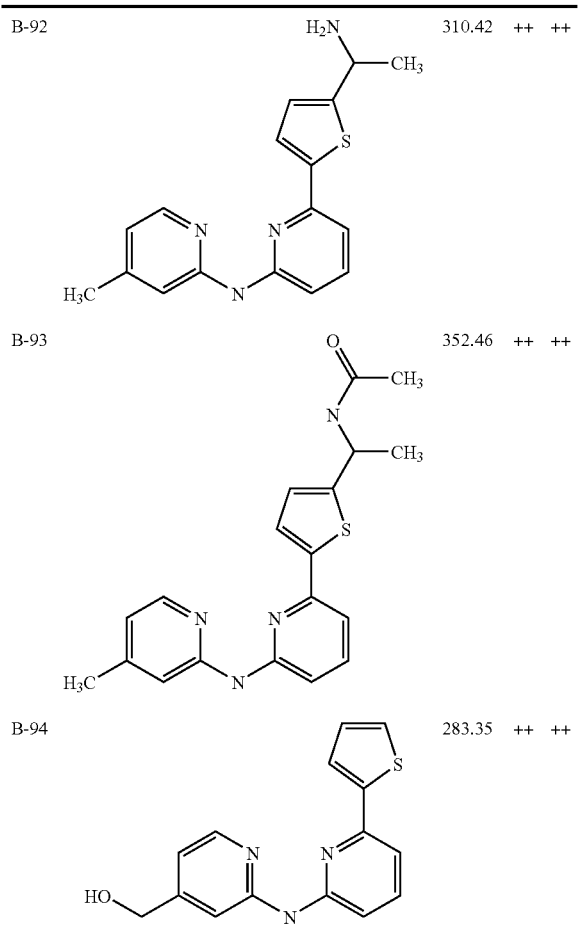
| | | |
|---|---|---|
| B-92 | 310.42 | ++ ++ |
| B-93 | 352.46 | ++ ++ |
| B-94 | 283.35 | ++ ++ |
TABLE 2-20-continued
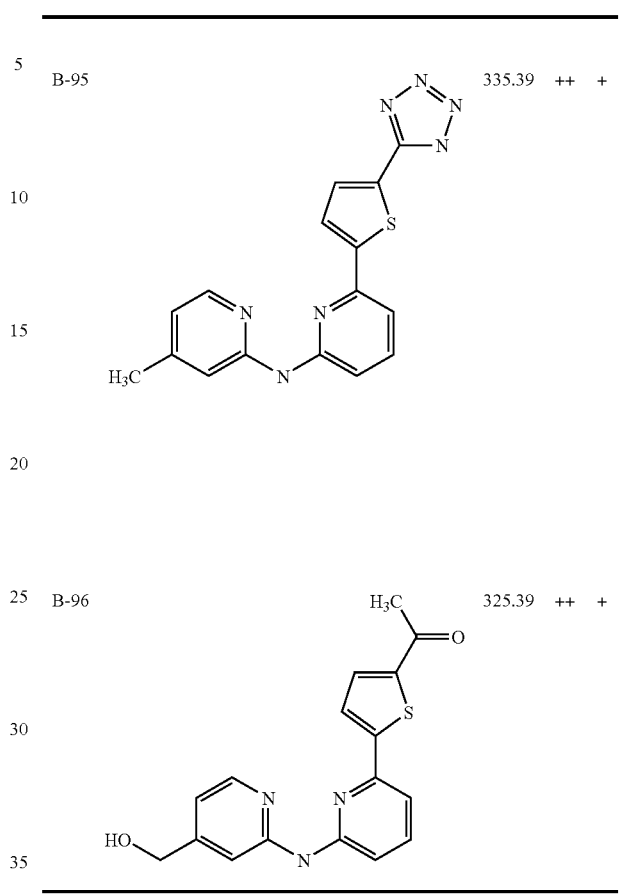
| | | |
|---|---|---|
| B-95 | 335.39 | ++ + |
| B-96 | 325.39 | ++ + |
TABLE 2-21
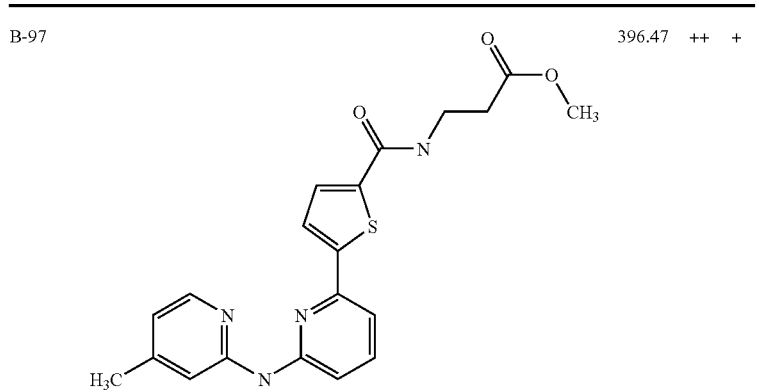
| | | |
|---|---|---|
| B-97 | 396.47 | ++ + |

TABLE 2-21-continued
B-98 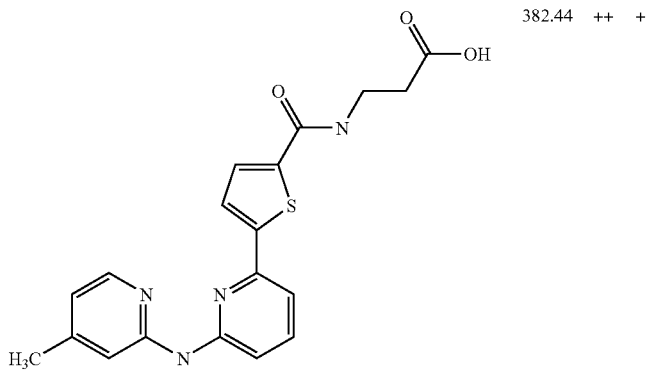 382.44 ++ +
B-99 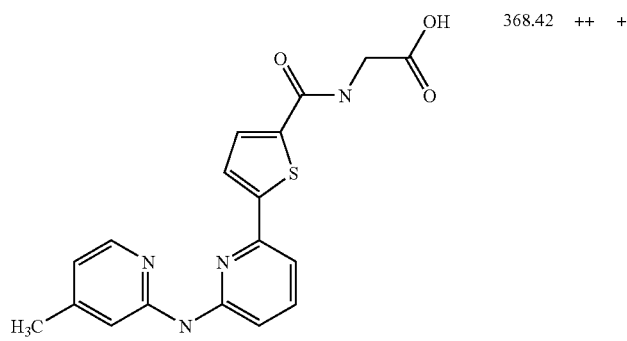 368.42 ++ +
B-100 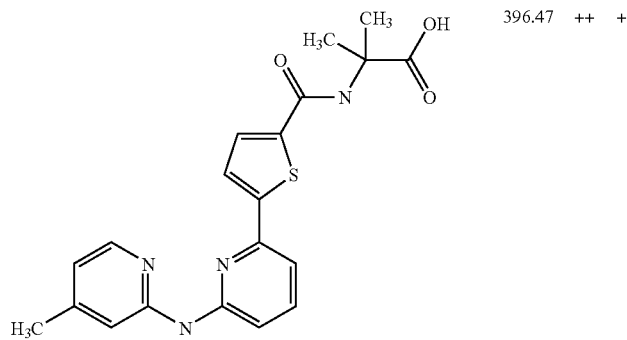 396.47 ++ +
TABLE 2-22
B-101 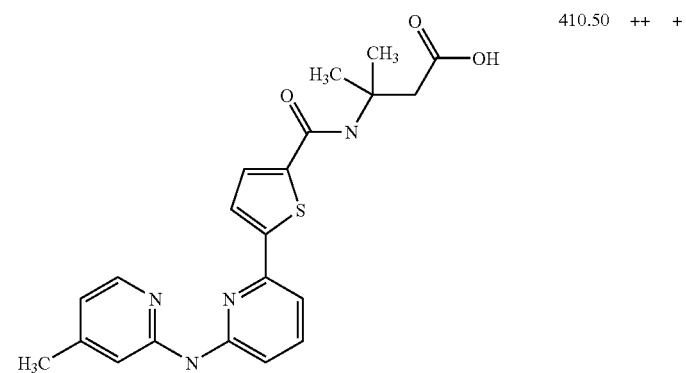 410.50 ++ +

TABLE 2-22-continued
| B-102 | 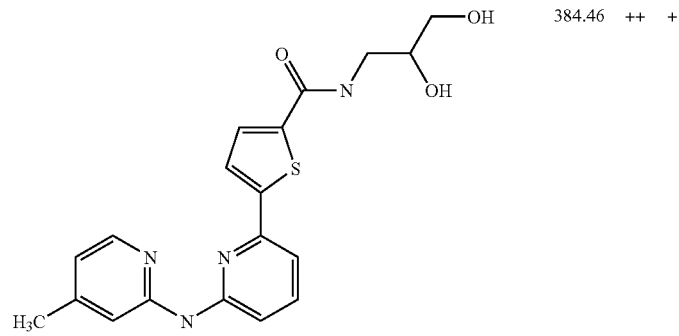 | 384.46 | ++ | + |
| B-103 | 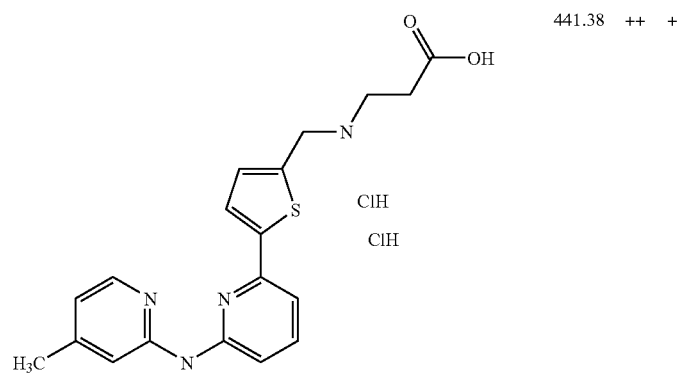 | 441.38 | ++ | + |
| B-104 | 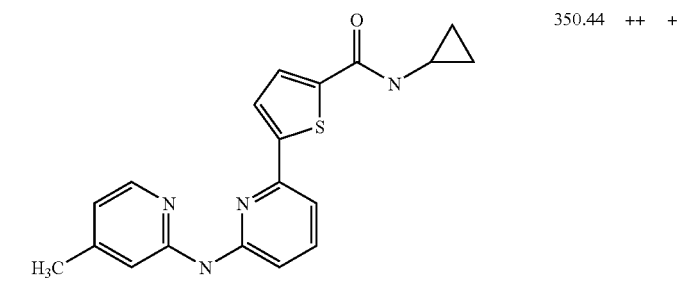 | 350.44 | ++ | + |
| B-105 | 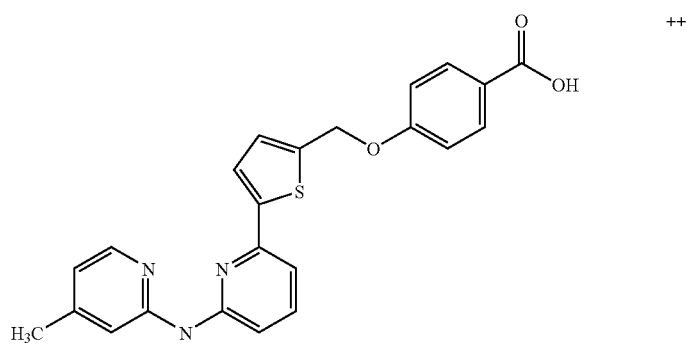 | | ++ | |

TABLE 2-23
| B-106 | 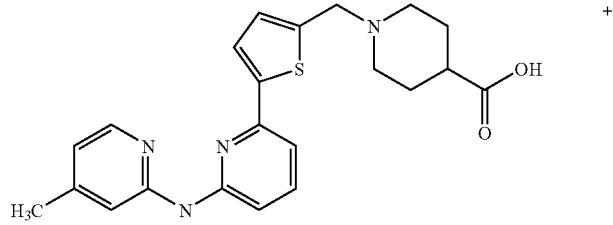 | ++ |
| B-107 | 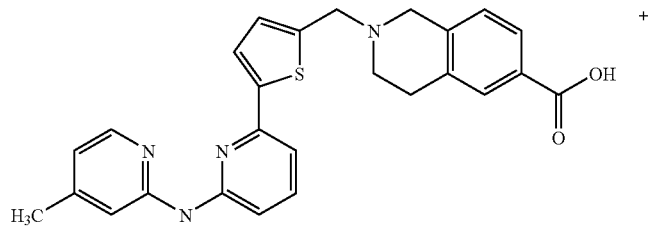 | ++ |
| B-108 | 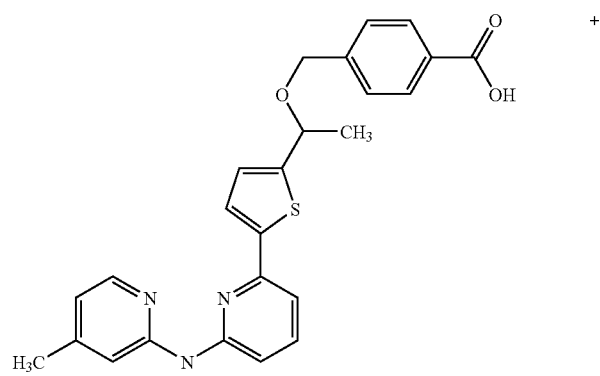 | ++ |
| B-109 | 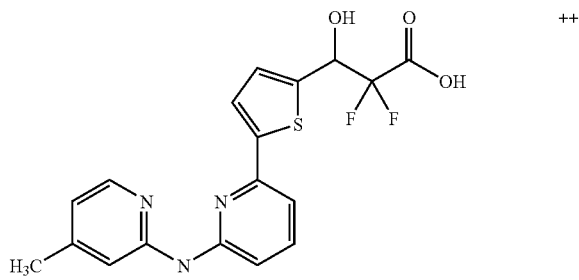 | +++ |
| B-110 | 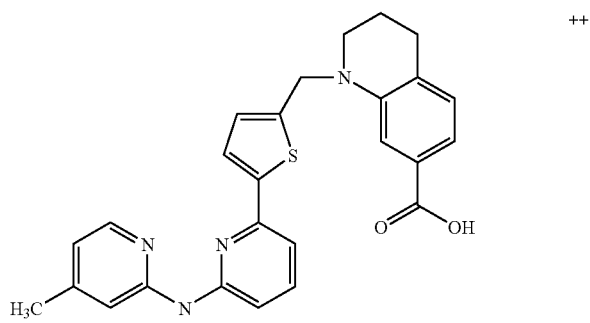 | ++ |

TABLE 2-24
| B-111 | 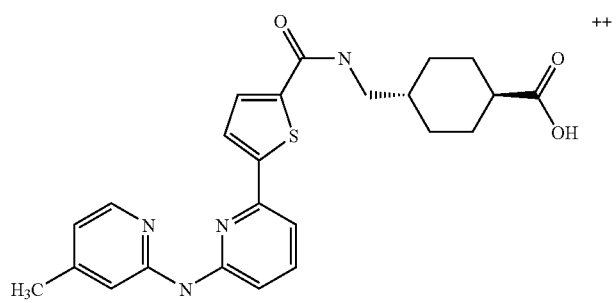 | ++ |
| B-112 | 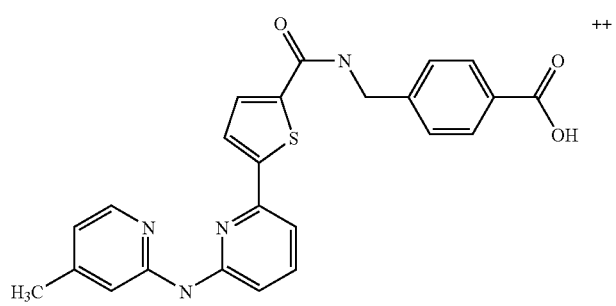 | ++ |
| B-113 | 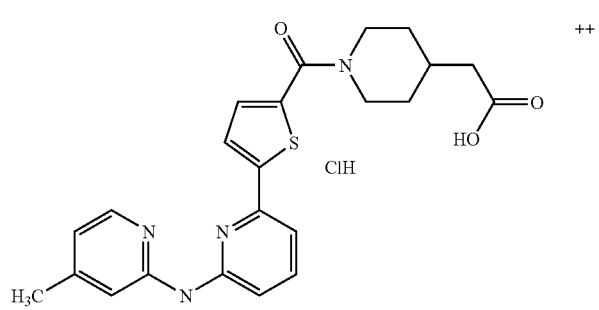 | ++ |
| B-114 | 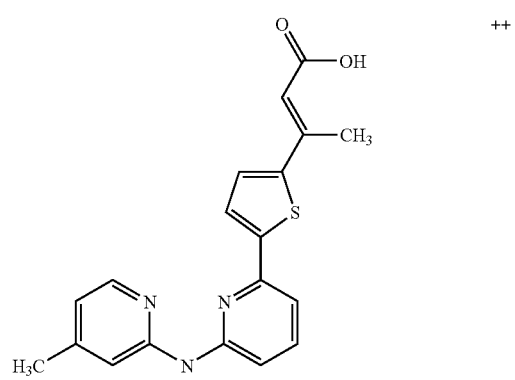 | ++ |
| B-115 | 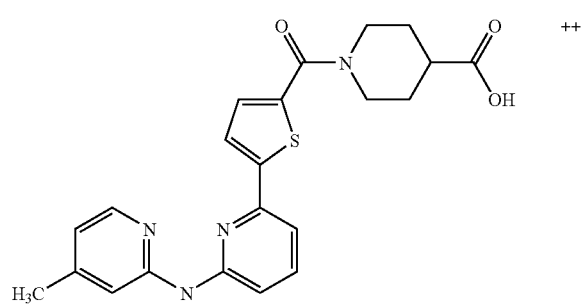 | ++ |

TABLE 2-25
B-116 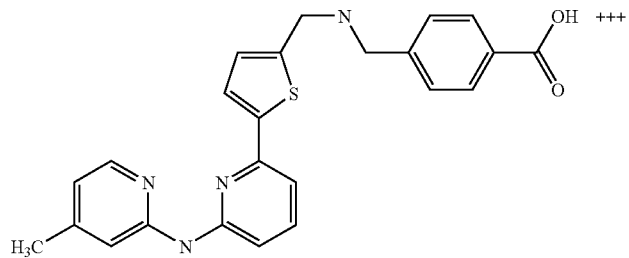 +++
B-117 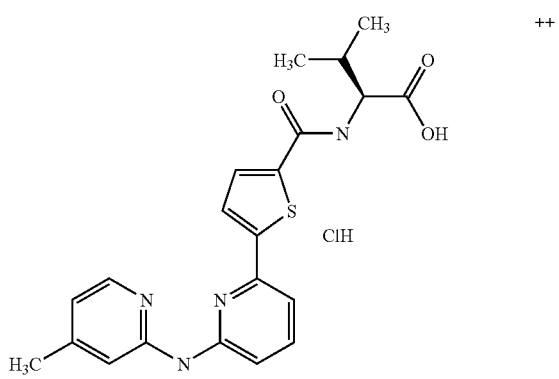 ++
B-118 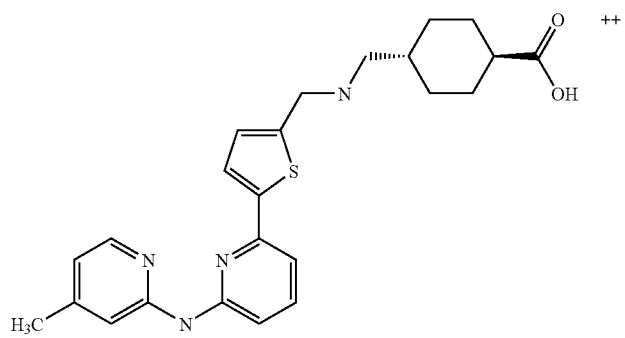 ++
B-119 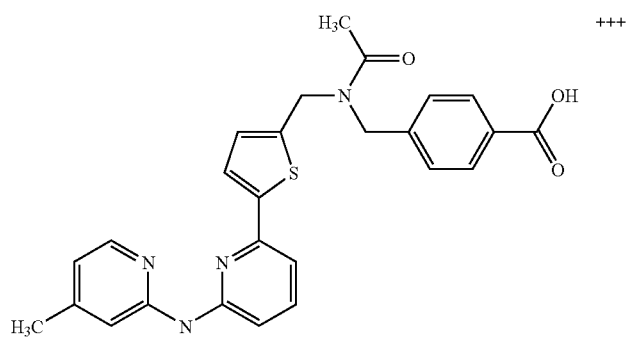 +++

TABLE 2-25-continued
| B-120 | 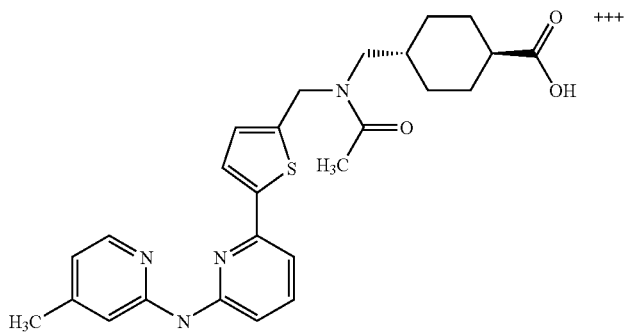 | +++ |
TABLE 2-26
| B-121 | 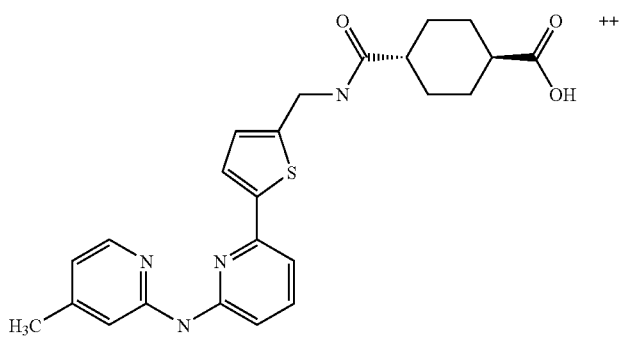 | ++ |
| B-122 | 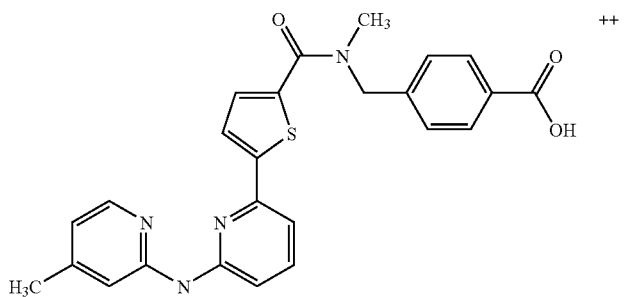 | ++ |
| B-123 | 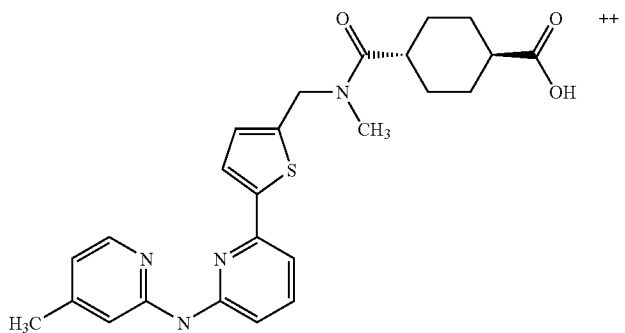 | ++ |

TABLE 2-26-continued
| B-124 | 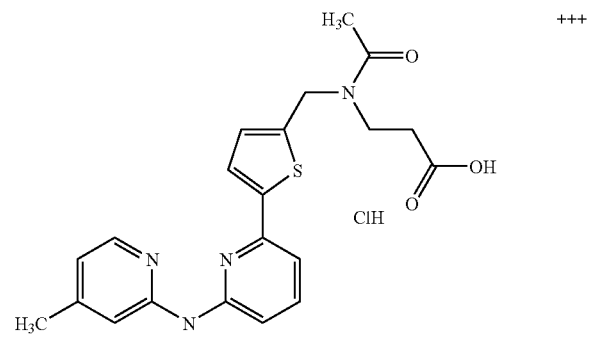 | +++ |
| B-125 | 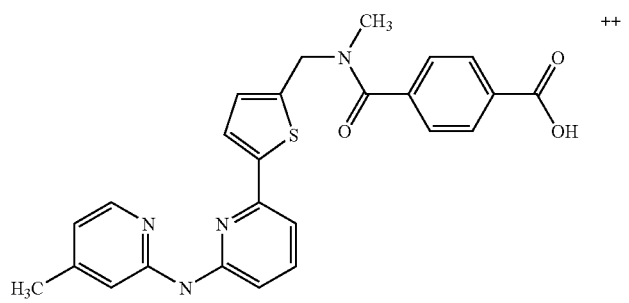 | ++ |
TABLE 2-27
| B-126 | 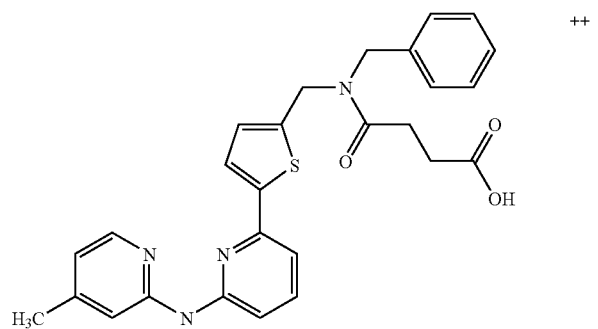 | ++ |
| B-127 | 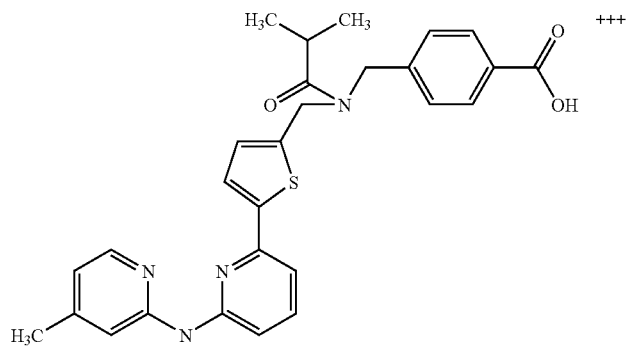 | +++ |

TABLE 2-27-continued

B-128     +++

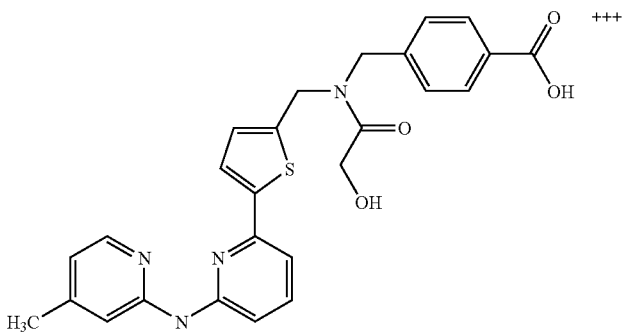

Syk kinase inhibitory activity of the compounds of the above example was examined. Test method is as follows and the inhibitory activity and the like are as described in the above tables.

Example 23

Syk Kinase Inhibition Test (HTRF Method)

After the compounds were serially diluted with dimethylsulfoxide (DMSO), 10 μL of those 10-fold diluted with kinase buffer (20 mM HEPES pH 7.0, 10 mM $MgCl_2$, 50 mM NaCl, 1 mM 2-ME, 0.05% BSA) was added to opti-plate HTRF-96 (Packard) (final DMSO concentration: 2%). 20 μL of a substrate solution (kinase buffer as mentioned above containing Syk Specific-Peptide Substrate Biot-EDPDYEWPSA-$NH_2$ (Peptide Laboratory) 625 nM, 250 μM ATP (SIGMA) was added (final substrate concentration 250 nM, 100 μM ATP), and further 20 μL of an enzyme solution (kinase buffer as mentioned above containing GST-Syk Full Protein (human) 16 nM) (final concentration 6.4 nM) was added and the mixture was immediately stirred with a plate shaker to start enzyme reaction. After reacted at room temperature (20 to 25° C.) for 30 minutes, the enzyme reaction was terminated by adding 100 μL/well of a buffer for terminating and detecting the reaction (30 mM HEPES pH 7.0, 150 mM KF, 0.15% BSA, 0.075% Tween-20, 75 mM EDTA) containing HTRF reagent (5 μg/ml XL665-Streptavidin (CIS bio), 170 ng/ml Eu(K)-anti-PhosphoTyrosin, PT-66 (CIS bio)) (final concentration 20 mM HEPES pH 7.0, 100 mM KF, 0.1% BSA, 0.05% Tween-20, 50 mM EDTA). After allowed to stand still at room temperature for 1 hour, inhibitory effect of a compound against Syk kinase enzymatic activity was evaluated by measuring 665/620 fluorescence ratio to excitation light at 337 nm by ARVO (Wallac).

Example 24

Degranulation Inhibition Test Using Cultured Human Mast Cells (1) Separation of Hematopoietic Stem Cells;

After 10 to 60 mL of umbilical cord blood collected with heparin was diluted with an equivalent amount of buffer (0.5% BSA, 2 mM EDTA/PBS-), it was superposed on Ficoll-Paque (Amersham Pharmacia Biotech) (Ficoll/Blood (1:2)) and mononuclear leukocyte fraction was collected by centri fuging it at 400 G (1350 rpm) 4° C. for 30 minutes. After centrifugal washing (1500 rpm, 5 min, 4° C.×3) with buffer, the number of cells was counted and 0.1 mL of CD34 Progenitor Cell Isolation Kit (Miltenyi Biotec), Reagent A1 (Fc blocking) was added for $1 \times 10^8$ cells. After agitation, 0.1 mL of Reagent A2 (CD34 antibody-hapten) was added (final volume 0.5 mL/$1 \times 10^8$ cells) and incubated at 9° C. for further 15 minutes after agitation. After centrifugal washing (1500 rpm, 5 min, 4° C.×3), it was resuspeded in a buffer (0.4 mL) and 0.1 mL of Reagent B (anti hapten antibody-microbeads) was added and agitated (final volume 0.5 mL/$1 \times 10^8$ cells) and incubated at 9° C. for further 15 minutes. After centrifugal washing (1500 rpm, 5 min, 4° C.×2), it was resuspeded in a buffer (0.5 mL) and loaded on CS column (Miltenyi Biotec) set in MACS (MAgnetic Cell Sorting system; Miltenyi Biotec, Daiichi Pure Chemicals) and washed with 30 mL of buffer to remove CD34⁻ cells. The column was separated from MACS and eluted with 30 mL of buffer and CD34⁺ cells bound to the column were collected and used as a hematopoietic stem cell population.

(2) Acquisition of Human Mast Cells by Long-Term Culturing of Hematopoietic Stem Cells;

The CD34⁺ cells separated in (1) were resuspended in Iscove's Modified Dulbecco's Medium (IMDM, Gibco) containing human (rh)SCF (1 μg/mL, Peprotech), rhIL-6 (0.5 μg/mL, Peprotech), rhIL-3 (10 ng/mL, Peprotech), 1% Insulin-Transferrin (Gibco), $5 \times 10^{-5}$M 2-ME (Gibco), 0.1% BSA (Sigma) in a density of $1 \times 10^6$ cells/ml and disseminated on 24-well culture plate with a dose of 0.1 mL/well and 0.9 ml of IMDM (Methocult SF$^{BIT}$ StemCell technology) containing 0.9% methyl cellulose was added and culturing was started. The above culture medium (excluding methyl cellulose) was added in a week and after that 100 μL/well of the above culture medium (further excluding IL-3) was added at an interval of every once a week so that cells were diluted to maintain $10^5$ cells/mL/well order and cultured more than about 8 weeks and thereby human culture mast cells were obtained.

(3) Expression Enhancement of FcεRI and Inhibition Test IgE Cross-Linking Stimulating Degranulation;

rhIL-4 (final concentration 1 ng/mL, R & D) and *Homo sapiens*(h) IgE (final concentration 0.5 μg/mL, CHEMICON) were added to the obtained human culture mast cells, and they were incubated for 5 days to enhance the expression of FcεRI. After incubation, cells were collected and, after centrifugal washing (IMDM), they were disseminated on 96-well culture plate in $5 \times 10^4$ cells/80 μL/well.

10 μL of a compound 10-fold diluted with IMDM after dissolved in DMSO (DMSO final concentration 0.1%) was added and reacted at 37° C. for 10 minutes. Further, 10 μL of anti-hIgE Ab (CHEMICON) adjusted to 100 μg/mL (final concentration 10 μg/mL) was added and degranulation was caused by being stimulated at 37° C. for 30 minutes. After centrifugation, 50 μL/well of the supernatant was collected and stored at −40° C. untill the quantity of degranulation was measured. The measurement of quantity of degranulation was performed using enzymatic activity of β-Hexosaminidase contained in the granulates as an index. That is, an equivalent amount of p-nitrophenyl-N-acetyl-β-D-glucosaminide (1 mM) (containing 0.1% Triton X-100) which is a substrate of β-Hexosaminidase was added to 50 μL of the culture filtrate, and after reacted at 37° C. for 2 hours, the reaction was terminated by using 100 μL of Carbonate buffer (0.1M, pH 10). Absorbance at a wavelength of 405 nm was measured and quantity (ratio) of degranulation was calculated from the value (Total) when the cells were crushed with water. Action of a test compound on the degranulation reaction was examined using this enzymatic activity as an index ($IC_{50}$ value (M)).

Example 25

Zap-70 Kinase Inhibition Test (HTRF Method)

After the compounds were serially diluted with DMSO, 10 μL of those 10-fold diluted with kinase buffer (20 mM HEPES pH 7.0, 10 mM $MgCl_2$, 50 mM NaCl, 1 mM 2-ME, 0.05% BSA) was added to opti-plate HTRF-96 (Packard) (final DMSO concentration: 2%).

20 μL of a substrate solution (kinase buffer as mentioned above containing Zap-70 Specific-Peptide Substrate Biot-EELQQDDYEMMEENLKKK-$NH_2$ (Peptide Laboratory) 625 nM, ATP (SIGMA) 25 μM) was added (final substrate concentration 250 nM, ATP 10 μM), and further 20 μL of an enzyme solution (kinase buffer as mentioned above containing Zap-70 active, UBI) 16 nM) (final concentration 6.4 nM) was added and the mixture was immediately stirred with a plate shaker to start enzyme reaction. After reacted at room temperature for 90 minutes, the enzyme reaction was terminated by adding 100 μL/well of a buffer for terminating and detecting the reaction (30 mM HEPES pH 7.0, 150 mM KF, 0.15% BSA, 0.075% Tween-20, 75 mM EDTA) containing HTRF reagent (5 μg/ml XL665-Streptavidin (CIS bio), 170 ng/ml Eu(K)-anti-PhosphoTyrosin, PT-66 (CIS bio)) (final concentration 20 mM HEPES pH 7.0, 100 mM KF, 0.1% BSA, 0.05% Tween-20, 50 mM EDTA). After allowed to stand still at room temperature for 1 hour, inhibitory effect of a compound against Zap-70 kinase enzymatic activity was evaluated by measuring 665/620 fluorescence ratio to excitation light at 337 nm by ARVO (Wallac).

INDUSTRIAL APPLICABILITY

The compound of the present invention is useful as an active ingredient of a pharmaceutical preparation. Since it has an Syk inhibitory effect, it is particularly useful as a preventive/therapeutic agent for diseases in which allergia or inflammatory reaction involved with Syk is a main etiological cause (asthma, nasal catarrh, atopic dermatitis, contact dermatitis, urticaria, food allergy, conjunctivitis, spring catarrh, etc.), diseases in which ADCC participates (autoimmune hemolytic anemia, myasthenia gravis, etc.) and thrombus in which platelet aggregation participate, etc.

The invention claimed is:
1. An aminopyridine compound represented by the following formula (I):

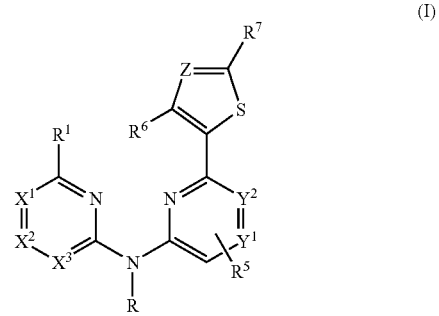

wherein $X^1$ represents
(1) —$C(R^2)$= or
(2) a nitrogen atom;
$X^2$ represents
(1) $C(R^3)$= or
(2) a nitrogen atom;
$X^3$ represents
(1) —$C(R^4)$= or
(2) a nitrogen atom;
Z represents
(1) a nitrogen atom or
(2) —$C(R^6)$=;
$Y^1$ represents
(1) —CH= or
(2) a nitrogen atom;
$Y^2$ represents
(1) —CH=, or,
(2) a nitrogen atom;
$R^1$ represents
(1) a hydrogen atom,
(2) a $C_{1-6}$ alkyl group or
(3) an acyl group;
$R^1$ represents
(1) a hydrogen atom,
(2) a $C_{1-6}$ alkyl group or
(3) a halogen atom;
$R^2$ represents
(1) a hydrogen atom,
(2) a $C_{1-6}$ alkyl group or
(3) a halogen atom;
$R^3$ represents
(1) a hydrogen atom,
(2) a halogen atom,
(3) —$N(R^{31})(R^{32})$,
wherein $R^{31}$ and $R^{32}$ represent a hydrogen atom or a $C_{1-6}$ alkyl group,
(4) a hydroxyl group,
(5) a $C_{1-6}$ alkoxy group, wherein the $C_{1-6}$ alkyl group in the $C_{1-6}$ alkoxy group may be substituted with a substituent selected from the following group Aa:
[Group Aa]
(a) a hydroxyl group,
(b) a $C_{1-6}$ alkoxy group,
(c) —$N(R^{31})(R^{32})$,
wherein $R^{31}$ and $R^{32}$ are the same as above,
(d) —$COOR^{33}$,
wherein $R^{33}$ represents a hydrogen atom or a $C_{1-6}$ alkyl group, (e) —CO—N($R^{31}$)($R^{32}$),
wherein $R^{31}$ and $R^{32}$ are the same as above, and
(f) a halogen atom,
(6) an aralkoxy group,
(7) an acyl group,
(8) a saturated heterocyclic group or an aromatic heterocyclic group, wherein the heterocyclic group may be substituted with a $C_{1-6}$ alkyl group, and the saturated heterocyclic group may partially have a double bond,
(9) a $C_{1-6}$ alkyl group, wherein the $C_{1-6}$ alkyl group may be substituted with a substituent selected from the following group Ab:
[group Ab]
(a) a hydroxyl group,
(b) —COO$R^{33}$, wherein $R^{33}$ is the same as the above,
(c) —CO—N($R^{31}$)($R^{32}$), wherein $R^{31}$ and $R^{32}$ are the same as above, and
(d) a halogen atom,
(10) —COO$R^{33}$,
wherein $R^{33}$ is the same as the above,
(11) —CO—N($R^{31}$)($R^{32}$), wherein $R^{31}$ and $R^{32}$ are the same as above, or
(12) a cyano group;
$R^3$ together with $R^2$ may form —C=C—C=C—;
$R^4$ represents
(1) a hydrogen atom,
(2) a $C_{1-6}$ alkyl group or
(3) a nitro group;
$R^5$ represents
(1) a hydrogen atom,
(2) a $C_{1-6}$ alkyl group, wherein the $C_{1-6}$ alkyl group may be substituted with a hydroxyl group or a $C_{1-6}$ alkoxy group,
(3) —COO$R^{51}$,
wherein $R^{51}$ represents a hydrogen atom or a $C_{1-6}$ alkyl group, or
(4) a nitro group;
$R^6$ and $R^{6'}$ may be the same or different and each represent
(1) a hydrogen atom,
(2) a $C_{1-6}$ alkyl group, wherein the $C_{1-6}$ alkyl group may be substituted with a hydroxyl group or a $C_{1-6}$ alkoxy group,
(3) —COO$R^{61}$,
wherein $R^{61}$ represents a hydrogen atom or a $C_{1-6}$ alkyl group,
(4) —N($R^{62}$)($R^{63}$),
wherein $R^{62}$ and $R^{63}$ may be the same or different and each represent a hydrogen atom, a $C_{1-6}$ alkyl group, a $C_{1-6}$ alkoxy group or an acyl group,
(5) —CO—N($R^{62}$)($R^{63}$),
wherein $R^{62}$ and $R^{63}$ are the same as above, or
(6) an acyl group;
$R^7$ represents a hydrogen atom, a halogen atom, a nitro group, a cyano group, or the following $R^a$, $R^b$, $R^c$, $R^d$, $R^e$, $R^f$, $R^g$ or $R^h$;
$R^a$ represents —$C_pH_{2(p-1)}$($R^{a1}$)($R^{a2}$)—O—$R^{a3}$,
wherein
(1) p represents an integer from 1 to 6,
(2) $R^{a1}$ represents a hydrogen atom or a $C_{1-6}$ alkyl group,
(3) $R^{a2}$ represents a hydrogen atom, a $C_{1-6}$ alkyl group, an aralkyl group or an aryl group, wherein the $C_{1-6}$ alkyl group, aralkyl group and aryl group may be substituted with a substituent respectively selected from the following group Ba:
[Group Ba]
(a) a hydroxyl group,
(b) a carboxy group,
(c) a $C_{1-6}$ alkoxycarbonyl group,
(d) an amino group,
(e) a $C_{1-6}$ alkylamino group,
(f) a di-$C_{1-6}$ alkylamino group,
(g) an acyloxy group and
(h) a halogen atom,
(4) $R^{a3}$ represents a hydrogen atom, an acyl group, —CON($R^{a31}$)($R^{a32}$) or a $C_{1-6}$ alkyl group, wherein the alkyl group may be substituted with a $C_{1-6}$ alkoxycarbonyl group or —CON($R^{a31}$)($R^{a32}$),
wherein $R^{a31}$ and $R^{a32}$ may be the same or different and each represent
a hydrogen atom,
an acyl group, wherein the acyl group may be substituted with a hydroxyl group or a carboxy group,
a $C_{1-6}$ alkyl group wherein $C_{1-6}$ alkyl group may be substituted with a substituent selected from a hydroxyl group, a carboxy group, a $C_{1-6}$ alkoxycarbonyl group, a carbamoyl group, a $C_{1-6}$ alkylcarbamoyl group and a di-$C_{1-6}$ alkylcarbamoyl group,
a $C_{1-6}$ alkoxycarbonyl group or
a $C_{1-6}$ alkylsulfonyl group, or
$R^{a31}$ and $R^{a32}$ together with the adjacent nitrogen atom may form a 5- or 6-membered saturated heterocyclic group which has one or more nitrogen atoms, wherein the saturated heterocyclic group may be substituted with a hydroxyl group, an oxo group, an aralkylamino group or an acylamino group;
$R^b$ represents —$C_pH_{2(p-1)}$($R^{b1}$)($R^{b2}$)—N—($R^{b3}$)($R^{b4}$),
wherein
(1) p represents an integer from 1 to 6,
(2) $R^{b1}$ represents a hydrogen atom or a $C_{1-6}$ alkyl group,
(3) $R^{b2}$ represents
(a) a hydrogen atom,
(b) an aralkyl group, wherein the aralkyl group may be substituted with a hydroxyl group, a $C_{1-6}$ alkoxy group which may be substituted with a hydroxyl group, an aralkyloxy group or —N($R^{b21}$)($R^{b22}$),
wherein $R^{b21}$ and $R^{b22}$ may be the same or different and each represent a hydrogen atom, a $C_{1-6}$ alkyl group, an acyl group, a carbonyl group, a $C_{1-6}$ alkoxycarbonyl group or an aralkoxycarbonyl group,
(c) an aryl group, wherein the aryl group may be substituted with a hydroxyl group, a $C_{1-6}$ alkoxy group or an aralkoxy group, or
(d) a $C_{1-6}$ alkyl group, wherein the $C_{1-6}$ alkyl group may be substituted with a substituent selected from the following group Ca:
[Group Ca]
a hydroxyl group,
an aralkoxy group,
—COO$R^{b23}$,
wherein $R^{b23}$ represents a hydrogen atom, a $C_{1-6}$ alkyl group or an aralkyl group,
—N($R^{b21}$)($R^{b22}$), wherein $R^{b21}$ and $R^{b22}$ are the same as above, and
an aryl group, wherein the aryl may be substituted with a substituent selected from a hydroxyl group, a $C_{1-6}$ alkoxy group, wherein the $C_{1-6}$ alkoxy group may be substituted with a hydroxyl group, an aralkoxy group, —N($R^{b21}$)($R^{b22}$) and an aralkoxycarbonylamino group,
wherein $R^{b21}$ and $R^{b22}$ are the same as above, and
(4) $R^{b3}$ and $R^{b4}$ may be the same or different and each represent
(a) a hydrogen atom,
(b) a $C_{1-6}$ alkyl group, wherein the $C_{1-6}$ alkyl group may be substituted with a substituent selected from a hydroxyl group, a carboxy group, a $C_{1-6}$ alkoxycarbonyl group, a carbamoyl group, a $C_{1-6}$ alkylcarbamoyl group and a di-$C_{1-6}$ alkylcarbamoyl group, (c) —COOR$^{b41}$, wherein R$^{b41}$ represents a hydrogen atom, a $C_{1-6}$ alkyl group or an aralkyl group, (d) —COR$^{b42}$, wherein R$^{b42}$ represents a $C_{1-6}$ alkyl group, wherein the $C_{1-6}$ alkyl group may be substituted with a substituent selected from a hydroxyl group, a carboxy group, a $C_{1-6}$ alkoxycarbonyl group, an acyl group, an acyloxy group, an amino group and an acylamino group, a $C_{3-8}$ cycloalkyl group, wherein the $C_{3-8}$ cycloalkyl group may be substituted with a hydroxyl group, a 5- or 6-membered aromatic heterocyclic group having 1 to 4 hetero atoms, wherein the heterocyclic group may be substituted with a $C_{1-6}$ alkyl group, or an aryl group, wherein the aryl group may be substituted with a hydroxyl group, (e) —CO—N(R$^{b43}$)(R$^{b44}$), wherein R$^{b43}$ and R$^{b44}$ may be the same or different and each represent a hydrogen atom, a $C_{1-6}$ alkyl group or an acyl group, or (f) —SO$_2$—R$^{b45}$, wherein R$^{b45}$ represents a $C_{1-6}$ alkyl group;

R$^c$ represents —C(=N—R$^{c1}$)—R$^{c2}$, wherein (1) R$^{c1}$ represents (a) a hydroxyl group, (b) a $C_{1-6}$ alkoxy group, wherein the $C_{1-6}$ alkyl group in the $C_{1-6}$ alkoxy group may be substituted with a hydroxyl group or a $C_{1-6}$ alkoxy group, or (c) an acyloxy group, and (2) R$^{c2}$ represents a $C_{1-6}$ alkyl group or an amino group;

R$^d$ represents —C(=O)—R$^{d1}$, wherein R$^{d1}$ represents (1) a hydrogen atom, (2) a $C_{1-6}$ alkyl group, wherein the $C_{1-6}$ alkyl group may be substituted with a hydroxyl group, a carboxy group or a $C_{1-6}$ alkoxycarbonyl group, (3) a hydroxyl group, (4) a $C_{1-6}$ alkoxy group, and (5) —N(R$^{d11}$)(R$^{d12}$), wherein R$^{d11}$ and R$^{d12}$ may be the same or different and each represent a substituent selected from the following group Da:

[Group Da]

(a) a hydrogen atom, (b) a $C_{1-6}$ alkoxy group, (c) a $C_{3-8}$ cycloalkyl group, wherein the cycloalkyl group may be substituted with a hydroxyl group, and (d) a $C_{1-6}$ alkyl group, wherein the $C_{1-6}$ alkyl group may be substituted with a hydroxyl group, a carboxy group, a $C_{1-6}$ alkoxycarbonyl group or an amino group, or R$^{d11}$ and R$^{d12}$ together with the adjacent nitrogen atom may form a 5- or 6-membered saturated heterocyclic group which has one or more nitrogen atoms, wherein the saturated heterocyclic group may be substituted with a $C_{1-6}$ alkyl groups, wherein the alkyl group may be substituted with a carboxy group, or a carboxy group;

R$^e$ represents the following Ring A:

wherein Ring A represents a 5- or 6-membered saturated heterocyclic group having 1 or 2 hetero atoms, a 5- or 6-membered aromatic heterocyclic group having 1 to 4 hetero atoms, a 9- to 12-membered condensed aromatic heterocyclic group having 1 or 2 hetero atoms which may be partially saturated a $C_{3-8}$ cycloalkyl group or a $C_{7-11}$ spiroheterocycloalkyl group having 1 or 2 hetero atoms);

which may be substituted with a substituent respectively selected from the following group Ea:

[Group Ea]

(a) —OR$^{e1}$, wherein R$^{e1}$ represents a hydrogen atom, a $C_{1-6}$ alkyl group, the $C_{1-6}$ alkyl group may be substituted with a carboxy group or —CON(R$^{e11}$)(R$^{e12}$), wherein R$^{e11}$ and R$^{e12}$ may be the same or different and each represent a hydrogen atom or a $C_{1-6}$ alkyl group, an acyl group, a carbamoyl group or an aralkyl group, (b) —COOR$^{e2}$, wherein R$^{e2}$ represents a hydrogen atom or a $C_{1-6}$ alkyl group, (c) —CO—N(R$^{e41}$)(R$^{e42}$), wherein R$^{e41}$ and R$^{e42}$ may be the same or different and each represent a hydrogen atom, a $C_{1-6}$ alkyl group, wherein the $C_{1-6}$ alkyl group may be substituted with a substituent selected from a hydroxyl group, a $C_{1-6}$ alkoxy group, an amino group, a $C_{1-6}$ alkylamino group, a di-$C_{1-6}$ alkylamino group, a halogen atom, a carboxy group, a carbamoyl group, a $C_{1-6}$ alkylcarbamoyl group, a di-$C_{1-6}$ alkylcarbamoyl group or a 5- or 6-membered saturated heterocyclic group or aromatic heterocyclic group having 1 or 2 hetero atoms, a hydroxyl group, a $C_{1-6}$ alkoxy group, a $C_{5-6}$ cycloalkyl group, wherein the $C_{5-6}$ cycloalkyl group may be substituted with a hydroxyl group or a $C_{1-6}$ alkyl group, wherein the $C_{1-6}$ alkyl group may be substituted with a hydroxyl group, or a $C_{1-6}$ alkylsulfonyl group, (d) —COR$^{e3}$, wherein R$^{e3}$ represents a hydrogen atom, a $C_{1-6}$ alkyl group, wherein the $C_{1-6}$ alkyl group may be substituted with a substituent selected from a hydroxyl group, a carboxy group, a $C_{1-6}$ alkoxycarbonyl group and a $C_{1-6}$ alkylsulfonyl group, a 5- or 6-membered saturated heterocyclic group or aromatic heterocyclic group having 1 or 2 hetero atoms, wherein the saturated heterocyclic group or aromatic heterocyclic group may be substituted with a hydroxyl group, an oxo group, a carboxy group, a $C_{1-6}$ alkoxy group, wherein the $C_{1-6}$ alkoxy group may be substituted with a carbamoyl group, a carbamoyl group, wherein the carbamoyl group may be substituted with a hydroxyl group, an acyl group, acyloxy group, an amino group, an acylamino group, wherein the acylamino group may be substituted with a hydroxyl group or carbamoyl group, a $C_{1-6}$ alkylamino group, a di-$C_{1-6}$ alkylamino group, a $C_{1-6}$ alkylsulfonylamino group, a 5- or 6-membered saturated heterocyclic group or aromatic heterocyclic group and a $C_{1-6}$ alkyl group, wherein the $C_{1-6}$ alkyl group may be substituted with a substituent selected from a hydroxyl group, a $C_{1-6}$ alkoxy group, wherein the $C_{1-6}$ alkoxy group may be substituted with a carbamoyl group, an acylamino group and a carbamoyl group, or a $C_{5-6}$ cycloalkyl group or aryl group, wherein the $C_{5-6}$ cycloalkyl group or aryl group may be substituted with a hydroxyl group, an oxo group, a $C_{1-6}$ alkoxy group, a carbamoyl group, an acylamino group, an oximino group or an acyloxy group, (e) an oxo group, (f) —N($R^{e51}$)($R^{e52}$), wherein $R^{e51}$ and $R^{e52}$ may be the same or different and each represent a hydrogen atom, a $C_{1-6}$ alkylsulfonyl group, a $C_{1-6}$ alkyl group, wherein the $C_{1-6}$ alkyl group may be substituted with a substituent selected from a hydroxyl group, a $C_{1-6}$ alkoxy group and a carbamoyl group, an acyl group, wherein the acyl group may be substituted with a hydroxyl group or a $C_{1-6}$ alkoxy group, —CON($R^{e11}$)($R^{e12}$) or, wherein $R^{e11}$ and $R^{e12}$ represent the same as above, —COR$^{e511}$, wherein $R^{e511}$ represents a 5- or 6-membered saturated heterocyclic group containing at least one nitrogen atom, a $C_{1-6}$ alkyl group, wherein the $C_{1-6}$ alkyl group may be substituted with a hydroxyl group, or a $C_{5-6}$ cycloalkyl group, wherein the cycloalkyl group may be substituted with a hydroxyl group, (g) a $C_{1-6}$ alkyl group, wherein the $C_{1-6}$ alkyl group may be substituted with a substituent selected from the following group Eb:

[Group Eb]

a hydroxyl group, a $C_{1-6}$ alkoxy group, wherein a $C_{1-6}$ alkyl group in the $C_{1-6}$ alkoxy group may be substituted with a carboxy group or —CO—N($R^{e11}$)($R^{e12}$), wherein $R^{e11}$ and $R^{e12}$ represent the same as above, —COOR$^{e2}$, wherein $R^{e2}$ represents the same as above, —N($R^{e51}$)($R^{e52}$), wherein $R^{e51}$ and $R^{e52}$ represent the same as above, —CO—N($R^{e51}$)($R^{e52}$), wherein $R^{e51}$ and $R^{e52}$ represent the same as above, a halogen atom, and a 5- or 6-membered saturated heterocyclic group having 1 or 2 hetero atoms, wherein the saturated heterocyclic group may be substituted with a hydroxyl group or a $C_{1-6}$ alkyl group, (h) —(CH$_2$)$_n$—N($R^{e61}$)—(CH$_2$)$_m$—CO($R^{e62}$), wherein n and m represent an integer of 0 or 1 to 4, and n+m is 1 to 6, $R^{e61}$ represents a hydrogen atom or a $C_{1-6}$ alkyl group and $R^{e62}$ is a $C_{1-6}$ alkyl group, wherein the $C_{1-6}$ alkyl group may be substituted with a hydroxyl group, a $C_{1-6}$ alkoxy group, an amino group, a $C_{1-6}$ alkylamino group or a di-$C_{1-6}$ alkylamino group, (i) a hydroxyimino group, (j) a $C_{1-6}$ alkylsulfonyl group, (k) a cyano group, (l) a 5- or 6-membered saturated heterocyclic group (which may be partially unsaturated) containing 1 or 2 hetero atoms selected from a nitrogen atom and an oxygen atom or a 5- or 6-membered aromatic heterocyclic group containing 1 to 4 hetero atoms selected from a nitrogen atom and an oxygen atom, wherein the saturated heterocyclic group and aromatic heterocyclic group may be substituted with an oxo group or a $C_{1-6}$ alkyl group, (m) an aminosulfonyl group and (n) a $C_{1-6}$ alkylidene group, wherein the $C_{1-6}$ alkylidene group may be substituted with a halogen atom or a carboxy group;

$R^f$ is a $C_{1-6}$ alkyl group or a $C_{2-6}$ alkenyl group, wherein these $C_{1-6}$ alkyl group and $C_{2-6}$ alkenyl group may be substituted with a substituent selected from the following group Fa:

[Group Fa]

(a) a $C_{1-6}$ alkoxy group, wherein the $C_{1-6}$ alkyl group in the alkoxy group may be substituted with a carboxy group, a $C_{1-6}$ alkoxycarbonyl group or —CON($R^{f21}$)($R^{f22}$), wherein $R^{f21}$ and $R^{f22}$ may be the same or different and each represent a hydrogen atom, an acyl group, wherein the acyl group may be substituted with a hydroxyl group or a carboxy group, a $C_{1-6}$ alkoxycarbonyl group, —O—COOR$^{f1}$, wherein $R^{f1}$ is a hydrogen atom or a $C_{1-6}$ alkyl group, a $C_{1-6}$ alkyl group, wherein the $C_{1-6}$ alkyl group may be substituted with a hydroxyl group, a carboxy group, a $C_{1-6}$ alkoxycarbonyl group, a carbamoyl group, a $C_{1-6}$ alkylsulfonyl group or a carbamoyl group, (b) —COOR$^{f1}$, wherein $R^{f1}$ is a hydrogen atom or a $C_{1-6}$ alkyl group, (c) —N($R^{f21}$)($R^{f22}$), wherein $R^{f21}$ and $R^{f22}$ represent the same as above, (d) —CON($R^{f21}$)($R^{f22}$), wherein $R^{f21}$ and $R^{f22}$ represent the same as above, (e) —N($R^{f23}$)CON($R^{f21}$)($R^{f22}$), wherein $R^{f23}$ represents a hydrogen atom or a $C_{1-6}$ alkyl group, and $R^{f21}$ and $R^{f22}$ represent the same as above, (f) an acyl group and (g) a halogen atom;

$R^g$ represents a substituent having Ring B represented by the following formula (II):

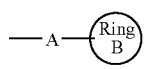

wherein A represents a linker selected from the following group Ga:

[Group Ga]

—(CH$_2$)$_k$-,

—(CH$_2$)$_k$—NR$^{g1}$—(CH$_2$)$_j$—,

—(CH$_2$)$_k$—O—(CO)NR$^{g1}$—(CH$_2$)$_j$—,

—(CH$_2$)$_k$—NR$^{g1}$(CO)—(CH$_2$)$_j$—,

—(CH$_2$)$_k$—(CO)—(CH$_2$)$_j$—,

—(CO)—,

—(CH$_2$)$_k$—O—(CH$_2$)$_j$—,

—(CH$_2$)$_k$—S—(CH$_2$)$_j$—,

—(CH$_2$)$_k$—O—(CO)—(CH$_2$)$_j$—,

—(CO)NR$^{g1}$—, and

—(CH$_2$)$_k$—O—(CH$_2$)$_j$(CO)—(CH$_2$)$_g$—, wherein k, j and g may be the same or different and represent an integer from 0 to 4 but k and j, or k and g are not 0 at the same time, R$^{g1}$ represents a hydrogen atom, a hydroxyl group, a C$_{1-6}$ alkoxy group, an acyl group, wherein the acyl group may be substituted with a hydroxyl group or a carboxy group, a C$_{3-8}$ cycloalkyl group, wherein the cycloalkyl group may be substituted with a C$_{1-6}$ alkyl group, wherein the alkyl group may be substituted with a carboxy group, an aralkyl group or a C$_{1-6}$ alkyl group, wherein the alkyl group may be substituted with a hydroxyl group, —N(R$^{g41}$)(R$^{g42}$) or —CON(R$^{g41}$)(R$^{g42}$), wherein R$^{g41}$ and R$^{g42}$ may be the same or different and represent a hydrogen atom, an acyl group, wherein the acyl group may be substituted with a hydroxyl group, an aralkyl group, a C$_{1-6}$ alkylsulfonyl group or, a C$_{1-6}$ alkyl group, wherein the C$_{1-6}$ alkyl group may be substituted with a hydroxyl group, a carboxy group, a C$_{1-6}$ alkoxycarbonyl group, —N(R$^{g51}$)(R$^{g52}$) or —CO—N(R$^{g51}$)(R$^{g52}$), wherein R$^{g51}$ and R$^{g52}$ may be the same or different and represent a hydrogen atom, an acyl group, wherein the acyl group may be substituted with a hydroxyl group, a C$_{1-6}$ alkyl group, wherein the C$_{1-6}$ alkyl group may be substituted with a hydroxyl group, a carboxy group, acylamino group, a C$_{1-6}$ alkoxycarbonyl group or a halogen atom, a C$_{1-6}$ alkoxycarbonyl group, a C$_{1-6}$ alkylsulfonyl group or a C$_{3-8}$ cycloalkyl group, wherein the cycloalkyl group may be substituted with a hydroxyl group or a C$_{1-6}$ alkoxy group, or R$^{g51}$ and R$^{g52}$ together with the adjacent nitrogen atom may form a 5- or 6-membered saturated heterocyclic group which has one or more nitrogen atoms, wherein the saturated heterocyclic group may be substituted with a hydroxyl group or a C$_{1-6}$ alkoxy group, Ring B represents a ring selected from the following group Ha:

[Group Ha]

an aryl group, a C$_{3-8}$ cycloalkyl group, a 5- to 7-membered saturated heterocyclic group containing one or more nitrogen atoms, a 5- or 6-membered aromatic heterocyclic group containing at least one hetero atoms, and an 8- to 11-membered condensed aromatic heterocyclic group containing at least one hetero atoms, and the Ring B may be substituted with a substituent selected from follows group Ia:

[Group Ia]

(a) —OR$^{g2}$, wherein R$^{g2}$ represents a hydrogen atom, a C$_{1-6}$ alkyl group or an aralkyl group, (b) —COOR$^{g3}$, wherein R$^{g3}$ represents a hydrogen atom, a C$_{1-6}$ alkyl group or an aralkyl group, wherein the alkyl group may be substituted with a hydroxyl group, (c) —N(R$^{g41}$)(R$^{g42}$), wherein R$^{g41}$ and R$^{g42}$ represent the same as above, (d) —CO—R$^{g53}$, wherein R$^{g53}$ represents a C$_{1-6}$ alkyl group, wherein the alkyl group may be substituted with a hydroxyl group, a carboxy group or an acylamino group, a C$_{3-8}$ cycloalkyl group, wherein the cycloalkyl group may be substituted with a hydroxyl group, a C$_{1-6}$ alkoxy group or oxo group, a 5- or 6-membered saturated heterocyclic group containing at least one hetero atoms, wherein the saturated heterocyclic group may be substituted with a hydroxyl group, a C$_{1-6}$ alkyl group or an oxo group, an aryl group, wherein the aryl may be substituted with a hydroxyl group, a 5- or 6-membered aromatic heterocyclic group containing at least one hetero atoms, an aralkyl group or a 5- or 6-membered saturated heterocyclic group containing 1 or 2 hetero atoms, (e) a C$_{1-6}$ alkyl group, wherein the C$_{1-6}$ alkyl group which may be substituted with a hydroxyl group, a C$_{1-6}$ alkoxy group, an aralkoxy group, a carboxy group, a C$_{1-6}$ alkoxycarbonyl group, —CO—R$^{g53}$, wherein R$^{g53}$ represents the same as above, —N(R$^{g51}$)(R$^{g52}$) or —CO—N(R$^{g51}$)(R$^{g52}$), wherein R$^{g51}$ and R$^{g52}$ represent the same as above, (f) —CO—N(R$^{g51}$)(R$^{g52}$), wherein R$^{g51}$ and R$^{g52}$ represent the same as above, (g) a C$_{1-6}$ alkylsulfonyl group, (h) an oxo group, (i) an aryl group, wherein the aryl group may be substituted with a hydroxyl group, (j) an aralkyl group and (k) a halogen atom; and R$^h$ represents —N(R$^{h1}$)(R$^{h2}$), wherein R$^{h1}$ represents (1) a hydrogen atom, (2) a C$_{1-6}$ alkyl group, wherein the C$_{1-6}$ alkyl group may be substituted with a hydroxyl group, a C$_{1-6}$ alkoxy group, —N(R$^{g51}$)(R$^{g52}$), —CO—N(R$^{g51}$)(R$^{g52}$), wherein R$^{g51}$ and R$^{g52}$ represent the same as above, a C$_{1-6}$ alkylsulfonyl group or a halogen atom, (3) a C$_{2-6}$ alkenyl group, (4) a C$_{3-8}$ cycloalkyl group, wherein the cycloalkyl group may be substituted with a hydroxyl group or a C$_{1-6}$ alkoxy group, or (5) an aralkyl group, R$^{h2}$ represents (1) a C$_{1-6}$ alkyl group, wherein the C$_{1-6}$ alkyl group may be substituted with a substituent selected from the following group Ja:

[Group Ja]

a hydroxyl group, a C$_{1-6}$ alkoxy group, a carboxy group, an aromatic carbocyclic group, wherein the aromatic carbocyclic group may be substituted with a hydroxyl group, a C$_{1-6}$ alkyl group, wherein the alkyl group may be substituted with a carboxy group, a halogen atom, a C$_{1-6}$ alkoxy group, a carboxy group, a C$_{1-6}$ alkoxycarbonyl group, $C_{2-6}$ alkenyl group, wherein the $C_{2-6}$ alkenyl group may be substituted with a carboxy group,
a $C_{3-8}$ cycloalkyl group, wherein the cycloalkyl group may be substituted with a carboxy group or an aralkoxy group,
a 5- or 6-membered aromatic heterocyclic group containing 1 or 2 hetero atoms, wherein the aromatic heterocyclic group may be substituted with a carboxy group,
a 5- or 6-membered saturated heterocyclic group containing 1 or 2 hetero atoms,
—N($R^{g51}$)($R^{g52}$),
wherein $R^{g51}$ and $R^{g52}$ represent the same as above,
—CON($R^{g51}$)($R^{g52}$),
wherein $R^{g51}$ and $R^{g52}$ represent the same as above,
—CO$R^{g53}$, wherein $R^{g53}$ represents the same as above, and
—COO$R^{g3}$, wherein $R^{g3}$ represents the same as above,
(2) an acyl group, wherein the acyl group may be substituted with a hydroxyl group,
(3) a $C_{1-6}$ alkoxycarbonyl group,
(4) a $C_{2-6}$ alkenyl group, wherein the alkenyl group may be substituted with a carboxy group or a halogen atom,
(5) a $C_{3-8}$ cycloalkyl group, wherein the cycloalkyl group may be substituted with a hydroxyl group, —COO$R^{g3}$, wherein $R^{g3}$ represents the same as above, —CO$R^{g53}$, wherein $R^{g53}$ represents the same as above, —CONR$^{g51}$R$^{g52}$, wherein $R^{g51}$ and $R^{g52}$ each represent the same as above, or a $C_{1-6}$ alkyl group, wherein the alkyl group may be substituted with a carboxy group,
(6) a 5- or 6-membered saturated heterocyclic group containing 1 or 2 hetero atoms, wherein the saturated heterocyclic group may be substituted with —CO$R^{g53}$, wherein $R^{g53}$ represents the same as above, —COO$R^{g3}$, wherein $R^{g3}$ represents the same as above, —CONR$^{g51}$R$^{g52}$, wherein $R^{g51}$ and $R^{g52}$ each represent the same as above or a $C_{1-6}$ alkylsulfonyl group, or
(7) an aromatic carbocyclic group, wherein the aromatic carbocyclic group may be substituted with a carboxy group, a $C_{1-6}$ alkyl group, wherein the alkyl group may be substituted with a carboxy group, or a $C_{2-6}$ alkenyl group, wherein the alkenyl group may be substituted with a carboxy group,
or a pharmaceutically acceptable salt thereof.

2. The aminopyridine compound or a pharmaceutically acceptable salt thereof according to claim 1, wherein Z is a nitrogen atom.

3. The aminopyridine compound or a pharmaceutically acceptable salt thereof according to claim 2, represented by the following formula (Ia-1):

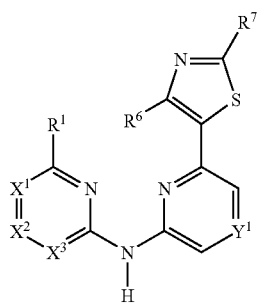

(Ia-1)

wherein
$X^1$ represents
(1) —C($R^2$)═;

$X^2$ represents
(1) —C($R^3$)═O or
(2) a nitrogen atom;
$X^3$ represents
(1) —C($R^4$)═ or
(2) a nitrogen atom;
$Y^1$ represents
(1) —CH═ or
(2) a nitrogen atom;
$R^1$ represents
(1) a hydrogen atom or
(2) a $C_{1-6}$ alkyl group;
$R^2$ represents
(1) a hydrogen atom,
(2) a halogen atom or
(3) a $C_{1-6}$ alkyl group;
$R^3$ represents
(1) a hydrogen atom,
(2) a halogen atom,
(3) a $C_{1-6}$ alkoxy group, wherein $C_{1-6}$ alkyl group in the $C_{1-6}$ alkoxy group may be substituted with a substituent selected from the following group Aa-1:
[Group Aa-1]
(a) a hydroxyl group,
(b) a $C_{1-6}$ alkoxy group,
(c) —N($R^{31}$)($R^{32}$),
wherein $R^{31}$ and $R^{32}$ are a hydrogen atom or a $C_{1-6}$ alkyl group,
(d) a halogen atom,
(4) an aralkoxy group,
(5) an acyl group,
(6) a saturated heterocyclic group or an aromatic heterocyclic group, wherein the heterocyclic group may be substituted with a $C_{1-6}$ alkyl group, and the saturated heterocyclic group may partially have a double bond,
(7) a $C_{1-6}$ alkyl group, wherein the $C_{1-6}$ alkyl group may be substituted with a substituent selected from the following group Ab-1:
[Group Ab-1]
(a) a hydroxyl group,
(b) —COO$R^{33}$, wherein $R^{33}$ is a hydrogen atom or a $C_{1-6}$ alkyl group,
(c) —CO—N($R^{31}$)($R^{32}$), wherein $R^{31}$ and $R^{32}$ represent the same as above, and
(d) a halogen atom, or
(8) a cyano group, or
$R^3$ together with $R^2$ may form —C═C—C═C—;
$R^4$ represents
(1) a hydrogen atom or
(2) a $C_{1-6}$ alkyl group;
$R^6$ represents
(1) a hydrogen atom,
(2) a $C_{1-6}$ alkyl group, wherein the $C_{1-6}$ alkyl group may be substituted with a hydroxyl group or a $C_{1-6}$ alkoxy group,
(3) —COO$R^{61}$,
wherein $R^{61}$ is a hydrogen atom or a $C_{1-6}$ alkyl group,
(4) —N($R^{62}$)($R^{63}$),
wherein $R^{62}$ and $R^{63}$ may be the same or different and each represent a hydrogen atom, a $C_{1-6}$ alkyl group, a $C_{1-6}$ alkoxy group or an acyl group,
(5) —CO—N($R^{62}$)($R^{63}$), wherein $R^{62}$ and $R^{63}$ are the same as above, or
(6) an acyl group; and
$R^7$ represent the same as in claim 1.

4. The aminopyridine compound or a pharmaceutically acceptable salt thereof according to claim 1, wherein the aminopyridine compound according to claim 1 is an aminopyridine compound represented by the following formula (Ia-2):

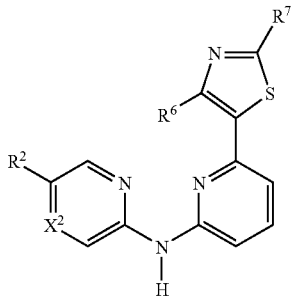

(Ia-2)

wherein
X² represents
(1) =C(R³)— or
(2) a nitrogen atom;
R² represents
(1) a hydrogen atom or
(2) a halogen atom;
R³ represents
(1) a hydrogen atom,
(2) a halogen atom,
(3) a $C_{1-6}$ alkoxy group,
wherein the $C_{1-6}$ alkyl group in the $C_{1-6}$ alkoxy group may be substituted with a substituent selected from the following group Aa-2:
[Group Aa-2]
(a) a hydroxyl group and
(b) a halogen atom,
(4) an acyl group,
(5) a saturated heterocyclic group or an aromatic heterocyclic group, wherein the heterocyclic group may be substituted with a $C_{1-6}$ alkyl group, and the saturated heterocyclic group may partially have a double bond,
(6) a $C_{1-6}$ alkyl group which may be substituted with a substituent selected from the following group Ab-2:
[Group Ab-2]
(a) a hydroxyl group and
(b) a halogen atom or
(7) a cyano group, or
R³ together with R² may form —C=C—C=C—;
R⁶ is
(1) a hydrogen atom or
(2) a $C_{1-6}$ alkyl group, wherein the $C_{1-6}$ alkyl group may be substituted with a hydroxyl group or a $C_{1-6}$ alkoxy group;
R⁷ is a hydrogen atom, or the following $R^a$, $R^b$, $R^c$, $R^d$, $R^e$, $R^f$, $R^g$ or $R^h$;
$R^a$ represents —$C_pH_{2(p-1)}(R^{a1})(R^{a2})$—O—$R^{a3}$,
wherein
(1) p represents an integer from 1 to 6,
(2) $R^{a1}$ represents a hydrogen atom,
(3) $R^{a2}$ represents
a $C_{1-6}$ alkyl group, wherein the $C_{1-6}$ alkyl group may be substituted with a hydroxyl group, a carboxy group, an acyloxy group, a $C_{1-6}$ alkylamino group or a di-$C_{1-6}$ alkylamino group,
an aralkyl group, wherein the aralkyl group may be substituted with a hydroxyl group, a carboxy group or an acyloxy group, or
an aryl group, (4) $R^{a3}$ is a hydrogen atom, an acyl group or —(CO)N($R^{a31}$)($R^{a32}$),
wherein $R^{a31}$ and $R^{a32}$ may be the same or different and are a hydrogen atom or a $C_{1-6}$ alkyl group;
$R^b$ represents —$C_pH_{2(p-1)}(R^{b1})(R^{b2})$—N—($R^{b3}$)($R^{b4}$),
wherein
(1) p is an integer from 1 to 6,
(2) $R^{b1}$ is a hydrogen atom,
(3) $R^{b2}$ is
(a) an aralkyl group, wherein the aralkyl group may be substituted with a hydroxyl group, a $C_{1-6}$ alkoxy group which may be substituted with a hydroxyl group, aralkoxy group or —N($R^{b21}$)($R^{b22}$),
wherein $R^{b21}$ and $R^{b22}$ are a hydrogen atom, a $C_{1-6}$ alkyl group, an acyl group or an aralkoxy carbonyl group,
(b) an aryl group, wherein the aryl group may be substituted with a hydroxyl group or an aralkoxygroup, or
(c) a $C_{1-6}$ alkyl group, wherein the $C_{1-6}$ alkyl group may be substituted with a hydroxyl group, a carboxy group, an aralkoxy group, an aralkoxycarbonyl group, an amino group, an acyl group or an aralkyl carbonyl group,
(4) $R^{b3}$ is a hydrogen atom or a $C_{1-6}$ alkyl group,
(5) $R^{b4}$
represents
(a) a hydrogen atom,
(b) a $C_{1-6}$ alkyl group, wherein the $C_{1-6}$ alkyl group may be substituted with a carboxy group or a $C_{1-6}$ alkoxycarbonyl group,
(c) —COR^{b32},
wherein $R^{b32}$ is a $C_{1-6}$ alkyl group, wherein the $C_{1-6}$ alkyl group may be substituted with a hydroxyl group, an acyl group, a carboxy group, a $C_{1-6}$ alkoxycarbonyl group or acyloxy group, or
(d) —CON($R^{b321}$)($R^{b322}$),
wherein $R^{b321}$ and $R^{b322}$ are a hydrogen atom or a $C_{1-6}$ alkyl group;
$R^c$ is —C(=N—$R^{c1}$)—$R^{c2}$,
wherein
(1) $R^{c1}$ represents
(a) a hydroxyl group,
(b) a $C_{1-6}$ alkoxy group, wherein the $C_{1-6}$ alkyl group in the $C_{1-6}$ alkoxy group may be substituted with a hydroxyl group, or
(c) an acyloxy group,
(2) $R^{c2}$ is a $C_{1-6}$ alkyl group;
$R^d$ is —C(=O)—$R^{d1}$
wherein $R^{d1}$ represents
(1) a $C_{1-6}$ alkyl group, wherein the $C_{1-6}$ alkyl group may be substituted with a hydroxyl group, a carboxy group or a $C_{1-6}$ alkoxycarbonyl group,
(2) a $C_{1-6}$ alkoxy group,
(3) a $C_{3-8}$ cycloalkyl group, wherein the $C_{3-8}$ cycloalkyl group may be substituted with a hydroxyl group,
(4) —N($R^{d11}$)($R^{d12}$),
wherein $R^{d11}$ and $R^{d12}$ may be the same or different and are each
a hydrogen atom,
a $C_{1-6}$ alkoxy group, or
a $C_{1-6}$ alkyl group, wherein the $C_{1-6}$ alkyl group may be substituted with a hydroxyl group, a carboxy group or a $C_{1-6}$ alkoxycarbonyl group;
$R^e$ represents
a 5- or 6-membered saturated heterocyclic group having 1 or 2 hetero atoms,
a 5- or 6-membered aromatic heterocyclic group having 1 to 4 hetero atoms, a 9- to 12-membered condensed aromatic heterocyclic group which may be partially saturated having 1 or 2 hetero atoms, a $C_{3-8}$ cycloalkyl group or a $C_{7-11}$ spiroheterocycloalkyl group having 1 or 2 hetero atoms, and may be each substituted with a substituent selected from the following group Ea-1:

[Group Ea-1]

(a) —$OR^{e1}$, wherein $R^{e1}$ represents a hydrogen atom, $C_{1-6}$ alkyl group, wherein the $C_{1-6}$ alkyl group may be substituted with a carboxy group or —$CON(R^{e11})(R^{e12})$, wherein $R^{e11}$ and $R^{e12}$ may be the same or different and each represent a hydrogen atom or a $C_{1-6}$ alkyl group, an acyl group, a carbamoyl group or an aralkyl group, (b) —$COOR^{e2}$, wherein $R^{e2}$ is a hydrogen atom or a $C_{1-6}$ alkyl group, (c) —$CO$—$N(R^{e41})(R^{e42})$, wherein $R^{e41}$ and $R^{e42}$ may be the same or different and each represent a hydrogen atom, a $C_{1-6}$ alkyl group, wherein the $C_{1-6}$ alkyl group may be substituted with a substituent selected from a hydroxyl group, a $C_{1-6}$ alkoxy group, a di-$C_{1-6}$ alkylamino group, a carboxy group, a halogen atom, a $C_{1-6}$ alkylcarbamoyl group and a 5- or 6-membered saturated heterocyclic group or an aromatic heterocyclic group having 1 or 2 hetero atoms, a hydroxyl group, a $C_{1-6}$ alkoxy group, an acyl group, wherein the acyl group may be substituted with a hydroxyl group, a $C_{3-8}$ cycloalkyl group, wherein the $C_{3-8}$ cycloalkyl group may be substituted with a hydroxyl group, or, a $C_{1-6}$ alkylsulfonyl group, (d) —$COR^{e3}$, wherein $R^{e3}$ is a hydrogen atom, a $C_{1-6}$ alkyl group, wherein a $C_{1-6}$ alkyl group may be substituted with a hydroxy group, a carboxy group or a $C_{1-6}$ alkylsulfonyl group, a 5- or 6-membered saturated heterocyclic group having 1 or 2 hetero atoms wherein the saturated heterocyclic group may be substituted with a hydroxyl group, a carboxy group, a $C_{1-6}$ alkyl group, an acyl group, a $C_{1-6}$ alkoxy group, a carbamoyl group, $N(R^{e41})(R^{e42})$, wherein $R^{e41}$ and $R^{e42}$ represent the same as above, an acylamino group or an oxo group, a $C_{3-8}$ cycloalkyl group, wherein the $C_{3-8}$ cycloalkyl group may be substituted with a hydroxyl group, an aromatic hydrocarbon group, wherein the aromatic hydrocarbon group may be substituted with a hydroxyl group, or a 5- or 6-membered aromatic heterocyclic group having 1 or 2 hetero atoms, (e) an oxo group, (f) —$N(R^{e51})(R^{e52})$, wherein $R^{e51}$ and $R^{e52}$ may be the same or different and each represent a hydrogen atom, a $C_{1-6}$ alkylsulfonyl group, a $C_{1-6}$ alkyl group, wherein the $C_{1-6}$ alkyl group may be substituted with a hydroxyl group, an acyl group, wherein the acyl group may be substituted with a hydroxyl group, or —$COR^{e511}$, wherein $R^{e511}$ represents a 5- or 6-membered saturated heterocyclic group containing at least one nitrogen atom or a $C_{3-8}$ cycloalkyl group, wherein the $C_{3-8}$ cycloalkyl group may be substituted with a hydroxyl group, (g) a $C_{1-6}$ alkyl group, wherein the $C_{1-6}$ alkyl group may be substituted with a substituent selected from the following group Eb-1:

[Group Eb-1]

a hydroxyl group, a $C_{1-6}$ alkoxy group, wherein the $C_{1-6}$ alkyl group in the $C_{1-6}$ alkoxy group may be substituted with a carboxy group or —$CO$—$N(R^{e11})(R^{e12})$, wherein $R^{e11}$ and $R^{e12}$ represent the same as above, —$COOR^{e2}$, wherein $R^{e2}$ represents the same as above, —$N(R^{e51})(R^{e52})$, wherein $R^{e51}$ and $R^{e52}$ represent the same as above, —$CO$—$N(R^{e51})(R^{e52})$, and wherein $R^{e51}$ and $R^{e52}$ represent the same as above, a halogen atom and a 5- or 6-membered saturated heterocyclic group having 1 or 2 hetero atoms, (h) a hydroxyimino group, (i) a $C_{1-6}$ alkylsulfonyl group, (j) a cyano group, (k) a 5- or 6-membered saturated heterocyclic group containing 1 or 2 hetero atoms selected from a nitrogen atom and an oxygen atom (which may be partially unsaturated and may be substituted with an oxo group or a $C_{1-6}$ alkyl group) or an aromatic heterocyclic group containing 1 to 4 hetero atoms selected from a nitrogen atom and an oxygen atom, (l) an aminosulfonyl group and (m) a $C_{1-6}$ alkylidene group, wherein the $C_{1-6}$ alkylidene group may be substituted with a halogen atom or a carboxy group;

$R^f$ is a $C_{1-6}$ alkyl group, wherein the $C_{1-6}$ alkyl group may be substituted with a substituent selected from the following group Fa-1:

[Group Fa-1]

(a) a $C_{1-6}$ alkoxy group, wherein $C_{1-6}$ alkyl group in the alkoxy group) may be substituted with a carboxy group $C_{1-6}$ alkoxycarbonyl group or —$CON(R^{f21})(R^{f22})$, wherein $R^{f21}$ and $R^{f22}$ may be the same or different and each represent a hydrogen atom, an acyl group, wherein the acyl group may be substituted with a hydroxyl group or a carboxy group, a $C_{1-6}$ alkoxycarbonyl group, —$O$—$COOR^{f1}$ wherein $R^{f1}$ is a hydrogen atom or a $C_{1-6}$ alkyl group, a $C_{1-6}$ alkyl group, wherein the $C_{1-6}$ alkyl group may be substituted with a hydroxyl group, a carboxy group, a $C_{1-6}$ alkoxycarbonyl group or a carbamoyl group, a $C_{1-6}$ alkylsulfonyl group or, a carbamoyl group, (b) —$COOR^{f1}$, wherein $R^{f1}$ represents the same as above, (c) —$N(R^{f21})(R^{f22})$, wherein $R^{f21}$ and $R^{f22}$ represent the same as above, (d) —$CON(R^{f21})(R^{f22})$, wherein $R^{f21}$ and $R^{f22}$ represent the same as above, (e) an acyl group and (f) a halogen atom;

$R^g$ represents a substituent having Ring B' represented by the following formula (IIa):

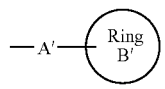
(IIa)

wherein A' is a linker selected from the following group Ga-1:
[Group Ga-1]
—$(CH_2)_k$—,
—$(CH_2)_k$—$NR^{g1}$—$(CH_2)_j$—,
—$(CH_2)_k$—O—(CO)$NR^{g1}$$(CH_2)_j$—,
—$(CH_2)_k$—$NR^{g1}$(CO)—$(CH_2)_j$—,
—$(CH_2)_k$—(CO)—$(CH_2)_j$—,
—(CO)—,
—$(CH_2)_k$—O—$(CH_2)_j$—,
—$(CH_2)_k$—S—$(CH_2)_j$—,
—$(CH_2)_k$—O—(CO)—$(CH_2)_j$—, and
$(CH_2)_k$—O—$(CH_2)_j$(CO)—$(CH_2)_g$—,
wherein k, j and g may be the same or different and represent an integer from 0 to 4 but k and j, or k and g are not 0 at the same time,
$R^{g1}$ is
a hydrogen atom,
an acyl group, wherein the acyl group may be substituted with a carboxy group or a hydroxyl group, or
a $C_{1-6}$ alkyl group,
wherein the alkyl group may be substituted with a carboxy group,
Ring B' is a ring selected from the following group Ha-1:
[Group Ha-1]
an aryl group,
a $C_{3-8}$ cycloalkyl group,
a 5- to 7-membered saturated heterocyclic group having at least one nitrogen atom, wherein the saturated heterocyclic ring may form a condensed ring with a phenyl group, and
a 5- or 6-membered aromatic heterocyclic group containing 1 or 2 hetero atoms, and
the Ring B' may be substituted with a substituent selected from follows group Ia-1:
[Group Ia-1]
(a) —$OR^{g2}$,
wherein $R^{g2}$ represents
a hydrogen atom,
a $C_{1-6}$ alkyl group or
an aralkyl group,
(b) —$COOR^{g3}$,
wherein $R^{g3}$ represents
a hydrogen atom or
a $C_{1-6}$ alkyl group, wherein the alkyl group may be substituted with a hydroxyl group,
(c) -N($R^{g41}$)($R^{g42}$),
wherein $R^{g41}$ and $R^{g42}$ represent the same as above,
(d) -CO—$R^{g53}$, wherein $R^{g53}$ represents
a $C_{1-6}$ alkyl group, wherein the alkyl group may be substituted with a hydroxyl group, a carboxy group or an acylamino group,
a $C_{3-8}$ cycloalkyl group, wherein the cycloalkyl group may be substituted with a hydroxyl group, a $C_{1-6}$ alkoxy group or an oxo group,
an aryl group, wherein the aryl group may be substituted with a hydroxyl group,
a 5- or 6-membered saturated heterocyclic group containing 1 or 2 hetero atoms, wherein the saturated heterocyclic group may be substituted with a hydroxyl group, a $C_{1-6}$ alkyl group or an oxo group,
an aralkyl group or
a 5- or 6-membered aromatic heterocyclic group containing 1 or 2 hetero atoms,
(e) a $C_{1-6}$ alkyl group, wherein the $C_{1-6}$ alkyl group may be substituted with a hydroxyl group, a carboxy group or —CO—$R^{g53}$, wherein $R^{g53}$ represents the same as above,
(f) —CO—N($R^{g51}$)($R^{g52}$),
wherein $R^{g51}$ and $R^{g52}$ may be the same or different and are
a hydrogen atom,
an acyl group, wherein the acyl group may be substituted with a hydroxyl group,
a $C_{1-6}$ alkyl group,
wherein the $C_{1-6}$ alkyl group may be substituted with a hydroxyl group, a carboxy group, an acylamino group, a $C_{1-6}$ alkoxycarbonyl group or a halogen atom,
a $C_{1-6}$ alkylsulfonyl group,
a $C_{1-6}$ alkoxycarbonyl group,
a carbamoyl group or
a $C_{3-8}$ cycloalkyl group, wherein the cycloalkyl group may be substituted with a hydroxyl group or a $C_{1-6}$ alkoxy group,
(g) a $C_{1-6}$ alkylsulfonyl group,
(h) an oxo group and
(i) a halogen atom; and
$R^h$ is —N($R^{h1}$)($R^{h2}$),
wherein $R^{h1}$ is
(1) a hydrogen atom,
(2) a $C_{1-6}$ alkyl group, wherein the $C_{1-6}$ alkyl group may be substituted with a hydroxyl group, a $C_{1-6}$ alkoxy group, —N($R^{g51}$)($R^{g52}$), —CO—N($R^{g51}$)($R^{g52}$), a $C_{1-6}$ alkylsulfonyl or a halogen atom,
wherein $R^{g51}$ and $R^{g52}$ represent the same as above,
(3) a $C_{2-6}$ alkenyl group,
(4) a $C_{3-8}$ cycloalkyl group, wherein the cycloalkyl group may be substituted with a hydroxyl group or a $C_{1-6}$ alkoxy group, or
(5) an aralkyl group,
$R^{h2}$ is
(1) a $C_{1-6}$ alkyl group, wherein the $C_{1-6}$ alkyl group may be substituted with a substituent selected from the following group Ja-1:
[Group Ja-1]
a hydroxyl group,
a $C_{1-6}$ alkoxy group,
a carboxy group,
an aromatic carbocyclic group, wherein the aromatic carbocyclic group may be substituted with a hydroxyl group, a $C_{1-6}$ alkyl group, wherein the alkyl group may be substituted with a carboxy group, a halogen atom, a $C_{1-6}$ alkoxy group, a carboxy group, a $C_{1-6}$ alkoxycarbonyl group, $C_{2-6}$ alkenyl group, wherein the $C_{2-6}$ alkenyl group may be substituted with a carboxy group,
a $C_{3-8}$ cycloalkyl group, wherein the cycloalkyl group may be substituted with a carboxy group or an aralkoxy group,
a 5- or 6-membered aromatic heterocyclic group containing 1 or 2 hetero atoms, wherein the aromatic heterocyclic group may be substituted with a carboxy group,
a 5- or 6-membered saturated heterocyclic group containing 1 or 2 hetero atoms,
—N($R^{g51}$)($R^{g52}$) and
—CON($R^{g51}$)($R^{g52}$), wherein $R^{g51}$ and $R^{g52}$ represent the same as above, (2) an acyl group, wherein the acyl group may be substituted with a hydroxyl group, (3) a $C_{2-6}$ alkenyl group, wherein the alkenyl group may be substituted with a carboxy group or a halogen atom, (4) a $C_{3-8}$ cycloalkyl group, wherein the cycloalkyl group may be substituted with a hydroxyl group, —COOR$^{g3}$, wherein R$^{g3}$ represents the same as above, —COR$^{g53}$, wherein R$^{g53}$ represents the same as above, —CONR$^{g51}$R$^{g52}$, wherein R$^{g51}$ and R$^{g52}$ each represent the same as above, or a $C_{1-6}$ alkyl group, wherein the alkyl group may be substituted with a carboxy group, (5) a 5- or 6-membered saturated heterocyclic group containing 1 or 2 hetero atoms, wherein the saturated heterocyclic group may be substituted with —COR$^{g53}$, herein R$^{g53}$ represents the same as above, —COOR$^{g3}$, wherein R$^{g3}$ represents the same as above, —CONR$^{g51}$R$^{g52}$, wherein R$^{g51}$ and R$^{g52}$ each represent the same as above, or a $C_{1-6}$ alkylsulfonyl group, or (6) an aromatic carbocyclic group, wherein the aromatic carbocyclic group may be substituted with a carboxy group, $C_{1-6}$ alkyl group, wherein the alkyl group may be substituted with a carboxy group, or a $C_{2-6}$ alkenyl group, wherein the alkenyl group may be substituted with a carboxy group.

5. The aminopyridine compound or a pharmaceutically acceptable salt thereof according to claim 4, wherein
$R^2$ is a hydrogen atom,
$R^3$ is a $C_{1-6}$ alkyl group, wherein the $C_{1-6}$ alkyl group may be substituted with a hydroxyl group or a halogen atom,
$R^6$ is a hydrogen atom, and
$R^7$ is $R^e$, $R^g$ or $R^h$.

6. The aminopyridine compound or a pharmaceutically acceptable salt thereof according to claim 5, wherein
$R^7$ is $R^e$, and
$R^e$ is
(1) a 5- or 6-membered saturated heterocyclic group containing 1 or 2 hetero atoms, wherein the saturated heterocyclic group may be substituted with a $C_{1-6}$ alkyl group, wherein the alkyl group may be substituted with a carboxy group, —COR$^{e3}$, wherein R$^{e3}$ is a 5- or 6-membered saturated heterocyclic group having 1 or 2 hetero atoms, wherein the 5- or 6-membered saturated heterocyclic group may be substituted with a hydroxyl group, or —CO—N(R$^{e41}$)(R$^{e42}$), wherein R$^{e41}$ and R$^{e42}$ may be the same or different and each represent a hydrogen atom or a $C_{1-6}$ alkyl group, or
(2) a $C_{3-8}$ cycloalkyl group, wherein the cycloalkyl group may be substituted with a $C_{1-6}$ alkyl group, wherein the alkyl group may be substituted with a carboxy group, —COR$^{e3}$, wherein R$^{e3}$ is a 5- or 6-membered saturated heterocyclic group having 1 or 2 hetero atoms, wherein the 5- or 6-membered saturated heterocyclic group may be substituted with a hydroxyl group, or —CO—N(R$^{e41}$)(R$^{e42}$), wherein R$^{e41}$ and R$^{e42}$ may be the same or different and each represent a hydrogen atom or a $C_{1-6}$ alkyl group.

7. The aminopyridine compound or a pharmaceutically acceptable salt thereof according to claim 6, wherein
$R^e$ is
(1) a 5- or 6-membered saturated heterocyclic group having 1 or 2 hetero atoms represented by the following Ring L, wherein the saturated heterocyclic group may be substituted with 1 or 2 identical or different substituents selected from a $C_{1-6}$ alkyl group, wherein the alkyl group may be substituted with a carboxy group, —COR$^{e3}$, wherein R$^{e3}$ is a 5- or 6-membered saturated heterocyclic group having 1 or 2 hetero atoms, wherein the 5- or 6-membered saturated heterocyclic group may be substituted with a hydroxyl group, or —CO—N(R$^{e41}$)(R$^{e42}$), wherein R$^{e41}$ and R$^{e42}$ may be the same or different and each represent a hydrogen atom or a $C_{1-6}$ alkyl group,

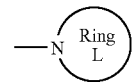

wherein Ring L is a 5- or 6-membered saturated heterocyclic group having 1 or 2 hetero atoms, or (2) a 5- or 6-membered cycloalkyl group, wherein the cycloalkyl group may be substituted with 1 or 2 identical or different substituents selected from a $C_{1-6}$ alkyl group, wherein the alkyl group may be substituted with a carboxy group, —COR$^{e3}$, wherein R$^{e3}$ is a 5- or 6-membered saturated heterocyclic group having 1 or 2 hetero atoms, wherein the 5- or 6-membered saturated heterocyclic group may be substituted with a hydroxyl group, or —CO—N(R$^{e41}$)(R$^{e42}$), wherein R$^{e41}$ and R$^{e42}$ may be the same or different and each represent a hydrogen atom or a $C_{1-6}$ alkyl group.

8. The aminopyridine compound or a pharmaceutically acceptable salt thereof according to claim 5, wherein
$R^h$ is —N(R$^{h1}$)(R$^{h2}$) and the R$^{h1}$ is a $C_{1-6}$ alkyl group, the R$^{h2}$ is a $C_{3-8}$ cycloalkyl group, wherein the cycloalkyl group may be substituted with —COOR$^{g3}$, wherein R$^{g3}$ is a hydrogen atom or a $C_{1-6}$ alkyl group, wherein the alkyl group may be substituted with a hydroxyl group.

9. The aminopyridine compound or a pharmaceutically acceptable salt thereof according to claim 1, wherein the aminopyridine compound is selected from the following compound group, (001) 1-methyl-4-{5-[6-(4-methylpyridin-2-ylamino)pyridin-2-yl]thiazol-2-yl}piperazin-2-one, (002) 1-{5-[6-(4-methylpyridin-2-ylamino)pyridin-2-yl]thiazol-2-yl}piperidine-4-carboxylic acid, (003) 1-{5-[6-(4-methylpyridin-2-ylamino)pyridin-2-yl]thiazol-2-yl}piperidine-4-carboxamide, (004) N-methyl-1-{5-[6-(4-methylpyridin-2-ylamino)pyridin-2-yl]thiazol-2-yl}piperidine-4-carboxamide, (005) N-(2-hydroxyethyl)-1-{5-[6-(4-methylpyridin-2-ylamino)pyridin-2-yl]thiazol-2-yl} piperidine-4-carboxamide, (006) trans-4-{5-[6-(4-methylpyridin-2-ylamino)pyridin-2-yl]thiazol-2-yl}cyclohexanecarboxylic acid methyl ester, (007) trans-4-{5-[6-(4-methylpyridin-2-ylamino)pyridin-2-yl]thiazol-2-yl}cyclohexanecarboxylic acid, (008) (4-hydroxypiperidin-1-yl)-(trans-4-{5-[6-(4-methylpyridin-2-ylamino)pyridin-2-yl]thiazol-2-yl}cyclohexyl)methanone, (009) N—((S)-1-{5-[6-(4-methylpyridin-2-ylamino)pyridin-2-yl]thiazol-2-yl}ethyl)amine, (010) N—((S)-1-{5-[6-(4-methylpyridin-2-ylamino)pyridin-2-yl]thiazol-2-yl}ethyl)acetamide, (011) (S)-3-methyl-4-{5-[6-(4-methylpyridin-2-ylamino)pyridin-2-yl]thiazol-2-yl}oxazolidin-2-one, (012) (5)-2,2-dimethyl-4-{5-[6-(4-methylpyridin-2-ylamino)pyridin-2-yl]thiazol-2-yl}oxazolidine-3-carboxylic acid tert-butyl ester, (013) (S)-2-amino-2-{5-[6-(4-methylpyridin-2-ylamino)pyridin-2-yl]thiazol-2-yl}ethanol, (014) (S)-4-{5-[6-(4-methylpyridin-2-ylamino)pyridin-2-yl]thiazol-2-yl}oxazolidin-2-one,
(015) (1-{5-[6-(4-methylpyridin-2-ylamino)pyridin-2-yl]thiazol-2-yl}piperidin-4-yl)acetic acid,
(016) trans-4-[N-methyl-N-{5-[6-(4-methylpyridin-2-ylamino)pyridin-2-yl]thiazol-2-yl}amino)methyl]cyclohexanecarboxylic acid,
(017) 3-(1-{5-[6-(4-methylpyridin-2-ylamino)pyridin-2-yl]thiazol-2-yl}piperidin-4-yl)propionic acid,
(018) 2-methyl-2-(1-{5-[6-(4-methylpyridin-2-ylamino)pyridin-2-yl]thiazol-2-yl}piperidin-4-yl)propionic acid,
(019) N-{4-methyl-5-[6-(4-methylpyridin-2-ylamino)pyridin-2-yl]thiazol-2-yl}propionamide,
(020) N-{4-methyl-5-[6-(4-methylpyridin-2-ylamino)pyridin-2-yl]thiazol-2-yl}acetamide,
(021) N-{4-methyl-5-[6-(4-methylpyridin-2-ylamino)pyrazin-2-yl]thiazol-2-yl}acetamide,
(022) acetic acid(S)-1-{5-[6-(4-methylpyridin-2-ylamino)pyridin-2-yl]thiazol-2-yl}ethyl ester,
(023) (S)-1-{5-[6-(4-methylpyridin-2-ylamino)pyridin-2-yl]thiazol-2-yl}ethanol,
(024) 1-{5-[6-(4-methylpyridin-2-ylamino)pyridin-2-yl]thiazol-2-yl}ethanone,
(025) 5-[6-(4-methylpyridin-2-ylamino)pyridin-2-yl]thiazole-2-carboxylic acid ethyl ester,
(026) 1-{5-[6-(4-methylpyridin-2-ylamino)pyridin-2-yl]thiazol-2-yl}ethanone oxime,
(027) (S)-5-{5-[6-(4-methylpyridin-2-ylamino)pyridin-2-yl]thiazol-2-yl}dihydrofuran-2-one,
(028) 1-{5-[6-(4-methylpyridin-2-ylamino)pyridin-2-yl]thiazol-2-yl}ethanone O-(2-hydroxyethyl)oxime,
(029) N-methoxy-N-methyl-5-[6-(4-methylpyridin-2-ylamino)pyridin-2-yl]thiazole-2-carboxamide,
(030) N-methyl-5-[6-(4-methylpyridin-2-ylamino)pyridin-2-yl]thiazole-2-carboxamide,
(031) N-methyl-N—((S)-1-{5-[6-(4-methylpyridin-2-ylamino)pyridin-2-yl]thiazol-2-yl}ethyl)acetamide,
(032) (S)-5-{5-[6-(4-methylpyridin-2-ylamino)pyridin-2-yl]thiazol-2-yl}pyrrolidin-2-one,
(033) 5-{5-[6-(4-methylpyridin-2-ylamino)pyridin-2-yl]thiazol-2-yl}pentanoic acid,
(034) 5-{5-[6-(4-methylpyridin-2-ylamino)pyridin-2-yl]thiazol-2-yl}pentan-1-ol,
(035) 5-{5-[6-(4-methylpyridin-2-ylamino)pyridin-2-yl]thiazol-2-yl}pentanamide,
(036) 4-{5-[6-(4-methylpyridin-2-ylamino)pyridin-2-yl]thiazol-2-yl}cyclohexanol,
(037) 4-{5-[6-(4-methylpyridin-2-ylamino)pyridin-2-yl]thiazol-2-yl}cyclohexanone oxime,
(038) N-{6-[2-((S)-1-aminoethyl)thiazol-5-yl]pyridin-2-yl}-N-([4,4']bipyridinyl-2-yl)amine,
(039) N—((S)-1-{5-[6-([4,4]bipyridinyl-2-ylamino)pyridin-2-yl]thiazol-2-yl}ethyl)acetamide,
(040) N—((S)-1-{5-[6-(4-chloropyridin-2-ylamino)pyridin-2-yl]thiazol-2-yl}ethyl)acetamide,
(041) (S)-2-methyl-1-{5-[6-(4-methylpyridin-2-ylamino)pyridin-2-yl]thiazol-2-yl}propan-1-ol,
(042) N—((S)-1-{5-[6-(isoquinolin-3-ylamino)pyridin-2-yl]thiazol-2-yl}ethyl)acetamide,
(043) (4-methylpyridin-2-yl)-[6-(2-piperidin-4-ylthiazol-5-yl)pyridin-2-yl]amine,
(044) trans-4-{5-[6-(4-methylpyridin-2-ylamino)pyridin-2-yl]thiazol-2-yl}cyclohexanecarboxamide,
(045) 5-{5-[6-(4-methylpyridin-2-ylamino)pyridin-2-yl]thiazol-2-yl}pentylamine,
(046) 4-{5-[6-(4-methylpyridin-2-ylamino)pyridin-2-yl]thiazol-2-yl}butan-1-ol,
(047) 4-(2-{5-[6-(4-methylpyridin-2-ylamino)pyridin-2-yl]thiazol-2-yl}ethyl)phenol,
(048) 2-hydroxy-N—((S)-1-{5-[6-(4-methylpyridin-2-ylamino)pyridin-2-yl]thiazol-2-yl}ethyl)acetamide,
(049) 3-({5-[6-(4-methylpyridin-2-ylamino)pyridin-2-yl]thiazole-2-carbonyl}amino)propionic acid,
(050) 4-(2-{5-[6-(4-methylpyridin-2-ylamino)pyridin-2-yl]thiazol-2-yl}ethyl)benzoic acid,
(051) 1-{5-[6-(4-methylpyridin-2-ylamino)pyridin-2-yl]thiazol-2-ylmethyl}piperidin-4-ol,
(052) 3,3-dimethyl-4-{5-[6-(4-methylpyridin-2-ylamino)pyridin-2-yl]thiazol-2-yl}butan-1-ol,
(053) [4-(2-{5-[6-(4-methylpyridin-2-ylamino)pyridin-2-yl]thiazol-2-yl}ethyl)phenyl]methanol,
(054) N—((R)-(4-hydroxyphenyl)-{5-[6-(4-methylpyridin-2-ylamino)pyridin-2-yl]thiazol-2-yl}methyl)acetamide,
(055) N-(2-hydroxyethyl)-4-(2-{5-[6-(4-methylpyridin-2-ylamino)pyridin-2-yl]thiazol-2-yl}ethyl)benzamide,
(056) 4-(2-{5-[6-(4-methylpyridin-2-ylamino)pyridin-2-yl]thiazol-2-yl}ethyl)cyclohexanone,
(057) 4-(2-{5-[6-(4-methylpyridin-2-ylamino)pyridin-2-yl]thiazol-2-yl}ethyl)cyclohexanol,
(058) ((3R,4S)-3,4-dihydroxypyrrolidin-1-yl)-(trans-4-{5-[6-(4-methylpyridin-2-ylamino)pyridin-2-yl]thiazol-2-yl}cyclohexyl)methanone,
(059) (trans-4-{5-[6-(4-methylpyridin-2-ylamino)pyridin-2-yl]thiazol-2-yl}cyclohexyl)-(piperazin-1-yl)methanone,
(060) 4-{5-[6-(4-methylpyridin-2-ylamino)pyridin-2-yl]thiazol-2-yl}piperidine-1-carboxamide,
(061) 2-hydroxy-1-(4-{5-[6-(4-methylpyridin-2-ylamino)pyridin-2-yl]thiazol-2-yl}piperidin-1-yl)ethanone,
(062) trans-4-{5-[6-(4-methoxypyridin-2-ylamino)pyridin-2-yl]thiazol-2-yl}cyclohexanecarboxylic acid,
(063) 3-(4-{5-[6-(4-methylpyridin-2-ylamino)pyridin-2-yl]thiazol-2-yl}piperidin-1-yl)-3-oxopropionic acid,
(064) N-(4-methylpyridin-2-yl)-N-{6-[2-(piperazin-1-ylmethyl)thiazol-5-yl]pyridin-2-yl}amine,
(065) 1-{5-[6-(4-methylpyridin-2-ylamino)pyridin-2-yl]thiazol-2-ylmethyl}piperidin-4-ylamine,
(066) N-{5-[6-(4-methylpyridin-2-ylamino)pyridin-2-yl]thiazol-2-ylmethyl}methanesulfonamide,
(067) N-(trans-4-{5-[6-(4-methylpyridin-2-ylamino)pyridin-2-yl]thiazol-2-yl}cyclohexyl)acetamide,
(068) trans-4-{5-[6-(4-chloropyridin-2-ylamino)pyridin-2-yl]thiazol-2-yl}cyclohexanecarboxylic acid,
(069) 2-{5-[6-(4-methylpyridin-2-ylamino)pyridin-2-yl]thiazol-2-yl}ethanol,
(070) (trans-4-{5-[6-(4-methylpyridin-2-ylamino)pyridin-2-yl]thiazol-2-yl}cyclohexyl)methanol,
(071) trans-4-{5-[6-(isoquinolin-3-ylamino)pyridin-2-yl]thiazol-2-yl}cyclohexanecarboxylic acid,
(072) trans-4-{5-[6-(4-methylpyridin-2-ylamino)pyridin-2-yl]thiazol-2-yl}cyclohexylmethylamine,
(073) ((3R,4S)-3,4-dihydroxypyrrolidin-1-yl)-[4-(2-{5-[6-(4-methylpyridin-2-ylamino)pyridin-2-yl]thiazol-2-yl}ethyl)phenyl]methanone,
(074) N-(trans-4-{5-[6-(4-methylpyridin-2-ylamino)pyridin-2-yl]thiazol-2-yl}cyclohexylmethyl)acetamide,
(075) N-(trans-4-{5-[6-(4-methylpyridin-2-ylamino)pyridin-2-yl]thiazol-2-yl}cyclohexylmethyl)methanesulfonamide, (076) 2-hydroxy-N-(trans-4-{5-[6-(4-methylpyridin-2-ylamino)pyridin-2-yl]thiazol-2-yl}cyclohexylmethyl)acetamide,
(077) 2-hydroxy-N-[4-(2-{5-[6-(4-methylpyridin-2-ylamino)pyridin-2-yl]thiazol-2-yl}ethyl)phenyl]acetamide,
(078) ((3R,4S)-3,4-dihydroxypiperidin-1-yl)-(trans-4-{5-[6-(4-methylpyridin-2-ylamino)pyridin-2-yl]thiazol-2-yl}cyclohexyl)methanone,
(079) ((R)-3-hydroxypyrrolidin-1-yl)-(trans-4-{5-[6-(4-methylpyridin-2-ylamino)pyridin-2-yl]thiazol-2-yl}cyclohexyl)metanone,
(080) (4-{5-[6-(4-methylpyridin-2-ylamino)pyridin-2-yl]thiazol-2-ylmethyl}phenyl)methanol,
(081) N-(4-methylpyridin-2-yl)-N-[6-(2-pyridin-3-ylmethylthiazol-5-yl)pyridin-2-yl]amine,
(082) N-(4-methylpyridin-2-yl)-N-{6-[2-(2-piperidin-4-ylethyl)thiazol-5-yl]pyridin-2-yl}amine,
(083) N-(6-{2-[2-(1-methanesulfonylpiperidin-4-yl)ethyl]thiazol-5-yl}pyridin-2-yl)-N-(4-methylpyridin-2-yl)amine,
(084) 2-hydroxy-1-[4-(2-{5-[6-(4-methylpyridin-2-ylamino)pyridin-2-yl]thiazol-2-yl}ethyl)piperidin-1-yl]ethanone,
(085) N-(2-hydroxyethyl)-trans-4-{5-[6-(4-methylpyridin-2-ylamino)pyridin-2-yl]thiazol-2-yl}cyclohexanecarboxamide,
(086) N-(2-morpholin-4-ylethyl)-trans-4-{5-[6-(4-methylpyridin-2-ylamino)pyridin-2-yl]thiazol-2-yl}cyclohexanecarboxamide,
(087) [3-(2-{5-[6-(4-methylpyridin-2-ylamino)pyridin-2-yl]thiazol-2-yl}ethyl)phenyl]methanol,
(088) (3-hydroxypyrrolidin-1-yl)-(trans-4-{5-[6-(4-methylpyridin-2-ylamino)pyridin-2-yl]thiazol-2-yl}cyclohexyl)methanone,
(089) 4-(trans-4-{5-[6-(4-methylpyridin-2-ylamino)pyridin-2-yl]thiazol-2-yl}cyclohexanecarbonyl)piperazin-2-one,
(090) ((R)-2-hydroxymethylpyrrolidin-1-yl)-(trans-4-{5-[6-(4-methylpyridin-2-ylamino)pyridin-2-yl]thiazol-2-yl}cyclohexyl)metanone,
(091) (4-aminopiperidin-1-yl)-(trans-4-{5-[6-(4-methylpyridin-2-ylamino)pyridin-2-yl]thiazol-2-yl}cyclohexyl)methanone,
(092) [4-(2-{5-[6-(4-methylpyridin-2-ylamino)pyridin-2-yl]thiazol-2-yl}ethyl)piperidin-1-yl]-(piperidin-4-yl)metanone,
(093) (trans-4-{5-[6-(4-chloropyridin-2-ylamino)pyridin-2-yl]thiazol-2-yl}cyclohexyl)-(4-hydroxypiperidin-1-yl)metanone,
(094) N-(4-hydroxypiperidin-1-yl)-(trans-4-{5-[6-(4-methylpyridin-2-ylamino)pyridin-2-yl]thiazol-2-yl}cyclohexanecarboxamide,
(095) N—[(R)-2-hydroxy-1-(3H-imidazol-4-ylmethyl)ethyl]-trans-4-{5-[6-(4-methylpyridin-2-ylamino)pyridin-2-yl]thiazol-2-yl}cyclohexanecarboxamide,
(096) N—[(S)-2-hydroxy-1-(3H-imidazol-4-ylmethyl)ethyl]-trans-4-{5-[6-(4-methylpyridin-2-ylamino)pyridin-2-yl]thiazol-2-yl}cyclohexanecarboxamide,
(097) N-(2-dimethylaminoethyl)-trans-4-{5-[6-(4-methylpyridin-2-ylamino)pyridin-2-yl]thiazol-2-yl}cyclohexanecarboxamide,
(098) (3-aminopyrrolidin-1-yl)-(trans-4-{5-[6-(4-methylpyridin-2-ylamino)pyridin-2-yl]thiazol-2-yl}cyclohexyl)methanone,
(099) N-[1-(trans-4-{5-[6-(4-methylpyridin-2-ylamino)pyridin-2-yl]thiazol-2-yl}cyclohexanecarbonyl)pyrrolidin-3-yl]methanesulfonamide,
(100) (3R,4S)-1-(trans-4-{5-[6-(4-methylpyridin-2-ylamino)pyridin-2-yl]thiazol-2-yl}cyclohexylmethyl)pyrrolidin-3,4-diol,
(101) trans-4-{5-[6-(4-methylpyridin-2-ylamino)pyridin-2-yl]thiazol-2-yl}cyclohexanecarbonitrile,
(102) cis-4-{5-[6-(4-methylpyridin-2-ylamino)pyridin-2-yl]thiazol-2-yl}cyclohexanecarbonitrile,
(103) (S)-5-{5-[6-(4-methoxypyridin-2-ylamino)pyridin-2-yl]thiazol-2-yl}pyrrolidin-2-one,
(104) (S)-1-{5-[6-(4-methoxypyridin-2-ylamino)pyridin-2-yl]thiazol-2-yl}ethanol,
(105) (5)-1-(5-{6-[4-(2-hydroxyethyl)pyridin-2-ylamino]pyridin-2-yl}thiazol-2-yl)ethanol,
(106) (S)-1-{5-[6-(4-chloropyridin-2-ylamino)pyridin-2-yl]thiazol-2-yl}ethanol,
(107) (S)-5-{5-[6-(4-chloropyridin-2-ylamino)pyridin-2-yl]thiazol-2-yl}pyrrolidin-2-one,
(108) 3-(trans-4-{5-[6-(4-methylpyridin-2-ylamino)pyridin-2-yl]thiazol-2-yl}cyclohexyl)-4H-[1,2,4]oxazol-5-one,
(109) N-(4-methylpyridin-2-yl)-N-(6-{2-[4-(1H-tetrazol-5-yl)cyclohexyl]thiazol-5-yl}pyridin-2-yl)amine,
(110) (5)-5-(5-{6-[4-(2-hydroxyethyl)pyridin-2-ylamino]pyridin-2-yl}thiazol-2-yl)pyrrolidin-2-one,
(111) N-(1,1-dimethyl-2-{5-[6-(4-methylpyridin-2-ylamino)pyridin-2-yl]thiazol-2-yl}ethyl)acetamide,
(112) (S)-1-(5-{6-[4-(2-methyl-[1,3]dioxolan-2-yl)pyridin-2-ylamino]pyridin-2-yl}thiazol-2-yl)ethanol,
(113) N-methyl-trans-4-{5-[6-(4-methylpyridin-2-ylamino)pyridin-2-yl]thiazol-2-yl}cyclohexanecarboxamide,
(114) N-(1,1-dimethyl-2-{5-[6-(4-methylpyridin-2-ylamino)pyridin-2-yl]thiazol-2-yl}ethyl)methanesulfonamide,
(115) trans-4-{5-[6-(4-chloropyridin-2-ylamino)pyridin-2-yl]thiazol-2-yl}cyclohexanecarboxamide,
(116) trans-4-{5-[6-(4-methoxypyridin-2-ylamino)pyridin-2-yl]thiazol-2-yl}cyclohexanecarboxamide,
(117) 4-{5-[6-(4-methylpyridin-2-ylamino)pyridin-2-yl]thiazol-2-ylmethyl}cyclohexanol,
(118) (S)-1-(5-{6-[4-(2-hydroxyethoxy)pyridin-2-ylamino]pyridin-2-yl}thiazol-2-yl)ethanol,
(119) dimethylcarbamic acid(S)-1-{5-[6-(4-methylpyridin-2-ylamino)pyridin-2-yl]thiazol-2-yl}ethyl ester,
(120) 4-{5-[6-(4-methylpyridin-2-ylamino)pyridin-2-yl]thiazol-2-ylmethyl}piperazin-2-one,
(121) 4-(2-hydroxy-2-{5-[6-(4-methylpyridin-2-ylamino)pyridin-2-yl]thiazol-2-yl}ethyl)phenol,
(122) 4-(2-{5-[6-(4-methylpyridin-2-ylamino)pyridin-2-yl]thiazol-2-ylmethoxy}acetyl)piperazin-2-one,
(123) N—((R)-(4-hydroxyphenyl)-{5-[6-(4-methylpyridin-2-ylamino)pyridin-2-yl]thiazol-2-yl}methyl)-N-methylacetamide,
(124) 4-{5-[6-(4-methylpyridin-2-ylamino)pyridin-2-yl]thiazol-2-ylmethyl}piperazin-2,6-dione,
(125) (S)-5-{5-[6-(4-methylpyridin-2-ylamino)pyridin-2-yl]thiazol-2-yl}oxazolidin-2-one,
(126) 4-{5-[6-(4-methylpyridin-2-ylamino)pyridin-2-yl]thiazol-2-ylmethyl}piperazin-2-one,
(127) N-(4-methylpyridin-2-yl)-N-[6-(2-morpholin-4-ylthiazol-5-yl)pyridin-2-yl]amine,
(128) 1-(4-{5-[6-(4-methylpyridin-2-ylamino)pyridin-2-yl]thiazol-2-yl}piperazin-1-yl)ethanone, (129) 4-{5-[6-(4-methylpyridin-2-ylamino)pyridin-2-yl]thiazol-2-yl}piperazine-1-sulfonamide,
(130) N-(4-methoxypyridin-2-yl)-N-{6-[2-(morpholin-4-yl)thiazol-5-yl]pyridin-2-yl}amine,
(131) (3R,4S)-1-{5-[6-(4-methylpyridin-2-ylamino)pyridin-2-yl]thiazol-2-yl}pyrrolidine-3,4-diol,
(132) N-methyl-N-{5-[6-(4-methylpyridin-2-ylamino)pyridin-2-yl]thiazol-2-yl}acetamide,
(133) N-[6-(4-methyl-2-morpholin-4-ylthiazol-5-yl)pyridin-2-yl]-N-(4-methylpyridin-2-yl)amine,
(134) N-methyl-N-{5-[6-(4-methylpyridin-2-ylamino)pyridin-2-yl]thiazol-2-yl}amine,
(135) N-methyl-4-{5-[6-(4-methylpyridin-2-ylamino)pyridin-2-yl]thiazol-2-yl}piperazine-1-carboxamide,
(136) 1-{4-methyl-5-[6-(4-methylpyridin-2-ylamino)pyridin-2-yl]thiazol-2-yl}piperidine-4-carboxamide,
(137) N-{6-[2-(4-methoxypiperidin-1-yl)thiazol-5-yl]pyridin-2-yl}-N-(4-methylpyridin-2-yl)amine,
(138) N-{6-[2-(4-methylpiperazin-1-yl)thiazol-5-yl]pyridin-2-yl}-N-(4-methylpyridin-2-yl)amine,
(139) 1-{5-[6-(4-methylpyridin-2-ylamino)pyridin-2-yl]thiazol-2-yl}piperidin-4-ol,
(140) N-methyl-1-{5-[6-(4-methoxypyridin-2-ylamino)pyridin-2-yl]thiazol-2-yl}piperidine-4-carboxamide,
(141) 4-{4-methyl-5-[6-(4-methylpyridin-2-ylamino)pyridin-2-yl]thiazol-2-yl}piperazine-1-carbaldehyde,
(142) 4-{5-[6-(4-methylpyridin-2-ylamino)pyridin-2-yl]thiazol-2-yl}piperazine-4-carboxylic methyl ester,
(143) 2-hydroxy-1-(4-{5-[6-(4-methylpyridin-2-ylamino)pyridin-2-yl]thiazol-2-yl}piperazin-1-yl)ethanone,
(144) 1-(4-{5-[6-(4-methylpyridin-2-ylamino)pyridin-2-yl]thiazol-2-yl}piperazin-1-yl)propan-1-one,
(145) N,N-dimethyl-4-{5-[6-(4-methylpyridin-2-ylamino)pyridin-2-yl]thiazol-2-yl}piperazine-1-carboxamide,
(146) 1-(4-{5-[6-(4-methoxypyridin-2-ylamino)pyridin-2-yl]thiazol-2-yl}piperazin-1-yl)ethanone,
(147) 1-(4-{5-[6-(4-chloropyridin-2-ylamino)pyridin-2-yl]thiazol-2-yl}piperazin-1-yl)ethanone,
(148) 4-(methyl-{5-[6-(4-methylpyridin-2-ylamino)pyridin-2-yl]thiazol-2-yl}amino)cyclohexanecarboxylic acid,
(149) 4-(N-methyl-N-{5-[6-(4-methylpyridin-2-ylamino)pyridin-2-yl]thiazol-2-yl}amino)cyclohexanecarboxamide,
(150) 3-(1-{5-[6-(4-methylpyridin-2-ylamino)pyridin-2-yl]thiazol-2-yl}piperidin-4-yl)-4H-[1,2,4]oxadiazole-5-one,
(151) N-methyl-N-{5-[6-(4-methylpyridin-2-ylamino)pyridin-2-yl]thiazol-2-yl}-N-piperidin-4-ylamine,
(152) 4-(1-{5-[6-(4-methylpyridin-2-ylamino)pyridin-2-yl]thiazol-2-yl}piperidine-4-carbonyl)piperazin-2-one,
(153) N-(2,2-dimethoxyethyl)-N-methyl-N-{5-[6-(4-methylpyridin-2-ylamino)pyridin-2-yl]thiazol-2-yl}amine,
(154) 1-[4-(N-methyl-N-{5-[6-(4-methylpyridin-2-ylamino)pyridin-2-yl]thiazol-2-yl}amino)piperidin-1-yl]ethanone,
(155) 2-hydroxy-1-[4-(N-methyl-N-{5-[6-(4-methylpyridin-2-ylamino)pyridin-2-yl]thiazol-2-yl}amino)piperidin-1-yl]ethanone,
(156) N-methyl-4-(N'-methyl-N'-{5-[6-(4-methylpyridin-2-ylamino)pyridin-2-yl]thiazol-2-yl}amino)piperidine-1-carboxamide,
(157) N-{2-[4-(N'-methyl-N'-{5-[6-(4-methylpyridin-2-ylamino)pyridin-2-yl]thiazol-2-yl}amino)piperidin-1-yl]-2-oxoethyl}acetamide,
(158) (4-{5-[6-(4-methylpyridin-2-ylamino)pyridin-2-yl]thiazol-2-yl}-2-oxopiperazin-1-yl)acetic acid,
(159) 2-(4-{5-[6-(4-methylpyridin-2-ylamino)pyridin-2-yl]thiazol-2-yl}-2-oxopiperazin-1-yl)acetamide,
(160) N-methyl-2-(4-{5-[6-(4-methylpyridin-2-ylamino)pyridin-2-yl]thiazol-2-yl}-2-oxopiperazin-1-yl)acetamide,
(161) N-(2-hydroxyethyl)-2-(4-{5-[6-(4-methylpyridin-2-ylamino)pyridin-2-yl]thiazol-2-yl}-2-oxopiperazin-1-yl)acetamide,
(162) N-methyl-N-methylcarbamoylmethyl-1-{5-[6-(4-methylpyridin-2-ylamino)pyridin-2-yl]thiazol-2-yl}piperidine-4-carboxamide,
(163) N-methyl-N-{5-[6-(4-methylpyridin-2-ylamino)pyridin-2-yl]thiazol-2-yl}-N-tetrahydropyran-4-ylamine,
(164) 4-[(N-methyl-N-{5-[6-(4-methylpyridin-2-ylamino)pyridin-2-yl]thiazol-2-yl}amino)methyl]phenol,
(165) N—((R)-1-{5-[6-(4-methylpyridin-2-ylamino)pyridin-2-yl]thiazol-2-yl}pyrrolidin-3-yl)acetamide,
(166) (R)-1-{5-[6-(4-methylpyridin-2-ylamino)pyridin-2-yl]thiazol-2-yl}pyrrolidin-3-ylamine,
(167) 1-{5-[6-(4-methylpyridin-2-ylamino)pyridin-2-yl]thiazol-2-yl}piperidine-3-carboxylic acid,
(168) 2-hydroxy-N—((R)-1-{5-[6-(4-methylpyridin-2-ylamino)pyridin-2-yl]thiazol-2-yl}pyrrolidin-3-yl)acetamide,
(169) 1-{5-[6-(4-methylpyridin-2-ylamino)pyridin-2-yl]thiazol-2-yl}piperidine-3-carboxamide,
(170) N-methyl-1-{5-[6-(4-methylpyridin-2-ylamino)pyridin-2-yl]thiazol-2-yl}piperidine-3-carboxamide,
(171) N-(2-hydroxyethyl)-1-{5-[6-(4-methylpyridin-2-ylamino)pyridin-2-yl]thiazol-2-yl}piperidine-3-carboxamide,
(172) (R)-1-{5-[6-(4-methylpyridin-2-ylamino)pyridin-2-yl]thiazol-2-yl}pyrrolidin-3-ol,
(173) trans-4-(N-methyl-N-{5-[6-(4-methylpyridin-2-ylamino)pyridin-2-yl]thiazol-2-yl}amino)cyclohexanol,
(174) N-{6-[2-(3-methoxymethylpiperidin-1-yl)thiazol-5-yl]pyridin-2-yl}-N-(4-methylpyridin-2-yl)amine,
(175) 2-hydroxy-N-(1-{5-[6-(4-methylpyridin-2-ylamino)pyridin-2-yl]thiazol-2-yl}piperidin-4-yl)acetamide,
(176) 2-hydroxy-N-methyl-N-(1-{5-[6-(4-methylpyridin-2-ylamino)pyridin-2-yl]thiazol-2-yl}piperidin-4-yl)acetamide,
(177) N-(1-{5-[6-(4-methylpyridin-2-ylamino)pyridin-2-yl]thiazol-2-yl}piperidin-4-yl)methanesulfonamide,
(178) N-methyl-N-(1-{5-[6-(4-methylpyridin-2-ylamino)pyridin-2-yl]thiazol-2-yl}piperidin-4-yl)methanesulfonamide,
(179) 2-hydroxy-N-(1-{5-[6-(4-methylpyridin-2-ylamino)pyridin-2-yl]thiazol-2-yl}piperidin-4-ylmethyl)acetamide,
(180) N-(1-{5-[6-(4-methylpyridin-2-ylamino)pyridin-2-yl]thiazol-2-yl}piperidin-4-ylmethyl)acetamide,
(181) N-methyl-(S)-1-{5-[6-(4-methylpyridin-2-ylamino)pyridin-2-yl]thiazol-2-yl}pyrrolidine-2-carboxamide,
(182) N—((R)-1-{5-[6-(4-methylpyridin-2-ylamino)pyridin-2-yl]thiazol-2-yl}pyrrolidin-3-yl)methanesulfonamide,
(183) N-{6-[2-((R)-3-methoxypyrrolidin-1-yl)thiazol-5-yl]pyridin-2-yl}-N-(4-methylpyridin-2-yl)amine,
(184) N-methyl-4-(N'-methyl-N'-{5-[6-(4-methylpyridin-2-ylamino)pyridin-2-yl]thiazol-2-yl}amino)cyclohexanecarboxamide, (185) N-(2-hydroxyethyl)-4-(N'-methyl-N'-{5-[6-(4-methylpyridin-2-ylamino)pyridin-2-yl]thiazol-2-yl}amino)cyclohexanecarboxamide,
(186) N-(2-acetylaminoethyl)-4-(N'-methyl-N'-{5-[6-(4-methylpyridin-2-ylamino)pyridin-2-yl]thiazol-2-yl}amino)cyclohexanecarboxamide,
(187) (1-{5-[6-(4-methylpyridin-2-ylamino)pyridin-2-yl]thiazol-2-yl}piperidin-3-ylmethoxy)acetic acid,
(188) (1-{5-[6-(4-methylpyridin-2-ylamino)pyridin-2-yl]thiazol-2-yl}piperidin-3-yl)methanol,
(189) 2-(1-{5-[6-(4-methylpyridin-2-ylamino)pyridin-2-yl]thiazol-2-yl}piperidin-3-ylmethoxy)acetamide,
(190) 4-methyl-1-{5-[6-(4-methylpyridin-2-ylamino)pyridin-2-yl]thiazol-2-yl}piperidine-4-carboxamide,
(191) N-methyl-4-methyl-1-{5-[6-(4-methylpyridin-2-ylamino)pyridin-2-yl]thiazol-2-yl}piperidine-4-carboxamide,
(192) N-methyl-2-(1-{5-[6-(4-methylpyridin-2-ylamino)pyridin-2-yl]thiazol-2-yl}piperidin-3-ylmethoxy)acetamide,
(193) N-(2-hydroxyethyl)-4-methyl-1-{5-[6-(4-methylpyridin-2-ylamino)pyridin-2-yl]thiazol-2-yl}-piperidine-4-carboxamide,
(194) 2-(1-{5-[6-(4-methylpyridin-2-ylamino)pyridin-2-yl]thiazol-2-yl}piperidin-4-yl)acetamide,
(195) N-methyl-2-(1-{5-[6-(4-methylpyridin-2-ylamino)pyridin-2-yl]thiazol-2-yl}piperidin-4-yl)acetamide,
(196) N-(2-hydroxyethyl)-2-(1-{5-[6-(4-methylpyridin-2-ylamino)pyridin-2-yl]thiazol-2-yl}piperidin-4-yl)acetamide,
(197) N,N-diallyl-N-{5-[6-(4-methylpyridin-2-ylamino)pyridin-2-yl]thiazol-2-yl}amine,
(198) N-[2-(N'-methyl-N'-{5-[6-(4-methylpyridin-2-ylamino)pyridin-2-yl]thiazol-2-yl}amino)ethyl]acetamide,
(199) 2-hydroxy-N-[2-(N'-methyl-{5-[6-(4-methylpyridin-2-ylamino)pyridin-2-yl]thiazol-2-yl}amino)ethyl]acetamide,
(200) N-(4-methanesulfonylpiperidin-1-yl)—N-methyl-N-{5-[6-(4-methylpyridin-2-ylamino)pyridin-2-yl]thiazol-2-yl} amine,
(201) N,N-dimethyl-4-(N'-methyl-N'-{5-[6-(4-methylpyridin-2-ylamino)pyridin-2-yl]thiazol-2-yl}amino)piperidine-1-carboxamide,
(202) (4-hydroxyphenyl)-[4-(N-methyl-N-{5-[6-(4-methylpyridin-2-ylamino)pyridin-2-yl]thiazol-2-yl}amino)piperidin-1-yl]methanone,
(203) 1-(4-{5-[6-(4-methylpyridin-2-ylamino)pyridin-2-yl]thiazol-2-ylamino}piperidin-1-yl)ethanone,
(204) 1-[4-(N-isopropyl-N-{5-[6-(4-methylpyridin-2-ylamino)pyridin-2-yl]thiazol-2-yl}amino)piperidin-1-yl]ethanone,
(205) N-methyl-2-((R)-1-{5-[6-(4-methylpyridin-2-ylamino)pyridin-2-yl]thiazol-2-yl}pyrrolidin-3-yloxy)acetamide,
(206) 1-{5-[6-(4-methoxypyridin-2-ylamino)pyridin-2-yl]thiazol-2-yl}piperidine-4-carboxamide,
(207) 1-{5-[6-(4-chloropyridin-2-ylamino)pyridin-2-yl]thiazol-2-yl}piperidine-4-carboxamide,
(208) 2-(N-methyl-N-{5-[6-(4-methylpyridin-2-ylamino)pyridin-2-yl]thiazol-2-yl}amino)ethanol,
(209) N-(2-methoxyethyl)-N-methyl-N-{5-[6-(4-methylpyridin-2-ylamino)pyridin-2-yl]thiazol-2-yl}amine,
(210) N-[2-(N'-(1-acetylpiperidin-4-yl)-N'-{5-[6-(4-methylpyridin-2-ylamino)pyridin-2-yl]thiazol-2-yl}amino)ethyl]methanesulfonamide,
(211) 1-[4-(N-(2-hydroxyethyl)-N-{5-[6-(4-methylpyridin-2-ylamino)pyridin-2-yl]thiazol-2-yl}amino)piperidin-1-yl]ethanone,
(212) 1-[4-(N-(2-methoxyethyl)-N-{5-[6-(4-methylpyridin-2-ylamino)pyridin-2-yl]thiazol-2-yl}amino)piperidin-1-yl]ethanone,
(213) (S)-1-{5-[6-(4-methylpyridin-2-ylamino)pyridin-2-yl]thiazol-2-yl}pyrrolidine-2-carboxamide,
(214) N-methyl-(S)-1-{5-[6-(4-methylpyridin-2-ylamino)pyridin-2-yl]thiazol-2-yl}pyrrolidine-2-carboxamide,
(215) N-(2,2,2-trifluoroethyl)-(S)-1-{5-[6-(4-methylpyridin-2-ylamino)pyridin-2-yl]thiazol-2-yl}pyrrolidine-2-carboxamide,
(216) (R)-1-{5-[6-(4-methylpyridin-2-ylamino)pyridin-2-yl]thiazol-2-yl}piperidine-3-carboxylic acid,
(217) ((R)-1-{5-[6-(4-methylpyridin-2-ylamino)pyridin-2-yl]thiazol-2-yl}piperidin-3-yl)methanol,
(218) (R)-1-{5-[6-(4-methylpyridin-2-ylamino)pyridin-2-yl]thiazol-2-yl}piperidine-3-carboxamide,
(219) 1-[4-(N-ethyl-N-{5-[6-(4-methylpyridin-2-ylamino)
(220) pyridin-2-yl]thiazol-2-yl}amino)piperidin-1-yl]ethanone,
(221) 1-{4-[N-{5-[6-(4-methylpyridin-2-ylamino)pyridin-2-yl]thiazol-2-yl}-N-(2,2,2-trifluoroethyl)amino]piperidin-1-yl}ethanone,
(222) 1-[4-(N-{5-[6-(4-chloropyridin-2-ylamino)pyridin-2-yl]thiazol-2-yl}-N-methylamino)piperidin-1-yl]ethanone,
(223) 1-[4-(N-{5-[6-(4-chloropyridin-2-ylamino)pyridin-2-yl]thiazol-2-yl}-N-methylamino)piperidin-1-yl]-2-hydroxyethanone,
(224) (R)-1-{5-[6-(4-methoxypyridin-2-ylamino)pyridin-2-yl]thiazol-2-yl}pyrrolidin-3-ol,
(225) (R)-1-{5-[6-(4-chloropyridin-2-ylamino)pyridin-2-yl]thiazol-2-yl}pyrrolidin-3-ol,
(226) 4-methyl-1-{5-[6-(4-methylpyridin-2-ylamino)pyridin-2-yl]thiazol-2-yl}piperidine-4-carboxylic acid,
(227) (S)-1-{5-[6-(4-methoxypyridin-2-ylamino)pyridin-2-yl]thiazol-2-yl}pyrrolidine-2-carboxamide,
(228) (S)-1-{5-[6-(4-chloropyridin-2-ylamino)pyridin-2-yl]thiazol-2-yl}pyrrolidine-2-carboxamide,
(229) 1-{5-[6-(4-acetylpyridin-2-ylamino)pyridin-2-yl]thiazol-2-yl}piperidine-4-carboxamide,
(230) 2-(N-(2-hydroxyethyl)-N-{5-[6-(4-methylpyridin-2-ylamino)pyridin-2-yl]thiazol-2-yl}amino)ethanol,
(231) 2-[N-{5-[6-(4-chloropyridin-2-ylamino)pyridin-2-yl]thiazol-2-yl}-N-(2-hydroxyethyl)amino]ethanol,
(232) (R)-1-{5-[6-(4-chloropyridin-2-ylamino)pyridin-2-yl]thiazol-2-yl}piperidine-3-carboxylic acid,
(233) 1-(5-{6-[4-(1-hydroxyethyl)pyridin-2-ylamino]pyridin-2-yl}thiazol-2-yl)piperidine-4-carboxamide,
(234) (R)-1-(5-{6-[4-(2-methyl-[1,3]dioxolan-2-yl)pyridin-2-ylamino]pyridin-2-yl}thiazol-2-yl)pyrrolidin-3-ol,
(235) 1-(2-{6-[2-((R)-3-hydroxypyrrolidin-1-yl)thiazol-5-yl]pyridin-2-ylamino}pyridin-4-yl)ethanone,
(236) 4-(4-{5-[6-(4-methylpyridin-2-ylamino)pyridin-2-yl]thiazol-2-yl}piperazin-1-yl)-4-oxobutyric acid,
(237) N-hydroxy-(R)-1-{5-[6-(4-chloropyridin-2-ylamino)pyridin-2-yl]thiazol-2-yl}piperidine-3-carboxamide,
(238) 4-[4-(N-methyl-N-{5-[6-(4-methylpyridin-2-ylamino)pyridin-2-yl]thiazol-2-yl}amino)piperidin-1-yl]-4-oxobutyric acid,
(239) (R)-1-(5-{6-[4-(1-hydroxyethyl)pyridin-2-ylamino]pyridin-2-yl}thiazol-2-yl)pyrrolidin-3-ol, (240) 2-(N-methyl-N-{5-[6-(4-methylpyridin-2-ylamino)pyridin-2-yl]thiazol-2-yl}amino)acetamide,
(241) (R)-1-(5-{6-[4-(2-methyl-[1,3]dioxolan-2-yl)pyridin-2-ylamino]pyridin-2-yl}thiazol-2-yl)piperidine-3-carboxylic acid,
(242) (R)-1-{5-[6-(4-acetylpyridin-2-ylamino)pyridin-2-yl]thiazol-2-yl}piperidine-3-carboxylic acid,
(243) (S)-1-{5-[6-(4-acetylpyridin-2-ylamino)pyridin-2-yl]thiazol-2-yl}pyrrolidine-2-carboxamide,
(244) (1-{5-[6-(4-chloropyridin-2-ylamino)pyridin-2-yl]thiazol-2-yl}pyrrolidin-3-yl)methanol,
(245) 1-[(R)-3-(N-methyl-N-{5-[6-(4-methylpyridin-2-ylamino)pyridin-2-yl]thiazol-2-yl}amino)pyrrolidin-1-yl]ethanone,
(246) (S)-1-{5-[6-(4-acetylpyridin-2-ylamino)pyridin-2-yl]thiazol-2-yl}pyrrolidine-2-carboxylic acid,
(247) (R)-1-(5-{6-[4-(2-methyl-[1,3]dioxolan-2-yl)pyridin-2-ylamino]pyridin-2-yl}thiazol-2-yl)piperidine-3-carboxamide,
(248) ((S)-1-{5-[6-(4-methylpyridin-2-ylamino)pyridin-2-yl]thiazol-2-yl}piperidin-3-yl)acetic acid,
(249) (S)-3-methyl-2-[2-(N-methyl-N-{5-[6-(4-methylpyridin-2-ylamino)pyridin-2-yl]thiazol-2-yl}amino)acetylamino]butyric acid,
(250) 3-[2-(N-methyl-N-{5-[6-(4-methylpyridin-2-ylamino)pyridin-2-yl]thiazol-2-yl}amino)acetylamino]propionic acid,
(251) [2-(N-methyl-N-{5-[6-(4-methylpyridin-2-ylamino)pyridin-2-yl]thiazol-2-yl}amino)acetylamino]acetic acid,
(252) [1-(5-{6-[4-(2-methyl-[1,3]dioxolan-2-yl)pyridin-2-ylamino]pyridin-2-yl}thiazol-2-yl)piperidin-4-yl]acetic acid,
(253) (1-{5-[6-(pyridin-2-ylamino)pyridin-2-yl]thiazol-2-yl}piperidin-4-yl)acetic acid,
(254) 4-[N-methyl-N-{5-[6-(4-methylpyridin-2-ylamino)pyridin-2-yl]thiazol-2-yl}amino)methyl]benzoic acid,
(255) ((R)-1-{5-[6-(4-methylpyridin-2-ylamino)pyridin-2-yl]thiazol-2-yl}pyrrolidin-3-yloxy)acetic acid,
(256) 1-{5-[6-(4-methylpyridin-2-ylamino)pyridin-2-yl]thiazol-2-yl}pyrrolidine-3-carboxylic acid,
(257) (R)-1-(5-{6-[4-(2-hydroxyethyl)pyridin-2-ylamino]pyridin-2-yl}thiazol-2-yl)pyrrolidin-3-ol,
(258) 4-(N-methyl-N-{5-[6-(4-methylpyridin-2-ylamino)pyridin-2-yl]thiazol-2-yl}amino)benzoic acid,
(259) (2S,4R)-4-(N-methyl-N-{5-[6-(4-methylpyridin-2-ylamino)pyridin-2-yl]thiazol-2-yl}amino)pyrrolidine-2-carboxylic acid,
(260) {N-methyl-N-[2-(N'-methyl-N'-{5-[6-(4-methylpyridin-2-ylamino)pyridin-2-yl]thiazol-2-yl}amino)acetyl]amino}acetic acid,
(261) 2-{5-[6-(4-methylpyridin-2-ylamino)pyridin-2-yl]thiazol-2-yl}-1,2,3,4-tetrahydroisoquinoline-5-carboxylic acid,
(262) 3-[N-methyl-N-{5-[6-(4-methylpyridin-2-ylamino)pyridin-2-yl]thiazol-2-yl}amino)methyl]benzoic acid,
(263) {4-[N-methyl-N-{5-[6-(4-methylpyridin-2-ylamino)pyridin-2-yl]thiazol-2-yl}amino)methyl]phenyl}acetic acid,
(264) (1-{5-[6-(4-methylpyridin-2-ylamino)pyridin-2-yl]thiazol-2-yl}pyrrolidin-3-yl)acetic acid,
(265) (4-{5-[6-(4-methylpyridin-2-ylamino)pyridin-2-yl]thiazol-2-yl}piperazin-1-yl)acetic acid,
(266) N-(4-methylpyridin-2-yl)-N-(6-{2-[(R)-3-(1H-tetrazol-5-yl)piperidin-1-yl]thiazol-5-yl}pyridin-2-yl)amine,
(267) cis-4-(N-methyl-N-{5-[6-(4-methylpyridin-2-ylamino)pyridin-2-yl]thiazol-2-yl}amino)cyclohexanecarboxylic acid,
(268) trans-4-(N-methyl-N-{5-[6-(4-methylpyridin-2-ylamino)pyridin-2-yl]thiazol-2-yl}amino)cyclohexanecarboxylic acid,
(269) 4-[2-(N-methyl-N-{5-[6-(4-methylpyridin-2-ylamino)pyridin-2-yl]thiazol-2-yl}amino)ethyl]benzoic acid,
(270) (1-{5-[6-(4-methylpyridin-2-ylamino)pyridin-2-yl]thiazol-2-yl}piperidin-4-yloxy)acetic acid,
(271) (4-{5-[6-(4-methylpyridin-2-ylamino)pyridin-2-yl]thiazol-2-yl}cyclohexyl)acetic acid,
(272) 4-{[N-methyl-N-(5-{6-[4-(2-methyl-[1,3]dioxolan-2-yl)pyridin-2-ylamino]pyridin-2-yl}thiazol-2-yl)amino]methyl}benzoic acid,
(273) 4-[(N-dimethylcarbamoylmethyl-N-{5-[6-(4-methylpyridin-2-ylamino)pyridin-2-yl]thiazol-2-yl}amino)methyl]benzoic acid,
(274) cis-4-(N-carbamoylmethyl-N-{5-[6-(4-methylpyridin-2-ylamino)pyridin-2-yl]thiazol-2-yl}amino)cyclohexanecarboxylic acid,
(275) trans-4-[(N-carbamoylmethyl-N-{5-[6-(4-methylpyridin-2-ylamino)pyridin-2-yl]thiazol-2-yl}amino)methyl]cyclohexanecarboxylic acid,
(276) 5-[(N-methyl-N-{5-[6-(4-methylpyridin-2-ylamino)pyridin-2-yl]thiazol-2-yl}amino)methyl]thiophene-2-carboxylic acid,
(277) 3-chloro-4-[(N-methyl-N-{5-[6-(4-methylpyridin-2-ylamino)pyridin-2-yl]thiazol-2-yl}amino)methyl]benzoic acid,
(278) 4-{5-[6-(4-methylpyridin-2-ylamino)pyridin-2-yl]thiazol-2-ylmethoxy}benzoic acid,
(279) 3-methoxy-4-[(N-methyl-N-{5-[6-(4-methylpyridin-2-ylamino)pyridin-2-yl]thiazol-2-yl}amino)methyl]benzoic acid,
(280) 2-{5-[6-(4-methylpyridin-2-ylamino)pyridin-2-yl]thiazol-2-yl}-1,2,3,4-tetrahydroisoquinoline-6-carboxylic acid,
(281) 2-[(N-methyl-N-{5-[6-(4-methylpyridin-2-ylamino)pyridin-2-yl]thiazol-2-yl}amino)methyl]thiazole-4-carboxylic acid,
(282) [trans-4-(N-methyl-N-{5-[6-(4-methylpyridin-2-ylamino)pyridin-2-yl]thiazol-2-yl}amino)cyclohexyl]acetic acid,
(283) [cis-4-(N-methyl-N-{5-[6-(4-methylpyridin-2-ylamino)pyridin-2-yl]thiazol-2-yl}amino)cyclohexyl]acetic acid,
(284) 4-(2-{5-[6-(4-methylpyridin-2-ylamino)pyridin-2-yl]thiazol-2-yl}ethyl)cyclohexanecarboxylic acid,
(285) (1-{5-[6-(4-methylpyridin-2-ylamino)pyridin-2-yl]thiazol-2-yl}piperidin-4-yl)acetic acid,
(286) 4-{5-[6-(4-methylpyridin-2-ylamino)pyridin-2-yl]thiazol-2-yl}-3,4-dihydro-2H-benzo[1,4]oxazine-8-carboxylic acid,
(287) {5-[6-(4-methylpyridin-2-ylamino)pyridin-2-yl]thiazol-2-ylmethoxy}acetic acid,
(288) 4-[1-methyl-1-(N-methyl-N-{5-[6-(4-methylpyridin-2-ylamino)pyridin-2-yl]thiazol-2-ylamino)ethyl]benzoic acid,
(289) [4-(N-methyl-N-{5-[6-(4-methylpyridin-2-ylamino)pyridin-2-yl]thiazol-2-yl}amino)phenyl]acetic acid,
(290) (1-{5-[6-(4-chloropyridin-2-ylamino)pyridin-2-yl]thiazol-2-yl}piperidin-4-yl)acetic acid, (291) trans-4-[(N-benzyl-N-{5-[6-(4-methylpyridin-2-ylamino)pyridin-2-yl]thiazol-2-yl}amino)methyl]cyclohexanecarboxylic acid,
(292) [trans-4-(N-benzyl-N-{5-[6-(4-methylpyridin-2-ylamino)pyridin-2-yl]thiazol-2-yl}amino)cyclohexyl]acetic acid,
(293) trans-4-[(N-isopropyl-N-{5-[6-(4-methylpyridin-2-ylamino)pyridin-2-yl]thiazol-2-yl}amino)methyl]cyclohexanecarboxylic acid,
(294) 1-{5-[6-(4-methylpyridin-2-ylamino)pyridin-2-yl]thiazol-2-yl}-1,2,3,4-tetrahydroquinoline-5-carboxylic acid,
(295) fluoro-(1-{5-[6-(4-methylpyridin-2-ylamino)pyridin-2-yl]thiazol-2-yl}piperidin-4-ylidene)acetic acid,
(296) 5-(N-methyl-N-{5-[6-(4-methylpyridin-2-ylamino)pyridin-2-yl]thiazol-2-yl}amino)pentanoic acid,
(297) N-[2-(1-{5-[6-(4-methylpyridin-2-ylamino)pyridin-2-yl]thiazol-2-yl}piperidin-4-yl)acetyl]methanesulfonamide,
(298) 4-(N-methyl-N-{5-[6-(4-methylpyridin-2-ylamino)pyridin-2-yl]thiazol-2-yl}amino)butyric acid,
(299) (1-{5-[6-(4-trifluoromethylpyridin-2-ylamino)pyridin-2-yl]thiazol-2-yl}piperidin-4-yl)acetic acid,
(300) (1-{5-[6-(5-chloropyridin-2-ylamino)pyridin-2-yl]thiazol-2-yl}piperidin-4-yl)acetic acid,
(301) (1-{5-[6-(4-methoxypyridin-2-ylamino)pyridin-2-yl]thiazol-2-yl}piperidin-4-yl)acetic acid,
(302) trans-4-(N-methyl-N-{5-[6-(4-trifluoromethylpyridin-2-ylamino)pyridin-2-yl]thiazol-2-yl}amino)cyclohexanecarboxylic acid,
(303) 3-[4-(N-methyl-N-{5-[6-(4-methylpyridin-2-ylamino)pyridin-2-yl]thiazol-2-yl}amino)phenyl]propionic acid,
(304) (E)-6-(N-methyl-N-{5-[6-(4-methylpyridin-2-ylamino)pyridin-2-yl]thiazol-2-yl}-amino)hex-2-enoic acid,
(305) (2-{5-[6-(4-methylpyridin-2-ylamino)pyridin-2-yl]thiazol-2-yl}-1,2,3,4-tetrahydroisoquinolin-6-yl)acetic acid,
(306) 3-(2-{5-[6-(4-methylpyridin-2-ylamino)pyridin-2-yl]thiazol-2-yl}-1,2,3,4-tetrahydroisoquinolin-5-yl)propionic acid,
(307) 5-(N-isopropyl-N-{5-[6-(4-methylpyridin-2-ylamino)pyridin-2-yl]thiazol-2-yl}amino)pentanoic acid,
(308) 5-{5-[6-(4-methylpyridin-2-ylamino)pyridin-2-yl]thiazol-2-ylamino}pentanoic acid,
(309) 6-(N-methyl-N-{5-[6-(4-methylpyridin-2-ylamino)pyridin-2-yl]thiazol-2-yl}amino)hexanoic acid,
(310) (Z)-2-fluoro-6-(N-methyl-N-{5-[6-(4-methylpyridin-2-ylamino)pyridin-2-yl]thiazol-2-yl}amino)hex-2-enoic acid,
(311) (8-{5-[6-(4-trifluoromethylpyridin-2-ylamino)pyridin-2-yl]thiazol-2-yl}-8-azabicyclo [3.2.1]oct-3-yl)acetic acid,
(312) (8-{5-[6-(4-methylpyridin-2-ylamino)pyridin-2-yl]thiazol-2-yl}-8-azabicyclo[3.2.1]oct-3-yl)acetic acid,
(313) (1-{5-[6-(4-cyanopyridin-2-ylamino)pyridin-2-yl]thiazol-2-yl}piperidin-4-yl)acetic acid,
(314) {4-[(N-methyl-N-{5-[6-(4-trifluoromethylpyridin-2-ylamino)pyridin-2-yl]thiazol-2-yl}-amino)methyl]phenyl}acetic acid,
(315) 2-(1-{5-[6-(4-methylpyridin-2-ylamino)pyridin-2-yl]thiazol-2-yl}piperidin-4-yl)propionic acid,
(316) (1-{5-[6-(4-methylpyridin-2-ylamino)pyridin-2-yl]thiazol-2-yl}piperidin-4-yl)acetic acid,
(317) 4-[1-methyl-1-(N-methyl-N-{5-[6-(4-trifluoromethylpyridin-2-ylamino)pyridin-2-yl]thiazol-2-yl}amino)ethyl]benzoic acid,
(318) 3-methyl-6-(N-methyl-N-{5-[6-(4-trifluoromethylpyridin-2-ylamino)pyridin-2-yl]thiazol-2-yl}amino)hex-2-enoic acid,
(319) 3-methyl-6-(N-methyl-N-{5-[6-(4-methylpyridin-2-ylamino)pyridin-2-yl]thiazol-2-yl}amino)hex-2-enoic acid,
(320) (E)-6-(N-methyl-N-{5-[6-(4-trifluoromethylpyridin-2-ylamino)pyridin-2-yl]thiazol-2-yl}amino)hex-2-enoic acid,
(321) N-(2-hydroxyethyl)-(S)-1-{5-[6-(4-methylpyridin-2-ylamino)pyridin-2-yl]thiazol-2-yl}pyrrolidine-2-carboxamide,
(322) 2-(N-isopropyl-N-{5-[6-(4-methylpyridin-2-ylamino)pyridin-2-yl]thiazol-2-yl}amino)acetamide,
(323) 3-methyl-2-(N-methyl-N-{5-[6-(4-methylpyridin-2-ylamino)pyridin-2-yl]thiazol-2-yl}amino)butylamide,
(324) 2-(1-{5-[6-(4-methylpyridin-2-ylamino)pyridin-2-yl]thiazol-2-yl}piperidin-4-yl)ethanol,
(325) 5-(N-isopropyl-N-{5-[6-(4-methylpyridin-2-ylamino)pyridin-2-yl]thiazol-2-yl}amino)pentan-1-ol,
(326) (1-{5-[6-(pyrazin-2-ylamino)pyridin-2-yl]thiazol-2-yl}piperidin-4-yl)acetic acid,
(327) [1-(5-{6-[4-(2-hydroxyethyl)pyridin-2-ylamino]pyridin-2-yl} thiazol-2-yl)piperidin-4-yl]acetic acid,
(328) fluoro-(1-{5-[6-(4-methylpyridin-2-ylamino)pyridin-2-yl]thiazol-2-yl}piperidin-4-yl)acetic acid,
(329) 1-{5-[6-(4-methylpyridin-2-ylamino)pyridin-2-yl]thiazol-2-ylmethyl}piperidine-4-carboxamide,
(330) (1-{5-[6-(4-ethylpyridin-2-ylamino)pyridin-2-yl]thiazol-2-yl}piperidin-4-yl)acetic acid,
(331) N-isopropyl-N-{5-[6-(4-methylpyridin-2-ylamino)pyridin-2-yl]thiazol-2-yl}amine,
(332) N-{5-[6-(4-methylpyridin-2-ylamino)pyridin-2-yl]thiazol-2-yl}-N-(2-morpholin-4-ylethyl)amine,
(333) 2-(N-methyl-N-{5-[6-(4-methylpyridin-2-ylamino)pyridin-2-yl]thiazol-2-ylmethyl}amino)acetamide,
(334) 2-(1-{5-[6-(4-methylpyridin-2-ylamino)pyridin-2-yl]thiazol-2-yl}piperidin-4-yl)butyric acid,
(335) trans-4-[(N-methyl-N-{5-[6-(pyridin-2-ylamino)pyridin-2-yl]thiazol-2-yl}amino)methyl]cyclohexanecarboxylic acid,
(336) [1-(5-{6-[4-(2,2,2-trifluoroethoxy)pyridin-2-ylamino]pyridin-2-yl}thiazol-2-yl)piperidin-4-yl]acetic acid,
(337) 2-methyl-1-(N-methyl-N-{5-[6-(4-methylpyridin-2-ylamino)pyridin-2-yl]thiazol-2-yl}amino)propan-2-ol,
(338) 3-(1-{5-[6-(4-methylpyridin-2-ylamino)pyridin-2-yl]thiazol-2-yl}piperidin-3-yl)propionic acid,
(339) N-(2-hydroxyethyl)-4-(N'-methyl-N'-{5-[6-(4-methylpyridin-2-ylamino)pyridin-2-yl]thiazol-2-yl}amino)piperidine-1-carboxamide,
(340) 2-methyl-2-(1-{5-[6-(pyrazin-2-ylamino)pyridin-2-yl]thiazol-2-yl}piperidin-4-yl)propionic acid,
(341) 4-[(N-acetyl-N-{5-[6-(4-methylpyridin-2-ylamino)pyridin-2-yl]thiazol-2-ylmethyl}amino)methyl]benzoic acid,
(342) (1-{5-[6-(4-tert-butylpyridin-2-ylamino)pyridin-2-yl]thiazol-2-yl}piperidin-4-yl)acetic acid,
(343) (1-{5-[6-(4-isopropylpyridin-2-ylamino)pyridin-2-yl]thiazol-2-yl}piperidin-4-yl)acetic acid,
(344) 2-ylamino)pyridin-2-yl]thiazol-2-yl}-6-azaspiro[2.5]octane-1-carboxylic acid, (345) 2-[1-(5-{6-[4-(2-hydroxyethyl)pyridin-2-ylamino]pyridin-2-yl}thiazol-2-yl)piperidin-4-yl]-2-methylpropionic acid,
(346) 2-methyl-2-(1-{5-[6-(pyridin-2-ylamino)pyridin-2-yl]thiazol-2-yl}piperidin-4-yl)propionic acid,
(347) fluoro-(1-{5-[6-(pyrazin-2-ylamino)pyridin-2-yl]thiazol-2-yl}piperidin-4-yl)acetic acid,
(348) fluoro-(1-{5-[6-(pyridin-2-ylamino)pyridin-2-yl]thiazol-2-yl}piperidin-4-yl)acetic acid,
(349) [1-(5-{6-[4-(1-hydroxy-1-methylethyl)pyridin-2-ylamino]pyridin-2-yl}thiazol-2-yl)piperidin-4-yl]acetic acid,
(350) 2-methyl-2-(1-{5-[6-(4-methylpyridin-2-ylamino)pyridin-2-yl]thiazol-2-yl}piperidin-4-yl)propionic acid,
(351) 5-(1-{5-[6-(4-methylpyridin-2-ylamino)pyridin-2-yl]thiazol-2-yl}piperidin-3-yl)pentanoic acid, and
(352) 2-methyl-2-(N-methyl-N-{5-[6-(4-methylpyridin-2-ylamino)pyridin-2-yl]thiazol-2-ylmethyl}amino)propionamide.

10. The aminopyridine compound or a pharmaceutically acceptable salt thereof according to claim 1, wherein Z is a carbon atom.

11. The aminopyridine compound or a pharmaceutically acceptable salt thereof according to claim 10, wherein the aminopyridine compound is an aminopyridine compound represented by the following formula (Ib-1):

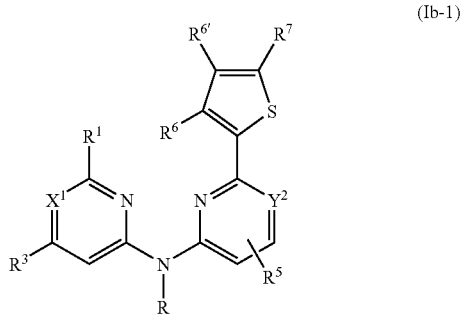

wherein
$X^1$ is
(1) —CH= or
(2) a nitrogen atom;
$Y^2$ is
(1) —CH= or
(2) a nitrogen atom;
R is
(1) a hydrogen atom,
(2) a $C_{1-6}$ alkyl group or
(3) an acyl group;
$R^1$ is
(1) a hydrogen atom or
(2) a halogen atom;
$R^3$ is
(1) a hydrogen atom,
(2) a halogen atom,
(3) —N($R^{31}$)($R^{32}$),
wherein $R^{31}$ and $R^{32}$ are a hydrogen atom or a $C_{1-6}$ alkyl group,
(4) a $C_{1-6}$ alkoxy group, wherein the $C_{1-6}$ alkyl group in the $C_{1-6}$ alkoxy group may be substituted with a substituent selected from the following group Aa-3:
[Group Aa-3]
(a) a hydroxyl group and
(b) —N($R^{31}$)($R^{32}$),
wherein $R^{31}$ and $R^{32}$ are the same as above,
(5) an acyl group,
(6) a saturated heterocyclic group or an aromatic heterocyclic group, wherein the heterocyclic group may be substituted with a $C_{1-6}$ alkyl group, and the saturated heterocyclic group may partially have a double bond,
(7) a $C_{1-6}$ alkyl group, wherein the $C_{1-6}$ alkyl group may be substituted with a substituent selected from the following group Ab-3:
[group Ab-3]
(a) a hydroxyl group,
(b) —COO$R^{33}$, wherein $R^{33}$ is a hydrogen atom or a $C_{1-6}$ alkyl group, and
(c) —CO—N($R^{31}$)($R^{32}$), wherein $R^{31}$ and $R^{32}$ are the same as above, or
(8) —COO$R^{33}$, wherein $R^{33}$ is the same as the above;
$R^5$ is
(1) a hydrogen atom,
(2) a $C_{1-6}$ alkyl group or
(3) —COO$R^{51}$,
wherein $R^{51}$ is a hydrogen atom or a $C_{1-6}$ alkyl group;
$R^6$ and $R^{6'}$ may be the same or different and each represent
(1) a hydrogen atom,
(2) a $C_{1-6}$ alkyl group or
(3) an acyl group; and
$R^7$ represent the same as in claim 1.

12. The aminopyridine compound or a pharmaceutically acceptable salt thereof according to claim 11, wherein the aminopyridine compound is an aminopyridine compound represented by the following formula (Ib-2):

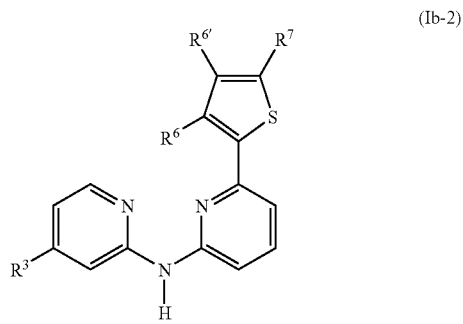

wherein $R^3$ is
(1) a halogen atom,
(2) —N($R^{31}$)($R^{32}$),
wherein $R^{31}$ and $R^{32}$ are hydrogen atom or a $C_{1-6}$ alkyl groups,
(3) a $C_{1-6}$ alkoxy group,
wherein the $C_{1-6}$ alkyl group in the $C_{1-6}$ alkoxy group may be substituted with a substituent selected from the following group Aa-3:
[Group Aa-3]
(a) a hydroxyl group and
(b) —N($R^{31}$)($R^{32}$),
wherein $R^{31}$ and $R^{32}$ are the same as above,
(4) an acyl group,
(5) a saturated heterocyclic group, wherein the heterocyclic group partially have a double bond and may be substituted with a $C_{1-6}$ alkyl group,
(6) a $C_{1-6}$ alkyl group which may be substituted with a substituent selected from the following group Ab-4:
[Group Ab-4]
(a) a hydroxyl group,
(b) —COO$R^{33}$, wherein $R^{33}$ is a hydrogen atom or a $C_{1-6}$ alkyl group, and
(c) —CO—N($R^{31}$)($R^{32}$),
wherein $R^{31}$ and $R^{32}$ are the same as above, or (7) —COOR$^{33}$,
wherein R$^{33}$ is the same as the above;
R$^6$ and R$^{6'}$ may be the same or different and each represent
(1) a hydrogen atom,
(2) a C$_{1-6}$ alkyl group which may be substituted with a hydroxyl group or a C$_{1-6}$ alkyl group which may be substituted with a C$_{1-6}$ alkoxy group or (3) an acyl group;
R$^7$ is a hydrogen atom, a halogen atom, a nitro group, a cyano group, or the following R$^a$, R$^b$, R$^c$, R$^d$, R$^e$, R$^f$, R$^g$ or R$^h$;
R$^a$ is —C$_p$H$_{2(p-1)}$(R$^{a1}$)(R$^{a2}$)—O—R$^{a3}$,
wherein
(1) p is an integer from 1 to 6,
(2) R$^{a1}$ is a hydrogen atom,
(3) R$^{a2}$ is a C$_{1-6}$ alkyl group, wherein the C$_{1-6}$ alkyl group may be substituted with a hydroxyl group, a halogen atom, a carboxy group, and
(4) R$^{a3}$ is a hydrogen atom or an acyl group;
R$^b$ is —C$_p$H$_{2(p-1)}$(R$^{b1}$)(R$^{b2}$)—N—(R$^{b3}$)(R$^{b4}$),
wherein
(1) p is an integer from 1 to 6,
(2) R$^{b1}$ is a hydrogen atom,
(3) R$^{b2}$ is a C$_{1-6}$ alkyl group,
(4) R$^{b3}$ is a hydrogen atom or a C$_{1-6}$ alkyl group, and
(5) R$^{b4}$ is
(a) a hydrogen atom or
(b) —OR$^{b42}$,
wherein R$^{b42}$ is a C$_{1-6}$ alkyl group;
R$^c$ is —C(=N—R$^{c1}$)—R$^{c2}$,
wherein
(1) R$^{c1}$ is
(a) a hydroxyl group,
(b) a C$_{1-6}$ alkoxy group, wherein C$_{1-6}$ alkyl group in the C$_{1-6}$ alkoxy group may be substituted with a hydroxyl group or a C$_{1-6}$ alkoxy group, or
(c) an acyloxy group, and
(2) R$^{c2}$ is a C$_{1-6}$ alkyl group or an amino group;
R$^d$ is —C(=O)—R$^{d1}$,
wherein R$^{d1}$ is
(1) a hydrogen atom,
(2) a C$_{1-6}$ alkyl group, wherein the C$_{1-6}$ alkyl group may be substituted with a hydroxyl group,
(3) a hydroxyl group,
(4) a C$_{1-6}$ alkoxy group,
(5) —N(R$^{d11}$)(R$^{d12}$),
wherein R$^{d11}$ and R$^{d12}$ may be the same or different and are
a hydrogen atom or
a C$_{1-6}$ alkyl group, wherein the C$_{1-6}$ alkyl group may be substituted with an amino group, a carboxy group or a hydroxyl group, or
R$^{d11}$ and R$^{d12}$ together with the adjacent nitrogen atom may form a 5- or 6-membered saturated heterocyclic ring, or
(6) a C$_{1-6}$ alkoxy group;
R$^e$ is a 5- or 6-membered aromatic heterocyclic group having 1 to 4 hetero atoms, wherein the aromatic heterocyclic group may be substituted with a C$_{1-6}$ alkyl group or an oxo group;
R$^f$ is a C$_{1-6}$ alkyl group or a C$_{2-6}$ alkenyl group, wherein these C$_{1-6}$ alkyl group and C$_{2-6}$ alkenyl group may be substituted with a substituent selected from the following group Fa-2:
[Group Fa-2]
(a) —COOH,
(b) —N(R$^{f21}$)(R$^{f22}$),
wherein R$^{f21}$ and R$^{f22}$ may be the same or different and are
a hydrogen atom,
an acyl group or
a C$_{1-6}$ alkyl group,
wherein the C$_{1-6}$ alkyl group may be substituted with a carboxy group, and
(c) a halogen atom,
R$^g$ is a substituent having Ring B" represented by the following formula (IIb);

(IIb)

wherein A" is a linker selected from the following group Ga-2:
[Group Ga-2]
—(CH$_2$)$_k$—,
—(CH$_2$)$_k$—NR$^{g1}$(CO)—,
—(CH$_2$)$_k$—NR$^{g1}$—(CH$_2$)$_j$—,
—(CH$_2$)$_k$—O—(CO)—,
—(CH$_2$)$_k$—O—,
—(CO)—NR$^{g1}$—(CH$_2$)$_j$—,
—(CO)— and
—(CO)—NR$^{g1}$—,
wherein k and j may be the same or different and represent an integer from 1 to 4,
R$^{g1}$ is
a hydrogen atom,
an acyl group, wherein the acyl group may be substituted with a hydroxyl group or a carboxy group, or
a C$_{1-6}$ alkyl group, wherein the alkyl group may be substituted with —CON(R$^{g41}$)(R$^{g42}$),
Ring B" is a ring selected from the following group Ha-2:
[Group Ha-2]
an aromatic hydrocarbon group,
a C$_{3-8}$ cycloalkyl group and
a 5- to 7-membered saturated heterocyclic group containing at least one nitrogen atoms, wherein the saturated heterocyclic ring may form a condensed ring with a phenyl group, and
the Ring B" may be substituted with a substituent selected from follows group Ia-2:
[Group Ia-2]
(a) —OR$^{g2}$,
wherein R$^{g2}$ is
a hydrogen atom,
a C$_{1-6}$ alkyl group or
an aralkyl group, and
(b) —COOR$^{g3}$,
wherein R$^{g3}$ is
a hydrogen atom or
a C$_{1-6}$ alkyl group, wherein the alkyl group may be substituted with a hydroxyl group; and
R$^h$ is —N(R$^{h1}$)(R$^{h2}$),
wherein R$^{h1}$ is a hydrogen atom, and R$^{h2}$ is an acyl group, wherein the acyl group may be substituted with a hydroxyl group, or a C$_{1-6}$ alkoxycarbonyl group.

13. A pharmaceutical composition comprising an aminopyridine compound or a pharmaceutically acceptable salt thereof according to claim 1 as an active ingredient.

* * * * *